(12) United States Patent
Yadav et al.

(10) Patent No.: US 9,029,122 B2
(45) Date of Patent: May 12, 2015

(54) LONG CHAIN OMEGA-3 AND OMEGA-6 POLYUNSATURATED FATTY ACID BIOSYNTHESIS BY EXPRESSION OF ACYL-COA LYSOPHOSPHOLIPID ACYLTRANSFERASES

(71) Applicant: E I du Pont de Nemours and Company, Wilmington, DE (US)

(72) Inventors: Narendra S Yadav, Wilmington, DE (US); Hongxiang Zhang, Chadds Ford, PA (US); Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/957,782

(22) Filed: Aug. 2, 2013

(65) Prior Publication Data

US 2014/0031572 A1 Jan. 30, 2014

Related U.S. Application Data

(62) Division of application No. 12/814,764, filed on Jun. 14, 2010, now Pat. No. 8,524,485.

(60) Provisional application No. 61/187,366, filed on Jun. 16, 2009, provisional application No. 61/187,368, filed on Jun. 16, 2009, provisional application No. 61/187,359, filed on Jun. 16, 2009.

(51) Int. Cl.
| | |
|---|---|
| *C12N 1/00* | (2006.01) |
| *C12N 1/10* | (2006.01) |
| *C12N 15/00* | (2006.01) |
| *C07H 21/04* | (2006.01) |
| *A23D 9/00* | (2006.01) |
| *C12N 9/10* | (2006.01) |
| *A21D 2/16* | (2006.01) |
| *A23K 1/16* | (2006.01) |
| *C12N 9/00* | (2006.01) |
| *C12P 7/64* | (2006.01) |

(52) U.S. Cl.
CPC ............. *C12N 9/1029* (2013.01); *A21D 2/165* (2013.01); *A23K 1/164* (2013.01); *C12N 9/00* (2013.01); *C12N 9/13* (2013.01); *C12N 9/93* (2013.01); *C12P 7/6427* (2013.01); *C12P 7/6472* (2013.01); *C12P 7/6481* (2013.01)

(58) Field of Classification Search
CPC .... C12N 9/1029; C12N 15/815; C12N 15/52; C12N 1/16; C12N 9/20; C12N 15/79; C12P 7/6472; C12P 7/6427; C12P 7/6481; C12P 7/64; C12P 7/6409; A23V 2002/00; A23V 2250/187; A23V 2250/1868; A23V 2250/1862; A23V 2250/1882; A23K 1/164
See application file for complete search history.

(56) References Cited

U.S. PATENT DOCUMENTS

| | | |
|---|---|---|
| 2006/0094090 A1 | 5/2006 | Damude et al. |
| 2006/0110806 A1 | 5/2006 | Damude et al. |
| 2006/0115881 A1 | 6/2006 | Damude et al. |
| 2006/0168687 A1 | 7/2006 | Renz et al. |
| 2006/0174376 A1 | 8/2006 | Renz et al. |
| 2008/0076377 A1 | 3/2008 | Golberg et al. |
| 2008/0145867 A1 | 6/2008 | Zou et al. |
| 2009/0093543 A1 | 4/2009 | Xue et al. |
| 2009/0094707 A1 | 4/2009 | Cirpus et al. |
| 2009/0325265 A1 | 12/2009 | Damude et al. |

FOREIGN PATENT DOCUMENTS

| | | |
|---|---|---|
| EP | 2169055 A1 | 3/2010 |
| EP | 2182071 A1 | 5/2010 |
| WO | 2004076617 A2 | 9/2004 |
| WO | 2004087902 A2 | 10/2004 |
| WO | 2006052870 A2 | 5/2006 |
| WO | 2006069936 A2 | 6/2006 |
| WO | 2008034648 A1 | 3/2008 |
| WO | 2008146745 A1 | 12/2008 |
| WO | 2009001315 A2 | 12/2008 |
| WO | 2009014140 A1 | 1/2009 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Co-Pending U.S. Appl. No. 61/187,359, filed Jun. 14, 2010, Narendra S. Yadav et al.
Co-Pending U.S. Appl. No. 61/187,366, filed Jun. 14, 2010, Seung-Pyo Hong et al.
Co-Pending U.S. Appl. No. 61/187,368, filed Jun. 14, 2010, Seung-Pyo Hong et al.
Shindou et al., Identification of Membrane O-Acyltransferase Family Motifs, Biochemical and Biophysical Research Communications, vol. 383 (2009), pp. 320-325.
Shindou et al., Recent Progress on Acyl CoA: Lysophospholipid Acyltransferase Research, Journal of Lipid Research, vol. 50, (April Supplement 2009), pp. S46-S51.
Shindou et al., Acyl-CoA: Lysophospholipid Acyltransferases, Journal of Biological Chemistry, vol. 284 (2009), pp. 1-5.
Lewin et al., Analysis of Amino Acid Motifs Diagnostic for the sn-Glycerol-3-Phosphate Acyltransferase Reaction, Biochemistry, vol. 38 (1999), pp. 5764-5771.
Yamashita et al., Topology of Acyltransferase Motifs and Substrate Specificity and Accessibility in 1-Acyl-Sn-Glycero-3-Phosphate Acyltransferase 1, Biochimica et Biophysics Acta, vol. 1771 (2007), pp. 1202-1215.

(Continued)

*Primary Examiner* — Iqbal H Chowdhury

(57) ABSTRACT

Methods for increasing $C_{18}$ to $C_{20}$ elongation conversion efficiency and/or Δ4 desaturation conversion efficiency in long-chain polyunsaturated fatty acid ["LC-PUFA"]-producing recombinant oleaginous microbial host cells are provided herein, based on over-expression of acyl-CoA:lysophospholipid acyltransferases ["LPLATs"] (e.g., Ale1, LPAAT, LPCAT). Production host cells and oils produced by the methods of the invention are also claimed.

12 Claims, 14 Drawing Sheets

(56) References Cited

OTHER PUBLICATIONS

Figure 1B:
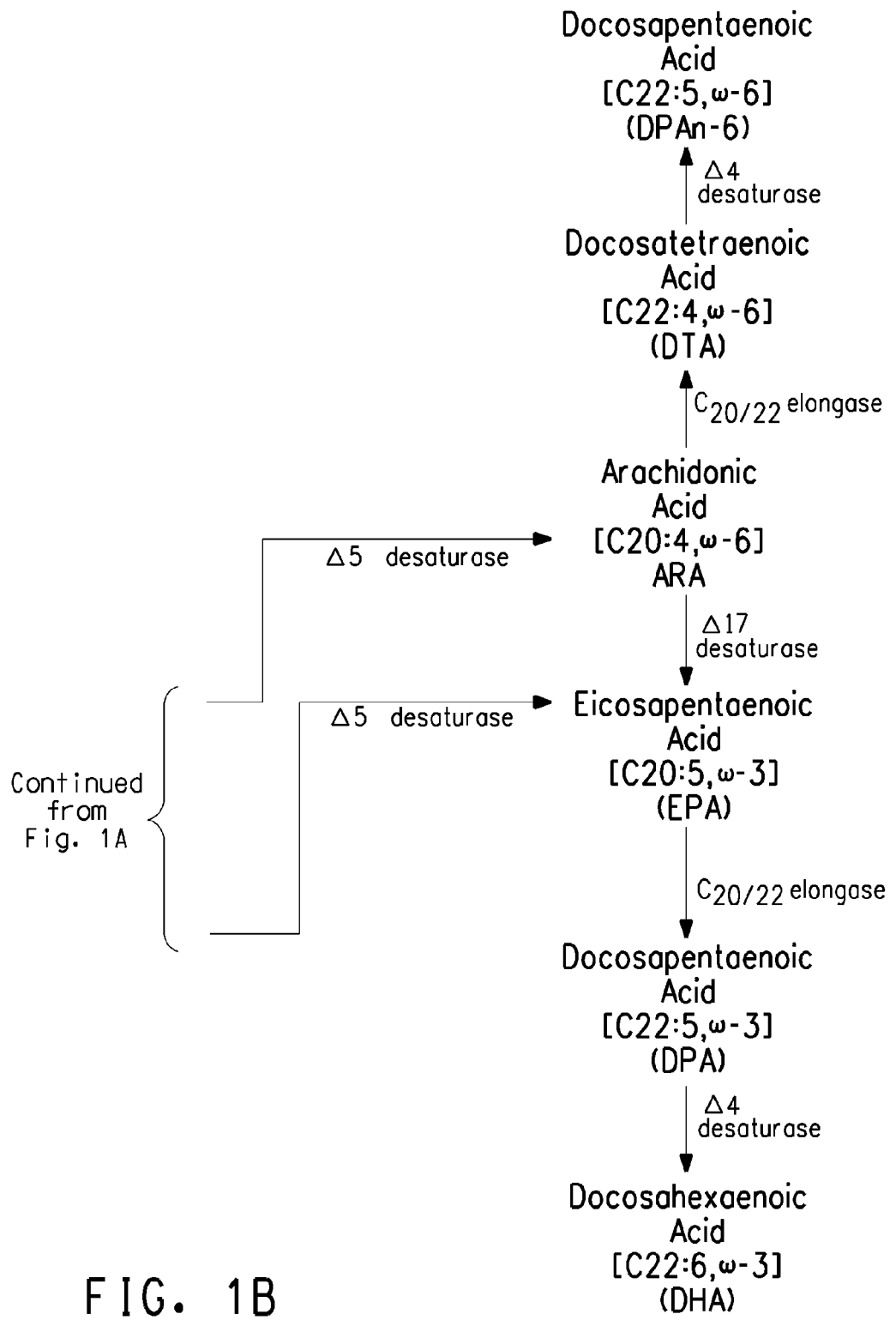

Kennedy et al., The Function of Cytidine Coenzymes in the Biosynthesis of Phospholipides, J. Biol. Chem., vol. 222 (1956), pp. 193-214.

Lands et al., Metabolism of Glycerolipides: A Comparison of Lecithin and Triglyceride Synthesis, J. Biol. Chem., vol. 231 (1958), pp. 883-888.

International Search Report, International Patent Application PCT/US2010/38527, Mailed Oct. 1, 2010.

* cited by examiner

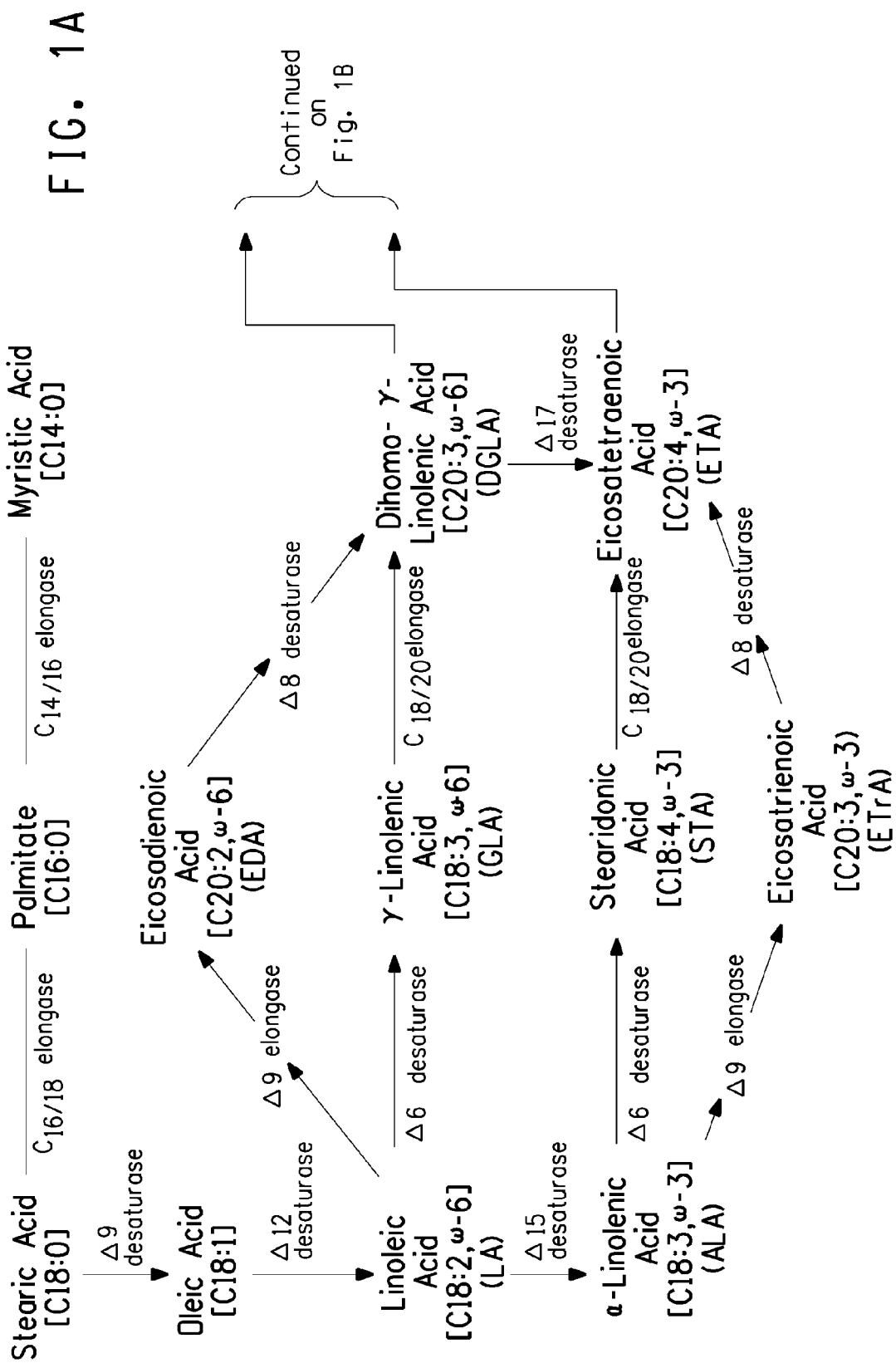

SEQUENCE LISTING

```
<160> NUMBER OF SEQ ID NOS: 101

<210> SEQ ID NO 1
<211> LENGTH: 849
<212> TYPE: DNA
<213> ORGANISM: Caenorhabditis elegans
<220> FEATURE:
<221> NAME/KEY: CDS
<222> LOCATION: (1)..(849)
<223> OTHER INFORMATION: GenBank Accession No. CAA98276; "clone T06E8.1"
<300> PUBLICATION INFORMATION:
<302> TITLE: METHOD FOR THE PRODUCTION OF POLYUNSATURATED FATTY ACIDS
<310> PATENT DOCUMENT NUMBER: US 2006-0168687-A1
<311> PATENT FILING DATE: 2004-01-29
<312> PUBLICATION DATE: 2006-07-27
<313> RELEVANT RESIDUES IN SEQ ID NO: (1)..(849)
<300> PUBLICATION INFORMATION:
<302> TITLE: METHOD FOR THE PRODUCTION OF POLYUNSATURATED FATTY ACIDS
<310> PATENT DOCUMENT NUMBER: WO 2004/076617
<311> PATENT FILING DATE: 2004-01-29
<312> PUBLICATION DATE: 2004-09-10
<313> RELEVANT RESIDUES IN SEQ ID NO: (1)..(849)
```

<400> SEQUENCE: 1

```
atg gag aac ttc tgg tcg atc gtc gtg ttt ttt cta ctc tca att ctc    48
Met Glu Asn Phe Trp Ser Ile Val Val Phe Phe Leu Leu Ser Ile Leu
1               5                   10                  15 ttc att tta tat aac ata tcg aca gta tgc cac tac tat atg cgg att    96
Phe Ile Leu Tyr Asn Ile Ser Thr Val Cys His Tyr Tyr Met Arg Ile
                20                  25                  30 tcg ttt tat tac ttc aca att tta ttg cat gga atg gaa gtt tgt gtt   144
Ser Phe Tyr Tyr Phe Thr Ile Leu Leu His Gly Met Glu Val Cys Val
            35                  40                  45 aca atg atc cct tct tgg cta aat ggg aag ggt gct gat tac gtg ttt   192
Thr Met Ile Pro Ser Trp Leu Asn Gly Lys Gly Ala Asp Tyr Val Phe
        50                  55                  60 cac tcg ttt ttc tat tgg tgt aaa tgg act ggt gtt cat aca aca gtc   240
His Ser Phe Phe Tyr Trp Cys Lys Trp Thr Gly Val His Thr Thr Val
65                  70                  75                  80 tat gga tat gaa aaa aca caa gtt gaa ggt ccg gct gta gtt att tgt   288
Tyr Gly Tyr Glu Lys Thr Gln Val Glu Gly Pro Ala Val Val Ile Cys
                85                  90                  95 aat cat cag agt tct ctc gac att cta tcg atg gca tca atc tgg ccg   336
Asn His Gln Ser Ser Leu Asp Ile Leu Ser Met Ala Ser Ile Trp Pro
                100                 105                 110 aag aat tgt gtt gta atg atg aaa cga att ctt gcc tat gtt cca ttc   384
Lys Asn Cys Val Val Met Met Lys Arg Ile Leu Ala Tyr Val Pro Phe
            115                 120                 125 ttc aat ctc gga gcc tac ttt tcc aac aca atc ttc atc gat cga tat   432
Phe Asn Leu Gly Ala Tyr Phe Ser Asn Thr Ile Phe Ile Asp Arg Tyr
        130                 135                 140 aac cgt gaa cgt gcg atg gct tca gtt gat tat tgt gca tct gaa atg   480
Asn Arg Glu Arg Ala Met Ala Ser Val Asp Tyr Cys Ala Ser Glu Met
145                 150                 155                 160 aag aac aga aat ctt aaa ctt tgg gta ttt ccg gaa gga aca aga aat   528
Lys Asn Arg Asn Leu Lys Leu Trp Val Phe Pro Glu Gly Thr Arg Asn
                165                 170                 175 cgt gaa gga ggg ttc att cca ttc aag aaa gga gca ttc aat att gca   576
Arg Glu Gly Gly Phe Ile Pro Phe Lys Lys Gly Ala Phe Asn Ile Ala
            180                 185                 190 gtt cgt gcg cag att ccc att att cca gtt gta ttc tca gac tat cgg   624
Val Arg Ala Gln Ile Pro Ile Ile Pro Val Val Phe Ser Asp Tyr Arg
        195                 200                 205 gat ttc tac tca aag cca ggc cga tat ttc aag aat gat gga gaa gtt   672
Asp Phe Tyr Ser Lys Pro Gly Arg Tyr Phe Lys Asn Asp Gly Glu Val
        210                 215                 220 gtt att cga gtt ctg gat gcg att cca aca aaa ggg ctc act ctt gat   720
Val Ile Arg Val Leu Asp Ala Ile Pro Thr Lys Gly Leu Thr Leu Asp
225                 230                 235                 240 gac gtc agc gag ttg tct gat atg tgt cgg gac gtt atg ttg gca gcc   768
Asp Val Ser Glu Leu Ser Asp Met Cys Arg Asp Val Met Leu Ala Ala
                245                 250                 255 tat aag gaa gtt act cta gaa gct cag caa cga aat gcg aca cgg cgt   816
Tyr Lys Glu Val Thr Leu Glu Ala Gln Gln Arg Asn Ala Thr Arg Arg
            260                 265                 270 gga gaa aca aaa gac ggg aag aaa tct gag taa                       849
Gly Glu Thr Lys Asp Gly Lys Lys Ser Glu
        275                 280
```

<210> SEQ ID NO 2
<211> LENGTH: 282
<212> TYPE: PRT
<213> ORGANISM: Caenorhabditis elegans

<400> SEQUENCE: 2

```
Met Glu Asn Phe Trp Ser Ile Val Val Phe Leu Leu Ser Ile Leu
1               5                   10                  15

Phe Ile Leu Tyr Asn Ile Ser Thr Val Cys His Tyr Tyr Met Arg Ile
            20                  25                  30

Ser Phe Tyr Tyr Phe Thr Ile Leu Leu His Gly Met Glu Val Cys Val
            35                  40                  45

Thr Met Ile Pro Ser Trp Leu Asn Gly Lys Gly Ala Asp Tyr Val Phe
    50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Val Ile Cys
                85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
            115                 120                 125

Phe Asn Leu Gly Ala Tyr Phe Ser Asn Thr Ile Phe Ile Asp Arg Tyr
130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
                165                 170                 175

Arg Glu Gly Gly Phe Ile Pro Phe Lys Lys Gly Ala Phe Asn Ile Ala
            180                 185                 190

Val Arg Ala Gln Ile Pro Ile Ile Pro Val Val Phe Ser Asp Tyr Arg
    195                 200                 205

Asp Phe Tyr Ser Lys Pro Gly Arg Tyr Phe Lys Asn Asp Gly Glu Val
    210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
            245                 250                 255

Tyr Lys Glu Val Thr Leu Glu Ala Gln Gln Arg Asn Ala Thr Arg Arg
            260                 265                 270

Gly Glu Thr Lys Asp Gly Lys Lys Ser Glu
            275                 280
```

<210> SEQ ID NO 3
<211> LENGTH: 7
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: MISC_FEATURE
<222> LOCATION: (2)..(2)
<223> OTHER INFORMATION: Xaa = Val [V] or Ile [I]
<220> FEATURE:
<221> NAME/KEY: misc_feature
<222> LOCATION: (4)..(5)
<223> OTHER INFORMATION: Xaa can be any naturally occurring amino acid

<400> SEQUENCE: 3

```
Met Xaa Leu Xaa Xaa Lys Leu
1               5
```

```
<210> SEQ ID NO 4
<211> LENGTH: 8
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 4

Arg Xaa Lys Tyr Tyr Xaa Xaa Trp
1               5

<210> SEQ ID NO 5
<211> LENGTH: 6
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 5

Ser Ala Xaa Trp His Gly
1               5

<210> SEQ ID NO 6
<211> LENGTH: 859
<212> TYPE: DNA
<213> ORGANISM: Caenorhabditis elegans
<220> FEATURE:
<221> NAME/KEY: CDS
<222> LOCATION: (3)..(851)
<223> OTHER INFORMATION: synthetic LPCAT (codon-optimized for Yarrowia
      lipolytica)

<400> SEQUENCE: 6 cc atg gag aac ttc tgg tcc atc gtc gtg ttc ttt ctg ctc tcc att        47
   Met Glu Asn Phe Trp Ser Ile Val Val Phe Phe Leu Leu Ser Ile
   1               5                   10                  15 ctg ttc atc ctc tac aac att tcg aca gtc tgc cac tac tac atg cga       95
Leu Phe Ile Leu Tyr Asn Ile Ser Thr Val Cys His Tyr Tyr Met Arg
                20                  25                  30 atc tcc ttc tac tac ttt acc atc ctg ctt cac ggc atg gag gtg tgc      143
Ile Ser Phe Tyr Tyr Phe Thr Ile Leu Leu His Gly Met Glu Val Cys
            35                  40                  45 gtt acc atg att ccc tct tgg ctc aac ggc aag ggt gcc gac tac gtg      191
Val Thr Met Ile Pro Ser Trp Leu Asn Gly Lys Gly Ala Asp Tyr Val
        50                  55                  60 ttt cac tcg ttc ttc tac tgg tgc aag tgg act gga gtc cac acc act      239
Phe His Ser Phe Phe Tyr Trp Cys Lys Trp Thr Gly Val His Thr Thr
    65                  70                  75 gtg tat ggc tac gag aag acc cag gtc gaa ggt cct gcc gtg gtc atc      287
Val Tyr Gly Tyr Glu Lys Thr Gln Val Glu Gly Pro Ala Val Val Ile
80                  85                  90                  95 tgc aac cat cag tcc tcg ctc gac att ctg tct atg gct tcc atc tgg      335
Cys Asn His Gln Ser Ser Leu Asp Ile Leu Ser Met Ala Ser Ile Trp
                100                 105                 110 ccc aag aac tgt gtt gtc atg atg aag cgg att ctt gcc tac gtt ccc      383
```

```
             Pro Lys Asn Cys Val Val Met Met Lys Arg Ile Leu Ala Tyr Val Pro
                         115                 120                 125 ttc ttc aac ctg gga gcc tac ttt tcc aac acc atc ttc atc gac cga        431
Phe Phe Asn Leu Gly Ala Tyr Phe Ser Asn Thr Ile Phe Ile Asp Arg
            130                 135                 140 tac aac cga gag cga gct atg gct tct gtc gac tac tgt gcc tcc gag        479
Tyr Asn Arg Glu Arg Ala Met Ala Ser Val Asp Tyr Cys Ala Ser Glu
145                 150                 155 atg aag aac cga aac ctg aag ctc tgg gtg ttt ccc gaa ggc act cgg        527
Met Lys Asn Arg Asn Leu Lys Leu Trp Val Phe Pro Glu Gly Thr Arg
160                 165                 170                 175 aat cga gag ggt gga ttc att ccc ttc aag aaa ggt gcc ttc aac atc        575
Asn Arg Glu Gly Gly Phe Ile Pro Phe Lys Lys Gly Ala Phe Asn Ile
                180                 185                 190 gct gtt cga gcc cag att ccc atc att cct gtc gtg ttc tct gac tat        623
Ala Val Arg Ala Gln Ile Pro Ile Ile Pro Val Val Phe Ser Asp Tyr
            195                 200                 205 cga gac ttc tac tcc aag cct ggc cga tac ttc aag aac gat gga gag        671
Arg Asp Phe Tyr Ser Lys Pro Gly Arg Tyr Phe Lys Asn Asp Gly Glu
        210                 215                 220 gtc gtg atc cga gtc ctg gat gcc att ccc acc aag ggt ctg acc ctc        719
Val Val Ile Arg Val Leu Asp Ala Ile Pro Thr Lys Gly Leu Thr Leu
225                 230                 235 gat gac gtc tct gag ctt tcg gac atg tgt cga gac gtc atg ctg gct        767
Asp Asp Val Ser Glu Leu Ser Asp Met Cys Arg Asp Val Met Leu Ala
240                 245                 250                 255 gcc tac aag gaa gtt acc ctc gag gct cag caa cga aac gcc act cga        815
Ala Tyr Lys Glu Val Thr Leu Glu Ala Gln Gln Arg Asn Ala Thr Arg
                260                 265                 270 aga gga gag acc aag gac ggc aag aaa tcc gag taa gcggccgc              859
Arg Gly Glu Thr Lys Asp Gly Lys Lys Ser Glu
            275                 280

<210> SEQ ID NO 7
<211> LENGTH: 282
<212> TYPE: PRT
<213> ORGANISM: Caenorhabditis elegans

<400> SEQUENCE: 7

Met Glu Asn Phe Trp Ser Ile Val Val Phe Leu Leu Ser Ile Leu
1               5                   10                  15

Phe Ile Leu Tyr Asn Ile Ser Thr Val Cys His Tyr Met Arg Ile
                20                  25                  30

Ser Phe Tyr Tyr Phe Thr Ile Leu Leu His Gly Met Glu Val Cys Val
            35                  40                  45

Thr Met Ile Pro Ser Trp Leu Asn Gly Lys Gly Ala Asp Tyr Val Phe
        50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Ile Cys
                85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
    130                 135                 140

Asn Arg Glu Arg Ala Met Ala Ser Val Asp Tyr Cys Ala Ser Glu Met
```

```
                145                 150                 155                 160
Lys Asn Arg Asn Leu Lys Leu Trp Val Phe Pro Glu Gly Thr Arg Asn
                    165                 170                 175
Arg Glu Gly Gly Phe Ile Pro Phe Lys Lys Gly Ala Phe Asn Ile Ala
                    180                 185                 190
Val Arg Ala Gln Ile Pro Ile Pro Val Val Phe Ser Asp Tyr Arg
                195                 200                 205
Asp Phe Tyr Ser Lys Pro Gly Arg Tyr Phe Lys Asn Asp Gly Glu Val
            210                 215                 220
Val Ile Arg Val Leu Asp Ala Ile Pro Thr Lys Gly Leu Thr Leu Asp
225                 230                 235                 240
Asp Val Ser Glu Leu Ser Asp Met Cys Arg Asp Val Met Leu Ala Ala
                245                 250                 255
Tyr Lys Glu Val Thr Leu Glu Ala Gln Gln Arg Asn Ala Thr Arg Arg
                260                 265                 270
Gly Glu Thr Lys Asp Gly Lys Lys Ser Glu
            275                 280
```

<210> SEQ ID NO 8
<211> LENGTH: 1860
<212> TYPE: DNA
<213> ORGANISM: Saccharomyces cerevisiae
<220> FEATURE:
<221> NAME/KEY: CDS
<222> LOCATION: (1)..(1860)
<223> OTHER INFORMATION: GenBank Accession No. NP_014818; "YOR175C"
<300> PUBLICATION INFORMATION:
<302> TITLE: Genes encoding a novel type of lysophophatidylcholine
      acyltransferases and their use to increase triacylglycerol
      production and/or modify fatty acid composition
<310> PATENT DOCUMENT NUMBER: US-2008-0145867-A1
<311> PATENT FILING DATE: 2007-06-15
<312> PUBLICATION DATE: 2008-06-19
<313> RELEVANT RESIDUES IN SEQ ID NO: (1)..(1860)
<300> PUBLICATION INFORMATION:
<302> TITLE: Genes encoding a novel type of lysophophatidylcholine
      acyltransferases and their use to increase triacylglycerol
      production and/or modify fatty acid composition
<310> PATENT DOCUMENT NUMBER: WO 2008/076377
<311> PATENT FILING DATE: 2007-12-13
<312> PUBLICATION DATE: 2008-06-26
<313> RELEVANT RESIDUES IN SEQ ID NO: (1)..(1860)
<300> PUBLICATION INFORMATION:
<302> TITLE: USE OF A CLASS OF GENES ENCODING LYSOPHOSPHOLIPID ACYL
      TRANSFERASES FOR APPLICATION IN AGRICULTURE, BIOTECHNOLOGY AND
      MEDICINE
<310> PATENT DOCUMENT NUMBER: WO 2009/001315
<311> PATENT FILING DATE: 2008-06-25
<312> PUBLICATION DATE: 2008-12-31
<313> RELEVANT RESIDUES IN SEQ ID NO: (1)..(1860)

<400> SEQUENCE: 8

```
atg tac aat cct gtg gac gct gtt tta aca aag ata att acc aac tat    48
Met Tyr Asn Pro Val Asp Ala Val Leu Thr Lys Ile Ile Thr Asn Tyr
1               5                   10                  15 ggg att gat agt ttt aca ctg cga tat gct atc tgc tta ttg gga tcg    96
Gly Ile Asp Ser Phe Thr Leu Arg Tyr Ala Ile Cys Leu Leu Gly Ser
                20                  25                  30 ttc cca ctg aat gct att ttg aag aga att ccc gag aag cgt ata ggt   144
Phe Pro Leu Asn Ala Ile Leu Lys Arg Ile Pro Glu Lys Arg Ile Gly
            35                  40                  45 tta aaa tgt tgt ttt atc att tct atg tcg atg ttt tac tta ttc ggt   192
Leu Lys Cys Cys Phe Ile Ile Ser Met Ser Met Phe Tyr Leu Phe Gly
    50                  55                  60 gtg ctg aat cta gta agt gga ttc agg acc ctg ttt att agt acc atg   240
```

|  |  |  |  |  |  |  |  |  |  |  |  |  |  |  |  |  |
|---|---|---|---|---|---|---|---|---|---|---|---|---|---|---|---|---|
| Val | Leu | Asn | Leu | Val | Ser | Gly | Phe | Arg | Thr | Leu | Phe | Ile | Ser | Thr | Met | |
| 65 | | | | 70 | | | | | 75 | | | | | | 80 | |

```
ttt act tac ttg atc tca aga ttt tac cgt tcc aag ttt atg cca cac       288
Phe Thr Tyr Leu Ile Ser Arg Phe Tyr Arg Ser Lys Phe Met Pro His
                85                  90                  95 ttg aat ttc atg ttt gtt atg ggt cat ttg gca ata aat cat ata cac       336
Leu Asn Phe Met Phe Val Met Gly His Leu Ala Ile Asn His Ile His
            100                 105                 110 gcc caa ttc ctt aac gaa cag act caa act acc gtt gac att aca agt       384
Ala Gln Phe Leu Asn Glu Gln Thr Gln Thr Thr Val Asp Ile Thr Ser
        115                 120                 125 tca caa atg gtt tta gcc atg aaa cta act tct ttt gca tgg tcg tac       432
Ser Gln Met Val Leu Ala Met Lys Leu Thr Ser Phe Ala Trp Ser Tyr
    130                 135                 140 tat gat ggt tca tgc act agc gaa agc gat ttc aaa gat ttg act gag       480
Tyr Asp Gly Ser Cys Thr Ser Glu Ser Asp Phe Lys Asp Leu Thr Glu
145                 150                 155                 160 cat caa aaa tct cgt gct gtc aga ggt cat cca ccc tta tta aag ttc       528
His Gln Lys Ser Arg Ala Val Arg Gly His Pro Pro Leu Leu Lys Phe
                165                 170                 175 ctg gca tat gca ttt ttc tat tca acg ttg cta act ggc cca agt ttc       576
Leu Ala Tyr Ala Phe Phe Tyr Ser Thr Leu Leu Thr Gly Pro Ser Phe
            180                 185                 190 gat tat gcc gat ttt gac agc tgg ttg aat tgt gag atg ttc cgt gac       624
Asp Tyr Ala Asp Phe Asp Ser Trp Leu Asn Cys Glu Met Phe Arg Asp
        195                 200                 205 ttg cct gaa agc aaa aag cct atg aga aga cac cac cct ggt gaa aga       672
Leu Pro Glu Ser Lys Lys Pro Met Arg Arg His His Pro Gly Glu Arg
    210                 215                 220 aga cag att cca aag aat ggt aaa ctt gca tta tgg aaa gtt gtt caa       720
Arg Gln Ile Pro Lys Asn Gly Lys Leu Ala Leu Trp Lys Val Val Gln
225                 230                 235                 240 ggt ctt gct tgg atg att tta agt aca cta gga atg aag cac ttc ccc       768
Gly Leu Ala Trp Met Ile Leu Ser Thr Leu Gly Met Lys His Phe Pro
                245                 250                 255 gta aaa tac gtt ttg gac aaa gat ggc ttc cca acg aga tct ttt ata       816
Val Lys Tyr Val Leu Asp Lys Asp Gly Phe Pro Thr Arg Ser Phe Ile
            260                 265                 270 ttc aga atc cat tac tta ttc ttg ctt ggt ttc atc cat aga ttc aag       864
Phe Arg Ile His Tyr Leu Phe Leu Leu Gly Phe Ile His Arg Phe Lys
        275                 280                 285 tac tac gct gcc tgg act att tcg gaa gga tct tgt att ttg tgc ggt       912
Tyr Tyr Ala Ala Trp Thr Ile Ser Glu Gly Ser Cys Ile Leu Cys Gly
    290                 295                 300 ttg ggt tat aat ggt tat gat tca aag aca caa aag atc aga tgg gat       960
Leu Gly Tyr Asn Gly Tyr Asp Ser Lys Thr Gln Lys Ile Arg Trp Asp
305                 310                 315                 320 cgt gtc aga aat att gac att tgg acc gta gaa acg gcg cag aat acg      1008
Arg Val Arg Asn Ile Asp Ile Trp Thr Val Glu Thr Ala Gln Asn Thr
                325                 330                 335 cgt gaa atg ttg gaa gca tgg aat atg aat act aac aag tgg cta aaa      1056
Arg Glu Met Leu Glu Ala Trp Asn Met Asn Thr Asn Lys Trp Leu Lys
            340                 345                 350 tac tct gtt tat tta cgt gtc aca aag aag ggc aaa aaa cct ggt ttc      1104
Tyr Ser Val Tyr Leu Arg Val Thr Lys Lys Gly Lys Lys Pro Gly Phe
        355                 360                 365 cgc tca act ttg ttt act ttc cta act tcc gca ttt tgg cat ggt acc      1152
Arg Ser Thr Leu Phe Thr Phe Leu Thr Ser Ala Phe Trp His Gly Thr
    370                 375                 380
```

```
aga cct ggg tac tat ctg act ttt gcg aca ggg gct ttg tac caa aca    1200
Arg Pro Gly Tyr Tyr Leu Thr Phe Ala Thr Gly Ala Leu Tyr Gln Thr
385                 390                 395                 400 tgt ggt aaa atc tac aga cgc aat ttt aga cca att ttc ttg cga gaa    1248
Cys Gly Lys Ile Tyr Arg Arg Asn Phe Arg Pro Ile Phe Leu Arg Glu
            405                 410                 415 gat ggt gtc act cct ttg cct tct aaa aaa atc tac gat tta gtt ggc    1296
Asp Gly Val Thr Pro Leu Pro Ser Lys Lys Ile Tyr Asp Leu Val Gly
                420                 425                 430 ata tat gca att aaa cta gca ttt ggt tac atg gtg caa cca ttt att    1344
Ile Tyr Ala Ile Lys Leu Ala Phe Gly Tyr Met Val Gln Pro Phe Ile
            435                 440                 445 atc ctt gat ttg aag cca tct tta atg gta tgg ggc tct gtt tat ttc    1392
Ile Leu Asp Leu Lys Pro Ser Leu Met Val Trp Gly Ser Val Tyr Phe
        450                 455                 460 tat gtt cat att att gtt gct ttc tca ttt ttc cta ttc aga gga cca    1440
Tyr Val His Ile Ile Val Ala Phe Ser Phe Phe Leu Phe Arg Gly Pro
465                 470                 475                 480 tat gct aaa caa gtt act gaa ttt ttt aaa tcc aaa caa cct aaa gaa    1488
Tyr Ala Lys Gln Val Thr Glu Phe Phe Lys Ser Lys Gln Pro Lys Glu
                485                 490                 495 ata ttc att aga aaa caa aag aag ttg gaa aaa gat att tct gca agc    1536
Ile Phe Ile Arg Lys Gln Lys Lys Leu Glu Lys Asp Ile Ser Ala Ser
            500                 505                 510 tct cca aac ttg ggt ggt ata ttg aag gca aag att gaa cat gaa aag    1584
Ser Pro Asn Leu Gly Gly Ile Leu Lys Ala Lys Ile Glu His Glu Lys
        515                 520                 525 gga aag aca gca gaa gaa gaa gaa atg aac tta ggt att cca cca att    1632
Gly Lys Thr Ala Glu Glu Glu Glu Met Asn Leu Gly Ile Pro Pro Ile
530                 535                 540 gag tta gaa aag tgg gac aat gct aag gaa gat tgg gaa gat ttc tgc    1680
Glu Leu Glu Lys Trp Asp Asn Ala Lys Glu Asp Trp Glu Asp Phe Cys
545                 550                 555                 560 aaa gat tac aaa gaa tgg aga aat aaa aat ggt ctt gaa ata gaa gag    1728
Lys Asp Tyr Lys Glu Trp Arg Asn Lys Asn Gly Leu Glu Ile Glu Glu
                565                 570                 575 gaa aac ctt tct aaa gct ttt gaa aga ttc aag cag gaa ttt tct aac    1776
Glu Asn Leu Ser Lys Ala Phe Glu Arg Phe Lys Gln Glu Phe Ser Asn
            580                 585                 590 gct gca agt gga tca ggt gaa cgt gtg aga aaa atg agt ttt agt ggt    1824
Ala Ala Ser Gly Ser Gly Glu Arg Val Arg Lys Met Ser Phe Ser Gly
        595                 600                 605 tac tca cca aag cct att tca aaa aag gaa gag tag                    1860
Tyr Ser Pro Lys Pro Ile Ser Lys Lys Glu Glu
    610                 615

<210> SEQ ID NO 9
<211> LENGTH: 619
<212> TYPE: PRT
<213> ORGANISM: Saccharomyces cerevisiae

<400> SEQUENCE: 9

Met Tyr Asn Pro Val Asp Ala Val Leu Thr Lys Ile Ile Thr Asn Tyr
1               5                   10                  15

Gly Ile Asp Ser Phe Thr Leu Arg Tyr Ala Ile Cys Leu Leu Gly Ser
            20                  25                  30

Phe Pro Leu Asn Ala Ile Leu Lys Arg Ile Pro Glu Lys Arg Ile Gly
        35                  40                  45

Leu Lys Cys Cys Phe Ile Ile Ser Met Ser Met Phe Tyr Leu Phe Gly
    50                  55                  60
```

```
Val Leu Asn Leu Val Ser Gly Phe Arg Thr Leu Phe Ile Ser Thr Met
 65                  70                  75                  80

Phe Thr Tyr Leu Ile Ser Arg Phe Tyr Arg Ser Lys Phe Met Pro His
                 85                  90                  95

Leu Asn Phe Met Phe Val Met Gly His Leu Ala Ile Asn His Ile His
            100                 105                 110

Ala Gln Phe Leu Asn Glu Gln Thr Gln Thr Thr Val Asp Ile Thr Ser
        115                 120                 125

Ser Gln Met Val Leu Ala Met Lys Leu Thr Ser Phe Ala Trp Ser Tyr
    130                 135                 140

Tyr Asp Gly Ser Cys Thr Ser Glu Ser Asp Phe Lys Asp Leu Thr Glu
145                 150                 155                 160

His Gln Lys Ser Arg Ala Val Arg Gly His Pro Pro Leu Leu Lys Phe
                165                 170                 175

Leu Ala Tyr Ala Phe Phe Tyr Ser Thr Leu Leu Thr Gly Pro Ser Phe
            180                 185                 190

Asp Tyr Ala Asp Phe Asp Ser Trp Leu Asn Cys Glu Met Phe Arg Asp
        195                 200                 205

Leu Pro Glu Ser Lys Lys Pro Met Arg Arg His His Pro Gly Glu Arg
210                 215                 220

Arg Gln Ile Pro Lys Asn Gly Lys Leu Ala Leu Trp Lys Val Val Gln
225                 230                 235                 240

Gly Leu Ala Trp Met Ile Leu Ser Thr Leu Gly Met Lys His Phe Pro
                245                 250                 255

Val Lys Tyr Val Leu Asp Lys Asp Gly Phe Pro Thr Arg Ser Phe Ile
            260                 265                 270

Phe Arg Ile His Tyr Leu Phe Leu Leu Gly Phe Ile His Arg Phe Lys
        275                 280                 285

Tyr Tyr Ala Ala Trp Thr Ile Ser Glu Gly Ser Cys Ile Leu Cys Gly
290                 295                 300

Leu Gly Tyr Asn Gly Tyr Asp Ser Lys Thr Gln Lys Ile Arg Trp Asp
305                 310                 315                 320

Arg Val Arg Asn Ile Asp Ile Trp Thr Val Glu Thr Ala Gln Asn Thr
                325                 330                 335

Arg Glu Met Leu Glu Ala Trp Asn Met Asn Thr Asn Lys Trp Leu Lys
            340                 345                 350

Tyr Ser Val Tyr Leu Arg Val Thr Lys Gly Lys Lys Pro Gly Phe
        355                 360                 365

Arg Ser Thr Leu Phe Thr Phe Leu Thr Ser Ala Phe Trp His Gly Thr
370                 375                 380

Arg Pro Gly Tyr Tyr Leu Thr Phe Ala Thr Gly Ala Leu Tyr Gln Thr
385                 390                 395                 400

Cys Gly Lys Ile Tyr Arg Arg Asn Phe Arg Pro Ile Phe Leu Arg Glu
                405                 410                 415

Asp Gly Val Thr Pro Leu Pro Ser Lys Lys Ile Tyr Asp Leu Val Gly
            420                 425                 430

Ile Tyr Ala Ile Lys Leu Ala Phe Gly Tyr Met Val Gln Pro Phe Ile
        435                 440                 445

Ile Leu Asp Leu Lys Pro Ser Leu Met Val Trp Gly Ser Val Tyr Phe
450                 455                 460

Tyr Val His Ile Ile Val Ala Phe Ser Phe Phe Leu Phe Arg Gly Pro
465                 470                 475                 480
```

```
Tyr Ala Lys Gln Val Thr Glu Phe Phe Lys Ser Lys Gln Pro Lys Glu
            485                 490                 495

Ile Phe Ile Arg Lys Gln Lys Lys Leu Glu Lys Asp Ile Ser Ala Ser
            500                 505                 510

Ser Pro Asn Leu Gly Gly Ile Leu Lys Ala Lys Ile Glu His Glu Lys
            515                 520                 525

Gly Lys Thr Ala Glu Glu Glu Met Asn Leu Gly Ile Pro Pro Ile
            530                 535                 540

Glu Leu Glu Lys Trp Asp Asn Ala Lys Glu Asp Trp Glu Asp Phe Cys
545                 550                 555                 560

Lys Asp Tyr Lys Glu Trp Arg Asn Lys Asn Gly Leu Glu Ile Glu Glu
                565                 570                 575

Glu Asn Leu Ser Lys Ala Phe Glu Arg Phe Lys Gln Glu Phe Ser Asn
            580                 585                 590

Ala Ala Ser Gly Ser Gly Glu Arg Val Arg Lys Met Ser Phe Ser Gly
            595                 600                 605

Tyr Ser Pro Lys Pro Ile Ser Lys Lys Glu Glu
            610                 615

<210> SEQ ID NO 10
<211> LENGTH: 1539
<212> TYPE: DNA
<213> ORGANISM: Yarrowia lipolytica
<220> FEATURE:
<221> NAME/KEY: CDS
<222> LOCATION: (1)..(1539)
<223> OTHER INFORMATION: GenBank Accession No. XP_505624; "YALI0F19514p"

<400> SEQUENCE: 10 atg gcc ttt cca tgg gca gat aag tgg gca gcc gat gcg tct gca tct     48
Met Ala Phe Pro Trp Ala Asp Lys Trp Ala Ala Asp Ala Ser Ala Ser
1               5                   10                  15 aca ggg ctg cct ccg gac ctc ctc aag att gca ttc act ctg gtc atg     96
Thr Gly Leu Pro Pro Asp Leu Leu Lys Ile Ala Phe Thr Leu Val Met
                20                  25                  30 tct tat ccg ctg agt tct ctc atg aaa cgg ctg cca gat gac gcc aaa    144
Ser Tyr Pro Leu Ser Ser Leu Met Lys Arg Leu Pro Asp Asp Ala Lys
            35                  40                  45 aac ctc aag atc atc tat atc atc tcc gtg tcc atc ttc tac atg gtg    192
Asn Leu Lys Ile Ile Tyr Ile Ile Ser Val Ser Ile Phe Tyr Met Val
    50                  55                  60 ggt gtc ttc tcc ctc tat ggc gga gct gcc act ctg ctc ttc tcc tca    240
Gly Val Phe Ser Leu Tyr Gly Gly Ala Ala Thr Leu Leu Phe Ser Ser
65                  70                  75                  80 atg ggt acc ttc ttc atc acc caa tgg aag agc cct tac atg ccc tgg    288
Met Gly Thr Phe Phe Ile Thr Gln Trp Lys Ser Pro Tyr Met Pro Trp
                85                  90                  95 gtc aat ttt ggt ttt gtc atg acc cat ctc ttc gtc aat cac ctg cgt    336
Val Asn Phe Gly Phe Val Met Thr His Leu Phe Val Asn His Leu Arg
                100                 105                 110 tcg cag ttt ttc ccc gaa aca tac gac ccc aat gtc att gac atc acc    384
Ser Gln Phe Phe Pro Glu Thr Tyr Asp Pro Asn Val Ile Asp Ile Thr
            115                 120                 125 gga gca cag atg gtt ctg tgt atg aag cta tcg tct ttt gga tgg aac    432
Gly Ala Gln Met Val Leu Cys Met Lys Leu Ser Ser Phe Gly Trp Asn
        130                 135                 140 gtc tac gat gga tgg cag att gag aag ggt gag cag ctc agc gag ttc    480
Val Tyr Asp Gly Trp Gln Ile Glu Lys Gly Glu Gln Leu Ser Glu Phe
145                 150                 155                 160
```

-continued

| | | |
|---|---|---|
| cag act aaa agg gct gtt ctc aag cac ccc agt ctt atg gac ttc cta<br>Gln Thr Lys Arg Ala Val Leu Lys His Pro Ser Leu Met Asp Phe Leu<br>            165                 170                 175 | | 528 |
| gct ttt gtg ttc tac ttc cct tcc att ctg aca ggt cct tct tac gac<br>Ala Phe Val Phe Tyr Phe Pro Ser Ile Leu Thr Gly Pro Ser Tyr Asp<br>        180                 185                 190 | | 576 |
| tat atg gag ttc cat aac tgg ctc gat ctc agc ctg ttc aag gag ctg<br>Tyr Met Glu Phe His Asn Trp Leu Asp Leu Ser Leu Phe Lys Glu Leu<br>    195                 200                 205 | | 624 |
| gag aaa gat aag gac ccc aag cga gct gct cga cga aag cga cac aag<br>Glu Lys Asp Lys Asp Pro Lys Arg Ala Ala Arg Arg Lys Arg His Lys<br>210                 215                 220 | | 672 |
| atc ccc cga tct gga atc gct gct tcc aag aaa ctc gcc gct ggt atc<br>Ile Pro Arg Ser Gly Ile Ala Ala Ser Lys Lys Leu Ala Ala Gly Ile<br>225                 230                 235                 240 | | 720 |
| ttc tgg atc gtt ctg tgg acc cag gtg gac tct cga atc tcc acc gcc<br>Phe Trp Ile Val Leu Trp Thr Gln Val Asp Ser Arg Ile Ser Thr Ala<br>                245                 250                 255 | | 768 |
| tac gct tac tca gac gca ttc acc aag gag cac aac atc ttt gga cga<br>Tyr Ala Tyr Ser Asp Ala Phe Thr Lys Glu His Asn Ile Phe Gly Arg<br>            260                 265                 270 | | 816 |
| att gtg tac ctc tac atg ctc ggt ttc atg tac cga ctc aag tac tac<br>Ile Val Tyr Leu Tyr Met Leu Gly Phe Met Tyr Arg Leu Lys Tyr Tyr<br>        275                 280                 285 | | 864 |
| gga gcc tgg tcc att tcc gag gga gcc tgc atc ttg tct ggc ctc gga<br>Gly Ala Trp Ser Ile Ser Glu Gly Ala Cys Ile Leu Ser Gly Leu Gly<br>    290                 295                 300 | | 912 |
| ttc cat ggc gtg gac ccc aaa act ggc aag tac aag tgg gac cgt gtc<br>Phe His Gly Val Asp Pro Lys Thr Gly Lys Tyr Lys Trp Asp Arg Val<br>305                 310                 315                 320 | | 960 |
| cag aac gtg gac ccg tgg gga ttc gaa act ggt caa aac aca aag gct<br>Gln Asn Val Asp Pro Trp Gly Phe Glu Thr Gly Gln Asn Thr Lys Ala<br>                325                 330                 335 | | 1008 |
| ctg ctg gag gcc tgg aac cag aac act aac aag tgg cta cga aac tat<br>Leu Leu Glu Ala Trp Asn Gln Asn Thr Asn Lys Trp Leu Arg Asn Tyr<br>            340                 345                 350 | | 1056 |
| gtg tac ctc cga gtg gtg ccc aaa ggc caa aag cct gga ttc cga gcc<br>Val Tyr Leu Arg Val Val Pro Lys Gly Gln Lys Pro Gly Phe Arg Ala<br>        355                 360                 365 | | 1104 |
| act atc ttc aca ttt gtg gtt tcc gcc ttc tgg cat gga act cga cct<br>Thr Ile Phe Thr Phe Val Val Ser Ala Phe Trp His Gly Thr Arg Pro<br>    370                 375                 380 | | 1152 |
| ggc tac tat ctc acc ttt gtg acc gct gcc atg tac cag tct gtt ggt<br>Gly Tyr Tyr Leu Thr Phe Val Thr Ala Ala Met Tyr Gln Ser Val Gly<br>385                 390                 395                 400 | | 1200 |
| aag ttc ttc cga cga tac ctg cga ccc ttc ttc atg gag tct gat gga<br>Lys Phe Phe Arg Arg Tyr Leu Arg Pro Phe Phe Met Glu Ser Asp Gly<br>                405                 410                 415 | | 1248 |
| aag act gcc ggt ccc tat aag atc tac tac gac att gtg tgt tgg atc<br>Lys Thr Ala Gly Pro Tyr Lys Ile Tyr Tyr Asp Ile Val Cys Trp Ile<br>            420                 425                 430 | | 1296 |
| gtt gtc caa acc gca ttt gga tac gct acc cag tcc ttt atg att cta<br>Val Val Gln Thr Ala Phe Gly Tyr Ala Thr Gln Ser Phe Met Ile Leu<br>        435                 440                 445 | | 1344 |
| gac ttc tgg ctg tcg ctc aag tgt tgg aag aac tcc tgg ttc ctg tac<br>Asp Phe Trp Leu Ser Leu Lys Cys Trp Lys Asn Ser Trp Phe Leu Tyr<br>    450                 455                 460 | | 1392 |
| cac att gct ctg ggc gcc atc ttt gca att tct agc ccc tac aag gca<br>His Ile Ala Leu Gly Ala Ile Phe Ala Ile Ser Ser Pro Tyr Lys Ala<br>465                 470                 475                 480 | | 1440 |

```
tgg gcg att ccc aag atc aag aaa aag cag gct gga gcc gtc act gac    1488
Trp Ala Ile Pro Lys Ile Lys Lys Lys Gln Ala Gly Ala Val Thr Asp
            485                 490                 495 aag aag gac gcc aag gag gag gtg aag aag gac acc atc aag acc aag    1536
Lys Lys Asp Ala Lys Glu Glu Val Lys Lys Asp Thr Ile Lys Thr Lys
            500                 505                 510 taa                                                                 1539

<210> SEQ ID NO 11
<211> LENGTH: 512
<212> TYPE: PRT
<213> ORGANISM: Yarrowia lipolytica

<400> SEQUENCE: 11

Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
50                  55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
            115                 120                 125

Gly Ala Gln Met Val Leu Cys Met Lys Leu Ser Ser Phe Gly Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
            195                 200                 205

Glu Lys Asp Lys Asp Pro Lys Arg Ala Ala Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
            275                 280                 285

Gly Ala Trp Ser Ile Ser Glu Gly Ala Cys Ile Leu Ser Gly Leu Gly
        290                 295                 300

Phe His Gly Val Asp Pro Lys Thr Gly Lys Tyr Lys Trp Asp Arg Val
305                 310                 315                 320
```

```
Gln Asn Val Asp Pro Trp Gly Phe Glu Thr Gly Gln Asn Thr Lys Ala
            325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
            355                 360                 365

Thr Ile Phe Thr Phe Val Val Ser Ala Phe Trp His Gly Thr Arg Pro
        370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
            405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
            435                 440                 445

Asp Phe Trp Leu Ser Leu Lys Cys Trp Lys Asn Ser Trp Phe Leu Tyr
        450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
            485                 490                 495

Lys Lys Asp Ala Lys Glu Glu Val Lys Asp Thr Ile Lys Thr Lys
            500                 505                 510

<210> SEQ ID NO 12
<211> LENGTH: 1870
<212> TYPE: DNA
<213> ORGANISM: Saccharomyces cerevisiae
<220> FEATURE:
<221> NAME/KEY: CDS
<222> LOCATION: (3)..(1862)
<223> OTHER INFORMATION: synthetic Ale1 (codon-optimized for Yarrowia
      lipolytica)

<400> SEQUENCE: 12 ac atg tac aac ccc gtg gac gca gtg ttg act aag att att aca aac        47
   Met Tyr Asn Pro Val Asp Ala Val Leu Thr Lys Ile Ile Thr Asn
   1               5                   10                  15 tac gga att gat tct ttt acc ctg cga tat gcc att tgt ctg ttg gga      95
Tyr Gly Ile Asp Ser Phe Thr Leu Arg Tyr Ala Ile Cys Leu Leu Gly
                20                  25                  30 tct ttt cct ctt aac gct att ctg aag cgg att cct gaa aag cga atc     143
Ser Phe Pro Leu Asn Ala Ile Leu Lys Arg Ile Pro Glu Lys Arg Ile
            35                  40                  45 ggc ctg aag tgt tgt ttt atc att tct atg tcc atg ttt tat ctc ttc     191
Gly Leu Lys Cys Cys Phe Ile Ile Ser Met Ser Met Phe Tyr Leu Phe
        50                  55                  60 ggc gtt ctg aat ctc gtg agc gga ttt cga acc ctc ttc att tcc aca     239
Gly Val Leu Asn Leu Val Ser Gly Phe Arg Thr Leu Phe Ile Ser Thr
65                  70                  75 atg ttc aca tac ctt atc tct cgg ttc tac cga tcc aag ttt atg ccc     287
Met Phe Thr Tyr Leu Ile Ser Arg Phe Tyr Arg Ser Lys Phe Met Pro
80                  85                  90                  95 cat ctc aac ttc atg ttc gtc atg ggc cac ttg gct atc aac cac att     335
His Leu Asn Phe Met Phe Val Met Gly His Leu Ala Ile Asn His Ile
                100                 105                 110 cat gct cag ttc ctg aac gaa caa act caa acg acc gtc gat att aca     383
His Ala Gln Phe Leu Asn Glu Gln Thr Gln Thr Thr Val Asp Ile Thr
```

-continued

|  |  | 115 |  |  | 120 |  |  | 125 |  |  |  |
|---|---|---|---|---|---|---|---|---|---|---|---|
| tcc | tcg | cag | atg | gtc | ctg | gct | atg | aag | ctg | aca | agc | ttt | gcc | tgg | tct | 431 |
| Ser | Ser | Gln | Met | Val | Leu | Ala | Met | Lys | Leu | Thr | Ser | Phe | Ala | Trp | Ser |  |
|  |  | 130 |  |  |  | 135 |  |  |  | 140 |  |  |  |  |  |

```
tcc tcg cag atg gtc ctg gct atg aag ctg aca agc ttt gcc tgg tct    431
Ser Ser Gln Met Val Leu Ala Met Lys Leu Thr Ser Phe Ala Trp Ser
        130                 135                 140 tac tat gac ggt tcg tgt acg agc gag tcc gac ttc aag gac ctt acc    479
Tyr Tyr Asp Gly Ser Cys Thr Ser Glu Ser Asp Phe Lys Asp Leu Thr
145                 150                 155 gaa cac cag aag tcc cga gcc gtc cga ggc cat cct ccc ctt ctg aaa    527
Glu His Gln Lys Ser Arg Ala Val Arg Gly His Pro Pro Leu Leu Lys
160                 165                 170                 175 ttt ttg gct tac gcc ttt ttc tac tct acc ctt ctc acc ggt ccc tcc    575
Phe Leu Ala Tyr Ala Phe Phe Tyr Ser Thr Leu Leu Thr Gly Pro Ser
                180                 185                 190 ttc gat tac gct gat ttc gac tct tgg ctg aac tgc gaa atg ttc cgg    623
Phe Asp Tyr Ala Asp Phe Asp Ser Trp Leu Asn Cys Glu Met Phe Arg
                195                 200                 205 gac ctt ccc gag tcc aag aaa ccc atg cga aga cat cat cct ggt gag    671
Asp Leu Pro Glu Ser Lys Lys Pro Met Arg Arg His His Pro Gly Glu
            210                 215                 220 cgg cgt cag att ccc aag aac ggc aag ctc gcc ctg tgg aag gtt gtc    719
Arg Arg Gln Ile Pro Lys Asn Gly Lys Leu Ala Leu Trp Lys Val Val
225                 230                 235 cag ggc ctc gcc tgg atg att ctg agc acg ttg ggt atg aag cac ttc    767
Gln Gly Leu Ala Trp Met Ile Leu Ser Thr Leu Gly Met Lys His Phe
240                 245                 250                 255 ccc gtg aag tac gtg ctg gac aag gac gga ttt cct acc cgt tcc ttt    815
Pro Val Lys Tyr Val Leu Asp Lys Asp Gly Phe Pro Thr Arg Ser Phe
                260                 265                 270 atc ttc cgt att cat tat ctg ttt ctg ctg gga ttc atc cac cga ttt    863
Ile Phe Arg Ile His Tyr Leu Phe Leu Leu Gly Phe Ile His Arg Phe
                275                 280                 285 aag tat tac gct gcg tgg acg att agc gaa ggt tcg tgc att ctc tgt    911
Lys Tyr Tyr Ala Ala Trp Thr Ile Ser Glu Gly Ser Cys Ile Leu Cys
            290                 295                 300 ggt ctt ggt tat aat gga tac gat tct aag acc cag aag atc cgg tgg    959
Gly Leu Gly Tyr Asn Gly Tyr Asp Ser Lys Thr Gln Lys Ile Arg Trp
305                 310                 315 gat cga gtg cgg aat att gat att tgg aca gtg gag act gca caa aac   1007
Asp Arg Val Arg Asn Ile Asp Ile Trp Thr Val Glu Thr Ala Gln Asn
320                 325                 330                 335 acc cga gag atg ctg gaa gcg tgg aac atg aat act aac aaa tgg ctg   1055
Thr Arg Glu Met Leu Glu Ala Trp Asn Met Asn Thr Asn Lys Trp Leu
                340                 345                 350 aag tat agc gtg tat ctt aga gtg act aag aag ggt aag aag cca ggt   1103
Lys Tyr Ser Val Tyr Leu Arg Val Thr Lys Lys Gly Lys Lys Pro Gly
            355                 360                 365 ttt cga tct acc ctg ttt acc ttc ctg acc tcc gcc ttt tgg cac ggt   1151
Phe Arg Ser Thr Leu Phe Thr Phe Leu Thr Ser Ala Phe Trp His Gly
370                 375                 380 acc cgt cct gga tac tac ctt acc ttc gca act ggt gcc ctg tac caa   1199
Thr Arg Pro Gly Tyr Tyr Leu Thr Phe Ala Thr Gly Ala Leu Tyr Gln
385                 390                 395 acc tgt gga aag atc tat aga cga aac ttt cgt ccc atc ttt ctg aga   1247
Thr Cys Gly Lys Ile Tyr Arg Arg Asn Phe Arg Pro Ile Phe Leu Arg
400                 405                 410                 415 gaa gat ggc gtg aca cct ctc ccg tcc aag aag att tac gac ctg gtc   1295
Glu Asp Gly Val Thr Pro Leu Pro Ser Lys Lys Ile Tyr Asp Leu Val
                420                 425                 430 ggc att tac gct att aag ctg gcc ttt ggt tac atg gtt caa ccc ttc   1343
Gly Ile Tyr Ala Ile Lys Leu Ala Phe Gly Tyr Met Val Gln Pro Phe
```

```
            Gly Ile Tyr Ala Ile Lys Leu Ala Phe Gly Tyr Met Val Gln Pro Phe
                            435                 440                 445 att atc ctt gac ctg aag ccc tct ctt atg gtt tgg gga tcc gtg tat               1391
Ile Ile Leu Asp Leu Lys Pro Ser Leu Met Val Trp Gly Ser Val Tyr
            450                 455                 460 ttc tac gtg cat att att gtg gcc ttc tcg ttc ttt ctg ttc cga gga               1439
Phe Tyr Val His Ile Ile Val Ala Phe Ser Phe Phe Leu Phe Arg Gly
465                 470                 475 cca tac gct aag cag gtt act gaa ttt ttc aaa agc aag caa ccg aag               1487
Pro Tyr Ala Lys Gln Val Thr Glu Phe Phe Lys Ser Lys Gln Pro Lys
480                 485                 490                 495 gag atc ttc atc cga aag cag aag aag ttg gaa aaa gac atc tct gcc               1535
Glu Ile Phe Ile Arg Lys Gln Lys Lys Leu Glu Lys Asp Ile Ser Ala
            500                 505                 510 tct tcc ccc aac ctc gga ggt att ctt aag gca aaa atc gaa cat gag               1583
Ser Ser Pro Asn Leu Gly Gly Ile Leu Lys Ala Lys Ile Glu His Glu
            515                 520                 525 aag gga aag acg gca gag gag gaa gag atg aac ttg ggc att cca ccc               1631
Lys Gly Lys Thr Ala Glu Glu Glu Met Asn Leu Gly Ile Pro Pro
            530                 535                 540 atc gaa ctg gag aag tgg gac aac gcc aag gag gac tgg gag gat ttc               1679
Ile Glu Leu Glu Lys Trp Asp Asn Ala Lys Glu Asp Trp Glu Asp Phe
545                 550                 555 tgc aag gac tac aag gag tgg cgg aac aag aac gga ctg gaa att gaa               1727
Cys Lys Asp Tyr Lys Glu Trp Arg Asn Lys Asn Gly Leu Glu Ile Glu
560                 565                 570                 575 gag gag aac ctg tcc aag gcc ttc gag cga ttt aag cag gaa ttt tcc               1775
Glu Glu Asn Leu Ser Lys Ala Phe Glu Arg Phe Lys Gln Glu Phe Ser
                580                 585                 590 aac gct gcg tcg ggc tct ggt gaa cgg gtt cgg aaa atg tcc ttc tcc               1823
Asn Ala Ala Ser Gly Ser Gly Glu Arg Val Arg Lys Met Ser Phe Ser
                595                 600                 605 gga tat tct cct aaa ccc atc tcg aag aaa gaa gaa tag gcggccgc                  1870
Gly Tyr Ser Pro Lys Pro Ile Ser Lys Lys Glu Glu
            610                 615

<210> SEQ ID NO 13
<211> LENGTH: 619
<212> TYPE: PRT
<213> ORGANISM: Saccharomyces cerevisiae

<400> SEQUENCE: 13

Met Tyr Asn Pro Val Asp Ala Val Leu Thr Lys Ile Ile Thr Asn Tyr
1               5                   10                  15

Gly Ile Asp Ser Phe Thr Leu Arg Tyr Ala Ile Cys Leu Leu Gly Ser
                20                  25                  30

Phe Pro Leu Asn Ala Ile Leu Lys Arg Ile Pro Glu Lys Arg Ile Gly
            35                  40                  45

Leu Lys Cys Cys Phe Ile Ile Ser Met Ser Met Phe Tyr Leu Phe Gly
        50                  55                  60

Val Leu Asn Leu Val Ser Gly Phe Arg Thr Leu Phe Ile Ser Thr Met
65                  70                  75                  80

Phe Thr Tyr Leu Ile Ser Arg Phe Tyr Arg Ser Lys Phe Met Pro His
                85                  90                  95

Leu Asn Phe Met Phe Val Met Gly His Leu Ala Ile Asn His Ile His
                100                 105                 110

Ala Gln Phe Leu Asn Glu Gln Thr Gln Thr Thr Val Asp Ile Thr Ser
            115                 120                 125
```

```
Ser Gln Met Val Leu Ala Met Lys Leu Thr Ser Phe Ala Trp Ser Tyr
    130                 135                 140

Tyr Asp Gly Ser Cys Thr Ser Glu Ser Asp Phe Lys Asp Leu Thr Glu
145                 150                 155                 160

His Gln Lys Ser Arg Ala Val Arg Gly His Pro Pro Leu Leu Lys Phe
                165                 170                 175

Leu Ala Tyr Ala Phe Phe Tyr Ser Thr Leu Thr Gly Pro Ser Phe
            180                 185                 190

Asp Tyr Ala Asp Phe Asp Ser Trp Leu Asn Cys Glu Met Phe Arg Asp
            195                 200                 205

Leu Pro Glu Ser Lys Lys Pro Met Arg Arg His His Pro Gly Glu Arg
210                 215                 220

Arg Gln Ile Pro Lys Asn Gly Lys Leu Ala Leu Trp Lys Val Val Gln
225                 230                 235                 240

Gly Leu Ala Trp Met Ile Leu Ser Thr Leu Gly Met Lys His Phe Pro
                245                 250                 255

Val Lys Tyr Val Leu Asp Lys Asp Gly Phe Pro Thr Arg Ser Phe Ile
                260                 265                 270

Phe Arg Ile His Tyr Leu Phe Leu Leu Gly Phe Ile His Arg Phe Lys
        275                 280                 285

Tyr Tyr Ala Ala Trp Thr Ile Ser Glu Gly Ser Cys Ile Leu Cys Gly
    290                 295                 300

Leu Gly Tyr Asn Gly Tyr Asp Ser Lys Thr Gln Lys Ile Arg Trp Asp
305                 310                 315                 320

Arg Val Arg Asn Ile Asp Ile Trp Thr Val Glu Thr Ala Gln Asn Thr
                325                 330                 335

Arg Glu Met Leu Glu Ala Trp Asn Met Asn Thr Asn Lys Trp Leu Lys
        340                 345                 350

Tyr Ser Val Tyr Leu Arg Val Thr Lys Gly Lys Lys Pro Gly Phe
    355                 360                 365

Arg Ser Thr Leu Phe Thr Phe Leu Thr Ser Ala Phe Trp His Gly Thr
        370                 375                 380

Arg Pro Gly Tyr Tyr Leu Thr Phe Ala Thr Gly Ala Leu Tyr Gln Thr
385                 390                 395                 400

Cys Gly Lys Ile Tyr Arg Arg Asn Phe Arg Pro Ile Phe Leu Arg Glu
                405                 410                 415

Asp Gly Val Thr Pro Leu Pro Ser Lys Ile Tyr Asp Leu Val Gly
                420                 425                 430

Ile Tyr Ala Ile Lys Leu Ala Phe Gly Tyr Met Val Gln Pro Phe Ile
        435                 440                 445

Ile Leu Asp Leu Lys Pro Ser Leu Met Val Trp Gly Ser Val Tyr Phe
450                 455                 460

Tyr Val His Ile Ile Val Ala Phe Ser Phe Phe Leu Phe Arg Gly Pro
465                 470                 475                 480

Tyr Ala Lys Gln Val Thr Glu Phe Phe Lys Ser Lys Gln Pro Lys Glu
                485                 490                 495

Ile Phe Ile Arg Lys Gln Lys Lys Leu Glu Lys Asp Ile Ser Ala Ser
                500                 505                 510

Ser Pro Asn Leu Gly Gly Ile Leu Lys Ala Lys Ile Glu His Glu Lys
                515                 520                 525

Gly Lys Thr Ala Glu Glu Glu Met Asn Leu Gly Ile Pro Pro Ile
530                 535                 540

Glu Leu Glu Lys Trp Asp Asn Ala Lys Glu Asp Trp Glu Asp Phe Cys
```

```
                 545                 550                 555                 560
Lys Asp Tyr Lys Glu Trp Arg Asn Lys Asn Gly Leu Glu Ile Glu Glu
                565                 570                 575

Glu Asn Leu Ser Lys Ala Phe Glu Arg Phe Lys Gln Glu Phe Ser Asn
                580                 585                 590

Ala Ala Ser Gly Ser Gly Glu Arg Val Arg Lys Met Ser Phe Ser Gly
                595                 600                 605

Tyr Ser Pro Lys Pro Ile Ser Lys Lys Glu Glu
                610                 615

<210> SEQ ID NO 14
<211> LENGTH: 945
<212> TYPE: DNA
<213> ORGANISM: Mortierella alpina
<220> FEATURE:
<221> NAME/KEY: CDS
<222> LOCATION: (1)..(945)
<223> OTHER INFORMATION: LPAAT1
<300> PUBLICATION INFORMATION:
<302> TITLE: High eicosapentaenoic acid producing strains of Yarrowia
       lipolytica
<310> PATENT DOCUMENT NUMBER: US-2006-0115881-A1
<311> PATENT FILING DATE: 2005-11-02
<312> PUBLICATION DATE: 2006-06-01
<313> RELEVANT RESIDUES IN SEQ ID NO: (1)..(945)
<300> PUBLICATION INFORMATION:
<302> TITLE: High eicosapentaenoic acid producing strains of Yarrowia
       lipolytica
<310> PATENT DOCUMENT NUMBER: WO 2006/052870
<311> PATENT FILING DATE: 2005-11-03
<312> PUBLICATION DATE: 2006-05-18
<313> RELEVANT RESIDUES IN SEQ ID NO: (1)..(945)

<400> SEQUENCE: 14 atg tcc ata ggt tct tcc aat cct gtc ctg ctg gca gcg atc ccc ttc      48
Met Ser Ile Gly Ser Ser Asn Pro Val Leu Leu Ala Ala Ile Pro Phe
1               5                   10                  15 gtc tac ctc ttc gtc ctc cct cgt gtc ctc gcc ttc ctc cct caa aag      96
Val Tyr Leu Phe Val Leu Pro Arg Val Leu Ala Phe Leu Pro Gln Lys
            20                  25                  30 gcc cag ttc ctc gca aaa tgc atc gtg gtc ttg atc gcc acc ctt atc     144
Ala Gln Phe Leu Ala Lys Cys Ile Val Val Leu Ile Ala Thr Leu Ile
        35                  40                  45 atg tcc gtc gca ggc tgc ttc att tcc atc gtc tgt gcg ctc ctc gat     192
Met Ser Val Ala Gly Cys Phe Ile Ser Ile Val Cys Ala Leu Leu Asp
    50                  55                  60 aaa cgc tat gtg atc aac tac gtc gtc tca aga ctc ttc tca ttc ctc     240
Lys Arg Tyr Val Ile Asn Tyr Val Val Ser Arg Leu Phe Ser Phe Leu
65                  70                  75                  80 gct gca aga ccc tgc ggt gtc acc tac aag atc gtc ggc gag gaa cat     288
Ala Ala Arg Pro Cys Gly Val Thr Tyr Lys Ile Val Gly Glu Glu His
                85                  90                  95 ctg gac aag tac ccc gcc att gtc gtc tgc aac cac cag agc tcc atg     336
Leu Asp Lys Tyr Pro Ala Ile Val Val Cys Asn His Gln Ser Ser Met
            100                 105                 110 gac atg atg gtc ctg gga cgc gtc ttc cca aag cac tgt gtc gtc atg     384
Asp Met Met Val Leu Gly Arg Val Phe Pro Lys His Cys Val Val Met
        115                 120                 125 gca aag aag gaa ctt ctt tac ttt ccg ttc ctg ggc atg ttt atg aag     432
Ala Lys Lys Glu Leu Leu Tyr Phe Pro Phe Leu Gly Met Phe Met Lys
    130                 135                 140 ctg agt aac gcc atc ttc att gac cgc aag aac cac aag aag gcg atc     480
Leu Ser Asn Ala Ile Phe Ile Asp Arg Lys Asn His Lys Lys Ala Ile
145                 150                 155                 160
```

```
gag tcc acc acc caa gct gtc gcc gac atg aag aag cac aac tct gga       528
Glu Ser Thr Thr Gln Ala Val Ala Asp Met Lys Lys His Asn Ser Gly
            165                 170                 175 atc tgg att ttc ccc gaa gga aca cgt tcc cgc ttg gac aag gcc gat       576
Ile Trp Ile Phe Pro Glu Gly Thr Arg Ser Arg Leu Asp Lys Ala Asp
        180                 185                 190 ctc ttg ccc ttc aag aag gga gcc ttc cac ctc gcc att caa gcc caa       624
Leu Leu Pro Phe Lys Lys Gly Ala Phe His Leu Ala Ile Gln Ala Gln
    195                 200                 205 ctc ccg atc ctc ccc atc atc tcg caa gga tac tca cac atc tac gat       672
Leu Pro Ile Leu Pro Ile Ile Ser Gln Gly Tyr Ser His Ile Tyr Asp
210                 215                 220 tcg tca aaa cgc tac ttc ccc ggt gga gag ctc gag atc aga gtc ctg       720
Ser Ser Lys Arg Tyr Phe Pro Gly Gly Glu Leu Glu Ile Arg Val Leu
225                 230                 235                 240 gaa cct atc ccc acc acg gga ttg acc aca gac gat gtg aac gac ctg       768
Glu Pro Ile Pro Thr Thr Gly Leu Thr Thr Asp Asp Val Asn Asp Leu
            245                 250                 255 atg gac aag act cgc aac ctg atg ctg aag cac ctc aag gag atg gat       816
Met Asp Lys Thr Arg Asn Leu Met Leu Lys His Leu Lys Glu Met Asp
        260                 265                 270 tct caa tac tcc tcc tcc acc gct gaa aac gga tcg acc cat att gac       864
Ser Gln Tyr Ser Ser Ser Thr Ala Glu Asn Gly Ser Thr His Ile Asp
    275                 280                 285 gcc gat atc gca aag tca act gcc aca tcg atc gga aac acg gac gat       912
Ala Asp Ile Ala Lys Ser Thr Ala Thr Ser Ile Gly Asn Thr Asp Asp
290                 295                 300 gct atc aca aag agg agg aca cca aaa gag tag                           945
Ala Ile Thr Lys Arg Arg Thr Pro Lys Glu
305                 310

<210> SEQ ID NO 15
<211> LENGTH: 314
<212> TYPE: PRT
<213> ORGANISM: Mortierella alpina

<400> SEQUENCE: 15

Met Ser Ile Gly Ser Ser Asn Pro Val Leu Leu Ala Ala Ile Pro Phe
1               5                   10                  15

Val Tyr Leu Phe Val Leu Pro Arg Val Leu Ala Phe Leu Pro Gln Lys
            20                  25                  30

Ala Gln Phe Leu Ala Lys Cys Ile Val Val Leu Ile Ala Thr Leu Ile
        35                  40                  45

Met Ser Val Ala Gly Cys Phe Ile Ser Ile Val Cys Ala Leu Leu Asp
    50                  55                  60

Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu Glu His
                85                  90                  95

Leu Asp Lys Tyr Pro Ala Ile Val Val Cys Asn His Gln Ser Ser Met
            100                 105                 110

Asp Met Met Val Leu Gly Arg Val Phe Pro Lys His Cys Val Val Met
        115                 120                 125

Ala Lys Lys Glu Leu Leu Tyr Phe Pro Phe Leu Gly Met Phe Met Lys
    130                 135                 140

Leu Ser Asn Ala Ile Phe Ile Asp Arg Lys Asn His Lys Lys Ala Ile
145                 150                 155                 160
```

```
Glu Ser Thr Thr Gln Ala Val Ala Asp Met Lys Lys His Asn Ser Gly
                165                 170                 175

Ile Trp Ile Phe Pro Glu Gly Thr Arg Ser Arg Leu Asp Lys Ala Asp
        180                 185                 190

Leu Leu Pro Phe Lys Lys Gly Ala Phe His Leu Ala Ile Gln Ala Gln
    195                 200                 205

Leu Pro Ile Leu Pro Ile Ile Ser Gln Gly Tyr Ser His Ile Tyr Asp
210                 215                 220

Ser Ser Lys Arg Tyr Phe Pro Gly Gly Glu Leu Gly Ile Arg Val Leu
225                 230                 235                 240

Glu Pro Ile Pro Thr Thr Gly Leu Thr Thr Asp Asp Val Asn Asp Leu
                245                 250                 255

Met Asp Lys Thr Arg Asn Leu Met Leu Lys His Leu Lys Glu Met Asp
            260                 265                 270

Ser Gln Tyr Ser Ser Ser Thr Ala Glu Asn Gly Ser Thr His Ile Asp
        275                 280                 285

Ala Asp Ile Ala Lys Ser Thr Ala Thr Ser Ile Gly Asn Thr Asp Asp
    290                 295                 300

Ala Ile Thr Lys Arg Arg Thr Pro Lys Glu
305                 310

<210> SEQ ID NO 16
<211> LENGTH: 1549
<212> TYPE: DNA
<213> ORGANISM: Yarrowia lipolytica
<220> FEATURE:
<221> NAME/KEY: CDS
<222> LOCATION: (501)..(1349)
<223> OTHER INFORMATION: LPAAT1
<300> PUBLICATION INFORMATION:
<302> TITLE: High eicosapentaenoic acid producing strains of Yarrowia
      lipolytica
<310> PATENT DOCUMENT NUMBER: US-2006-0115881-A1
<311> PATENT FILING DATE: 2005-11-02
<312> PUBLICATION DATE: 2006-06-01
<313> RELEVANT RESIDUES IN SEQ ID NO: (1)..(1549)
<300> PUBLICATION INFORMATION:
<302> TITLE: High eicosapentaenoic acid producing strains of Yarrowia
      lipolytica
<310> PATENT DOCUMENT NUMBER: WO 2006/052870
<311> PATENT FILING DATE: 2005-11-03
<312> PUBLICATION DATE: 2006-05-18
<313> RELEVANT RESIDUES IN SEQ ID NO: (1)..(1549)

<400> SEQUENCE: 16
cacagcataa taccacggca tgaccccgct gactccaacc ttcatttcgg cacatgtagg      60
tgcacaaggg acttcaagag gggccaattt catgcggaca catggcgcaa aaaacgcccg    120
actttgatta cacagacacg taataacgac gaagccgaga tgagcacacg tggccaagtc    180
tgccaatggc cccctggacc ccctgacaa agtttcccaa caagcccagc cgtgcatggt    240 gtgttttgt gcggagacac acgccaatta ggctcatttg agggtatgca gcgaaaaaaa    300
attagtgtgg gtagtttgtt tgcaggaatc aagtgggtgg ttgaaaaaca agaaagagcg    360
acgacaagag agagagaaaa agagagagag actccataaa gcgtgcatca aaattaaggt    420
gtgtgactat ccgaaaacca aacatgaaca gttggatata tgtcgctgtg attgcagttg    480
ctgccgttct cattgcccga atg tcc gtt gca tcc aag ctc gtc ttc tac gtc    533
                        Met Ser Val Ala Ser Lys Leu Val Phe Tyr Val
                          1               5                      10 cgc gcc gcc atc gcc gtg gtc atc ttt gcc gcc tgt gcc acc tac ggc    581
Arg Ala Ala Ile Ala Val Val Ile Phe Ala Ala Cys Ala Thr Tyr Gly
         15                  20                  25
```

```
gtg ctg gcg tcc acc att ctc acc gcc atc ggc aag cag ggc ctg gcc    629
Val Leu Ala Ser Thr Ile Leu Thr Ala Ile Gly Lys Gln Gly Leu Ala
         30                  35                  40 caa tgg acc gtt gcc aga gcc ttc tac tac tcg gtg cgc atc ttc ctg    677
Gln Trp Thr Val Ala Arg Ala Phe Tyr Tyr Ser Val Arg Ile Phe Leu
 45                  50                  55 ggt atc agc atc aag ctg cgt agc cgg cag gtg acc gga acc gcc ggt    725
Gly Ile Ser Ile Lys Leu Arg Ser Arg Gln Val Thr Gly Thr Ala Gly
 60                  65                  70                  75 ctg gat gcc tcc aag atc cag gtc gcc aac acc acc aag ccc att gac    773
Leu Asp Ala Ser Lys Ile Gln Val Ala Asn Thr Thr Lys Pro Ile Asp
                 80                  85                  90 gac atc acc aaa cac ctg ccc cga cca tgc att ctg att tcc aac cac    821
Asp Ile Thr Lys His Leu Pro Arg Pro Cys Ile Leu Ile Ser Asn His
         95                 100                 105 cag aac gaa atg gac att ctg gtg ctc ggt cgc atc ttc ccc cag tac    869
Gln Asn Glu Met Asp Ile Leu Val Leu Gly Arg Ile Phe Pro Gln Tyr
    110                 115                 120 tgc tcc gtc acc gcc aaa aag gcc ctc aag tgg tac cct ctg ctg ggc    917
Cys Ser Val Thr Ala Lys Lys Ala Leu Lys Trp Tyr Pro Leu Leu Gly
125                 130                 135 cag ttc atg gcg ctg tcc ggc acc atc ttc ctg gac cga aag gac cga    965
Gln Phe Met Ala Leu Ser Gly Thr Ile Phe Leu Asp Arg Lys Asp Arg
140                 145                 150                 155 acc aag tcc gtg cag acc ctc ggc ggc gcc gtc aag acc atc cag agc   1013
Thr Lys Ser Val Gln Thr Leu Gly Gly Ala Val Lys Thr Ile Gln Ser
                160                 165                 170 ggc aac gga ggc aag ggc cag agc gtc ttc atg ttc ccc gag gga acc   1061
Gly Asn Gly Gly Lys Gly Gln Ser Val Phe Met Phe Pro Glu Gly Thr
        175                 180                 185 cga tcc tac tcc aag gac gtc ggc atc atg ccc ttc aag aag ggc tgt   1109
Arg Ser Tyr Ser Lys Asp Val Gly Ile Met Pro Phe Lys Lys Gly Cys
    190                 195                 200 ttc cac ctg gcg gtc cag tcg ggc gct ccc att gtc ccc gtg gtg gtc   1157
Phe His Leu Ala Val Gln Ser Gly Ala Pro Ile Val Pro Val Val Val
205                 210                 215 cag aac acc tcc cga atg ttt tct ttc ggc cga ggc aag ctg gac gcc   1205
Gln Asn Thr Ser Arg Met Phe Ser Phe Gly Arg Gly Lys Leu Asp Ala
220                 225                 230                 235 gga gag atc ctt gtc gac gtc ctg agc ccc att gag acc aag ggt ctg   1253
Gly Glu Ile Leu Val Asp Val Leu Ser Pro Ile Glu Thr Lys Gly Leu
                240                 245                 250 gac gcc agc aac gtc gac gct ctc atg gcc acc act tat aag gcc atg   1301
Asp Ala Ser Asn Val Asp Ala Leu Met Ala Thr Thr Tyr Lys Ala Met
        255                 260                 265 tgc gag act gcc gac cag att ggc tac gct ggc cag aag act cag tag   1349
Cys Glu Thr Ala Asp Gln Ile Gly Tyr Ala Gly Gln Lys Thr Gln
    270                 275                 280 agactgcagc acaagaagtg cttgtagcta ctttaggaga gagataggta atatgaaaca   1409 ttttcagat cgacacccac ggcgaaccat tggctgtgga gctatgggtg aatggattaa   1469
tatagcaacg aaatctacct cgattaccaa cgcaaaacga gcccactttc tctgtactgt   1529
gctatatcgt gtatacccca                                              1549

<210> SEQ ID NO 17
<211> LENGTH: 282
<212> TYPE: PRT
<213> ORGANISM: Yarrowia lipolytica
```

<400> SEQUENCE: 17

Met Ser Val Ala Ser Lys Leu Val Phe Tyr Val Arg Ala Ala Ile Ala
1               5                   10                  15

Val Val Ile Phe Ala Ala Cys Ala Thr Tyr Gly Val Leu Ala Ser Thr
            20                  25                  30

Ile Leu Thr Ala Ile Gly Lys Gln Gly Leu Ala Gln Trp Thr Val Ala
        35                  40                  45

Arg Ala Phe Tyr Tyr Ser Val Arg Ile Phe Leu Gly Ile Ser Ile Lys
    50                  55                  60

Leu Arg Ser Arg Gln Val Thr Gly Thr Ala Gly Leu Asp Ala Ser Lys
65                  70                  75                  80

Ile Gln Val Ala Asn Thr Thr Lys Pro Ile Asp Asp Ile Thr Lys His
                85                  90                  95

Leu Pro Arg Pro Cys Ile Leu Ile Ser Asn His Gln Asn Glu Met Asp
            100                 105                 110

Ile Leu Val Leu Gly Arg Ile Phe Pro Gln Tyr Cys Ser Val Thr Ala
        115                 120                 125

Lys Lys Ala Leu Lys Trp Tyr Pro Leu Leu Gly Gln Phe Met Ala Leu
    130                 135                 140

Ser Gly Thr Ile Phe Leu Asp Arg Lys Asp Arg Thr Lys Ser Val Gln
145                 150                 155                 160

Thr Leu Gly Gly Ala Val Lys Thr Ile Gln Ser Gly Asn Gly Gly Lys
                165                 170                 175

Gly Gln Ser Val Phe Met Phe Pro Glu Gly Thr Arg Ser Tyr Ser Lys
            180                 185                 190

Asp Val Gly Ile Met Pro Phe Lys Lys Gly Cys Phe His Leu Ala Val
        195                 200                 205

Gln Ser Gly Ala Pro Ile Val Pro Val Val Gln Asn Thr Ser Arg
    210                 215                 220

Met Phe Ser Phe Gly Arg Gly Lys Leu Asp Ala Gly Glu Ile Leu Val
225                 230                 235                 240

Asp Val Leu Ser Pro Ile Glu Thr Lys Gly Leu Asp Ala Ser Asn Val
                245                 250                 255

Asp Ala Leu Met Ala Thr Thr Tyr Lys Ala Met Cys Glu Thr Ala Asp
            260                 265                 270

Gln Ile Gly Tyr Ala Gly Gln Lys Thr Gln
        275                 280

<210> SEQ ID NO 18
<211> LENGTH: 303
<212> TYPE: PRT
<213> ORGANISM: Saccharomyces cerevisiae
<220> FEATURE:
<221> NAME/KEY: MISC_FEATURE
<222> LOCATION: (1)..(303)
<223> OTHER INFORMATION: Slc1p; GenBank Accession No. NP_010231

<400> SEQUENCE: 18

Met Ser Val Ile Gly Arg Phe Leu Tyr Tyr Leu Arg Ser Val Leu Val
1               5                   10                  15

Val Leu Ala Leu Ala Gly Cys Gly Phe Tyr Gly Val Ile Ala Ser Ile
            20                  25                  30

Leu Cys Thr Leu Ile Gly Lys Gln His Leu Ala Gln Trp Ile Thr Ala
        35                  40                  45

Arg Cys Phe Tyr His Val Met Lys Leu Met Leu Gly Leu Asp Val Lys
    50                  55                  60

```
Val Val Gly Glu Glu Asn Leu Ala Lys Lys Pro Tyr Ile Met Ile Ala
 65                  70                  75                  80

Asn His Gln Ser Thr Leu Asp Ile Phe Met Leu Gly Arg Ile Phe Pro
             85                  90                  95

Pro Gly Cys Thr Val Thr Ala Lys Lys Ser Leu Lys Tyr Val Pro Phe
            100                 105                 110

Leu Gly Trp Phe Met Ala Leu Ser Gly Thr Tyr Phe Leu Asp Arg Ser
            115                 120                 125

Lys Arg Gln Glu Ala Ile Asp Thr Leu Asn Lys Gly Leu Glu Asn Val
            130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
                165                 170                 175

Leu Ala Gln Gln Gly Lys Ile Pro Ile Val Pro Val Val Ser Asn
            180                 185                 190

Thr Ser Thr Leu Val Ser Pro Lys Tyr Gly Val Phe Asn Arg Gly Cys
            195                 200                 205

Met Ile Val Arg Ile Leu Lys Pro Ile Ser Thr Glu Asn Leu Thr Lys
210                 215                 220

Asp Lys Ile Gly Glu Phe Ala Glu Lys Val Arg Asp Gln Met Val Asp
225                 230                 235                 240

Thr Leu Lys Glu Ile Gly Tyr Ser Pro Ala Ile Asn Asp Thr Thr Leu
                245                 250                 255

Pro Pro Gln Ala Ile Glu Tyr Ala Ala Leu Gln His Asp Lys Lys Val
            260                 265                 270

Asn Lys Lys Ile Lys Asn Glu Pro Val Pro Ser Val Ser Ile Ser Asn
            275                 280                 285

Asp Val Asn Thr His Asn Glu Gly Ser Ser Val Lys Lys Met His
            290                 295                 300

<210> SEQ ID NO 19
<211> LENGTH: 7
<212> TYPE: PRT
<213> ORGANISM: Artificial Sequence
<220> FEATURE:
<223> OTHER INFORMATION: 1-acyl-sn-glycerol-3-phosphate acyltransferase
      motif
<220> FEATURE:
<221> NAME/KEY: misc_feature
<222> LOCATION: (3)..(6)
<223> OTHER INFORMATION: Xaa can be any naturally occurring amino acid

<400> SEQUENCE: 19

Asn His Xaa Xaa Xaa Xaa Asp
1               5

<210> SEQ ID NO 20
<211> LENGTH: 4
<212> TYPE: PRT
<213> ORGANISM: Artificial Sequence
<220> FEATURE:
<223> OTHER INFORMATION: 1-acyl-sn-glycerol-3-phosphate acyltransferase
      motif

<400> SEQUENCE: 20

Glu Gly Thr Arg
1
```

```
<210> SEQ ID NO 21
<211> LENGTH: 955
<212> TYPE: DNA
<213> ORGANISM: Mortierella alpina
<220> FEATURE:
<221> NAME/KEY: CDS
<222> LOCATION: (3)..(947)
<223> OTHER INFORMATION: synthetic LPAAT1 (codon-optimized for Yarrowia
      lipolytica)

<400> SEQUENCE: 21 ac atg tct att ggt tcg tcc aac ccc gtg ctc ttg gct gcg att ccc       47
   Met Ser Ile Gly Ser Ser Asn Pro Val Leu Leu Ala Ala Ile Pro
   1               5                  10                  15 ttc gtc tac ctg ttt gtc ctc cca cga gtc ctg gct ttc ctg cct cag      95
Phe Val Tyr Leu Phe Val Leu Pro Arg Val Leu Ala Phe Leu Pro Gln
                20                  25                  30 aag gct cag ttc ctg gcc aaa tgt att gtg gtc ctg att gcc acg ctt     143
Lys Ala Gln Phe Leu Ala Lys Cys Ile Val Val Leu Ile Ala Thr Leu
            35                  40                  45 atc atg tcc gtt gca ggc tgc ttc atc tcg atc gtg tgc gct ctt ctg     191
Ile Met Ser Val Ala Gly Cys Phe Ile Ser Ile Val Cys Ala Leu Leu
        50                  55                  60 gac aag aga tac gtc atc aat tac gtt gtg tcg cga ttg ttc tcc ttc     239
Asp Lys Arg Tyr Val Ile Asn Tyr Val Val Ser Arg Leu Phe Ser Phe
65                  70                  75 ctt gcc gct cga ccg tgt ggt gtg acc tat aag att gtt ggt gag gaa     287
Leu Ala Ala Arg Pro Cys Gly Val Thr Tyr Lys Ile Val Gly Glu Glu
80                  85                  90                  95 cac ctc gat aag tac cct gct atc gtg gtc tgt aac cat caa tcc tct     335
His Leu Asp Lys Tyr Pro Ala Ile Val Val Cys Asn His Gln Ser Ser
                100                 105                 110 atg gat atg atg gtt ttg gga cga gtt ttt cca aag cac tgc gtt gtc     383
Met Asp Met Met Val Leu Gly Arg Val Phe Pro Lys His Cys Val Val
            115                 120                 125 atg gcg aag aag gaa ctc ctg tac ttt ccc ttt ttg gga atg ttt atg     431
Met Ala Lys Lys Glu Leu Leu Tyr Phe Pro Phe Leu Gly Met Phe Met
        130                 135                 140 aaa ctg agc aac gct atc ttc atc gac cgg aag aac cac aag aaa gcc     479
Lys Leu Ser Asn Ala Ile Phe Ile Asp Arg Lys Asn His Lys Lys Ala
145                 150                 155 atc gag tct acc acc caa gcc gtg gcg gac atg aag aag cac aac tct     527
Ile Glu Ser Thr Thr Gln Ala Val Ala Asp Met Lys Lys His Asn Ser
160                 165                 170                 175 gga atc tgg att ttc cca gag ggc acc cgg tct aga ctg gac aag gca     575
Gly Ile Trp Ile Phe Pro Glu Gly Thr Arg Ser Arg Leu Asp Lys Ala
                180                 185                 190 gac ctg ctg ccc ttc aag aaa ggt gcc ttt cat ctt gca att cag gcc     623
Asp Leu Leu Pro Phe Lys Lys Gly Ala Phe His Leu Ala Ile Gln Ala
            195                 200                 205 cag ctc cct att ctc ccc att atc tcg cag ggc tat tcc cat atc tac     671
Gln Leu Pro Ile Leu Pro Ile Ile Ser Gln Gly Tyr Ser His Ile Tyr
        210                 215                 220 gac tct tcg aag cgg tac ttc ccc ggt gga gag ctc gag atc aga gtc     719
Asp Ser Ser Lys Arg Tyr Phe Pro Gly Gly Glu Leu Glu Ile Arg Val
225                 230                 235 ctg gag ccc att cct aca act ggc ctc act act gat gat gtg aac gac     767
Leu Glu Pro Ile Pro Thr Thr Gly Leu Thr Thr Asp Asp Val Asn Asp
240                 245                 250                 255 ctg atg gac aag aca cga aac ctt atg ctc aag cac ttg aag gag atg     815
Leu Met Asp Lys Thr Arg Asn Leu Met Leu Lys His Leu Lys Glu Met
                260                 265                 270
```

```
gat tcc cag tat tcg tcg agc act gct gaa aat gga tcc acg cac atc    863
Asp Ser Gln Tyr Ser Ser Ser Thr Ala Glu Asn Gly Ser Thr His Ile
        275                 280                 285 gac gcc gat att gcc aag tct aca gcc acc agc att ggc aac act gac    911
Asp Ala Asp Ile Ala Lys Ser Thr Ala Thr Ser Ile Gly Asn Thr Asp
    290                 295                 300 gac gca att aca aaa cgt cgt acc cct aag gaa taa gcggccgc           955
Asp Ala Ile Thr Lys Arg Arg Thr Pro Lys Glu
        305                 310
```

<210> SEQ ID NO 22
<211> LENGTH: 314
<212> TYPE: PRT
<213> ORGANISM: Mortierella alpina

<400> SEQUENCE: 22

```
Met Ser Ile Gly Ser Ser Asn Pro Val Leu Ala Ala Ile Pro Phe
1               5                   10                  15

Val Tyr Leu Phe Val Leu Pro Arg Val Leu Ala Phe Leu Pro Gln Lys
            20                  25                  30

Ala Gln Phe Leu Ala Lys Cys Ile Val Val Leu Ile Ala Thr Leu Ile
            35                  40                  45

Met Ser Val Ala Gly Cys Phe Ile Ser Ile Val Cys Ala Leu Leu Asp
    50                  55                  60

Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu Glu His
            85                  90                  95

Leu Asp Lys Tyr Pro Ala Ile Val Val Cys Asn His Gln Ser Ser Met
            100                 105                 110

Asp Met Met Val Leu Gly Arg Val Phe Pro Lys His Cys Val Val Met
        115                 120                 125

Ala Lys Lys Glu Leu Leu Tyr Phe Pro Phe Leu Gly Met Phe Met Lys
    130                 135                 140

Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
            165                 170                 175

Ile Trp Ile Phe Pro Glu Gly Thr Arg Ser Arg Leu Asp Lys Ala Asp
            180                 185                 190

Leu Leu Pro Phe Lys Lys Gly Ala Phe His Leu Ala Ile Gln Ala Gln
        195                 200                 205

Leu Pro Ile Leu Pro Ile Ile Ser Gln Gly Tyr Ser His Ile Tyr Asp
    210                 215                 220

Ser Ser Lys Arg Tyr Phe Pro Gly Gly Glu Leu Glu Ile Arg Val Leu
225                 230                 235                 240

Glu Pro Ile Pro Thr Thr Gly Leu Thr Thr Asp Asp Val Asn Asp Leu
            245                 250                 255

Met Asp Lys Thr Arg Asn Leu Met Leu Lys His Leu Lys Glu Met Asp
            260                 265                 270

Ser Gln Tyr Ser Ser Ser Thr Ala Glu Asn Gly Ser Thr His Ile Asp
        275                 280                 285

Ala Asp Ile Ala Lys Ser Thr Ala Thr Ser Ile Gly Asn Thr Asp Asp
    290                 295                 300

Ala Ile Thr Lys Arg Arg Thr Pro Lys Glu
```

```
<210> SEQ ID NO 23
<211> LENGTH: 12
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<300> PUBLICATION INFORMATION:
<301> AUTHORS: Hideo Shindou, Miki Etoa, Ryo Morimotoa and Takao
       Shimizua
<302> TITLE: Identification of membrane O-acyltransferase family motifs
<303> JOURNAL: Biochemical and Biophysical Research Communications
<304> VOLUME: 383
<305> ISSUE: 3
<306> PAGES: 320-325
<307> DATE: 2009-04-08
<313> RELEVANT RESIDUES IN SEQ ID NO: (1)..(12)

<400> SEQUENCE: 23

Trp His Gly Xaa Xaa Xaa Gly Tyr Xaa Xaa Xaa Phe
1               5                   10

<210> SEQ ID NO 24
<211> LENGTH: 6
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (2)..(5)
<223> OTHER INFORMATION: Xaa can be any naturally occurring amino acid
<300> PUBLICATION INFORMATION:
<301> AUTHORS: Hideo Shindou, Miki Etoa, Ryo Morimotoa and Takao
       Shimizua
<302> TITLE: Identification of membrane O-acyltransferase family motifs
<303> JOURNAL: Biochemical and Biophysical Research Communications
<304> VOLUME: 383
<305> ISSUE: 3
<306> PAGES: 320-325
<307> DATE: 2009-04-08
<313> RELEVANT RESIDUES IN SEQ ID NO: (1)..(6)

<400> SEQUENCE: 24

Tyr Xaa Xaa Xaa Xaa Phe
1               5

<210> SEQ ID NO 25
<211> LENGTH: 9
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<300> PUBLICATION INFORMATION:
<301> AUTHORS: Hideo Shindou, Miki Etoa, Ryo Morimotoa and Takao
       Shimizua
<302> TITLE: Identification of membrane O-acyltransferase family motifs
```

```
<303> JOURNAL: Biochemical and Biophysical Research Communications
<304> VOLUME: 383
<305> ISSUE: 3
<306> PAGES: 320-325
<307> DATE: 2009-04-08
<313> RELEVANT RESIDUES IN SEQ ID NO: (1)..(9)

<400> SEQUENCE: 25

Tyr Xaa Xaa Xaa Tyr Phe Xaa Xaa His
1               5

<210> SEQ ID NO 26
<211> LENGTH: 15
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (2)..(2)
<223> OTHER INFORMATION: Xaa = Val [V] or Ile [I]
<220> FEATURE:
<221> NAME/KEY: MISC_FEATURE
<222> LOCATION: (3)..(3)
<223> OTHER INFORMATION: Xaa = Leu [L] or Ile [I]
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa = Leu [L] or Ile [I] or Val [V]
<220> FEATURE:
<221> NAME/KEY: misc_feature
<222> LOCATION: (8)..(13)
<223> OTHER INFORMATION: Xaa can be any naturally occurring amino acid
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent Publication No.
      2008-0145867-A1
<311> PATENT FILING DATE: 2007-06-15
<312> PUBLICATION DATE: 2008-06-19
<313> RELEVANT RESIDUES IN SEQ ID NO: (1)..(15)

<400> SEQUENCE: 26

Met Xaa Xaa Xaa Xaa Lys Xaa Xaa Xaa Xaa Xaa Xaa Xaa Asp Gly
1               5                   10                  15

<210> SEQ ID NO 27
<211> LENGTH: 24
<212> TYPE: PRT
<213> ORGANISM: Artificial Sequence
<220> FEATURE:
<223> OTHER INFORMATION: motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa = Glu [E] or Asp [D]
<220> FEATURE:
<221> NAME/KEY: MISC_FEATURE
```

```
<222> LOCATION: (13)..(13)
<223> OTHER INFORMATION: Xaa = Ala [A] or Gly [G]
<220> FEATURE:
<221> NAME/KEY: misc_feature
<222> LOCATION: (14)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: Xaa = Phe [F] or Tyr [Y]
<220> FEATURE:
<221> NAME/KEY: misc_feature
<222> LOCATION: (23)..(23)
<223> OTHER INFORMATION: Xaa can be any naturally occurring amino acid
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent Publication No.
      2008-0145867-A1
<311> PATENT FILING DATE: 2007-06-15
<312> PUBLICATION DATE: 2008-06-19
<313> RELEVANT RESIDUES IN SEQ ID NO: (1)..(15)

<400> SEQUENCE: 27

Arg Xaa Lys Tyr Tyr Xaa Xaa Trp Xaa Xaa Xaa Xaa Xaa Xaa Xaa Xaa
1               5                   10                  15

Xaa Xaa Gly Xaa Gly Xaa Xaa Gly
            20

<210> SEQ ID NO 28
<211> LENGTH: 20
<212> TYPE: PRT
<213> ORGANISM: Artificial Sequence
<220> FEATURE:
<223> OTHER INFORMATION: motif
<220> FEATURE:
<221> NAME/KEY: misc_feature
<222> LOCATION: (2)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: Xaa = Thr [T] or Val [V]
<220> FEATURE:
<221> NAME/KEY: misc_feature
<222> LOCATION: (18)..(19)
<223> OTHER INFORMATION: Xaa can be any naturally occurring amino acid
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent Publication No.
      2008-0145867-A1
<311> PATENT FILING DATE: 2007-06-15
<312> PUBLICATION DATE: 2008-06-19
<313> RELEVANT RESIDUES IN SEQ ID NO: (1)..(15)

<400> SEQUENCE: 28

Glu Xaa Xaa Xaa Xaa Xaa Xaa Xaa Xaa Xaa Xaa Xaa Trp Asn Xaa Xaa
1               5                   10                  15

Xaa Xaa Xaa Trp
            20

<210> SEQ ID NO 29
```

```
<211> LENGTH: 15
<212> TYPE: PRT
<213> ORGANISM: Artificial Sequence
<220> FEATURE:
<223> OTHER INFORMATION: motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa = Thr [T] or Phe [F]
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent Publication No.
      2008-0145867-A1
<311> PATENT FILING DATE: 2007-06-15
<312> PUBLICATION DATE: 2008-06-19
<313> RELEVANT RESIDUES IN SEQ ID NO: (1)..(15)

<400> SEQUENCE: 29

Ser Ala Xaa Trp His Gly Xaa Xaa Pro Gly Tyr Xaa Xaa Xaa Phe
1               5                   10                  15

<210> SEQ ID NO 30
<211> LENGTH: 7
<212> TYPE: PRT
<213> ORGANISM: Artificial Sequence
<220> FEATURE:
<223> OTHER INFORMATION: 1-acyl-sn-glycerol-3-phosphate acyltransferase
      motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = Asp [D] or Arg [R]
<300> PUBLICATION INFORMATION:
<301> AUTHORS: Tal M. Lewin, Ping Wang, and Rosalind A. Coleman
<302> TITLE: Analysis of Amino Acid Motifs Diagnostic for the
      sn-Glycerol-3-phosphate Acyltransferase Reaction
<303> JOURNAL: Biochemistry
<304> VOLUME: 38
<305> ISSUE: 18
<306> PAGES: 57645771
<307> DATE: 1999-04-15
<313> RELEVANT RESIDUES IN SEQ ID NO: (1)..(7)
<300> PUBLICATION INFORMATION:
<301> AUTHORS: Atsushi Yamashita, Hiroki Nakanishia, Hiroshi Suzukia,
      Ryo Kamataa, Ken Tanakaa, Keizo Wakua and Takayuki Sugiura
<302> TITLE: Topology of acyltransferase motifs and substrate
      specificity and accessibility in 1-acyl-sn-glycero-3-phosphate
      acyltransferase 1
<303> JOURNAL: Biochimica et Biophysica Acta
<304> VOLUME: 1771
<305> ISSUE: 9
<306> PAGES: 1202-1215
<307> DATE: 2007-07-17
<313> RELEVANT RESIDUES IN SEQ ID NO: (1)..(7)

<400> SEQUENCE: 30

Gly Xaa Xaa Phe Ile Xaa Arg
1               5
```

```
<210> SEQ ID NO 31
<211> LENGTH: 6
<212> TYPE: PRT
<213> ORGANISM: Artificial Sequence
<220> FEATURE:
<223> OTHER INFORMATION: 1-acyl-sn-glycerol-3-phosphate acyltransferase
      motif
<220> FEATURE:
<221> NAME/KEY: MISC_FEATURE
<222> LOCATION: (1)..(1)
<223> OTHER INFORMATION: Xaa = Val [V] or Ile [I]
<220> FEATURE:
<221> NAME/KEY: MISC_FEATURE
<222> LOCATION: (2)..(2)
<223> OTHER INFORMATION: Xaa = Pro [P] or Xaa
<220> FEATURE:
<221> NAME/KEY: MISC_FEATURE
<222> LOCATION: (3)..(3)
<223> OTHER INFORMATION: Xaa = Ile [I] or Val [V] or Leu [L]
<220> FEATURE:
<221> NAME/KEY: MISC_FEATURE
<222> LOCATION: (4)..(4)
<223> OTHER INFORMATION: Xaa = Ile [I] or Val [V]
<220> FEATURE:
<221> NAME/KEY: MISC_FEATURE
<222> LOCATION: (6)..(6)
<223> OTHER INFORMATION: Xaa =  Val [V] or Ile [I]
<300> PUBLICATION INFORMATION:
<301> AUTHORS: Atsushi Yamashita, Hiroki Nakanishia, Hiroshi Suzukia,
      Ryo Kamataa, Ken Tanakaa, Keizo Wakua and Takayuki Sugiura
<302> TITLE: Topology of acyltransferase motifs and substrate
      specificity and accessibility in 1-acyl-sn-glycero-3-phosphate
      acyltransferase 1
<303> JOURNAL: Biochimica et Biophysica Acta
<304> VOLUME: 1771
<305> ISSUE: 9
<306> PAGES: 1202-1215
<307> DATE: 2007-07-17
<313> RELEVANT RESIDUES IN SEQ ID NO: (1)..(6)

<400> SEQUENCE: 31

Xaa Xaa Xaa Xaa Pro Xaa
1               5

<210> SEQ ID NO 32
<211> LENGTH: 6
<212> TYPE: PRT
<213> ORGANISM: Artificial Sequence
<220> FEATURE:
<223> OTHER INFORMATION: 1-acyl-sn-glycerol-3-phosphate acyltransferase
      motif
<300> PUBLICATION INFORMATION:
<301> AUTHORS: Atsushi Yamashita, Hiroki Nakanishia, Hiroshi Suzukia,
      Ryo Kamataa, Ken Tanakaa, Keizo Wakua and Takayuki Sugiura
<302> TITLE: Topology of acyltransferase motifs and substrate
      specificity and accessibility in 1-acyl-sn-glycero-3-phosphate
      acyltransferase 1
<303> JOURNAL: Biochimica et Biophysica Acta
<304> VOLUME: 1771
<305> ISSUE: 9
<306> PAGES: 1202-1215
<307> DATE: 2007-07-17
<313> RELEVANT RESIDUES IN SEQ ID NO: (1)..(6)

<400> SEQUENCE: 32

Ile Val Pro Ile Val Met
1               5

<210> SEQ ID NO 33
<211> LENGTH: 8739
<212> TYPE: DNA
<213> ORGANISM: Artificial Sequence
<220> FEATURE:
```

<223> OTHER INFORMATION: Plasmid pY116

<400> SEQUENCE: 33

```
ggccgccacc gcggcccgag attccggcct cttcggccgc caagcgaccc gggtggacgt      60
ctagaggtac ctagcaatta acagatagtt tgccggtgat aattctctta acctcccaca     120
ctcctttgac ataacgattt atgtaacgaa actgaaattt gaccagatat tgtgtccgcg     180
gtggagctcc agcttttgtt ccctttagtg agggtttaaa cgagcttggc gtaatcatgg     240
tcatagctgt ttcctgtgtg aaattgttat ccgctcacaa ttccacacaa cgtacgagcc     300
ggaagcataa agtgtaaagc ctggggtgcc taatgagtga gctaactcac attaattgcg     360
ttgcgctcac tgcccgcttt ccagtcggga acctgtcgt gccagctgca ttaatgaatc      420
ggccaacgcg cggggagagg cggtttgcgt attgggcgct cttccgcttc ctcgctcact     480
gactcgctgc gctcggtcgt tcggctgcgg cgagcggtat cagctcactc aaaggcggta     540
atacggttat ccacagaatc aggggataac gcaggaaaga acatgtgagc aaaaggccag     600
caaaaggcca ggaaccgtaa aaaggccgcg ttgctggcgt ttttccatag gctccgcccc     660
cctgacgagc atcacaaaaa tcgacgctca agtcagaggt ggcgaaaccc gacaggacta     720
taaagatacc aggcgtttcc ccctggaagc tccctcgtgc gctctcctgt tccgaccctg     780
ccgcttaccg gatacctgtc cgcctttctc ccttcgggaa gcgtggcgct ttctcatagc     840
tcacgctgta ggtatctcag ttcggtgtag gtcgttcgct ccaagctggg ctgtgtgcac     900
gaaccccccg ttcagcccga ccgctgcgcc ttatccggta actatcgtct tgagtccaac     960
ccggtaagac acgacttatc gccactggca gcagccactg gtaacaggat tagcagagcg    1020
aggtatgtag gcggtgctac agagttcttg aagtggtggc ctaactacgg ctacactaga    1080
aggacagtat ttggtatctg cgctctgctg aagccagtta ccttcggaaa aagagttggt    1140
agctcttgat ccggcaaaca aaccaccgct ggtagcggtg gtttttttgt ttgcaagcag    1200
cagattacgc gcagaaaaaa aggatctcaa gaagatcctt tgatcttttc tacgggtct     1260
gacgctcagt ggaacgaaaa ctcacgttaa gggattttgg tcatgagatt atcaaaaagg    1320
atcttcacct agatcctttt aaattaaaaa tgaagtttta atcaatcta aagtatatat      1380
gagtaaactt ggtctgacag ttaccaatgc ttaatcagtg aggcacctat ctcagcgatc    1440
tgtctatttc gttcatccat agttgcctga ctccccgtcg tgtagataac tacgatacgg    1500
gagggcttac catctggccc cagtgctgca atgataccgc gagacccacg ctcaccggct    1560
ccagatttat cagcaataaa ccagccagcc ggaagggccg agcgcagaag tggtcctgca    1620
actttatccg cctccatcca gtctattaat tgttgccggg aagctagagt aagtagttcg    1680
ccagttaata gtttgcgcaa cgttgttgcc attgctacag gcatcgtggt gtcacgctcg    1740
tcgtttggta tggcttcatt cagctccggt tcccaacgat caaggcgagt tacatgatcc    1800
cccatgttgt gcaaaaaagc ggttagctcc ttcggtcctc cgatcgttgt cagaagtaag    1860
ttggccgcag tgttatcact catggttatg gcagcactgc ataattctct tactgtcatg    1920
ccatccgtaa gatgcttttc tgtgactggt gagtactcaa ccaagtcatt ctgagaatag    1980
tgtatgcggc gaccgagttg ctcttgcccg gcgtcaatac gggataatac cgcgccacat    2040
agcagaactt taaaagtgct catcattgga aaacgttctt cggggcgaaa actctcaagg    2100
atcttaccgc tgttgagatc cagttcgatg taacccactc gtgcacccaa ctgatcttca    2160
gcatctttta ctttcaccag cgtttctggg tgagcaaaaa caggaaggca aaatgccgca    2220
aaaaagggaa taagggcgac acggaaatgt tgaatactca tactcttcct ttttcaatat    2280
```

```
tattgaagca tttatcaggg ttattgtctc atgagcggat acatatttga atgtatttag    2340
aaaaataaac aaatagggt tccgcgcaca tttccccgaa aagtgccacc tgacgcgccc    2400
tgtagcggcg cattaagcgc ggcgggtgtg gtggttacgc gcagcgtgac cgctacactt    2460
gccagcgccc tagcgcccgc tcctttcgct ttcttcsctt cctttctcgc cacgttcgcc    2520
ggctttcccc gtcaagctct aaatcggggg ctcccttag ggttccgatt tagtgcttta    2580
cggcacctcg accccaaaaa acttgattag ggtgatggtt cacgtagtgg gccatcgccc    2640
tgatagacgg ttttttcgccc tttgacgttg gagtccacgt tctttaatag tggactcttg    2700
ttccaaactg gaacaacact caaccctatc tcggtctatt cttttgattt ataagggatt    2760
ttgccgattt cggcctattg gttaaaaaat gagctgattt aacaaaaatt taacgcgaat    2820
tttaacaaaa tattaacgct tacaatttcc attcgccatt caggctgcgc aactgttggg    2880
aagggcgatc ggtgcgggcc tcttcgctat tacgccagct ggcgaaaggg ggatgtgctg    2940
caaggcgatt aagttgggta acgccagggt tttcccagtc acgacgttgt aaaacgacgg    3000
ccagtgaatt gtaatacgac tcactatagg gcgaattggg taccgggccc cccctcgagg    3060
tcgatggtgt cgataagctt gatatcgaat tcatgtcaca caaaccgatc ttcgcctcaa    3120
ggaaacctaa ttctacatcc gagagactgc cgagatccag tctacactga ttaattttcg    3180
ggccaataat ttaaaaaaat cgtgttatat aatattatat gtattatata tatacatcat    3240
gatgatactg acagtcatgt cccattgcta aatagacaga ctccatctgc cgcctccaac    3300
tgatgttctc aatatttaag gggtcatctc gcattgttta ataataaaca gactccatct    3360
accgcctcca aatgatgttc tcaaaatata ttgtatgaac ttattttat tacttagtat    3420 tattagacaa cttacttgct ttatgaaaaa cacttcctat ttaggaaaca atttataatg    3480
gcagttcgtt catttaacaa tttatgtaga ataaatgtta taaatgcgta tgggaaatct    3540
taaatatgga tagcataaat gatatctgca ttgcctaatt cgaaatcaac agcaacgaaa    3600
aaaatccctt gtacaacata aatagtcatc gagaaatatc aactatcaaa gaacagctat    3660
tcacacgtta ctattgagat tattattgga cgagaatcac acactcaact gtctttctct    3720
cttctagaaa tacaggtaca agtatgtact attctcattg ttcatacttc tagtcatttc    3780
atcccacata ttccttggat ttctctccaa tgaatgacat tctatcttgc aaattcaaca    3840
attataataa gatataccaa agtagcggta tagtggcaat caaaaagctt ctctggtgtg    3900
cttctcgtat ttatttttat tctaatgatc cattaaaggt atatatttat ttcttgttat    3960
ataatccttt tgtttattac atgggctgga tacataaagg tattttgatt taattttttg    4020
cttaaattca atccccctc gttcagtgtc aactgtaatg gtaggaaatt accatacttt    4080
tgaagaagca aaaaaatga agaaaaaaa aaatcgtatt tccaggttag acgttccgca    4140
gaatctagaa tgcggtatgc ggtacattgt tcttcgaacg taaaagttgc gctccctgag    4200
atattgtaca ttttgctttt tacaagtaca agtacatcgt acaactatgt actactgttg    4260
atgcatccac aacagtttgt tttgtttttt tttgtttttt ttttttctaa tgattcatta    4320
ccgctatgta tacctacttg tacttgtagt aagcccgggtt attggcgttc aattaatcat    4380
agacttatga atctgcacgg tgtgcgctgc gagttacttt tagcttatgc atgctacttg    4440
ggtgtaatat tgggatctgt tcggaaatca acggatgctc aaccgatttc gacagtaatt    4500
aattaatttg aatcgaatcg gagcctaaaa tgaacccgag tatatctcat aaaattctcg    4560
gtgagaggtc tgtgactgtc agtacaaggt gccttcatta tgccctcaac cttaccatac    4620
```

```
ctcactgaat gtagtgtacc tctaaaaatg aaatacagtg ccaaaagcca aggcactgag   4680
ctcgtctaac ggacttgata tacaaccaat taaaacaaat gaaaagaaat acagttcttt   4740
gtatcatttg taacaattac cctgtacaaa ctaaggtatt gaaatcccac aatattccca   4800
aagtccaccc ctttccaaat tgtcatgcct acaactcata taccaagcac taacctacca   4860
aacaccacta aaccccaca aaatatatct taccgaatat acagtaacaa gctaccacca   4920
cactcgttgg gtgcagtcgc cagcttaaag atatctatcc acatcagcca caactccctt   4980
cctttaataa accgactaca cccttggcta ttgaggttat gagtgaatat actgtagaca   5040
agacactttc aagaagactg tttccaaaac gtaccactgt cctccactac aaacacaccc   5100
aatctgcttc ttctagtcaa ggttgctaca ccggtaaatt ataaatcatc atttcattag   5160
cagggcaggg ccctttttat agagtcttat acactagcgg accctgccgg tagaccaacc   5220
cgcaggcgcg tcagtttgct ccttccatca atgcgtcgta gaaacgactt actccttctt   5280
gagcagctcc ttgaccttgt tggcaacaag tctccgacct cggaggtgga ggaagagcct   5340
ccgatatcgg cggtagtgat accagcctcg acggactcct tgacgcagc ctcaacagcg    5400 tcaccggcgg gcttcatgtt aagagagaac ttgagcatca tggcggcaga cagaatggtg   5460
gcaatggggt tgaccttctg cttgccgaga tcggggcag atccgtgaca gggctcgtac    5520
agaccgaacg cctcgttggt gtcgggcaga aagccagag aggcggaggg cagcagaccc    5580
agagaaccgg ggatgacgga ggcctcgtcg gagatgatat cgccaaacat gttggtggtg   5640
atgatgatac cattcatctt ggagggctgc ttgatgagga tcatggcggc cgagtcgatc   5700
agctggtggt tgagctcgag ctgggggaat tcgtccttga ggactcgagt gacagtcttt   5760
cgccaaagtc gagaggaggc cagcacgttg gccttgtcaa gagaccacac gggaagaggg   5820 ggggttgtgct gaagggccag gaaggcggcc attcgggcaa ttcgctcaac ctcaggaacg   5880
gagtaggtct cggtgtcgga agcgacgcca gatccgtcat cctcctttcg ctctccaaag   5940
tagataccct cgacgagctc tcggacaatg atgaagtcgg tgccctcaac gtttcggatg   6000
ggggagagat cggcgagctt gggcgacagc agctggcagg gtcgcaggtt ggcgtacagg   6060
ttcaggtcct ttcgcagctt gaggagaccc tgctcgggtc gcacgtcggt tcgtccgtcg   6120
ggagtggtcc atacggtgtt ggcagcgcct ccgacagcac cgagcataat agagtcagcc   6180
tttcggcaga tgtcgagagt agcgtcggtg atgggctcgc cctccttctc aatggcagct   6240
cctccaatga gtcggtcctc aaacacaaac tcggtgccgg aggcctcagc aacagacttg   6300
agcaccttga cggcctcggc aatcacctcg gggccacaga agtcgccgcc gagaagaaca   6360
atcttcttgg agtcagtctt ggtcttctta gtttcgggtt ccattgtgga tgtgtgtggt   6420
tgtatgtgtg atgtggtgtg tggagtgaaa atctgtggct ggcaaacgct cttgtatata   6480
tacgcacttt tgcccgtgct atgtggaaga ctaaacctcc gaagattgtg actcaggtag   6540
tgcggtatcg gctagggacc caaaccttgt cgatgccgat agcgctatcg aacgtaccc    6600 agccggccgg gagtatgtcg gagggacat acgagatcgt caagggtttg tggccaactg     6660
gtatttaaat gtagctaacg gtagcaggcg aactactggt acatacctcc cccggaatat   6720
gtacaggcat aatgcgtatc tgtgggacat gtggtcgttg cgccattatg taagcagcgt   6780
gtactcctct gactgtccat atggtttgct ccatctcacc ctcatcgttt tcattgttca   6840
caggcggcca caaaaaaact gtcttctctc cttctctctt cgccttagtc tactcggacc   6900
agttttagtt tagcttggcg ccactggata aatgagacct caggccttgt gatgaggagg   6960
tcacttatga agcatgttag gaggtgcttg tatggataga gaagcaccca aaataataag   7020
```

```
aataataata aaacaggggg cgttgtcatt tcatatcgtg ttttcaccat caatacacct    7080
ccaaacaatg cccttcatgt ggccagcccc aatattgtcc tgtagttcaa ctctatgcag    7140
ctcgtatctt attgagcaag taaaactctg tcagccgata ttgcccgacc cgcgacaagg    7200
gtcaacaagg tggtgtaagg ccttcgcaga agtcaaaact gtgccaaaca acatctaga    7260 gtctctttgg tgtttctcgc atatatttwa tcggctgtct tacgtatttg cgcctcggta    7320
ccggactaat ttcggatcat ccccaatacg cttttcttc gcagctgtca acagtgtcca    7380
tgatctatcc acctaaatgg gtcatatgag gcgtataatt tcgtggtgct gataataatt    7440
cccatatatt tgacacaaaa cttccccccc tagacataca tctcacaatc tcacttcttg    7500
tgcttctgtc acacatctcc tccagctgac ttcaactcac acctctgccc cagttggtct    7560
acagcggtat aaggtttctc cgcatagagg tgcaccactc ctcccgatac ttgtttgtgt    7620
gacttgtggg tcacgacata tatatctaca cacattgcgc caccctttgg ttcttccagc    7680
acaacaaaaa cacgacacgc taaccatggc caatttactg accgtacacc aaaatttgcc    7740
tgcattaccg gtcgatgcaa cgagtgatga ggttcgcaag aacctgatgg acatgttcag    7800
ggatcgccag gcgttttctg agcatacctg gaaaatgctt ctgtccgttt gccggtcgtg    7860
ggcggcatgg tgcaagttga ataaccggaa atggtttccc gcagaacctg aagatgttcg    7920
cgattatctt ctatatcttc aggcgcgcgg tctggcagta aaaactatcc agcaacattt    7980
gggccagcta acatgcttc atcgtcggtc cgggctgcca cgaccaagtg acagcaatgc    8040
tgtttcactg gttatgcggc ggatccgaaa agaaaacgtt gatgccggtg aacgtgcaaa    8100
acaggctcta gcgttcgaac gcactgattt cgaccaggtt cgttcactca tggaaaatag    8160
cgatcgctgc caggatatac gtaatctggc atttctgggg attgcttata cacccctgtt    8220
acgtatagcc gaaattgcca ggatcagggt taaagatatc tcacgtactg acggtgggag    8280
aatgttaatc catattggca gaacgaaaac gctggttagc accgcaggtg tagagaaggc    8340
acttagcctg ggggtaacta aactggtcga gcgatggatt tccgtctctg gtgtagctga    8400
tgatccgaat aactacctgt tttgccgggt cagaaaaaat ggtgttgccg cgccatctgc    8460
caccagccag ctatcaactc gcgccctgga agggattttt gaagcaactc atcgattgat    8520
ttacggcgct aaggatgact ctggtcagag atacctggcc tggtctggac acagtgcccg    8580
tgtcggagcc gcgcgagata tggcccgcgc tggagtttca ataccggaga tcatgcaagc    8640
tggtggctgg accaatgtaa atattgtcat gaactatatc cgtaacctgg atagtgaaac    8700
aggggcaatg tgcgcctgc tggaagatgg cgattaagc                            8739

<210> SEQ ID NO 34
<211> LENGTH: 13975
<212> TYPE: DNA
<213> ORGANISM: Artificial Sequence
<220> FEATURE:
<223> OTHER INFORMATION: Plasmid pZKSL-5S5A5

<400> SEQUENCE: 34
cgatggttaa tgctgctgtg tgctgtgtgt gtgtgttgtt tggcgctcat tgttgcgtta      60
tgcagcgtac accacaatat tggaagctta ttagccttc tattttttcg tttgcaaggc     120
ttaacaacat tgctgtggag agggatgggg atatggaggc cgctggaggg agtcggagag     180
gcgttttgga gcggcttggc ctggcgccca gctcgcgaaa cgcacctagg acccttggc     240 acgccgaaat gtgccacttt tcagtctagt aacgccttac ctacgtcatt ccatgcgtgc     300
```

```
atgtttgcgc cttttttccc ttgcccttga tcgccacaca gtacagtgca ctgtacagtg      360
gaggttttgg gggggtctta gatgggagct aaaagcggcc tagcggtaca ctagtgggat      420
tgtatggagt ggcatggagc ctaggtggag cctgacagga cgcacgaccg gctagcccgt      480
gacagacgat gggtggctcc tgttgtccac cgcgtacaaa tgtttgggcc aaagtcttgt      540
cagccttgct tgcgaaccta attcccaatt ttgtcacttc gcaccccat tgatcgagcc       600 ctaacccctg cccatcaggc aatccaatta agctcgcatt gtctgccttg tttagtttgg      660
ctcctgcccg tttcggcgtc cacttgcaca aacacaaaca agcattatat ataaggctcg      720
tctctccctc ccaaccacac tcactttttt gcccgtcttc ccttgctaac acaaaagtca      780
agaacacaaa caaccacccc aacccccctta cacacaagac atatctacag caatggccat      840
ggctctcagt cttaccacag aacagctgtt agaacgccct gatttggttg cgattgatgg      900
catcctctac gaccttgaag ggcttgccaa agttcatcca ggatccgatt tgattctcgc      960
ttctggtgcc tctgatgcct cccctctctt ttattcaatg catccatacg tcaaaccgga     1020
gaactccaaa ttgcttcaac agttcgtccg agggaagcat gaccgcacct cgaaggacat     1080
tgtctacacg tatgattctc ccttcgcaca agacgttaag cggacaatgc gcgaggtgat     1140
gaaagggagg aactggtacg caacccctgg cttctggctg cgcaccgttg ggatcatcgc     1200
cgtgacggcc ttttgcgagt ggcactgggc taccacgggg atggtgctgt ggggcctgtt     1260
gactggattc atgcacatgc agatcggctt atccatccag catgatgcgt cccacggggc     1320
catcagcaag aagccttggg tcaacgccct cttcgcctac ggcattgacg tcatcggatc     1380
gtcccggtgg atttggctgc agtcgcacat catgcggcac cacacctaca ccaaccagca     1440
cggcctcgac ctggatgcgg agtcggcaga gccgttcctg gtgttccaca actacccgc      1500 cgcaaacacc gcccgaaagt ggttccaccg cttccaggct tggtacatgt accttgtgct     1560
gggggcatac ggggtatcgc tggtgtacaa cccgctctac attttccgga tgcagcacaa     1620
tgacaccatc ccagagtctg tcacggccat gcgggaaaat ggctttctgc ggcgctaccg     1680
cacacttgca ttcgtgatgc gagctttctt catcttccgg accgcattct tgccctggta     1740
cctcactggg acctcattgc tgatcaccat tcctctggtg cccaccgcaa ctggtgcctt     1800
cttgacgttc ttcttcattt tgtcccacaa ttttgatggc tccgaacgga tccccgacaa     1860
gaactgcaag gttaagcgat ctgagaagga cgttgaggct gaccaaattg actggtatcg     1920
ggcgcaggtg gagacgtcct ccacatacgg tggccccatc gccatgttct tcactggcgg     1980
tctcaatttc cagatcgagc accacctctt tcccggatg tcgtcttggc actacccctt      2040
cgtccagcag gcggtccggg agtgttgcga acgacatgga gtgcgatatg ttttctaccc     2100
taccatcgtc ggcaacatca tctccaccct gaagtacatg cataaggtgg gtgtcgtcca     2160
ctgcgtgaag gacgcacagg attcctaagc ggccgcattg atgattggaa acacacacat     2220
gggttatatc taggtgagag ttagttggac agttatatat taaatcagct atgccaacgg     2280
taacttcatt catgtcaacg aggaaccagt gactgcaagt aatatagaat ttgaccacct     2340
tgccattctc ttgcactcct ttactatatc tcatttattt cttatataca aatcacttct     2400
tcttcccagc atcgagctcg gaaacctcat gagcaataac atcgtggatc tcgtcaatag     2460
agggcttttt ggactccttg ctgttggcca ccttgtcctt gctgtctggc tcattctgtt     2520
tcaacgccct ttaattaact ctcctgcagc ttcctcagcg agacactgct cctgtctgga     2580
cccgagctaa ggctctgttc gacaaacacg ttctgcgaat tggcgagtaa tttcattaat     2640
gcaaatagac gtgtatttga aaaggaggag atgatggtac cagtaattta cggtgtttga     2700
```

```
atagacaaat tatatatata aaattaacct gatgaatgag tgtatgaatg gattgcttaa    2760
tataccgagg gagagccggc attatcaata tttattgtcc taagaagcta aaatatgctg    2820
ttccgttgat agcgatgtct gtttgagagt caatggcaga acgcggagga gtattgttag    2880
ttggtgatcg gtttactcga catcgagtag ggggcgagac agaagatatc ccgaatccat    2940
tgcattgttt attaggatgt tcacaacaca actccctcta gactctgggg atgtgcgtta    3000
gaagaatgac ctggagcaag agtgttcaga ttgatccgtt caaattttca agattactgt    3060
tggggttgtt tttgaatcca cattagctgg acgactattg catctgagcg ctcggaacgt    3120
ctccctttcc cttcagcttt atacgagtcg attccataag cgcgacctct cgaattgcct    3180
tcggttgtga agccataggc aaaggtgtgg ctatggaatg catgcgacgt cgggcccaat    3240
tcgccctata gtgagtcgta ttacaattca ctggccgtcg ttttacaacg tcgtgactgg    3300
gaaaaccctg gcgttaccca acttaatcgc cttgcagcac atccccettt cgccagctgg    3360 cgtaatagcg aagaggcccg caccgatcgc ccttcccaac agttgcgcag cctgaatggc    3420
gaatggacgc gccctgtagc ggcgcattaa gcgcggcggg tgtggtggtt acgcgcagcg    3480
tgaccgctac acttgccagc gccctagcgc ccgctccttt cgctttcttc ccttcctttc    3540
tcgccacgtt cgccggcttt ccccgtcaag ctctaaatcg ggggctccct ttagggttcc    3600
gatttagtgc tttacggcac ctcgacccca aaaaacttga ttagggtgat ggttcacgta    3660
gtgggccatc gccctgatag acggtttttc gccctttgac gttggagtcc acgttcttta    3720
atagtggact cttgttccaa actggaacaa cactcaaccc tatctcggtc tattcttttg    3780
atttataagg gattttgccg atttcggcct attggttaaa aaatgagctg atttaacaaa    3840
aatttaacgc gaattttaac aaaatattaa cgcttacaat ttcctgatgc ggtattttct    3900
ccttacgcat ctgtgcggta tttcacaccg catcaggtgg cacttttcgg ggaaatgtgc    3960
gcggaacccc tatttgttta ttttctaaa tacattcaaa tatgtatccg ctcatgagac    4020
aataaccctg ataaatgctt caataatatt gaaaaaggaa gagtatgagt attcaacatt    4080
tccgtgtcgc ccttattccc ttttttgcgg cattttgcct tcctgttttt gctcacccag    4140
aaacgctggt gaaagtaaaa gatgctgaag atcagttggg tgcacgagtg ggttacatcg    4200
aactggatct caacagcggt aagatccttg agagttttcg ccccgaagaa cgttttccaa    4260
tgatgagcac ttttaaagtt ctgctatgtg gcgcggtatt atcccgtatt gacgccgggc    4320
aagagcaact cggtcgccgc atacactatt ctcagaatga cttggttgag tactcaccag    4380
tcacagaaaa gcatcttacg gatggcatga cagtaagaga attatgcagt gctgccataa    4440
ccatgagtga taacactgcg gccaacttac ttctgacaac gatcggagga ccgaaggagc    4500
taaccgcttt tttgcacaac atgggggatc atgtaactcg ccttgatcgt tgggaaccgg    4560
agctgaatga agccatacca aacgacgagc gtgacaccac gatgcctgta gcaatggcaa    4620
caacgttgcg caaactatta actggcgaac tacttactct agcttcccgg caacaattaa    4680
tagactggat ggaggcggat aaagttgcag gaccacttct gcgctcggcc cttccggctg    4740
gctggtttat tgctgataaa tctggagccg gtgagcgtgg gtctcgcggt atcattgcag    4800
cactggggcc agatggtaag ccctcccgta tcgtagttat ctacacgacg gggagtcagg    4860
caactatgga tgaacgaaat agacagatcg ctgagatagg tgcctcactg attaagcatt    4920
ggtaactgtc agaccaagtt tactcatata ctttagat tgatttaaaa cttcattttt    4980
aatttaaaag gatctaggtg aagatccttt ttgataatct catgaccaaa atcccttaac    5040
```

```
gtgagttttc gttccactga gcgtcagacc ccgtagaaaa gatcaaagga tcttcttgag    5100
atccttttt  tctgcgcgta atctgctgct tgcaaacaaa aaaaccaccg ctaccagcgg    5160
tggtttgttt gccggatcaa gagctaccaa ctcttttcc  gaaggtaact ggcttcagca    5220
gagcgcagat accaaatact gttcttctag tgtagccgta gttaggccac cacttcaaga    5280
actctgtagc accgcctaca tacctcgctc tgctaatcct gttaccagtg gctgctgcca    5340
gtggcgataa gtcgtgtctt accgggttgg actcaagacg atagttaccg gataaggcgc    5400
agcggtcggg ctgaacgggg ggttcgtgca cacagcccag cttggagcga acgacctaca    5460
ccgaactgag atacctacag cgtgagctat gagaaagcgc cacgcttccc gaagggagaa    5520
aggcggacag gtatccggta agcggcaggg tcggaacagg agagcgcacg agggagcttc    5580
cagggggaaa cgcctggtat ctttatagtc ctgtcgggtt tcgccacctc tgacttgagc    5640
gtcgattttt gtgatgctcg tcagggggc  ggagcctatg gaaaaacgcc agcaacgcgg    5700
cctttttacg gttcctggcc ttttgctggc cttttgctca catgttcttt cctgcgttat    5760
cccctgattc tgtggataac cgtattaccg cctttgagtg agctgatacc gctcgccgca    5820
gccgaacgac cgagcgcagc gagtcagtga gcgaggaagc ggaagagcgc ccaatacgca    5880
aaccgcctct ccccgcgcgt tggccgattc attaatgcag ctggcgcgcc gaggtttcca    5940
acgagataac atcgtggcag ctgccaccat gaccgatatg cctgaaataa gtgaattgac    6000
catcagaagt tctgcattca aatagaacta tatcatattc ggctcagttt tttcaataat    6060
agtccaatcc ctaagtctcc tatccaaaat ggttcctgac cagccacatc catgatcatg    6120
actgcgtgac aggaacagtc attccgtgga tgaacgactt tacgctcagg tactgtaaat    6180
atctgtaaag ggcagacaac caaccaattg agtaacctgt gagacttgaa cgtaagatg     6240
acttcacaca caaagtcact tgactcaacc gtggctctca attgcacaaa atcactctgc    6300
actaatctat tgcaggagtc aggctatgaa caactagacg acagctactt atgtgttata    6360
tagaggaata ttaaaaaatc taagaataat cataaagtta caaataatt  atcagatttc    6420
gagccacagg tcacccctaa catgtgttat tgcacaccca caatcctcag cttgatgtca    6480
tttaattctt ccagccacca tctctctctc caaccctaat ggcaaacttt attttggtgg    6540
agcgatgact cttactcaac tgcagcatac ttaagcacaa ttgttcccca gcctgatacg    6600
acacaccatc cattgtcaag cttcaccaca tacaacaaca cagcgtacgc aactaacatg    6660
aatgaatacg atatacatca aagactatga tacgcagtat tgcacactgt acgagtaaga    6720
gcactagcca ctgcactcaa gtgaaaccgt tgcccgggta cgagtatgag tatgtacagt    6780
atgtttagta ttgtacttgg acagtgcttg tatcgtacat tctcaagtgt caaacataaa    6840
tatccgttgc tatatcctcg caccaccacg tagctcgcta tatccctgtg ttgaatccat    6900
ccatcttgga ttgccaattg tgcacacaga accgggcact cacttcccca tccacacttg    6960
cggccgctta ggaatcctga gcgtccttga cacagtgaac cacaccgact ttgtgcatgt    7020
acttgagggt ggaaatgatg ttgcccacaa tggtagggta gaagacgtac cgaactccgt    7080
gtcgttcgca acactctcgg acagcttgct gcacgaaggg atagtgccaa gacgacattc    7140
gaggaaagag gtgatgctcg atctggaagt tgagaccgcc agtaaagaac atggcaatgg    7200
gtccaccgta ggtggaagag gtctccacct gagctctgta ccagtcgatc tgatcggctt    7260
caacgtcctt ctcggagctc ttgacccttgc agttcttgtc gggattcgc  tccgagccat    7320
cgaagttgtg agacaagatg aaaaagaagg tgaggaaggc accggtagca gtgggcacca    7380
gaggaatggt gatgagcagg gaggttccag tgagatacca gggcaagaag gcggttcgaa    7440
```

```
agatgaagaa agctcgcata acgaatgcaa gggttcggta ccgtcgcaga aagccgttct    7500
ctcgcatggc tgtgacagac tcgggaatgg tgtcgttgtg ctgcattcgg aagatgtaga    7560
gagggttgta caccagcgaa acgccgtagg ctccaagcac gaggtacatg taccaggcct    7620
ggaatcggtg aaaccacttt cgagcagtgt tggcagcagg gtagttgtgg aacacaagga    7680
atggttctgc ggactcggca tccaggtcga gaccatgctg attggtgtag gtgtgatgtc    7740
gcatgatgtg agactgcagc cagatccatc tggacgatcc aatgacgtcg atgccgtagg    7800
caaagagagc gttgacccag ggcttttttgc tgatggcacc atgagaggca tcgtgctgaa    7860
tggacaggcc gatctgcatg tgcatgaatc cagtcaagag accccacagc accattccgg    7920
tagtagccca gtgccactcg caaaaggcgg tgacagcaat gatgccaacg gttcgcagcc    7980
agaatccagg tgtggcatac cagttccgac ctttcatgac ctctcgcata gttcgcttga    8040
cgtcctgtgc aaagggagag tcgtaggtgt agacaatgtc cttggaggtt cggtcgtgct    8100
tgcctcgcac gaactgttga agcagcttcg agttctcggg cttgacgtaa gggtgcatgg    8160
agtagaacag aggagaagca tcggaggcac cagaagcgag gatcaagtcg gatccgggat    8220
ggaccttggc aagaccttcc agatcgtaga gaatgccgtc gatggcaacc aggtcgggtc    8280
gctcgagcag ctgctcggta gtaagggaga gagccatgga gagctgggtt agtttgtgta    8340
gagagtgtgt gttgctagcg actttcggat tgtgtcatta cacaaaacgc gtcgtctcga    8400
cactgatctt gtcgtggata ctcacggctc ggacatcgtc gccgacgatg acaccggact    8460
ttcgcttaag gacgtcagta acaggcattg tgtgatgtgt agtttagatt tcgaatctgt    8520
ggggaaagaa aggaaaaaag agactggcaa ccgattggga gagccactgt ttatatatac    8580
cctagacaag cccccccgctt gtaagatgtt ggtcaatgta aaccagtatt aaggttggca    8640
agtgcaggag aagcaaggtg tgggtaccga gcaatggaaa tgtgcggaag gcaaaaaaat    8700
gaggccacgg cctattgtcg gggctatatc caggggggcga ttgaagtaca ctaacatgac    8760
atgtgtccac agaccctcaa tctggcctga tgagccaaat ccatacgcgc tttcgcagct    8820
ctaaaggcta taacaagtca caccaccctg ctcgacctca gcgccctcac ttttttgttaa    8880 gacaaactgt acacgctgtt ccagcgtttt ctgcctgcac ctggtgggac atttggtgca    8940
acctaaagtg ctcggaacct ctgtggtgtc cagatcagcg cagcagttcc gaggtagttt    9000 tgaggcccett agatgatgca atggtgtcag tcgctggatc acgagtctta atggcagtat    9060
tcgttcttat ttgtgccatt gagccccgtt atcctcgtat cttctacccc ccatcccatc    9120
cctttgttgg tgcaacccta cccatttatt gttgggtgca gcccaaccga cgtggagagc    9180
ttggcttggc catataaaaa ggcccccccc tagtggcaat ggcagaaagt cagctgtgag    9240
ttgttgaatt tgtcatctag gcggcctggc cgtcttctcc ggggcaattg gggctgtttt    9300
ttgggacaca aatacgccgc caacccggtc tctcctgaat tctgcagatg ggctgcagga    9360
attccgtcgt cgcctgagtc gactccaact tttcacactg agcgtaaaat gtggagaaga    9420
aatcggcact aaaaagtcag gtagactgga aaatgcgcca tgaaatgaat atctcttgct    9480
acagtaatgc ccagcatcga ggggtattgt gtcaccaaca ctatagtggc agctgaagcg    9540
ctcgtgattg tagtatgagt ctttattggt gatgggaaga gttcactcaa tattctcgtt    9600
actgccaaaa caccacggta atcggccaga caccatggat gtagatcacc aagcctgtga    9660
atgttattcg agctaaaatg cacatggttg gtgaaaggag tagttgctgt cgaattccgt    9720
cgtcgcctga gtcatcattt atttaccagt tggccacaaa cccttgacga tctcgtatgt    9780
```

```
cccctccgac atactcccgg ccggctgggg tacgttcgat agcgctatcg gcatcgacaa    9840
ggtttgggtc cctagccgat accgcactac ctgagtcaca atcttcggag gtttagtctt    9900
ccacatagca cgggcaaaag tgcgtatata tacaagagcg tttgccagcc acagattttc    9960
actccacaca ccacatcaca catacaacca cacacatcca caatggaacc cgaaactaag   10020
aagaccaaga ctgactccaa gaagattgtt cttctcggcg gcgacttctg tggccccgag   10080
gtgattgccg aggccgtcaa ggtgctcaag tctgttgctg aggcctccgg caccgagttt   10140
gtgtttgagg accgactcat tggaggagct gccattgaga aggagggcga gcccatcacc   10200
gacgctactc tcgacatctg ccgaaaggct gactctatta tgctcggtgc tgtcggaggc   10260
gctgccaaca ccgtatggac cactcccgac ggacgaaccg acgtgcgacc cgagcagggt   10320
ctcctcaagc tgcgaaagga cctgaacctg tacgccaacc tgcgaccctg ccagctgctg   10380
tcgcccaagc tcgccgatct ctcccccatc cgaaacgttg agggcaccga cttcatcatt   10440
gtccgagagc tcgtcggagg tatctacttt ggagagcgaa aggaggatga cggatctggc   10500
gtcgcttccg acaccgagac ctactccgtt cctgaggttg agcgaattgc ccgaatggcc   10560
gccttcctgg cccttcagca caacccccct cttcccgtgt ggtctcttga caaggccaac   10620
gtgctggcct cctctcgact ttggcgaaag actgtcactc gagtcctcaa ggacgaattc   10680
ccccagctcg agctcaacca ccagctgatc gactcggccg ccatgatcct catcaagcag   10740
ccctccaaga tgaatggtat catcatcacc accaacatgt ttggcgatat catctccgac   10800
gaggcctccg tcatccccgg ttctctgggt ctgctgccct ccgcctctct ggcttctctg   10860
cccgacacca acgaggcgtt cggtctgtac gagccctgtc acggatctgc ccccgatctc   10920
ggcaagcaga aggtcaaccc cattgccacc attctgtctg ccgccatgat gctcaagttc   10980
tctcttaaca tgaagcccgc cggtgacgct gttgaggctg ccgtcaagga gtccgtcgag   11040
gctggtatca ctaccgccga tatcggaggc tcttcctcca cctccgaggt cggagacttg   11100
ttgccaacaa ggtcaaggag ctgctcaaga aggagtaagt cgtttctacg acgcattgat   11160
ggaaggagca aactgacgcg cctgcgggtt ggtctaccgg cagggtccgc tagtgtataa   11220
gactctataa aaagggccct gccctgctaa tgaaatgatg atttataatt taccggtgta   11280
gcaaccttga ctagaagaag cagattgggt gtgtttgtag tggaggacag tggtacgttt   11340
tggaaacagt cttcttgaaa gtgtcttgtc tacagtatat tcactcataa cctcaatagc   11400
caagggtgta gtcggtttat taaaggaagg gagttgtggc tgatgtggat agatatcttt   11460
aagctggcga ctgcacccaa cgagtgtggt ggtagcttgt ttaaacagag tgtgaaagac   11520
tcactatggt ccgggcttat ctcgaccaat agccaaagtc tggagtttct gagagaaaaa   11580
ggcaagatac gtatgtaaca aagcgacgca tggtacaata taccggagg catgtatcat   11640
agagagttag tggttcgatg atggcactgg tgcctggtat gactttatac ggctgactac   11700
atatttgtcc tcagacatac aattacagtc aagcacttac ccttggacat ctgtaggtac   11760
cccccggcca agacgatctc agcgtgtcgt atgtcggatt ggcgtagctc cctcgctcgt   11820
caattggctc ccatctactt tcttctgctt ggctacaccc agcatgtctg ctatggctcg   11880
ttttcgtgcc ttatctatcc tcccagtatt accaactcta atgacatga tgtgattggg   11940
tctacacttt catatcagag ataaggagta gcacagttgc ataaaaagcc caactctaat   12000
cagcttcttc ctttcttgta attagtacaa aggtgattag cgaaatctgg aagcttagtt   12060
ggccctaaaa aaatcaaaaa aagcaaaaaa cgaaaaacga aaaccacag ttttgagaac   12120
agggaggtaa cgaaggatcg tatatatata tatatatata tatacccacg gatcccgaga   12180
```

```
ccggcctttg attcttccct acaaccaacc attctcacca ccctaattca caaccatggc   12240
caccatctcc ctgactaccg agcagctcct ggaacacccc gagctcgttg ccatcgacgg   12300
agtcctgtac gatctcttcg gtctggccaa ggtccatgcc ggaggcaacc tcatcgaagc   12360
tgccggtgca tccgacggaa ccgctctgtt ctactccatg catcctggag tcaagccaga   12420
gaactcgaag cttctgcagc aatttgcccg aggcaagcac gaacgaagct ccaaggatcc   12480
cgtgtacacc ttcgactctc cctttgctca ggacgtcaag cagtccgttc gagaggtcat   12540
gaagggtcga aactggtacg ccactcctgg cttctggctg agaaccgcac tcatcatcgc   12600
ttgtactgcc attggcgagt ggtactggat cacaaccgga gcagtgatgt ggggtatctt   12660
tactggatac ttccactcgc agattggctt ggccattcaa cacgatgctt ctcacggagc   12720
catcagcaaa aagccctggg tcaacgcctt tttcgcttat ggcatcgacg ccattggttc   12780
ctctcgttgg atctggctgc agtcccacat tatgcgacat cacacttaca ccaaccagca   12840
tggcctcgac ctggatgctg cctcggcaga gccgttcatc ttgttccact cctatcctgc   12900
taccaacgcc tctcgaaagt ggtaccaccg atttcaggcg tggtacatgt acatcgttct   12960
gggaatgtat ggtgtctcga tggtgtacaa tcccatgtac ctcttcacaa tgcagcacaa   13020
cgacaccatt cccgaggcca cttctctcag accaggcagc tttttcaatc ggcagcgagc   13080
tttcgccgtt tcccttcgac tgctcttcat cttccgaaac gcctttcttc cctggtacat   13140
tgctggtgcc tctcctctgc tcaccattct tctggtgccc acggtcacag gcatcttcct   13200 caccttttgtg ttcgttctgt cccataactt cgagggagcc gaacggaccc cagagaagaa   13260
ctgcaaggcc aaacgagcta aggaaggcaa ggaggtcaga gacgtggaag aggatcgagt   13320
cgactggtac cgagcacagg ccgagactgc tgccacctac ggtggcagcg tgggaatgat   13380
gcttacaggc ggtctcaacc tgcagatcga gcatcacttg tttccccgaa tgtcctcttg   13440
gcactatccc ttcattcaag acaccgttcg ggagtgttgc aagcgacatg gcgtccgtta   13500
cacatactat cctaccattc tcgagaacat catgtccact cttcgataca tgcagaaggt   13560
gggtgttgct cacaccattc aggatgccca ggagttctaa gcggccgcat gtacatacaa   13620
gattatttat agaaatgaat cgcgatcgaa caaagagtac gagtgtacga gtagggggatg   13680 atgataaaag tggaagaagt tccgcatctt tggatttatc aacgtgtagg acgatacttc   13740
ctgtaaaaat gcaatgtctt taccataggt tctgctgtag atgttattaa ctaccattaa   13800
catgtctact tgtacagttg cagaccagtt ggagtataga atggtacact taccaaaaag   13860
tgttgatggt tgtaactacg atatataaaa ctgttgacgg gatccccgct gatatgccta   13920
aggaacaatc aaagaggaag atattaattc agaatgctag tatacagtta gggat         13975
```

<210> SEQ ID NO 35
<211> LENGTH: 1350
<212> TYPE: DNA
<213> ORGANISM: Euglena gracilis
<220> FEATURE:
<221> NAME/KEY: CDS
<222> LOCATION: (1)..(1350)
<223> OTHER INFORMATION: synthetic mutant delta-5 desaturase
      (codon-optimized for Yarrowia lipolytica)

<400> SEQUENCE: 35

```
atg gct ctc tcc ctt act acc gag cag ctg ctc gag cga ccc gac ctg      48
Met Ala Leu Ser Leu Thr Thr Glu Gln Leu Leu Glu Arg Pro Asp Leu
1               5                   10                  15 gtt gcc atc gac ggc att ctc tac gat ctg gaa ggt ctt gcc aag gtc      96
```

```
                Val Ala Ile Asp Gly Ile Leu Tyr Asp Leu Glu Gly Leu Ala Lys Val
                                20                  25                  30 cat ccc gga tcc gac ttg atc ctc gct tct ggt gcc tcc gat gct tct         144
His Pro Gly Ser Asp Leu Ile Leu Ala Ser Gly Ala Ser Asp Ala Ser
            35                  40                  45 cct ctg ttc tac tcc atg cac cct tac gtc aag ccc gag aac tcg aag         192
Pro Leu Phe Tyr Ser Met His Pro Tyr Val Lys Pro Glu Asn Ser Lys
    50                  55                  60 ctg ctt caa cag ttc gtg cga ggc aag cac gac cga acc tcc aag gac         240
Leu Leu Gln Gln Phe Val Arg Gly Lys His Asp Arg Thr Ser Lys Asp
65                  70                  75                  80 att gtc tac acc tac gac tct ccc ttt gca cag gac gtc aag cga act         288
Ile Val Tyr Thr Tyr Asp Ser Pro Phe Ala Gln Asp Val Lys Arg Thr
                85                  90                  95 atg cga gag gtc atg aaa ggt cgg aac tgg tat gcc aca cct gga ttc         336
Met Arg Glu Val Met Lys Gly Arg Asn Trp Tyr Ala Thr Pro Gly Phe
            100                 105                 110 tgg ctg cga acc gtt ggc atc att gct gtc acc gcc ttt tgc gag tgg         384
Trp Leu Arg Thr Val Gly Ile Ile Ala Val Thr Ala Phe Cys Glu Trp
    115                 120                 125 cac tgg gct act acc gga atg gtg ctg tgg ggt ctc ttg act gga ttc         432
His Trp Ala Thr Thr Gly Met Val Leu Trp Gly Leu Leu Thr Gly Phe
130                 135                 140 atg cac atg cag atc ggc ctg tcc att cag cac gat gcc tct cat ggt         480
Met His Met Gln Ile Gly Leu Ser Ile Gln His Asp Ala Ser His Gly
145                 150                 155                 160 gcc atc agc aaa aag ccc tgg gtc aac gct ctc ttt gcc tac ggc atc         528
Ala Ile Ser Lys Lys Pro Trp Val Asn Ala Leu Phe Ala Tyr Gly Ile
                165                 170                 175 gac gtc att gga tcg tcc aga tgg atc tgg ctg cag tct cac atc atg         576
Asp Val Ile Gly Ser Ser Arg Trp Ile Trp Leu Gln Ser His Ile Met
            180                 185                 190 cga cat cac acc tac acc aat cag cat ggt ctc gac ctg gat gcc gag         624
Arg His His Thr Tyr Thr Asn Gln His Gly Leu Asp Leu Asp Ala Glu
    195                 200                 205 tcc gca gaa cca ttc ctt gtg ttc cac aac tac cct gct gcc aac act         672
Ser Ala Glu Pro Phe Leu Val Phe His Asn Tyr Pro Ala Ala Asn Thr
210                 215                 220 gct cga aag tgg ttt cac cga ttc cag gcc tgg tac atg tac ctc gtg         720
Ala Arg Lys Trp Phe His Arg Phe Gln Ala Trp Tyr Met Tyr Leu Val
225                 230                 235                 240 ctt gga gcc tac ggc gtt tcg ctg gtg tac aac cct ctc tac atc ttc         768
Leu Gly Ala Tyr Gly Val Ser Leu Val Tyr Asn Pro Leu Tyr Ile Phe
                245                 250                 255 cga atg cag cac aac gac acc att ccc gag tct gtc aca gcc atg cga         816
Arg Met Gln His Asn Asp Thr Ile Pro Glu Ser Val Thr Ala Met Arg
            260                 265                 270 gag aac ggc ttt ctg cga cgg tac cga acc ctt gca ttc gtt atg cga         864
Glu Asn Gly Phe Leu Arg Arg Tyr Arg Thr Leu Ala Phe Val Met Arg
    275                 280                 285 gct ttc ttc atc ttt cga acc gcc ttc ctg ccc tgg tat ctc act gga         912
Ala Phe Phe Ile Phe Arg Thr Ala Phe Leu Pro Trp Tyr Leu Thr Gly
290                 295                 300 acc tcc ctg ctc atc acc att cct ctg gtg ccc act gct acc ggt gcc         960
Thr Ser Leu Leu Ile Thr Ile Pro Leu Val Pro Thr Ala Thr Gly Ala
305                 310                 315                 320 ttc ctc acc ttc ttt ttc atc ttg tct cac aac ttc gat ggc tcg gag         1008
Phe Leu Thr Phe Phe Phe Ile Leu Ser His Asn Phe Asp Gly Ser Glu
                325                 330                 335
```

```
cga atc ccc gac aag aac tgc aag gtc aag agc tcc gag aag gac gtt    1056
Arg Ile Pro Asp Lys Asn Cys Lys Val Lys Ser Ser Glu Lys Asp Val
            340                 345                 350 gaa gcc gat cag atc gac tgg tac aga gct cag gtg gag acc tct tcc    1104
Glu Ala Asp Gln Ile Asp Trp Tyr Arg Ala Gln Val Glu Thr Ser Ser
        355                 360                 365 acc tac ggt gga ccc att gcc atg ttc ttt act ggc ggt ctc aac ttc    1152
Thr Tyr Gly Gly Pro Ile Ala Met Phe Phe Thr Gly Gly Leu Asn Phe
    370                 375                 380 cag atc gag cat cac ctc ttt cct cga atg tcg tct tgg cac tat ccc    1200
Gln Ile Glu His His Leu Phe Pro Arg Met Ser Ser Trp His Tyr Pro
385                 390                 395                 400 ttc gtg cag caa gct gtc cga gag tgt tgc gaa cga cac gga gtt cgg    1248
Phe Val Gln Gln Ala Val Arg Glu Cys Cys Glu Arg His Gly Val Arg
                405                 410                 415 tac gtc ttc tac cct acc att gtg ggc aac atc att tcc acc ctc aag    1296
Tyr Val Phe Tyr Pro Thr Ile Val Gly Asn Ile Ile Ser Thr Leu Lys
            420                 425                 430 tac atg cac aaa gtc ggt gtg gtt cac tgt gtc aag gac gct cag gat    1344
Tyr Met His Lys Val Gly Val Val His Cys Val Lys Asp Ala Gln Asp
        435                 440                 445 tcc taa                                                             1350
Ser

<210> SEQ ID NO 36
<211> LENGTH: 449
<212> TYPE: PRT
<213> ORGANISM: Euglena gracilis

<400> SEQUENCE: 36

Met Ala Leu Ser Leu Thr Thr Glu Gln Leu Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Ser Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
        115                 120                 125

His Trp Ala Thr Thr Gly Met Val Leu Trp Gly Leu Leu Thr Gly Phe
    130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
```

```
        210                 215                 220
Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
                260                 265                 270

Glu Asn Gly Phe Leu Arg Arg Tyr Arg Thr Leu Ala Phe Val Met Arg
                275                 280                 285

Ala Phe Phe Ile Phe Arg Thr Ala Phe Leu Pro Trp Tyr Leu Thr Gly
290                 295                 300

Thr Ser Leu Leu Ile Thr Ile Pro Leu Val Pro Thr Ala Thr Gly Ala
305                 310                 315                 320

Phe Leu Thr Phe Phe Ile Leu Ser His Asn Phe Asp Gly Ser Glu
                325                 330                 335

Arg Ile Pro Asp Lys Asn Cys Lys Val Lys Ser Ser Glu Lys Asp Val
                340                 345                 350

Glu Ala Asp Gln Ile Asp Trp Tyr Arg Ala Gln Val Glu Thr Ser Ser
                355                 360                 365

Thr Tyr Gly Gly Pro Ile Ala Met Phe Phe Thr Gly Leu Asn Phe
                370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg
                405                 410                 415

Tyr Val Phe Tyr Pro Thr Ile Val Gly Asn Ile Ile Ser Thr Leu Lys
                420                 425                 430

Tyr Met His Lys Val Gly Val Val His Cys Val Lys Asp Ala Gln Asp
                435                 440                 445

Ser

<210> SEQ ID NO 37
<211> LENGTH: 1365
<212> TYPE: DNA
<213> ORGANISM: Euglena anabaena UTEX 373
<220> FEATURE:
<221> NAME/KEY: CDS
<222> LOCATION: (1)..(1365)
<223> OTHER INFORMATION: synthetic mutant delta-5 desaturase
      (codon-optimized for Yarrowia lipolytica)

<400> SEQUENCE: 37 atg gcc acc atc tcc ctg act acc gag cag ctc ctg gaa cac ccc gag      48
Met Ala Thr Ile Ser Leu Thr Thr Glu Gln Leu Leu Glu His Pro Glu
1               5                   10                  15 ctc gtt gcc atc gac gga gtc ctg tac gat ctc ttc ggt ctg gcc aag      96
Leu Val Ala Ile Asp Gly Val Leu Tyr Asp Leu Phe Gly Leu Ala Lys
            20                  25                  30 gtc cat gcc gga ggc aac ctc atc gaa gct gcc ggt gca tcc gac gga     144
Val His Ala Gly Gly Asn Leu Ile Glu Ala Ala Gly Ala Ser Asp Gly
        35                  40                  45 acc gct ctg ttc tac tcc atg cat cct gga gtc aag cca gag aac tcg     192
Thr Ala Leu Phe Tyr Ser Met His Pro Gly Val Lys Pro Glu Asn Ser
    50                  55                  60 aag ctt ctg cag caa ttt gcc cga ggc aag cac gaa cga agc tcc aag     240
Lys Leu Leu Gln Gln Phe Ala Arg Gly Lys His Glu Arg Ser Ser Lys
65                  70                  75                  80
```

```
gat ccc gtg tac acc ttc gac tct ccc ttt gct cag gac gtc aag cag      288
Asp Pro Val Tyr Thr Phe Asp Ser Pro Phe Ala Gln Asp Val Lys Gln
            85                  90                  95 tcc gtt cga gag gtc atg aag ggt cga aac tgg tac gcc act cct ggc      336
Ser Val Arg Glu Val Met Lys Gly Arg Asn Trp Tyr Ala Thr Pro Gly
        100                 105                 110 ttc tgg ctg aga acc gca ctc atc atc gct tgt act gcc att ggc gag      384
Phe Trp Leu Arg Thr Ala Leu Ile Ile Ala Cys Thr Ala Ile Gly Glu
        115                 120                 125 tgg tac tgg atc aca acc gga gca gtg atg tgg ggt atc ttt act gga      432
Trp Tyr Trp Ile Thr Thr Gly Ala Val Met Trp Gly Ile Phe Thr Gly
    130                 135                 140 tac ttc cac tcg cag att ggc ttg gcc att caa cac gat gct tct cac      480
Tyr Phe His Ser Gln Ile Gly Leu Ala Ile Gln His Asp Ala Ser His
145                 150                 155                 160 gga gcc atc agc aaa aag ccc tgg gtc aac gcc ttt ttc gct tat ggc      528
Gly Ala Ile Ser Lys Lys Pro Trp Val Asn Ala Phe Phe Ala Tyr Gly
            165                 170                 175 atc gac gcc att ggt tcc tct cgt tgg atc tgg ctg cag tcc cac att      576
Ile Asp Ala Ile Gly Ser Ser Arg Trp Ile Trp Leu Gln Ser His Ile
        180                 185                 190 atg cga cat cac act tac acc aac cag cat ggc ctc gac ctg gat gct      624
Met Arg His His Thr Tyr Thr Asn Gln His Gly Leu Asp Leu Asp Ala
        195                 200                 205 gcc tcg gca gag ccg ttc atc ttg ttc cac tcc tat cct gct acc aac      672
Ala Ser Ala Glu Pro Phe Ile Leu Phe His Ser Tyr Pro Ala Thr Asn
    210                 215                 220 gcc tct cga aag tgg tac cac cga ttt cag gcg tgg tac atg tac atc      720
Ala Ser Arg Lys Trp Tyr His Arg Phe Gln Ala Trp Tyr Met Tyr Ile
225                 230                 235                 240 gtt ctg gga atg tat ggt gtc tcg atg gtg tac aat ccc atg tac ctc      768
Val Leu Gly Met Tyr Gly Val Ser Met Val Tyr Asn Pro Met Tyr Leu
            245                 250                 255 ttc aca atg cag cac aac gac acc att ccc gag gcc act tct ctc aga      816
Phe Thr Met Gln His Asn Asp Thr Ile Pro Glu Ala Thr Ser Leu Arg
        260                 265                 270 cca ggc agc ttt ttc aat cgg cag cga gct ttc gcc gtt tcc ctt cga      864
Pro Gly Ser Phe Phe Asn Arg Gln Arg Ala Phe Ala Val Ser Leu Arg
        275                 280                 285 ctg ctc ttc atc ttc cga aac gcc ttt ctt ccc tgg tac att gct ggt      912
Leu Leu Phe Ile Phe Arg Asn Ala Phe Leu Pro Trp Tyr Ile Ala Gly
    290                 295                 300 gcc tct cct ctg ctc acc att ctt ctg gtg ccc acg gtc aca ggc atc      960
Ala Ser Pro Leu Leu Thr Ile Leu Leu Val Pro Thr Val Thr Gly Ile
305                 310                 315                 320 ttc ctc acc ttt gtg ttc gtt ctg tcc cat aac ttc gag gga gcc gaa     1008
Phe Leu Thr Phe Val Phe Val Leu Ser His Asn Phe Glu Gly Ala Glu
            325                 330                 335 cgg acc cca gag aag aac tgc aag gcc aaa cga gct aag gaa ggc aag     1056
Arg Thr Pro Glu Lys Asn Cys Lys Ala Lys Arg Ala Lys Glu Gly Lys
        340                 345                 350 gag gtc aga gac gtg gaa gag gat cga gtc gac tgg tac cga gca cag     1104
Glu Val Arg Asp Val Glu Glu Asp Arg Val Asp Trp Tyr Arg Ala Gln
        355                 360                 365 gcc gag act gct gcc acc tac ggt ggc agc gtg gga atg atg ctt aca     1152
Ala Glu Thr Ala Ala Thr Tyr Gly Gly Ser Val Gly Met Met Leu Thr
    370                 375                 380 ggc ggt ctc aac ctg cag atc gag cat cac ttg ttt ccc cga atg tcc     1200
Gly Gly Leu Asn Leu Gln Ile Glu His His Leu Phe Pro Arg Met Ser
385                 390                 395                 400
```

```
tct tgg cac tat ccc ttc att caa gac acc gtt cgg gag tgt tgc aag    1248
Ser Trp His Tyr Pro Phe Ile Gln Asp Thr Val Arg Glu Cys Cys Lys
            405                 410                 415 cga cat ggc gtc cgt tac aca tac tat cct acc att ctc gag aac atc    1296
Arg His Gly Val Arg Tyr Thr Tyr Tyr Pro Thr Ile Leu Glu Asn Ile
        420                 425                 430 atg tcc act ctt cga tac atg cag aag gtg ggt gtt gct cac acc att    1344
Met Ser Thr Leu Arg Tyr Met Gln Lys Val Gly Val Ala His Thr Ile
    435                 440                 445 cag gat gcc cag gag ttc taa                                        1365
Gln Asp Ala Gln Glu Phe
    450
```

<210> SEQ ID NO 38
<211> LENGTH: 454
<212> TYPE: PRT
<213> ORGANISM: Euglena anabaena UTEX 373

<400> SEQUENCE: 38

```
Met Ala Thr Ile Ser Leu Thr Thr Glu Gln Leu Leu Glu His Pro Glu
1               5                   10                  15

Leu Val Ala Ile Asp Gly Val Leu Tyr Asp Leu Phe Gly Leu Ala Lys
            20                  25                  30

Val His Ala Gly Gly Asn Leu Ile Glu Ala Ala Gly Ala Ser Asp Gly
        35                  40                  45

Thr Ala Leu Phe Tyr Ser Met His Pro Gly Val Lys Pro Glu Asn Ser
    50                  55                  60

Lys Leu Leu Gln Gln Phe Ala Arg Gly Lys His Glu Arg Ser Ser Lys
65                  70                  75                  80

Asp Pro Val Tyr Thr Phe Asp Ser Pro Phe Ala Gln Asp Val Lys Gln
                85                  90                  95

Ser Val Arg Glu Val Met Lys Gly Arg Asn Trp Tyr Ala Thr Pro Gly
            100                 105                 110

Phe Trp Leu Arg Thr Ala Leu Ile Ile Ala Cys Thr Ala Ile Gly Glu
        115                 120                 125

Trp Tyr Trp Ile Thr Thr Gly Ala Val Met Trp Gly Ile Phe Thr Gly
    130                 135                 140

Tyr Phe His Ser Gln Ile Gly Leu Ala Ile Gln His Asp Ala Ser His
145                 150                 155                 160

Gly Ala Ile Ser Lys Lys Pro Trp Val Asn Ala Phe Ala Tyr Gly
                165                 170                 175

Ile Asp Ala Ile Gly Ser Ser Arg Trp Ile Trp Leu Gln Ser His Ile
            180                 185                 190

Met Arg His His Thr Tyr Thr Asn Gln His Gly Leu Asp Leu Asp Ala
        195                 200                 205

Ala Ser Ala Glu Pro Phe Ile Leu Phe His Ser Tyr Pro Ala Thr Asn
    210                 215                 220

Ala Ser Arg Lys Trp Tyr His Arg Phe Gln Ala Trp Tyr Met Tyr Ile
225                 230                 235                 240

Val Leu Gly Met Tyr Gly Val Ser Met Val Tyr Asn Pro Met Tyr Leu
                245                 250                 255

Phe Thr Met Gln His Asn Asp Thr Ile Pro Glu Ala Thr Ser Leu Arg
            260                 265                 270

Pro Gly Ser Phe Phe Asn Arg Gln Arg Ala Phe Ala Val Ser Leu Arg
        275                 280                 285
```

```
Leu Leu Phe Ile Phe Arg Asn Ala Phe Leu Pro Trp Tyr Ile Ala Gly
    290                 295                 300
Ala Ser Pro Leu Leu Thr Ile Leu Leu Val Pro Thr Val Thr Gly Ile
305                 310                 315                 320
Phe Leu Thr Phe Val Phe Val Leu Ser His Asn Phe Glu Gly Ala Glu
                325                 330                 335
Arg Thr Pro Glu Lys Asn Cys Lys Ala Lys Arg Ala Lys Glu Gly Lys
            340                 345                 350
Glu Val Arg Asp Val Glu Asp Arg Val Asp Trp Tyr Arg Ala Gln
        355                 360                 365
Ala Glu Thr Ala Ala Thr Tyr Gly Gly Ser Val Gly Met Met Leu Thr
370                 375                 380
Gly Gly Leu Asn Leu Gln Ile Glu His His Leu Phe Pro Arg Met Ser
385                 390                 395                 400
Ser Trp His Tyr Pro Phe Ile Gln Asp Thr Val Arg Glu Cys Cys Lys
                405                 410                 415
Arg His Gly Val Arg Tyr Thr Tyr Tyr Pro Thr Ile Leu Glu Asn Ile
            420                 425                 430
Met Ser Thr Leu Arg Tyr Met Gln Lys Val Gly Val Ala His Thr Ile
        435                 440                 445
Gln Asp Ala Gln Glu Phe
    450
```

<210> SEQ ID NO 39
<211> LENGTH: 13066
<212> TYPE: DNA
<213> ORGANISM: Artificial Sequence
<220> FEATURE:
<223> OTHER INFORMATION: Plasmid pZP3-Pa777U

<400> SEQUENCE: 39

```
tctcggtcta ttcttttgat ttataaggga ttttgccgat ttcggcctat tggttaaaaa     60
atgagctgat ttaacaaaaa tttaacgcga attttaacaa aatattaacg cttacaattt    120
cctgatgcgg tattttctcc ttacgcatct gtgcggtatt tcacaccgca tcaggtggca    180
cttttcgggg aaatgtgcgc ggaacccta tttgttatt tttctaaata cattcaaata    240
tgtatccgct catgagacaa taaccctgat aaatgcttca ataatattga aaaggaaga    300
gtatgagtat tcaacatttc cgtgtcgccc ttattccctt ttttgcggca ttttgccttc    360
ctgtttttgc tcacccagaa acgctggtga agtaaaaga tgctgaagat cagttgggtg    420
cacgagtggg ttacatcgaa ctggatctca acagcggtaa gatccttgag agttttcgcc    480
ccgaagaacg ttttccaatg atgagcactt taaagttct gctatgtggc gcggtattat    540
cccgtattga cgccgggcaa gagcaactcg gtcgccgcat acactattct cagaatgact    600
tggttgagta ctcaccagtc acagaaaagc atcttacgga tggcatgaca gtaagagaat    660
tatgcagtgc tgccataacc atgagtgata acactgcggc caacttactt ctgacaacga    720
tcggaggacc gaaggagcta accgcttttt tgcacaacat ggggatcat gtaactcgcc    780
ttgatcgttg ggaaccggag ctgaatgaag ccataccaaa cgacgagcgt gacaccacga    840
tgcctgtagc aatggcaaca acgttgcgca aactattaac tggcgaacta cttactctag    900
cttcccggca acaattaata gactggatgg aggcggataa agttgcagga ccacttctgc    960
gctcggccct tccggctggc tggtttattg ctgataaatc tggagccggt gagcgtgggt   1020
ctcgcggtat cattgcagca ctggggccag atggtaagcc ctcccgtatc gtagttatct   1080
```

```
acacgacggg gagtcaggca actatggatg aacgaaatag acagatcgct gagataggtg   1140
cctcactgat taagcattgg taactgtcag accaagttta ctcatatata ctttagattg   1200
atttaaaact tcatttttaa tttaaaagga tctaggtgaa gatcctttt gataatctca   1260 tgaccaaaat cccttaacgt gagttttcgt tccactgagc gtcagacccc gtagaaaaga   1320
tcaaaggatc ttcttgagat cctttttttc tgcgcgtaat ctgctgcttg caaacaaaaa   1380
aaccaccgct accagcggtg gtttgtttgc cggatcaaga gctaccaact cttttccga   1440 aggtaactgg cttcagcaga gcgcagatac caaatactgt tcttctagtg tagccgtagt   1500
taggccacca cttcaagaac tctgtagcac cgcctacata cctcgctctg ctaatcctgt   1560
taccagtggc tgctgccagt ggcgataagt cgtgtcttac cgggttggac tcaagacgat   1620
agttaccgga taaggcgcag cggtcgggct gaacggggg ttcgtgcaca cagcccagct   1680
tggagcgaac gacctacacc gaactgagat acctacagcg tgagctatga gaaagcgcca   1740
cgcttcccga agggagaaag gcggacaggt atccggtaag cggcagggtc ggaacaggag   1800
agcgcacgag ggagcttcca gggggaaacg cctggtatct ttatagtcct gtcgggtttc   1860
gccacctctg acttgagcgt cgatttttgt gatgctcgtc agggggggcgg agcctatgga   1920 aaaacgccag caacgcggcc ttttacggtt cctggcctt ttgctggcct tttgctcaca   1980
tgttctttcc tgcgttatcc cctgattctg tggataaccg tattaccgcc tttgagtgag   2040
ctgataccgc tcgccgcagc cgaacgaccg agcgcagcga gtcagtgagc gaggaagcgg   2100
aagagcgccc aatacgcaaa ccgcctctcc ccgcgcgttg gccgattcat taatgcagct   2160
ggcgcgccca caatcacaat tctgaaaagc acatcttgat ctcctcattg cggggagtcc   2220
aacggtggtc ttattccccc gaatttcccg ctcaatctcg ttccagaccg acccggacac   2280
agtgcttaac gccgttccga aactctaccg cagatatgct ccaacggact gggctgcata   2340
gatgtgatcc tcggcttgga gaaatggata aaagccggcc aaaaaaaaag cggaaaaaag   2400
cggaaaaaaa gagaaaaaaa atcgcaaaat ttgaaaaata ggggaaaag acgcaaaaac   2460 gcaaggaggg gggagtatat gacactgata agcaagctca caacggttcc tcttattttt   2520
ttcctcatct tctgcctagg ttcccaaaat cccagatgct tctctccagt gccaaaagta   2580
agtaccccac aggttttcgg ccgaaaattc cacgtgcagc aacgtcgtgt ggggtgttaa   2640
aatgtggggg gggggaacca ggacaagagg ctcttgtggg agccgaatga gagcacaaag   2700
cgggcgggtg tgataagggc attttttgccc attttcccctt ctcctgtctc tccgacggtg   2760
atggcgttgt gcgtcctcta ttttcttttta ttttcttttttg ttttattttct ctgactaccg   2820 atttggtttg atttcctcaa ccccacacaa ataagctcgg gccgaggaat atatatatac   2880
acggacacag tcgccctgtg gacaacacgt cactacctct acgatacaca ccgtacgttg   2940
tgtggaagct tgtgagcgga taacaatttc acacaggaaa cagctatgac catgattacg   3000
ccaagctcga aattaaccct cactaaaggg aacaaaagct ggagctccac cgcggacaca   3060
atatctggtc aaatttcagt ttcgttacat ttaaattcct tcacttcaag ttcattcttc   3120
atctgcttct gttttacttt gacaggcaaa tgaagacatg gtacgacttg atggaggcca   3180
agaacgccat tcaccccgga gacaccgaag tgcctgaaat cctggctgcc ccattgata   3240 acatcggaaa ctacggtatt ccggaaagtg tatatagaac ctttccccag cttgtgtctg   3300
tggatatgga tggtgtaatc ccctttgagt actcgtcttg gcttctctcc gagcagtatg   3360
aggctctcta atctagcgca tttaatatct caatgtatt atatattat cttctcatgc   3420 ggccgcttag ttggctttgg tcttggcagc cttggcctcc ttgagggtaa acatcttggc   3480
```

```
atccttgtcg accacgccgt acttggcgta cataagacca attcggatga aggtgggaat    3540
gatgggagaa gccgactttc gcaccagttc gggaaaggcc tgagcgaagg cagcagtggc    3600
ctcgttgagc ttgtagtgag gaatgatggg aaacagatgg tggatctgat gtgtaccaat    3660
gttgtgggac aggttgtcga tgagggctcc gtagcttcgg tccacagagg acaagttgcc    3720
cttgacatag gtccactccg aatcggcgta ccagggagtt tcctcgtcgt tgtgatggag    3780
gaaggtagtg acaaccagca tggtggcgaa tccaaagaga ggtgcgaagt aatacagagc    3840
catggtcttg aggccgtaga cgtaggtaag gtaggcgtac agaccagcaa aggccacgag    3900
agagccgagg gaaatgatga cggcagacat tcttcgcagg tagagaggct cccagggatt    3960
gaagtggttg acctttcggg gaggaaatcc agcaacgagg taggcaaacc aagccgaacc    4020
aagggagatg accatgtgtc gggacagggg atgagagtcg gcttctcgct gagggtagaa    4080
gatctcatcc ttgtcgatgt tgccggtgtt cttgtgatgg tgtcgatggc tgatcttcca    4140
cgactcgtag ggagtcagaa tgatggagtg aatgagtgtg ccaacagaga agttgagcag    4200
gtgggatcgc gagaaggcac catgtccaca gtcgtgaccg atggtaaaga atccccagaa    4260
cacgataccc tggagcagaa tgtagccagt gcaaaggacg gcatcgagca gtgcaaactc    4320
ctgcacgata gcaagggctc gagcatagta cagtccgaga gcaagggaac cggcaatgcc    4380
cagagctcgc acggtatagt agagggacca gggaacagag gcttcgaagc agtgggcagg    4440
cagggatcgc ttgatctcgg tgagagtagg gaactcgtag ggagcggcaa cggtagagga    4500
agccatggtt gtgaattagg gtggtgagaa tggttggttg tagggaagaa tcaaaggccg    4560
gtctcgggat ccgtgggtat atatatatat atatatatat acgatccttc gttacctccc    4620
tgttctcaaa actgtggttt ttcgtttttc gttttttgct ttttttgatt tttttagggc    4680
caactaagct tccagatttc gctaatcacc tttgtactaa ttacaagaaa ggaagaagct    4740
gattagagtt gggcttttta tgcaactgtg ctactcctta tctctgatat gaaagtgtag    4800
acccaatcac atcatgtcat ttagagttgg taatactggg aggatagata aggcacgaaa    4860
acgagccata gcagacatgc tgggtgtagc caagcagaag aaagtagatg ggagccaatt    4920
gacgagcgag ggagctacgc caatccgaca tacgacacgc tgagatcgtc ttggccgggg    4980
ggtacctaca gatgtccaag ggtaagtgct tgactgtaat tgtatgtctg aggacaaata    5040
tgtagtcagc cgtataaagt cataccaggc accagtgcca tcatcgaacc actaactctc    5100
tatgatacat gcctccggta ttattgtacc atgcgtcgct tgttacata cgtatcttgc     5160 cttttctct cagaaactcc agactttggc tattggtcga gataagcccg gaccatagtg    5220
agtctttcac actctacatt tctcccttgc tccaactatc gattgttgtc tactaactat    5280
cgtacgataa cttcgtatag catacattat acgaagttat cgcgtcgacg agtatctgtc    5340
tgactcgtca ttgccgcctt tggagtacga ctccaactat gagtgtgctt ggatcacttt    5400
gacgatacat tcttcgttgg aggctgtggg tctgacagct gcgttttcgg cgcggttggc    5460
cgacaacaat atcagctgca acgtcattgc tggctttcat catgatcaca ttttttgtcgg   5520 caaaggcgac gcccagagag ccattgacgt tctttctaat ttggaccgat agccgtatag    5580
tccagtctat ctataagttc aactaactcg taactattac cataacatat acttcactgc    5640
cccagataag gttccgataa aaagttctgc agactaaatt tatttcagtc tcctcttcac    5700
caccaaaatg ccctcctacg aagctcgagc taacgtccac aagtccgcct ttgccgctcg    5760
agtgctcaag ctcgtggcag ccaagaaaac caacctgtgt gcttctctgg atgttaccac    5820
```

```
caccaaggag ctcattgagc ttgccgataa ggtcggacct tatgtgtgca tgatcaaaac   5880
ccatatcgac atcattgacg acttcaccta cgccggcact gtgctccccc tcaaggaact   5940
tgctcttaag cacggtttct tcctgttcga ggacagaaag ttcgcagata ttggcaacac   6000
tgtcaagcac cagtaccggt gtcaccgaat cgccgagtgg tccgatatca ccaacgccca   6060
cggtgtaccc ggaaccggaa tcattgctgg cctgcgagct ggtgccgagg aaactgtctc   6120
tgaacagaag aaggaggacg tctctgacta cgagaactcc cagtacaagg agttcctagt   6180
cccctctccc aacgagaagc tggccagagg tctgctcatg ctggccgagc tgtcttgcaa   6240
gggctctctg ccactggcg agtactccaa gcagaccatt gagcttgccc gatccgaccc   6300
cgagtttgtg gttggcttca ttgcccagaa ccgacctaag ggcgactctg aggactggct   6360
tattctgacc cccggggtgg gtcttgacga caagggagac gctctcggac agcagtaccg   6420
aactgttgag gatgtcatgt ctaccggaac ggatatcata attgtcggcc gaggtctgta   6480
cggccagaac cgagatccta ttgaggaggc caagcgatac cagaaggctg ctgggaggc   6540 ttaccagaag attaactgtt agaggttaga ctatggatat gtaatttaac tgtgtatata   6600
gagagcgtgc aagtatggag cgcttgttca gcttgtatga tggtcagacg acctgtctga   6660
tcgagtatgt atgatactgc acaacctgtg tatccgcatg atctgtccaa tggggcatgt   6720
tgttgtgttt ctcgatacgg agatgctggg tacagtgcta atacgttgaa ctacttatac   6780
ttatatgagg ctcgaagaaa gctgacttgt gtatgactta ttctcaacta catccccagt   6840
cacaatacca ccactgcact accactacac caaaaccatg atcaaaccac ccatggactt   6900
cctggaggca gaagaacttg ttatggaaaa gctcaagaga gagatcataa cttcgtatag   6960
catacattat acgaagttat cctgcaggta aaggaattca tgctgttcat cgtggttaat   7020
gctgctgtgt gctgtgtgtg tgtgttgttt ggcgctcatt gttgcgttat gcagcgtaca   7080
ccacaatatt ggaagcttat tagccttttct atttttttcgt ttgcaaggct taacaacatt   7140
gctgtggaga gggatgggga tatggaggcc gctggaggga gtcggagagg cgttttggag   7200
cggcttggcc tggcgcccag ctcgcgaaac gcacctagga cccttggca cgccgaaatg   7260 tgccactttt cagtctagta acgccttacc tacgtcattc catgcgtgca tgtttgcgcc   7320
ttttttccct tgcccttgat cgccacacag tacagtgcac tgtacagtgg aggttttggg   7380
ggggtcttag atgggagcta aaagcggcct agcggtacac tagtgggatt gtatggagtg   7440
gcatggagcc taggtggagc ctgacaggac gcacgaccgg ctagcccgtg acagacgatg   7500
ggtggctcct gttgtccacc gcgtacaaat gtttgggcca aagtcttgtc agccttgctt   7560
gcgaacctaa ttcccaattt tgtcacttcg cacccccatt gatcgagccc taaccctgc   7620 ccatcaggca atccaattaa gctcgcattg tctgccttgt ttagtttggc tcctgcccgt   7680
ttcggcgtcc acttgcacaa acacaaacaa gcattatata taaggctcgt ctctccctcc   7740
caaccacact cactttttg cccgtcttcc cttgctaaca caaagtcaa gaacacaaac   7800 aaccacccca accccttac acacaagaca tatctacagc aatggccatg gcttcttcca   7860
ctgttgctgc gccgtacgag ttcccgacgc tgacggagat caagcgctcg ctgccagcgc   7920
actgctttga ggcctcggtc ccgtggtcgc tctactacac cgtgcgcgcg ctgggcatcg   7980
ccggctcgct cgcgctcggc ctctactacg cgcgcgcgct cgcgatcgtg caggagtttg   8040
ccctgctgga tgcggtgctc tgcacggggt acattctgct gcagggcatc gtattctggg   8100
ggttcttcac catcggccat gactgcggcc acggcgcgtt ctcgcgttcg cacctgctca   8160
acttcagcgt cggcacgctc attcactcga tcatcctcac gccgtacgag tcatggaaga   8220
```

```
tctcgcaccg ccaccaccac aagaacacgg gcaacatcga caaggacgag attttctacc    8280
cgcagcgcga ggccgactcg cacccactgt cccgacacat ggtgatctcg ctcggctcgg    8340
cctggttcgc gtacctcgtt gcgggcttcc ctcctcgcaa ggtgaaccac ttcaacccttt   8400 gggaaccgtt gtacctgcgc cgcatgtctg ccgtcatcat ctcactcggc tcgctcgtgg    8460
cgttcgcggg cttgtatgcg tatctcacct acgtctatgg ccttaagacc atggcgctgt    8520
actacttcgc ccctctcttt gggttcgcca cgatgctcgt ggtcactacc tttttgcacc    8580
acaatgacga ggaaacgcca tggtacgccg actcggagtg gacgtacgtc aagggcaacc    8640
tctcgtccgt ggaccgctcg tacgcgcgc tcatcgacaa cctgagccac aacatcggca     8700
cgcaccagat ccaccacctg tttccgatca tcccgcacta caagctgaac gaggcgacgg    8760
cagcgttcgc gcaggcgttc ccggagctcg tgcgcaagag cgcgtcgccg atcatcccga    8820
cgttcatccg catcgggctc atgtacgcca agtacggcgt cgtggacaag gacgccaaga    8880
tgtttacgct caaggaggcc aaggccgcca agaccaaggc caactaggcg gccgcattga    8940
tgattggaaa cacacacatg ggttatatct aggtgagagt tagttggaca gttatatatt    9000
aaatcagcta tgccaacggt aacttcattc atgtcaacga ggaaccagtg actgcaagta    9060
atatagaatt tgaccacctt gccattctct tgcactcctt tactatatct catttatttc    9120
ttatatacaa atcacttctt cttcccagca tcgagctcgg aaacctcatg agcaataaca    9180
tcgtggatct cgtcaataga gggcttttttg gactccttgc tgttggccac cttgtccttg    9240
ctgtttaaac agtgtacgca gatctactat agaggaacat ttaaattgcc ccggagaaga    9300
cggccaggcc gcctagatga caaattcaac aactcacagc tgactttctg ccattgccac    9360
tagggggggg ccttttttata tggccaagcc aagctctcca cgtcggttgg gctgcaccca    9420
acaataaatg ggtagggttg caccaacaaa gggatgggat gggggggtaga agatacgagg    9480 ataacgggcc tcaatggcac aaataagaac gaatactgcc attaagactc gtgatccagc    9540
gactgacacc attgcatcat ctaagggcct caaaactacc tcggaactgc tgcgctgatc    9600
tggacaccac agaggttccg agcactttag gttgcaccaa atgtcccacc aggtgcaggc    9660
agaaaacgct ggaacagcgt gtacagtttg tcttaacaaa aagtgagggc gctgaggtcg    9720
agcagggtgg tgtgacttgt tatagccttt agagctgcga aagcgcgtat ggatttggct    9780
catcaggcca gattgagggt ctgtggacac atgtcatgtt agtgtacttc aatcgccccc    9840
tggatatagc cccgacaata ggccgtggcc tcattttttt gccttccgca catttccatt    9900
gctcggtacc cacaccttgc ttctcctgca cttgccaacc ttaatactgg tttacattga    9960
ccaacatctt acaagcgggg ggcttgtcta gggtatatat aaacagtggc tctcccaatc   10020
ggttgccagt ctctttttttc ctttctttcc ccacagattc gaaatctaaa ctacacatca   10080
cagaattccg agccgtgagt atccacgaca agatcagtgt cgagacgacg cgttttgtgt   10140
aatgacacaa tccgaaagtc gctagcaaca cacactctct acacaaacta acccagctct   10200
ggtaccatgg cttcttccac tgttgctgcg ccgtacgagt tcccgacgct gacggagatc   10260
aagcgctcgc tgccagcgca ctgctttgag gcctcggtcc cgtggtcgct ctactacacc   10320
gtgcgcgcgc tgggcatcgc cggctcgctc gcgctcggcc tctactacgc gcgcgcgctc   10380
gcgatcgtgc aggagtttgc cctgctggat gcggtgctct gcacggggta cattctgctg   10440
cagggcatcg tattctgggg gttcttcacc atcggccatg actgcggcca cggcgcgttc   10500
tcgcgttcgc acctgctcaa cttcagcgtc ggcacgctca ttcactcgat catcctcacg   10560
```

```
ccgtacgagt catggaagat ctcgcaccgc caccaccaca agaacacggg caacatcgac    10620
aaggacgaga ttttctaccc gcagcgcgag gccgactcgc acccactgtc ccgacacatg    10680
gtgatctcgc tcggctcggc ctggttcgcg tacctcgttg cgggcttccc tcctcgcaag    10740
gtgaaccact tcaacccttg ggaaccgttg tacctgcgcc gcatgtctgc cgtcatcatc    10800
tcactcggct cgctcgtggc gttcgcgggc ttgtatgcgt atctcaccta cgtctatggc    10860
cttaagacca tggcgctgta ctacttcgcc cctctctttg ggttcgccac gatgctcgtg    10920
gtcactacct ttttgcacca caatgacgag gaaacgccat ggtacgccga ctcggagtgg    10980
acgtacgtca agggcaacct ctcgtccgtg gaccgctcgt acggcgcgct catcgacaac    11040
ctgagccaca acatcggcac gcaccagatc caccacctgt ttccgatcat cccgcactac    11100
aagctgaacg aggcgacggc agcgttcgcg caggcgttcc cggagctcgt gcgcaagagc    11160
gcgtcgccga tcatcccgac gttcatccgc atcgggctca tgtacgccaa gtacggcgtc    11220
gtggacaagg acgccaagat gtttacgctc aaggaggcca aggccgccaa gaccaaggcc    11280
aactaggcgg ccgcatggag cgtgtgttct gagtcgatgt tttctatgga gttgtgagtg    11340
ttagtagaca tgatgggttt atatatgatg aatgaataga tgtgattttg atttgcacga    11400
tggaattgag aactttgtaa acgtacatgg gaatgtatga atgtggggt tttgtgactg    11460
gataactgac ggtcagtgga cgccgttgtt caaatatcca agagatgcga gaaactttgg    11520
gtcaagtgaa catgtcctct ctgttcaagt aaaccatcaa ctatgggtag tatatttagt    11580
aaggacaaga gttgagattc tttggagtcc tagaaacgta ttttcgcgtt ccaagatcaa    11640
attagtagag taatacgggc acgggaatcc attcatagtc tcaatcctgc aggtgagtta    11700
attaagatga cgacatttgc gagctggacg aggaatagat ggagcgtgtg ttctgagtcg    11760
atgttttcta tggagttgtg agtgttagta gacatgatgg gtttatatat gatgaatgaa    11820
tagatgtgat tttgatttgc acgatggaat tgagaacttt gtaaacgtac atgggaatgt    11880
atgaatgtgg gggttttgtg actggataac tgacggtcag tggacgccgt tgttcaaata    11940
tccaagagat gcgagaaact ttgggtcaag tgaacatgtc ctctctgttc aagtaaacca    12000
tcaactatgg gtagtatatt tagtaaggac aagagttgag attctttgga gtcctagaaa    12060
cgtattttcg cgttccaaga tcaaattagt agagtaatac gggcacggga atccattcat    12120
agtctcaatt tcccataggg tgtgctacaa ggtgttgaga tgtggtacag taccaccatg    12180
attcgaggta aagagcccag aagtcattga tgaggtcaag aaatacacag atctacagct    12240
caatacaatg aatatcttct ttcatattct tcaggtgaca ccaagggtgt ctatttttccc    12300
cagaaatgcg tgaaaaggcg cgtgtgtagc gtggagtatg ggttcggttg gcgtatcctt    12360
catatatcga cgaaatagta gggcaagaga tgacaaaaag tatctatatg tagacagcgt    12420
agaatatgga tttgattggt ataaattcat ttattgcgtg tctcacaaat actctcgata    12480
agttggggtt aaactggaga tggaacaatg tcgatatctc gacgcatgcg acgtcgggcc    12540
caattcgccc tatagtgagt cgtattacaa ttcactggcc gtcgttttac aacgtcgtga    12600
ctgggaaaac cctggcgtta cccaacttaa tcgccttgca gcacatcccc ctttcgccag    12660
ctggcgtaat agcgaagagg cccgcaccga tcgcccttcc caacagttgc gcagcctgaa    12720
tggcgaatgg acgcgccctg tagcggcgca ttaagcgcgg cgggtgtggt ggttacgcgc    12780
agcgtgaccg ctacacttgc cagcgcccta gcgcccgctc ctttcgcttt cttcccttcc    12840
tttctcgcca cgttcgccgg ctttccccgt caagctctaa atcgggggct ccctttaggg    12900
ttccgattta gtgctttacg gcacctcgac cccaaaaaac ttgattaggg tgatggttca    12960
```

```
cgtagtgggc catcgccctg atagacggtt tttcgccctt tgacgttgga gtccacgttc    13020
tttaatagtg gactcttgtt ccaaactgga acaacactca accta                   13066

<210> SEQ ID NO 40
<211> LENGTH: 4313
<212> TYPE: DNA
<213> ORGANISM: Artificial Sequence
<220> FEATURE:
<223> OTHER INFORMATION: Plasmid pZKUM

<400> SEQUENCE: 40
taatcgagct tggcgtaatc atggtcatag ctgtttcctg tgtgaaattg ttatccgctc      60
acaattccac acaacatacg agccggaagc ataaagtgta aagcctgggg tgcctaatga     120
gtgagctaac tcacattaat tgcgttgcgc tcactgcccg ctttccagtc gggaaacctg     180
tcgtgccagc tgcattaatg aatcggccaa cgcgcgggga gaggcggttt gcgtattggg     240
cgctcttccg cttcctcgct cactgactcg ctgcgctcgg tcgttcggct gcggcgagcg     300
gtatcagctc actcaaaggc ggtaatacgg ttatccacag aatcagggga taacgcagga     360
aagaacatgt gagcaaaagg ccagcaaaag gccaggaacc gtaaaaaggc cgcgttgctg     420 gcgttttttcc ataggctccg ccccctgac gagcatcaca aaaatcgacg ctcaagtcag     480
aggtggcgaa acccgacagg actataaaga taccaggcgt ttccccctgg aagctccctc     540
gtgcgctctc ctgttccgac cctgccgctt accggatacc tgtccgcctt tctcccttcg     600
ggaagcgtgg cgctttctca tagctcacgc tgtaggtatc tcagttcggt gtaggtcgtt     660
cgctccaagc tgggctgtgt gcacgaaccc cccgttcagc ccgaccgctg cgccttatcc     720
ggtaactatc gtcttgagtc aacccggta agacacgact tatcgccact ggcagcagcc     780
actggtaaca ggattagcag agcgaggtat gtaggcggtg ctacagagtt cttgaagtgg     840
tggcctaact acggctacac tagaaggaca gtatttggta tctgcgctct gctgaagcca     900
gttaccttcg gaaaaagagt tggtagctct tgatccggca acaaaccac cgctggtagc     960 ggtggttttt ttgtttgcaa gcagcagatt acgcgcagaa aaaaaggatc tcaagaagat    1020
cctttgatct tttctacggg gtctgacgct cagtggaacg aaaactcacg ttaagggatt    1080
ttggtcatga gattatcaaa aaggatcttc acctagatcc ttttaaatta aaaatgaagt    1140
tttaaatcaa tctaaagtat atatgagtaa acttggtctg acagttacca atgcttaatc    1200
agtgaggcac ctatctcagc gatctgtcta tttcgttcat ccatagttgc ctgactcccc    1260
gtcgtgtaga taactacgat acgggagggc ttaccatctg gccccagtgc tgcaatgata    1320
ccgcgagacc cacgctcacc ggctccagat ttatcagcaa taaaccagcc agccggaagg    1380
gccgagcgca gaagtggtcc tgcaacttta tccgcctcca tccagtctat taattgttgc    1440
cgggaagcta gagtaagtag ttcgccagtt aatagtttgc gcaacgttgt tgccattgct    1500
acaggcatcg tggtgtcacg ctcgtcgttt ggtatggctt cattcagctc cggttcccaa    1560
cgatcaaggc gagttacatg atcccccatg ttgtgcaaaa aagcggttag ctccttcggt    1620
cctccgatcg ttgtcagaag taagttggcc gcagtgttat cactcatggt tatggcagca    1680
ctgcataatt ctcttactgt catgccatcc gtaagatgct tttctgtgac tggtgagtac    1740
tcaaccaagt cattctgaga atagtgtatg cggcgaccga gttgctcttg cccggcgtca    1800
atacgggata taccgcgcc acatagcaga actttaaaag tgctcatcat tggaaaacgt    1860
tcttcggggc gaaaactctc aaggatctta ccgctgttga gatccagttc gatgtaaccc    1920
```

```
actcgtgcac ccaactgatc ttcagcatct tttactttca ccagcgtttc tgggtgagca    1980
aaaacaggaa ggcaaaatgc cgcaaaaaag ggaataaggg cgacacgaaa atgttgaata    2040
ctcatactct tcctttttca atattattga agcatttatc agggttattg tctcatgagc    2100
ggatacatat ttgaatgtat ttagaaaaat aaacaaatag gggttccgcg cacatttccc    2160
cgaaaagtgc cacctgacgc gccctgtagc ggcgcattaa gcgcggcggg tgtggtggtt    2220
acgcgcagcg tgaccgctac acttgccagc gccctagcgc ccgctccttt cgctttcttc    2280
ccttcctttc tcgccacgtt cgccggcttt ccccgtcaag ctctaaatcg ggggctccct    2340
ttagggttcc gatttagtgc tttacggcac ctcgacccca aaaaacttga ttagggtgat    2400
ggttcacgta gtgggccatc gccctgatag acggtttttc gccctttgac gttggagtcc    2460
acgttcttta atagtggact cttgttccaa actggaacaa cactcaaccc tatctcggtc    2520
tattcttttg atttataagg gattttgccg atttcggcct attggttaaa aaatgagctg    2580
atttaacaaa aatttaacgc gaattttaac aaaatattaa cgcttacaat ttccattcgc    2640
cattcaggct gcgcaactgt tgggaagggc gatcggtgcg ggcctcttcg ctattacgcc    2700
agctggcgaa aggggatgt gctgcaaggc gattaagttg ggtaacgcca gggttttccc    2760
agtcacgacg ttgtaaaacg acggccagtg aattgtaata cgactcacta tagggcgaat    2820
tgggtaccgg gccccccctc gaggtcgacg agtatctgtc tgactcgtca ttgccgcctt    2880
tggagtacga ctccaactat gagtgtgctt ggatcacttt gacgatacat tcttcgttgg    2940
aggctgtggg tctgacagct gcgttttcgg cgcggttggc cgacaacaat atcagctgca    3000
acgtcattgc tggctttcat catgatcaca tttttgtcgg caaaggcgac gcccagagag    3060
ccattgacgt tctttctaat ttggaccgat agccgtatag tccagtctat ctataagttc    3120
aactaactcg taactattac cataacatat acttcactgc cccagataag gttccgataa    3180
aaagttctgc agactaaatt tatttcagtc tcctcttcac caccaaaatg ccctcctacg    3240
aagctcgagt gctcaagctc gtggcagcca agaaaaccaa cctgtgtgct tctctggatg    3300
ttaccaccac caaggagctc attgagcttg ccgataaggt cggaccttat gtgtgcatga    3360
tcaaaaccca tatcgacatc attgacgact tcacctacgc cggcactgtg ctccccctca    3420
aggaacttgc tcttaagcac ggtttcttcc tgttcgagga cagaaagttc gcagatattg    3480
gcaacactgt caagcaccag taccggtgtc accgaatcgc cgagtggtcc gatatcacca    3540
acgcccacgg tgtacccgga accggaatcg attgctggcc tgcgagctgg tgcgtacgag    3600
gaaactgtct ctgaacagaa gaaggaggac gtctctgact acgagaactc ccagtacaag    3660
gagttcctag tcccctctcc caacgagaag ctggccagag gtctgctcat gctggccgag    3720
ctgtcttgca agggctctct ggccactggc gagtactcca agcagaccat tgagcttgcc    3780
cgatccgacc ccgagtttgt ggttggcttc attgcccaga accgacctaa gggcgactct    3840
gaggactggc ttattctgac ccccggggtg ggtcttgacg acaagggaga cgctctcgga    3900
cagcagtacc gaactgttga ggatgtcatg tctaccggaa cggatatcat aattgtcggc    3960
cgaggtctgt acggccagaa ccgagatcct attgaggagg ccaagcgata ccagaaggct    4020
ggctgggagg cttaccagaa gattaactgt tagaggttag actatggata tgtaatttaa    4080
ctgtgtatat agagagcgtg caagtatgga gcgcttgttc agcttgtatg atggtcagac    4140
gacctgtctg atcgagtatg tatgatactg cacaacctgt gtatccgcat gatctgtcca    4200
atggggcatg ttgttgtgtt tctcgatacg gagatgctgg gtacagtgct aatacgttga    4260
actacttata cttatatgag gctcgaagaa agctgacttg tgtatgactt aat          4313
```

<210> SEQ ID NO 41
<211> LENGTH: 15991
<212> TYPE: DNA
<213> ORGANISM: Artificial Sequence
<220> FEATURE:
<223> OTHER INFORMATION: Plasmid pZKL2-5mB89C

<400> SEQUENCE: 41

| | | | | | |
|---|---|---|---|---|---|
| gtacgttatc | atttgaacag | tgaaaggcta | cagtaacaga | agcagttgta | aacttcattc | 60 |
| cgttgattct | gtactacagt | accccactac | gccgcttccg | ctgacactgt | tcaacccaaa | 120 |
| aactacatct | gcgtgcgctg | tgtaaggcta | tcatcagata | catactgtag | attctgtaga | 180 |
| tgcgaacctg | cttgtatcat | atacatcccc | ctcccctga | cctgcacaag | caagcaatgt | 240 |
| gacattgata | ttgctgctta | tctagtgccg | aggatgtgaa | agccgagact | caaacatttc | 300 |
| ttttactctc | ttgttcctga | ccagacctgg | cggagattac | gccagtatga | ttcttgcagg | 360 |
| tctgagacaa | gcctggaaca | gccaacattt | attttcgaa | gcgagaaaca | tgccacaccc | 420 |
| cggcacgttc | agagatgcat | atgatttgtt | tttcgagtaa | cagtaccccc | ccccccccc | 480 |
| ccaatgaaac | cagtattact | cacaccatcc | tcattcaaag | cgttacactg | attacgcgcc | 540 |
| catcaacgac | agcatgaggg | gactgctgat | ctgatctaat | caaatgacta | caaaaatcgc | 600 |
| aataatgaag | agcaaacgac | aaaaaagaaa | caggttaacc | aatcccgctt | caatgtctca | 660 |
| ccacaatcca | gcactgtttc | tcattacctc | ctccctctaa | tttcagagtt | gcatcagggt | 720 |
| ccttgatggc | gcgccagctg | cattaatgaa | tcggccaacg | cgcggggaga | ggcggtttgc | 780 |
| gtattgggcg | ctcttccgct | tcctcgctca | ctgactcgct | gcgctcggtc | gttcggctgc | 840 |
| ggcgagcggt | atcagctcac | tcaaaggcgg | taatacggtt | atccacagaa | tcagggggata | 900 |
| acgcaggaaa | gaacatgtga | gcaaaaggcc | agcaaaaggc | caggaaccgt | aaaaaggccg | 960 |
| cgttgctggc | gtttttccat | aggctccgcc | cccctgacga | gcatcacaaa | aatcgacgct | 1020 |
| caagtcagag | gtggcgaaac | ccgacaggac | tataaagata | ccaggcgttt | cccctggaa | 1080 |
| gctccctcgt | gcgctctcct | gttccgaccc | tgccgcttac | cggatacctg | tccgcctttc | 1140 |
| tcccttcggg | aagcgtggcg | ctttctcata | gctcacgctg | taggtatctc | agttcggtgt | 1200 |
| aggtcgttcg | ctccaagctg | ggctgtgtgc | acgaacccc | cgttcagccc | gaccgctgcg | 1260 |
| ccttatccgg | taactatcgt | cttgagtcca | acccggtaag | acacgactta | tcgccactgg | 1320 |
| cagcagccac | tggtaacagg | attagcagag | cgaggtatgt | aggcggtgct | acagagttct | 1380 |
| tgaagtggtg | gcctaactac | ggctacacta | gaagaacagt | atttggtatc | tgcgctctgc | 1440 |
| tgaagccagt | taccttcgga | aaaagagttg | gtagctcttg | atccggcaaa | caaaccaccg | 1500 |
| ctggtagcgg | tggttttttt | gtttgcaagc | agcagattac | gcgcagaaaa | aaaggatctc | 1560 |
| aagaagatcc | tttgatcttt | tctacggggt | ctgacgctca | gtggaacgaa | aactcacgtt | 1620 |
| aagggatttt | ggtcatgaga | ttatcaaaaa | ggatcttcac | ctagatcctt | ttaaattaaa | 1680 |
| aatgaagttt | taaatcaatc | taaagtatat | atgagtaaac | ttggtctgac | agttaccaat | 1740 |
| gcttaatcag | tgaggcacct | atctcagcga | tctgtctatt | tcgttcatcc | atagttgcct | 1800 |
| gactccccgt | cgtgtagata | actacgatac | gggagggctt | accatctggc | cccagtgctg | 1860 |
| caatgatacc | gcgagaccca | cgctcaccgg | ctccagattt | atcagcaata | aaccagccag | 1920 |
| ccggaagggc | cgagcgcaga | agtggtcctg | caactttatc | cgcctccatc | cagtctatta | 1980 |
| attgttgccg | ggaagctaga | gtaagtagtt | cgccagttaa | tagtttgcgc | aacgttgttg | 2040 |

```
ccattgctac aggcatcgtg gtgtcacgct cgtcgtttgg tatggcttca ttcagctccg   2100
gttcccaacg atcaaggcga gttacatgat cccccatgtt gtgcaaaaaa gcggttagct   2160
ccttcggtcc tccgatcgtt gtcagaagta agttggccgc agtgttatca ctcatggtta   2220
tggcagcact gcataattct cttactgtca tgccatccgt aagatgcttt tctgtgactg   2280
gtgagtactc aaccaagtca ttctgagaat agtgtatgcg gcgaccgagt tgctcttgcc   2340
cggcgtcaat acgggataat accgcgccac atagcagaac tttaaaagtg ctcatcattg   2400
gaaaacgttc ttcggggcga aaactctcaa ggatcttacc gctgttgaga tccagttcga   2460
tgtaacccac tcgtgcaccc aactgatctt cagcatcttt tactttcacc agcgtttctg   2520
ggtgagcaaa aacaggaagg caaaatgccg caaaaaaggg aataagggcg acacggaaat   2580
gttgaatact catactcttc cttttcaat attattgaag catttatcag gttattgtc     2640 tcatgagcgg atacatattt gaatgtattt agaaaaataa acaaataggg gttccgcgca   2700
catttccccg aaaagtgcca cctgatgcgg tgtgaaatac cgcacagatg cgtaaggaga   2760
aaataccgca tcaggaaatt gtaagcgtta atattttgtt aaaattcgcg ttaaattttt   2820
gttaaatcag ctcattttt aaccaatagg ccgaaatcgg caaaatccct tataaatcaa    2880
aagaatagac cgagataggg ttgagtgttg ttccagtttg gaacaagagt ccactattaa   2940
agaacgtgga ctccaacgtc aaagggcgaa aaaccgtcta tcagggcgat ggcccactac   3000
gtgaaccatc accctaatca agttttttgg ggtcgaggtg ccgtaaagca ctaaatcgga   3060
accctaaagg gagcccccga tttagagctt gacggggaaa gccggcgaac gtggcgagaa   3120
aggaagggaa gaaagcgaaa ggagcgggcg ctagggcgct ggcaagtgta gcggtcacgc   3180
tgcgcgtaac caccacaccc gccgcgctta atgcgccgct acagggcgcg tccattcgcc   3240
attcaggctg cgcaactgtt gggaagggcg atcggtgcgg gcctcttcgc tattacgcca   3300
gctggcgaaa ggggggatgtg ctgcaaggcg attaagttgg gtaacgccag gttttcccca   3360
gtcacgacgt tgtaaaacga cggccagtga attgtaatac gactcactat agggcgaatt   3420
gggcccgacg tcgcatgctg gtttcgattt gtcttagagg aacgcatata cagtaatcat   3480
agagaataaa cgatattcat ttattaaagt agatagttga ggtagaagtt gtaaagagtg   3540
ataaatagct tagataccac agacaccctc ggtgacgaag tactgcagat ggtttccaat   3600
cacattgacc tgctggagca gagtgttacc ggcagagcac tgtttattgc tctgccctg    3660 gcacatgaca acgttggaga gaggagggtg gatcaggggc cagtcaataa agacctcacc   3720
agagcagtgc tggtaaccgt cccagaaggg cacttgaggg acgatatctc ctcggtgggt   3780
gattcggtag agctttcggt cttttggacac cttggagaca tcggggttct cctggccaaa   3840
gaagagttta tcgacccagt tagcaaagcc agcgttaccg acaatgggct gaccaagagt   3900
aacaacgagg ggatcgtggc cgttaacctt gaggttgatt ccgaacagaa gggctgcagc   3960
tcctccgaga gagtgaccgg tgacagcaat ctggtagtcg ggatactgct caatcacaga   4020
gtcgagcttg gggccgatct gattgtaggt gttgttgtag gactggatga agccattgtg   4080
gacaagacag tcatcacaag tagcagtaga agagatgtta gcagcaagat caaagttaat   4140
taactcacct gcaggattga gactatgaat ggattcccgt gcccgtatta ctctactaat   4200
ttgatcttgg aacgcgaaaa tacgtttcta ggactccaaa gaatctcaac tcttgtcctt   4260
actaaatata ctacccatag ttgatggttt acttgaacag agaggacatg ttcacttgac   4320
ccaaagtttc tcgcatctct tggatatttg aacaacggcg tccactgacc gtcagttatc   4380
cagtcacaaa accccacat tcatacattc ccatgtacgt ttacaaagtt ctcaattcca    4440
```

```
tcgtgcaaat caaaatcaca tctattcatt catcatatat aaacccatca tgtctactaa    4500
cactcacaac tccatagaaa acatcgactc agaacacacg ctccatgcgg ccgcttagga    4560
atcctgagcg tccttgacac agtgaaccac accgactttg tgcatgtact tgagggtgga    4620
aatgatgttg cccacaatgg tagggtagaa gacgtaccga actccgtgtc gttcgcaaca    4680
ctctcggaca gcttgctgca cgaagggata gtgccaagac gacattcgag gaaagaggtg    4740
atgctcgatc tggaagttga gaccgccagt aaagaacatg gcaatgggtc caccgtaggt    4800
ggaagaggtc tccacctgag ctctgtacca gtcgatctga tcggcttcaa cgtccttctc    4860
ggagctcttg accttgcagt tcttgtcggg gattcgctcc gagccatcga agttgtgaga    4920
caagatgaaa aagaaggtga ggaaggcacc ggtagcagtg gcaccagag gaatggtgat     4980
gagcagggag gttccagtga gataccaggg caagaaggcg gttcgaaaga tgaagaaagc    5040
tcgcataacg aatgcaaggg ttcggtaccg tcgcagaaag ccgttctctc gcatggctgt    5100
gacagactcg ggaatggtgt cgttgtgctg cattcggaag atgtagagag ggttgtacac    5160
cagcgaaacg ccgtaggctc caagcacgag gtacatgtac caggcctgga atcggtgaaa    5220
ccactttcga gcagtgttgg cagcagggta gttgtggaac acaaggaatg gttctgcgga    5280
ctcggcatcc aggtcgagac catgctgatt ggtgtaggtg tgatgtcgca tgatgtgaga    5340
ctgcagccag atccatctgg acgatccaat gacgtcgatg ccgtaggcaa agagagcgtt    5400
gacccagggc tttttgctga tggcaccatg agaggcatcg tgctgaatgg acaggccgat    5460
ctgcatgtgc atgaatccag tcaagagacc ccacagcacc attccggtag tagcccagtg    5520
ccactcgcaa aaggcggtga cagcaatgat gccaacggtt cgcagccaga atccaggtgt    5580
ggcataccag ttccgacctt tcatgacctc tcgcatagtt cgcttgacgt cctgtgcaaa    5640
gggagagtcg taggtgtaga caatgtcctt ggaggttcgg tcgtgcttgc ctcgcacgaa    5700
ctgttgaagc agcttcgagt tctcgggctt gacgtaaggg tgcatggagt agaacagagg    5760
agaagcatcg gaggcaccag aagcgaggat caagtcggat ccgggatgga ccttggcaag    5820
accttccaga tcgtagagaa tgccgtcgat ggcaaccagg tcgggtcgct cgagcagctg    5880
ctcggtagta agggagagag ccatgggcag gacctgtgtt agtacattgt cggggagtca    5940
tcaattggtt cgacaggttg tcgactgtta gtatgagctc aattgggctc tggtgggtcg    6000
atgacacttg tcatctgttt ctgttgggtc atgtttccat caccttctat ggtactcaca    6060
attcgtccga ttcgcccgaa tccgttaata ccgactttga tggccatgtt gatgtgtgtt    6120
taattcaaga atgaatatag agaagagaag aagaaaaaag attcaattga ccggcgatg    6180
cagacccta tataaatgtt gccttggaca gacggagcaa gcccgcccaa acctacgttc    6240
ggtataatat gttaagcttt ttaacacaaa ggtttggctt ggggtaacct gatgtggtgc    6300
aaaagaccgg gcgttggcga gccattgcgc gggcgaatgg ggccgtgact cgtctcaaat    6360
tcgagggcgt gcctcaattc gtgcccccgt ggcttttcc cgccgtttcc gccccgtttg    6420
caccactgca gccgcttctt tggttcggac accttgctgc gagctaggtg ccttgtgcta    6480
cttaaaaagt ggcctcccaa caccaacatg acatgagtgc gtgggccaag acacgttggc    6540
ggggtcgcag tcggctcaat ggcccggaaa aaacgctgct ggagctggtt cggacgcagt    6600
ccgccgcggc gtatggatat ccgcaaggtt ccatagcgcc attgccctcc gtcggcgtct    6660
atcccgcaac ctctaaatag agcgggaata aacccaagc ttcttttttt tcctttaaca     6720
cgcacacccc caactatcat gttgctgctg ctgtttgact ctactctgtg gaggggtgct    6780
```

```
cccacccaac ccaacctaca ggtggatccg gcgctgtgat tggctgataa gtctcctatc    6840
cggactaatt ctgaccaatg ggacatgcgc gcaggaccca aatgccgcaa ttacgtaacc    6900
ccaacgaaat gcctacccct cttttggagcc cagcggcccc aaatcccccc aagcagcccg   6960
gttctaccgg cttccatctc caagcacaag cagcccggaa ttctctctct tgagcttttc    7020
cataacaagt tcttctgcct ccaggaagtc catgggtggt ttgatcatgg ttttggtgta    7080
gtggtagtgc agtggtggta ttgtgactgg ggatgtagtt gagaataagt catacacaag    7140
tcagctttct tcgagcctca tataagtata agtagttcaa cgtattagca ctgtacccag    7200
catctccgta tcgagaaaca caacaacatg ccccattgga cagatcatgc ggatacacag    7260
gttgtgcagt atcatacata ctcgatcaga caggtcgtct gaccatcata caagctgaac    7320
aagcgctcca tacttgcacg ctctctatat acacagttaa attacatatc catagtctaa    7380
cctctaacag ttaatcttct ggtaagcctc ccagccagcc ttctggtatc gcttggcctc    7440
ctcaatagga tctcggttct ggccgtacag acctcggccg acaattatga tatccgttcc    7500
ggtagacatg acatcctcaa cagttcggta ctgctgtccg agagcgtctc ccttgtcgtc    7560
aagacccacc ccgggggtca gaataagcca gtcctcagag tcgcccttag gtcggttctg    7620
ggcaatgaag ccaaccacaa actcggggtc ggatcgggca agctcaatgg tctgcttgga    7680
gtactcgcca gtggccagag agcccttgca agacagctcg gccagcatga gcagacctct    7740
ggccagcttc tcgttgggag aggggactag gaactccttg tactgggagt tctcgtagtc    7800
agagacgtcc tccttcttct gttcagagac agtttcctcg gcaccagctc gcaggccagc    7860
aatgattccg gttccgggta caccgtgggc gttggtgata tcggaccact cggcgattcg    7920
gtgacaccgg tactggtgct tgacagtgtt gccaatatct gcgaactttc tgtcctcgaa    7980
caggaagaaa ccgtgcttaa gagcaagttc cttgaggggg agcacagtgc cggcgtaggt    8040
gaagtcgtca atgatgtcga tatgggtttt gatcatgcac ataaggtc cgaccttatc     8100
ggcaagctca atgagctcct tggtggtggt aacatccaga gaagcacaca ggttggtttt   8160
cttggctgcc acgagcttga gcactcgagc ggcaaaggcg gacttgtgga cgttagctcg   8220
agcttcgtag gagggcattt tggtggtgaa gaggagactg aaataaattt agtctgcaga   8280
acttttatc ggaaccttat ctggggcagt gaagtatatg ttatggtaat agttacgagt    8340
tagttgaact tatagataga ctggactata cggctatcgg tccaaattag aaagaacgtc   8400
aatggctctc tgggcgtcgc cttttgccgac aaaaatgtga tcatgatgaa agccagcaat  8460
gacgttgcag ctgatattgt tgtcggccaa ccgcgccgaa aacgcagctg tcagacccac   8520
agcctccaac gaagaatgta tcgtcaaagt gatccaagca cactcatagt tggagtcgta  8580
ctccaaaggc ggcaatgacg agtcagacag atactcgtcg acctttcct tgggaaccac  8640
caccgtcagc ccttctgact cacgtattgt agccaccgac acaggcaaca gtccgtggat 8700
agcagaatat gtcttgtcgg tccatttctc accaacttta ggcgtcaagt gaatgttgca  8760
gaagaagtat gtgccttcat tgagaatcgg tgttgctgat tcaataaag tcttgagatc   8820
agtttggcca gtcatgttgt gggggtaat tggattgagt tatcgcctac agtctgtaca  8880
ggtatactcg ctgcccactt tatacttttt gattccgctg cacttgaagc aatgtcgttt  8940
accaaaagtg agaatgctcc acagaacaca ccccagggta tggttgagca aaaataaac   9000
actccgatac ggggaatcga accccggtct ccacggttct caagaagtat tcttgatgag 9060
agcgtatcga tcgaggaaga ggacaagcgg ctgcttctta gtttgtgac atcagtatcc   9120
aaggcaccat tgcaaggatt caaggctttg aacccgtcat ttgccattcg taacgctggt  9180
```

```
agacaggttg atcggttccc tacggcctcc acctgtgtca atcttctcaa gctgcctgac  9240
tatcaggaca ttgatcaact tcggaagaaa cttttgtatg ccattcgatc acatgctggt  9300
ttcgatttgt cttagaggaa cgcatataca gtaatcatag agaataaacg atattcattt  9360
attaaagtag atagttgagg tagaagttgt aaagagtgat aaatagcggc cgctcactga  9420 atcttttttgg ctcccttgtg ctttcggacg atgtaggtct gcacgtagaa gttgaggaac  9480
agacacagga cagtaccaac gtagaagtag ttgaaaaacc agccaaacat tctcattcca  9540
tcttgtcggt agcagggaat gttccggtac ttccagacga tgtagaagcc aacgttgaac  9600
tgaatgatct gcatagaagt aatcaggac ttgggcatag gaacttgag cttgatcagt  9660 cgggtccaat agtagccgta catgatccag tgaatgaagc cgttgagcag cacaaagatc  9720
caaacggctt cgtttcggta gttgtagaac agccacatgt ccataggagc tccgagatgg  9780
tgaaagaact gcaaccaggt cagaggcttg cccatgaggg gcagatagaa ggagtcaatg  9840
tactcgagga acttgctgag gtagaacagc tgagtggtga ttcggaagac attgttgtcg  9900
aaagccttct cgcagttgtc ggacatgaca ccaatggtgt acatggcgta ggccatagag  9960
aggaaggagc ccagcgagta gatggacatg agcaggttgt agttggtgaa cacaaacttc  10020
attcgagact gacccttggg tccgagagga ccaagggtga acttcaggat gacgaaggcg  10080
atggagaggt acagcacctc gcagtgcgag gcatcagacc agagctgagc atagtcgacc  10140
ttgggaagaa cctcctggcc aatggagacg atttcgttca cgacctccat ggttgtgaat  10200
tagggtggtg agaatggttg gttgtaggga agaatcaaag gccggtctcg ggatccgtgg  10260
gtatatatat atatatatat atatacgatc cttcgttacc tccctgttct caaaactgtg  10320 gttttttcgtt tttcgttttt tgctttttttt gattttttttta gggccaacta agcttccaga  10380
tttcgctaat caccttttgta ctaattacaa gaaaggaaga agctgattag agttgggctt  10440
tttatgcaac tgtgctactc cttatctctg atatgaaagt gtagacccaa tcacatcatg  10500
tcatttagag ttggtaatac tgggaggata gataaggcac gaaaacgagc catagcagac  10560
atgctgggtg tagccaagca gaagaaagta gatgggagcc aattgacgag cgagggagct  10620
acgccaatcc gacatacgac acgctgagat cgtcttggcc gggggtacc tacagatgtc  10680 caagggtaag tgcttgactg taattgtatg tctgaggaca aatatgtagt cagccgtata  10740
aagtcatacc aggcaccagt gccatcatcg aaccactaac tctctatgat acatgcctcc  10800
ggtattattg taccatgcgt cgctttgtta catacgtatc ttgcctttttt ctctcagaaa  10860 ctccagactt tggctattgg tcgagataag cccggaccat agtgagtctt tcacactctg  10920
tttaaacacc actaaaaccc cacaaaatat atcttaccga atatacagat ctactataga  10980
ggaacaattg ccccgagaa gacggccagg ccgcctagat gacaaattca acaactcaca  11040
gctgactttc tgccattgcc actagggggg ggccttttta tatggccaag ccaagctctc  11100
cacgtcggtt gggctgcacc caacaataaa tgggtagggt tgcaccaaca aagggatggg  11160 atgggggggta gaagatacga ggataacggg gctcaatggc acaaataaga acgaatactg  11220
ccattaagac tcgtgatcca gcgactgaca ccattgcatc atctaagggc ctcaaaacta  11280
cctcggaact gctgcgctga tctggacacc acagaggttc cgagcacttt aggttgcacc  11340
aaatgtccca ccaggtgcag gcagaaaacg ctggaacagc gtgtacagtt tgtcttaaca  11400
aaaagtgagg gcgctgaggt cgagcagggt ggtgtgactt gttatagcct ttagagctgc  11460
gaaagcgcgt atggatttgg ctcatcaggc cagattgagg gtctgtggac acatgtcatg  11520
```

```
ttagtgtact tcaatcgccc cctggatata gccccgacaa taggccgtgg cctcattttt    11580
ttgccttccg cacatttcca ttgctcggta cccacacctt gcttctcctg cacttgccaa    11640
ccttaatact ggtttacatt gaccaacatc ttacaagcgg ggggcttgtc tagggtatat    11700
ataaacagtg gctctcccaa tcggttgcca gtctcttttt tcctttcttt ccccacagat    11760
tcgaaatcta aactacacat cacacaatgc ctgttactga cgtccttaag cgaaagtccg    11820
gtgtcatcgt cggcgacgat gtccgagccg tgagtatcca cgacaagatc agtgtcgaga    11880
cgacgcgttt tgtgtaatga cacaatccga aagtcgctag caacacacac tctctacaca    11940
aactaaccca gctctccatg gtgaaggctt ctcgacaggc tctgcccctc gtcatcgacg    12000
gaaaggtgta cgacgtctcc gcttgggtga acttccaccc tggtggagct gaaatcattg    12060
agaactacca gggacgagat gctactgacg ccttcatggt tatgcactct caggaagcct    12120
tcgacaagct caagcgaatg cccaagatca accaggcttc cgagctgcct ccccaggctg    12180
ccgtcaacga agctcaggag gatttccgaa agctccgaga agagctgatc gccactggca    12240
tgtttgacgc ctctcccctc tggtactcgt acaagatctt gaccaccctg ggtcttggcg    12300
tgcttgcctt cttcatgctg gtccagtacc acctgtactt cattggtgct ctcgtgctcg    12360
gtatgcacta ccagcaaatg ggatggctgt ctcatgacat ctgccaccac cagaccttca    12420
agaaccgaaa ctggaataac gtcctgggtc tggtctttgg caacggactc cagggcttct    12480
ccgtgacctg gtgaaggac agacacaacg cccatcattc tgctaccaac gttcagggtc    12540
acgatcccga cattgataac ctgcctctgc tcgcctggtc cgaggacgat gtcactcgag    12600
cttctcccat ctcccgaaag ctcattcagt tccaacagta ctatttcctg gtcatctgta    12660
ttctcctgcg attcatctgg tgtttccagt ctgtgctgac cgttcgatcc ctcaaggacc    12720
gagacaacca gttctaccga tctcagtaca agaaagaggc cattggactc gctctgcact    12780
ggactctcaa gaccctgttc cacctcttct ttatgccctc catcctgacc tcgatgctgg    12840
tgttctttgt ttccgagctc gtcggtggct tcggaattgc catcgtggtc ttcatgaacc    12900
actaccctct ggagaagatc ggtgattccg tctgggacgg acatggcttc tctgtgggtc    12960
agatccatga gaccatgaac attcgacgag gcatcattac tgactggttc tttggaggcc    13020
tgaactacca gatcgagcac catctctggc ccaccctgcc tcgacacaac ctcactgccg    13080
tttcctacca ggtggaacag ctgtgccaga agcacaacct ccctaccga aaccctctgc    13140
cccatgaagg tctcgtcatc ctgctccgat acctgtccca gttcgctcga atggccgaga    13200
agcagcccgg tgccaaggct cagtaagcgg ccgcatgaga agataaatat ataaatacat    13260
tgagatatta aatgcgctag attagagagc ctcatactgc tcggagagaa gccaagacga    13320
gtactcaaag gggattacac catccatatc cacagacaca agctggggaa aggttctata    13380
tacactttcc ggaataccgt agtttccgat gttatcaatg ggggcagcca ggatttcagg    13440
cacttcggtg tctcggggtg aaatggcgtt cttggcctcc atcaagtcgt accatgtctt    13500
catttgcctg tcaaagtaaa acagaagcag atgaagaatg aacttgaagt gaaggaattt    13560
aaatagttgg agcaagggag aaatgtagag tgtgaaagac tcactatggt ccgggcttat    13620
ctcgaccaat agccaaagtc tggagttttct gagagaaaaa ggcaagatac gtatgtaaca    13680
aagcgacgca tggtacaata ataccggagg catgtatcat agagagttag tggttcgatg    13740
atggcactgg tgcctggtat gactttatac ggctgactac atatttgtcc tcagacatac    13800
aattacagtc aagcacttac ccttggacat ctgtaggtac cccccggcca agacgatctc    13860
agcgtgtcgt atgtcggatt ggcgtagctc cctcgctcgt caattggctc ccatctactt    13920
```

```
tcttctgctt ggctacaccc agcatgtctg ctatggctcg ttttcgtgcc ttatctatcc   13980
tcccagtatt accaactcta aatgacatga tgtgattggg tctacacttt catatcagag   14040
ataaggagta gcacagttgc ataaaaagcc caactctaat cagcttcttc ctttcttgta   14100
attagtacaa aggtgattag cgaaatctgg aagcttagtt ggccctaaaa aaatcaaaaa   14160
aagcaaaaaa cgaaaaacga aaaccacag ttttgagaac agggaggtaa cgaaggatcg   14220
tatatatata tatatatata tatcccacg gatcccgaga ccggcctttg attcttccct   14280
acaaccaacc attctcacca ccctaattca caaccatggg cgtattcatt aaacaggagc   14340
agcttccggc tctcaagaag tacaagtact ccgccgagga tcactcgttc atctccaaca   14400
acattctgcg ccccttctgg cgacagtttg tcaaaatctt ccctctgtgg atggccccca   14460
acatggtgac tctgctgggc ttcttctttg tcattgtgaa cttcatcacc atgctcattg   14520
ttgatcccac ccacgaccgc gagcctccca gatgggtcta cctcacctac gctctgggtc   14580 tgttcctta ccagacattt gatgcctgtg acggatccca tgcccgacga actggccaga   14640
gtggacccct tggagagctg tttgaccact gtgtcgacgc catgaatacc tctctgattc   14700
tcacggtggt ggtgtccacc acccatatgg gatataacat gaagctactg attgtgcaga   14760
ttgccgctct cggaaacttc tacctgtcga cctgggagac ctaccatacc ggaactctgt   14820
acctttctgg cttctctggt cctgttgaag gtatcttgat tctggtggct cttttcgtcc   14880
tcaccttctt cactggtccc aacgtgtacg ctctgaccgt ctacgaggct cttcccgagt   14940
ccatcacttc gctgctgcct gccagcttcc tggacgtcac catcacccag atctacattg   15000
gattcggagt gctgggcatg gtgttcaaca tctacggcgc ctgcggaaac gtgatcaagt   15060
actacaacaa caagggcaag agcgctctcc ccgccattct cggaatcgcc ccctttggca   15120
tcttctacgt cggcgtcttt gcctgggccc atgttgctcc tctgcttctc tccaagtacg   15180
ccatcgtcta tctgttttgcc attggggctg ccttttgccat gcaagtcggc cagatgattc   15240
ttgcccatct cgtgcttgct ccctttcccc actggaacgt gctgctcttc ttcccctttg   15300
tgggactggc agtgcactac attgcacccg tgtttggctg ggacgccgat atcgtgtcgg   15360
ttaacactct cttcacctgt tttggcgcca ccctctccat ttacgccttc tttgtgcttg   15420
agatcatcga cgagatcacc aactacctcg atatctggtg tctgcgaatc aagtaccctc   15480
aggagaagaa gaccgaataa gcggccgcat ggagcgtgtg ttctgagtcg atgttttcta   15540
tggagttgtg agtgttagta gacatgatgg gtttatatat gatgaatgaa tagatgtgat   15600
tttgatttgc acgatggaat tgagaacttt gtaaacgtac atgggaatgt atgaatgtgg   15660
gggttttgtg actggataac tgacggtcag tggacgccgt tgttcaaata tccaagagat   15720
gcgagaaact ttgggtcaag tgaacatgtc ctctctgttc aagtaaacca tcaactatgg   15780
gtagtatatt tagtaaggac aagagttgag attctttgga gtcctagaaa cgtattttcg   15840
cgttccaaga tcaaattagt agagtaatac gggcacggga atccattcat agtctcaatc   15900
ctgcaggtga gttaattaat cgagcttggc gtaatcatgg tcatagctgt ttcctgtgtg   15960
aaattgttat ccgctcacaa ttccacacaa c                                 15991
```

<210> SEQ ID NO 42
<211> LENGTH: 1185
<212> TYPE: DNA
<213> ORGANISM: Yarrowia lipolytica
<220> FEATURE:
<221> NAME/KEY: CDS
<222> LOCATION: (1)..(1185)

<223> OTHER INFORMATION: diacylglycerol cholinephosphotransferase (YlCPT1)
<300> PUBLICATION INFORMATION:
<302> TITLE: HIGH EICOSAPENTAENOIC ACID PRODUCING STRAINS OF
<310> PATENT DOCUMENT NUMBER: WO 2006/052870
<311> PATENT FILING DATE: 2005-11-03
<312> PUBLICATION DATE: 2006-05-18
<313> RELEVANT RESIDUES IN SEQ ID NO: (1)..(1185)
<300> PUBLICATION INFORMATION:
<302> TITLE: HIGH EICOSAPENTAENOIC ACID PRODUCING STRAINS OF
<310> PATENT DOCUMENT NUMBER: US 2006-0115881-A1
<311> PATENT FILING DATE: 2005-11-02
<312> PUBLICATION DATE: 2006-06-01
<313> RELEVANT RESIDUES IN SEQ ID NO: (1)..(1185)

<400> SEQUENCE: 42

```
atg ggc gta ttc att aaa cag gag cag ctt ccg gct ctc aag aag tac       48
Met Gly Val Phe Ile Lys Gln Glu Gln Leu Pro Ala Leu Lys Lys Tyr
1               5                   10                  15 aag tac tcc gcc gag gat cac tcg ttc atc tcc aac aac att ctg cgc       96
Lys Tyr Ser Ala Glu Asp His Ser Phe Ile Ser Asn Asn Ile Leu Arg
            20                  25                  30 ccc ttc tgg cga cag ttt gtc aaa atc ttc cct ctg tgg atg gcc ccc      144
Pro Phe Trp Arg Gln Phe Val Lys Ile Phe Pro Leu Trp Met Ala Pro
        35                  40                  45 aac atg gtg act ctg ttg ggc ttc ttc ttt gtc att gtg aac ttc atc      192
Asn Met Val Thr Leu Leu Gly Phe Phe Phe Val Ile Val Asn Phe Ile
    50                  55                  60 acc atg ctc att gtt gat ccc acc cac gac cgc gag cct ccc aga tgg      240
Thr Met Leu Ile Val Asp Pro Thr His Asp Arg Glu Pro Pro Arg Trp
65                  70                  75                  80 gtc tac ctc acc tac gct ctg ggt ctg ttc ctt tac cag aca ttt gat      288
Val Tyr Leu Thr Tyr Ala Leu Gly Leu Phe Leu Tyr Gln Thr Phe Asp
                85                  90                  95 gcc tgt gac gga tcc cat gcc cga cga act ggc cag agt gga ccc ctt      336
Ala Cys Asp Gly Ser His Ala Arg Arg Thr Gly Gln Ser Gly Pro Leu
            100                 105                 110 gga gag ctg ttt gac cac tgt gtc gac gcc atg aat acc tct ctg att      384
Gly Glu Leu Phe Asp His Cys Val Asp Ala Met Asn Thr Ser Leu Ile
        115                 120                 125 ctc acg gtg gtg gtg tcc acc acc cat atg gga tat aac atg aag ctg      432
Leu Thr Val Val Val Ser Thr Thr His Met Gly Tyr Asn Met Lys Leu
    130                 135                 140 ctg att gtg cag att gcc gct ctc gga aac ttc tac ctg tcg acc tgg      480
Leu Ile Val Gln Ile Ala Ala Leu Gly Asn Phe Tyr Leu Ser Thr Trp
145                 150                 155                 160 gag acc tac cat acc gga act ctg tac ctt tct ggc ttc tct ggt cct      528
Glu Thr Tyr His Thr Gly Thr Leu Tyr Leu Ser Gly Phe Ser Gly Pro
                165                 170                 175 gtt gaa ggt atc ttg att ctg gtg gct ctt ttc gtc ctc acc ttc ttc      576
Val Glu Gly Ile Leu Ile Leu Val Ala Leu Phe Val Leu Thr Phe Phe
            180                 185                 190 act ggt ccc aac gtg tac gct ctg acc gtc tac gag gct ctt ccc gaa      624
Thr Gly Pro Asn Val Tyr Ala Leu Thr Val Tyr Glu Ala Leu Pro Glu
        195                 200                 205 tcc atc act tcg ctg ctg cct gcc agc ttc ctg gac gtc acc atc acc      672
Ser Ile Thr Ser Leu Leu Pro Ala Ser Phe Leu Asp Val Thr Ile Thr
    210                 215                 220 cag atc tac att gga ttc gga gtg ctg ggc atg gtg ttc aac atc tac      720
Gln Ile Tyr Ile Gly Phe Gly Val Leu Gly Met Val Phe Asn Ile Tyr
225                 230                 235                 240 ggc gcc tgc gga aac gtg atc aag tac tac aac aac aag ggc aag agc      768
Gly Ala Cys Gly Asn Val Ile Lys Tyr Tyr Asn Asn Lys Gly Lys Ser
```

```
                    245                 250                 255
gct ctc ccc gcc att ctc gga atc gcc ccc ttt ggc atc ttc tac gtc      816
Ala Leu Pro Ala Ile Leu Gly Ile Ala Pro Phe Gly Ile Phe Tyr Val
            260                 265                 270 ggc gtc ttt gcc tgg gcc cat gtt gct cct ctg ctt ctc tcc aag tac      864
Gly Val Phe Ala Trp Ala His Val Ala Pro Leu Leu Leu Ser Lys Tyr
            275                 280                 285 gcc atc gtc tat ctg ttt gcc att ggg gct gcc ttt gcc atg caa gtc      912
Ala Ile Val Tyr Leu Phe Ala Ile Gly Ala Ala Phe Ala Met Gln Val
            290                 295                 300 ggc cag atg att ctt gcc cat ctc gtg ctt gct ccc ttc ccc cac tgg      960
Gly Gln Met Ile Leu Ala His Leu Val Leu Ala Pro Phe Pro His Trp
305                 310                 315                 320 aac gtg ctg ctc ttc ttc ccc ttt gtg gga ctg gca gtg cac tac att     1008
Asn Val Leu Leu Phe Phe Pro Phe Val Gly Leu Ala Val His Tyr Ile
                325                 330                 335 gca ccc gtg ttt ggc tgg gac gcc gat atc gtg tcg gtt aac act ctc     1056
Ala Pro Val Phe Gly Trp Asp Ala Asp Ile Val Ser Val Asn Thr Leu
            340                 345                 350 ttc acc tgt ttt ggc gcc acc ctc tcc att tac gcc ttc ttt gtg ctt     1104
Phe Thr Cys Phe Gly Ala Thr Leu Ser Ile Tyr Ala Phe Phe Val Leu
            355                 360                 365 gag atc atc gac gag atc acc aac tac ctc gat atc tgg tgt ctg cga     1152
Glu Ile Ile Asp Glu Ile Thr Asn Tyr Leu Asp Ile Trp Cys Leu Arg
370                 375                 380 atc aag tac cct cag gag aag aag act gag taa                          1185
Ile Lys Tyr Pro Gln Glu Lys Lys Thr Glu
385                 390
```

<210> SEQ ID NO 43
<211> LENGTH: 394
<212> TYPE: PRT
<213> ORGANISM: Yarrowia lipolytica

<400> SEQUENCE: 43

```
Met Gly Val Phe Ile Lys Gln Glu Gln Leu Pro Ala Leu Lys Lys Tyr
1               5                   10                  15

Lys Tyr Ser Ala Glu Asp His Ser Phe Ile Ser Asn Asn Ile Leu Arg
            20                  25                  30

Pro Phe Trp Arg Gln Phe Val Lys Ile Phe Pro Leu Trp Met Ala Pro
        35                  40                  45

Asn Met Val Thr Leu Leu Gly Phe Phe Val Ile Val Asn Phe Ile
    50                  55                  60

Thr Met Leu Ile Val Asp Pro Thr His Asp Arg Glu Pro Pro Arg Trp
65                  70                  75                  80

Val Tyr Leu Thr Tyr Ala Leu Gly Leu Phe Leu Tyr Gln Thr Phe Asp
                85                  90                  95

Ala Cys Asp Gly Ser His Ala Arg Arg Thr Gly Gln Ser Gly Pro Leu
            100                 105                 110

Gly Glu Leu Phe Asp His Cys Val Asp Ala Met Asn Thr Ser Leu Ile
        115                 120                 125

Leu Thr Val Val Ser Thr Thr His Met Gly Tyr Asn Met Lys Leu
    130                 135                 140

Leu Ile Val Gln Ile Ala Ala Leu Gly Asn Phe Tyr Leu Ser Thr Trp
145                 150                 155                 160

Glu Thr Tyr His Thr Gly Thr Leu Tyr Leu Ser Gly Phe Ser Gly Pro
                165                 170                 175
```

```
Val Glu Gly Ile Leu Ile Leu Val Ala Leu Phe Val Leu Thr Phe Phe
            180                 185                 190

Thr Gly Pro Asn Val Tyr Ala Leu Thr Val Tyr Glu Ala Leu Pro Glu
        195                 200                 205

Ser Ile Thr Ser Leu Leu Pro Ala Ser Phe Leu Asp Val Thr Ile Thr
    210                 215                 220

Gln Ile Tyr Ile Gly Phe Gly Val Leu Gly Met Val Phe Asn Ile Tyr
225                 230                 235                 240

Gly Ala Cys Gly Asn Val Ile Lys Tyr Tyr Asn Asn Lys Gly Lys Ser
                245                 250                 255

Ala Leu Pro Ala Ile Leu Gly Ile Ala Pro Phe Gly Ile Phe Tyr Val
            260                 265                 270

Gly Val Phe Ala Trp Ala His Val Ala Pro Leu Leu Leu Ser Lys Tyr
        275                 280                 285

Ala Ile Val Tyr Leu Phe Ala Ile Gly Ala Ala Phe Ala Met Gln Val
    290                 295                 300

Gly Gln Met Ile Leu Ala His Leu Val Leu Ala Pro Phe Pro His Trp
305                 310                 315                 320

Asn Val Leu Leu Phe Phe Pro Phe Val Gly Leu Ala Val His Tyr Ile
                325                 330                 335

Ala Pro Val Phe Gly Trp Asp Ala Asp Ile Val Ser Val Asn Thr Leu
            340                 345                 350

Phe Thr Cys Phe Gly Ala Thr Leu Ser Ile Tyr Ala Phe Phe Val Leu
        355                 360                 365

Glu Ile Ile Asp Glu Ile Thr Asn Tyr Leu Asp Ile Trp Cys Leu Arg
    370                 375                 380

Ile Lys Tyr Pro Gln Glu Lys Lys Thr Glu
385                 390

<210> SEQ ID NO 44
<211> LENGTH: 1272
<212> TYPE: DNA
<213> ORGANISM: Artificial Sequence
<220> FEATURE:
<223> OTHER INFORMATION: mutant EgD8S-23 delta-8 desaturase
<220> FEATURE:
<221> NAME/KEY: CDS
<222> LOCATION: (2)..(1270)
<300> PUBLICATION INFORMATION:
<302> TITLE: MUTANT DELTA-8 DESATURASE GENES ENGINEERED BY TARGETED
       MUTAGENSIS AND THEIR USE IN MAKING POLYUNSATURATED FATTY ACIDS
<310> PATENT DOCUMENT NUMBER: WO 2008/073271
<311> PATENT FILING DATE: 2007-12-05
<312> PUBLICATION DATE: 2008-06-19
<313> RELEVANT RESIDUES IN SEQ ID NO: (1)..(1272)
<300> PUBLICATION INFORMATION:
<302> TITLE: MUTANT DELTA-8 DESATURASE GENES ENGINEERED BY TARGETED
       MUTAGENSIS AND THEIR USE IN MAKING POLYUNSATURATED FATTY ACIDS
<310> PATENT DOCUMENT NUMBER: US 2008-0138868-A1
<311> PATENT FILING DATE: 2006-12-07
<312> PUBLICATION DATE: 2008-06-12
<313> RELEVANT RESIDUES IN SEQ ID NO: (1)..(1272)

<400> SEQUENCE: 44 c atg gtg aag gct tct cga cag gct ctg ccc ctc gtc atc gac gga aag      49
  Met Val Lys Ala Ser Arg Gln Ala Leu Pro Leu Val Ile Asp Gly Lys
  1               5                  10                  15 gtg tac gac gtc tcc gct tgg gtg aac ttc cac cct ggt gga gct gaa      97
Val Tyr Asp Val Ser Ala Trp Val Asn Phe His Pro Gly Gly Ala Glu
             20                  25                  30 atc att gag aac tac cag gga cga gat gct act gac gcc ttc atg gtt     145
Ile Ile Glu Asn Tyr Gln Gly Arg Asp Ala Thr Asp Ala Phe Met Val
```

-continued

```
               35                  40                  45
atg cac tct cag gaa gcc ttc gac aag ctc aag cga atg ccc aag atc      193
Met His Ser Gln Glu Ala Phe Asp Lys Leu Lys Arg Met Pro Lys Ile
 50                  55                  60 aac cag gct tcc gag ctg cct ccc cag gct gcc gtc aac gaa gct cag      241
Asn Gln Ala Ser Glu Leu Pro Pro Gln Ala Ala Val Asn Glu Ala Gln
 65                  70                  75                  80 gag gat ttc cga aag ctc cga gaa gag ctg atc gcc act ggc atg ttt      289
Glu Asp Phe Arg Lys Leu Arg Glu Glu Leu Ile Ala Thr Gly Met Phe
                 85                  90                  95 gac gcc tct ccc ctc tgg tac tcg tac aag atc ttg acc acc ctg ggt      337
Asp Ala Ser Pro Leu Trp Tyr Ser Tyr Lys Ile Leu Thr Thr Leu Gly
            100                 105                 110 ctt ggc gtg ctt gcc ttc ttc atg ctg gtc cag tac cac ctg tac ttc      385
Leu Gly Val Leu Ala Phe Phe Met Leu Val Gln Tyr His Leu Tyr Phe
        115                 120                 125 att ggt gct ctc gtg ctc ggt atg cac tac cag caa atg gga tgg ctg      433
Ile Gly Ala Leu Val Leu Gly Met His Tyr Gln Gln Met Gly Trp Leu
130                 135                 140 tct cat gac atc tgc cac cac cag acc ttc aag aac cga aac tgg aat      481
Ser His Asp Ile Cys His His Gln Thr Phe Lys Asn Arg Asn Trp Asn
145                 150                 155                 160 aac gtc ctg ggt ctg gtc ttt ggc aac gga ctc cag ggc ttc tcc gtg      529
Asn Val Leu Gly Leu Val Phe Gly Asn Gly Leu Gln Gly Phe Ser Val
                165                 170                 175 acc tgg tgg aag gac aga cac aac gcc cat cat tct gct acc aac gtt      577
Thr Trp Trp Lys Asp Arg His Asn Ala His His Ser Ala Thr Asn Val
            180                 185                 190 cag ggt cac gat ccc gac att gat aac ctg cct ctg ctc gcc tgg tcc      625
Gln Gly His Asp Pro Asp Ile Asp Asn Leu Pro Leu Leu Ala Trp Ser
        195                 200                 205 gag gac gat gtc act cga gct tct ccc atc tcc cga aag ctc att cag      673
Glu Asp Asp Val Thr Arg Ala Ser Pro Ile Ser Arg Lys Leu Ile Gln
210                 215                 220 ttc caa cag tac tat ttc ctg gtc atc tgt att ctc ctg cga ttc atc      721
Phe Gln Gln Tyr Tyr Phe Leu Val Ile Cys Ile Leu Leu Arg Phe Ile
225                 230                 235                 240 tgg tgt ttc cag tct gtg ctg acc gtt cga tcc ctc aag gac cga gac      769
Trp Cys Phe Gln Ser Val Leu Thr Val Arg Ser Leu Lys Asp Arg Asp
                245                 250                 255 aac cag ttc tac cga tct cag tac aag aaa gag gcc att gga ctc gct      817
Asn Gln Phe Tyr Arg Ser Gln Tyr Lys Lys Glu Ala Ile Gly Leu Ala
            260                 265                 270 ctg cac tgg act ctc aag acc ctg ttc cac ctc ttc ttt atg ccc tcc      865
Leu His Trp Thr Leu Lys Thr Leu Phe His Leu Phe Phe Met Pro Ser
        275                 280                 285 atc ctg acc tcg atg ctg gtg ttc ttt gtt tcc gag ctc gtc ggt ggc      913
Ile Leu Thr Ser Met Leu Val Phe Phe Val Ser Glu Leu Val Gly Gly
290                 295                 300 ttc gga att gcc atc gtg gtc ttc atg aac cac tac cct ctg gag aag      961
Phe Gly Ile Ala Ile Val Val Phe Met Asn His Tyr Pro Leu Glu Lys
305                 310                 315                 320 atc ggt gat tcc gtc tgg gac gga cat ggc ttc tct gtg ggt cag atc     1009
Ile Gly Asp Ser Val Trp Asp Gly His Gly Phe Ser Val Gly Gln Ile
                325                 330                 335 cat gag acc atg aac att cga cga ggc atc att act gac tgg ttc ttt     1057
His Glu Thr Met Asn Ile Arg Arg Gly Ile Ile Thr Asp Trp Phe Phe
            340                 345                 350 gga ggc ctg aac tac cag atc gag cac cat ctc tgg ccc acc ctg cct     1105
```

```
Gly Gly Leu Asn Tyr Gln Ile Glu His His Leu Trp Pro Thr Leu Pro
        355                 360                 365 cga cac aac ctc act gcc gtt tcc tac cag gtg gaa cag ctg tgc cag      1153
Arg His Asn Leu Thr Ala Val Ser Tyr Gln Val Glu Gln Leu Cys Gln
        370                 375                 380 aag cac aac ctc ccc tac cga aac cct ctg ccc cat gaa ggt ctc gtc      1201
Lys His Asn Leu Pro Tyr Arg Asn Pro Leu Pro His Glu Gly Leu Val
385                 390                 395                 400 atc ctg ctc cga tac ctg tcc cag ttc gct cga atg gcc gag aag cag      1249
Ile Leu Leu Arg Tyr Leu Ser Gln Phe Ala Arg Met Ala Glu Lys Gln
                405                 410                 415 ccc ggt gcc aag gct cag taa gc                                       1272
Pro Gly Ala Lys Ala Gln
            420

<210> SEQ ID NO 45
<211> LENGTH: 422
<212> TYPE: PRT
<213> ORGANISM: Artificial Sequence
<220> FEATURE:
<223> OTHER INFORMATION: Synthetic Construct

<400> SEQUENCE: 45

Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Gln Ala Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Leu Thr Thr Leu Gly
            100                 105                 110

Leu Gly Val Leu Ala Phe Phe Met Leu Val Gln Tyr His Leu Tyr Phe
        115                 120                 125

Ile Gly Ala Leu Val Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Val Leu Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270
```

```
Leu His Trp Thr Leu Lys Thr Leu Phe His Leu Phe Met Pro Ser
        275                 280                 285

Ile Leu Thr Ser Met Leu Val Phe Phe Val Ser Glu Leu Val Gly Gly
        290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415

Pro Gly Ala Lys Ala Gln
            420

<210> SEQ ID NO 46
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: synthetic delta-9 elongase (codon-optimized for
      Yarrowia lipolytica)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(777)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: US-2007-0117190-A1
<311> PATENT FILING DATE: 2006-11-16
<312> PUBLICATION DATE: 2007-05-24
<313> RELEVANT RESIDUES IN SEQ ID NO: (1)..(777)

<400> SEQUENCE: 46 atg gag gtc gtg aac gaa atc gtc tcc att ggc cag gag gtt ctt ccc      48
Met Glu Val Val Asn Glu Ile Val Ser Ile Gly Gln Glu Val Leu Pro
1               5                   10                  15 aag gtc gac tat gct cag ctc tgg tct gat gcc tcg cac tgc gag gtg      96
Lys Val Asp Tyr Ala Gln Leu Trp Ser Asp Ala Ser His Cys Glu Val
            20                  25                  30 ctg tac ctc tcc atc gcc ttc gtc atc ctg aag ttc acc ctt ggt cct     144
Leu Tyr Leu Ser Ile Ala Phe Val Ile Leu Lys Phe Thr Leu Gly Pro
        35                  40                  45 ctc gga ccc aag ggt cag tct cga atg aag ttt gtg ttc acc aac tac     192
Leu Gly Pro Lys Gly Gln Ser Arg Met Lys Phe Val Phe Thr Asn Tyr
    50                  55                  60 aac ctg ctc atg tcc atc tac tcg ctg ggc tcc ttc ctc tct atg gcc     240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct     288
```

```
                Tyr Ala Met Tyr Thr Ile Gly Val Met Ser Asp Asn Cys Glu Lys Ala
                                85                  90                  95 ttc gac aac aat gtc ttc cga atc acc act cag ctg ttc tac ctc agc              336
Phe Asp Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag              384
Lys Phe Leu Glu Tyr Ile Asp Ser Phe Tyr Leu Pro Leu Met Gly Lys
        115                 120                 125 cct ctg acc tgg ttg cag ttc ttt cac cat ctc gga gct cct atg gac              432
Pro Leu Thr Trp Leu Gln Phe Phe His His Leu Gly Ala Pro Met Asp
    130                 135                 140 atg tgg ctg ttc tac aac tac cga aac gaa gcc gtt tgg atc ttt gtg              480
Met Trp Leu Phe Tyr Asn Tyr Arg Asn Glu Ala Val Trp Ile Phe Val
145                 150                 155                 160 ctg ctc aac ggc ttc att cac tgg atc atg tac ggc tac tat tgg acc              528
Leu Leu Asn Gly Phe Ile His Trp Ile Met Tyr Gly Tyr Tyr Trp Thr
                165                 170                 175 cga ctg atc aag ctc aag ttc cct atg ccc aag tcc ctg att act tct              576
Arg Leu Ile Lys Leu Lys Phe Pro Met Pro Lys Ser Leu Ile Thr Ser
            180                 185                 190 atg cag atc att cag ttc aac gtt ggc ttc tac atc gtc tgg aag tac              624
Met Gln Ile Ile Gln Phe Asn Val Gly Phe Tyr Ile Val Trp Lys Tyr
        195                 200                 205 cgg aac att ccc tgc tac cga caa gat gga atg aga atg ttt ggc tgg              672
Arg Asn Ile Pro Cys Tyr Arg Gln Asp Gly Met Arg Met Phe Gly Trp
    210                 215                 220 ttt ttc aac tac ttc tac gtt ggt act gtc ctg tgt ctg ttc ctc aac              720
Phe Phe Asn Tyr Phe Tyr Val Gly Thr Val Leu Cys Leu Phe Leu Asn
225                 230                 235                 240 ttc tac gtg cag acc tac atc gtc cga aag cac aag gga gcc aaa aag              768
Phe Tyr Val Gln Thr Tyr Ile Val Arg Lys His Lys Gly Ala Lys Lys
                245                 250                 255 att cag tga                                                                   777
Ile Gln <210> SEQ ID NO 47
<211> LENGTH: 258
<212> TYPE: PRT
<213> ORGANISM: Euglena gracilis

<400> SEQUENCE: 47

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
```

```
            130                 135                 140
Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 48
<211> LENGTH: 14554
<212> TYPE: DNA
<213> ORGANISM: Artificial Sequence
<220> FEATURE:
<223> OTHER INFORMATION: Plasmid pZKL1-2SR9G85

<400> SEQUENCE: 48
cgatagttgg agcaagggag aaatgtagag tgtgaaagac tcactatggt ccgggcttat    60
ctcgaccaat agccaaagtc tggagtttct gagagaaaaa ggcaagatac gtatgtaaca   120
aagcgacgca tggtacaata ataccggagg catgtatcat agagagttag tggttcgatg   180
atggcactgg tgcctggtat gactttatac ggctgactac atatttgtcc tcagacatac   240
aattacagtc aagcacttac ccttggacat ctgtaggtac ccccggcca agacgatctc    300 agcgtgtcgt atgtcggatt ggcgtagctc cctcgctcgt caattggctc ccatctactt   360
tcttctgctt ggctacaccc agcatgtctg ctatggctcg ttttcgtgcc ttatctatcc   420
tcccagtatt accaactcta atgacatga tgtgattggg tctacacttt catatcagag    480
ataaggagta gcacagttgc ataaaaagcc caactctaat cagcttcttc ctttcttgta   540
attagtacaa aggtgattag cgaaatctgg aagcttagtt ggccctaaaa aaatcaaaaa   600
aagcaaaaaa cgaaaacga aaaccacag ttttgagaac agggaggtaa cgaaggatcg    660
tatatatata tatatatata tatacccacg gatcccgaga ccggcctttg attcttccct   720
acaaccaacc attctcacca ccctaattca caaccatggc tgccgtcatc gaggtggcca   780
acgagttcgt cgctatcact gccgagaccc ttcccaaggt ggactatcag cgactctggc   840
gagacatcta ctcctgcgag ctcctgtact tctccattgc tttcgtcatc ctcaagttta   900
cccttggcga gctctcggat tctggcaaaa agattctgcg agtgctgttc aagtggtaca   960
acctcttcat gtccgtcttt tcgctggtgt ccttcctctg tatgggttac gccatctaca  1020
ccgttggact gtactccaac gaatgcgaca gagctttcga caacagcttg ttccgatttg  1080
ccaccaaggt cttctactat tccaagtttc tggagtacat cgactctttc taccttcccc  1140
tcatggccaa gctctgtcc tttctgcagt tctttcatca cttgggagct cctatggaca  1200
tgtggctctt cgtgcagtac tctggcgaat ccatttggat ctttgtgttc ctgaacggat  1260
tcattcactt tgtcatgtac ggctactatt ggacacggct gatgaagttc aactttccca  1320
```

```
tgcccaagca gctcattacc gcaatgcaga tcacccagtt caacgttggc ttctacctcg   1380
tgtggtggta caaggacatt ccctgttacc gaaaggatcc catgcgaatg ctggcctgga   1440
tcttcaacta ctggtacgtc ggtaccgttc ttctgctctt catcaacttc tttgtcaagt   1500
cctacgtgtt tcccaagcct aagactgccg acaaaaaggt ccagggcgcc ggtcccgctc   1560
gacctgccgg acttcctccc gctacctact acgactctct ggccgtcatg ggatccgtga   1620
aggcttctcg acaggctctg cccctcgtca tcgacggaaa ggtgtacgac gtctccgctt   1680
gggtgaactt ccaccctggt ggagctgaaa tcattgagaa ctaccaggga cgagatgcta   1740
ctgacgcctt catggttatg cactctcagg aagccttcga caagctcaag cgaatgccca   1800
agatcaacca ggcttccgag ctgcctcccc aggctgccgt caacgaagct caggaggatt   1860
tccgaaagct ccgagaagag ctgatcgcca ctggcatgtt tgacgcctct ccctctggt    1920
actcgtacaa gatcttgacc accctgggtc ttggcgtgct tgccttcttc atgctggtcc   1980
agtaccacct gtacttcatt ggtgctctcg tgctcggtat gcactaccag caaatgggat   2040
ggctgtctca tgacatctgc caccaccaga ccttcaagaa ccgaaactgg aataacgtcc   2100
tgggtctggt cttggcaac ggactccagg gcttctccgt gacctggtgg aaggacagac    2160
acaacgccca tcattctgct accaacgttc agggtcacga tccgacatt gataacctgc     2220
ctctgctcgc ctggtccgag gacgatgtca ctcgagcttc tcccatctcc cgaaagctca   2280
ttcagttcca acagtactat ttcctggtca tctgtattct cctgcgattc atctggtgtt   2340
tccagtctgt gctgaccgtt cgatccctca aggaccgaga caaccagttc taccgatctc   2400
agtacaagaa gaggccatt ggactcgctc tgcactggac tctcaagacc ctgttccacc     2460
tcttctttat gcctccatc ctgacctcga tgctggtgtt cttgtttcc gagctcgtcg      2520
gtggcttcgg aattgccatc gtggtcttca tgaaccacta ccctctggag aagatcggtg   2580
attccgtctg ggacggacat ggcttctctg tgggtcagat ccatgagacc atgaacattc   2640
gacgaggcat cattactgac tggttctttg gaggcctgaa ctaccagatc gagcaccatc   2700
tctggcccac cctgcctcga cacaacctca ctgccgtttc ctaccaggtg aacagctgt    2760
gccagaagca caacctcccc taccgaaacc ctctgcccca tgaaggtctc gtcatcctgc   2820
tccgatacct gtcccagttc gctcgaatgg ccgagaagca gcccggtgcc aaggctcagt   2880
aagcggccgc atgagaagat aaatatataa atacattgag atattaaatg cgctagatta   2940
gagagcctca tactgctcgg agagaagcca agacgagtac tcaaagggga ttacaccatc   3000
catatccaca gacacaagct ggggaaaggt tctatataca ctttccggaa taccgtagtt   3060
tccgatgtta tcaatggggg cagccaggat ttcaggcact tcggtgtctc ggggtgaaat   3120
ggcgttcttg gcctccatca agtcgtacca tgtcttcatt tgcctgtcaa agtaaaacag   3180
aagcagatga agaatgaact tgaagtgaag gaatttaaat gtaacgaaac tgaaatttga   3240
ccagatattg tgtccgcggt ggagctccag cttttgttcc ctttagtgag ggttaatttc   3300
gagcttggcg taatcatggt catagctgtt tcctgtgtga aattgttatc cgctcacaag   3360
cttccacaca acgtacgata gttagtagac aacaatcaga acatctccct ccttatataa   3420
tcacacaggc cagaacgcgc taaactaaag cgctttggac actatgttac attggcattg   3480
attgaactga accacagtc tccctcgcct gaatcgagca atggatgttg tcggaagtca    3540
acttcactag aagagcggtt ctatgccttg tcaagatcat atcataaact cactctgtat   3600
taccccatct atagaaacact tgttatgaat gggcggaaac attccgctat atgcaccttt   3660
ccacactaat gcaaagatgt gcatcttcaa cgggtagtaa gactggttcc gacttccgtt   3720
```

```
gcatggagag caatgacctc gataatgcga acatccccca catatacact cttacacagg    3780
ccaatataat ctgtgcattt actaaatatt taagtctatg cacctgcttg atgaaaagcg    3840
gcacggatgg tatcatctag tttccgccaa tccaagaacc aactgtgttg gcagtggtgt    3900
agcccatggc acacagacca aagatgaaaa tacagacatc ggcggttcga gccgtggtgc    3960
ctcgagcaac acccttgtaa tgcaaaagag gagggtaaat gtacaccaga ggcacacatg    4020
caaacgatcc ggtgagagcg acgaaccgat cgagatcgtc ggcacctccc catgcaacaa    4080
aggcggtgac aaacacaagg aagaaccgga aaatgttctt ctgccacttg atggtagagt    4140
tgtacttgcc tgatcgggtg aagagaccat tctcgatgat tcggatggcg cgccagctgc    4200
attaatgaat cggccaacgc gcggggagag gcggtttgcg tattgggcgc tcttccgctt    4260
cctcgctcac tgactcgctg cgctcggtcg ttcggctgcg gcgagcggta tcagctcact    4320
caaaggcggt aatacggtta ccacagaat cagggataa cgcaggaaag aacatgtgag    4380
caaaaggcca gcaaaaggcc aggaaccgta aaaaggccgc gttgctggcg ttttccata    4440 ggctccgccc ccctgacgag catcacaaaa atcgacgctc aagtcagagg tggcgaaacc    4500
cgacaggact ataagatac caggcgtttc cccctggaag ctccctcgtg cgctctcctg    4560
ttccgaccct gccgcttacc ggatacctgt ccgcctttct cccttcggga agcgtggcgc    4620
tttctcatag ctcacgctgt aggtatctca gttcggtgta ggtcgttcgc tccaagctgg    4680
gctgtgtgca cgaaccccc gttcagcccg accgctgcgc cttatccggt aactatcgtc    4740
ttgagtccaa cccggtaaga cacgacttat cgccactggc agcagccact ggtaacagga    4800
ttagcagagc gaggtatgta ggcggtgcta cagagttctt gaagtggtgg cctaactacg    4860
gctacactag aagaacagta tttggtatct gcgctctgct gaagccagtt accttcggaa    4920
aaagagttgg tagctcttga tccggcaaac aaaccaccgc tggtagcggt ggtttttttg    4980
tttgcaagca gcagattacg cgcagaaaaa aaggatctca agaagatcct ttgatctttt    5040
ctacggggtc tgacgctcag tggaacgaaa actcacgtta agggattttg gtcatgagat    5100
tatcaaaaag gatcttcacc tagatccttt taaattaaaa atgaagtttt aaatcaatct    5160
aaagtatata tgagtaaact tggtctgaca gttaccaatg cttaatcagt gaggcaccta    5220
tctcagcgat ctgtctattt cgttcatcca tagttgcctg actccccgtc gtgtagataa    5280
ctacgatacg ggagggctta ccatctggcc ccagtgctgc aatgataccg cgagacccac    5340
gctcaccggc tccagattta tcagcaataa accagccagc cggaagggcc gagcgcagaa    5400
gtggtcctgc aactttatcc gcctccatcc agtctattaa ttgttgccgg gaagctagag    5460
taagtagttc gccagttaat agtttgcgca acgttgttgc cattgctaca ggcatcgtgg    5520
tgtcacgctc gtcgtttggt atggcttcat tcagctccgg ttcccaacga tcaaggcgag    5580
ttacatgatc ccccatgttg tgcaaaaaag cggttagctc cttcggtcct ccgatcgttg    5640
tcagaagtaa gttggccgca gtgttatcac tcatggttat ggcagcactg cataattctc    5700
ttactgtcat gccatccgta agatgctttt ctgtgactgg tgagtactca accaagtcat    5760
tctgagaata gtgtatgcgg cgaccgagtt gctcttgccc ggcgtcaata cgggataata    5820
ccgcgccaca tagcagaact ttaaaagtgc tcatcattg aaaacgttct tcggggcgaa    5880
aactctcaag gatcttaccg ctgttgagat ccagttcgat gtaacccact cgtgcaccca    5940
actgatcttc agcatctttt actttcacca gcgtttctgg gtgagcaaaa acaggaaggc    6000
aaaatgccgc aaaaaaggga ataagggcga cacggaaatg ttgaatactc atactcttcc    6060
```

```
tttttcaata ttattgaagc atttatcagg gttattgtct catgagcgga tacatatttg   6120
aatgtattta gaaaataaaa caaatagggg ttccgcgcac atttccccga aaagtgccac   6180
ctgatgcggt gtgaaatacc gcacagatgc gtaaggagaa ataccgcat caggaaattg    6240 taagcgttaa tattttgtta aaattcgcgt taaattttg ttaaatcagc tcattttta    6300 accaataggc cgaaatcggc aaaatccctt ataaatcaaa agaatagacc gagatagggt   6360
tgagtgttgt tccagtttgg aacaagagtc cactattaaa gaacgtggac tccaacgtca   6420
aagggcgaaa aaccgtctat cagggcgatg gcccactacg tgaaccatca ccctaatcaa   6480
gttttttggg gtcgaggtgc cgtaaagcac taaatcggaa ccctaaaggg agcccccgat   6540
ttagagcttg acggggaaag ccggcgaacg tggcgagaaa ggaagggaag aaagcgaaag   6600
gagcgggcgc tagggcgctg gcaagtgtag cggtcacgct gcgcgtaacc accacacccg   6660
ccgcgcttaa tgcgccgcta cagggcgcgt ccattcgcca ttcaggctgc gcaactgttg   6720
ggaagggcga tcggtgcggg cctcttcgct attacgccag ctggcgaaag ggggatgtgc   6780
tgcaaggcga ttaagttggg taacgccagg gttttcccag tcacgacgtt gtaaaacgac   6840
ggccagtgaa ttgtaatacg actcactata gggcgaattg ggcccgacgt cgcatgctta   6900
gaagtgagga ttacaagaag cctctggata tcaatgatga acgtactcag cggctggtca   6960
agcatttcga ccgtcgaatc gacgaggtgt tcacctttga caagcgaggg ttcccaattg   7020
atcacgttct cgagttgttc aaatcttctc tcaacatctc tctgcatgaa ctatctctgt   7080
tgacgaacgt gtcacccact gttcctcgaa cgcccttctc cgagtttggt ctgaacatct   7140
tcgatctcaa actgaccccc gcagtgatca atagtgccat gccactgccg atgcggtgcg   7200
aacatccctg gagggattct cggagctcta cacaatgcag attctgtcgt cgagtactct   7260
ctaccttgct cgaatgactt attgtgctac tactgcactc atgcttcgat catgtgccct   7320
actgcacccc aaatttggtg atctgattga gacagagtac cctcttcagc tgattcagaa   7380
gatcatcagc aacatgaatg atgtggttga ccaggcaggc tgttgtagtc acgtccttca   7440
cttcaagttc attcttcatc tgcttctgtt ttactttgac aggcaaatga agacatggta   7500
cgacttgatg gaggccaaga acgccatttc accccgagac accgaagtgc ctgaaatcct   7560
ggctgccccc attgataaca tcggaaacta cggtattccg gaaagtgtat atagaacctt   7620
tccccagctt gtgtctgtgg atatggatgg tgtaatcccc ttaattaact cacctgcagg   7680
attgagacta tgaatggatt cccgtgcccg tattactcta ctaatttgat cttggaacgc   7740
gaaaatacgt ttctaggact ccaaagaatc tcaactcttg tccttactaa atatactacc   7800
catagttgat ggtttacttg aacagagagg acatgttcac ttgacccaaa gtttctcgca   7860
tctcttggat atttgaacaa cggcgtccac tgaccgtcag ttatccagtc acaaaacccc   7920
cacattcata cattcccatg tacgtttaca aagttctcaa ttccatcgtg caaatcaaaa   7980
tcacatctat tcattcatca tatataaacc catcatgtct actaacactc acaactccat   8040
agaaaacatc gactcagaac acacgctcca tgcggccgct aggcaacgg gcttgatgac    8100 agcgggagga gtgcccacat tgtttcggtt tcgaagaac aggacaccct tgccagctcc    8160
ctcggcacca gcggagggtt caacccactg gcacattcgt gcagatcggt acatggctcg   8220
aatgaatcct cgaggaccgt cctggacatc agctcgatag tgcttgccca tgataggttt   8280
gatggcctcg gtagcttcgt ccgcattgta gaagggaatg gaagagacgt agtgatgcag   8340
gacgtgagtc tcgataatgc cgtggagcag atgacgtcca atgaagccca tctctcggtc   8400
gatggttgca gcggcaccct gcacaaagtt ccactcgtcg ttggtgtagt ggggaagagt   8460
```

```
aggatctgtg tgctgcagaa aggtaatggc gacgagccag tggttaaccc acaagtaggg    8520
aacgaagtac cagatggcca tgttgtagaa tccgaacttc tgaacgagaa agtacagagc    8580
ggtggccata agaccaatgc caatgtcgga gagcacgatg agcttggcgt cgctgttctc    8640
gtacagagga gatcggggat cgaaatggtt aactccaccg ccaagaccgt tgtgctttcc    8700
cttgcctcga ccctctcgct gccgctcatg gtagttgtgt ccagtaacgt tggtaatgag    8760
atagttgggc caaccgacca gttgctgaag cacaagcatg agcagggtga aagcaggagt    8820
ttcctcggta agatgggcga gttcgtgggt catcttgccg agtcgagtag cttgctgctc    8880
tcgggttcga ggaacgaaga ccatgtctcg ctccatgttt ccagtggcct tgtgatgctt    8940
ccggtgggag atttgccagc tgaagtaggg aacaagcagg gaagagtgaa gcacccagcc    9000
agtaatgtcg ttgatgattc gggaatcgga gaaagcacca tgtccacact cgtgggcaat    9060
gacccacagt ccagtaccga agagtccctg aagaacggtg tacacagccc acagaccggc    9120
tcgagcagga gtggagggaa tgtactcggg tgtcacaaag ttgtaccaga tgctgaaagt    9180
ggtagtcagg aggacaatgt ctcgaagaat gtagccgtat cccttgagag cagatcgctt    9240
gaagcagtgc ttgggaatag cgttgtagat gtccttgatg gtgaagtcgg gaacttcgaa    9300
ctggttgccg taggtatcca gcatgacacc gtactcggac ttgggcttgg caatgtccac    9360
ctcggacatg gaagacagcg atgtagagga ggccgagtgt ctgggagaat cggagggaga    9420
gacggcagca gactccgagt cggtcacagt ggtggaagtg acggttcgtc ggagggcagg    9480
gttctgcttg gcagagccg aggtggaggc catggccatt gctgtagata tgtcttgtgt    9540
gtaagggggt tggggtggtt gtttgtgttc ttgacttttg tgttagcaag ggaagacggg    9600
caaaaaagtg agtgtggttg ggagggagag acgagcctta tatataatgc ttgtttgtgt    9660
ttgtgcaagt ggacgccgaa acgggcagga gccaaactaa acaaggcaga caatgcgagc    9720
ttaattggat tgcctgatgg gcaggggtta gggctcgatc aatgggggtg cgaagtgaca    9780
aaattgggaa ttaggttcgc aagcaaggct gacaagactt tggcccaaac atttgtacgc    9840
ggtggacaac aggagccacc catcgtctgt cacgggctag ccggtcgtgc gtcctgtcag    9900
gctccaccta ggctccatgc cactccatac aatcccacta gtgtaccgct aggccgcttt    9960
tagctcccat ctaagacccc cccaaaacct ccactgtaca gtgcactgta ctgtgtggcg   10020
atcaagggca agggaaaaaa ggcgcaaaca tgcacgcatg gaatgacgta ggtaaggcgt   10080
tactagactg aaaagtggca catttcggcg tgccaaaggg tcctaggtgc gtttcgcgag   10140
ctgggcgcca ggcaagccg ctccaaaacg cctctccgac tccctccagc ggcctccata   10200
tccccatccc tctccacagc aatgttgtta agccttgcaa acgaaaaaat agaaaggcta   10260
ataagcttcc aatattgtgg tgtacgctgc ataacgcaac aatgagcgcc aaacaacaca   10320
cacacacagc acacagcagc attaaccacg atgaacagca tgaattctct ctcttgagct   10380
tttccataac aagttcttct gcctccagga agtccatggg tggtttgatc atggttttgg   10440
tgtagtggta gtgcagtggt ggtattgtga ctggggatgt agttgagaat aagtcataca   10500
caagtcagct ttcttcgagc ctcatataag tataagtagt tcaacgtatt agcactgtac   10560
ccagcatctc cgtatcgaga aacacaacaa catgccccat tggacagatc atgcggatac   10620
acaggttgtg cagtatcata catactcgat cagacaggtc gtctgaccat catacaagct   10680
gaacaagcgc tccatacttg cacgctctct atatacacag ttaaattaca tatccatagt   10740
ctaacctcta acagttaatc ttctggtaag cctcccagcc agccttctgg tatcgcttgg   10800
```

```
cctcctcaat aggatctcgg ttctggccgt acagacctcg gccgacaatt atgatatccg   10860
ttccggtaga catgacatcc tcaacagttc ggtactgctg tccgagagcg tctcccttgt   10920
cgtcaagacc cacccccgggg gtcagaataa gccagtcctc agagtcgccc ttaggtcggt   10980
tctgggcaat gaagccaacc acaaactcgg ggtcggatcg ggcaagctca atggtctgct   11040
tggagtactc gccagtggcc agagagccct tgcaagacag ctcggccagc atgagcagac   11100
ctctggccag cttctcgttg ggagagggga ctaggaactc cttgtactgg gagttctcgt   11160
agtcagagac gtcctccttc ttctgttcag agacagtttc ctcggcacca gctcgcaggc   11220
cagcaatgat tccggttccg ggtacaccgt gggcgttggt gatatcggac cactcggcga   11280
ttcggtgaca ccggtactgg tgcttgacag tgttgccaat atctgcgaac tttctgtcct   11340
cgaacaggaa gaaaccgtgc ttaagagcaa gttccttgag ggggagcaca gtgccggcgt   11400
aggtgaagtc gtcaatgatg tcgatatggg ttttgatcat gcacacataa ggtccgacct   11460
tatcggcaag ctcaatgagc tccttggtgg tggtaacatc cagagaagca cacaggttgg   11520
ttttcttggc tgccacgagc ttgagcactc gagcggcaaa ggcggacttg tggacgttag   11580
ctcgagcttc gtaggagggc attttggtgg tgaagaggag actgaaataa atttagtctg   11640
cagaactttt tatcggaacc ttatctgggg cagtgaagta tatgttatgg taatagttac   11700
gagttagttg aacttataga tagactggac tatacggcta tcggtccaaa ttagaaagaa   11760
cgtcaatggc tctctgggcg tcgcctttgc cgacaaaaat gtgatcatga tgaaagccaa   11820
caatgacgtt gcagctgata ttgttgtcgg ccaaccgcgc cgaaaacgca gctgtcagac   11880
ccacagcctc caacgaagaa tgtatcgtca aagtgatcca agcacactca tagttggagt   11940
cgtactccaa aggcggcaat gacgagtcag acagatactc gtcgaccatt aattctcacg   12000
tgacacagat tattaacgtc tcgtaccaac cacagattac gacccattcg cagtcacagt   12060
tcactagggt ttgggttgca tccgttgaga gcggtttgtt tttaaccttc tccatgtgct   12120
cactcaggtt ttgggttcag atcaaatcaa ggcgtgaacc actttgtttg aggacaaatg   12180
tgacacaacc aaccagtgtc aggggcaagt ccgtgacaaa ggggaagata caatgcaatt   12240
actgacagtt acagactgcc tcgatgccct aaccttgccc caaaataaga caactgtcct   12300
cgtttaagcg caaccctatt cagcgtcacg tcataatagc gtttggatag cactagtcta   12360
tgaggagcgt tttatgttgc ggtgagggcg attggtgctc atatgggttc aattgaggtg   12420
gcggaacgag cttagtcttc aattgaggtg cgagcgacac aattgggtgt cacgtggcct   12480
aattgacctc gggtcgtgga gtccccagtt atacagcaac cacgaggtgc atgggtagga   12540
gacgtcacca gacaataggg tttttttttgg actggagagg gttgggcaaa agcgctcaac   12600
gggctgtttg gggagctgtg ggggaggaat tggcgatatt tgtgaggtta acggctccga   12660
tttgcgtgtt ttgtcgctcc tgcatctccc catacccata tcttccctcc ccacctcttt   12720
ccacgataat tttacggatc agcaataagg ttccttctcc tagtttccac gtccatatat   12780
atctatgctg cgtcgtcctt ttcgtgacat caccaaaaca catacaacca tggctctctc   12840
ccttactacc gagcagctgc tcgagcgacc cgacctggtt gccatcgacg gcattctcta   12900
cgatctggaa ggtcttgcca aggtccatcc cggatccgac ttgatcctcg cttctggtgc   12960
ctccgatgct tctcctctgt tctactccat gcacccttac gtcaagcccg agaactcgaa   13020
gctgcttcaa cagttcgtgc gaggcaagca cgaccgaacc tccaaggaca ttgtctacac   13080
ctacgactct ccctttgcac aggacgtcaa gcgaactatg cgagaggtca tgaaaggtcg   13140
gaactggtat gccacacctg gattctggct gcgaaccgtt ggcatcattg ctgtcaccgc   13200
```

```
ctttttgcgag tggcactggg ctactaccgg aatggtgctg tggggtctct tgactggatt    13260
catgcacatg cagatcggcc tgtccattca gcacgatgcc tctcatggtg ccatcagcaa    13320
aaagccctgg gtcaacgctc tctttgccta cggcatcgac gtcattggat cgtccagatg    13380
gatctggctg cagtctcaca tcatgcgaca tcacacctac accaatcagc atggtctcga    13440
cctggatgcc gagtccgcag aaccattcct tgtgttccac aactaccctg ctgccaacac    13500
tgctcgaaag tggtttcacc gattccaggc tggtacatg tacctcgtgc ttggagccta     13560
cggcgtttcg ctggtgtaca accctctcta catcttccga atgcagcaca acgacaccat    13620
tcccgagtct gtcacagcca tgcgagagaa cggctttctg cgacggtacc gaacccttgc    13680
attcgttatg cgagctttct tcatctttcg aaccgccttc ttgccctggt atctcactgg    13740
aacctccctg ctcatcacca ttcctctggt gcccactgct accggtgcct tcctcacctt    13800 cttttttcatc ttgtctcaca acttcgatgg ctcggagcga atccccgaca agaactgcaa    13860
ggtcaagagc tccgagaagg acgttgaagc cgatcagatc gactggtaca gagctcaggt    13920
ggagacctct tccacctacg gtggacccat tgccatgttc tttactggcg gtctcaactt    13980
ccagatcgag catcacctct ttcctcgaat gtcgtcttgg cactatccct tcgtgcagca    14040
agctgtccga gagtgttgcg aacgacacgg agttcggtac gtcttctacc ctaccattgt    14100
gggcaacatc atttccaccc tcaagtacat gcacaaagtc ggtgtggttc actgtgtcaa    14160
ggacgctcag gattcctaag cggccgcatg tacatacaag attatttata gaaatgaatc    14220
gcgatcgaac aaagagtacg agtgtacgag taggggatga tgataaaagt ggaagaagtt    14280
ccgcatcttt ggatttatca acgtgtagga cgatacttcc tgtaaaaatg caatgtcttt    14340
accataggtt ctgctgtaga tgttattaac taccattaac atgtctactt gtacagttgc    14400
agaccagttg gagtatagaa tggtacactt accaaaaagt gttgatggtt gtaactacga    14460
tatataaaac tgttgacggg atccccgctg atatgcctaa ggaacaatca aagaggaaga    14520
tattaattca gaatgctagt atacagttag ggat                                14554
```

<210> SEQ ID NO 49
<211> LENGTH: 2127
<212> TYPE: DNA
<213> ORGANISM: Artificial Sequence
<220> FEATURE:
<223> OTHER INFORMATION: Multizyme: E389D9eS/EgD8M gene fusion
<220> FEATURE:
<221> NAME/KEY: CDS
<222> LOCATION: (1)..(2127)
<223> OTHER INFORMATION: Multizyme: E389D9eS/EgD8M gene fusion
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: US-2008-0254191-A1
<311> PATENT FILING DATE: 2008-04-03
<312> PUBLICATION DATE: 2008-10-16
<313> RELEVANT RESIDUES IN SEQ ID NO: (1)..(2127)
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: WO 2008/124048
<311> PATENT FILING DATE: 2008-04-03
<312> PUBLICATION DATE: 2008-10-16
<313> RELEVANT RESIDUES IN SEQ ID NO: (1)..(2127)

<400> SEQUENCE: 49

```
atg gct gcc gtc atc gag gtg gcc aac gag ttc gtc gct atc act gcc    48
Met Ala Ala Val Ile Glu Val Ala Asn Glu Phe Val Ala Ile Thr Ala
1               5                   10                  15
```

-continued

| | | |
|---|---|---|
| gag acc ctt ccc aag gtg gac tat cag cga ctc tgg cga gac atc tac<br>Glu Thr Leu Pro Lys Val Asp Tyr Gln Arg Leu Trp Arg Asp Ile Tyr<br>20      25          30 | | 96 |
| tcc tgc gag ctc ctg tac ttc tcc att gct ttc gtc atc ctc aag ttt<br>Ser Cys Glu Leu Leu Tyr Phe Ser Ile Ala Phe Val Ile Leu Lys Phe<br>35          40          45 | | 144 |
| acc ctt ggc gag ctc tcg gat tct ggc aaa aag att ctg cga gtg ctg<br>Thr Leu Gly Glu Leu Ser Asp Ser Gly Lys Lys Ile Leu Arg Val Leu<br>50          55          60 | | 192 |
| ttc aag tgg tac aac ctc ttc atg tcc gtc ttt tcg ctg gtg tcc ttc<br>Phe Lys Trp Tyr Asn Leu Phe Met Ser Val Phe Ser Leu Val Ser Phe<br>65          70          75          80 | | 240 |
| ctc tgt atg ggt tac gcc atc tac acc gtt gga ctg tac tcc aac gaa<br>Leu Cys Met Gly Tyr Ala Ile Tyr Thr Val Gly Leu Tyr Ser Asn Glu<br>85          90          95 | | 288 |
| tgc gac aga gct ttc gac aac agc ttg ttc cga ttt gcc acc aag gtc<br>Cys Asp Arg Ala Phe Asp Asn Ser Leu Phe Arg Phe Ala Thr Lys Val<br>100         105         110 | | 336 |
| ttc tac tat tcc aag ttt ctg gag tac atc gac tct ttc tac ctt ccc<br>Phe Tyr Tyr Ser Lys Phe Leu Glu Tyr Ile Asp Ser Phe Tyr Leu Pro<br>115         120         125 | | 384 |
| ctc atg gcc aag cct ctg tcc ttt ctg cag ttc ttt cat cac ttg gga<br>Leu Met Ala Lys Pro Leu Ser Phe Leu Gln Phe Phe His His Leu Gly<br>130         135         140 | | 432 |
| gct cct atg gac atg tgg ctc ttc gtg cag tac tct ggc gaa tcc att<br>Ala Pro Met Asp Met Trp Leu Phe Val Gln Tyr Ser Gly Glu Ser Ile<br>145         150         155         160 | | 480 |
| tgg atc ttt gtg ttc ctg aac gga ttc att cac ttt gtc atg tac ggc<br>Trp Ile Phe Val Phe Leu Asn Gly Phe Ile His Phe Val Met Tyr Gly<br>165         170         175 | | 528 |
| tac tat tgg aca cgg ctg atg aag ttc aac ttt ccc atg ccc aag cag<br>Tyr Tyr Trp Thr Arg Leu Met Lys Phe Asn Phe Pro Met Pro Lys Gln<br>180         185         190 | | 576 |
| ctc att acc gca atg cag atc acc cag ttc aac gtt ggc ttc tac ctc<br>Leu Ile Thr Ala Met Gln Ile Thr Gln Phe Asn Val Gly Phe Tyr Leu<br>195         200         205 | | 624 |
| gtg tgg tgg tac aag gac att ccc tgt tac cga aag gat ccc atg cga<br>Val Trp Trp Tyr Lys Asp Ile Pro Cys Tyr Arg Lys Asp Pro Met Arg<br>210         215         220 | | 672 |
| atg ctg gcc tgg atc ttc aac tac tgg tac gtc ggt acc gtt ctt ctg<br>Met Leu Ala Trp Ile Phe Asn Tyr Trp Tyr Val Gly Thr Val Leu Leu<br>225         230         235         240 | | 720 |
| ctc ttc atc aac ttc ttt gtc aag tcc tac gtg ttt ccc aag cct aag<br>Leu Phe Ile Asn Phe Phe Val Lys Ser Tyr Val Phe Pro Lys Pro Lys<br>245         250         255 | | 768 |
| act gcc gac aaa aag gtc cag ggc gcc ggt ccc gct cga cct gcc gga<br>Thr Ala Asp Lys Lys Val Gln Gly Ala Gly Pro Ala Arg Pro Ala Gly<br>260         265         270 | | 816 |
| ctt cct ccc gct acc tac tac gac tct ctg gcc gtc atg gga tcc gtg<br>Leu Pro Pro Ala Thr Tyr Tyr Asp Ser Leu Ala Val Met Gly Ser Val<br>275         280         285 | | 864 |
| aag gct tct cga cag gct ctg ccc ctc gtc atc gac gga aag gtg tac<br>Lys Ala Ser Arg Gln Ala Leu Pro Leu Val Ile Asp Gly Lys Val Tyr<br>290         295         300 | | 912 |
| gac gtc tcc gct tgg gtg aac ttc cac cct ggt gga gct gaa atc att<br>Asp Val Ser Ala Trp Val Asn Phe His Pro Gly Gly Ala Glu Ile Ile<br>305         310         315         320 | | 960 |
| gag aac tac cag gga cga gat gct act gac gcc ttc atg gtt atg cac<br>Glu Asn Tyr Gln Gly Arg Asp Ala Thr Asp Ala Phe Met Val Met His<br>325         330         335 | | 1008 |

-continued

```
tct cag gaa gcc ttc gac aag ctc aag cga atg ccc aag atc aac cag      1056
Ser Gln Glu Ala Phe Asp Lys Leu Lys Arg Met Pro Lys Ile Asn Gln
            340                 345                 350 gct tcc gag ctg cct ccc cag gct gcc gtc aac gaa gct cag gag gat      1104
Ala Ser Glu Leu Pro Pro Gln Ala Ala Val Asn Glu Ala Gln Glu Asp
        355                 360                 365 ttc cga aag ctc cga gaa gag ctg atc gcc act ggc atg ttt gac gcc      1152
Phe Arg Lys Leu Arg Glu Glu Leu Ile Ala Thr Gly Met Phe Asp Ala
    370                 375                 380 tct ccc ctc tgg tac tcg tac aag atc ttg acc acc ctg ggt ctt ggc      1200
Ser Pro Leu Trp Tyr Ser Tyr Lys Ile Leu Thr Thr Leu Gly Leu Gly
385                 390                 395                 400 gtg ctt gcc ttc ttc atg ctg gtc cag tac cac ctg tac ttc att ggt      1248
Val Leu Ala Phe Phe Met Leu Val Gln Tyr His Leu Tyr Phe Ile Gly
                405                 410                 415 gct ctc gtg ctc ggt atg cac tac cag caa atg gga tgg ctg tct cat      1296
Ala Leu Val Leu Gly Met His Tyr Gln Gln Met Gly Trp Leu Ser His
            420                 425                 430 gac atc tgc cac cac cag acc ttc aag aac cga aac tgg aat aac gtc      1344
Asp Ile Cys His His Gln Thr Phe Lys Asn Arg Asn Trp Asn Asn Val
        435                 440                 445 ctg ggt ctg gtc ttt ggc aac gga ctc cag ggc ttc tcc gtg acc tgg      1392
Leu Gly Leu Val Phe Gly Asn Gly Leu Gln Gly Phe Ser Val Thr Trp
    450                 455                 460 tgg aag gac aga cac aac gcc cat cat tct gct acc aac gtt cag ggt      1440
Trp Lys Asp Arg His Asn Ala His His Ser Ala Thr Asn Val Gln Gly
465                 470                 475                 480 cac gat ccc gac att gat aac ctg cct ctc gcc tgg tcc gag gac          1488
His Asp Pro Asp Ile Asp Asn Leu Pro Leu Ala Trp Ser Glu Asp
                485                 490                 495 gat gtc act cga gct tct ccc atc tcc cga aag ctc att cag ttc caa      1536
Asp Val Thr Arg Ala Ser Pro Ile Ser Arg Lys Leu Ile Gln Phe Gln
            500                 505                 510 cag tac tat ttc ctg gtc atc tgt att ctc ctg cga ttc atc tgg tgt      1584
Gln Tyr Tyr Phe Leu Val Ile Cys Ile Leu Leu Arg Phe Ile Trp Cys
        515                 520                 525 ttc cag tct gtg ctg acc gtt cga tcc ctc aag gac cga gac aac cag      1632
Phe Gln Ser Val Leu Thr Val Arg Ser Leu Lys Asp Arg Asp Asn Gln
    530                 535                 540 ttc tac cga tct cag tac aag aaa gag gcc att gga ctc gct ctg cac      1680
Phe Tyr Arg Ser Gln Tyr Lys Lys Glu Ala Ile Gly Leu Ala Leu His
545                 550                 555                 560 tgg act ctc aag acc ctg ttc cac ctc ttc ttt atg ccc tcc atc ctg      1728
Trp Thr Leu Lys Thr Leu Phe His Leu Phe Phe Met Pro Ser Ile Leu
                565                 570                 575 acc tcg atg ctg gtg ttc ttt gtt tcc gag ctc gtc ggt ggc ttc gga      1776
Thr Ser Met Leu Val Phe Phe Val Ser Glu Leu Val Gly Gly Phe Gly
            580                 585                 590 att gcc atc gtg gtc ttc atg aac cac tac cct ctg gag aag atc ggt      1824
Ile Ala Ile Val Val Phe Met Asn His Tyr Pro Leu Glu Lys Ile Gly
        595                 600                 605 gat tcc gtc tgg gac gga cat ggc ttc tct gtg ggt cag atc cat gag      1872
Asp Ser Val Trp Asp Gly His Gly Phe Ser Val Gly Gln Ile His Glu
    610                 615                 620 acc atg aac att cga cga ggc atc att act gac tgg ttc ttt gga ggc      1920
Thr Met Asn Ile Arg Arg Gly Ile Ile Thr Asp Trp Phe Phe Gly Gly
625                 630                 635                 640 ctg aac tac cag atc gag cac cat ctc tgg ccc acc ctg cct cga cac      1968
Leu Asn Tyr Gln Ile Glu His His Leu Trp Pro Thr Leu Pro Arg His
```

|   |   |   |   |   |   |   |   |   |   |   |   |   |   |   |   |      |
|---|---|---|---|---|---|---|---|---|---|---|---|---|---|---|---|------|
|   |   |   |   | 645 |   |   |   |   | 650 |   |   |   |   | 655 |   |      |
| aac | ctc | act | gcc | gtt | tcc | tac | cag | gtg | gaa | cag | ctg | tgc | cag | aag | cac | 2016 |
| Asn | Leu | Thr | Ala | Val | Ser | Tyr | Gln | Val | Glu | Gln | Leu | Cys | Gln | Lys | His |      |
|   |   |   | 660 |   |   |   |   | 665 |   |   |   |   | 670 |   |   |      |
| aac | ctc | ccc | tac | cga | aac | cct | ctg | ccc | cat | gaa | ggt | ctc | gtc | atc | ctg | 2064 |
| Asn | Leu | Pro | Tyr | Arg | Asn | Pro | Leu | Pro | His | Glu | Gly | Leu | Val | Ile | Leu |      |
|   |   | 675 |   |   |   |   | 680 |   |   |   |   | 685 |   |   |   |      |
| ctc | cga | tac | ctg | tcc | cag | ttc | gct | cga | atg | gcc | gag | aag | cag | ccc | ggt | 2112 |
| Leu | Arg | Tyr | Leu | Ser | Gln | Phe | Ala | Arg | Met | Ala | Glu | Lys | Gln | Pro | Gly |      |
|   | 690 |   |   |   |   | 695 |   |   |   |   | 700 |   |   |   |   |      |
| gcc | aag | gct | cag | taa |   |   |   |   |   |   |   |   |   |   |   | 2127 |
| Ala | Lys | Ala | Gln |   |   |   |   |   |   |   |   |   |   |   |   |      |
| 705 |   |   |   |   |   |   |   |   |   |   |   |   |   |   |   |      |

<210> SEQ ID NO 50
<211> LENGTH: 708
<212> TYPE: PRT
<213> ORGANISM: Artificial Sequence
<220> FEATURE:
<223> OTHER INFORMATION: Synthetic Construct

<400> SEQUENCE: 50

Met Ala Ala Val Ile Glu Val Ala Asn Glu Phe Val Ala Ile Thr Ala
1               5                   10                  15

Glu Thr Leu Pro Lys Val Asp Tyr Gln Arg Leu Trp Arg Asp Ile Tyr
            20                  25                  30

Ser Cys Glu Leu Leu Tyr Phe Ser Ile Ala Phe Val Ile Leu Lys Phe
        35                  40                  45

Thr Leu Gly Glu Leu Ser Asp Ser Gly Lys Lys Ile Leu Arg Val Leu
    50                  55                  60

Phe Lys Trp Tyr Asn Leu Phe Met Ser Val Phe Ser Leu Val Ser Phe
65                  70                  75                  80

Leu Cys Met Gly Tyr Ala Ile Tyr Thr Val Gly Leu Tyr Ser Asn Glu
                85                  90                  95

Cys Asp Arg Ala Phe Asp Asn Ser Leu Phe Arg Phe Ala Thr Lys Val
            100                 105                 110

Phe Tyr Tyr Ser Lys Phe Leu Glu Tyr Ile Asp Ser Phe Tyr Leu Pro
        115                 120                 125

Leu Met Ala Lys Pro Leu Ser Phe Leu Gln Phe Phe His His Leu Gly
    130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Val Met Tyr Gly
                165                 170                 175

Tyr Tyr Trp Thr Arg Leu Met Lys Phe Asn Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
    210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp Lys Lys Val Gln Gly Ala Gly Pro Ala Arg Pro Ala Gly
            260                 265                 270

-continued

```
Leu Pro Pro Ala Thr Tyr Tyr Asp Ser Leu Ala Val Met Gly Ser Val
        275                 280                 285

Lys Ala Ser Arg Gln Ala Leu Pro Leu Val Ile Asp Gly Lys Val Tyr
        290                 295                 300

Asp Val Ser Ala Trp Val Asn Phe His Pro Gly Ala Glu Ile Ile
305                 310                 315                 320

Glu Asn Tyr Gln Gly Arg Asp Ala Thr Asp Ala Phe Met Val Met His
                325                 330                 335

Ser Gln Glu Ala Phe Asp Lys Leu Lys Arg Met Pro Lys Ile Asn Gln
                340                 345                 350

Ala Ser Glu Leu Pro Pro Gln Ala Ala Val Asn Glu Ala Gln Glu Asp
            355                 360                 365

Phe Arg Lys Leu Arg Glu Glu Leu Ile Ala Thr Gly Met Phe Asp Ala
        370                 375                 380

Ser Pro Leu Trp Tyr Ser Tyr Lys Ile Leu Thr Thr Leu Gly Leu Gly
385                 390                 395                 400

Val Leu Ala Phe Phe Met Leu Val Gln Tyr His Leu Tyr Phe Ile Gly
                405                 410                 415

Ala Leu Val Leu Gly Met His Tyr Gln Gln Met Gly Trp Leu Ser His
            420                 425                 430

Asp Ile Cys His His Gln Thr Phe Lys Asn Arg Asn Trp Asn Asn Val
        435                 440                 445

Leu Gly Leu Val Phe Gly Asn Gly Leu Gln Gly Phe Ser Val Thr Trp
        450                 455                 460

Trp Lys Asp Arg His Asn Ala His His Ser Ala Thr Asn Val Gln Gly
465                 470                 475                 480

His Asp Pro Asp Ile Asp Asn Leu Pro Leu Leu Ala Trp Ser Glu Asp
                485                 490                 495

Asp Val Thr Arg Ala Ser Pro Ile Ser Arg Lys Leu Ile Gln Phe Gln
            500                 505                 510

Gln Tyr Tyr Phe Leu Val Ile Cys Ile Leu Leu Arg Phe Ile Trp Cys
        515                 520                 525

Phe Gln Ser Val Leu Thr Val Arg Ser Leu Lys Asp Arg Asp Asn Gln
        530                 535                 540

Phe Tyr Arg Ser Gln Tyr Lys Lys Glu Ala Ile Gly Leu Ala Leu His
545                 550                 555                 560

Trp Thr Leu Lys Thr Leu Phe His Leu Phe Phe Met Pro Ser Ile Leu
                565                 570                 575

Thr Ser Met Leu Val Phe Phe Val Ser Glu Leu Val Gly Gly Phe Gly
            580                 585                 590

Ile Ala Ile Val Val Phe Met Asn His Tyr Pro Leu Glu Lys Ile Gly
        595                 600                 605

Asp Ser Val Trp Asp Gly His Gly Phe Ser Val Gly Gln Ile His Glu
610                 615                 620

Thr Met Asn Ile Arg Arg Gly Ile Ile Thr Asp Trp Phe Phe Gly Gly
625                 630                 635                 640

Leu Asn Tyr Gln Ile Glu His His Leu Trp Pro Thr Leu Pro Arg His
                645                 650                 655

Asn Leu Thr Ala Val Ser Tyr Gln Val Glu Gln Leu Cys Gln Lys His
            660                 665                 670

Asn Leu Pro Tyr Arg Asn Pro Leu Pro His Glu Gly Leu Val Ile Leu
        675                 680                 685

Leu Arg Tyr Leu Ser Gln Phe Ala Arg Met Ala Glu Lys Gln Pro Gly
```

Ala Lys Ala Gln
705

<210> SEQ ID NO 51
<211> LENGTH: 1434
<212> TYPE: DNA
<213> ORGANISM: Fusarium moniliforme
<220> FEATURE:
<221> NAME/KEY: CDS
<222> LOCATION: (1)..(1434)
<223> OTHER INFORMATION: synthetic delta-12 desaturase (codon-optimized for Yarrowia lipolytica)
<300> PUBLICATION INFORMATION:
<302> TITLE: DELTA-12 DESATURASES SUITABLE FOR ALTERING LEVELS OF POLYUNSATURATED FATTY ACIDS IN OLEAGINOUS YEAST
<310> PATENT DOCUMENT NUMBER: WO 2005/047485
<311> PATENT FILING DATE: 2004-11-12
<312> PUBLICATION DATE: 2005-05-26
<313> RELEVANT RESIDUES IN SEQ ID NO: (1)..(1434)
<300> PUBLICATION INFORMATION:
<302> TITLE: DELTA-12 DESATURASES SUITABLE FOR ALTERING LEVELS OF POLYUNSATURATED FATTY ACIDS IN OLEAGINOUS YEAST
<310> PATENT DOCUMENT NUMBER: US 2005-0216975-A1
<311> PATENT FILING DATE: 2004-11-10
<312> PUBLICATION DATE: 2005-09-29
<313> RELEVANT RESIDUES IN SEQ ID NO: (1)..(1434)

<400> SEQUENCE: 51

```
atg gcc tcc acc tcg gct ctg ccc aag cag aac cct gcc ctc cga cga      48
Met Ala Ser Thr Ser Ala Leu Pro Lys Gln Asn Pro Ala Leu Arg Arg
1               5                  10                  15 acc gtc act tcc acc act gtg acc gac tcg gag tct gct gcc gtc tct      96
Thr Val Thr Ser Thr Thr Val Thr Asp Ser Glu Ser Ala Ala Val Ser
            20                  25                  30 ccc tcc gat tct ccc aga cac tcg gcc tcc tct aca tcg ctg tct tcc     144
Pro Ser Asp Ser Pro Arg His Ser Ala Ser Ser Thr Ser Leu Ser Ser
        35                  40                  45 atg tcc gag gtg gac att gcc aag ccc aag tcc gag tac ggt gtc atg     192
Met Ser Glu Val Asp Ile Ala Lys Pro Lys Ser Glu Tyr Gly Val Met
    50                  55                  60 ctg gat acc tac ggc aac cag ttc gaa gtt ccc gac ttc acc atc aag     240
Leu Asp Thr Tyr Gly Asn Gln Phe Glu Val Pro Asp Phe Thr Ile Lys
65                  70                  75                  80 gac atc tac aac gct att ccc aag cac tgc ttc aag cga tct gct ctc     288
Asp Ile Tyr Asn Ala Ile Pro Lys His Cys Phe Lys Arg Ser Ala Leu
                85                  90                  95 aag gga tac ggc tac att ctt cga gac att gtc ctc ctg act acc act     336
Lys Gly Tyr Gly Tyr Ile Leu Arg Asp Ile Val Leu Leu Thr Thr Thr
            100                 105                 110 ttc agc atc tgg tac aac ttt gtg aca ccc gag tac att ccc tcc act     384
Phe Ser Ile Trp Tyr Asn Phe Val Thr Pro Glu Tyr Ile Pro Ser Thr
        115                 120                 125 cct gct cga gcc ggt ctg tgg gct gtg tac acc gtt ctt cag gga ctc     432
Pro Ala Arg Ala Gly Leu Trp Ala Val Tyr Thr Val Leu Gln Gly Leu
    130                 135                 140 ttc ggt act gga ctg tgg gtc att gcc cac gag tgt gga cat ggt gct     480
Phe Gly Thr Gly Leu Trp Val Ile Ala His Glu Cys Gly His Gly Ala
145                 150                 155                 160 ttc tcc gat tcc cga atc atc aac gac att act ggc tgg gtg ctt cac     528
Phe Ser Asp Ser Arg Ile Ile Asn Asp Ile Thr Gly Trp Val Leu His
                165                 170                 175 tct tcc ctg ctt gtt ccc tac ttc agc tgg caa atc tcc cac cgg aag     576
Ser Ser Leu Leu Val Pro Tyr Phe Ser Trp Gln Ile Ser His Arg Lys
            180                 185                 190
```

```
cat cac aag gcc act gga aac atg gag cga gac atg gtc ttc gtt cct      624
His His Lys Ala Thr Gly Asn Met Glu Arg Asp Met Val Phe Val Pro
        195                 200                 205 cga acc cga gag cag caa gct act cga ctc ggc aag atg acc cac gaa      672
Arg Thr Arg Glu Gln Gln Ala Thr Arg Leu Gly Lys Met Thr His Glu
210                 215                 220 ctc gcc cat ctt acc gag gaa act cct gct ttc acc ctg ctc atg ctt      720
Leu Ala His Leu Thr Glu Glu Thr Pro Ala Phe Thr Leu Leu Met Leu
225                 230                 235                 240 gtg ctt cag caa ctg gtc ggt tgg ccc aac tat ctc att acc aac gtt      768
Val Leu Gln Gln Leu Val Gly Trp Pro Asn Tyr Leu Ile Thr Asn Val
            245                 250                 255 act gga cac aac tac cat gag cgg cag cga gag ggt cga ggc aag gga      816
Thr Gly His Asn Tyr His Glu Arg Gln Arg Glu Gly Arg Gly Lys Gly
                260                 265                 270 aag cac aac ggt ctt ggc ggt gga gtt aac cat ttc gat ccc cga tct      864
Lys His Asn Gly Leu Gly Gly Gly Val Asn His Phe Asp Pro Arg Ser
        275                 280                 285 cct ctg tac gag aac agc gac gcc aag ctc atc gtg ctc tcc gac att      912
Pro Leu Tyr Glu Asn Ser Asp Ala Lys Leu Ile Val Leu Ser Asp Ile
290                 295                 300 ggc att ggt ctt atg gcc acc gct ctg tac ttt ctc gtt cag aag ttc      960
Gly Ile Gly Leu Met Ala Thr Ala Leu Tyr Phe Leu Val Gln Lys Phe
305                 310                 315                 320 gga ttc tac aac atg gcc atc tgg tac ttc gtt ccc tac ttg tgg gtt     1008
Gly Phe Tyr Asn Met Ala Ile Trp Tyr Phe Val Pro Tyr Leu Trp Val
            325                 330                 335 aac cac tgg ctc gtc gcc att acc ttt ctg cag cac aca gat cct act     1056
Asn His Trp Leu Val Ala Ile Thr Phe Leu Gln His Thr Asp Pro Thr
                340                 345                 350 ctt ccc cac tac acc aac gac gag tgg aac ttt gtg cga ggt gcc gct     1104
Leu Pro His Tyr Thr Asn Asp Glu Trp Asn Phe Val Arg Gly Ala Ala
        355                 360                 365 gca acc atc gac cga gag atg ggc ttc att gga cgt cat ctg ctc cac     1152
Ala Thr Ile Asp Arg Glu Met Gly Phe Ile Gly Arg His Leu Leu His
370                 375                 380 ggc att atc gag act cac gtc ctg cat cac tac gtc tct tcc att ccc     1200
Gly Ile Ile Glu Thr His Val Leu His His Tyr Val Ser Ser Ile Pro
385                 390                 395                 400 ttc tac aat gcg gac gaa gct acc gag gcc atc aaa cct atc atg ggc     1248
Phe Tyr Asn Ala Asp Glu Ala Thr Glu Ala Ile Lys Pro Ile Met Gly
            405                 410                 415 aag cac tat cga gct gat gtc cag gac ggt cct cga gga ttc att cga     1296
Lys His Tyr Arg Ala Asp Val Gln Asp Gly Pro Arg Gly Phe Ile Arg
                420                 425                 430 gcc atg tac cga tct gca cga atg tgc cag tgg gtt gaa ccc tcc gct     1344
Ala Met Tyr Arg Ser Ala Arg Met Cys Gln Trp Val Glu Pro Ser Ala
        435                 440                 445 ggt gcc gag gga gct ggc aag ggt gtc ctg ttc ttt cga aac cga aac     1392
Gly Ala Glu Gly Ala Gly Lys Gly Val Leu Phe Phe Arg Asn Arg Asn
450                 455                 460 aat gtg ggc act cct ccc gct gtc atc aag ccc gtt gcc taa              1434
Asn Val Gly Thr Pro Pro Ala Val Ile Lys Pro Val Ala
465                 470                 475

<210> SEQ ID NO 52
<211> LENGTH: 477
<212> TYPE: PRT
<213> ORGANISM: Fusarium moniliforme
```

<400> SEQUENCE: 52

```
Met Ala Ser Thr Ser Ala Leu Pro Lys Gln Asn Pro Ala Leu Arg Arg
1               5                   10                  15

Thr Val Thr Ser Thr Val Thr Asp Ser Glu Ser Ala Ala Val Ser
            20                  25                  30

Pro Ser Asp Ser Pro Arg His Ser Ala Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
                100                 105                 110

Phe Ser Ile Trp Tyr Asn Phe Val Thr Pro Glu Tyr Ile Pro Ser Thr
            115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
    195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
                260                 265                 270

Lys His Asn Gly Leu Gly Gly Val Asn His Phe Asp Pro Arg Ser
    275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415
```

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475

<210> SEQ ID NO 53
<211> LENGTH: 15119
<212> TYPE: DNA
<213> ORGANISM: Artificial Sequence
<220> FEATURE:
<223> OTHER INFORMATION: Plasmid pZSCP-Ma83

<400> SEQUENCE: 53

| | | | | |
|---|---|---|---|---|
| gtacgacccc | tctcaggcca | agcagaaggc | tgagtccatc | aagaaggcca | acgctatcat | 60 |
| tgtcttcaac | ctcaagaaca | aggctggcaa | gaccgagtct | tggtaccttg | acctcaagaa | 120 |
| cgacggtgac | gtcggcaagg | gcaacaagtc | ccccaagggt | gatgctgaca | tccagctcac | 180 |
| tctctctgac | gaccacttcc | agcagctcgt | tgagggtaag | gctaacgccc | agcgactctt | 240 |
| catgaccggc | aagctcaagg | ttaagggcaa | cgtcatgaag | gctgccgcca | ttgagggtat | 300 |
| cctcaagaac | gctcagaaca | acctctaagc | gcatcattta | ttgattaatt | gatgatttac | 360 |
| tatattgatt | tcgcaactgt | agtgtgattg | tatgtgatct | ggctcgtagg | cttcagtaaa | 420 |
| tactagacgg | gtatcctacg | tagttgtatc | atacatcgag | cctgtggtta | cttgtacaat | 480 |
| aattcgtaat | gtagagatac | cccttgatcc | attgcctgtt | tctaacatac | aatgatctcc | 540 |
| acgcaataat | cccactcttg | actaaaagtt | gctactcttg | cacggttacc | tcggcatagt | 600 |
| cacgcctctc | ttgtctcgtc | tcgaacgcac | aaagtcaatt | gacaacgcca | ctcactcgag | 660 |
| tgtgccccaa | cagggcacca | tatcgactaa | tttgaggcca | actagggtga | ttttggatgg | 720 |
| aatttgatcg | gaaaaaatag | ctgcagaaat | tcctggagag | aaaaattgac | cgcatccaca | 780 |
| tggtttgacc | aaaaaatcgt | ctccatctct | gtgctcaact | ctcctgacga | gatatgcgcg | 840 |
| cgcacccca | catgatgtga | ttgatctcaa | caaacttcac | ccagacccct | atctttccgg | 900 |
| gaaacttact | gtataagtgg | tcgtgcgaac | agaaagtgtg | cgcactttag | gtgtctagat | 960 |
| ccgattgttc | tcgttctgat | aatgagccag | ccccgcgagg | caatgttttt | tacaattgaa | 1020 |
| aacttcgtta | accactcaca | ttaccgtttt | tgccccatat | ttaccctctg | gtacactccc | 1080 |
| tcttgcatac | acacacactg | cagtgaaaat | gcactccgtt | agcaccgttg | tgattggttc | 1140 |
| agggcacgag | tttggtggtt | taaggcgcaa | ctacatcaat | atgaaaacag | agacgctga | 1200 |
| aaagggtaa | tatcggactg | ctgctatgtt | gtatgtactg | catgacgaat | tggtgttatt | 1260 |
| caagaccgtg | gcacaggttg | ctgcggtacg | agacctggta | gcttctctaa | acggcatgtc | 1320 |
| taggtggcgc | gccagctgca | ttaatgaatc | ggccaacgcg | cggggagagg | cggtttgcgt | 1380 |
| attgggcgct | cttccgcttc | ctcgctcact | gactcgctgc | gctcggtcgt | tcggctgcgg | 1440 |
| cgagcggtat | cagctcactc | aaaggcggta | atacggttat | ccacagaatc | aggggataac | 1500 |
| gcaggaaaga | acatgtgagc | aaaaggccag | caaaaggcca | ggaaccgtaa | aaaggccgcg | 1560 |
| ttgctggcgt | ttttccatag | gctccgcccc | cctgacgagc | atcacaaaaa | tcgacgctca | 1620 |
| agtcagaggt | ggcgaaaccc | gacaggacta | taaagatacc | aggcgtttcc | ccctggaagc | 1680 |

```
tccctcgtgc gctctcctgt tccgaccctg ccgcttaccg gataccctgtc cgcctttctc   1740
ccttcgggaa gcgtggcgct ttctcatagc tcacgctgta ggtatctcag ttcggtgtag   1800
gtcgttcgct ccaagctggg ctgtgtgcac gaaccccccg ttcagcccga ccgctgcgcc   1860
ttatccggta actatcgtct tgagtccaac ccggtaagac acgacttatc gccactggca   1920
gcagccactg gtaacaggat tagcagagcg aggtatgtag gcggtgctac agagttcttg   1980
aagtggtggc ctaactacgg ctacactaga agaacagtat ttggtatctg cgctctgctg   2040
aagccagtta ccttcggaaa aagagttggt agctcttgat ccggcaaaca accaccgct   2100
ggtagcggtg ttttttttgt ttgcaagcag cagattacgc gcagaaaaaa aggatctcaa   2160
gaagatcctt tgatcttttc tacggggtct gacgctcagt ggaacgaaaa ctcacgttaa   2220
gggattttgg tcatgagatt atcaaaaagg atcttcacct agatcctttt aaattaaaaa   2280
tgaagtttta aatcaatcta agtatatat gagtaaactt ggtctgacag ttaccaatgc   2340
ttaatcagtg aggcacctat ctcagcgatc tgtctatttc gttcatccat agttgcctga   2400
ctccccgtcg tgtagataac tacgatacgg gagggcttac catctggccc cagtgctgca   2460
atgataccgc gagacccacg ctcaccggct ccagatttat cagcaataaa ccagccagcc   2520
ggaagggccg agcgcagaag tggtcctgca actttatccg cctccatcca gtctattaat   2580
tgttgccggg aagctagagt aagtagttcg ccagttaata gtttgcgcaa cgttgttgcc   2640
attgctacag gcatcgtggt gtcacgctcg tcgtttggta tggcttcatt cagctccggt   2700
tcccaacgat caaggcgagt tacatgatcc cccatgttgt gcaaaaaagc ggttagctcc   2760
ttcggtcctc cgatcgttgt cagaagtaag ttggccgcag tgttatcact catggttatg   2820
gcagcactgc ataattctct tactgtcatg ccatccgtaa gatgcttttc tgtgactggt   2880
gagtactcaa ccaagtcatt ctgagaatag tgtatgcggc gaccgagttg ctcttgcccg   2940
gcgtcaatac gggataatac cgcgccacat agcagaactt taaaagtgct catcattgga   3000
aaacgttctt cggggcgaaa actctcaagg atcttaccgc tgttgagatc cagttcgatg   3060
taacccactc gtgcacccaa ctgatcttca gcatctttta ctttcaccag cgtttctggg   3120
tgagcaaaaa caggaaggca aaatgccgca aaaaagggaa taagggcgac acggaaatgt   3180
tgaatactca tactcttcct ttttcaatat tattgaagca tttatcaggg ttattgtctc   3240
atgagcggat acatatttga atgtatttag aaaaataaac aaataggggt tccgcgcaca   3300
tttccccgaa aagtgccacc tgatgcggtg tgaaataccg cacagatgcg taaggagaaa   3360
ataccgcatc aggaaattgt aagcgttaat attttgttaa aattcgcgtt aaattttgt   3420
taaatcagct cattttttaa ccaataggcc gaaatcggca aaatccctta taatcaaaa   3480
gaatagaccg agatagggtt gagtgttgtt ccagtttgga acaagagtcc actattaaag   3540
aacgtggact ccaacgtcaa agggcgaaaa accgtctatc agggcgatgg cccactacgt   3600
gaaccatcac cctaatcaag ttttttgggg tcgaggtgcc gtaaagcact aaatcggaac   3660
cctaaaggga gccccccgatt tagagcttga cggggaaagc cggcgaacgt ggcgagaaag   3720
gaagggaaga aagcgaaagg agcgggcgct agggcgctgg caagtgtagc ggtcacgctg   3780
cgcgtaacca ccacacccgc cgcgcttaat gcgccgctac agggcgcgtc cattcgccat   3840
tcaggctgcg caactgttgg gaagggcgat cggtgcgggc ctcttcgcta ttacgccagc   3900
tggcgaaagg gggatgtgct gcaaggcgat taagttgggt aacgccaggg ttttcccagt   3960
cacgacgttg taaaacgacg gccagtgaat tgtaatacga ctcactatag ggcgaattgg   4020
gcccgacgtc gcatgcgtca ctaatcaagg ataccctacca tgccactatg atgtttgcag   4080
```

```
gaggtgtacc tcggcagtca tcaaaaaatg gaactactgg ctttagatct tgttgtatgg   4140
catcgcgcct aaaaaagaaa ccccttcca gcgagctact acaagtagtt gtagttgcgg    4200
gcgttggata ccgaaagtca caagcacatg tcgaagctct catctgaaac accgacagtc   4260
gtctgcaccc cgcaagtctc ggttcgtacc agcaccaatg ttaggcagaa ctatacacaa   4320
gagggcggac gatcacttcg gcgttaggca actgaaggct attttcggct ggtactgtag   4380
gggacagagg aaacgcaagt gattagtaaa tcggataata ggcctgttag tttaccgaaa   4440
tggtggggga ggggttccgt ggatatcttg aagttatgga ggctgatcgt tatttgtggg   4500
gatggatatc attgtatgga catactgtag ctactgtata aacaacggat cttacacctg   4560
cctcttgtat gcccattgct tgatcatcta tcgtgttact gtacatatac aatagatata   4620
gggaagaaaa gccggaagta gagaccatag tctggcagaa gtaacggcct cgggtcgaga   4680
gaactataac aaagtccaac ggcgggtctt agaatagccc caaggatcac acagttccgc   4740
aatccagttt cacatgttcc gttgcatgga cttttgcatg tctactgttg ctacgattcc   4800
cccattgcaa ccacagtttg gggttacccc gcattatatt agcatgatta cgaaagagat   4860
aagtatcata tggaacatgt gaagggtagt atgcaggtcc ggcggagaaa gagaatgacg   4920
ttttcattaa gcgattcgct tggcggcttg tgggggatgt gacgatactt acggtaaaga   4980
ccctgtgtga gagctggtac tcgctcgtta cttcgctgat ctgttgggcc gtcaatcgaa   5040
tctcgtggaa cttgcattct tcttaactgt gtctatacaa gacacctaat gaaacataca   5100
agctaccgaa atcattttac tcgtactgac cggtacggta cttgcacaag tagtgaaact   5160
tccgaaaata gccagcctca tgcatcatcg cttcacccct tctgttgacc tcaaaagcat   5220
tccaacggta aaaattata acgccgccaa ctggatggtt gtgacggcgt tgaccaccaa    5280
tgtgtggggg ctggcggtag gaccgagctt attcgtccca ataagctctt tggatttgat   5340 tctttgggt gtgtggtaaa attcacatgg ggaagaacac ggtggcagtt tgaggcagag    5400
gcccagcgtg tagttcctag ggcatgaata taccgaactc atggcgcaga attgagctga   5460
atgcgcaaaa agctacagga tcaaccgcgt tagaaatgcc gcaaatgtcc actaattccc   5520
cggactgttc caaatgattc tgtggggata aatctcaaac tgggttaggc tttgtcacgt   5580
ttctttgtgt cgtgtcggtt cgtccggggc aatgtgccca cgcttggctg tctccctaca   5640
cctcggtaaa aactatcaca tgctgcccct ctcgagcaag cattaaatgc atatagtcaa   5700
tctaacgaca tatatatagg tagggtgcat cctccggttt agctccccag aatatctctt   5760
attcattaca caaaaacaac aatgtctctc aaggtcgacg gcttcacttc ttaattaagt   5820
tgcgacacat gtcttgatag tatcttgaat tctctctctt gagcttttcc ataacaagtt   5880
cttctgcctc caggaagtcc atgggtggtt tgatcatggt tttggtgtag tggtagtgca   5940
gtggtggtat tgtgactggg gatgtagttg agaataagtc atacacaagt cagctttctt   6000
cgagcctcat ataagtataa gtagttcaac gtattagcac tgtacccagc atctccgtat   6060
cgagaaacac aacaacatgc cccattggac agatcatgcg gatacacagg ttgtgcagta   6120
tcatacatac tcgatcagac aggtcgtctg accatcatac aagctgaaca agcgctccat   6180
acttgcacgc tctctatata cacagttaaa ttacatatcc atagtctaac ctctaacagt   6240
taatcttctg gtaagcctcc cagccagcct tctggtatcg cttggcctcc tcaataggat   6300
ctcggttctg gccgtacaga cctcggccga caattatgat atccgttccg gtagacatga   6360
catcctcaac agttcggtac tgctgtccga gagcgtctcc cttgtcgtca agacccaccc   6420
```

```
cggggggtcag aataagccag tcctcagagt cgcccttagg tcggttctgg gcaatgaagc    6480
caaccacaaa ctcggggtcg gatcgggcaa gctcaatggt ctgcttggag tactcgccag    6540
tggccagaga gcccttgcaa gacagctcgg ccagcatgag cagacctctg gccagcttct    6600
cgttgggaga ggggactagg aactccttgt actgggagtt ctcgtagtca gagacgtcct    6660
ccttcttctg ttcagagaca gtttcctcgg caccagctcg caggccagca atgattccgg    6720
ttccgggtac accgtgggcg ttggtgatat cggaccactc ggcgattcgg tgacaccggt    6780
actggtgctt gacagtgttg ccaatatctg cgaactttct gtcctcgaac aggaagaaac    6840
cgtgcttaag agcaagttcc ttgaggggga gcacagtgcc ggcgtaggtg aagtcgtcaa    6900
tgatgtcgat atgggttttg atcatgcaca cataaggtcc gaccttatcg gcaagctcaa    6960
tgagctcctt ggtggtggta acatccagag aagcacacag gttggttttc ttggctgcca    7020
cgagcttgag cactcgagcg gcaaaggcgg acttgtggac gttagctcga gcttcgtagg    7080
agggcatttt ggtggtgaag aggagactga ataaaattta gtctgcagaa cttttatcg    7140 gaaccttatc tgggggcagtg aagtatatgt tatggtaata gttacgagtt agttgaactt    7200
atagatagac tggactatac ggctatcggt ccaaattaga aagaacgtca atggctctct    7260
gggcgtcgcc tttgccgaca aaaatgtgat catgatgaaa gccagcaatg acgttgcagc    7320
tgatattgtt gtcggccaac cgcgccgaaa acgcagctgt cagacccaca gcctccaacg    7380
aagaatgtat cgtcaaagtg atccaagcac actcatagtt ggagtcgtac tccaaaggcg    7440
gcaatgacga gtcagacaga tactcgtcga cctttttcctt gggaaccacc accgtcagcc    7500
cttctgactc acgtattgta gccaccgaca caggcaacag tccgtggata gcagaatatg    7560
tcttgtcggt ccatttctca ccaactttag gcgtcaagtg aatgttgcag aagaagtatg    7620
tgccttcatt gagaatcggt gttgctgatt tcaataaagt cttgagatca gtttggccag    7680
tcatgttgtg gggggtaatt ggattgagtt atcgcctaca gtctgtacag gtatactcgc    7740
tgcccacttt atactttttg attccgctgc acttgaagca atgtcgttta ccaaaagtga    7800
gaatgctcca cagaacacac cccagggtat ggttgagcaa aaaataaaca ctccgatacg    7860
gggaatcgaa ccccggtctc cacggttctc aagaagtatt cttgatgaga gcgtatcgat    7920
ggaagccggt agaaccgggc tgcttgtgct tggagatgga agccggtaga accgggctgc    7980 ttgggggggat ttggggccgc tgggctccaa agaggggtag gcatttcgtt ggggttacgt    8040
aattgcggca tttgggtcct cgcgcatgt cccattggtc agaattagtc cggataggag    8100
acttatcagc caatcacagc gccggatcca cctgtaggtt gggttgggtg ggagcacccc    8160
tccacagagt agagtcaaac agcagcagca acatgatagt tgggggtgtg cgtgttaaag    8220
gaaaaaaaag aagcttgggt tatattcccg ctctatttag aggttgcggg atagacgccg    8280
acggagggca atggcgctat ggaaccttgc ggatatccat acgccgcggc ggactgcgtc    8340
cgaaccagct ccagcagcgt ttttccccggg ccattgagcc gactgcgacc ccgccaacgt    8400
gtcttggccc acgcactcat gtcatgttgg tgttgggagg ccacttttta agtagcacaa    8460
ggcacctagc tcgcagcaag gtgtccgaac caaagaagcg gctgcagtgg tgcaaacggg    8520
gcggaaacgg cggaaaaag ccacgggggc acgaattgag gcacgccctc gaatttgaga    8580
cgagtcacgg ccccattcgc ccgcgcaatg gctcgccaac gcccggtctt ttgcaccaca    8640
tcaggttacc ccaagccaaa ccttttgtgtt aaaaagctta acatattata ccgaacgtag    8700
gtttgggcgg gcttgctccg tctgtccaag gcaacattta tataagggtc tgcatcgccg    8760
gctcaattga atcttttttc ttcttctctt ctctatattc attcttgaat taaacacaca    8820
```

```
tcaaccatgg tcaagcgacc cgctctgcct ctcaccgtgg acggtgtcac ctacgacgtt   8880
tctgcctggc tcaaccacca tcccggaggt gccgacatta tcgagaacta ccgaggtcgg   8940
gatgctaccg acgtcttcat ggttatgcac tccgagaacg ccgtgtccaa actcagacga   9000
atgcccatca tggaaccttc ctctcccctg actccaacac ctcccaagcc aaactccgac   9060
gaacctcagg aggatttccg aaagctgcga gacgagctca ttgctgcagg catgttcgat   9120
gcctctccca tgtggtacgc ttacaagacc ctgtcgactc tcggactggg tgtccttgcc   9180
gtgctgttga tgacccagtg gcactggtac ctggttggtg ctatcgtcct cggcattcac   9240
tttcaacaga tgggatggct ctcgcacgac atttgccatc accagctgtt caaggaccga   9300
tccatcaaca atgccattgg cctgctcttc ggaaacgtgc ttcagggctt ttctgtcact   9360
tggtggaagg accgacacaa cgctcatcac tccgccacca acgtgcaggg tcacgatccc   9420
gacatcgaca acctgcctct cctggcgtgg tccaaggagg acgtcgagcg agctggcccg   9480
ttttctcgac ggatgatcaa gtaccaacag tattacttct ttttcatctg tgcccttctg   9540
cgattcatct ggtgctttca gtccattcat actgccacgg gtctcaagga tcgaagcaat   9600
cagtactatc gaagacagta cgagaaggag tccgtcggtc tggcactcca ctggggtctc   9660
aaggccttgt tctactattt ctacatgccc tcgtttctca ccggactcat ggtgttcttt   9720
gtctccgagc tgcttggtgg cttcggaatt gccatcgttg tcttcatgaa ccactaccct   9780
ctggagaaga ttcaggactc cgtgtgggat ggtcatggct tctgtgctgg acagattcac   9840
gagaccatga acgttcagcg aggcctcgtc acagactggt ttttcggtgg cctcaactac   9900
cagatcgaac atcacctgtg gcctactctt cccagacaca acctcaccgc tgcctccatc   9960
aaagtggagc agctgtgcaa gaagcacaac ctgccctacc gatctcctcc catgctcgaa  10020
ggtgtcggca ttcttatctc ctacctgggc accttcgctc gaatggttgc caaggcagac  10080
aaggcctaag cggccgcatt gatgattgga acacacaca tgggttatat ctaggtgaga  10140
gttagttgga cagttatata ttaaatcagc tatgccaacg gtaacttcat tcatgtcaac  10200
gaggaaccag tgactgcaag taatatagaa tttgaccacc ttgccattct cttgcactcc  10260
tttactatat ctcatttatt tcttatatac aaatcacttc ttcttcccag catcgagctc  10320
ggaaacctca tgagcaataa catcgtggat ctcgtcaata gagggctttt tggactcctt  10380
gctgttggcc accttgtcct tgctgtttaa acagagtgtg aaagactcac tatggtccgg  10440
gcttatctcg accaatagcc aaagtctgga gtttctgaga gaaaaaggca agatacgtat  10500
gtaacaaagc gacgcatggt acaataatac cggaggcatg tatcatagag agttagtggt  10560
tcgatgatgg cactggtgcc tggtatgact ttatacggct gactacatat ttgtcctcag  10620
acatacaatt acagtcaagc acttacccct ggacatctgt aggtaccccc cggccaagac  10680
gatctcagcg tgtcgtatgt cggattggcg tagctccctc gctcgtcaat ggctcccat   10740 ctactttctt ctgcttggct acacccagca tgtctgctat ggctcgtttt cgtgccttat  10800
ctatcctccc agtattacca actctaaatg acatgatgtg attgggtcta cactttcata  10860
tcagagataa ggagtagcac agttgcataa aaagcccaac tctaatcagc ttcttccttt  10920
cttgtaatta gtacaaaggt gattagcgaa atctggaagc ttagttggcc ctaaaaaaat  10980 caaaaaagc aaaaaacgaa aaacgaaaaa ccacagtttt gagaacaggg aggtaacgaa   11040
ggatcgtata tatatatata tatatatata cccacggatc ccgagaccgg cctttgattc  11100
ttccctacaa ccaaccattc tcaccaccct aattcacaac catggtctcc aaccacctgt  11160
```

```
tcgacgccat gcgagctgcc gctcccggag acgcaccttt cattcgaatc gacaacgctc    11220
ggacctggac ttacgatgac gccattgctc tttccggtcg aatcgctgga gctatggacg    11280
cactcggcat tcgacccgga gacagagttg ccgtgcaggt cgagaagtct gccgaggcgt    11340
tgattctcta cctggcctgt cttcgaaccg gagctgtcta cctgcctctc aacactgcct    11400
acaccctggc cgagctcgac tacttcatcg gcgatgccga accgcgtctg gtggtcgttg    11460
ctcccgcagc tcgaggtggc gtggagacaa ttgccaagcg acacggtgct atcgtcgaaa    11520
ccctcgacgc cgatggacga ggctccttgc tggaccttgc tagagatgag cctgccgact    11580
ttgtcgatgc ttcgcgatct gccgacgatc tggctgctat tctctacact tccggtacaa    11640
ccggacgatc gaagggtgcc atgcttactc atggcaatct gctctccaac gctctcacct    11700
tgcgagacta ttggagagtt accgcagacg atcgactcat ccatgccttg ccaatctttc    11760
acactcatgg tctgttcgtt gctacgaacg tcacactgct tgcaggagcc tcgatgtttc    11820
tgctctccaa gttcgatgcc gacgaggtcg tttctctcat gccacaggcc accatgctta    11880
tgggcgtgcc cacattctac gttcgattgc tgcagagtcc tcgactcgag aagggtgctg    11940
tggccagcat cagactgttc atttctggat cagctcccctt gcttgccgaa acccacgccg    12000
agtttcatgc tcgtactggt cacgccattc tcgagcgata cggcatgacg gaaaccaaca    12060
tgaatacttc caaccctac gagggcaagc gtattgccgg aaccgttggt tttcctctgc    12120
ccgacgtcac tgtgcgagtc accgatcccg ccaccggtct cgttcttcca cctgaagaga    12180
ctggcatgat cgagatcaag ggacccaacg tcttcaaggg ctattggcga atgcccgaaa    12240
agaccgctgc cgagtttacc gcagacggtt tctttatctc tggagatctc ggcaagatcg    12300
accgagaagg ttacgttcac attgtgggac gaggcaagga cctggtcatt tccggtggct    12360
acaacatcta tcccaaagag gtcgaaggcg agatcgacca gatcgagggt gtggtcgagt    12420
ctgctgtcat tggtgttcct catcccgatt tcggagaagg tgtcaccgct gttgtcgtgt    12480
gcaaacctgg tgccgttctc gacgaaaaga ccatcgtgtc tgctctgcag gaccgtcttg    12540
cccgatacaa gcaacccaag cggattatct ttgccgacga tctgcctcga aacactatgg    12600
gaaaggttca gaagaacatt cttcgacagc aatacgccga tctctacacc agacgataag    12660
cggccgcatg agaagataaa tatataaata cattgagata ttaaatgcgc tagattagag    12720
agcctcatac tgctcggaga gaagccaaga cgagtactca aaggggatta ccaccatccat    12780 atccacagac acaagctggg gaaaggttct atatacactt tccggaatac cgtagtttcc    12840
gatgttatca atggggggcag ccaggatttc aggcacttcg gtgtctcggg gtgaaatggc    12900
gttcttggcc tccatcaagt cgtaccatgt cttcatttgc ctgtcaaagt aaaacagaag    12960
cagatgaaga atgaacttga agtgaaggaa tttaaatgat gtcgacgcag taggatgtcc    13020
tgcacgggtc tttttgtggg gtgtggagaa aggggtgctt ggagatggaa gccggtagaa    13080
ccgggctgct tgtgcttgga gatggaagcc ggtagaaccg gctgcttgg ggggatttgg    13140 ggccgctggg ctccaaagag gggtaggcat ttcgttgggg ttacgtaatt gcggcatttg    13200
ggtcctgcgc gcatgtccca ttggtcagaa ttagtccgga taggagactt atcagccaat    13260
cacagcgccg gatccacctg taggttgggt tgggtgggag caccccctcca cagagtagag    13320 tcaaacagca gcagcaacat gatagttggg ggtgtgcgtg ttaaaggaaa aaaagaagc    13380 ttgggttata ttcccgctct atttagaggt tgcgggatag acgccgacgg agggcaatgg    13440
cgctatggaa ccttgcggat atccatacgc cgcggcggac tgcgtccgaa ccagctccag    13500
cagcgttttt tccgggccat tgagccgact gcgaccccgc caacgtgtct tggcccacgc    13560
```

```
actcatgtca tgttggtgtt gggaggccac tttttaagta gcacaaggca cctagctcgc    13620
agcaaggtgt ccgaaccaaa gaagcggctg cagtggtgca acggggcgg aaacggcggg    13680 aaaaagccac gggggcacga attgaggcac gccctcgaat ttgagacgag tcacggcccc    13740
attcgcccgc gcaatggctc gccaacgccc ggtcttttgc accacatcag gttaccccaa    13800
gccaaacctt tgtgttaaaa agcttaacat attataccga acgtaggttt gggcgggctt    13860
gctccgtctg tccaaggcaa catttatata agggtctgca tcgccggctc aattgaatct    13920
tttttcttct tctcttctct atattcattc ttgaattaaa cacacatcaa ccatggagtc    13980
tggacccatg cctgctggca ttcccttccc tgagtactat gacttcttta tggactggaa    14040
gactcccctg gccatcgctg ccacctacac tgctgccgtc ggtctcttca accccaaggt    14100
tggcaaggtc tcccgagtgg ttgccaagtc ggctaacgca aagcctgccg agcgaaccca    14160
gtccggagct gccatgactg ccttcgtctt tgtgcacaac ctcattctgt gtgtctactc    14220
tggcatcacc ttctactaca tgtttcctgc tatggtcaag aacttccgaa cccacacact    14280
gcacgaagcc tactgcgaca cggatcagtc cctctggaac aacgcacttg gctactgggg    14340
ttacctcttc tacctgtcca agttctacga ggtcattgac accatcatca tcatcctgaa    14400
gggacgacgg tcctcgctgc ttcagaccta ccaccatgct ggagccatga ttaccatgtg    14460
gtctggcatc aactaccaag ccactcccat ttggatcttt gtggtcttca actccttcat    14520
tcacaccatc atgtactgtt actatgcctt cacctctatc ggattccatc ctcctggcaa    14580
aaagtacctg acttcgatgc agattactca gtttctggtc ggtatcacca ttgccgtgtc    14640
ctacctcttc gttcctggct gcatccgaac acccggtgct cagatggctg tctggatcaa    14700
cgtcggctac ctgttttccct tgacctatct gttcgtggac tttgccaagc gaacctactc    14760
caagcgatct gccattgccg ctcagaaaaa ggctcagtaa gcggccgcaa gtgtggatgg    14820
ggaagtgagt gcccggttct gtgtgcacaa ttggcaatcc aagatggatg gattcaacac    14880
agggatatag cgagctacgt ggtggtgcga ggatatagca acggatattt atgtttgaca    14940
cttgagaatg tacgatacaa gcactgtcca agtacaatac taaacatact gtacatactc    15000
atactcgtac ccgggcaacg gtttcacttg agtgcagtgg ctagtgctct tactcgtaca    15060
gtgtgcaata ctgcgtatca tagtctttga tgtatatcgt attcattcat gttagttgc     15119
```

<210> SEQ ID NO 54
<211> LENGTH: 828
<212> TYPE: DNA
<213> ORGANISM: Mortierella alpina
<220> FEATURE:
<221> NAME/KEY: CDS
<222> LOCATION: (1)..(828)
<223> OTHER INFORMATION: synthetic C16/18 elongase (codon-optimized for Yarrowia lipolytica)
<300> PUBLICATION INFORMATION:
<302> TITLE: A MORTIERELLA ALPINA C16/18 FATTY ACID ELONGASE
<310> PATENT DOCUMENT NUMBER: U.S. 7,470,532
<311> PATENT FILING DATE: 2005-10-19
<312> PUBLICATION DATE: 2008-12-30
<313> RELEVANT RESIDUES IN SEQ ID NO: (1)..(828)
<300> PUBLICATION INFORMATION:
<302> TITLE: A MORTIERELLA ALPINA C16/18 FATTY ACID ELONGASE
<310> PATENT DOCUMENT NUMBER: WO 2007/046817
<311> PATENT FILING DATE: 2005-11-04
<312> PUBLICATION DATE: 2007-04-26
<313> RELEVANT RESIDUES IN SEQ ID NO: (1)..(828)

<400> SEQUENCE: 54

```
atg gag tct gga ccc atg cct gct ggc att ccc ttc cct gag tac tat    48
```

```
Met Glu Ser Gly Pro Met Pro Ala Gly Ile Pro Phe Pro Glu Tyr Tyr
1               5                   10                  15 gac ttc ttt atg gac tgg aag act ccc ctg gcc atc gct gcc acc tac    96
Asp Phe Phe Met Asp Trp Lys Thr Pro Leu Ala Ile Ala Ala Thr Tyr
            20                  25                  30 act gct gcc gtc ggt ctc ttc aac ccc aag gtt ggc aag gtc tcc cga   144
Thr Ala Ala Val Gly Leu Phe Asn Pro Lys Val Gly Lys Val Ser Arg
        35                  40                  45 gtg gtt gcc aag tcg gct aac gca aag cct gcc gag cga acc cag tcc   192
Val Val Ala Lys Ser Ala Asn Ala Lys Pro Ala Glu Arg Thr Gln Ser
    50                  55                  60 gga gct gcc atg act gcc ttc gtc ttt gtg cac aac ctc att ctg tgt   240
Gly Ala Ala Met Thr Ala Phe Val Phe Val His Asn Leu Ile Leu Cys
65                  70                  75                  80 gtc tac tct ggc atc acc ttc tac tac atg ttt cct gct atg gtc aag   288
Val Tyr Ser Gly Ile Thr Phe Tyr Tyr Met Phe Pro Ala Met Val Lys
                85                  90                  95 aac ttc cga acc cac aca ctg cac gaa gcc tac tgc gac acg gat cag   336
Asn Phe Arg Thr His Thr Leu His Glu Ala Tyr Cys Asp Thr Asp Gln
            100                 105                 110 tcc ctc tgg aac aac gca ctt ggc tac tgg ggt tac ctc ttc tac ctg   384
Ser Leu Trp Asn Asn Ala Leu Gly Tyr Trp Gly Tyr Leu Phe Tyr Leu
        115                 120                 125 tcc aag ttc tac gag gtc att gac acc atc atc atc ctg aag gga       432
Ser Lys Phe Tyr Glu Val Ile Asp Thr Ile Ile Ile Leu Lys Gly
    130                 135                 140 cga cgg tcc tcg ctg ctt cag acc tac cac cat gct gga gcc atg att   480
Arg Arg Ser Ser Leu Leu Gln Thr Tyr His His Ala Gly Ala Met Ile
145                 150                 155                 160 acc atg tgg tct ggc atc aac tac caa gcc act ccc att tgg atc ttt   528
Thr Met Trp Ser Gly Ile Asn Tyr Gln Ala Thr Pro Ile Trp Ile Phe
                165                 170                 175 gtg gtc ttc aac tcc ttc att cac acc atc atg tac tgt tac tat gcc   576
Val Val Phe Asn Ser Phe Ile His Thr Ile Met Tyr Cys Tyr Tyr Ala
            180                 185                 190 ttc acc tct atc gga ttc cat cct cct ggc aaa aag tac ctg act tcg   624
Phe Thr Ser Ile Gly Phe His Pro Pro Gly Lys Lys Tyr Leu Thr Ser
        195                 200                 205 atg cag att act cag ttt ctg gtc ggt atc acc att gcc gtg tcc tac   672
Met Gln Ile Thr Gln Phe Leu Val Gly Ile Thr Ile Ala Val Ser Tyr
210                 215                 220 ctc ttc gtt cct ggc tgc atc cga aca ccc ggt gct cag atg gct gtc   720
Leu Phe Val Pro Gly Cys Ile Arg Thr Pro Gly Ala Gln Met Ala Val
225                 230                 235                 240 tgg atc aac gtc ggc tac ctg ttt ccc ttg acc tat ctg ttc gtg gac   768
Trp Ile Asn Val Gly Tyr Leu Phe Pro Leu Thr Tyr Leu Phe Val Asp
                245                 250                 255 ttt gcc aag cga acc tac tcc aag cga tct gcc att gcc gct cag aaa   816
Phe Ala Lys Arg Thr Tyr Ser Lys Arg Ser Ala Ile Ala Ala Gln Lys
            260                 265                 270 aag gct cag taa                                                   828
Lys Ala Gln
        275

<210> SEQ ID NO 55
<211> LENGTH: 275
<212> TYPE: PRT
<213> ORGANISM: Mortierella alpina

<400> SEQUENCE: 55
```

```
Met Glu Ser Gly Pro Met Pro Ala Gly Ile Pro Phe Pro Glu Tyr Tyr
1               5                   10                  15

Asp Phe Phe Met Asp Trp Lys Thr Pro Leu Ala Ile Ala Ala Thr Tyr
            20                  25                  30

Thr Ala Ala Val Gly Leu Phe Asn Pro Lys Val Gly Lys Val Ser Arg
        35                  40                  45

Val Val Ala Lys Ser Ala Asn Ala Lys Pro Ala Glu Arg Thr Gln Ser
50                  55                  60

Gly Ala Ala Met Thr Ala Phe Val Phe Val His Asn Leu Ile Leu Cys
65                  70                  75                  80

Val Tyr Ser Gly Ile Thr Phe Tyr Tyr Met Phe Pro Ala Met Val Lys
                85                  90                  95

Asn Phe Arg Thr His Thr Leu His Glu Ala Tyr Cys Asp Thr Asp Gln
            100                 105                 110

Ser Leu Trp Asn Asn Ala Leu Gly Tyr Trp Gly Tyr Leu Phe Tyr Leu
        115                 120                 125

Ser Lys Phe Tyr Glu Val Ile Asp Thr Ile Ile Ile Leu Lys Gly
    130                 135                 140

Arg Arg Ser Ser Leu Leu Gln Thr Tyr His His Ala Gly Ala Met Ile
145                 150                 155                 160

Thr Met Trp Ser Gly Ile Asn Tyr Gln Ala Thr Pro Ile Trp Ile Phe
                165                 170                 175

Val Val Phe Asn Ser Phe Ile His Thr Ile Met Tyr Cys Tyr Tyr Ala
            180                 185                 190

Phe Thr Ser Ile Gly Phe His Pro Pro Gly Lys Lys Tyr Leu Thr Ser
        195                 200                 205

Met Gln Ile Thr Gln Phe Leu Val Gly Ile Thr Ile Ala Val Ser Tyr
    210                 215                 220

Leu Phe Val Pro Gly Cys Ile Arg Thr Pro Gly Ala Gln Met Ala Val
225                 230                 235                 240

Trp Ile Asn Val Gly Tyr Leu Phe Pro Leu Thr Tyr Leu Phe Val Asp
                245                 250                 255

Phe Ala Lys Arg Thr Tyr Ser Lys Arg Ser Ala Ile Ala Ala Gln Lys
            260                 265                 270

Lys Ala Gln
        275

<210> SEQ ID NO 56
<211> LENGTH: 1518
<212> TYPE: DNA
<213> ORGANISM: Rhizobium leguminosarum bv. viciae 3841
<220> FEATURE:
<221> NAME/KEY: CDS
<222> LOCATION: (1)..(1518)
<223> OTHER INFORMATION: synthetic malonyl-CoA synthetase
      (codon-optimized for Yarrowia lipolytica)

<400> SEQUENCE: 56 atg gtc tcc aac cac ctg ttc gac gcc atg cga gct gcc gct ccc gga      48
Met Val Ser Asn His Leu Phe Asp Ala Met Arg Ala Ala Ala Pro Gly
1               5                   10                  15 gac gca cct ttc att cga atc gac aac gct cgg acc tgg act tac gat      96
Asp Ala Pro Phe Ile Arg Ile Asp Asn Ala Arg Thr Trp Thr Tyr Asp
            20                  25                  30 gac gcc att gct ctt tcc ggt cga atc gct gga gct atg gac gca ctc     144
Asp Ala Ile Ala Leu Ser Gly Arg Ile Ala Gly Ala Met Asp Ala Leu
        35                  40                  45
```

```
ggc att cga ccc gga gac aga gtt gcc gtg cag gtc gag aag tct gcc    192
Gly Ile Arg Pro Gly Asp Arg Val Ala Val Gln Val Glu Lys Ser Ala
    50              55                  60 gag gcg ttg att ctc tac ctg gcc tgt ctt cga acc gga gct gtc tac    240
Glu Ala Leu Ile Leu Tyr Leu Ala Cys Leu Arg Thr Gly Ala Val Tyr
65              70                  75                  80 ctg cct ctc aac act gcc tac acc ctg gcc gag ctc gac tac ttc atc    288
Leu Pro Leu Asn Thr Ala Tyr Thr Leu Ala Glu Leu Asp Tyr Phe Ile
                85                  90                  95 ggc gat gcc gaa ccg cgt ctg gtg gtc gtt gct ccc gca gct cga ggt    336
Gly Asp Ala Glu Pro Arg Leu Val Val Val Ala Pro Ala Ala Arg Gly
            100                 105                 110 ggc gtg gag aca att gcc aag cga cac ggt gct atc gtc gaa acc ctc    384
Gly Val Glu Thr Ile Ala Lys Arg His Gly Ala Ile Val Glu Thr Leu
        115                 120                 125 gac gcc gat gga cga ggc tcc ttg ctg gac ctt gct aga gat gag cct    432
Asp Ala Asp Gly Arg Gly Ser Leu Leu Asp Leu Ala Arg Asp Glu Pro
    130                 135                 140 gcc gac ttt gtc gat gct tcg cga tct gcc gac gat ctg gct gct att    480
Ala Asp Phe Val Asp Ala Ser Arg Ser Ala Asp Asp Leu Ala Ala Ile
145                 150                 155                 160 ctc tac act tcc ggt aca acc gga cga tcg aag ggt gcc atg ctt act    528
Leu Tyr Thr Ser Gly Thr Thr Gly Arg Ser Lys Gly Ala Met Leu Thr
                165                 170                 175 cat ggc aat ctg ctc tcc aac gct ctc acc ttg cga gac tat tgg aga    576
His Gly Asn Leu Leu Ser Asn Ala Leu Thr Leu Arg Asp Tyr Trp Arg
            180                 185                 190 gtt acc gca gac gat cga ctc atc cat gcc ttg cca atc ttt cac act    624
Val Thr Ala Asp Asp Arg Leu Ile His Ala Leu Pro Ile Phe His Thr
        195                 200                 205 cat ggt ctg ttc gtt gct acg aac gtc aca ctg ctt gca gga gcc tcg    672
His Gly Leu Phe Val Ala Thr Asn Val Thr Leu Leu Ala Gly Ala Ser
    210                 215                 220 atg ttt ctg ctc tcc aag ttc gat gcc gac gag gtc gtt tct ctc atg    720
Met Phe Leu Leu Ser Lys Phe Asp Ala Asp Glu Val Val Ser Leu Met
225                 230                 235                 240 cca cag gcc acc atg ctt atg ggc gtg ccc aca ttc tac gtt cga ttg    768
Pro Gln Ala Thr Met Leu Met Gly Val Pro Thr Phe Tyr Val Arg Leu
                245                 250                 255 ctg cag agt cct cga ctc gag aag ggt gct gtg gcc agc atc aga ctg    816
Leu Gln Ser Pro Arg Leu Glu Lys Gly Ala Val Ala Ser Ile Arg Leu
            260                 265                 270 ttc att tct gga tca gct ccc ttg ctt gcc gaa acc cac gcc gag ttt    864
Phe Ile Ser Gly Ser Ala Pro Leu Leu Ala Glu Thr His Ala Glu Phe
        275                 280                 285 cat gct cgt act ggt cac gcc att ctc gag cga tac ggc atg acg gaa    912
His Ala Arg Thr Gly His Ala Ile Leu Glu Arg Tyr Gly Met Thr Glu
    290                 295                 300 acc aac atg aat act tcc aac ccc tac gag ggc aag cgt att gcc gga    960
Thr Asn Met Asn Thr Ser Asn Pro Tyr Glu Gly Lys Arg Ile Ala Gly
305                 310                 315                 320 acc gtt ggt ttt cct ctg ccc gac gtc act gtg cga gtc acc gat ccc    1008
Thr Val Gly Phe Pro Leu Pro Asp Val Thr Val Arg Val Thr Asp Pro
                325                 330                 335 gcc acc ggt ctc gtt ctt cca cct gaa gag act ggc atg atc gag atc    1056
Ala Thr Gly Leu Val Leu Pro Pro Glu Glu Thr Gly Met Ile Glu Ile
            340                 345                 350 aag gga ccc aac gtc ttc aag ggc tat tgg cga atg ccc gaa aag acc    1104
Lys Gly Pro Asn Val Phe Lys Gly Tyr Trp Arg Met Pro Glu Lys Thr
        355                 360                 365
```

```
gct gcc gag ttt acc gca gac ggt ttc ttt atc tct gga gat ctc ggc      1152
Ala Ala Glu Phe Thr Ala Asp Gly Phe Phe Ile Ser Gly Asp Leu Gly
    370                 375                 380 aag atc gac cga gaa ggt tac gtt cac att gtg gga cga ggc aag gac      1200
Lys Ile Asp Arg Glu Gly Tyr Val His Ile Val Gly Arg Gly Lys Asp
385                 390                 395                 400 ctg gtc att tcc ggt ggc tac aac atc tat ccc aaa gag gtc gaa ggc      1248
Leu Val Ile Ser Gly Gly Tyr Asn Ile Tyr Pro Lys Glu Val Glu Gly
                405                 410                 415 gag atc gac cag atc gag ggt gtg gtc gag tct gct gtc att ggt gtt      1296
Glu Ile Asp Gln Ile Glu Gly Val Val Glu Ser Ala Val Ile Gly Val
            420                 425                 430 cct cat ccc gat ttc gga gaa ggt gtc acc gct gtt gtc gtg tgc aaa      1344
Pro His Pro Asp Phe Gly Glu Gly Val Thr Ala Val Val Val Cys Lys
        435                 440                 445 cct ggt gcc gtt ctc gac gaa aag acc atc gtg tct gct ctg cag gac      1392
Pro Gly Ala Val Leu Asp Glu Lys Thr Ile Val Ser Ala Leu Gln Asp
    450                 455                 460 cgt ctt gcc cga tac aag caa ccc aag cgg att atc ttt gcc gac gat      1440
Arg Leu Ala Arg Tyr Lys Gln Pro Lys Arg Ile Ile Phe Ala Asp Asp
465                 470                 475                 480 ctg cct cga aac act atg gga aag gtt cag aag aac att ctt cga cag      1488
Leu Pro Arg Asn Thr Met Gly Lys Val Gln Lys Asn Ile Leu Arg Gln
                485                 490                 495 caa tac gcc gat ctc tac acc aga cga taa                              1518
Gln Tyr Ala Asp Leu Tyr Thr Arg Arg
            500                 505

<210> SEQ ID NO 57
<211> LENGTH: 505
<212> TYPE: PRT
<213> ORGANISM: Rhizobium leguminosarum bv. viciae 3841

<400> SEQUENCE: 57

Met Val Ser Asn His Leu Phe Asp Ala Met Arg Ala Ala Ala Pro Gly
1               5                   10                  15

Asp Ala Pro Phe Ile Arg Ile Asp Asn Ala Arg Thr Trp Thr Tyr Asp
            20                  25                  30

Asp Ala Ile Ala Leu Ser Gly Arg Ile Ala Gly Ala Met Asp Ala Leu
        35                  40                  45

Gly Ile Arg Pro Gly Asp Arg Val Ala Val Gln Val Glu Lys Ser Ala
    50                  55                  60

Glu Ala Leu Ile Leu Tyr Leu Ala Cys Leu Arg Thr Gly Ala Val Tyr
65                  70                  75                  80

Leu Pro Leu Asn Thr Ala Tyr Thr Leu Ala Glu Leu Asp Tyr Phe Ile
                85                  90                  95

Gly Asp Ala Glu Pro Arg Leu Val Val Val Ala Pro Ala Ala Arg Gly
            100                 105                 110

Gly Val Glu Thr Ile Ala Lys Arg His Gly Ala Ile Val Glu Thr Leu
        115                 120                 125

Asp Ala Asp Gly Arg Gly Ser Leu Leu Asp Leu Ala Arg Asp Glu Pro
    130                 135                 140

Ala Asp Phe Val Asp Ala Ser Arg Ser Ala Asp Leu Ala Ala Ile
145                 150                 155                 160

Leu Tyr Thr Ser Gly Thr Thr Gly Arg Ser Lys Gly Ala Met Leu Thr
                165                 170                 175

His Gly Asn Leu Leu Ser Asn Ala Leu Thr Leu Arg Asp Tyr Trp Arg
```

```
                180                 185                 190
Val Thr Ala Asp Asp Arg Leu Ile His Ala Leu Pro Ile Phe His Thr
            195                 200                 205

His Gly Leu Phe Val Ala Thr Asn Val Thr Leu Leu Ala Gly Ala Ser
        210                 215                 220

Met Phe Leu Leu Ser Lys Phe Asp Ala Asp Glu Val Val Ser Leu Met
225                 230                 235                 240

Pro Gln Ala Thr Met Leu Met Gly Val Pro Thr Phe Tyr Val Arg Leu
                245                 250                 255

Leu Gln Ser Pro Arg Leu Glu Lys Gly Ala Val Ala Ser Ile Arg Leu
            260                 265                 270

Phe Ile Ser Gly Ser Ala Pro Leu Leu Ala Glu Thr His Ala Glu Phe
        275                 280                 285

His Ala Arg Thr Gly His Ala Ile Leu Glu Arg Tyr Gly Met Thr Glu
        290                 295                 300

Thr Asn Met Asn Thr Ser Asn Pro Tyr Glu Gly Lys Arg Ile Ala Gly
305                 310                 315                 320

Thr Val Gly Phe Pro Leu Pro Asp Val Thr Val Arg Val Thr Asp Pro
                325                 330                 335

Ala Thr Gly Leu Val Leu Pro Pro Glu Glu Thr Gly Met Ile Glu Ile
            340                 345                 350

Lys Gly Pro Asn Val Phe Lys Gly Tyr Trp Arg Met Pro Glu Lys Thr
        355                 360                 365

Ala Ala Glu Phe Thr Ala Asp Gly Phe Phe Ile Ser Gly Asp Leu Gly
        370                 375                 380

Lys Ile Asp Arg Glu Gly Tyr Val His Ile Val Gly Arg Gly Lys Asp
385                 390                 395                 400

Leu Val Ile Ser Gly Gly Tyr Asn Ile Tyr Pro Lys Glu Val Glu Gly
                405                 410                 415

Glu Ile Asp Gln Ile Glu Gly Val Val Glu Ser Ala Val Ile Gly Val
            420                 425                 430

Pro His Pro Asp Phe Gly Glu Gly Val Thr Ala Val Val Cys Lys
        435                 440                 445

Pro Gly Ala Val Leu Asp Glu Lys Thr Ile Val Ser Ala Leu Gln Asp
        450                 455                 460

Arg Leu Ala Arg Tyr Lys Gln Pro Lys Arg Ile Ile Phe Ala Asp Asp
465                 470                 475                 480

Leu Pro Arg Asn Thr Met Gly Lys Val Gln Lys Asn Ile Leu Arg Gln
                485                 490                 495

Gln Tyr Ala Asp Leu Tyr Thr Arg Arg
            500                 505

<210> SEQ ID NO 58
<211> LENGTH: 1260
<212> TYPE: DNA
<213> ORGANISM: Euglena anabaena UTEX 373
<220> FEATURE:
<221> NAME/KEY: CDS
<222> LOCATION: (1)..(1260)
<223> OTHER INFORMATION: synthetic delta-8 desaturase (codon-optimized
      for Yarrowia lipolytica)
<300> PUBLICATION INFORMATION:
<302> TITLE: DELTA-8 DESATURASES AND THEIR USE IN MAKING POLYUNSATURATED
      FATTY ACIDS
<310> PATENT DOCUMENT NUMBER: US-2008-0254521-A1
<311> PATENT FILING DATE: 2008-04-09
<312> PUBLICATION DATE: 2008-10-16
<313> RELEVANT RESIDUES IN SEQ ID NO: (1)..(1260)
```

```
<300> PUBLICATION INFORMATION:
<302> TITLE: DELTA-8 DESATURASES AND THEIR USE IN MAKING POLYUNSATURATED
      FATTY ACIDS
<310> PATENT DOCUMENT NUMBER: WO 2008/124194
<311> PATENT FILING DATE: 2008-04-10
<312> PUBLICATION DATE: 2008-10-16
<313> RELEVANT RESIDUES IN SEQ ID NO: (1)..(1260)

<400> SEQUENCE: 58 atg gtc aag cga ccc gct ctg cct ctc acc gtg gac ggt gtc acc tac        48
Met Val Lys Arg Pro Ala Leu Pro Leu Thr Val Asp Gly Val Thr Tyr
1               5                   10                  15 gac gtt tct gcc tgg ctc aac cac cat ccc gga ggt gcc gac att atc        96
Asp Val Ser Ala Trp Leu Asn His His Pro Gly Gly Ala Asp Ile Ile
            20                  25                  30 gag aac tac cga ggt cgg gat gct acc gac gtc ttc atg gtt atg cac       144
Glu Asn Tyr Arg Gly Arg Asp Ala Thr Asp Val Phe Met Val Met His
        35                  40                  45 tcc gag aac gcc gtg tcc aaa ctc aga cga atg ccc atc atg gaa cct       192
Ser Glu Asn Ala Val Ser Lys Leu Arg Arg Met Pro Ile Met Glu Pro
50                  55                  60 tcc tct ccc ctg act cca aca cct ccc aag cca aac tcc gac gaa cct       240
Ser Ser Pro Leu Thr Pro Thr Pro Pro Lys Pro Asn Ser Asp Glu Pro
65                  70                  75                  80 cag gag gat ttc cga aag ctg cga gac gag ctc att gct gca ggc atg       288
Gln Glu Asp Phe Arg Lys Leu Arg Asp Glu Leu Ile Ala Ala Gly Met
                85                  90                  95 ttc gat gcc tct ccc atg tgg tac gct tac aag acc ctg tcg act ctc       336
Phe Asp Ala Ser Pro Met Trp Tyr Ala Tyr Lys Thr Leu Ser Thr Leu
            100                 105                 110 gga ctg ggt gtc ctt gcc gtg ctg ttg atg acc cag tgg cac tgg tac       384
Gly Leu Gly Val Leu Ala Val Leu Leu Met Thr Gln Trp His Trp Tyr
        115                 120                 125 ctg gtt ggt gct atc gtc ctc ggc att cac ttt caa cag atg gga tgg       432
Leu Val Gly Ala Ile Val Leu Gly Ile His Phe Gln Gln Met Gly Trp
    130                 135                 140 ctc tcg cac gac att tgc cat cac cag ctg ttc aag gac cga tcc atc       480
Leu Ser His Asp Ile Cys His His Gln Leu Phe Lys Asp Arg Ser Ile
145                 150                 155                 160 aac aat gcc att ggc ctg ctc ttc gga aac gtg ctt cag ggc ttt tct       528
Asn Asn Ala Ile Gly Leu Leu Phe Gly Asn Val Leu Gln Gly Phe Ser
                165                 170                 175 gtc act tgg tgg aag gac cga cac aac gct cat cac tcc gcc acc aac       576
Val Thr Trp Trp Lys Asp Arg His Asn Ala His His Ser Ala Thr Asn
            180                 185                 190 gtg cag ggt cac gat ccc gac atc gac aac ctg cct ctc ctg gcg tgg       624
Val Gln Gly His Asp Pro Asp Ile Asp Asn Leu Pro Leu Leu Ala Trp
        195                 200                 205 tcc aag gag gac gtc gag cga gct ggc ccg ttt tct cga cgg atg atc       672
Ser Lys Glu Asp Val Glu Arg Ala Gly Pro Phe Ser Arg Arg Met Ile
    210                 215                 220 aag tac caa cag tat tac ttc ttt atc tgt gcc ctt ctg cga ttc           720
Lys Tyr Gln Gln Tyr Tyr Phe Phe Ile Cys Ala Leu Leu Arg Phe
225                 230                 235                 240 atc tgg tgc ttt cag tcc att cat act gcc acg ggt ctc aag gat cga       768
Ile Trp Cys Phe Gln Ser Ile His Thr Ala Thr Gly Leu Lys Asp Arg
                245                 250                 255 agc aat cag tac tat cga aga cag tac gag aag gag tcc gtc ggt ctg       816
Ser Asn Gln Tyr Tyr Arg Arg Gln Tyr Glu Lys Glu Ser Val Gly Leu
            260                 265                 270 gca ctc cac tgg ggt ctc aag gcc ttg ttc tac tat ttc tac atg ccc       864
```

```
Ala Leu His Trp Gly Leu Lys Ala Leu Phe Tyr Tyr Phe Tyr Met Pro
            275                 280                 285 tcg ttt ctc acc gga ctc atg gtg ttc ttt gtc tcc gag ctg ctt ggt       912
Ser Phe Leu Thr Gly Leu Met Val Phe Phe Val Ser Glu Leu Leu Gly
            290                 295                 300 ggc ttc gga att gcc atc gtt gtc ttc atg aac cac tac cct ctg gag       960
Gly Phe Gly Ile Ala Ile Val Val Phe Met Asn His Tyr Pro Leu Glu
305                 310                 315                 320 aag att cag gac tcc gtg tgg gat ggt cat ggc ttc tgt gct gga cag      1008
Lys Ile Gln Asp Ser Val Trp Asp Gly His Gly Phe Cys Ala Gly Gln
                325                 330                 335 att cac gag acc atg aac gtt cag cga ggc ctc gtc aca gac tgg ttt      1056
Ile His Glu Thr Met Asn Val Gln Arg Gly Leu Val Thr Asp Trp Phe
            340                 345                 350 ttc ggt ggc ctc aac tac cag atc gaa cat cac ctg tgg cct act ctt      1104
Phe Gly Gly Leu Asn Tyr Gln Ile Glu His His Leu Trp Pro Thr Leu
            355                 360                 365 ccc aga cac aac ctc acc gct gcc tcc atc aaa gtg gag cag ctg tgc      1152
Pro Arg His Asn Leu Thr Ala Ala Ser Ile Lys Val Glu Gln Leu Cys
370                 375                 380 aag aag cac aac ctg ccc tac cga tct cct ccc atg ctc gaa ggt gtc      1200
Lys Lys His Asn Leu Pro Tyr Arg Ser Pro Pro Met Leu Glu Gly Val
385                 390                 395                 400 ggc att ctt atc tcc tac ctg ggc acc ttc gct cga atg gtt gcc aag      1248
Gly Ile Leu Ile Ser Tyr Leu Gly Thr Phe Ala Arg Met Val Ala Lys
                405                 410                 415 gca gac aag gcc                                                      1260
Ala Asp Lys Ala
            420

<210> SEQ ID NO 59
<211> LENGTH: 420
<212> TYPE: PRT
<213> ORGANISM: Euglena anabaena UTEX 373

<400> SEQUENCE: 59

Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
                20                  25                  30

Glu Asn Tyr Arg Gly Arg Asp Ala Thr Asp Val Phe Met Val Met His
            35                  40                  45

Ser Glu Asn Ala Val Ser Lys Leu Arg Arg Met Pro Ile Met Glu Pro
    50                  55                  60

Ser Ser Pro Leu Thr Pro Thr Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95

Phe Asp Ala Ser Pro Met Trp Tyr Ala Tyr Lys Thr Leu Ser Thr Leu
            100                 105                 110

Gly Leu Gly Val Leu Ala Val Leu Leu Met Thr Gln Trp His Trp Tyr
            115                 120                 125

Leu Val Gly Ala Ile Val Leu Gly Ile His Phe Gln Gln Met Gly Trp
        130                 135                 140

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
                165                 170                 175
```

```
Val Thr Trp Trp Lys Asp Arg His Asn Ala His His Ser Ala Thr Asn
            180                 185                 190

Val Gln Gly His Asp Pro Asp Ile Asp Asn Leu Pro Leu Leu Ala Trp
        195                 200                 205

Ser Lys Glu Asp Val Glu Arg Ala Gly Pro Phe Ser Arg Arg Met Ile
    210                 215                 220

Lys Tyr Gln Gln Tyr Tyr Phe Phe Ile Cys Ala Leu Leu Arg Phe
225                 230                 235                 240

Ile Trp Cys Phe Gln Ser Ile His Thr Ala Thr Gly Leu Lys Asp Arg
                245                 250                 255

Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
        275                 280                 285

Ser Phe Leu Thr Gly Leu Met Val Phe Phe Val Ser Glu Leu Leu Gly
    290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
        355                 360                 365

Pro Arg His Asn Leu Thr Ala Ala Ser Ile Lys Val Glu Gln Leu Cys
    370                 375                 380

Lys Lys His Asn Leu Pro Tyr Arg Ser Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
            420

<210> SEQ ID NO 60
<211> LENGTH: 16424
<212> TYPE: DNA
<213> ORGANISM: Artificial Sequence
<220> FEATURE:
<223> OTHER INFORMATION: Plasmid pZKL4-220EA41B

<400> SEQUENCE: 60
aattctctct cttgagcttt tccataacaa gttcttctgc ctccaggaag tccatgggtg      60
gtttgatcat ggttttggtg tagtggtagt gcagtggtgg tatttgtgact ggggatgtag    120 ttgagaataa gtcatacaca agtcagcttt cttcgagcct catataagta taagtagttc    180
aacgtattag cactgtaccc agcatctccg tatcgagaaa cacaacaaca tgccccattg    240
gacagatcat gcggatacac aggttgtgca gtatcataca tactcgatca gacaggtcgt    300
ctgaccatca tacaagctga acaagcgctc catacttgca cgctctctat atacacagtt    360
aaattacata tccatagtct aacctctaac agtaatctt ctggtaagcc tcccagccag    420
ccttctggta tcgcttggcc tcctcaatag gatctcggtt ctggccgtac agacctcggc    480
cgacaattat gatatccgtt ccggtagaca tgacatcctc aacagttcgg tactgctgtc    540
cgagagcgtc tcccttgtcg tcaagaccca ccccgggggt cagaataagc cagtcctcag    600
```

```
agtcgccctt aggtcggttc tgggcaatga agccaaccac aaactcgggg tcggatcggg    660
caagctcaat ggtctgcttg gagtactcgc cagtggccag agagcccttg caagacagct    720
cggccagcat gagcagacct ctggccagct tctcgttggg agaggggact aggaactcct    780
tgtactggga gttctcgtag tcagagacgt cctccttctt ctgttcagag acagtttcct    840
cggcaccagc tcgcaggcca gcaatgattc cggttccggg tacaccgtgg gcgttggtga    900
tatcggacca ctcggcgatt cggtgacacc ggtactggtg cttgacagtg ttgccaatat    960
ctgcgaactt tctgtcctcg aacaggaaga aaccgtgctt aagagcaagt tccttgaggg   1020
ggagcacagt gccggcgtag gtgaagtcgt caatgatgtc gatatgggtt ttgatcatgc   1080
acacataagg tccgaccctta tcggcaagct caatgagctc cttggtggtg gtaacatcca   1140
gagaagcaca caggttggtt ttcttggctg ccacgagctt gagcactcga gcggcaaagg   1200
cggacttgtg gacgttagct cgagcttcgt aggagggcat tttggtggtg aagaggagac   1260
tgaaataaat ttagtctgca gaactttta tcggaacctt atctggggca gtgaagtata   1320
tgttatggta atagttacga gttagttgaa cttatagata gactggacta tacggctatc   1380
ggtccaaatt agaagaacg tcaatggctc tctgggcgtc gcctttgccg acaaaaatgt   1440
gatcatgatg aaagccagca atgacgttgc agctgatatt ttgtcggcc aaccgcgccg   1500 aaaacgcagc tgtcagaccc acagcctcca acgaagaatg tatcgtcaaa gtgatccaag   1560
cacactcata gttggagtcg tactccaaag gcggcaatga cgagtcagac agatactcgt   1620
cgaccttttc cttgggaacc accaccgtca gcccttctga ctcacgtatt gtagccaccg   1680
acacaggcaa cagtccgtgg atagcagaat atgtcttgtc ggtccatttc tcaccaactt   1740
taggcgtcaa gtgaatgttg cagaagaagt atgtgccttc attgagaatc ggtgttgctg   1800
atttcaataa agtcttgaga tcagtttggc cagtcatgtt gtgggggggta attggattga   1860 gttatcgcct acagtctgta caggtatact cgctgcccac tttatacttt ttgattccgc   1920
tgcacttgaa gcaatgtcgt ttaccaaaag tgagaatgct ccacagaaca cccccaggg   1980 tatggttgag caaaaaataa acactccgat acggggaatc gaaccccggt ctccacggtt   2040
ctcaagaagt attcttgatg agagcgtatc gatcgaggaa gaggacaagc ggctgcttct   2100
taagtttgtg acatcagtat ccaaggcacc attgcaagga ttcaaggctt gaacccgtc   2160 atttgccatt cgtaacgctg gtagacaggt tgatcggttc cctacggcct ccacctgtgt   2220
caatcttctc aagctgcctg actatcagga cattgatcaa cttcggaaga aacttttgta   2280
tgccattcga tcacatgctg gtttcgattt gtcttagagg aacgcatata cagtaatcat   2340
agagaataaa cgatattcat ttattaaagt agatagttga ggtagaagtt gtaaagagtg   2400
ataaatagcg gccgcttaag ccagagtggc gacagcagga caaccggcag cagatccgtc   2460
ggtggagccg tcgggttggg cagcaacggc agcagagagc acaggacaaa catcctccag   2520
ggaacctgca gtgggagcaa gcttgtcgtt gtctgcaggt ttggtgccca tagctcgcaa   2580
gtgctcgacc attccgtaca gagcatcgga aaactgagag tagttcttgt agggaagacc   2640
gtattcctcg cacacgccct tgacaacagg agcaatggtg ggatagttgg cgtgagaaat   2700
gctgggaaac aggtgatgct cgatctggtg gttgagtcca ccagaaaggt ggtttgaaaa   2760
gtagccacca gatcgccagt tgacgcaaca cagaacttgg gaggcagccc agtcgttggg   2820
aggtggagtg gggtgcttct gtttcgcctt ggcttcctgc tcggcctgct tgagcatttc   2880
ggtccgtcgg gcagcgataa cggaagaggg attgaggtag tcgcacgact cggaaatgtg   2940
gttgataatg aaacagacgg caaggtactc gccagaaacc agatgagctg taatgaagag   3000
```

```
ggccaatccg tgagcgatgc catgcaggta gcagggaagc acaatctgca tgagaaagcc   3060
catgatcttt gcaccccaga acagcatctg accctcgagg ggaacgagtc tggcagagaa   3120
gtcgatggga ccacgtcgct tggcaagaca aaacgtgaaa tcggagataa tgaccttgct   3180
gatggtcatg agagcgaaca acggaaaggc gtacacgtgt tgcagctgat ggtggggttt   3240
ccaaggagtg tccggatgca tccgcatgag gggataggtt ccgaaaacgt ctggatcgtt   3300
ctcgggaaga gcaaactcgg gatcggacac caggttggtg tactggtgat gaccaatgac   3360
gtgttggtac tcccaggcag tcgaggaggc tccgataacg tccatacccc agccagcaag   3420
acggttgagt cgtccagact tggagaaagc accatgattg ccgtcgtgct ggatgctgag   3480
tccaatgtga gagcctgcca gaccccagac ggcagcccaa agaaggatcc cctgtgtcac   3540
catgaggtag aacgaggcag caaaggcagc cataacaagg gctgccttga cagacaggcc   3600
accacgtcga ggttgtccag cctccttgag agtctgaacc actcgctgct tgagctcggc   3660
gtagaaagcg gaggcctgcc agtcgtagaa ggttctgtga tcctgaagtg taccgattcg   3720
gtacttctcc ataaccttgt cgggtcgtcc tgcaggatgg tacgattcga ccagaatagt   3780
ggagtctcgt ccgagaccga gagagataac atctccaccg gatgcttgc caatgaactc   3840 ggtgatgtcg tacacaccgt cgtgacaggc caaccagcca tcggtgggaa caatgtgtcg   3900
agcgacctct cgcatggtaa actttcggtc ctgtccagta ccggaggtgg ccagagcgtc   3960
gtaataggct gcaggtgggt tgccaacagg tcgaatggga ggtggaagag aagcgatctc   4020
cgagggcttg ccaggtccac cgggtttgac cttggccatg ccattgctg tagatatgtc   4080 ttgtgtgtaa gggggttggg gtggttgttt gtgttcttga cttttgtgtt agcaagggaa   4140
gacgggcaaa aaagtgagtg tggttgggag ggagagacga gccttatata taatgcttgt   4200
ttgtgtttgt gcaagtggac gccgaaacgg gcaggagcca aactaaacaa ggcagacaat   4260
gcgagcttaa ttggattgcc tgatgggcag gggttagggc tcgatcaatg ggggtgcgaa   4320
gtgacaaaat tgggaattag gttcgcaagc aaggctgaca agactttggc ccaaacattt   4380
gtacgcggtg gacaacagga gccacccatc gtctgtcacg ggctagccgg tcgtgcgtcc   4440
tgtcaggctc cacctaggct ccatgccact ccatacaatc ccactagtgt accgctaggc   4500
cgcttttagc tcccatctaa gaccccccca aaacctccac tgtacagtgc actgtactgt   4560
gtggcgatca agggcaaggg aaaaaaggcg caaacatgca cgcatggaat gacgtaggta   4620
aggcgttact agactgaaaa gtggcacatt tcggcgtgcc aaagggtcct aggtgcgttt   4680
cgcgagctgg gcgccaggcc aagccgctcc aaaacgcctc tccgactccc tccagcggcc   4740
tccatatccc catccctctc cacagcaatg ttgttaagcc ttgcaaacga aaaaatagaa   4800
aggctaataa gcttccaata ttgtggtgta cgctgcataa cgcaacaatg agcgccaaac   4860
aacacacaca cacagcacac agcagcatta accacgatgt ttaaacagag tgtgaaagac   4920
tcactatggt ccgggcttat ctcgaccaat agccaaagtc tggagtttct gagagaaaaa   4980
ggcaagatac gtatgtaaca aagcgacgca tggtacaata ataccggagg catgtatcat   5040
agagagttag tggttcgatg atggcactgg tgcctggtat gactttatac ggctgactac   5100
atatttgtcc tcagacatac aattacagtc aagcacttac ccttggacat ctgtaggtac   5160
cccccggcca agacgatctc agcgtgtcgt atgtcggatt ggcgtagctc cctcgctcgt   5220
caattggctc ccatctactt tcttctgctt ggctacaccc agcatgtctg ctatggctcg   5280
ttttcgtgcc ttatctatcc tcccagtatt accaactcta aatgacatga tgtgattggg   5340
```

```
tctacactttt catatcagag ataaggagta gcacagttgc ataaaaagcc caactctaat    5400
cagcttcttc ctttcttgta attagtacaa aggtgattag cgaaatctgg aagcttagtt    5460
ggccctaaaa aaatcaaaaa aagcaaaaaa cgaaaaacga aaaccacag ttttgagaac     5520
agggaggtaa cgaaggatcg tatatatata tatatatata tacccacg gatcccgaga     5580
ccggcctttg attcttccct acaaccaacc attctcacca ccctaattca caaccatggc    5640
tgactctccc gtcatcaacc tctccaccat gtggaagcct ctgtcgctca tggccttgga    5700
tcttgctgtt ctgggacacg tctggaagca ggcacaacag gagggctcca tctcggctta    5760
cgccgactct gtgtggactc ccctcatcat gtccggtctg tacctctcca tgatcttcgt    5820
gggatgtcga tggatgaaga accgagagcc cttcgaaatc aagacctaca tgtttgccta    5880
caacctgtac cagaccctca tgaacctttg cattgtgctg gcttcctct accaggtcca     5940
cgctaccggt atgcgattct ggggatctgg cgtggaccga tcgcccaagg gtctgggaat    6000
tggcttttc atctatgccc attaccacaa caagtacgtc gagtacttcg acacactctt    6060
catggtgctg cggaaaaaga caaccagat ttccttcttt cacgtctacc atcacgctct    6120
gctcacctgg gcttggtttg ccgtggtcta cttcgctcct ggaggtgacg gctggtttgg    6180
agcctgctac aattcctcca ttcatgtcct gatgtactct tactatctgc ttgccacctt    6240
cggcatctcc tgtccctgga aaagatcct cacccagctg caaatggttc agttctgctt    6300
ttgcttcacc cactcgatct acgtgtggat ttgcggttcc gaaatctacc ctcgaccctt    6360
gactgctctc cagtccttcg tgatggtcaa catgctggtt ctctttggca acttctacgt    6420
caagcagtat tctcagaaga atggaaagcc cgagaacggt gccactcctg agaacggtgc    6480
caagcctcag ccctgcgaga acggcaccgt cgagaagcga gagaacgaca ctgccaacgt    6540
tcgataagcg gccgcatgag aagataaata tataaataca ttgagatatt aaatgcgcta    6600
gattagagag cctcatactg ctcggagaga agccaagacg agtactcaaa ggggattaca    6660
ccatccatat ccacagacac aagctgggga aaggttctat atacactttc cggaataccg    6720
tagtttccga tgttatcaat gggggcagcc aggatttcag gcacttcggt gtctcgggt     6780
gaaatggcgt tcttggcctc catcaagtcg taccatgtct tcatttgcct gtcaaagtaa    6840
aacagaagca gatgaagaat gaacttgaag tgaaggaatt taaattgccc cggagaagac    6900
ggccaggccg cctagatgac aaattcaaca actcacagct gactttctgc cattgccact    6960
aggggggggc ctttttatat ggccaagcca agctctccac gtcggttggg ctgcacccaa    7020
caataaatgg gtagggttgc accaacaaag ggatgggatg gggggtagaa gatacgagga    7080
taacggggct caatggcaca aataagaacg aatactgcca ttaagactcg tgatccagcg    7140
actgacacca ttgcatcatc taagggcctc aaaaactacct cggaactgct gcgctgatct    7200
ggacaccaca gaggttccga gcactttagg ttgcaccaaa tgtcccacca ggtgcaggca    7260
gaaaacgctg gaacagcgtg tacagtttgt cttaacaaaa agtgagggcg ctgaggtcga    7320
gcagggtggt gtgacttgtt atagccttta gagctgcgaa agcgcgtatg gatttggctc    7380
atcaggccag attgagggtc tgtggacaca tgtcatgtta gtgtacttca atcgccccct    7440
ggatatagcc ccgacaatag gccgtggcct catttttttg ccttccgcac atttccattg    7500
ctcggtaccc acaccttgct tctcctgcac ttgccaacct taatactggt ttacattgac    7560
caacatctta caagcgggg gcttgtctag ggtatatata aacagtggct ctcccaatcg    7620
gttgccagtc tcttttttcc tttctttccc cacagattcg aaatctaaac tacacatcac    7680
agaactccga gccgtgagta tccacgacaa gatcagtgtc gagacgacgc gttttgtgta    7740
```

```
atgacacaat ccgaaagtcg ctagcaacac acactctcta cacaaactaa cccagctctg   7800
gtaccatggc cgagggcaag tccgacggtc ccgtcgttac cctccagtcc atgtggaagc   7860
ccctggctct catggccatc gacgtcggca tcctggtcaa cgtgcgacgg aaggccttca   7920
ccgagttcga cggacactcg aacgtcttcg ccgatcccgt gtacattccc tttgtcatga   7980
acctgttcta cctcaccatg atctttgctg gctgccgatg gatgaagact cgagaaccct   8040
tcgagatcaa gtcctacatg tttgcctaca acgcttacca gacaatgatg aactttctca   8100
ttgtggtcgg cttcatgtat gaggttcact ccaccggtat gcgatactgg ggatccagaa   8160
tcgacacttc taccaagggc ttgggactgg gtttcctcat ctatgcccat taccacaaca   8220
agtacgtgga gtacgtcgac accctgttca tgattctgcg gaagaaaaac aatcagatct   8280
cgttccttca cgtttaccac cattccctgc tcacttgggc atggtgggct gtggtctact   8340
gggctcctgg cggagatgcc tggttcggtg cctgttacaa ctccttcatc cacgttctca   8400
tgtactccta ctatctgttt gccaccttcg gcattcgatg tccctggaaa agatgctca   8460 cccagttgca aatggtccag ttctgctttt gcttcgctca tgccatgtac gttggatggc   8520
ttggtcacga ggtgtaccct cgatggctca ctgctctgca ggcctttgtg atgctcaaca   8580
tgctggtcct cttttggcaac ttctacatga agtcttactc caaggcgagc aagctcgaac   8640
cagcctctcc cgtgtcgcct gcctctcttg ctcagaagcc cttcgagaac gccaaggtca   8700
agtaagcggc cgcaagtgtg gatggggaag tgagtgcccg gttctgtgtg cacaattggc   8760
aatccaagat ggatggattc aacacaggga tatagcgagc tacgtggtgg tgcgaggata   8820
tagcaacgga tatttatgtt tgacacttga gaatgtacga tacaagcact gtccaagtac   8880
aatactaaac atactgtaca tactcatact cgtacccggg caacggtttc acttgagtgc   8940
agtggctagt gctcttactc gtacagtgtg caatactgcg tatcatagtc tttgatgtat   9000
atcgtattca ttcatgttag ttgcgtacgt agggatcagg tgcttaggaa gctcgaccaa   9060
ccacggagac tgttgaaact ggatgtcggt aacagcatct ggaatgctga atgttcctcg   9120
aataacaaca tatttctcct tgttgaggtg atcataagct atgtatccgg tgattgaagt   9180
ggaatagaag tctcctccga agactgagtc caacgtcatg ttcgggaaat accgacaact   9240
ctctccacat gtaaaatcag ttcgtagagg agtgactggc gcattgacac agtaggcgat   9300
gtttgcaatc cgagaaaact tggccgtaaa gttgtacagc tcctgggagg cttgaactcg   9360 agttttttgaa agtgtcgctg gtggctcgcc gaagagggag gcatagaggt acgcaaccac   9420
ttgcccgagc gtgaggttca tgatgccaat agtgaatgtc atttatcacc gtactgcgca   9480
gtatttatat agggctcatc ggtccatgta tagatctgtc cacttatgac accccatgt   9540 ctcattaatg tgtaaaggtg gagacgggtg gagtacaggt acagagttgg aggaaatcag   9600
gatagtgggg ttaagacatg ctccgagtcc aaatttcaac tctccattgt cacaagacct   9660
ctggtttcag agttattaca gatctaggcc tgtttcaagg tgagggacc tcatctggat   9720 cggcacgacg atcgtcacct tacagaggac gtctgtcgca gggaaaggtg atgtggcgcg   9780
ccagctgcat taatgaatcg gccaacgcgc ggggagaggc ggtttgcgta ttgggcgctc   9840
ttccgcttcc tcgctcactg actcgctgcg ctcggtcgtt cggctgcggc gagcggtatc   9900
agctcactca aaggcggtaa tacggttatc cacagaatca ggggataacg caggaaagaa   9960
catgtgagca aaaggccagc aaaaggccag gaaccgtaaa aaggccgcgt tgctggcgtt  10020
tttccatagg ctccgccccc ctgacgagca tcacaaaaat cgacgctcaa gtcagaggtg  10080
```

```
gcgaaacccg acaggactat aaagatacca ggcgtttccc cctggaagct ccctcgtgcg    10140
ctctcctgtt ccgaccctgc cgcttaccgg atacctgtcc gcctttctcc cttcgggaag    10200
cgtggcgctt tctcatagct cacgctgtag gtatctcagt tcggtgtagg tcgttcgctc    10260
caagctgggc tgtgtgcacg aaccccccgt tcagcccgac cgctgcgcct tatccggtaa    10320
ctatcgtctt gagtccaacc cggtaagaca cgacttatcg ccactggcag cagccactgg    10380
taacaggatt agcagagcga ggtatgtagg cggtgctaca gagttcttga agtggtggcc    10440
taactacggc tacactagaa gaacagtatt tggtatctgc gctctgctga agccagttac    10500
cttcggaaaa agagttggta gctcttgatc cggcaaacaa accaccgctg gtagcggtgg    10560
tttttttgtt tgcaagcagc agattacgcg cagaaaaaaa ggatctcaag aagatccttt    10620
gatcttttct acggggtctg acgctcagtg gaacgaaaac tcacgttaag ggattttggt    10680
catgagatta tcaaaaagga tcttcaccta gatcctttta aattaaaaat gaagttttaa    10740
atcaatctaa agtatatatg agtaaacttg gtctgacagt taccaatgct taatcagtga    10800
ggcacctatc tcagcgatct gtctatttcg ttcatccata gttgcctgac tccccgtcgt    10860
gtagataact acgatacggg agggcttacc atctggcccc agtgctgcaa tgataccgcg    10920
agacccacgc tcaccggctc cagatttatc agcaataaac cagccagccg aagggccga    10980 gcgcagaagt ggtcctgcaa ctttatccgc ctccatccag tctattaatt gttgccggga    11040
agctagagta agtagttcgc cagttaatag tttgcgcaac gttgttgcca ttgctacagg    11100
catcgtggtg tcacgctcgt cgtttggtat ggcttcattc agctccggtt cccaacgatc    11160
aaggcgagtt acatgatccc ccatgttgtg caaaaaagcg gttagctcct tcggtcctcc    11220
gatcgttgtc agaagtaagt tggccgcagt gttatcactc atggttatgg cagcactgca    11280
taattctctt actgtcatgc catccgtaag atgcttttct gtgactggtg agtactcaac    11340
caagtcattc tgagaatagt gtatgcggcg accgagttgc tcttgcccgg cgtcaatacg    11400
ggataatacc gcgccacata gcagaacttt aaaagtgctc atcattggaa aacgttcttc    11460
ggggcgaaaa ctctcaagga tcttaccgct gttgagatcc agttcgatgt aacccactcg    11520
tgcacccaac tgatcttcag catcttttac tttcaccagc gtttctgggt gagcaaaaac    11580
aggaaggcaa aatgccgcaa aaaagggaat aagggcgaca cggaaatgtt gaatactcat    11640
actcttcctt tttcaatatt attgaagcat ttatcagggt tattgtctca tgagcggata    11700
catatttgaa tgtatttaga aaaataaaca aataggggtt ccgcgcacat ttccccgaaa    11760
agtgccacct gatgcggtgt gaaataccgc acagatgcgt aaggagaaaa taccgcatca    11820
ggaaattgta agcgttaata ttttgttaaa attcgcgtta aattttttgtt aaatcagctc    11880 attttttaac caataggccg aaatcggcaa aatcccttat aaatcaaaag aatagaccga    11940
gatagggttg agtgttgttc cagtttggaa caagagtcca ctattaaaga acgtggactc    12000
caacgtcaaa gggcgaaaaa ccgtctatca gggcgatggc ccactacgtg aaccatcacc    12060
ctaatcaagt ttttttgggt cgaggtgccg taaagcacta atcggaacc ctaaagggag    12120 cccccgattt agagcttgac ggggaaagcc ggcgaacgtg gcgagaaagg aagggaagaa    12180
agcgaaagga gcggcgcta gggcgctggc aagtgtagcg gtcacgctgc gcgtaaccac    12240
cacacccgcc gcgcttaatg cgccgctaca gggcgcgtcc attcgccatt caggctgcgc    12300
aactgttggg aagggcgatc ggtgcgggcc tcttcgctat tacgccagct ggcgaaaggg    12360
ggatgtgctg caaggcgatt aagttgggta acgccagggt tttcccagtc acgacgttgt    12420
aaaacgacgg ccagtgaatt gtaatacgac tcactatagg gcgaattggg cccgacgtcg    12480
```

```
catgccaagg cgtatattag ttggtgggaa ccagtgtacg accgggtcct gtataaccag   12540
gttcagtggc atacttgtag gagttgttcc cgtggtattt gggcatggct aagacatttc   12600
gccgaccaat gttaagtgca caatagccga tgtagtagat gtaagccaga tggttttgga   12660
gcaggtcgat tcgagaccac agattgaaag tgcctcgatg gcaggcctcg ttttctcctc   12720
cttcacagac agacactttg tcgagtgcag ggtagacgct ttcttggtca atgtacactt   12780
ctccaatggc gtgtgtgtaa ttggaccaat ctggcagtcc aacgaagata tcgttccagt   12840
gggtgagcct gtagtttcgt cgcttgtcgt ttacttcaag gcctgtgtca ttaaaccaca   12900
gctggttgat gtagtttgca aactctgagt ttcctactct cggctggcca agttgatca    12960 tggtaggatc atgtccaagt aatttgaagt gagttgcgaa aagaagagct tgagcagcgc   13020
ccagcgagtg accagtaaca tacattttgt agtcagtgtg gttggtgagg aacttttcaa   13080
actgaggagc agcattgacc atagtttcgt tgaaggcctt ggcgaaccca tcatggatca   13140
tgcagccttt gcactcacta gttttgatgg gaataagacg ggggtcttca accaccagag   13200
cccgctcttt gaggttgtca agacctttgt tctccacttc caagtctggt cggactgccc   13260
atctctgtta attaactcac ctgcaggatt gagactatga atggattccc gtgcccgtat   13320
tactctacta atttgatctt ggaacgcgaa aatacgtttc taggactcca aagaatctca   13380
actcttgtcc ttactaaata tactacccat agttgatggt ttacttgaac agagaggaca   13440
tgttcacttg acccaaagtt tctcgcatct cttggatatt tgaacaacgg cgtccactga   13500
ccgtcagtta tccagtcaca aaaccccccac attcatacat tcccatgtac gtttacaaag   13560
ttctcaattc catcgtgcaa atcaaaatca catctattca ttcatcatat ataaacccat   13620
catgtctact aacactcaca actccataga aaacatcgac tcagaacaca cgctccatgc   13680
ggccgcttag gcgagagtag caacggcagg acatccagcg gcagagccgt cggtagaacc   13740
gtcgggttgg gcagccacgg cagcagacag aacagggcag acatcctcca aagatccagc   13800
agtaggagca agtttgtcgt tgtccgcagg cttggtaccc attgctcgca ggtgctccac   13860
catgccgtag agggcatcgg agaactgaga gtagttcttg tagggaagtc cgtactcttc   13920
gcacacaccc ttgacaacgg gagcaatggt gggatagttg gcgtggctga tagaaggaaa   13980
cagatggtgc tcgatctgat gattgagacc tcctgacaag tggttcgaga agtaaccgcc   14040
agatcgccag ttgacacagc aaagaacctg ggaagctgcc cagtcgttgg gtggaggtgt   14100
gggatgcttc tgtttcgcct tggcctcctg ttcggcttgc ttgagcatct ccgttcgtct   14160
ggcagcgatg acagaggagg ggttgaggta gtcacaagac tcgaaatgt ggttgataat    14220 gaagcaaaact gccaggtact cgcctgaaac gaggtgggca gtgatgaaca gagccaaacc   14280
atgtgcaatg ccgtgcaggt aacagggaag aacgatctgc atgagaaagc ccatgatctt   14340
tgctccccag aaaagcatct ggccctcgag aggcacaagt cgggcagaaa agtcgatcgg   14400
acctcgacgc ttggcgaggc agaaggtgaa atcgctaatg ataaccttgg agatagtcat   14460
gagggcgaac aggggaaagg catagacgtg ctgcagttgg tgatgaggtt tccacggagt   14520
gtcgggatgc attcgcatga gagggtaggt tccgaacacg tcgggatcgt tctctggaag   14580
ggcaaattcg ggatcggaaa caaggttggt gtattgatgg tggccaatga catgctggta   14640
ctcccaggct gtggacgaag caccaatgac gtccataccc catccggcca gtcgattgag   14700
acggccagac ttcgaaaagg caccgtggtt tccgtcgtgc tgaatggaga ggccgatgtg   14760
acttccagca agacccccaca cagctgccca gaaaaacgag ccctgagtga ccatgagata   14820
```

| | | |
|---|---|---|
| gaaggaagcg gcaaacgcag ccataaccag tgcagccttg actgacagtc cgcctcgtct | 14880 | |
| gggctgacca gcctccttga gggttttgcac gactcgctgc ttgagttccg cgtaaaaggc | 14940 | |
| agaagcctgc cagtcgtaga aagttcgatg atcctgaaga gtgccgattc tgtacttctc | 15000 | |
| cataaccttg tcgggtcgac cagcagggtg gtaggactcc acgagaatgg tagagtctcg | 15060 | |
| acccagtcca agggaaatga catcgccacc gggatgcttt ccgataaact ctgtaatgtc | 15120 | |
| gtaaacgccg tcgtgacagg ccagccaacc atcggtggga acgatgtgtc gtgcgacttc | 15180 | |
| tcgcatggtg aactttcggt cctgaccggt tccagaagta gcgagggcgt catagtaggc | 15240 | |
| agctggaggg tttcccacgg gtcggatggg tggaggcagc gaggcaatct cggagggttt | 15300 | |
| gccaggacct ccaggcttga ccttggccat gggcaggacc tgtgttagta cattgtcggg | 15360 | |
| gagtcatcaa ttggttcgac aggttgtcga ctgttagtat gagctcaatt gggctctggt | 15420 | |
| gggtcgatga cacttgtcat ctgtttctgt tgggtcatgt ttccatcacc ttctatggta | 15480 | |
| ctcacaattc gtccgattcg cccgaatccg ttaataccga ctttgatggc catgttgatg | 15540 | |
| tgtgtttaat tcaagaatga atatagagaa gagaagaaga aaaagattc aattgagccg | 15600 | |
| gcgatgcaga cccttatata aatgttgcct tggacagacg gagcaagccc gcccaaacct | 15660 | |
| acgttcggta taatatgtta agcttttttaa cacaaaggtt tggcttgggg taacctgatg | 15720 | |
| tggtgcaaaa gaccgggcgt tggcgagcca ttgcgcgggc gaatgggggcc gtgactcgtc | 15780 | |
| tcaaattcga gggcgtgcct caattcgtgc ccccgtggct ttttcccgcc gtttccgccc | 15840 | |
| cgtttgcacc actgcagccg cttctttggt tcggacacct tgctgcgagc taggtgcctt | 15900 | |
| gtgctactta aaaagtggcc tcccaacacc aacatgacat gagtgcgtgg gccaagacac | 15960 | |
| gttggcgggg tcgcagtcgg ctcaatggcc cggaaaaaac gctgctggag ctggttcgga | 16020 | |
| cgcagtccgc cgcggcgtat ggatatccgc aaggttccat agcgccattg ccctccgtcg | 16080 | |
| gcgtctatcc cgcaacctct aaatagagcg ggaatataac ccaagcttct ttttttttcct | 16140 | |
| ttaacacgca caccccccaac tatcatgttg ctgctgctgt ttgactctac tctgtggagg | 16200 | |
| ggtgctccca cccaacccaa cctacaggtg gatccggcgc tgtgattggc tgataagtct | 16260 | |
| cctatccgga ctaattctga ccaatgggac atgcgcgcag gacccaaatg ccgcaattac | 16320 | |
| gtaaccccaa cgaaatgcct accctctttt ggagcccagc ggccccaaat cccccaagc | 16380 | |
| agcccggttc taccggcttc catctccaag cacaagcagc ccgg | 16424 | |

<210> SEQ ID NO 61
<211> LENGTH: 900
<212> TYPE: DNA
<213> ORGANISM: Euglena anabaena
<220> FEATURE:
<221> NAME/KEY: CDS
<222> LOCATION: (1)..(900)
<223> OTHER INFORMATION: synthetic C20 elongase (codon-optimized for
    Yarrowia lipolytica) ("EaC20ES")
<300> PUBLICATION INFORMATION:
<302> TITLE: MULTIZYMES AND THEIR USE IN MAKING POLYUNSATURATED FATTY
    ACIDS
<310> PATENT DOCUMENT NUMBER: US-2008-0254191-A1
<311> PATENT FILING DATE: 2008-04-03
<312> PUBLICATION DATE: 2008-10-16
<313> RELEVANT RESIDUES IN SEQ ID NO: (1)..(900)

<400> SEQUENCE: 61

```
atg gcc gag ggc aag tcc gac ggt ccc gtc gtt acc ctc cag tcc atg        48
Met Ala Glu Gly Lys Ser Asp Gly Pro Val Val Thr Leu Gln Ser Met
1               5                   10                  15 tgg aag ccc ctg gct ctc atg gcc atc gac gtc ggc atc ctg gtc aac        96
```

```
                Trp Lys Pro Leu Ala Leu Met Ala Ile Asp Val Gly Ile Leu Val Asn
                         20                  25                  30 gtg cga cgg aag gcc ttc acc gag ttc gac gga cac tcg aac gtc ttc       144
Val Arg Arg Lys Ala Phe Thr Glu Phe Asp Gly His Ser Asn Val Phe
         35                  40                  45 gcc gat ccc gtg tac att ccc ttt gtc atg aac ctg ttc tac ctc acc       192
Ala Asp Pro Val Tyr Ile Pro Phe Val Met Asn Leu Phe Tyr Leu Thr
 50                  55                  60 atg atc ttt gct ggc tgc cga tgg atg aag act cga gaa ccc ttc gag       240
Met Ile Phe Ala Gly Cys Arg Trp Met Lys Thr Arg Glu Pro Phe Glu
 65                  70                  75                  80 atc aag tcc tac atg ttt gcc tac aac gct tac cag aca atg atg aac       288
Ile Lys Ser Tyr Met Phe Ala Tyr Asn Ala Tyr Gln Thr Met Met Asn
                 85                  90                  95 ttt ctc att gtg gtc ggc ttc atg tat gag gtt cac tcc acc ggt atg       336
Phe Leu Ile Val Val Gly Phe Met Tyr Glu Val His Ser Thr Gly Met
            100                 105                 110 cga tac tgg gga tcc aga atc gac act tct acc aag ggc ttg gga ctg       384
Arg Tyr Trp Gly Ser Arg Ile Asp Thr Ser Thr Lys Gly Leu Gly Leu
        115                 120                 125 ggt ttc ctc atc tat gcc cat tac cac aac aag tac gtg gag tac gtc       432
Gly Phe Leu Ile Tyr Ala His Tyr His Asn Lys Tyr Val Glu Tyr Val
130                 135                 140 gac acc ctg ttc atg att ctg cgg aag aaa aac aat cag atc tcg ttc       480
Asp Thr Leu Phe Met Ile Leu Arg Lys Lys Asn Asn Gln Ile Ser Phe
145                 150                 155                 160 ctt cac gtt tac cac cat tcc ctg ctc act tgg gca tgg tgg gct gtg       528
Leu His Val Tyr His His Ser Leu Leu Thr Trp Ala Trp Trp Ala Val
                165                 170                 175 gtc tac tgg gct cct ggc gga gat gcc tgg ttc ggt gcc tgt tac aac       576
Val Tyr Trp Ala Pro Gly Gly Asp Ala Trp Phe Gly Ala Cys Tyr Asn
            180                 185                 190 tcc ttc atc cac gtt ctc atg tac tcc tac tat ctg ttt gcc acc ttc       624
Ser Phe Ile His Val Leu Met Tyr Ser Tyr Tyr Leu Phe Ala Thr Phe
        195                 200                 205 ggc att cga tgt ccc tgg aaa aag atg ctc acc cag ttg caa atg gtc       672
Gly Ile Arg Cys Pro Trp Lys Lys Met Leu Thr Gln Leu Gln Met Val
210                 215                 220 cag ttc tgc ttt tgc ttc gct cat gcc atg tac gtt gga tgg ctt ggt       720
Gln Phe Cys Phe Cys Phe Ala His Ala Met Tyr Val Gly Trp Leu Gly
225                 230                 235                 240 cac gag gtg tac cct cga tgg ctc act gct ctg cag gcc ttt gtg atg       768
His Glu Val Tyr Pro Arg Trp Leu Thr Ala Leu Gln Ala Phe Val Met
                245                 250                 255 ctc aac atg ctg gtc ctc ttt ggc aac ttc tac atg aag tct tac tcc       816
Leu Asn Met Leu Val Leu Phe Gly Asn Phe Tyr Met Lys Ser Tyr Ser
            260                 265                 270 aag gcg agc aag ctc gaa cca gcc tct ccc gtg tcg cct gcc tct ctt       864
Lys Ala Ser Lys Leu Glu Pro Ala Ser Pro Val Ser Pro Ala Ser Leu
        275                 280                 285 gct cag aag ccc ttc gag aac gcc aag gtc aag taa                       900
Ala Gln Lys Pro Phe Glu Asn Ala Lys Val Lys
        290                 295

<210> SEQ ID NO 62
<211> LENGTH: 299
<212> TYPE: PRT
<213> ORGANISM: Euglena anabaena

<400> SEQUENCE: 62
```

```
Met Ala Glu Gly Lys Ser Asp Gly Pro Val Thr Leu Gln Ser Met
 1               5                  10                  15

Trp Lys Pro Leu Ala Leu Met Ala Ile Asp Val Gly Ile Leu Val Asn
            20                  25                  30

Val Arg Arg Lys Ala Phe Thr Glu Phe Asp Gly His Ser Asn Val Phe
        35                  40                  45

Ala Asp Pro Val Tyr Ile Pro Phe Val Met Asn Leu Phe Tyr Leu Thr
 50                  55                  60

Met Ile Phe Ala Gly Cys Arg Trp Met Lys Thr Arg Glu Pro Phe Glu
 65                  70                  75                  80

Ile Lys Ser Tyr Met Phe Ala Tyr Asn Ala Tyr Gln Thr Met Met Asn
                85                  90                  95

Phe Leu Ile Val Val Gly Phe Met Tyr Glu Val His Ser Thr Gly Met
            100                 105                 110

Arg Tyr Trp Gly Ser Arg Ile Asp Thr Ser Thr Lys Gly Leu Gly Leu
        115                 120                 125

Gly Phe Leu Ile Tyr Ala His Tyr His Asn Lys Tyr Val Glu Tyr Val
130                 135                 140

Asp Thr Leu Phe Met Ile Leu Arg Lys Lys Asn Asn Gln Ile Ser Phe
145                 150                 155                 160

Leu His Val Tyr His His Ser Leu Leu Thr Trp Ala Trp Ala Val
                165                 170                 175

Val Tyr Trp Ala Pro Gly Gly Asp Ala Trp Phe Gly Ala Cys Tyr Asn
            180                 185                 190

Ser Phe Ile His Val Leu Met Tyr Ser Tyr Tyr Leu Phe Ala Thr Phe
        195                 200                 205

Gly Ile Arg Cys Pro Trp Lys Lys Met Leu Thr Gln Leu Gln Met Val
210                 215                 220

Gln Phe Cys Phe Cys Phe Ala His Ala Met Tyr Val Gly Trp Leu Gly
225                 230                 235                 240

His Glu Val Tyr Pro Arg Trp Leu Thr Ala Leu Gln Ala Phe Val Met
                245                 250                 255

Leu Asn Met Leu Val Leu Phe Gly Asn Phe Tyr Met Lys Ser Tyr Ser
            260                 265                 270

Lys Ala Ser Lys Leu Glu Pro Ala Ser Pro Val Ser Pro Ala Ser Leu
        275                 280                 285

Ala Gln Lys Pro Phe Glu Asn Ala Lys Val Lys
290                 295
```

<210> SEQ ID NO 63
<211> LENGTH: 912
<212> TYPE: DNA
<213> ORGANISM: Euglena gracilis
<220> FEATURE:
<221> NAME/KEY: CDS
<222> LOCATION: (1)..(912)
<223> OTHER INFORMATION: synthetic C20 elongase (codon-optimized for
      Yarrowia lipolytica) ("EgC20ES")
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: US-2008-0254191-A1
<311> PATENT FILING DATE: 2008-04-03
<312> PUBLICATION DATE: 2008-10-16
<313> RELEVANT RESIDUES IN SEQ ID NO: (1)..(912)

<400> SEQUENCE: 63

```
atg gct gac tct ccc gtc atc aac ctc tcc acc atg tgg aag cct ctg    48
Met Ala Asp Ser Pro Val Ile Asn Leu Ser Thr Met Trp Lys Pro Leu
```

```
1               5                   10                  15
tcg ctc atg gcc ttg gat ctt gct gtt ctg gga cac gtc tgg aag cag       96
Ser Leu Met Ala Leu Asp Leu Ala Val Leu Gly His Val Trp Lys Gln
            20                  25                  30 gca caa cag gag ggc tcc atc tcg gct tac gcc gac tct gtg tgg act      144
Ala Gln Gln Glu Gly Ser Ile Ser Ala Tyr Ala Asp Ser Val Trp Thr
        35                  40                  45 ccc ctc atc atg tcc ggt ctg tac ctc tcc atg atc ttc gtg gga tgt      192
Pro Leu Ile Met Ser Gly Leu Tyr Leu Ser Met Ile Phe Val Gly Cys
    50                  55                  60 cga tgg atg aag aac cga gag ccc ttc gaa atc aag acc tac atg ttt      240
Arg Trp Met Lys Asn Arg Glu Pro Phe Glu Ile Lys Thr Tyr Met Phe
65                  70                  75                  80 gcc tac aac ctg tac cag acc ctc atg aac ctt tgc att gtg ctg ggc      288
Ala Tyr Asn Leu Tyr Gln Thr Leu Met Asn Leu Cys Ile Val Leu Gly
                85                  90                  95 ttc ctc tac cag gtc cac gct acc ggt atg cga ttc tgg gga tct ggc      336
Phe Leu Tyr Gln Val His Ala Thr Gly Met Arg Phe Trp Gly Ser Gly
            100                 105                 110 gtg gac cga tcg ccc aag ggt ctg gga att ggc ttt ttc atc tat gcc      384
Val Asp Arg Ser Pro Lys Gly Leu Gly Ile Gly Phe Phe Ile Tyr Ala
        115                 120                 125 cat tac cac aac aag tac gtc gag tac ttc gac aca ctc ttc atg gtg      432
His Tyr His Asn Lys Tyr Val Glu Tyr Phe Asp Thr Leu Phe Met Val
    130                 135                 140 ctg cgg aaa aag aac aac cag att tcc ttt ctt cac gtc tac cat cac      480
Leu Arg Lys Lys Asn Asn Gln Ile Ser Phe Leu His Val Tyr His His
145                 150                 155                 160 gct ctg ctc acc tgg gct tgg ttt gcc gtg gtc tac ttc gct cct gga      528
Ala Leu Leu Thr Trp Ala Trp Phe Ala Val Val Tyr Phe Ala Pro Gly
                165                 170                 175 ggt gac ggc tgg ttt gga gcc tgc tac aat tcc tcc att cat gtc ctg      576
Gly Asp Gly Trp Phe Gly Ala Cys Tyr Asn Ser Ser Ile His Val Leu
            180                 185                 190 atg tac tct tac tat ctg ctt gcc acc ttc ggc atc tcc tgt ccc tgg      624
Met Tyr Ser Tyr Tyr Leu Leu Ala Thr Phe Gly Ile Ser Cys Pro Trp
        195                 200                 205 aaa aag atc ctc acc cag ctg caa atg gtt cag ttc tgc ttt tgc ttc      672
Lys Lys Ile Leu Thr Gln Leu Gln Met Val Gln Phe Cys Phe Cys Phe
    210                 215                 220 acc cac tcg atc tac gtg tgg att tgc ggt tcc gaa atc tac cct cga      720
Thr His Ser Ile Tyr Val Trp Ile Cys Gly Ser Glu Ile Tyr Pro Arg
225                 230                 235                 240 ccc ttg act gct ctc cag tcc ttc gtg atg gtc aac atg ctg gtt ctc      768
Pro Leu Thr Ala Leu Gln Ser Phe Val Met Val Asn Met Leu Val Leu
                245                 250                 255 ttt ggc aac ttc tac gtc aag cag tat tct cag aag aat gga aag ccc      816
Phe Gly Asn Phe Tyr Val Lys Gln Tyr Ser Gln Lys Asn Gly Lys Pro
            260                 265                 270 gag aac ggt gcc act cct gag aac ggt gcc aag cct cag ccc tgc gag      864
Glu Asn Gly Ala Thr Pro Glu Asn Gly Ala Lys Pro Gln Pro Cys Glu
        275                 280                 285 aac ggc acc gtc gag aag cga gag aac gac act gcc aac gtt cga taa      912
Asn Gly Thr Val Glu Lys Arg Glu Asn Asp Thr Ala Asn Val Arg
    290                 295                 300

<210> SEQ ID NO 64
<211> LENGTH: 303
<212> TYPE: PRT
<213> ORGANISM: Euglena gracilis
```

<400> SEQUENCE: 64

```
Met Ala Asp Ser Pro Val Ile Asn Leu Ser Thr Met Trp Lys Pro Leu
1               5                   10                  15

Ser Leu Met Ala Leu Asp Leu Ala Val Leu Gly His Val Trp Lys Gln
            20                  25                  30

Ala Gln Gln Glu Gly Ser Ile Ser Ala Tyr Ala Asp Ser Val Trp Thr
        35                  40                  45

Pro Leu Ile Met Ser Gly Leu Tyr Leu Ser Met Ile Phe Val Gly Cys
    50                  55                  60

Arg Trp Met Lys Asn Arg Glu Pro Phe Glu Ile Lys Thr Tyr Met Phe
65                  70                  75                  80

Ala Tyr Asn Leu Tyr Gln Thr Leu Met Asn Leu Cys Ile Val Leu Gly
                85                  90                  95

Phe Leu Tyr Gln Val His Ala Thr Gly Met Arg Phe Trp Gly Ser Gly
            100                 105                 110

Val Asp Arg Ser Pro Lys Gly Leu Gly Ile Gly Phe Phe Ile Tyr Ala
        115                 120                 125

His Tyr His Asn Lys Tyr Val Glu Tyr Phe Asp Thr Leu Phe Met Val
    130                 135                 140

Leu Arg Lys Lys Asn Asn Gln Ile Ser Phe Leu His Val Tyr His His
145                 150                 155                 160

Ala Leu Leu Thr Trp Ala Trp Phe Ala Val Val Tyr Phe Ala Pro Gly
                165                 170                 175

Gly Asp Gly Trp Phe Gly Ala Cys Tyr Asn Ser Ser Ile His Val Leu
            180                 185                 190

Met Tyr Ser Tyr Tyr Leu Leu Ala Thr Phe Gly Ile Ser Cys Pro Trp
        195                 200                 205

Lys Lys Ile Leu Thr Gln Leu Gln Met Val Gln Phe Cys Phe Cys Phe
    210                 215                 220

Thr His Ser Ile Tyr Val Trp Ile Cys Gly Ser Glu Ile Tyr Pro Arg
225                 230                 235                 240

Pro Leu Thr Ala Leu Gln Ser Phe Val Met Val Asn Met Leu Val Leu
                245                 250                 255

Phe Gly Asn Phe Tyr Val Lys Gln Tyr Ser Gln Lys Asn Gly Lys Pro
            260                 265                 270

Glu Asn Gly Ala Thr Pro Glu Asn Gly Ala Lys Pro Gln Pro Cys Glu
        275                 280                 285

Asn Gly Thr Val Glu Lys Arg Glu Asn Asp Thr Ala Asn Val Arg
    290                 295                 300
```

<210> SEQ ID NO 65
<211> LENGTH: 1644
<212> TYPE: DNA
<213> ORGANISM: Euglena anabaena
<220> FEATURE:
<221> NAME/KEY: CDS
<222> LOCATION: (1)..(1644)
<223> OTHER INFORMATION: synthetic truncated delta-4 desaturase
      (codon-optimized for Yarrowia lipolytica)

<400> SEQUENCE: 65

```
atg gcc aag gtc aaa ccc ggt gga cct ggc aag ccc tcg gag atc gct    48
Met Ala Lys Val Lys Pro Gly Gly Pro Gly Lys Pro Ser Glu Ile Ala
1               5                   10                  15 tct ctt cca cct ccc att cga cct gtt ggc aac cca cct gca gcc tat    96
Ser Leu Pro Pro Pro Ile Arg Pro Val Gly Asn Pro Pro Ala Ala Tyr
```

```
            20                  25                  30
tac gac gct ctg gcc acc tcc ggt act gga cag gac cga aag ttt acc      144
Tyr Asp Ala Leu Ala Thr Ser Gly Thr Gly Gln Asp Arg Lys Phe Thr
         35                  40                  45 atg cga gag gtc gct cga cac att gtt ccc acc gat ggc tgg ttg gcc      192
Met Arg Glu Val Ala Arg His Ile Val Pro Thr Asp Gly Trp Leu Ala
 50                  55                  60 tgt cac gac ggt gtg tac gac atc acc gag ttc att ggc aag cat ccc      240
Cys His Asp Gly Val Tyr Asp Ile Thr Glu Phe Ile Gly Lys His Pro
 65                  70                  75                  80 ggt gga gat gtt atc tct ctc ggt ctc gga cga gac tcc act att ctg      288
Gly Gly Asp Val Ile Ser Leu Gly Leu Gly Arg Asp Ser Thr Ile Leu
                 85                  90                  95 gtc gaa tcg tac cat cct gca gga cga ccc gac aag gtt atg gag aag      336
Val Glu Ser Tyr His Pro Ala Gly Arg Pro Asp Lys Val Met Glu Lys
            100                 105                 110 tac cga atc ggt aca ctt cag gat cac aga acc ttc tac gac tgg cag      384
Tyr Arg Ile Gly Thr Leu Gln Asp His Arg Thr Phe Tyr Asp Trp Gln
        115                 120                 125 gcc tcc gct ttc tac gcc gag ctc aag cag cga gtg gtt cag act ctc      432
Ala Ser Ala Phe Tyr Ala Glu Leu Lys Gln Arg Val Val Gln Thr Leu
130                 135                 140 aag gag gct gga caa cct cga cgt ggt ggc ctg tct gtc aag gca gcc      480
Lys Glu Ala Gly Gln Pro Arg Arg Gly Gly Leu Ser Val Lys Ala Ala
145                 150                 155                 160 ctt gtt atg gct gcc ttt gct gcc tcg ttc tac ctc atg gtg aca cag      528
Leu Val Met Ala Ala Phe Ala Ala Ser Phe Tyr Leu Met Val Thr Gln
                165                 170                 175 gga tcc ttc ttt tgg gct gcc gtc tgg ggt ctg gca ggc tct cac att      576
Gly Ser Phe Phe Trp Ala Ala Val Trp Gly Leu Ala Gly Ser His Ile
            180                 185                 190 gga ctc agc atc cag cac gac ggc aat cat ggt gct ttc tcc aag tct      624
Gly Leu Ser Ile Gln His Asp Gly Asn His Gly Ala Phe Ser Lys Ser
        195                 200                 205 gga cga ctc aac cgt ctt gct ggc tgg ggt atg gac gtt atc gga gcc      672
Gly Arg Leu Asn Arg Leu Ala Gly Trp Gly Met Asp Val Ile Gly Ala
210                 215                 220 tcc tcg act gcc tgg gag tac caa cac gtc att ggt cat cac cag tac      720
Ser Ser Thr Ala Trp Glu Tyr Gln His Val Ile Gly His His Gln Tyr
225                 230                 235                 240 acc aac ctg gtg tcc gat ccc gag ttt gct ctt ccc gag aac gat cca      768
Thr Asn Leu Val Ser Asp Pro Glu Phe Ala Leu Pro Glu Asn Asp Pro
                245                 250                 255 gac gtt ttc gga acc tat ccc ctc atg cgg atg cat ccg gac act cct      816
Asp Val Phe Gly Thr Tyr Pro Leu Met Arg Met His Pro Asp Thr Pro
            260                 265                 270 tgg aaa ccc cac cat cag ctg caa cac gtg tac gcc ttt ccg ttg ttc      864
Trp Lys Pro His His Gln Leu Gln His Val Tyr Ala Phe Pro Leu Phe
        275                 280                 285 gct ctc atg acc atc agc aag gtc att atc tcc gat ttc acg ttt tgt      912
Ala Leu Met Thr Ile Ser Lys Val Ile Ile Ser Asp Phe Thr Phe Cys
290                 295                 300 ctt gcc aag cga cgt ggt ccc atc gac ttc tct gcc aga ctc gtt ccc      960
Leu Ala Lys Arg Arg Gly Pro Ile Asp Phe Ser Ala Arg Leu Val Pro
305                 310                 315                 320 ctc gag ggt cag atg ctg ttc tgg ggt gca aag atc atg ggc ttt ctc     1008
Leu Glu Gly Gln Met Leu Phe Trp Gly Ala Lys Ile Met Gly Phe Leu
                325                 330                 335 atg cag att gtg ctt ccc tgc tac ctg cat ggc atc gct cac gga ttg     1056
```

```
                                                    -continued

Met Gln Ile Val Leu Pro Cys Tyr Leu His Gly Ile Ala His Gly Leu
            340                 345                 350 gcc ctc ttc att aca gct cat ctg gtt tct ggc gag tac ctt gcc gtc      1104
Ala Leu Phe Ile Thr Ala His Leu Val Ser Gly Glu Tyr Leu Ala Val
            355                 360                 365 tgt ttc att atc aac cac att tcc gag tcg tgc gac tac ctc aat ccc      1152
Cys Phe Ile Ile Asn His Ile Ser Glu Ser Cys Asp Tyr Leu Asn Pro
370                 375                 380 tct tcc gtt atc gct gcc cga cgg acc gaa atg ctc aag cag gcc gag      1200
Ser Ser Val Ile Ala Ala Arg Arg Thr Glu Met Leu Lys Gln Ala Glu
385                 390                 395                 400 cag gaa gcc aag gcg aaa cag aag cac ccc act cca cct ccc aac gac      1248
Gln Glu Ala Lys Ala Lys Gln Lys His Pro Thr Pro Pro Pro Asn Asp
                405                 410                 415 tgg gct gcc tcc caa gtt ctg tgt tgc gtc aac tgg cga tct ggt ggc      1296
Trp Ala Ala Ser Gln Val Leu Cys Cys Val Asn Trp Arg Ser Gly Gly
            420                 425                 430 tac ttt tca aac cac ctt tct ggt gga ctc aac cac cag atc gag cat      1344
Tyr Phe Ser Asn His Leu Ser Gly Gly Leu Asn His Gln Ile Glu His
        435                 440                 445 cac ctg ttt ccc agc att tct cac gcc aac tat ccc acc att gct cct      1392
His Leu Phe Pro Ser Ile Ser His Ala Asn Tyr Pro Thr Ile Ala Pro
450                 455                 460 gtt gtc aag ggc gtg tgc gag gaa tac ggt ctt ccc tac aag aac tac      1440
Val Val Lys Gly Val Cys Glu Glu Tyr Gly Leu Pro Tyr Lys Asn Tyr
465                 470                 475                 480 tct cag ttt tcc gat gct ctg tac gga atg gtc gag cac ttg cga gct      1488
Ser Gln Phe Ser Asp Ala Leu Tyr Gly Met Val Glu His Leu Arg Ala
                485                 490                 495 atg ggc acc aaa cct gca gac aac gac aag ctt gct ccc act gca ggt      1536
Met Gly Thr Lys Pro Ala Asp Asn Asp Lys Leu Ala Pro Thr Ala Gly
            500                 505                 510 tcc ctg gag gat gtt tgt cct gtg ctc tct gct gcc gtt gct gcc caa      1584
Ser Leu Glu Asp Val Cys Pro Val Leu Ser Ala Ala Val Ala Ala Gln
        515                 520                 525 ccc gac ggc tcc acc gac gga tct gct gcc ggt tgt cct gct gtc gcc      1632
Pro Asp Gly Ser Thr Asp Gly Ser Ala Ala Gly Cys Pro Ala Val Ala
530                 535                 540 act ctg gct taa                                                      1644
Thr Leu Ala
545

<210> SEQ ID NO 66
<211> LENGTH: 547
<212> TYPE: PRT
<213> ORGANISM: Euglena anabaena

<400> SEQUENCE: 66

Met Ala Lys Val Lys Pro Gly Gly Pro Gly Lys Pro Ser Glu Ile Ala
1               5                   10                  15

Ser Leu Pro Pro Pro Ile Arg Pro Val Gly Asn Pro Ala Ala Tyr
            20                  25                  30

Tyr Asp Ala Leu Ala Thr Ser Gly Thr Gly Gln Asp Arg Lys Phe Thr
        35                  40                  45

Met Arg Glu Val Ala Arg His Ile Val Pro Thr Asp Gly Trp Leu Ala
    50                  55                  60

Cys His Asp Gly Val Tyr Asp Ile Thr Glu Phe Ile Gly Lys His Pro
65                  70                  75                  80

Gly Gly Asp Val Ile Ser Leu Gly Leu Gly Arg Asp Ser Thr Ile Leu
```

```
                     85                  90                  95
Val Glu Ser Tyr His Pro Ala Gly Arg Pro Asp Lys Val Met Glu Lys
                100                 105                 110

Tyr Arg Ile Gly Thr Leu Gln Asp His Arg Thr Phe Tyr Asp Trp Gln
            115                 120                 125

Ala Ser Ala Phe Tyr Ala Glu Leu Lys Gln Arg Val Val Gln Thr Leu
        130                 135                 140

Lys Glu Ala Gly Gln Pro Arg Arg Gly Gly Leu Ser Val Lys Ala Ala
145                 150                 155                 160

Leu Val Met Ala Ala Phe Ala Ala Ser Phe Tyr Leu Met Val Thr Gln
                165                 170                 175

Gly Ser Phe Phe Trp Ala Ala Val Trp Gly Leu Ala Gly Ser His Ile
            180                 185                 190

Gly Leu Ser Ile Gln His Asp Gly Asn His Gly Ala Phe Ser Lys Ser
        195                 200                 205

Gly Arg Leu Asn Arg Leu Ala Gly Trp Gly Met Asp Val Ile Gly Ala
    210                 215                 220

Ser Ser Thr Ala Trp Glu Tyr Gln His Val Ile Gly His His Gln Tyr
225                 230                 235                 240

Thr Asn Leu Val Ser Asp Pro Glu Phe Ala Leu Pro Glu Asn Asp Pro
                245                 250                 255

Asp Val Phe Gly Thr Tyr Pro Leu Met Arg Met His Pro Asp Thr Pro
            260                 265                 270

Trp Lys Pro His His Gln Leu Gln His Val Tyr Ala Phe Pro Leu Phe
        275                 280                 285

Ala Leu Met Thr Ile Ser Lys Val Ile Ile Ser Asp Phe Thr Phe Cys
    290                 295                 300

Leu Ala Lys Arg Arg Gly Pro Ile Asp Phe Ser Ala Arg Leu Val Pro
305                 310                 315                 320

Leu Glu Gly Gln Met Leu Phe Trp Gly Ala Lys Ile Met Gly Phe Leu
                325                 330                 335

Met Gln Ile Val Leu Pro Cys Tyr Leu His Gly Ile Ala His Gly Leu
            340                 345                 350

Ala Leu Phe Ile Thr Ala His Leu Val Ser Gly Glu Tyr Leu Ala Val
        355                 360                 365

Cys Phe Ile Ile Asn His Ile Ser Glu Ser Cys Asp Tyr Leu Asn Pro
    370                 375                 380

Ser Ser Val Ile Ala Ala Arg Arg Thr Glu Met Leu Lys Gln Ala Glu
385                 390                 395                 400

Gln Glu Ala Lys Ala Lys Gln Lys His Pro Thr Pro Pro Asn Asp
                405                 410                 415

Trp Ala Ala Ser Gln Val Leu Cys Cys Val Asn Trp Arg Ser Gly Gly
            420                 425                 430

Tyr Phe Ser Asn His Leu Ser Gly Gly Leu Asn His Gln Ile Glu His
        435                 440                 445

His Leu Phe Pro Ser Ile Ser His Ala Asn Tyr Pro Thr Ile Ala Pro
    450                 455                 460

Val Val Lys Gly Val Cys Glu Glu Tyr Gly Leu Pro Tyr Lys Asn Tyr
465                 470                 475                 480

Ser Gln Phe Ser Asp Ala Leu Tyr Gly Met Val Glu His Leu Arg Ala
                485                 490                 495

Met Gly Thr Lys Pro Ala Asp Asn Asp Lys Leu Ala Pro Thr Ala Gly
            500                 505                 510
```

Ser Leu Glu Asp Val Cys Pro Val Leu Ser Ala Ala Val Ala Ala Gln
            515                 520                 525

Pro Asp Gly Ser Thr Asp Gly Ser Ala Ala Gly Cys Pro Ala Val Ala
        530                 535                 540

Thr Leu Ala
545

<210> SEQ ID NO 67
<211> LENGTH: 1644
<212> TYPE: DNA
<213> ORGANISM: Euglena anabaena
<220> FEATURE:
<221> NAME/KEY: CDS
<222> LOCATION: (1)..(1644)
<223> OTHER INFORMATION: synthetic truncated delta-4 desaturase
      (codon-optimized for Yarrowia lipolytica)

<400> SEQUENCE: 67

| | | | | | | | | | | | | | | | | |
|---|---|---|---|---|---|---|---|---|---|---|---|---|---|---|---|---|
| atg | gcc | aag | gtc | aag | cct | gga | ggt | cct | ggc | aaa | ccc | tcc | gag | att | gcc | 48 |
| Met | Ala | Lys | Val | Lys | Pro | Gly | Gly | Pro | Gly | Lys | Pro | Ser | Glu | Ile | Ala | |
| 1 | | | | 5 | | | | | 10 | | | | | 15 | | |
| tcg | ctg | cct | cca | ccc | atc | cga | ccc | gtg | gga | aac | cct | cca | gct | gcc | tac | 96 |
| Ser | Leu | Pro | Pro | Pro | Ile | Arg | Pro | Val | Gly | Asn | Pro | Pro | Ala | Ala | Tyr | |
| | | 20 | | | | | 25 | | | | | 30 | | | | |
| tat | gac | gcc | ctc | gct | act | tct | gga | acc | ggt | cag | gac | cga | aag | ttc | acc | 144 |
| Tyr | Asp | Ala | Leu | Ala | Thr | Ser | Gly | Thr | Gly | Gln | Asp | Arg | Lys | Phe | Thr | |
| | | | 35 | | | | | 40 | | | | | 45 | | | |
| atg | cga | gaa | gtc | gca | cga | cac | atc | gtt | ccc | acc | gat | ggt | tgg | ctg | gcc | 192 |
| Met | Arg | Glu | Val | Ala | Arg | His | Ile | Val | Pro | Thr | Asp | Gly | Trp | Leu | Ala | |
| | 50 | | | | | 55 | | | | | 60 | | | | | |
| tgt | cac | gac | ggc | gtt | tac | gac | att | aca | gag | ttt | atc | gga | aag | cat | ccc | 240 |
| Cys | His | Asp | Gly | Val | Tyr | Asp | Ile | Thr | Glu | Phe | Ile | Gly | Lys | His | Pro | |
| 65 | | | | 70 | | | | | 75 | | | | | 80 | | |
| ggt | ggc | gat | gtc | att | tcc | ctt | gga | ctg | ggt | cga | gac | tct | acc | att | ctc | 288 |
| Gly | Gly | Asp | Val | Ile | Ser | Leu | Gly | Leu | Gly | Arg | Asp | Ser | Thr | Ile | Leu | |
| | | | | 85 | | | | | 90 | | | | | 95 | | |
| gtg | gag | tcc | tac | cac | cct | gct | ggt | cga | ccc | gac | aag | gtt | atg | gag | aag | 336 |
| Val | Glu | Ser | Tyr | His | Pro | Ala | Gly | Arg | Pro | Asp | Lys | Val | Met | Glu | Lys | |
| | | | 100 | | | | | 105 | | | | | 110 | | | |
| tac | aga | atc | ggc | act | ctt | cag | gat | cat | cga | act | ttc | tac | gac | tgg | cag | 384 |
| Tyr | Arg | Ile | Gly | Thr | Leu | Gln | Asp | His | Arg | Thr | Phe | Tyr | Asp | Trp | Gln | |
| | | 115 | | | | | 120 | | | | | 125 | | | | |
| gct | tct | gcc | ttt | tac | gcg | gaa | ctc | aag | cag | cga | gtc | gtg | caa | acc | ctc | 432 |
| Ala | Ser | Ala | Phe | Tyr | Ala | Glu | Leu | Lys | Gln | Arg | Val | Val | Gln | Thr | Leu | |
| | 130 | | | | | 135 | | | | | 140 | | | | | |
| aag | gag | gct | ggt | cag | ccc | aga | cga | ggc | gga | ctg | tca | gtc | aag | gct | gca | 480 |
| Lys | Glu | Ala | Gly | Gln | Pro | Arg | Arg | Gly | Gly | Leu | Ser | Val | Lys | Ala | Ala | |
| 145 | | | | | 150 | | | | | 155 | | | | | 160 | |
| ctg | gtt | atg | gct | gcg | ttt | gcc | gct | tcc | ttc | tat | ctc | atg | gtc | act | cag | 528 |
| Leu | Val | Met | Ala | Ala | Phe | Ala | Ala | Ser | Phe | Tyr | Leu | Met | Val | Thr | Gln | |
| | | | | 165 | | | | | 170 | | | | | 175 | | |
| ggc | tcg | ttt | ttc | tgg | gca | gct | gtg | tgg | ggt | ctt | gct | gga | agt | cac | atc | 576 |
| Gly | Ser | Phe | Phe | Trp | Ala | Ala | Val | Trp | Gly | Leu | Ala | Gly | Ser | His | Ile | |
| | | | 180 | | | | | 185 | | | | | 190 | | | |
| ggc | ctc | tcc | att | cag | cac | gac | gga | aac | cac | ggt | gcc | ttt | tcg | aag | tct | 624 |
| Gly | Leu | Ser | Ile | Gln | His | Asp | Gly | Asn | His | Gly | Ala | Phe | Ser | Lys | Ser | |
| | | 195 | | | | | 200 | | | | | 205 | | | | |
| ggc | cgt | ctc | aat | cga | ctg | gcc | gga | tgg | ggt | atg | gac | gtc | att | ggt | gct | 672 |
| Gly | Arg | Leu | Asn | Arg | Leu | Ala | Gly | Trp | Gly | Met | Asp | Val | Ile | Gly | Ala | |
| | 210 | | | | | 215 | | | | | 220 | | | | | |

-continued

| | | |
|---|---|---|
| tcg tcc aca gcc tgg gag tac cag cat gtc att ggc cac cat caa tac<br>Ser Ser Thr Ala Trp Glu Tyr Gln His Val Ile Gly His His Gln Tyr<br>225                                        230                                  235                        240 | 720 |
| acc aac ctt gtt tcc gat ccc gaa ttt gcc ctt cca gag aac gat ccc<br>Thr Asn Leu Val Ser Asp Pro Glu Phe Ala Leu Pro Glu Asn Asp Pro<br>                           245                                  250                                255 | 768 |
| gac gtg ttc gga acc tac cct ctc atg cga atg cat ccc gac act ccg<br>Asp Val Phe Gly Thr Tyr Pro Leu Met Arg Met His Pro Asp Thr Pro<br>                    260                                  265                                270 | 816 |
| tgg aaa cct cat cac caa ctg cag cac gtc tat gcc ttt ccc ctg ttc<br>Trp Lys Pro His His Gln Leu Gln His Val Tyr Ala Phe Pro Leu Phe<br>      275                                  280                                285 | 864 |
| gcc ctc atg act atc tcc aag gtt atc att agc gat ttc acc ttc tgc<br>Ala Leu Met Thr Ile Ser Lys Val Ile Ile Ser Asp Phe Thr Phe Cys<br>290                                        295                                  300 | 912 |
| ctc gcc aag cgt cga ggt ccg atc gac ttt tct gcc cga ctt gtg cct<br>Leu Ala Lys Arg Arg Gly Pro Ile Asp Phe Ser Ala Arg Leu Val Pro<br>305                                310                              315                    320 | 960 |
| ctc gag ggc cag atg ctt ttc tgg gga gca aag atc atg ggc ttt ctc<br>Leu Glu Gly Gln Met Leu Phe Trp Gly Ala Lys Ile Met Gly Phe Leu<br>                          325                                330                              335 | 1008 |
| atg cag atc gtt ctt ccc tgt tac ctg cac ggc att gca cat ggt ttg<br>Met Gln Ile Val Leu Pro Cys Tyr Leu His Gly Ile Ala His Gly Leu<br>                    340                                  345                                350 | 1056 |
| gct ctg ttc atc act gcc cac ctc gtt tca ggc gag tac ctg gca gtt<br>Ala Leu Phe Ile Thr Ala His Leu Val Ser Gly Glu Tyr Leu Ala Val<br>      355                                  360                                365 | 1104 |
| tgc ttc att atc aac cac att tcc gag tct tgt gac tac ctc aac ccc<br>Cys Phe Ile Ile Asn His Ile Ser Glu Ser Cys Asp Tyr Leu Asn Pro<br>370                                        375                                  380 | 1152 |
| tcc tct gtc atc gct gcc aga cga acg gag atg ctc aag caa gcc gaa<br>Ser Ser Val Ile Ala Ala Arg Arg Thr Glu Met Leu Lys Gln Ala Glu<br>385                                390                              395                    400 | 1200 |
| cag gag gcc aag gcg aaa cag aag cat ccc aca cct cca ccc aac gac<br>Gln Glu Ala Lys Ala Lys Gln Lys His Pro Thr Pro Pro Pro Asn Asp<br>                           405                                  410                                415 | 1248 |
| tgg gca gct tcc cag gtt ctt tgc tgt gtc aac tgg cga tct ggc ggt<br>Trp Ala Ala Ser Gln Val Leu Cys Cys Val Asn Trp Arg Ser Gly Gly<br>                    420                                  425                                430 | 1296 |
| tac ttc tcg aac cac ttg tca gga ggt ctc aat cat cag atc gag cac<br>Tyr Phe Ser Asn His Leu Ser Gly Gly Leu Asn His Gln Ile Glu His<br>      435                                  440                                445 | 1344 |
| cat ctg ttt cct tct atc agc cac gcc aac tat ccc acc att gct ccc<br>His Leu Phe Pro Ser Ile Ser His Ala Asn Tyr Pro Thr Ile Ala Pro<br>450                                        455                                  460 | 1392 |
| gtt gtc aag ggt gtg tgc gaa gag tac gga ctt ccc tac aag aac tac<br>Val Val Lys Gly Val Cys Glu Glu Tyr Gly Leu Pro Tyr Lys Asn Tyr<br>465                                470                              475                                480 | 1440 |
| tct cag ttc tcc gat gcc ctc tac ggc atg gtg gag cac ctg cga gca<br>Ser Gln Phe Ser Asp Ala Leu Tyr Gly Met Val Glu His Leu Arg Ala<br>                    485                                  490                                495 | 1488 |
| atg ggt acc aag cct gcg gac aac gac aaa ctt gct cct act gct gga<br>Met Gly Thr Lys Pro Ala Asp Asn Asp Lys Leu Ala Pro Thr Ala Gly<br>                           500                                  505                                510 | 1536 |
| tct ttg gag gat gtc tgc cct gtt ctg tct gct gcc gtg gct gcc caa<br>Ser Leu Glu Asp Val Cys Pro Val Leu Ser Ala Ala Val Ala Ala Gln<br>                    515                                  520                                525 | 1584 |
| ccc gac ggt tct acc gac ggc tct gcc gct gga tgt cct gcc gtt gct<br>Pro Asp Gly Ser Thr Asp Gly Ser Ala Ala Gly Cys Pro Ala Val Ala<br>      530                                  535                                540 | 1632 |

```
act ctc gcc taa                                                          1644
Thr Leu Ala
545
```

<210> SEQ ID NO 68
<211> LENGTH: 547
<212> TYPE: PRT
<213> ORGANISM: Euglena anabaena

<400> SEQUENCE: 68

```
Met Ala Lys Val Lys Pro Gly Gly Pro Gly Lys Pro Ser Glu Ile Ala
1               5                   10                  15

Ser Leu Pro Pro Pro Ile Arg Pro Val Gly Asn Pro Pro Ala Ala Tyr
            20                  25                  30

Tyr Asp Ala Leu Ala Thr Ser Gly Thr Gly Gln Asp Arg Lys Phe Thr
        35                  40                  45

Met Arg Glu Val Ala Arg His Ile Val Pro Thr Asp Gly Trp Leu Ala
50                  55                  60

Cys His Asp Gly Val Tyr Asp Ile Thr Glu Phe Ile Gly Lys His Pro
65                  70                  75                  80

Gly Gly Asp Val Ile Ser Leu Gly Leu Gly Arg Asp Ser Thr Ile Leu
                85                  90                  95

Val Glu Ser Tyr His Pro Ala Gly Arg Pro Asp Lys Val Met Glu Lys
            100                 105                 110

Tyr Arg Ile Gly Thr Leu Gln Asp His Arg Thr Phe Tyr Asp Trp Gln
        115                 120                 125

Ala Ser Ala Phe Tyr Ala Glu Leu Lys Gln Arg Val Val Gln Thr Leu
130                 135                 140

Lys Glu Ala Gly Gln Pro Arg Arg Gly Gly Leu Ser Val Lys Ala Ala
145                 150                 155                 160

Leu Val Met Ala Ala Phe Ala Ala Ser Phe Tyr Leu Met Val Thr Gln
                165                 170                 175

Gly Ser Phe Phe Trp Ala Ala Val Trp Gly Leu Ala Gly Ser His Ile
            180                 185                 190

Gly Leu Ser Ile Gln His Asp Gly Asn His Gly Ala Phe Ser Lys Ser
        195                 200                 205

Gly Arg Leu Asn Arg Leu Ala Gly Trp Gly Met Asp Val Ile Gly Ala
210                 215                 220

Ser Ser Thr Ala Trp Glu Tyr Gln His Val Ile Gly His His Gln Tyr
225                 230                 235                 240

Thr Asn Leu Val Ser Asp Pro Glu Phe Ala Leu Pro Glu Asn Asp Pro
                245                 250                 255

Asp Val Phe Gly Thr Tyr Pro Leu Met Arg Met His Pro Asp Thr Pro
            260                 265                 270

Trp Lys Pro His His Gln Leu Gln His Val Tyr Ala Phe Pro Leu Phe
        275                 280                 285

Ala Leu Met Thr Ile Ser Lys Val Ile Ser Asp Phe Thr Phe Cys
290                 295                 300

Leu Ala Lys Arg Arg Gly Pro Ile Asp Phe Ser Ala Arg Leu Val Pro
305                 310                 315                 320

Leu Glu Gly Gln Met Leu Phe Trp Gly Ala Lys Ile Met Gly Phe Leu
                325                 330                 335

Met Gln Ile Val Leu Pro Cys Tyr Leu His Gly Ile Ala His Gly Leu
            340                 345                 350
```

```
Ala Leu Phe Ile Thr Ala His Leu Val Ser Gly Glu Tyr Leu Ala Val
            355                 360                 365
Cys Phe Ile Ile Asn His Ile Ser Glu Ser Cys Asp Tyr Leu Asn Pro
370                 375                 380
Ser Ser Val Ile Ala Ala Arg Arg Thr Glu Met Leu Lys Gln Ala Glu
385                 390                 395                 400
Gln Glu Ala Lys Ala Lys Gln Lys His Pro Thr Pro Pro Asn Asp
                405                 410                 415
Trp Ala Ala Ser Gln Val Leu Cys Cys Val Asn Trp Arg Ser Gly Gly
                420                 425                 430
Tyr Phe Ser Asn His Leu Ser Gly Gly Leu Asn His Gln Ile Glu His
            435                 440                 445
His Leu Phe Pro Ser Ile Ser His Ala Asn Tyr Pro Thr Ile Ala Pro
450                 455                 460
Val Val Lys Gly Val Cys Glu Glu Tyr Gly Leu Pro Tyr Lys Asn Tyr
465                 470                 475                 480
Ser Gln Phe Ser Asp Ala Leu Tyr Gly Met Val Glu His Leu Arg Ala
                485                 490                 495
Met Gly Thr Lys Pro Ala Asp Asn Asp Lys Leu Ala Pro Thr Ala Gly
                500                 505                 510
Ser Leu Glu Asp Val Cys Pro Val Leu Ser Ala Ala Val Ala Ala Gln
            515                 520                 525
Pro Asp Gly Ser Thr Asp Gly Ser Ala Ala Gly Cys Pro Ala Val Ala
            530                 535                 540
Thr Leu Ala
545

<210> SEQ ID NO 69
<211> LENGTH: 17088
<212> TYPE: DNA
<213> ORGANISM: Artificial Sequence
<220> FEATURE:
<223> OTHER INFORMATION: Plasmid pZKL3-4GER44

<400> SEQUENCE: 69
aattctctct cttgagcttt tccataacaa gttcttctgc ctccaggaag tccatgggtg     60
gtttgatcat ggttttggtg tagtggtagt gcagtggtgg tattgtgact ggggatgtag    120
ttgagaataa gtcatacaca agtcagcttt cttcgagcct catataagta taagtagttc    180
aacgtattag cactgtaccc agcatctccg tatcgagaaa cacaacaaca tgccccattg    240
gacagatcat gcggatacac aggttgtgca gtatcataca tactcgatca gacaggtcgt    300
ctgaccatca tacaagctga acaagcgctc catacttgca cgctctctat atacacagtt    360
aaattacata tccatagtct aacctctaac agttaatctt ctggtaagcc tcccagccag    420
ccttctggta tcgcttggcc tcctcaatag gatctcggtt ctggccgtac agacctcggc    480
cgacaattat gatatccgtt ccggtagaca tgacatcctc aacagttcgg tactgctgtc    540
cgagagcgtc tcccttgtcg tcaagaccca ccccgggggt cagaataagc cagtcctcag    600
agtcgccctt aggtcggttc tgggcaatga agccaaccac aaactcgggg tcggatcggg    660
caagctcaat ggtctgcttg gagtactcgc cagtggccag agagcccttg caagacagct    720
cggccagcat gagcagacct ctggccagct tctcgttggg agaggggact aggaactcct    780
tgtactggga gttctcgtag tcagagacgt cctccttctt ctgttcagag acagtttcct    840
cggcaccagc tcgcaggcca gcaatgattc cggttccggg tacaccgtgg gcgttggtga    900
```

```
tatcggacca ctcggcgatt cggtgacacc ggtactggtg cttgacagtg ttgccaatat    960
ctgcgaactt tctgtcctcg aacaggaaga aaccgtgctt aagagcaagt tccttgaggg   1020
ggagcacagt gccggcgtag gtgaagtcgt caatgatgtc gatatgggtt ttgatcatgc   1080
acacataagg tccgacctta tcggcaagct caatgagctc cttggtggtg gtaacatcca   1140
gagaagcaca caggttggtt ttcttggctg ccacgagctt gagcactcga gcggcaaagg   1200
cggacttgtg gacgttagct cgagcttcgt aggagggcat tttggtggtg aagaggagac   1260
tgaaataaat ttagtctgca gaactttttta tcggaacctt atctgggca gtgaagtata   1320
tgttatggta atagttacga gttagttgaa cttatagata gactggacta tacggctatc   1380
ggtccaaatt agaaagaacg tcaatggctc tctgggcgtc gcctttgccg acaaaaatgt   1440
gatcatgatg aaagccagca atgacgttgc agctgatatt ttgtcggcc aaccgcgccg   1500
aaaacgcagc tgtcagaccc acagcctcca acgaagaatg tatcgtcaaa gtgatccaag   1560
cacactcata gttggagtcg tactccaaag gcggcaatga cgagtcagac agatactcgt   1620
cgaccttttc cttgggaacc accaccgtca gcccttctga ctcacgtatt gtagccaccg   1680
acacaggcaa cagtccgtgg atagcagaat atgtcttgtc ggtccatttc tcaccaactt   1740
taggcgtcaa gtgaatgttg cagaagaagt atgtgccttc attgagaatc ggtgttgctg   1800
atttcaataa agtcttgaga tcagtttggc cagtcatgtt gtgggggta attggattga   1860
gttatcgcct acagtctgta caggtatact cgctgcccac tttatacttt ttgattccgc   1920
tgcacttgaa gcaatgtcgt ttaccaaaag tgagaatgct ccacagaaca caccccaggg   1980
tatggttgag caaaaaataa acactccgat acggggaatc gaaccccggt ctccacggtt   2040
ctcaagaagt attcttgatg agagcgtatc gatggttaat gctgctgtgt gctgtgtgtg   2100
tgtgttgttt ggcgctcatt gttgcgttat gcagcgtaca ccacaatatt ggaagcttat   2160
tagcctttct attttttcgt ttgcaaggct taacaacatt gctgtggaga gggatgggga   2220
tatggaggcc gctggaggga gtcggagagg cgttttggag cggcttggcc tggcgcccag   2280
ctcgcgaaac gcacctagga ccctttggca cgccgaaatg tgccactttt cagtctagta   2340
acgccttacc tacgtcattc catgcgtgca tgtttgcgcc ttttttccct tgcccttgat   2400
cgccacacag tacagtgcac tgtacagtgg aggttttggg ggggtcttag atgggagcta   2460
aaagcggcct agcggtacac tagtgggatt gtatggagtg gcatggagcc taggtggagc   2520
ctgacaggac gcacgaccgg ctagcccgtg acagacgatg ggtggctcct gttgtccacc   2580
gcgtacaaat gtttgggcca agtcttgtc agccttgctt cgaacctaa ttcccaattt   2640
tgtcacttcg cacccccatt gatcgagccc taaccctgc ccatcaggca atccaattaa   2700
gctcgcattg tctgccttgt ttagtttggc tcctgcccgt ttcggcgtcc acttgcacaa   2760
acacaaacaa gcattatata taaggctcgt ctctccctcc caaccacact cactttttg   2820
cccgtcttcc cttgctaaca caaagtcaa gaacacaaac aaccacccca accccttac   2880
acacaagaca tatctacagc aatggccatg gctcagtcca ccaaggctgc cgacactgct   2940
gccaccgaca agtctctcga caagaaccga ctcatctccc gagacgagct gcggtctcac   3000
aacgttcccc aggatgcctg ggctgccgtc cacggcagag tcatcaacat taccgagttc   3060
gcccgacggc atcctggtgg cgacatcatt ctgcttgccg caggaaagga tgccaccgtg   3120
ctcttcgaga cttaccatcc tcgaggtgtt cccacctcga tcctcgacaa gctgcaggtc   3180
ggcaagatga aggacggaga acttccctcc tcgttctact cgtgggattc cgactttac   3240
aagaccctgc gagctcgagt ggtcgagcga ttggacaagc tcaacctgcc tcgaagaggt   3300
```

```
ggctacgaga tttgggtcaa ggcagtattc ctcctggctg gattctggtt cagcctctac   3360
aagatgtccg tcaacgagac ctactgggct gcctcgctgt ggtccgtgtc tatgggagtc   3420
tttgctgcct tcatcggcac ttgcattcaa cacgatggaa accacggtgc cttctcgacc   3480
agccctgctc tcaacaaggt tgcaggctgg actctggaca tgatcggtgc ttctggcttt   3540
acatgggaga ttcagcatat gctcggacac catccctaca ccaacgtcct ggacgtggac   3600
gaagagaagc gaaaggaagc tggcgacgat tgtcctatgg aggacaagga tcaggagtcc   3660
gacccagatg tcttctcttc gtttcctctc atgcgaatgc acccctacca caaggccgag   3720
tggtaccacc gatatcagca cctgtacgca cccgttctct tgctttcat  gactcttgcc   3780
aaggtgttcc aacaggacat cgaagtcgct accactcagc gactgtacca catcgacgcc   3840
aagtgccgat acaattccat tctcaatgtc cttcggtttt ggtcgatgaa ggtgctctcc   3900
atcggctaca tgctggctgt tccctgctac ttccacggaa tccttggtgg ccttggactg   3960
tttctcatcg gccactttgc ctgtggagag cttctggcaa ccatgttcat tgtcaatcac   4020
gtcatcgagg gtgtgtcctt tggcaaaaag ggagaatctc tcggtctgtc caaggacgtg   4080
gagttcaagc ctacaaccgt ttctggacga actccaatgg agcagacccg tgccgaggcc   4140
aaaaaggctg ccaatggagg caacgtcaag gatgttccct acaacgactg ggctgccgtt   4200
cagtgtcaaa cgagcgtcaa ctggtctcct ggatcgtggt tctggaatca cttctccggt   4260
ggcctctccc accagatcga gcaccatctg tttcccagca tttgtcacac caactacgct   4320
cacatccagg acgttgtcca gaagacttgc gaagagtacg tgttcctta  ccagtccgaa   4380
ccctctttgt tctccgccta tggcaagatg ctgtctcatc tcaagtacct cggaaacgag   4440
aaaaaggtcg cttaagcggc cgcatgtaca tacaagatta tttatagaaa tgaatcgcga   4500
tcgaacaaag agtacgagtg tacgagtagg ggatgatgat aaaagtggaa gaagttccgc   4560
atctttggat ttatcaacgt gtaggacgat acttcctgta aaaatgcaat gtctttacca   4620
taggttctgc tgtagatgtt attaactacc attaacatgt ctacttgtac agttgcagac   4680
cagtggagt  atagaatggt acacttacca aaaagtgttg atggttgtaa ctacgatata   4740
taaaactgtt gacgggatct gcgtacactg tttaaacaga gtgtgaaaga ctcactatgg   4800
tccgggctta tctcgaccaa tagccaaagt ctggagtttc tgagagaaaa aggcaagata   4860
cgtatgtaac aaaagcgacg catggtacaa tataccggag gcatgtatca tagagagtta   4920
gtggttcgat gatggcactg gtgcctggta tgactttata cggctgacta catatttgtc   4980
ctcagacata caattacagt caagcactta cccttggaca tctgtaggta ccccccggcc   5040
aagacgatct cagcgtgtcg tatgtcggat tggcgtagct ccctcgctcg tcaattggct   5100
cccatctact ttcttctgct tggctacacc cagcatgtct gctatggctc gttttcgtgc   5160
cttatctatc ctcccagtat taccaactct aaatgacatg atgtgattgg gtctacactt   5220
tcatatcaga gataaggagt agcacagttg cataaaaagc ccaactctaa tcagcttctt   5280
cctttcttgt aattagtaca aaggtgatta gcgaaatctg gaagcttagt tggccctaaa   5340
aaaatcaaaa aaagcaaaaa acgaaaaacg aaaaaccaca gttttgagaa cagggaggta   5400
acgaaggatc gtatatatat atatatatat atatacccac ggatcccgag accggccttt   5460
gattcttccc tacaaccaac cattctcacc accctaattc acaaccatgg ccaaggtcaa   5520
acccggtgga cctggcaagc cctcggagat cgcttctctt ccacctccca ttcgacctgt   5580
tggcaaccca cctgcagcct attacgacgc tctggccacc tccggtactg acaggaccg   5640
```

```
aaagtttacc atgcgagagg tcgctcgaca cattgttccc accgatggct ggttggcctg    5700
tcacgacggt gtgtacgaca tcaccgagtt cattggcaag catcccggtg gagatgttat    5760
ctctctcggt ctcggacgag actccactat tctggtcgaa tcgtaccatc ctgcaggacg    5820
acccgacaag gttatggaga agtaccgaat cggtacactt caggatcaca gaaccttcta    5880
cgactggcag gcctccgctt tctacgccga gctcaagcag cgagtggttc agactctcaa    5940
ggaggctgga caacctcgac gtggtggcct gtctgtcaag gcagcccttg ttatggctgc    6000
ctttgctgcc tcgttctacc tcatggtgac acagggatcc ttcttttggg ctgccgtctg    6060
gggtctggca ggctctcaca ttggactcag catccagcac gacggcaatc atggtgcttt    6120
ctccaagtct ggacgactca accgtcttgc tggctggggt atggacgtta tcggagcctc    6180
ctcgactgcc tgggagtacc aacacgtcat tggtcatcac cagtacacca acctggtgtc    6240
cgatcccgag tttgctcttc ccgagaacga tccagacgtt ttcggaacct atcccctcat    6300
gcggatgcat ccggacactc cttggaaacc ccaccatcag ctgcaacacg tgtacgcctt    6360
tccgttgttc gctctcatga ccatcagcaa ggtcattatc tccgatttca cgttttgtct    6420
tgccaagcga cgtggtccca tcgacttctc tgccagactc gttcccctcg agggtcagat    6480
gctgttctgg ggtgcaaaga tcatgggctt tctcatgcag attgtgcttc cctgctacct    6540
gcatggcatc gctcacggat tggccctctt cattacagct catctggttt ctggcgagta    6600
ccttgccgtc tgtttcatta tcaaccacat ttccgagtcg tgcgactacc tcaatccctc    6660
ttccgttatc gctgcccgac ggaccgaaat gctcaagcag gccgagcagg aagccaaggc    6720
gaaacagaag cacccactc cacctcccaa cgactgggct gcctcccaag ttctgtgttg    6780
cgtcaactgg cgatctggtg gctacttttc aaaccacctt tctggtggac tcaaccacca    6840
gatcgagcat cacctgtttc ccagcatttc tcacgccaac tatcccacca ttgctcctgt    6900
tgtcaagggc gtgtgcgagg aatacggtct tccctacaag aactactctc agttttccga    6960
tgctctgtac ggaatggtcg agcacttgcg agctatgggc accaaacctg cagacaacga    7020
caagcttgct cccactgcag gttccctgga ggatgtttgt cctgtgctct ctgctgccgt    7080
tgctgcccaa cccgacggct ccaccgacgg atctgctgcc ggttgtcctg ctgtcgccac    7140
tctggcttaa gcggccgcat gagaagataa atatataaat acattgagat attaaatgcg    7200
ctagattaga gagcctcata ctgctcggag agaagccaag acgagtactc aaagggatt    7260 acaccatcca tatccacaga cacaagctgg ggaaaggttc tatatacact ttccggaata    7320
ccgtagtttc cgatgttatc aatgggggca gccaggattt caggcacttc ggtgtctcgg    7380
ggtgaaatgg cgttcttggc ctccatcaag tcgtaccatg tcttcatttg cctgtcaaag    7440
taaaacagaa gcagatgaag aatgaacttg aagtgaagga atttaaattg ccccggagaa    7500
gacggccagg ccgcctagat gacaaattca acaactcaca gctgactttc tgccattgcc    7560 actaggggg ggcctttta tatggccaag ccaagctctc cacgtcggtt gggctgcacc    7620
caacaataaa tgggtagggt tgcaccaaca aagggatggg atgggggta gaagatacga    7680 ggataacggg gctcaatggc acaaataaga acgaatactg ccattaagac tcgtgatcca    7740
gcgactgaca ccattgcatc atctaagggc ctcaaaacta cctcggaact gctgcgctga    7800
tctggacacc acagaggttc cgagcacttt aggttgcacc aaatgtccca ccaggtgcag    7860
gcagaaaacg ctggaacagc gtgtacagtt tgtcttaaca aaaagtgagg gcgctgaggt    7920
cgagcagggt ggtgtgactt gttatagcct ttagagctgc gaaagcgcgt atggatttgg    7980
ctcatcaggc cagattgagg gtctgtggac acatgtcatg ttagtgtact tcaatcgccc    8040
```

```
cctggatata gccccgacaa taggccgtgg cctcattttt ttgccttccg cacatttcca    8100
ttgctcggta cccacacctt gcttctcctg cacttgccaa ccttaatact ggtttacatt    8160
gaccaacatc ttacaagcgg ggggcttgtc tagggtatat ataaacagtg gctctcccaa    8220
tcggttgcca gtctcttttt tcctttcttt ccccacagat tcgaaatcta aactacacat    8280
cacagaactc cgagccgtga gtatccacga caagatcagt gtcgagacga cgcgttttgt    8340
gtaatgacac aatccgaaag tcgctagcaa cacacactct ctacacaaac taacccagct    8400
ctggtaccat ggctgactct cccgtcatca acctctccac catgtggaag cctctgtcgc    8460
tcatggcctt ggatcttgct gttctgggac acgtctggaa gcaggcacaa caggagggct    8520
ccatctcggc ttacgccgac tctgtgtgga ctcccctcat catgtccggt ctgtacctct    8580
ccatgatctt cgtgggatgt cgatggatga agaaccgaga gcccttcgaa atcaagacct    8640
acatgtttgc ctacaacctg taccagaccc tcatgaacct ttgcattgtg ctgggcttcc    8700
tctaccaggt ccacgctacc ggtatgcgat tctggggatc tggcgtggac cgatcgccca    8760
agggtctggg aattggcttt ttcatctatg cccattacca caacaagtac gtcgagtact    8820
tcgacacact cttcatggtg ctgcggaaaa agaacaacca gatttccttt cttcacgtct    8880
accatcacgc tctgctcacc tgggcttggt ttgccgtggt ctacttcgct cctggaggtg    8940
acggctggtt tggagcctgc tacaattcct ccattcatgt cctgatgtac tcttactatc    9000
tgcttgccac cttcggcatc tcctgtccct ggaaaaagat cctcacccag ctgcaaatgg    9060
ttcagttctg cttttgcttc acccactcga tctacgtgtg gatttgcggt tccgaaatct    9120
accctcgacc cttgactgct ctccagtcct tcgtgatggt caacatgctg gttctctttg    9180
gcaacttcta cgtcaagcag tattctcaga agaatggaaa gcccgagaac ggtgccactc    9240
ctgagaacgg tgccaagcct cagccctgcg agaacggcac cgtcgagaag cgagagaacg    9300
acactgccaa cgttcgataa gcggccgcaa gtgtggatgg ggaagtgagt gcccggttct    9360
gtgtgcacaa ttggcaatcc aagatggatg gattcaacac agggatatag cgagctacgt    9420
ggtggtgcga ggatatagca acggatattt atgtttgaca cttgagaatg tacgatacaa    9480
gcactgtcca agtacaatac taaacatact gtacatactc atactcgtac ccgggcaacg    9540
gtttcacttg agtgcagtgg ctagtgctct tactcgtaca gtgtgcaata ctgcgtatca    9600
tagtctttga tgtatatcgt attcattcat gttagttgcg tacggattgt gtatgtccct    9660
gtacctgcat cttgatggag agagctccgg aaagcggatc aggagctgtc caattttaat    9720
tttataacat ggaaacgagt ccttggagct agaagaccat ttttcaact gccctatcga    9780
ctatatttat ctactccaaa accgactgct tcccaagaat cttcagccaa ggcttccaaa    9840
gtaacccctc gcttcccgac acttaattga aaccttagat gcagtcactg cgagtgaagt    9900
ggactctaac atctccaaca tagcgacgat attgcgaggg tttgaatata actaagatgc    9960
atgatccatt acatttgtag aaatatcata acaacgaag cacatagaca gaatgctgtt   10020
ggttgttaca tctgaagccg aggtaccgat gtcattttca gctgtcactg cagagacagg   10080
ggtatgtcac atttgaagat catacaaccg acgtttatga aaaccagaga tatagagaat   10140
gtattgacgg ttgtggctat gtcataagtg cagtgaagtg cagtgattat aggtatagta   10200
cacttactgt agctacaagt acatactgct acagtaatac tcatgtatgc aaaccgtatt   10260
ctgtgtctac agaaggcgat acggaagagt caatctctta tgtagagcca tttctataat   10320
cgaaggggcc ttgtaatttc caaacgagta attgagtaat tgaagagcat cgtagacatt   10380
```

```
acttatcatg tattgtgaga gggaggagat gcagctgtag ctactgcaca tactgtactc   10440
gcccatgcag ggataatgca tagcgagact tggcagtagg tgacagttgc tagctgctac   10500
ttgtagtcgg gtgggtgata gcatggcgcg ccagctgcat taatgaatcg gccaacgcgc   10560
ggggagaggc ggtttgcgta ttgggcgctc ttccgcttcc tcgctcactg actcgctgcg   10620
ctcggtcgtt cggctgcggc gagcggtatc agctcactca aaggcggtaa tacggttatc   10680
cacagaatca ggggataacg caggaaagaa catgtgagca aaaggccagc aaaaggccag   10740
gaaccgtaaa aaggccgcgt tgctggcgtt tttccatagg ctccgccccc ctgacgagca   10800
tcacaaaaat cgacgctcaa gtcagaggtg gcgaaacccg acaggactat aaagatacca   10860
ggcgtttccc cctggaagct ccctcgtgcg ctctcctgtt ccgaccctgc cgcttaccgg   10920
atacctgtcc gcctttctcc cttcgggaag cgtggcgctt tctcatagct cacgctgtag   10980
gtatctcagt tcggtgtagg tcgttcgctc caagctgggc tgtgtgcacg aacccccgt    11040 tcagcccgac cgctgcgcct tatccggtaa ctatcgtctt gagtccaacc cggtaagaca   11100
cgacttatcg ccactggcag cagccactgg taacaggatt agcagagcga ggtatgtagg   11160
cggtgctaca gagttcttga agtggtggcc taactacggc tacactagaa gaacagtatt   11220
tggtatctgc gctctgctga agccagttac cttcggaaaa agagttggta gctcttgatc   11280
cggcaaacaa accaccgctg gtagcggtgg ttttttttgtt tgcaagcagc agattacgcg   11340
cagaaaaaaa ggatctcaag aagatccttt gatcttttct acggggtctg acgctcagtg   11400
gaacgaaaac tcacgttaag ggattttggt catgagatta tcaaaaagga tcttcaccta   11460 gatccttta aattaaaaat gaagttttaa atcaatctaa agtatatatg agtaaacttg   11520
gtctgacagt taccaatgct taatcagtga ggcacctatc tcagcgatct gtctatttcg   11580
ttcatccata gttgcctgac tccccgtcgt gtagataact acgatacggg agggcttacc   11640
atctggcccc agtgctgcaa tgataccgcg agacccacgc tcaccggctc cagatttatc   11700
agcaataaac cagccagccg gaagggccga gcgcagaagt ggtcctgcaa ctttatccgc   11760
ctccatccag tctattaatt gttgccggga agctagagta agtagttcgc cagttaatag   11820
tttgcgcaac gttgttgcca ttgctacagg catcgtggtg tcacgctcgt cgtttggtat   11880
ggcttcattc agctccggtt cccaacgatc aaggcgagtt acatgatccc ccatgttgtg   11940
caaaaaagcg gttagctcct tcggtcctcc gatcgttgtc agaagtaagt tggccgcagt   12000
gttatcactc atggttatgg cagcactgca taattctctt actgtcatgc catccgtaag   12060
atgcttttct gtgactggtg agtactcaac caagtcattc tgagaatagt gtatgcggcg   12120
accgagttgc tcttgcccgg cgtcaatacg ggataatacc gcgccacata gcagaacttt   12180
aaaagtgctc atcattggaa aacgttcttc ggggcgaaaa ctctcaagga tcttaccgct   12240
gttgagatcc agttcgatgt aacccactcg tgcacccaac tgatcttcag catcttttac   12300
tttcaccagc gtttctgggt gagcaaaaac aggaaggcaa aatgccgcaa aaaagggaat   12360
aagggcgaca cggaaatgtt gaatactcat actcttcctt tttcaatatt attgaagcat   12420
ttatcagggt tattgtctca tgagcggata catatttgaa tgtatttaga aaaataaaca   12480
aataggggtt ccgcgcacat ttccccgaaa agtgccacct gatgcggtgt gaaataccgc   12540
acagatgcgt aaggagaaaa taccgcatca ggaaattgta agcgttaata ttttgttaaa   12600
attcgcgtta aatttttgtt aaatcagctc attttttaac caataggccg aaatcggcaa   12660
aatcccttat aaatcaaaag aatagaccga gatagggttg agtgttgttc cagtttggaa   12720
caagagtcca ctattaaaga acgtggactc caacgtcaaa gggcgaaaaa ccgtctatca   12780
```

```
gggcgatggc ccactacgtg aaccatcacc ctaatcaagt tttttggggt cgaggtgccg   12840
taaagcacta aatcggaacc ctaaagggag cccccgattt agagcttgac ggggaaagcc   12900
ggcgaacgtg gcgagaaagg aagggaagaa agcgaaagga gcgggcgcta gggcgctggc   12960
aagtgtagcg gtcacgctgc gcgtaaccac cacacccgcc gcgcttaatg cgccgctaca   13020
gggcgcgtcc attcgccatt caggctgcgc aactgttggg aagggcgatc ggtgcgggcc   13080
tcttcgctat tacgccagct ggcgaaaggg ggatgtgctg caaggcgatt aagttgggta   13140
acgccagggt tttcccagtc acgacgttgt aaaacgacgg ccagtgaatt gtaatacgac   13200
tcactatagg gcgaattggg cccgacgtcg catgcaggaa tagacatctt caataggagc   13260
attaatacct gtgggatcac tgatgtaaac ttctcccaga gtatgtgaat aaccagcggg   13320
ccatccaaca aagaagtcgt tccagtgagt gactcggtac atccgtcttt cggggttgat   13380
ggtaagtccg tcgtctcctt gcttaaagaa cagagcgtcc acgtagtctg caaaagcctt   13440
gtttccaagt cgaggctgcc catagttgat tagcgttgga tcatatccaa gattcttcag   13500
gttgatgccc atgaatagag cagtgacagc tcctagagag tggccagtta cgatcaattt   13560
gtagtcagtg ttgtttccaa ggaagtcgac cagacgatcc tgtacgttca ccatagtctc   13620
tctgtatgcc ttctgaaagc catcatgaac ttggcagcca ggacaattga tactggcaga   13680
agggtttgtg gagtttatgt cagtagtgtt aagaggaggg atactggtca tgtagggttg   13740
ttggatcgtt tggatgtcag taatagcgtc tgcaatggag aaagtgcctc ggaaaacaat   13800
atacttttcc ttttggtgt gatcgtgggc caaaaatcca gtaactgaag tcgagaagaa   13860
atttcctcca aactggtagt caagagtcac atcgggaaaa tgagcgcaag agtttccaca   13920
ggtaaaatcg ctctgcaggg caaatgggcc aggggctctg acacaatagg ccacgttaga   13980
tagccatccg tacttgagaa caaagtcgta tgtctcctgg gtgataggag ccgttaatta   14040
actcacctgc aggattgaga ctatgaatgg attcccgtgc ccgtattact ctactaattt   14100
gatcttggaa cgcgaaaata cgtttctagg actccaaaga atctcaactc ttgtccttac   14160
taaatatact acccatagtt gatggtttac ttgaacagag aggacatgtt cacttgaccc   14220
aaagtttctc gcatctcttg gatatttgaa caacggcgtc cactgaccgt cagttatcca   14280
gtcacaaaac ccccacattc atacattccc atgtacgttt acaaagttct caattccatc   14340
gtgcaaatca aaatcacatc tattcattca tcatatataa acccatcatg tctactaaca   14400
ctcacaactc catagaaaac atcgactcag aacacacgct ccatgcggcc gcttaggact   14460
ttttgtcgcc gttggtaggc acgggaggag cacccatgag tcgcagatgc tgaaccatgc   14520
cacacacggc atcccagaac gtaacgtagt tcttgtaggg caatccgtat tcctcgcaca   14580
cttccttgac aactcgagca atgatgggat agttcgcgtg agagatgctg ggaaacagat   14640
ggtgctcgat ctgatggttg aggccaccgg agaggtgatt ggccagcacg cctccagatc   14700
gccagttgac acagcactgg acttgtgtca cagcccaatc gttgggtgga ggagtgggct   14760
tgaccttttt cgcctcggct gcctgatgag ctgcctggag catctcggtc cgtcgggcag   14820
cagtttgaaa ggaggtattc ataaattcgc aagactcgga gatgtggtta atgatgaaac   14880
agatggccag gtactctcca gacacaaggt gggcaacaga gaacagagca aggcccatag   14940
cagttccgtg gaggtagcag ggcagcacaa tctgcaagag aaagttcgcc agcttggctc   15000
cccagaacaa cagctggcct tcgagtggaa ccagtctgga cgaacagtcg atagaaccct   15060
ttttcatgga gagacaaaca gcaaagtcgc tggtgagcac cttggaaatg gtcataagag   15120
```

```
cgaagagagg aaaggcgaac aggtgttgaa atcggtgatg aggctgccaa gcagtgtcgg    15180
gatgcattcg catgagagga tagctggaaa acacatctgg gtcgttctcg ggaaggctga    15240
acagcgtatc ggaaacgaga ttcgtgtact gatggtgtcc aatgacatgc tggtactccc    15300
acacggtgga cgaggcaccg atcaagtcca tgcccatcc tgcgagtctg ttgaccaggg     15360
tggatcgaga gaaagcaccg tggttgccat cgtgttgaat gctcagtccg acatgcgaac    15420
cggcaaagcc ccagacggca gcccacagga aagacttgtg ggcaacccac atgtaccagg    15480
agacaaagaa gagggtaagc accaggagag ccttgactcc cagtccacct cgacgtgcct    15540
gtccagcctc cttgagtcgt gcaagagccc gtcgtttgag ctcagggtaa aagtccgatt    15600
ctccccaagc gtagaaagtc ttgggatcct ggagtgtgcc gatacggtac ttctccatga    15660
ccttgtctgg tcgtccagcg ggatggtagg actcgaccag aatggtgcag tctcgaccaa    15720
gtccgagagt gatgacgcca cctccaggat gcttggccag gaaatcggtg acgtcgtaca    15780
caccttcgtg acaggtgagc catccatcgg tgggaagaat gtgtcgtctg acctcgtctg    15840
tggtgaacag tcgctccttg ccctgtcccg acacggcgag agagtcatag taagttgcgg    15900
gtggaagacc ggcaggtcta gcgggtcgaa cattggcggt gtcgttttct cgcttctcca    15960
cggtaccgtt ctcgcaaggt tgcggtttgg ccatgggcag gacctgtgtt agtacattgt    16020
cggggagtca tcaattggtt cgacaggttg tcgactgtta gtatgagctc aattgggctc    16080
tggtgggtcg atgacacttg tcatctgttt ctgtttgggtc atgtttccat caccttctat    16140
ggtactcaca attcgtccga ttcgcccgaa tccgttaata ccgactttga tggccatgtt    16200
gatgtgtgtt taattcaaga atgaatatag agaagagaag aagaaaaaag attcaattga    16260
gccggcgatg cagacccta tataaatgtt gccttggaca gacggagcaa gcccgcccaa     16320
acctacgttc ggtataatat gttaagcttt ttaacacaaa ggtttggctt ggggtaacct    16380
gatgtggtgc aaaagaccgg gcgttggcga gccattgcgc gggcgaatgg ggccgtgact    16440
cgtctcaaat tcgagggcgt gcctcaattc gtgcccccgt ggcttttttcc cgccgtttcc    16500 gccccgtttg caccactgca gccgcttctt tggttcggac accttgctgc gagctaggtg    16560
ccttgtgcta cttaaaaagt ggcctcccaa caccaacatg acatgagtgc gtgggccaag    16620
acacgttggc ggggtcgcag tcggctcaat ggcccggaaa aaacgctgct ggagctggtt    16680
cggacgcagt ccgccgcggc gtatggatat ccgcaaggtt ccatagcgcc attgccctcc    16740
gtcggcgtct atcccgcaac tctaaatag agcgggaata taccccaagc ttcttttttt    16800
tcctttaaca cgcacacccc caactatcat gttgctgctg ctgtttgact ctactctgtg    16860 gagggggtgct cccacccaac ccaacctaca ggtggatccg gcgctgtgat tggctgataa    16920
gtctcctatc cggactaatt ctgaccaatg ggacatgcgc gcaggaccca aatgccgcaa    16980
ttacgtaacc ccaacgaaat gcctacccct ctttggagcc cagcggcccc aaatcccccc    17040
aagcagcccg gttctaccgg cttccatctc caagcacaag cagcccgg               17088
```

<210> SEQ ID NO 70
<211> LENGTH: 1548
<212> TYPE: DNA
<213> ORGANISM: Eutreptiella cf_gymnastica CCMP1594
<220> FEATURE:
<221> NAME/KEY: CDS
<222> LOCATION: (1)..(1548)
<223> OTHER INFORMATION: synthetic delta-4 desaturase (codon-optimized for Yarrowia lipolytica) ("E1594D4S")

<400> SEQUENCE: 70

| | | |
|---|---|---|
| atg gct cag tcc acc aag gct gcc gac act gct gcc acc gac aag tct<br>Met Ala Gln Ser Thr Lys Ala Ala Asp Thr Ala Ala Thr Asp Lys Ser<br>1                         5                      10                    15 | 48 | |
| ctc gac aag aac cga ctc atc tcc cga gac gag ctg cgg tct cac aac<br>Leu Asp Lys Asn Arg Leu Ile Ser Arg Asp Glu Leu Arg Ser His Asn<br>             20                      25                    30 | 96 | |
| gtt ccc cag gat gcc tgg gct gcc gtc cac ggc aga gtc atc aac att<br>Val Pro Gln Asp Ala Trp Ala Ala Val His Gly Arg Val Ile Asn Ile<br>        35                      40                    45 | 144 | |
| acc gag ttc gcc cga cgg cat cct ggt ggc gac atc att ctg ctt gcc<br>Thr Glu Phe Ala Arg Arg His Pro Gly Gly Asp Ile Ile Leu Leu Ala<br>    50                      55                    60 | 192 | |
| gca gga aag gat gcc acc gtg ctc ttc gag act tac cat cct cga ggt<br>Ala Gly Lys Asp Ala Thr Val Leu Phe Glu Thr Tyr His Pro Arg Gly<br>65                       70                    75                    80 | 240 | |
| gtt ccc acc tcg atc ctc gac aag ctg cag gtc ggc aag atg aag gac<br>Val Pro Thr Ser Ile Leu Asp Lys Leu Gln Val Gly Lys Met Lys Asp<br>             85                      90                    95 | 288 | |
| gga gaa ctt ccc tcc tcg ttc tac tcg tgg gat tcc gac ttt tac aag<br>Gly Glu Leu Pro Ser Ser Phe Tyr Ser Trp Asp Ser Asp Phe Tyr Lys<br>        100                     105                   110 | 336 | |
| acc ctg cga gct cga gtg gtc gag cga ttg gac aag ctc aac ctg cct<br>Thr Leu Arg Ala Arg Val Val Glu Arg Leu Asp Lys Leu Asn Leu Pro<br>      115                     120                   125 | 384 | |
| cga aga ggt ggc tac gag att tgg gtc aag gca gta ttc ctg ctg gct<br>Arg Arg Gly Gly Tyr Glu Ile Trp Val Lys Ala Val Phe Leu Leu Ala<br>130                      135                    140 | 432 | |
| gga ttc tgg ttc agc ctc tac aag atg tcc gtc aac gag acc tac tgg<br>Gly Phe Trp Phe Ser Leu Tyr Lys Met Ser Val Asn Glu Thr Tyr Trp<br>145                      150                    155                  160 | 480 | |
| gct gcc tcg ctg tgg tcc gtg tct atg gga gtc ttt gct gcc ttc atc<br>Ala Ala Ser Leu Trp Ser Val Ser Met Gly Val Phe Ala Ala Phe Ile<br>                 165                     170                    175 | 528 | |
| ggc act tgc att caa cac gat gga aac cac ggt gcc ttc tcg acc agc<br>Gly Thr Cys Ile Gln His Asp Gly Asn His Gly Ala Phe Ser Thr Ser<br>            180                     185                    190 | 576 | |
| cct gct ctc aac aag gtt gca ggc tgg act ctg gac atg atc ggt gct<br>Pro Ala Leu Asn Lys Val Ala Gly Trp Thr Leu Asp Met Ile Gly Ala<br>          195                     200                    205 | 624 | |
| tct ggc ttt aca tgg gag att cag cat atg ctc gga cac cat ccc tac<br>Ser Gly Phe Thr Trp Glu Ile Gln His Met Leu Gly His His Pro Tyr<br>    210                      215                    220 | 672 | |
| acc aac gtc ctg gac gtg gac gaa gag aag cga aag gaa gct ggc gac<br>Thr Asn Val Leu Asp Val Asp Glu Glu Lys Arg Lys Glu Ala Gly Asp<br>225                       230                    235                  240 | 720 | |
| gat tgt cct atg gag gac aag gat cag gag tcc gac cca gat gtc ttc<br>Asp Cys Pro Met Glu Asp Lys Asp Gln Glu Ser Asp Pro Asp Val Phe<br>                 245                     250                    255 | 768 | |
| tct tcg ttt cct ctc atg cga atg cac ccc tac cac aag gcc gag tgg<br>Ser Ser Phe Pro Leu Met Arg Met His Pro Tyr His Lys Ala Glu Trp<br>            260                     265                    270 | 816 | |
| tac cac cga tat cag cac ctg tac gca ccc gtt ctc ttt gct ttc atg<br>Tyr His Arg Tyr Gln His Leu Tyr Ala Pro Val Leu Phe Ala Phe Met<br>        275                     280                    285 | 864 | |
| act ctt gcc aag gtg ttc caa cag gac atc gaa gtc gct acc act cag<br>Thr Leu Ala Lys Val Phe Gln Gln Asp Ile Glu Val Ala Thr Thr Gln<br>    290                      295                    300 | 912 | |
| cga ctg tac cac atc gac gcc aag tgc cga tac aat tcc att ctc aat<br>Arg Leu Tyr His Ile Asp Ala Lys Cys Arg Tyr Asn Ser Ile Leu Asn<br>305                       310                    315                  320 | 960 | |

```
gtc ctt cgg ttt tgg tcg atg aag gtg ctc tcc atc ggc tac atg ctg      1008
Val Leu Arg Phe Trp Ser Met Lys Val Leu Ser Ile Gly Tyr Met Leu
            325                 330                 335 gct gtt ccc tgc tac ttc cac gga atc ctt ggt ggc ctt gga ctg ttt      1056
Ala Val Pro Cys Tyr Phe His Gly Ile Leu Gly Gly Leu Gly Leu Phe
        340                 345                 350 ctc atc ggc cac ttt gcc tgt gga gag ctt ctg gca acc atg ttc att      1104
Leu Ile Gly His Phe Ala Cys Gly Glu Leu Leu Ala Thr Met Phe Ile
    355                 360                 365 gtc aat cac gtc atc gag ggt gtg tcc ttt ggc aaa aag gga gaa tct      1152
Val Asn His Val Ile Glu Gly Val Ser Phe Gly Lys Lys Gly Glu Ser
370                 375                 380 ctc ggt ctg tcc aag gac gtg gag ttc aag cct aca acc gtt tct gga      1200
Leu Gly Leu Ser Lys Asp Val Glu Phe Lys Pro Thr Thr Val Ser Gly
385                 390                 395                 400 cga act cca atg gag cag acc cgt gcc gag gcc aaa aag gct gcc aat      1248
Arg Thr Pro Met Glu Gln Thr Arg Ala Glu Ala Lys Lys Ala Ala Asn
            405                 410                 415 gga ggc aac gtc aag gat gtt ccc tac aac gac tgg gct gcc gtt cag      1296
Gly Gly Asn Val Lys Asp Val Pro Tyr Asn Asp Trp Ala Ala Val Gln
        420                 425                 430 tgt caa acg agc gtc aac tgg tct cct gga tcg tgg ttc tgg aat cac      1344
Cys Gln Thr Ser Val Asn Trp Ser Pro Gly Ser Trp Phe Trp Asn His
    435                 440                 445 ttc tcc ggt ggc ctc tcc cac cag atc gag cac cat ctg ttt ccc agc      1392
Phe Ser Gly Gly Leu Ser His Gln Ile Glu His His Leu Phe Pro Ser
450                 455                 460 att tgt cac acc aac tac gct cac atc cag gac gtt gtc cag aag act      1440
Ile Cys His Thr Asn Tyr Ala His Ile Gln Asp Val Val Gln Lys Thr
465                 470                 475                 480 tgc gaa gag tac ggt gtt cct tac cag tcc gaa ccc tct ttg ttc tcc      1488
Cys Glu Glu Tyr Gly Val Pro Tyr Gln Ser Glu Pro Ser Leu Phe Ser
            485                 490                 495 gcc tat ggc aag atg ctg tct cat ctc aag tac ctc gga aac gag aaa      1536
Ala Tyr Gly Lys Met Leu Ser His Leu Lys Tyr Leu Gly Asn Glu Lys
        500                 505                 510 aag gtc gct taa                                                      1548
Lys Val Ala
    515

<210> SEQ ID NO 71
<211> LENGTH: 515
<212> TYPE: PRT
<213> ORGANISM: Eutreptiella cf_gymnastica CCMP1594

<400> SEQUENCE: 71

Met Ala Gln Ser Thr Lys Ala Ala Asp Thr Ala Thr Asp Lys Ser
1               5                   10                  15

Leu Asp Lys Asn Arg Leu Ile Ser Arg Asp Glu Leu Arg Ser His Asn
            20                  25                  30

Val Pro Gln Asp Ala Trp Ala Ala Val His Gly Arg Val Ile Asn Ile
        35                  40                  45

Thr Glu Phe Ala Arg Arg His Pro Gly Gly Asp Ile Ile Leu Leu Ala
    50                  55                  60

Ala Gly Lys Asp Ala Thr Val Leu Phe Glu Thr Tyr His Pro Arg Gly
65                  70                  75                  80

Val Pro Thr Ser Ile Leu Asp Lys Leu Gln Val Gly Lys Met Lys Asp
            85                  90                  95
```

```
Gly Glu Leu Pro Ser Ser Phe Tyr Ser Trp Asp Ser Asp Phe Tyr Lys
            100                 105                 110
Thr Leu Arg Ala Arg Val Val Glu Arg Leu Asp Lys Leu Asn Leu Pro
        115                 120                 125
Arg Arg Gly Gly Tyr Glu Ile Trp Val Lys Ala Val Phe Leu Leu Ala
    130                 135                 140
Gly Phe Trp Phe Ser Leu Tyr Lys Met Ser Val Asn Glu Thr Tyr Trp
145                 150                 155                 160
Ala Ala Ser Leu Trp Ser Val Ser Met Gly Val Phe Ala Ala Phe Ile
                165                 170                 175
Gly Thr Cys Ile Gln His Asp Gly Asn His Gly Ala Phe Ser Thr Ser
            180                 185                 190
Pro Ala Leu Asn Lys Val Ala Gly Trp Thr Leu Asp Met Ile Gly Ala
        195                 200                 205
Ser Gly Phe Thr Trp Glu Ile Gln His Met Leu Gly His His Pro Tyr
    210                 215                 220
Thr Asn Val Leu Asp Val Asp Glu Glu Lys Arg Lys Glu Ala Gly Asp
225                 230                 235                 240
Asp Cys Pro Met Glu Asp Lys Asp Gln Glu Ser Asp Pro Asp Val Phe
                245                 250                 255
Ser Ser Phe Pro Leu Met Arg Met His Pro Tyr His Lys Ala Glu Trp
            260                 265                 270
Tyr His Arg Tyr Gln His Leu Tyr Ala Pro Val Leu Phe Ala Phe Met
        275                 280                 285
Thr Leu Ala Lys Val Phe Gln Gln Asp Ile Glu Val Ala Thr Thr Gln
    290                 295                 300
Arg Leu Tyr His Ile Asp Ala Lys Cys Arg Tyr Asn Ser Ile Leu Asn
305                 310                 315                 320
Val Leu Arg Phe Trp Ser Met Lys Val Leu Ser Ile Gly Tyr Met Leu
                325                 330                 335
Ala Val Pro Cys Tyr Phe His Gly Ile Leu Gly Leu Gly Leu Phe
            340                 345                 350
Leu Ile Gly His Phe Ala Cys Gly Glu Leu Leu Ala Thr Met Phe Ile
        355                 360                 365
Val Asn His Val Ile Glu Gly Val Ser Phe Gly Lys Lys Gly Glu Ser
    370                 375                 380
Leu Gly Leu Ser Lys Asp Val Glu Phe Lys Pro Thr Thr Val Ser Gly
385                 390                 395                 400
Arg Thr Pro Met Glu Gln Thr Arg Ala Glu Ala Lys Lys Ala Ala Asn
                405                 410                 415
Gly Gly Asn Val Lys Asp Val Pro Tyr Asn Asp Trp Ala Ala Val Gln
            420                 425                 430
Cys Gln Thr Ser Val Asn Trp Ser Pro Gly Ser Trp Phe Trp Asn His
        435                 440                 445
Phe Ser Gly Gly Leu Ser His Gln Ile Glu His Leu Phe Pro Ser
    450                 455                 460
Ile Cys His Thr Asn Tyr Ala His Ile Gln Asp Val Val Gln Lys Thr
465                 470                 475                 480
Cys Glu Glu Tyr Gly Val Pro Tyr Gln Ser Glu Pro Ser Leu Phe Ser
                485                 490                 495
Ala Tyr Gly Lys Met Leu Ser His Leu Lys Tyr Leu Gly Asn Glu Lys
            500                 505                 510
Lys Val Ala
```

<210> SEQ ID NO 72
<211> LENGTH: 1542
<212> TYPE: DNA
<213> ORGANISM: Euglena gracilis
<220> FEATURE:
<221> NAME/KEY: CDS
<222> LOCATION: (1)..(1542)
<223> OTHER INFORMATION: synthetic truncated delta-4 desaturase
      (codon-optimized for Yarrowia lipolytica)
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: U.S. Pat. Pub. No. 2008-0254191-A1
<311> PATENT FILING DATE: 2008-04-03
<312> PUBLICATION DATE: 2008-10-16
<313> RELEVANT RESIDUES IN SEQ ID NO: (1)..(1542)
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: WO 2008/124048
<311> PATENT FILING DATE: 2008-04-03
<312> PUBLICATION DATE: 2008-10-16
<313> RELEVANT RESIDUES IN SEQ ID NO: (1)..(1542)

<400> SEQUENCE: 72

```
atg gcc aaa ccg caa cct tgc gag aac ggt acc gtg gag aag cga gaa      48
Met Ala Lys Pro Gln Pro Cys Glu Asn Gly Thr Val Glu Lys Arg Glu
1               5                   10                  15 aac gac acc gcc aat gtt cga ccc gct aga cct gcc ggt ctt cca ccc      96
Asn Asp Thr Ala Asn Val Arg Pro Ala Arg Pro Ala Gly Leu Pro Pro
            20                  25                  30 gca act tac tat gac tct ctc gcc gtg tcg gga cag ggc aag gag cga     144
Ala Thr Tyr Tyr Asp Ser Leu Ala Val Ser Gly Gln Gly Lys Glu Arg
        35                  40                  45 ctg ttc acc aca gac gag gtc aga cga cac att ctt ccc acc gat gga     192
Leu Phe Thr Thr Asp Glu Val Arg Arg His Ile Leu Pro Thr Asp Gly
    50                  55                  60 tgg ctc acc tgt cac gaa ggt gtg tac gac gtc acc gat ttc ctg gcc     240
Trp Leu Thr Cys His Glu Gly Val Tyr Asp Val Thr Asp Phe Leu Ala
65                  70                  75                  80 aag cat cct gga ggt ggc gtc atc act ctc gga ctt ggt cga gac tgc     288
Lys His Pro Gly Gly Gly Val Ile Thr Leu Gly Leu Gly Arg Asp Cys
                85                  90                  95 acc att ctg gtc gag tcc tac cat ccc gct gga cga cca gac aag gtc     336
Thr Ile Leu Val Glu Ser Tyr His Pro Ala Gly Arg Pro Asp Lys Val
            100                 105                 110 atg gag aag tac cgt atc ggc aca ctc cag gat ccc aag act ttc tac     384
Met Glu Lys Tyr Arg Ile Gly Thr Leu Gln Asp Pro Lys Thr Phe Tyr
        115                 120                 125 gct tgg gga gaa tcg gac ttt tac cct gag ctc aaa cga cgg gct ctt     432
Ala Trp Gly Glu Ser Asp Phe Tyr Pro Glu Leu Lys Arg Arg Ala Leu
    130                 135                 140 gca cga ctc aag gag gct gga cag gca cgt cga ggt gga ctg gga gtc     480
Ala Arg Leu Lys Glu Ala Gly Gln Ala Arg Arg Gly Gly Leu Gly Val
145                 150                 155                 160 aag gct ctc ctg gtg ctt acc ctc ttt gtc tcc tgg tac atg tgg         528
Lys Ala Leu Leu Val Leu Thr Leu Phe Phe Val Ser Trp Tyr Met Trp
                165                 170                 175 gtt gcc cac aag tct ttc ctg tgg gct gcc gtc tgg ggc ttt gcc ggt     576
Val Ala His Lys Ser Phe Leu Trp Ala Ala Val Trp Gly Phe Ala Gly
            180                 185                 190 tcg cat gtc gga ctg agc att caa cac gat ggc aac cac ggt gct ttc     624
Ser His Val Gly Leu Ser Ile Gln His Asp Gly Asn His Gly Ala Phe
```

|  |  |  |  |  |  |  |  |  |  |  |  |  |  |  |
|---|---|---|---|---|---|---|---|---|---|---|---|---|---|---|
|  |  | 195 |  |  |  | 200 |  |  |  | 205 |  |  |  |  |
| tct | cga | tcc | acc | ctg | gtc | aac | aga | ctc | gca | gga | tgg | ggc | atg | gac ttg | 672 |
| Ser | Arg | Ser | Thr | Leu | Val | Asn | Arg | Leu | Ala | Gly | Trp | Gly | Met | Asp Leu |  |
|  | 210 |  |  |  |  | 215 |  |  |  |  | 220 |  |  |  |  |
| atc | ggt | gcc | tcg | tcc | acc | gtg | tgg | gag | tac | cag | cat | gtc | att | gga cac | 720 |
| Ile | Gly | Ala | Ser | Ser | Thr | Val | Trp | Glu | Tyr | Gln | His | Val | Ile | Gly His |  |
| 225 |  |  |  |  | 230 |  |  |  |  | 235 |  |  |  | 240 |  |
| cat | cag | tac | acg | aat | ctc | gtt | tcc | gat | acg | ctg | ttc | agc | ctt | ccc gag | 768 |
| His | Gln | Tyr | Thr | Asn | Leu | Val | Ser | Asp | Thr | Leu | Phe | Ser | Leu | Pro Glu |  |
|  |  |  |  | 245 |  |  |  |  | 250 |  |  |  |  | 255 |  |
| aac | gac | cca | gat | gtg | ttt | tcc | agc | tat | cct | ctc | atg | cga | atg | cat ccc | 816 |
| Asn | Asp | Pro | Asp | Val | Phe | Ser | Ser | Tyr | Pro | Leu | Met | Arg | Met | His Pro |  |
|  |  |  | 260 |  |  |  |  | 265 |  |  |  |  | 270 |  |  |
| gac | act | gct | tgg | cag | cct | cat | cac | cga | ttt | caa | cac | ctg | ttc | gcc ttt | 864 |
| Asp | Thr | Ala | Trp | Gln | Pro | His | His | Arg | Phe | Gln | His | Leu | Phe | Ala Phe |  |
|  |  | 275 |  |  |  |  | 280 |  |  |  |  | 285 |  |  |  |
| cct | ctc | ttc | gct | ctt | atg | acc | att | tcc | aag | gtg | ctc | acc | agc | gac ttt | 912 |
| Pro | Leu | Phe | Ala | Leu | Met | Thr | Ile | Ser | Lys | Val | Leu | Thr | Ser | Asp Phe |  |
|  | 290 |  |  |  |  | 295 |  |  |  |  | 300 |  |  |  |  |
| gct | gtt | tgt | ctc | tcc | atg | aaa | aag | ggt | tct | atc | gac | tgt | tcg | tcc aga | 960 |
| Ala | Val | Cys | Leu | Ser | Met | Lys | Lys | Gly | Ser | Ile | Asp | Cys | Ser | Ser Arg |  |
| 305 |  |  |  |  | 310 |  |  |  |  | 315 |  |  |  | 320 |  |
| ctg | gtt | cca | ctc | gaa | ggc | cag | ctg | ttg | ttc | tgg | gga | gcc | aag | ctg gcg | 1008 |
| Leu | Val | Pro | Leu | Glu | Gly | Gln | Leu | Leu | Phe | Trp | Gly | Ala | Lys | Leu Ala |  |
|  |  |  |  | 325 |  |  |  |  | 330 |  |  |  |  | 335 |  |
| aac | ttt | ctc | ttg | cag | att | gtg | ctg | ccc | tgc | tac | ctc | cac | gga | act gct | 1056 |
| Asn | Phe | Leu | Leu | Gln | Ile | Val | Leu | Pro | Cys | Tyr | Leu | His | Gly | Thr Ala |  |
|  |  |  | 340 |  |  |  |  | 345 |  |  |  |  | 350 |  |  |
| atg | ggc | ctt | gct | ctg | ttc | tct | gtt | gcc | cac | ctt | gtg | tct | gga | gag tac | 1104 |
| Met | Gly | Leu | Ala | Leu | Phe | Ser | Val | Ala | His | Leu | Val | Ser | Gly | Glu Tyr |  |
|  |  | 355 |  |  |  |  | 360 |  |  |  |  | 365 |  |  |  |
| ctg | gcc | atc | tgt | ttc | atc | att | aac | cac | atc | tcc | gag | tct | tgc | gaa ttt | 1152 |
| Leu | Ala | Ile | Cys | Phe | Ile | Ile | Asn | His | Ile | Ser | Glu | Ser | Cys | Glu Phe |  |
|  | 370 |  |  |  |  | 375 |  |  |  |  | 380 |  |  |  |  |
| atg | aat | acc | tcc | ttt | caa | act | gct | gcc | cga | cgg | acc | gag | atg | ctc cag | 1200 |
| Met | Asn | Thr | Ser | Phe | Gln | Thr | Ala | Ala | Arg | Arg | Thr | Glu | Met | Leu Gln |  |
| 385 |  |  |  |  | 390 |  |  |  |  | 395 |  |  |  | 400 |  |
| gca | gct | cat | cag | gca | gcc | gag | gcg | aaa | aag | gtc | aag | ccc | act | cct cca | 1248 |
| Ala | Ala | His | Gln | Ala | Ala | Glu | Ala | Lys | Lys | Val | Lys | Pro | Thr | Pro Pro |  |
|  |  |  |  | 405 |  |  |  |  | 410 |  |  |  |  | 415 |  |
| ccc | aac | gat | tgg | gct | gtg | aca | caa | gtc | cag | tgc | tgt | gtc | aac | tgg cga | 1296 |
| Pro | Asn | Asp | Trp | Ala | Val | Thr | Gln | Val | Gln | Cys | Cys | Val | Asn | Trp Arg |  |
|  |  |  | 420 |  |  |  |  | 425 |  |  |  |  | 430 |  |  |
| tct | gga | ggc | gtg | ctg | gcc | aat | cac | ctc | tcc | ggt | ggc | ctc | aac | cat cag | 1344 |
| Ser | Gly | Gly | Val | Leu | Ala | Asn | His | Leu | Ser | Gly | Gly | Leu | Asn | His Gln |  |
|  |  | 435 |  |  |  |  | 440 |  |  |  |  | 445 |  |  |  |
| atc | gag | cac | cat | ctg | ttt | ccc | agc | atc | tct | cac | gcg | aac | tat | ccc atc | 1392 |
| Ile | Glu | His | His | Leu | Phe | Pro | Ser | Ile | Ser | His | Ala | Asn | Tyr | Pro Ile |  |
|  | 450 |  |  |  |  | 455 |  |  |  |  | 460 |  |  |  |  |
| att | gct | cga | gtt | gtc | aag | gaa | gtg | tgc | gag | gaa | tac | gga | ttg | ccc tac | 1440 |
| Ile | Ala | Arg | Val | Val | Lys | Glu | Val | Cys | Glu | Glu | Tyr | Gly | Leu | Pro Tyr |  |
| 465 |  |  |  |  | 470 |  |  |  |  | 475 |  |  |  | 480 |  |
| aag | aac | tac | gtt | acg | ttc | tgg | gat | gcc | gtg | tgt | ggc | atg | gtt | cag cat | 1488 |
| Lys | Asn | Tyr | Val | Thr | Phe | Trp | Asp | Ala | Val | Cys | Gly | Met | Val | Gln His |  |
|  |  |  |  | 485 |  |  |  |  | 490 |  |  |  |  | 495 |  |
| ctg | cga | ctc | atg | ggt | gct | cct | ccc | gtg | cct | acc | aac | ggc | gac | aaa aag | 1536 |
| Leu | Arg | Leu | Met | Gly | Ala | Pro | Pro | Val | Pro | Thr | Asn | Gly | Asp | Lys Lys |  |
|  |  |  | 500 |  |  |  |  | 505 |  |  |  |  | 510 |  |  |
| tcc | taa |  |  |  |  |  |  |  |  |  |  |  |  |  | 1542 |

Ser

<210> SEQ ID NO 73
<211> LENGTH: 513
<212> TYPE: PRT
<213> ORGANISM: Euglena gracilis

<400> SEQUENCE: 73

```
Met Ala Lys Pro Gln Pro Cys Glu Asn Gly Thr Val Glu Lys Arg Glu
1               5                   10                  15

Asn Asp Thr Ala Asn Val Arg Pro Ala Arg Pro Ala Gly Leu Pro Pro
            20                  25                  30

Ala Thr Tyr Tyr Asp Ser Leu Ala Val Ser Gly Gln Gly Lys Glu Arg
        35                  40                  45

Leu Phe Thr Thr Asp Glu Val Arg Arg His Ile Leu Pro Thr Asp Gly
    50                  55                  60

Trp Leu Thr Cys His Glu Gly Val Tyr Asp Val Thr Asp Phe Leu Ala
65                  70                  75                  80

Lys His Pro Gly Gly Gly Val Ile Thr Leu Gly Leu Gly Arg Asp Cys
                85                  90                  95

Thr Ile Leu Val Glu Ser Tyr His Pro Ala Gly Arg Pro Asp Lys Val
            100                 105                 110

Met Glu Lys Tyr Arg Ile Gly Thr Leu Gln Asp Pro Lys Thr Phe Tyr
        115                 120                 125

Ala Trp Gly Glu Ser Asp Phe Tyr Pro Glu Leu Lys Arg Arg Ala Leu
    130                 135                 140

Ala Arg Leu Lys Glu Ala Gly Gln Ala Arg Arg Gly Gly Leu Gly Val
145                 150                 155                 160

Lys Ala Leu Leu Val Leu Thr Leu Phe Phe Val Ser Trp Tyr Met Trp
                165                 170                 175

Val Ala His Lys Ser Phe Leu Trp Ala Ala Val Trp Gly Phe Ala Gly
            180                 185                 190

Ser His Val Gly Leu Ser Ile Gln His Asp Gly Asn His Gly Ala Phe
        195                 200                 205

Ser Arg Ser Thr Leu Val Asn Arg Leu Ala Gly Trp Gly Met Asp Leu
    210                 215                 220

Ile Gly Ala Ser Ser Thr Val Trp Glu Tyr Gln His Val Ile Gly His
225                 230                 235                 240

His Gln Tyr Thr Asn Leu Val Ser Asp Thr Leu Phe Ser Leu Pro Glu
                245                 250                 255

Asn Asp Pro Asp Val Phe Ser Ser Tyr Pro Leu Met Arg Met His Pro
            260                 265                 270

Asp Thr Ala Trp Gln Pro His His Arg Phe Gln His Leu Phe Ala Phe
        275                 280                 285

Pro Leu Phe Ala Leu Met Thr Ile Ser Lys Val Leu Thr Ser Asp Phe
    290                 295                 300

Ala Val Cys Leu Ser Met Lys Lys Gly Ser Ile Asp Cys Ser Ser Arg
305                 310                 315                 320

Leu Val Pro Leu Glu Gly Gln Leu Leu Phe Trp Gly Ala Lys Leu Ala
                325                 330                 335

Asn Phe Leu Leu Gln Ile Val Leu Pro Cys Tyr Leu His Gly Thr Ala
            340                 345                 350

Met Gly Leu Ala Leu Phe Ser Val Ala His Leu Val Ser Gly Glu Tyr
        355                 360                 365
```

```
Leu Ala Ile Cys Phe Ile Ile Asn His Ile Ser Glu Ser Cys Glu Phe
        370                 375                 380
Met Asn Thr Ser Phe Gln Thr Ala Ala Arg Arg Thr Glu Met Leu Gln
385                 390                 395                 400
Ala Ala His Gln Ala Ala Glu Ala Lys Lys Val Lys Pro Thr Pro Pro
                405                 410                 415
Pro Asn Asp Trp Ala Val Thr Gln Val Gln Cys Cys Val Asn Trp Arg
            420                 425                 430
Ser Gly Gly Val Leu Ala Asn His Leu Ser Gly Leu Asn His Gln
        435                 440                 445
Ile Glu His His Leu Phe Pro Ser Ile Ser His Ala Asn Tyr Pro Ile
450                 455                 460
Ile Ala Arg Val Val Lys Glu Val Cys Glu Glu Tyr Gly Leu Pro Tyr
465                 470                 475                 480
Lys Asn Tyr Val Thr Phe Trp Asp Ala Val Cys Gly Met Val Gln His
                485                 490                 495
Leu Arg Leu Met Gly Ala Pro Pro Val Pro Thr Asn Gly Asp Lys Lys
            500                 505                 510
Ser
```

```
<210> SEQ ID NO 74
<211> LENGTH: 15617
<212> TYPE: DNA
<213> ORGANISM: Artificial Sequence
<220> FEATURE:
<223> OTHER INFORMATION: Plasmid pZKLY-G20444

<400> SEQUENCE: 74
aattctctct cttgagcttt tccataacaa gttcttctgc ctccaggaag tccatgggtg      60
gtttgatcat ggttttggtg tagtggtagt gcagtggtgg tattgtgact ggggatgtag     120
ttgagaataa gtcatacaca agtcagcttt cttcgagcct catataagta taagtagttc     180
aacgtattag cactgtaccc agcatctccg tatcgagaaa cacaacaaca tgccccattg     240
gacagatcat gcggatacac aggttgtgca gtatcataca tactcgatca gacaggtcgt     300
ctgaccatca tacaagctga acaagcgctc catacttgca cgctctctat atacacagtt     360
aaattacata tccatagtct aacctctaac agttaatctt ctggtaagcc tcccagccag     420
ccttctggta tcgcttggcc tcctcaatag gatctcggtt ctggccgtac agaccctcggc     480
cgacaattat gatatccgtt ccggtagaca tgacatcctc aacagttcgg tactgctgtc     540
cgagagcgtc tcccttgtcg tcaagaccca ccccgggggt cagaataagc cagtcctcag     600
agtcgccctt aggtcggttc tgggcaatga agccaaccac aaactcgggg tcggatcggg     660
caagctcaat ggtctgcttg gagtactcgc cagtggccag agagcccttg caagacagct     720
cggccagcat gagcagacct ctggccagct tctcgttggg agaggggact aggaactcct     780
tgtactggga gttctcgtag tcagagacgt cctccttctt ctgttcagag acagtttcct     840
cggcaccagc tcgcaggcca gcaatgattc cggttccggg tacaccgtgg gcgttggtga     900
tatcggacca ctcggcgatt cggtgacacc ggtactggtg cttgacagtg ttgccaatat     960
ctgcgaactt tctgtcctcg aacaggaaga aaccgtgctt aagagcaagt tccttgaggg    1020
ggagcacagt gccggcgtag gtgaagtcgt caatgatgtc gatatgggtt ttgatcatgc    1080
acacataagg tccgacccta tcggcaagct caatgagctc cttggtggtg gtaacatcca    1140
gagaagcaca caggttggtt ttcttggctg ccacgagctt gagcactcga gcggcaaagg    1200
```

```
cggacttgtg gacgttagct cgagcttcgt aggagggcat tttggtggtg aagaggagac    1260
tgaaataaat ttagtctgca gaactttta tcggaacctt atctgggca gtgaagtata      1320 tgttatggta atagttacga gttagttgaa cttatagata gactggacta tacggctatc   1380
ggtccaaatt agaagaacg tcaatggctc tctgggcgtc gcctttgccg acaaaaatgt    1440
gatcatgatg aaagccagca atgacgttgc agctgatatt gttgtcggcc aaccgcgccg   1500
aaaacgcagc tgtcagaccc acagcctcca acgaagaatg tatcgtcaaa gtgatccaag   1560
cacactcata gttggagtcg tactccaaag gcggcaatga cgagtcagac agatactcgt   1620
cgaccttttc cttgggaacc accaccgtca gcccttctga ctcacgtatt gtagccaccg   1680
acacaggcaa cagtccgtgg atagcagaat atgtcttgtc ggtccatttc tcaccaactt   1740
taggcgtcaa gtgaatgttg cagaagaagt atgtgccttc attgagaatc ggtgttgctg   1800
atttcaataa agtcttgaga tcagtttggc cagtcatgtt gtgggggta attggattga    1860 gttatcgcct acagtctgta caggtatact cgctgcccac tttatacttt ttgattccgc   1920
tgcacttgaa gcaatgtcgt ttaccaaaag tgagaatgct ccacagaaca caccccaggg   1980
tatggttgag caaaaaataa acactccgat acggggaatc gaaccccggt ctccacggtt   2040
ctcaagaagt attcttgatg agagcgtatc gatggttaat gctgctgtgt gctgtgtgtg   2100
tgtgttgttt ggcgctcatt gttgcgttat gcagcgtaca ccacaatatt ggaagcttat   2160 tagccttttct atttttttcgt ttgcaaggct taacaacatt gctgtggaga gggatgggga   2220
tatggaggcc gctggaggga gtcggagagg cgttttggag cggcttggcc tggcgcccag   2280
ctcgcgaaac gcacctagga ccctttggca cgccgaaatg tgccactttt cagtctagta   2340
acgccttacc tacgtcattc catgcgtgca tgtttgcgcc tttttccct tgcccttgat    2400 cgccacacag tacagtgcac tgtacagtgg aggttttggg gggtcttag atgggagcta    2460 aaagcggcct agcggtacac tagtgggatt gtatggagtg catggagcc taggtggagc    2520 ctgacaggac gcacgaccgg ctagcccgtg acagacgatg ggtggctcct gttgtccacc   2580
gcgtacaaat gttttgggcca aagtcttgtc agccttgctt gcgaacctaa ttcccaatttt  2640 tgtcacttcg cacccccatt gatcgagccc taaccccctgc ccatcaggca atccaattaa   2700
gctcgcattg tctgccttgt ttagtttggc tcctgcccgt ttcggcgtcc acttgcacaa   2760
acacaaacaa gcattatata taaggctcgt ctctccctcc caaccacact cacttttttg   2820
cccgtcttcc cttgctaaca caaaagtcaa gaacacaaac aaccacccca accccttac    2880 acacaagaca tatctacagc aatggccatg gccaaggtca aacccggtgg acctggcaag   2940
ccctcggaga tcgcttctct tccacctccc attcgacctg ttggcaaccc acctgcagcc   3000
tattacgacg ctctggccac ctccggtact ggacaggacc gaaagtttac catgcgagag   3060
gtcgctcgac acattgttcc caccgatggc tggttggcct gtcacgacgg tgtgtacgac   3120
atcaccgagt tcattggcaa gcatcccggt ggagatgtta tctctctcgg tctcggacga   3180
gactccacta ttctggtcga atcgtaccat cctgcaggac gacccgacaa ggttatggag   3240
aagtaccgaa tcggtacact tcaggatcac agaaccttct acgactggca ggcctccgct   3300
ttctacgccg agctcaagca gcgagtggtt cagactctca aggaggctgg acaacctcga   3360
cgtggtggcc tgtctgtcaa ggcagccctt gttatggctg cctttgctgc ctcgttctac   3420
ctcatggtga cacagggatc cttcttttgg gctgccgtct ggggtctggc aggctctcac   3480
attggactca gcatccagca cgacggcaat catggtgctt tctccaagtc tggacgactc   3540
aaccgtcttg ctggctgggg tatggacgtt atcggagcct cctcgactgc ctgggagtac   3600
```

```
caacacgtca ttggtcatca ccagtacacc aacctggtgt ccgatcccga gtttgctctt    3660
cccgagaacg atccagacgt tttcggaacc tatcccctca tgcggatgca tccggacact    3720
ccttggaaac cccaccatca gctgcaacac gtgtacgcct ttccgttgtt cgctctcatg    3780
accatcagca aggtcattat ctccgatttc acgttttgtc ttgccaagcg acgtggtccc    3840
atcgacttct ctgccagact cgttcccctc gagggtcaga tgctgttctg gggtgcaaag    3900
atcatgggct ttctcatgca gattgtgctt ccctgctacc tgcatggcat cgctcacgga    3960
ttggccctct tcattacagc tcatctggtt tctggcgagt accttgccgt ctgtttcatt    4020
atcaaccaca tttccgagtc gtgcgactac ctcaatccct cttccgttat cgctgcccga    4080
cggaccgaaa tgctcaagca ggccgagcag gaagccaagg cgaaacagaa gcaccccact    4140
ccacctccca cgactgggc tgcctcccaa gttctgtgtt gcgtcaactg gcgatctggt    4200
ggctactttt caaaccacct ttctggtgga ctcaaccacc agatcgagca tcacctgttt    4260
cccagcattt ctcacgccaa ctatcccacc attgctcctg ttgtcaaggg cgtgtgcgag    4320
gaatacggtc ttccctacaa gaactactct cagttttccg atgctctgta cggaatggtc    4380
gagcacttgc gagctatggg caccaaacct gcagacaacg acaagcttgc tcccactgca    4440
ggttccctgg aggatgtttg tcctgtgctc tctgctgccg ttgctgccca cccgacggc    4500 tccaccgacg gatctgctgc cggttgtcct gctgtcgcca ctctggctta gcggccgca    4560 ttgatgattg gaaacacaca catgggttat atctaggtga gagttagttg gacagttata    4620
tattaaatca gctatgccaa cggtaacttc attcatgtca acgaggaacc agtgactgca    4680
agtaatatag aatttgacca ccttgccatt ctcttgcact cctttactat atctcattta    4740
tttcttatat acaaatcact tcttcttccc agcatcgagc tcggaaacct catgagcaat    4800
aacatcgtgg atctcgtcaa tagagggctt tttggactcc ttgctgttgg ccaccttgtc    4860
cttgctgttt aaacagagtg tgaaagactc actatggtcc gggcttatct cgaccaatag    4920
ccaaagtctg gagtttctga gagaaaaagg caagatacgt atgtaacaaa gcgacgcatg    4980
gtacaataat accggaggca tgtatcatag agagttagtg gttcgatgat ggcactggtg    5040
cctggtatga ctttatacgg ctgactacat atttgtcctc agacatacaa ttacagtcaa    5100
gcacttaccc ttggacatct gtaggtaccc cccggccaag acgatctcag cgtgtcgtat    5160
gtcggattgg cgtagctccc tcgctcgtca attggctccc atctactttc ttctgcttgg    5220
ctacacccag catgtctgct atggctcgtt ttcgtgcctt atctatcctc ccagtattac    5280
caactctaaa tgacatgatg tgattgggtc tacactttca tatcagagat aaggagtagc    5340
acagttgcat aaaaagccca actctaatca gcttcttcct ttcttgtaat tagtacaaag    5400
gtgattagcg aaatctggaa gcttagttgg ccctaaaaaa atcaaaaaaa gcaaaaaacg    5460
aaaaacgaaa aaccacagtt ttgagaacag ggaggtaacg aaggatcgta tatatatata    5520
tatatatata tacccacgga tcccgagacc ggcctttgat tcttccctac aaccaaccat    5580
tctcaccacc ctaattcaca accatggctg actctcccgt catcaacctc tccaccatgt    5640
ggaagcctct gtcgctcatg gccttggatc ttgctgttct gggacacgtc tggaagcagg    5700
cacaacagga gggctccatc tcggcttacg ccgactctgt gtggactccc ctcatcatgt    5760
ccggtctgta cctctccatg atcttcgtgg gatgtcgatg gatgaagaac cgagagccct    5820
tcgaaatcaa gacctacatg tttgcctaca acctgtacca gaccctcatg aacctttgca    5880
ttgtgctggg cttcctctac caggtccacg ctaccggtat gcgattctgg ggatctggcg    5940
```

```
tggaccgatc gcccaagggt ctgggaattg cttttttcat ctatgcccat taccacaaca    6000
agtacgtcga gtacttcgac acactcttca tggtgctgcg gaaaaagaac aaccagattt    6060
cctttcttca cgtctaccat cacgctctgc tcacctgggc ttggtttgcc gtggtctact    6120
tcgctcctgg aggtgacggc tggtttggag cctgctacaa ttcctccatt catgtcctga    6180
tgtactctta ctatctgctt gccaccttcg gcatctcctg tccctggaaa aagatcctca    6240
cccagctgca atggttcag ttctgctttt gcttcaccca ctcgatctac gtgtggattt    6300
gcggttccga atctaccct cgacccttga ctgctctcca gtccttcgtg atggtcaaca    6360
tgctggttct ctttggcaac ttctacgtca agcagtattc tcagaagaat ggaaagcccg    6420
agaacggtgc cactcctgag aacggtgcca agcctcagcc ctgcgagaac ggtaccgtgg    6480
agaagcgaga aaacgacacc gccaatgttc gacccgctag acctgccggt cttccacccg    6540
caacttacta tgactctctc gccgtgtcgg acagggcaa ggagcgactg ttcaccacag    6600
acgaggtcag acgacacatt cttcccaccg atggatggct cacctgtcac gaaggtgtgt    6660
acgacgtcac cgatttcctg gccaagcatc ctggaggtgg cgtcatcact ctcggacttg    6720
gtcgagactg caccattctg gtcgagtcct accatcccgc tggacgacca gacaaggtca    6780
tggagaagta ccgtatcggc acactccagg atcccaagac tttctacgct tggggagaat    6840 cggacttta ccctgagctc aaacgacggg ctcttgcacg actcaaggag gctggacagg    6900
cacgtcgagg tggactggga gtcaaggctc tcctggtgct taccctcttc tttgtctcct    6960
ggtacatgtg ggttgcccac aagtctttcc tgtgggctgc cgtctggggc tttgccggtt    7020
cgcatgtcgg actgagcatt caacacgatg gcaaccacgg tgctttctct cgatccaccc    7080
tggtcaacag actcgcagga tggggcatgg acttgatcgg tgcctcgtcc accgtgtggg    7140
agtaccagca tgtcattgga caccatcagt acacgaatct cgtttccgat acgctgttca    7200
gccttcccga gaacgaccca gatgtgtttt ccagctatcc tctcatgcga atgcatcccg    7260
acactgcttg gcagcctcat caccgatttc aacacctgtt cgcctttcct ctcttcgctc    7320
ttatgaccat ttccaaggtg ctcaccagcg actttgctgt tgtctctcc atgaaaaagg    7380 gttctatcga ctgttcgtcc agactggttc cactcgaagg ccagctgttg ttctggggag    7440
ccaagctggc gaactttctc ttgcagattg tgctgccctg ctacctccac ggaactgcta    7500
tgggccttgc tctgttctct gttgcccacc ttgtgtctgg agagtacctg gccatctgtt    7560
tcatcattaa ccacatctcc gagtcttgcg aatttatgaa tacctccttt caaactgctg    7620
cccgacggac cgagatgctc caggcagctc atcaggcagc cgaggcgaaa aaggtcaagc    7680
ccactcctcc acccaacgat tgggctgtga cacaagtcca gtgctgtgtc aactggcgat    7740
ctggaggcgt gctggccaat cacctctccg gtggcctcaa ccatcagatc gagcaccatc    7800
tgtttcccag catctctcac gcgaactatc ccatcattgc tcgagttgtc aaggaagtgt    7860
gcgaggaata cggattgccc tacaagaact acgttacgtt ctgggatgcc gtgtgtggca    7920
tggttcagca tctgcgactc atgggtgctc ctcccgtgcc taccaacggc gacaaaaagt    7980
cctaagcggc cgcatgagaa gataaatata taaatacatt gagatattaa atgcgctaga    8040
ttagagagcc tcatactgct cggagagaag ccaagacgag tactcaaagg ggattacacc    8100
atccatatcc acagacacaa gctggggaaa ggttctatat acactttccg gaataccgta    8160
gtttccgatg ttatcaatgg gggcagccag gatttcaggc acttcggtgt ctcggggtga    8220
aatggcgttc ttgcctcca tcaagtcgta ccatgtcttc atttgcctgt caaagtaaaa    8280
cagaagcaga tgaagaatga acttgaagtg aaggaattta aatgtaacga aactgaaatt    8340
```

```
tgaccagata ttgtgtccgc ggtggagctc cagcttttgt tccctttagt gagggttaat   8400
ttcgagcttg gcgtaatcat ggtcatagct gtttcctgtg tgaaattgtt atccgctcac   8460
aagcttccac acaacgtacg ttgattgagg tggagccaga tgggctattg tttcatatat   8520
agactggcag ccacctcttt ggcccagcat gtttgtatac ctggaaggga aaactaaaga   8580
agctggctag tttagtttga ttattatagt agatgtccta atcactagag attagaatgt   8640
cttggcgatg attagtcgtc gtcccctgta tcatgtctag accaactgtg tcatgaagtt   8700
ggtgctggtg ttttacctgt gtactacaag taggtgtcct agatctagtg tacagagccg   8760
tttagaccca tgtggacttc accattaacg atggaaaatg ttcattatat gacagtatat   8820
tacaatggac ttgctccatt tcttccttgc atcacatgtt ctccacctcc atagttgatc   8880
aacacatcat agtagctaag gctgctgctc tcccactaca gtccaccaca agttaagtag   8940
caccgtcagt acagctaaaa gtacacgtct agtacgtttc ataactagtc aagtagcccc   9000
tattacagat atcagcacta tcacgcacga gttttttctct gtgctatcta atcaacttgc   9060
caagtattcg gagaagatac actttcttgg catcaggtat acgagggagc ctatcagatg   9120
aaaaagggta tattggatcc attcatatcc acctacacgt tgtcataatc tcctcattca   9180
cgtgattcat ttcgtgacac tagtttctca ctttccccccc cgcacctata gtcaacttgg   9240
cggacacgct acttgtagct gacgttgatt tatagaccca atcaaagcgg ttatcggtc    9300
aggtagcact tatcattcat cgttcatact acgatgagca atctcgggca tgtccggaaa   9360
agtgtcgggc gcgccagctg cattaatgaa tcggccaacg cgcggggaga ggcggtttgc   9420
gtattgggcg ctcttccgct tcctcgctca ctgactcgct gcgctcggtc gttcggctgc   9480
ggcgagcggt atcagctcac tcaaaggcgg taatacggtt atccacagaa tcaggggata   9540
acgcaggaaa gaacatgtga gcaaaaggcc agcaaaaggc caggaaccgt aaaaaggccg   9600
cgttgctggc gtttttccat aggctccgcc cccctgacga gcatcacaaa aatcgacgct   9660
caagtcagag gtggcgaaac ccgacaggac tataaagata ccaggcgttt ccccctggaa   9720
gctccctcgt gcgctctcct gttccgaccc tgccgcttac cggatacctg tccgcctttc   9780
tcccttcggg aagcgtggcg ctttctcata gctcacgctg taggtatctc agttcggtgt   9840
aggtcgttcg ctccaagctg ggctgtgtgc acgaaccccc cgttcagccc gaccgctgcg   9900
ccttatccgg taactatcgt cttgagtcca acccggtaag acacgactta tcgccactgg   9960
cagcagccac tggtaacagg attagcagag cgaggtatgt aggcggtgct acagagttct  10020
tgaagtggtg gcctaactac ggctacacta agaacagat ttggtatc tgcgctctgc   10080
tgaagccagt taccttcgga aaaagagttg gtagctcttg atccggcaaa caaaccaccg  10140
ctggtagcgg tggtttttt gtttgcaagc agcagattac gcgcagaaaa aaggatctc   10200
aagaagatcc tttgatcttt tctacggggt ctgacgctca gtggaacgaa aactcacgtt  10260
aagggatttt ggtcatgaga ttatcaaaaa ggatcttcac ctagatcctt ttaaattaaa  10320
aatgaagttt taaatcaatc taaagtatat atgagtaaac ttggtctgac agttaccaat  10380
gcttaatcag tgaggcacct atctcagcga tctgtctatt tcgttcatcc atagttgcct  10440
gactccccgt cgtgtagata actacgatac gggagggctt accatctggc cccagtgctg  10500
caatgatacc gcgagaccca cgctcaccgg ctccagattt atcagcaata aaccagccag  10560
ccggaagggc cgagcgcaga agtggtcctg caacttatc cgcctccatc cagtctatta  10620
attgttgccg ggaagctaga gtaagtagtt cgccagttaa tagtttgcgc aacgttgttg  10680
```

```
ccattgctac aggcatcgtg gtgtcacgct cgtcgtttgg tatggcttca ttcagctccg   10740
gttcccaacg atcaaggcga gttacatgat cccccatgtt gtgcaaaaaa gcggttagct   10800
ccttcggtcc tccgatcgtt gtcagaagta agttggccgc agtgttatca ctcatggtta   10860
tggcagcact gcataattct cttactgtca tgccatccgt aagatgcttt tctgtgactg   10920
gtgagtactc aaccaagtca ttctgagaat agtgtatgcg gcgaccgagt tgctcttgcc   10980
cggcgtcaat acgggataat accgcgccac atagcagaac tttaaaagtg ctcatcattg   11040
gaaaacgttc ttcggggcga aaactctcaa ggatcttacc gctgttgaga tccagttcga   11100
tgtaacccac tcgtgcaccc aactgatctt cagcatcttt tactttcacc agcgtttctg   11160
ggtgagcaaa aacaggaagg caaaatgccg caaaaaaggg aataagggcg acacggaaat   11220
gttgaatact catactcttc cttttcaat attattgaag catttatcag gttattgtc    11280
tcatgagcgg atacatattt gaatgtattt agaaaaataa acaaataggg gttccgcgca   11340
catttccccg aaaagtgcca cctgatgcgg tgtgaaatac cgcacagatg cgtaaggaga   11400
aaataccgca tcaggaaatt gtaagcgtta atattttgtt aaaattcgcg ttaaattttt   11460
gttaaatcag ctcattttt aaccaatagg ccgaaatcgg caaaatccct tataaatcaa   11520
aagaatagac cgagataggg ttgagtgttg ttccagtttg gaacaagagt ccactattaa   11580
agaacgtgga ctccaacgtc aaagggcgaa aaaccgtcta tcagggcgat ggcccactac   11640
gtgaaccatc accctaatca agttttttgg ggtcgaggtg ccgtaaagca ctaaatcgga   11700
accctaaagg gagccccga tttagagctt gacggggaaa gccggcgaac gtggcgagaa   11760
aggaagggaa gaaagcgaaa ggagcgggcg ctagggcgct ggcaagtgta gcggtcacgc   11820
tgcgcgtaac caccacaccc gccgcgctta atgcgccgct acagggcgcg tccattcgcc   11880
attcaggctg cgcaactgtt gggaagggcg atcggtgcgg gcctcttcgc tattacgcca   11940
gctggcgaaa ggggatgtg ctgcaaggcg attaagttgg gtaacgccag gttttccca    12000
gtcacgacgt tgtaaaacga cggccagtga attgtaatac gactcactat agggcgaatt   12060
gggcccgacg tcgcatgcat tccgacagca gcgactgggc accatgatca agcgaaacac   12120
cttcccccag ctgccctggc aaaccatcaa gaaccctact ttcatcaagt gcaagaacgg   12180
ttctactctt ctcacctccg gtgtctacgg ctggtgccga aagcctaact acaccgctga   12240
tttcatcatg tgcctcacct gggctctcat gtgcggtgtt gcttctcccc tgccttactt   12300
ctacccggtc ttcttcttcc tggtgctcat ccaccgagct taccgagact tgagcgact   12360
ggagcgaaag tacggtgagg actaccagga gttcaagcga caggtccctt ggatcttcat   12420
cccttatgtt ttctaaacga taagcttagt gagcgaatgg tgaggttact taattgagtg   12480
gccagcctat gggattgtat aacagacagt caatatatta ctgaaaagac tgaacagcca   12540
gacggagtga ggttgtgagt gaatcgtaga gggcggctat tacagcaagt ctactctaca   12600
gtgtactaac acagcagaga acaaatacag gtgtgcattc ggctatctga gaattagttg   12660
gagagctcga gaccctcggc gataaactgc tcctcggttt tgtgtccata cttgtacgga   12720
ccattgtaat ggggcaagtc gttgagttct cgtcgtccga cgttcagagc acagaaacca   12780
atgtaatcaa tgtagcagag atggttctgc aaaagattga tttgtgcgag caggttaatt   12840
aaaaggcgtt gaaacagaat gagccagttt aaacagcaag acaaggtgg ccaacagcaa    12900
ggagtccaaa aagccctcta ttgacgagat ccacgatgtt attgctcatg aggtttccga   12960
gctcgatgct gggaagaaga agtgatttgt atataagaaa taaatgagat atagtaaagg   13020
agtgcaagag aatggcaagg tggtcaaatt ctatattact tgcagtcact ggttcctcgt   13080
```

```
tgacatgaat gaagttaccg ttggcatagc tgatttaata tataactgtc caactaactc    13140
tcacctagat ataacccatg tgtgtgtttc caatcatcaa tgcggccgct taagcgacct    13200
ttttctcgtt tccgaggtac ttgagatgag acagcatctt gccataggcg gagaacaaag    13260
agggttcgga ctggtaagga acaccgtact cttcgcaagt cttctggaca acgtcctgga    13320
tgtgagcgta gttggtgtga caaatgctgg gaaacagatg gtgctcgatc tggtgggaga    13380
ggccaccgga gaagtgattc cagaaccacg atccaggaga ccagttgacg ctcgtttgac    13440
actgaacggc agcccagtcg ttgtagggaa catccttgac gttgcctcca ttggcagcct    13500
ttttggcctc ggcacgggtc tgctccattg gagttcgtcc agaaacggtt gtaggcttga    13560
actccacgtc cttggacaga ccgagagatt ctccttttt gccaaaggac acaccctcga     13620
tgacgtgatt gacaatgaac atggttgcca gaagctctcc acaggcaaag tggccgatga    13680
gaaacagtcc aaggccacca aggattccgt ggaagtagca gggaacagcc agcatgtagc    13740
cgatggagag caccttcatc gaccaaaacc gaaggacatt gagaatggaa ttgtatcggc    13800
acttggcgtc gatgtggtac agtcgctgag tggtagcgac ttcgatgtcc tgttggaaca    13860
ccttggcaag agtcatgaaa gcaaagagaa cgggtgcgta caggtgctga tatcggtggt    13920
accactcggc cttgtggtag gggtgcattc gcatgagagg aaacgaagag aagacatctg    13980
ggtcggactc ctgatccttg tcctccatag acaatcgtc gccagcttcc tttcgcttct     14040
cttcgtccac gtccaggacg ttggtgtagg gatggtgtcc gagcatatgc tgaatctccc    14100
atgtaaagcc agaagcaccg atcatgtcca gagtccagcc tgcaaccttg ttgagagcag    14160
ggctggtcga gaaggcaccg tggtttccat cgtgttgaat gcaagtgccg atgaaggcag    14220
caaagactcc catagacacg gaccacagcg aggcagccca gtaggtctcg ttgacggaca    14280
tcttgtagag gctgaaccag aatccagcca ggaggaatac tgccttgacc caaatctcgt    14340
agccacctct tcgaggcagg ttgagcttgt ccaatcgctc gaccactcga gctcgcaggg    14400
tcttgtaaaa gtcggaatcc cacgagtaga acgaggaggg aagttctccg tccttcatct    14460
tgccgacctg cagcttgtcg aggatcgagg tgggaacacc tcgaggatgg taagtctcga    14520
agagcacggt ggcatccttt cctgcggcaa gcagaatgat gtcgccacca ggatgccgtc    14580
gggcgaactc ggtaatgttg atgactctgc cgtggacggc agcccaggca tcctggggaa    14640
cgttgtgaga ccgcagctcg tctcgggaga tgagtcggtt cttgtcgaga gcttgtcgg    14700 tggcagcagt gtcggcagcc ttggtggact gagccatggt accagagctg ggttagtttg    14760
tgtagagagt gtgtgttgct agcgactttc ggattgtgtc attacacaaa acgcgtcgtc    14820
tcgacactga tcttgtcgtg gatactcacg gctcggaact ctgtgatgtg tagtttagat    14880
ttcgaatctg tggggaaaga aaggaaaaaa gagactggca accgattggg agagccactg    14940
tttatatata ccctagacaa gccccccgct tgtaagatgt tggtcaatgt aaaccagtat    15000
taaggttggc aagtgcagga gaagcaaggt gtgggtaccg agcaatggaa atgtgcgaa     15060 ggcaaaaaaa tgaggccacg gcctattgtc ggggctatat ccaggggcg attgaagtac     15120 actaacatga catgtgtcca cagaccctca atctggcctg atgagccaaa tccatacgcg    15180
ctttcgcagc tctaaaggct ataacaagtc acaccaccct gctcgacctc agcgccctca    15240 cttttttgtta agacaaactg tacacgctgt tccagcgttt tctgcctgca cctggtggga    15300
catttggtgt aacctaaagt gctcggaacc tctgtggtgt ccagatcagc gcagcagttc    15360
cgaggtagtt ttgaggccct tagatgatgc aatggtgtca gtcgctggat cacgagtctt    15420
```

```
aatggcagta ttcgttctta tttgtgccat tgagccccgt tatcctcgta tcttctaccc    15480
cccatcccat cccttttgttg gtgcaaccct acccatttat tgttgggtgc agcccaaccg    15540
acgtggagag cttggcttgg ccatataaaa aggcccccccc ctagtggcaa tggcagaaag    15600
tcagctgtga gttgttg                                                   15617
```

<210> SEQ ID NO 75
<211> LENGTH: 2382
<212> TYPE: DNA
<213> ORGANISM: Euglena gracilis
<220> FEATURE:
<221> NAME/KEY: CDS
<222> LOCATION: (1)..(2382)
<223> OTHER INFORMATION: synthetic DHA synthase (codon-optimized for
      Yarrowia lipolytica)
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: U.S. Pat. Pub. No. 2008-0254191-A1
<311> PATENT FILING DATE: 2008-04-03
<312> PUBLICATION DATE: 2008-10-16
<313> RELEVANT RESIDUES IN SEQ ID NO: (1)..(2382)
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: WO 2008/124048
<311> PATENT FILING DATE: 2008-04-03
<312> PUBLICATION DATE: 2008-10-16
<313> RELEVANT RESIDUES IN SEQ ID NO: (1)..(2382)

<400> SEQUENCE: 75

```
atg gct gac tct ccc gtc atc aac ctc tcc acc atg tgg aag cct ctg         48
Met Ala Asp Ser Pro Val Ile Asn Leu Ser Thr Met Trp Lys Pro Leu
1               5                   10                  15 tcg ctc atg gcc ttg gat ctt gct gtt ctg gga cac gtc tgg aag cag         96
Ser Leu Met Ala Leu Asp Leu Ala Val Leu Gly His Val Trp Lys Gln
                20                  25                  30 gca caa cag gag ggc tcc atc tcg gct tac gcc gac tct gtg tgg act        144
Ala Gln Gln Glu Gly Ser Ile Ser Ala Tyr Ala Asp Ser Val Trp Thr
            35                  40                  45 ccc ctc atc atg tcc ggt ctg tac ctc tcc atg atc ttc gtg gga tgt        192
Pro Leu Ile Met Ser Gly Leu Tyr Leu Ser Met Ile Phe Val Gly Cys
        50                  55                  60 cga tgg atg aag aac cga gag ccc ttc gaa atc aag acc tac atg ttt        240
Arg Trp Met Lys Asn Arg Glu Pro Phe Glu Ile Lys Thr Tyr Met Phe
65                  70                  75                  80 gcc tac aac ctg tac cag acc ctc atg aac ctt tgc att gtg ctg ggc        288
Ala Tyr Asn Leu Tyr Gln Thr Leu Met Asn Leu Cys Ile Val Leu Gly
                85                  90                  95 ttc ctc tac cag gtc cac gct acc ggt atg cga ttc tgg gga tct ggc        336
Phe Leu Tyr Gln Val His Ala Thr Gly Met Arg Phe Trp Gly Ser Gly
                100                 105                 110 gtg gac cga tcg ccc aag ggt ctg gga att ggc ttt ttc atc tat gcc        384
Val Asp Arg Ser Pro Lys Gly Leu Gly Ile Gly Phe Phe Ile Tyr Ala
            115                 120                 125 cat tac cac aac aag tac gtc gag tac ttc gac aca ctc ttc atg gtg        432
His Tyr His Asn Lys Tyr Val Glu Tyr Phe Asp Thr Leu Phe Met Val
        130                 135                 140 ctg cgg aaa aag aac aac cag att tcc ttt ctt cac gtc tac cat cac        480
Leu Arg Lys Lys Asn Asn Gln Ile Ser Phe Leu His Val Tyr His His
145                 150                 155                 160 gct ctg ctc acc tgg gct tgg ttt gcc gtg gtc tac ttc gct cct gga        528
Ala Leu Leu Thr Trp Ala Trp Phe Ala Val Val Tyr Phe Ala Pro Gly
                165                 170                 175
```

-continued

| | |
|---|---|
| ggt gac ggc tgg ttt gga gcc tgc tac aat tcc tcc att cat gtc ctg<br>Gly Asp Gly Trp Phe Gly Ala Cys Tyr Asn Ser Ser Ile His Val Leu<br>           180                          185                          190 | 576 |
| atg tac tct tac tat ctg ctt gcc acc ttc ggc atc tcc tgt ccc tgg<br>Met Tyr Ser Tyr Tyr Leu Leu Ala Thr Phe Gly Ile Ser Cys Pro Trp<br>              195                         200                        205 | 624 |
| aaa aag atc ctc acc cag ctg caa atg gtt cag ttc tgc ttt tgc ttc<br>Lys Lys Ile Leu Thr Gln Leu Gln Met Val Gln Phe Cys Phe Cys Phe<br>210                          215                         220 | 672 |
| acc cac tcg atc tac gtg tgg att tgc ggt tcc gaa atc tac cct cga<br>Thr His Ser Ile Tyr Val Trp Ile Cys Gly Ser Glu Ile Tyr Pro Arg<br>225                          230                        235                        240 | 720 |
| ccc ttg act gct ctc cag tcc ttc gtg atg gtc aac atg ctg gtt ctc<br>Pro Leu Thr Ala Leu Gln Ser Phe Val Met Val Asn Met Leu Val Leu<br>                        245                        250                        255 | 768 |
| ttt ggc aac ttc tac gtc aag cag tat tct cag aag aat gga aag ccc<br>Phe Gly Asn Phe Tyr Val Lys Gln Tyr Ser Gln Lys Asn Gly Lys Pro<br>              260                         265                        270 | 816 |
| gag aac ggt gcc act cct gag aac ggt gcc aag cct cag ccc tgc gag<br>Glu Asn Gly Ala Thr Pro Glu Asn Gly Ala Lys Pro Gln Pro Cys Glu<br>                      275                        280                        285 | 864 |
| aac ggt acc gtg gag aag cga gaa aac gac acc gcc aat gtt cga ccc<br>Asn Gly Thr Val Glu Lys Arg Glu Asn Asp Thr Ala Asn Val Arg Pro<br>290                          295                         300 | 912 |
| gct aga cct gcc ggt ctt cca ccc gca act tac tat gac tct ctc gcc<br>Ala Arg Pro Ala Gly Leu Pro Pro Ala Thr Tyr Tyr Asp Ser Leu Ala<br>305                          310                        315                        320 | 960 |
| gtg tcg gga cag ggc aag gag cga ctg ttc acc aca gac gag gtc aga<br>Val Ser Gly Gln Gly Lys Glu Arg Leu Phe Thr Thr Asp Glu Val Arg<br>                      325                        330                        335 | 1008 |
| cga cac att ctt ccc acc gat gga tgg ctc acc tgt cac gaa ggt gtg<br>Arg His Ile Leu Pro Thr Asp Gly Trp Leu Thr Cys His Glu Gly Val<br>                      340                        345                        350 | 1056 |
| tac gac gtc acc gat ttc ctg gcc aag cat cct gga ggt ggc gtc atc<br>Tyr Asp Val Thr Asp Phe Leu Ala Lys His Pro Gly Gly Gly Val Ile<br>                      355                        360                        365 | 1104 |
| act ctc gga ctt ggt cga gac tgc acc att ctg gtc gag tcc tac cat<br>Thr Leu Gly Leu Gly Arg Asp Cys Thr Ile Leu Val Glu Ser Tyr His<br>370                          375                        380 | 1152 |
| ccc gct gga cga cca gac aag gtc atg gag aag tac cgt atc ggc aca<br>Pro Ala Gly Arg Pro Asp Lys Val Met Glu Lys Tyr Arg Ile Gly Thr<br>385                          390                        395                        400 | 1200 |
| ctc cag gat ccc aag act ttc tac gct tgg gga gaa tcg gac ttt tac<br>Leu Gln Asp Pro Lys Thr Phe Tyr Ala Trp Gly Glu Ser Asp Phe Tyr<br>                      405                        410                        415 | 1248 |
| cct gag ctc aaa cga cgg gct ctt gca cga ctc aag gag gct gga cag<br>Pro Glu Leu Lys Arg Arg Ala Leu Ala Arg Leu Lys Glu Ala Gly Gln<br>                      420                        425                        430 | 1296 |
| gca cgt cga ggt gga ctg gga gtc aag gct ctc ctg gtg ctt acc ctc<br>Ala Arg Arg Gly Gly Leu Gly Val Lys Ala Leu Leu Val Leu Thr Leu<br>                      435                        440                        445 | 1344 |
| ttc ttt gtc tcc tgg tac atg tgg gtt gcc cac aag tct ttc ctg tgg<br>Phe Phe Val Ser Trp Tyr Met Trp Val Ala His Lys Ser Phe Leu Trp<br>450                          455                        460 | 1392 |
| gct gcc gtc tgg ggc ttt gcc ggt tcg cat gtc gga ctg agc att caa<br>Ala Ala Val Trp Gly Phe Ala Gly Ser His Val Gly Leu Ser Ile Gln<br>465                          470                        475                        480 | 1440 |
| cac gat ggc aac cac ggt gct ttc tct cga tcc acc ctg gtc aac aga<br>His Asp Gly Asn His Gly Ala Phe Ser Arg Ser Thr Leu Val Asn Arg<br>                      485                        490                        495 | 1488 |

```
ctc gca gga tgg ggc atg gac ttg atc ggt gcc tcg tcc acc gtg tgg    1536
Leu Ala Gly Trp Gly Met Asp Leu Ile Gly Ala Ser Ser Thr Val Trp
            500                 505                 510 gag tac cag cat gtc att gga cac cat cag tac acg aat ctc gtt tcc    1584
Glu Tyr Gln His Val Ile Gly His His Gln Tyr Thr Asn Leu Val Ser
            515                 520                 525 gat acg ctg ttc agc ctt ccc gag aac gac cca gat gtg ttt tcc agc    1632
Asp Thr Leu Phe Ser Leu Pro Glu Asn Asp Pro Asp Val Phe Ser Ser
530                 535                 540 tat cct ctc atg cga atg cat ccc gac act gct tgg cag cct cat cac    1680
Tyr Pro Leu Met Arg Met His Pro Asp Thr Ala Trp Gln Pro His His
545                 550                 555                 560 cga ttt caa cac ctg ttc gcc ttt cct ctc ttc gct ctt atg acc att    1728
Arg Phe Gln His Leu Phe Ala Phe Pro Leu Phe Ala Leu Met Thr Ile
                565                 570                 575 tcc aag gtg ctc acc agc gac ttt gct gtt tgt ctc tcc atg aaa aag    1776
Ser Lys Val Leu Thr Ser Asp Phe Ala Val Cys Leu Ser Met Lys Lys
            580                 585                 590 ggt tct atc gac tgt tcg tcc aga ctg gtt cca ctc gaa ggc cag ctg    1824
Gly Ser Ile Asp Cys Ser Ser Arg Leu Val Pro Leu Glu Gly Gln Leu
            595                 600                 605 ttg ttc tgg gga gcc aag ctg gcg aac ttt ctc ttg cag att gtg ctg    1872
Leu Phe Trp Gly Ala Lys Leu Ala Asn Phe Leu Leu Gln Ile Val Leu
610                 615                 620 ccc tgc tac ctc cac gga act gct atg ggc ctt gct ctg ttc tct gtt    1920
Pro Cys Tyr Leu His Gly Thr Ala Met Gly Leu Ala Leu Phe Ser Val
625                 630                 635                 640 gcc cac ctt gtg tct gga gag tac ctg gcc atc tgt ttc atc att aac    1968
Ala His Leu Val Ser Gly Glu Tyr Leu Ala Ile Cys Phe Ile Ile Asn
                645                 650                 655 cac atc tcc gag tct tgc gaa ttt atg aat acc tcc ttt caa act gct    2016
His Ile Ser Glu Ser Cys Glu Phe Met Asn Thr Ser Phe Gln Thr Ala
            660                 665                 670 gcc cga cgg acc gag atg ctc cag gca gct cat cag gca gcc gag gcg    2064
Ala Arg Arg Thr Glu Met Leu Gln Ala Ala His Gln Ala Ala Glu Ala
            675                 680                 685 aaa aag gtc aag ccc act cct cca ccc aac gat tgg gct gtg aca caa    2112
Lys Lys Val Lys Pro Thr Pro Pro Pro Asn Asp Trp Ala Val Thr Gln
690                 695                 700 gtc cag tgc tgt gtc aac tgg cga tct gga ggc gtg ctg gcc aat cac    2160
Val Gln Cys Cys Val Asn Trp Arg Ser Gly Gly Val Leu Ala Asn His
705                 710                 715                 720 ctc tcc ggt ggc ctc aac cat cag atc gag cac cat ctg ttt ccc agc    2208
Leu Ser Gly Gly Leu Asn His Gln Ile Glu His His Leu Phe Pro Ser
                725                 730                 735 atc tct cac gcg aac tat ccc atc att gct cga gtt gtc aag gaa gtg    2256
Ile Ser His Ala Asn Tyr Pro Ile Ile Ala Arg Val Val Lys Glu Val
            740                 745                 750 tgc gag gaa tac gga ttg ccc tac aag aac tac gtt acg ttc tgg gat    2304
Cys Glu Glu Tyr Gly Leu Pro Tyr Lys Asn Tyr Val Thr Phe Trp Asp
            755                 760                 765 gcc gtg tgt ggc atg gtt cag cat ctg cga ctc atg ggt gct cct ccc    2352
Ala Val Cys Gly Met Val Gln His Leu Arg Leu Met Gly Ala Pro Pro
770                 775                 780 gtg cct acc aac ggc gac aaa aag tcc taa                            2382
Val Pro Thr Asn Gly Asp Lys Lys Ser
785                 790
```

<210> SEQ ID NO 76

```
<211> LENGTH: 793
<212> TYPE: PRT
<213> ORGANISM: Euglena gracilis

<400> SEQUENCE: 76
```

| | | | | | | | | | | | | | | | |
|---|---|---|---|---|---|---|---|---|---|---|---|---|---|---|---|
| Met | Ala | Asp | Ser | Pro | Val | Ile | Asn | Leu | Ser | Thr | Met | Trp | Lys | Pro | Leu |
| 1 | | | | 5 | | | | | 10 | | | | | 15 | |
| Ser | Leu | Met | Ala | Leu | Asp | Leu | Ala | Val | Leu | Gly | His | Val | Trp | Lys | Gln |
| | | | 20 | | | | | 25 | | | | | 30 | | |
| Ala | Gln | Gln | Glu | Gly | Ser | Ile | Ser | Ala | Tyr | Ala | Asp | Ser | Val | Trp | Thr |
| | | | 35 | | | | | 40 | | | | 45 | | | |
| Pro | Leu | Ile | Met | Ser | Gly | Leu | Tyr | Leu | Ser | Met | Ile | Phe | Val | Gly | Cys |
| 50 | | | | | 55 | | | | | 60 | | | | | |
| Arg | Trp | Met | Lys | Asn | Arg | Glu | Pro | Phe | Glu | Ile | Lys | Thr | Tyr | Met | Phe |
| 65 | | | | | 70 | | | | 75 | | | | | 80 | |
| Ala | Tyr | Asn | Leu | Tyr | Gln | Thr | Leu | Met | Asn | Leu | Cys | Ile | Val | Leu | Gly |
| | | | | 85 | | | | | 90 | | | | | 95 | |
| Phe | Leu | Tyr | Gln | Val | His | Ala | Thr | Gly | Met | Arg | Phe | Trp | Gly | Ser | Gly |
| | | | 100 | | | | | 105 | | | | | 110 | | |
| Val | Asp | Arg | Ser | Pro | Lys | Gly | Leu | Gly | Ile | Gly | Phe | Ile | Tyr | Ala |
| | | 115 | | | | | 120 | | | | | 125 | | | |
| His | Tyr | His | Asn | Lys | Tyr | Val | Glu | Tyr | Phe | Asp | Thr | Leu | Phe | Met | Val |
| 130 | | | | | 135 | | | | | 140 | | | | | |
| Leu | Arg | Lys | Lys | Asn | Asn | Gln | Ile | Ser | Phe | Leu | His | Val | Tyr | His | His |
| 145 | | | | | 150 | | | | | 155 | | | | | 160 |
| Ala | Leu | Leu | Thr | Trp | Ala | Trp | Phe | Ala | Val | Val | Tyr | Phe | Ala | Pro | Gly |
| | | | | 165 | | | | | 170 | | | | | 175 | |
| Gly | Asp | Gly | Trp | Phe | Gly | Ala | Cys | Tyr | Asn | Ser | Ser | Ile | His | Val | Leu |
| | | | 180 | | | | | 185 | | | | | 190 | | |
| Met | Tyr | Ser | Tyr | Tyr | Leu | Leu | Ala | Thr | Phe | Gly | Ile | Ser | Cys | Pro | Trp |
| | | 195 | | | | | 200 | | | | | 205 | | | |
| Lys | Lys | Ile | Leu | Thr | Gln | Leu | Gln | Met | Val | Gln | Phe | Cys | Phe | Cys | Phe |
| 210 | | | | | 215 | | | | | 220 | | | | | |
| Thr | His | Ser | Ile | Tyr | Val | Trp | Ile | Cys | Gly | Ser | Glu | Ile | Tyr | Pro | Arg |
| 225 | | | | | 230 | | | | | 235 | | | | | 240 |
| Pro | Leu | Thr | Ala | Leu | Gln | Ser | Phe | Val | Met | Val | Asn | Met | Leu | Val | Leu |
| | | | | 245 | | | | | 250 | | | | | 255 | |
| Phe | Gly | Asn | Phe | Tyr | Val | Lys | Gln | Tyr | Ser | Gln | Lys | Asn | Gly | Lys | Pro |
| | | | 260 | | | | | 265 | | | | | 270 | | |
| Glu | Asn | Gly | Ala | Thr | Pro | Glu | Asn | Gly | Ala | Lys | Pro | Gln | Pro | Cys | Glu |
| | | 275 | | | | | 280 | | | | | 285 | | | |
| Asn | Gly | Thr | Val | Glu | Lys | Arg | Glu | Asn | Asp | Thr | Ala | Asn | Val | Arg | Pro |
| | 290 | | | | | 295 | | | | | 300 | | | | |
| Ala | Arg | Pro | Ala | Gly | Leu | Pro | Pro | Ala | Thr | Tyr | Tyr | Asp | Ser | Leu | Ala |
| 305 | | | | | 310 | | | | | 315 | | | | | 320 |
| Val | Ser | Gly | Gln | Gly | Lys | Glu | Arg | Leu | Phe | Thr | Thr | Asp | Glu | Val | Arg |
| | | | | 325 | | | | | 330 | | | | | 335 | |
| Arg | His | Ile | Leu | Pro | Thr | Asp | Gly | Trp | Leu | Thr | Cys | His | Glu | Gly | Val |
| | | | 340 | | | | | 345 | | | | | 350 | | |
| Tyr | Asp | Val | Thr | Asp | Phe | Leu | Ala | Lys | His | Pro | Gly | Gly | Val | Ile |
| | | | 355 | | | | | 360 | | | | | 365 | | |
| Thr | Leu | Gly | Leu | Gly | Arg | Asp | Cys | Thr | Ile | Leu | Val | Glu | Ser | Tyr | His |
| | 370 | | | | | 375 | | | | | 380 | | | | |
| Pro | Ala | Gly | Arg | Pro | Asp | Lys | Val | Met | Glu | Lys | Tyr | Arg | Ile | Gly | Thr |

```
                385                 390                 395                 400
Leu Gln Asp Pro Lys Thr Phe Tyr Ala Trp Gly Glu Ser Asp Phe Tyr
                    405                 410                 415

Pro Glu Leu Lys Arg Arg Ala Leu Ala Arg Leu Lys Glu Ala Gly Gln
                    420                 425                 430

Ala Arg Arg Gly Gly Leu Gly Val Lys Ala Leu Leu Val Leu Thr Leu
                435                 440                 445

Phe Phe Val Ser Trp Tyr Met Trp Val Ala His Lys Ser Phe Leu Trp
450                 455                 460

Ala Ala Val Trp Gly Phe Ala Gly Ser His Val Gly Leu Ser Ile Gln
465                 470                 475                 480

His Asp Gly Asn His Gly Ala Phe Ser Arg Ser Thr Leu Val Asn Arg
                485                 490                 495

Leu Ala Gly Trp Gly Met Asp Leu Ile Gly Ala Ser Ser Thr Val Trp
                500                 505                 510

Glu Tyr Gln His Val Ile Gly His His Gln Tyr Thr Asn Leu Val Ser
                515                 520                 525

Asp Thr Leu Phe Ser Leu Pro Glu Asn Asp Pro Asp Val Phe Ser Ser
530                 535                 540

Tyr Pro Leu Met Arg Met His Pro Asp Thr Ala Trp Gln Pro His His
545                 550                 555                 560

Arg Phe Gln His Leu Phe Ala Phe Pro Leu Phe Ala Leu Met Thr Ile
                565                 570                 575

Ser Lys Val Leu Thr Ser Asp Phe Ala Val Cys Leu Ser Met Lys Lys
                580                 585                 590

Gly Ser Ile Asp Cys Ser Ser Arg Leu Val Pro Leu Glu Gly Gln Leu
                595                 600                 605

Leu Phe Trp Gly Ala Lys Leu Ala Asn Phe Leu Leu Gln Ile Val Leu
                610                 615                 620

Pro Cys Tyr Leu His Gly Thr Ala Met Gly Leu Ala Leu Phe Ser Val
625                 630                 635                 640

Ala His Leu Val Ser Gly Glu Tyr Leu Ala Ile Cys Phe Ile Ile Asn
                    645                 650                 655

His Ile Ser Glu Ser Cys Glu Phe Met Asn Thr Ser Phe Gln Thr Ala
                660                 665                 670

Ala Arg Arg Thr Glu Met Leu Gln Ala Ala His Gln Ala Ala Glu Ala
                675                 680                 685

Lys Lys Val Lys Pro Thr Pro Pro Asn Asp Trp Ala Val Thr Gln
690                 695                 700

Val Gln Cys Cys Val Asn Trp Arg Ser Gly Gly Val Leu Ala Asn His
705                 710                 715                 720

Leu Ser Gly Gly Leu Asn His Gln Ile Glu His Leu Phe Pro Ser
                725                 730                 735

Ile Ser His Ala Asn Tyr Pro Ile Ile Ala Arg Val Val Lys Glu Val
                740                 745                 750

Cys Glu Glu Tyr Gly Leu Pro Tyr Lys Asn Tyr Val Thr Phe Trp Asp
                755                 760                 765

Ala Val Cys Gly Met Val Gln His Leu Arg Leu Met Gly Ala Pro Pro
                770                 775                 780

Val Pro Thr Asn Gly Asp Lys Lys Ser
785                 790

<210> SEQ ID NO 77
```

<211> LENGTH: 9641
<212> TYPE: DNA
<213> ORGANISM: Artificial Sequence
<220> FEATURE:
<223> OTHER INFORMATION: Plasmid pY201

<400> SEQUENCE: 77

```
gtacgataac ttcgtatagc atacattata cgaagttatc gcgtcgacga gtatctgtct      60
gactcgtcat tgccgccttt ggagtacgac tccaactatg agtgtgcttg gatcactttg     120
acgatacatt cttcgttgga ggctgtgggt ctgacagctg cgttttcggc gcggttggcc     180
gacaacaata tcagctgcaa cgtcattgct ggctttcatc atgatcacat ttttgtcggc     240
aaaggcgacg cccagagagc cattgacgtt ctttctaatt tggaccgata gccgtatagt     300
ccagtctatc tataagttca actaactcgt aactattacc ataacatata cttcactgcc     360
ccagataagg ttccgataaa aagttctgca gactaaattt atttcagtct cctcttcacc     420
accaaaatgc cctcctacga agctcgagct aacgtccaca agtccgcctt tgccgctcga     480
gtgctcaagc tcgtggcagc caagaaaacc aacctgtgtg cttctctgga tgttaccacc     540
accaaggagc tcattgagct tgccgataag gtcggacctt atgtgtgcat gatcaaaacc     600
catatcgaca tcattgacga cttcacctac gccggcactg tgctcccccct caaggaactt     660
gctcttaagc acggtttctt cctgttcgag gacagaaagt cgcagatatt ggcaacact      720
gtcaagcacc agtaccggtg tcaccgaatc gccgagtggt ccgatatcac caacgcccac     780
ggtgtacccg gaaccggaat cattgctggc ctgcgagctg gtgccgagga aactgtctct     840
gaacagaaga aggaggacgt ctctgactac gagaactccc agtacaagga gttcctagtc     900
ccctctccca acgagaagct ggccagaggt ctgctcatgc tggccgagct gtcttgcaag     960
ggctctctgg ccactggcga gtactccaag cagaccattg agcttgcccg atccgacccc    1020
gagtttgtgg ttggcttcat tgcccagaac cgacctaagg gcgactctga ggactggctt    1080
attctgaccc ccggggtggg tcttgacgac aaggagacg ctctcggaca gcagtaccga    1140
actgttgagg atgtcatgtc taccggaacg gatatcataa ttgtcggccg aggtctgtac    1200
ggccagaacc gagatcctat tgaggaggcc aagcgatacc agaaggctgg ctgggaggct    1260
taccagaaga ttaactgtta gaggttagac tatggatatg taatttaact gtgtatatag    1320
agagcgtgca agtatggagc gcttgttcag cttgtatgat ggtcagacga cctgtctgat    1380
cgagtatgta tgatactgca caacctgtgt atccgcatga tctgtccaat ggggcatgtt    1440
gttgtgtttc tcgatacgga gatgctgggt acagtgctaa tacgttgaac tacttatact    1500
tatatgaggc tcgaagaaag ctgacttgtg tatgacttat tctcaactac atccccagtc    1560
acaataccac cactgcacta ccactacacc aaaaccatga tcaaaccacc catggacttc    1620
ctggaggcag aagaacttgt tatggaaaag ctcaagagag agatcataac ttcgtatagc    1680
atacattata cgaagttatc ctgcaggtaa aggaattcag gagagaccgg gttggcggcg    1740
tatttgtgtc ccaaaaaaca gccccaattg ccccaattga ccccaaattg acccagtagc    1800
gggcccaacc ccggcgagag ccccccttcac cccacatatc aaacctcccc cggttcccac    1860
acttgccgtt aagggcgtag ggtactgcag tctggaatct acgcttgttc agactttgta    1920
ctagttttctt tgtctggcca tccgggtaac ccatgccgga cgcaaaatag actactgaaa    1980
atttttttgc tttgtggttg ggactttagc caagggtata aaagaccacc gtccccgaat    2040
tacctttcct cttcttttct ctctctcctt gtcaactcac acccgaaatc gttaagcatt    2100
tccttctgag tataagaatc attcaccatg gacttcctgg aggcagaaga acttgttatg    2160
```

```
gaaaagctca agagagagaa gccaagatac tatcaagaca tgtgtcgcaa cttaattaag    2220
atgacgacat ttgcgagctg gacgaggaat agatggagcg tgtgttctga gtcgatgttt    2280
tctatggagt tgtgagtgtt agtagacatg atgggtttat atatgatgaa tgaatagatg    2340
tgattttgat ttgcacgatg gaattgagaa ctttgtaaac gtacatggga atgtatgaat    2400
gtggggtttt tgtgactgga taactgacgg tcagtggacg ccgttgttca aatatccaag    2460
agatgcgaga aactttgggt caagtgaaca tgtcctctct gttcaagtaa accatcaact    2520
atgggtagta tatttagtaa ggacaagagt tgagattctt tggagtccta gaaacgtatt    2580
ttcgcgttcc aagatcaaat tagtagagta atacgggcac gggaatccat tcatagtctc    2640
aattttccca taggtgtgct acaaggtgtt gagatgtggt acagtaccac catgattcga    2700
ggtaaagagc ccagaagtca ttgatgaggt caagaaatac acagatctac agctcaatac    2760
aatgaatatc ttctttcata ttcttcaggt gacaccaagg gtgtctattt tccccagaaa    2820
tgcgtgaaaa ggcgcgtgtg tagcgtggag tatgggttcg gttggcgtat ccttcatata    2880
tcgacgaaat agtagggcaa gagatgacaa aaagtatcta tatgtagaca gcgtagaata    2940
tggatttgat tggtataaat tcatttattg cgtgtctcac aaatactctc gataagttgg    3000
ggttaaactg gagatggaac aatgtcgata tctcgacgca tgcgacgtcg ggcccaattc    3060
gccctatagt gagtcgtatt acaattcact ggccgtcgtt ttacaacgtc gtgactggga    3120
aaaccctggc gttacccaac ttaatcgcct tgcagcacat ccccctttcg ccagctggcg    3180
taatagcgaa gaggcccgca ccgatcgccc ttcccaacag ttgcgcagcc tgaatggcga    3240
atggacgcgc cctgtagcgg cgcattaagc gcggcgggtg tggtggttac gcgcagcgtg    3300
accgctacac ttgccagcgc cctagcgccc gctcctttcg ctttcttccc ttcctttctc    3360
gccacgttcg ccggctttcc ccgtcaagct ctaaatcggg ggctcccttt agggttccga    3420
tttagtgctt tacggcacct cgaccccaaa aaacttgatt agggtgatgg ttcacgtagt    3480
gggccatcgc cctgatagac ggttttttcgc cctttgacgt tggagtccac gttctttaat    3540
agtggactct tgttccaaac tggaacaaca ctcaaccccta tctcggtcta ttcttttgat    3600
ttataaggga ttttgccgat ttcggcctat tggttaaaaa atgagctgat ttaacaaaaa    3660
tttaacgcga attttaacaa aatattaacg cttacaattt cctgatgcgg tattttctcc    3720
ttacgcatct gtgcggtatt tcacaccgca tcaggtggca cttttcgggg aaatgtgcgc    3780
ggaaccccta tttgtttatt tttctaaata cattcaaata tgtatccgct catgagacaa    3840
taaccctgat aaatgcttca ataatattga aaaggaaga gtatgagtat tcaacatttc    3900
cgtgtcgccc ttattccctt ttttgcggca ttttgccttc ctgtttttgc tcacccagaa    3960
acgctggtga agtaaaaga tgctgaagat cagttgggtg cacgagtggg ttacatcgaa    4020
ctggatctca acagcggtaa gatccttgag agttttcgcc ccgaagaacg ttttccaatg    4080
atgagcactt ttaaagttct gctatgtggc gcggtattat cccgtattga cgccgggcaa    4140
gagcaactcg gtcgccgcat acactattct cagaatgact tggttgagta ctcaccagtc    4200
acagaaaagc atcttacgga tggcatgaca gtaagagaat tatgcagtgc tgccataacc    4260
atgagtgata acactgcggc caacttactt ctgacaacga tcgaggacc gaaggagcta    4320
accgcttttt tgcacaacat gggggatcat gtaactcgcc ttgatcgttg ggaaccggag    4380
ctgaatgaag ccataccaaa cgacgagcgt gacaccacga tgcctgtagc aatggcaaca    4440
acgttgcgca aactattaac tggcgaacta cttactctag cttcccggca acaattaata    4500
```

```
gactggatgg aggcggataa agttgcagga ccacttctgc gctcggccct tccggctggc    4560
tggtttattg ctgataaatc tggagccggt gagcgtgggt ctcgcggtat cattgcagca    4620
ctggggccag atggtaagcc ctcccgtatc gtagttatct acacgacggg gagtcaggca    4680
actatggatg aacgaaatag acagatcgct gagataggtg cctcactgat taagcattgg    4740
taactgtcag accaagttta ctcatatata ctttagattg atttaaaact tcattttttaa   4800 tttaaaagga tctaggtgaa gatcctttt gataatctca tgaccaaaat cccttaacgt    4860
gagttttcgt tccactgagc gtcagacccc gtagaaaaga tcaaaggatc ttcttgagat    4920
cctttttttc tgcgcgtaat ctgctgcttg caaacaaaaa aaccaccgct accagcggtg    4980
gtttgtttgc cggatcaaga gctaccaact cttttccga aggtaactgg cttcagcaga    5040
gcgcagatac caaatactgt tcttctagtg tagccgtagt taggccacca cttcaagaac    5100
tctgtagcac cgcctacata cctcgctctg ctaatcctgt taccagtggc tgctgccagt    5160
ggcgataagt cgtgtcttac cgggttggac tcaagacgat agttaccgga taaggcgcag    5220
cggtcgggct gaacggggg ttcgtgcaca cagcccagct tggagcgaac gacctacacc    5280
gaactgagat acctacagcg tgagctatga gaaagcgcca cgcttcccga agggagaaag    5340
gcggacaggt atccggtaag cggcagggtc ggaacaggag agcgcacgag ggagcttcca    5400
gggggaaacg cctggtatct ttatagtcct gtcgggtttc gccacctctg acttgagcgt    5460
cgatttttgt gatgctcgtc aggggggcgg agcctatgga aaaacgccag caacgcggcc    5520
tttttacggt tcctggcctt tgctggcct tttgctcaca tgttctttcc tgcgttatcc    5580
cctgattctg tggataaccg tattaccgcc tttgagtgag ctgataccgc tcgccgcagc    5640
cgaacgaccg agcgcagcga gtcagtgagc gaggaagcgg aagagcgccc aatacgcaaa    5700
ccgcctctcc ccgcgcgttg gccgattcat taatgcagct ggcgcgccac caatcacaat    5760
tctgaaaagc acatcttgat ctcctcattg cggggagtcc aacggtggtc ttattccccc    5820
gaatttcccg ctcaatctcg ttccagaccg acccggacac agtgcttaac gccgttccga    5880
aactctaccg cagatatgct ccaacggact gggctgcata gatgtgatcc tcggcttgga    5940
gaaatggata aaagccggcc aaaaaaaag cggaaaaaag cggaaaaaaa gagaaaaaaa    6000
atcgcaaaat ttgaaaaata ggggaaaag acgcaaaaac gcaaggaggg gggagtatat    6060
gacactgata agcaagctca caacggttcc tcttattttt ttcctcatct tctgcctagg    6120
ttcccaaaat cccagatgct tctctccagt gccaaaagta agtacccac aggttttcgg    6180 ccgaaaattc cacgtgcagc aacgtcgtgt ggggtgttaa aatgtggggg ggggaacca    6240 ggacaagagg ctcttgtggg agccgaatga gagcacaaag cgggcgggtg tgataagggc    6300 attttttgccc atttttccctt ctcctgtctc tccgacggtg atggcgttgt gcgtcctcta    6360
tttcttttta tttctttttg ttttatttct ctgactaccg atttggtttg atttcctcaa    6420
ccccacacaa ataagctcgg gccgaggaat atatatatac acggacacag tcgcctgtg    6480 gacaacacgt cactacctct acgatacaca ccgtacgata gttagtagac aacaatcgat    6540
agttggagca agggagaaat gtagagtgtg aaagactcac tatggtccgg gcttatctcg    6600
accaatagcc aaagtctgga gtttctgaga gaaaaaggca agatacgtat gtaacaaagc    6660
gacgcatggt acaataatac cggaggcatg tatcatagag agttagtggt tcgatgatgg    6720
cactggtgcc tggtatgact ttatacggct gactacatat ttgtcctcag acatacaatt    6780
acagtcaagc acttaccctt ggacatcgtg aggtacccc cggccaagac gatctcagcg    6840
tgtcgtatgt cggattggcg tagctccctc gctcgtcaat tggctcccat ctactttctt    6900
```

```
ctgcttggct acacccagca tgtctgctat ggctcgtttt cgtgccttat ctatcctccc   6960
agtattacca actctaaatg acatgatgtg attgggtcta cactttcata tcagagataa   7020
ggagtagcac agttgcataa aaagcccaac tctaatcagc ttcttccttt cttgtaatta   7080
gtacaaaggt gattagcgaa atctggaagc ttagttggcc ctaaaaaaat caaaaaaagc   7140
aaaaaacgaa aaacgaaaaa ccacagtttt gagaacaggg aggtaacgaa ggatcgtata   7200
tatatatata tatatatata cccacggatc ccgagaccgg cctttgattc ttccctacaa   7260
ccaaccattc tcaccaccct aattcacaac catgtacaac cccgtggacg cagtgttgac   7320
taagattatt acaaactacg gaattgattc ttttaccctg cgatatgcca tttgtctgtt   7380
gggatctttt cctcttaacg ctattctgaa gcggattcct gaaaagcgaa tcggcctgaa   7440
gtgttgtttt atcatttcta tgtccatgtt ttatctcttc ggcgttctga atctcgtgag   7500
cggatttcga accctcttca tttccacaat gttcacatac cttatctctc ggttctaccg   7560
atccaagttt atgccccatc tcaacttcat gttcgtcatg gccacttgg ctatcaacca    7620 cattcatgct cagttcctga acgaacaaac tcaaacgacc gtcgatatta catcctcgca   7680
gatggtcctg gctatgaagc tgacaagctt tgcctggtct tactatgacg gttcgtgtac   7740
gagcgagtcc gacttcaagg accttaccga acaccagaag tcccgagccg tccgaggcca   7800
tcctcccctt ctgaaatttt tggcttacgc ctttttctac tctacccttc tcaccggtcc   7860
ctccttcgat tacgctgatt tcgactcttg gctgaactgc gaaatgttcc gggaccttcc   7920
cgagtccaag aaacccatgc gaagacatca tcctggtgag cggcgtcaga ttcccaagaa   7980
cggcaagctc gccctgtgga aggttgtcca gggcctcgcc tggatgattc tgagcacgtt   8040
gggtatgaag cacttccccg tgaagtacgt gctggacaag gacggatttc ctacccgttc   8100
ctttatcttc cgtattcatt atctgtttct gctgggattc atccaccgat ttaagtatta   8160
cgctgcgtgg acgattagcg aaggttcgtg cattctctgt ggtcttggtt ataatggata   8220
cgattctaag acccagaaga tccggtggga tcgagtgcgg aatattgata tttggacagt   8280
ggagactgca caaaacaccc gagagatgct ggaagcgtgg aacatgaata ctaacaaatg   8340
gctgaagtat agcgtgtatc ttagagtgac taagaagggg aagaagccag ttttcgatc    8400 taccctgttt accttcctga cctccgcctt ttggcacggt acccgtcctg gatactacct   8460
taccttcgca actggtgccc tgtaccaaac ctgtggaaag atctatagac gaaactttcg   8520
tcccatcttt ctgagagaag atggcgtgac acctctcccg tccaagaaga tttacgacct   8580
ggtcggcatt tacgctatta agctggcctt tggttacatg gttcaaccct tcattatcct   8640
tgacctgaag ccctctctta tggtttgggg atccgtgtat ttctacgtgc atattattgt   8700
ggccttctcg ttctttctgt tccgaggacc atacgctaag caggttactg aattttcaa    8760 aagcaagcaa ccgaaggaga tcttcatccg aaagcagaag aagttggaaa agacatctc    8820 tgcctcttcc cccaacctcg gaggtattct taaggcaaaa atcgaacatg agaagggaaa   8880
gacggcagag gaggaagaga tgaacttggg cattccaccc atcgaactgg agaagtggga   8940
caacgccaag gaggactggg aggatttctg caaggactac aaggagtggc ggaacaagaa   9000
cggactggaa attgaagagg agaacctgtc caaggccttc gagcgattta gcaggaatt    9060 ttccaacgct gcgtcgggct ctggtgaacg ggttcggaaa atgtccttct ccggatattc   9120
tcctaaaccc atctcgaaga aagaagaata ggcggccgca tgagaagata aatatataaa   9180
tacattgaga tattaaatgc gctagattag agagcctcat actgctcgga gagaagccaa   9240
```

-continued

```
gacgagtact caaaggggat tacaccatcc atatccacag acacaagctg gggaaaggtt    9300
ctatatacac tttccggaat accgtagttt ccgatgttat caatggggc agccaggatt     9360 tcaggcactt cggtgtctcg gggtgaaatg gcgttcttgg cctccatcaa gtcgtaccat    9420
gtcttcattt gcctgtcaaa gtaaaacaga agcagatgaa gaatgaactt gaagtgaagg    9480
aatttaaatg taacgaaact gaaatttgac cagatattgt gtccgcggtg gagctccagc    9540
ttttgttccc tttagtgagg gttaatttcg agcttggcgt aatcatggtc atagctgttt    9600
cctgtgtgaa attgttatcc gctcacaagc ttccacacaa c                       9641
```

<210> SEQ ID NO 78
<211> LENGTH: 34
<212> TYPE: DNA
<213> ORGANISM: Escherichia coli

<400> SEQUENCE: 78

```
ataacttcgt ataatgtatg ctatacgaag ttat                                34
```

<210> SEQ ID NO 79
<211> LENGTH: 40
<212> TYPE: DNA
<213> ORGANISM: Artificial Sequence
<220> FEATURE:
<223> OTHER INFORMATION: Primer 798

<400> SEQUENCE: 79

```
ctaattcaca accatggcct ttccatgggc agataagtgg                          40
```

<210> SEQ ID NO 80
<211> LENGTH: 36
<212> TYPE: DNA
<213> ORGANISM: Artificial Sequence
<220> FEATURE:
<223> OTHER INFORMATION: Primer 799

<400> SEQUENCE: 80

```
ctcatgcggc cgcttacttg gtcttgatgg tgtcct                              36
```

<210> SEQ ID NO 81
<211> LENGTH: 40
<212> TYPE: DNA
<213> ORGANISM: Artificial Sequence
<220> FEATURE:
<223> OTHER INFORMATION: Primer 800

<400> SEQUENCE: 81

```
cgatagttag tagacaacaa tcgatagttg gagcaaggga                          40
```

<210> SEQ ID NO 82
<211> LENGTH: 36
<212> TYPE: DNA
<213> ORGANISM: Artificial Sequence
<220> FEATURE:
<223> OTHER INFORMATION: Primer 801

<400> SEQUENCE: 82

```
gaaaggccat ggttgtgaat tagggtggtg agaatg                              36
```

<210> SEQ ID NO 83
<211> LENGTH: 9320
<212> TYPE: DNA
<213> ORGANISM: Artificial Sequence
<220> FEATURE:
<223> OTHER INFORMATION: Plasmid pY168

<400> SEQUENCE: 83

```
gtacgataac ttcgtatagc atacattata cgaagttatc gcgtcgacga gtatctgtct      60
gactcgtcat tgccgccttt ggagtacgac tccaactatg agtgtgcttg gatcactttg     120
acgatacatt cttcgttgga ggctgtgggt ctgacagctg cgttttcggc gcggttggcc     180
gacaacaata tcagctgcaa cgtcattgct ggctttcatc atgatcacat ttttgtcggc     240
aaaggcgacg cccagagagc cattgacgtt ctttctaatt tggaccgata gccgtatagt     300
ccagtctatc tataagttca actaactcgt aactattacc ataacatata cttcactgcc     360
ccagataagg ttccgataaa aagttctgca gactaaattt atttcagtct cctcttcacc     420
accaaaatgc cctcctacga agctcgagct aacgtccaca agtccgcctt gccgctcga      480
gtgctcaagc tcgtggcagc caagaaaacc aacctgtgtg cttctctgga tgttaccacc     540
accaaggagc tcattgagct tgccgataag gtcggacctt atgtgtgcat gatcaaaacc     600
catatcgaca tcattgacga cttcacctac gccggcactg tgctcccct caaggaactt     660
gctcttaagc acggtttctt cctgttcgag gacagaaagt tcgcagatat tggcaacact     720
gtcaagcacc agtaccggtg tcaccgaatc gccgagtggt ccgatatcac caacgcccac     780
ggtgtacccg gaaccggaat cattgctggc ctgcgagctg gtgccgagga aactgtctct     840
gaacagaaga aggaggacgt ctctgactac gagaactccc agtacaagga gttcctagtc     900
ccctctccca acgagaagct ggccagaggt ctgctcatgc tggccgagct gtcttgcaag     960
ggctctctgg ccactggcga gtactccaag cagaccattg agcttgcccg atccgacccc    1020
gagtttgtgg ttggcttcat tgcccagaac cgacctaagg gcgactctga ggactggctt    1080
attctgaccc ccggggtggg tcttgacgac aagggagacg ctctcggaca gcagtaccga    1140
actgttgagg atgtcatgtc taccggaacg gatatcataa ttgtcggccg aggtctgtac    1200
ggccagaacc gagatcctat tgaggaggcc aagcgatacc agaaggctgg ctgggaggct    1260
taccagaaga ttaactgtta gaggttagac tatggatatg taatttaact gtgtatatag    1320
agagcgtgca agtatggagc gcttgttcag cttgtatgat ggtcagacga cctgtctgat    1380
cgagtatgta tgatactgca caacctgtgt atccgcatga tctgtccaat ggggcatgtt    1440
gttgtgtttc tcgatacgga gatgctgggt acagtgctaa tacgttgaac tacttatact    1500
tatatgaggc tcgaagaaag ctgacttgtg tatgacttat tctcaactac atccccagtc    1560
acaataccac cactgcacta ccactacacc aaaaccatga tcaaaccacc catggacttc    1620
ctggaggcag aagaacttgt tatggaaaag ctcaagagag agatcataac ttcgtatagc    1680
atacattata cgaagttatc ctgcaggtaa aggaattcag gagagaccgg gttggcggcg    1740
tatttgtgtc ccaaaaaaca gccccaattg ccccaattga cccaaattg acccagtagc     1800
gggcccaacc ccggcgagag ccccttcac cccacatatc aaacctcccc cggttcccac    1860
acttgccgtt aagggcgtag ggtactgcag tctggaatct acgcttgttc agactttgta    1920
ctagttctt tgtctggcca tccgggtaac ccatgccgga cgcaaaatag actactgaaa     1980
attttttgc tttgtggttg ggactttagc caagggtata aaagaccacc gtccccgaat     2040
tacctttcct cttcttttct ctctctcctt gtcaactcac acccgaaatc gttaagcatt    2100
tccttctgag tataagaatc attcaccatg gacttcctgg aggcagaaga acttgttatg    2160
gaaaagctca agagagagaa gccaagatac tatcaagaca tgtgtcgcaa cttaattaag    2220
atgacgacat ttgcgagctg gacgaggaat agatggagcg tgtgttctga gtcgatgttt    2280
```

```
tctatggagt tgtgagtgtt agtagacatg atgggtttat atatgatgaa tgaatagatg   2340
tgattttgat ttgcacgatg gaattgagaa ctttgtaaac gtacatggga atgtatgaat   2400 gtggggggttt tgtgactgga taactgacgg tcagtggacg ccgttgttca aatatccaag   2460
agatgcgaga aactttgggt caagtgaaca tgtcctctct gttcaagtaa accatcaact   2520
atgggtagta tatttagtaa ggacaagagt tgagattctt tggagtccta gaaacgtatt   2580
ttcgcgttcc aagatcaaat tagtagagta atacgggcac gggaatccat tcatagtctc   2640
aattttccca taggtgtgct acaaggtgtt gagatgtggt acagtaccac catgattcga   2700
ggtaaagagc ccagaagtca ttgatgaggt caagaaatac acagatctac agctcaatac   2760
aatgaatatc ttctttcata ttcttcaggt gacaccaagg gtgtctattt tccccagaaa   2820
tgcgtgaaaa ggcgcgtgtg tagcgtggag tatgggttcg gttggcgtat ccttcatata   2880
tcgacgaaat agtagggcaa gagatgacaa aaagtatcta tatgtagaca gcgtagaata   2940
tggatttgat tggtataaat tcatttattg cgtgtctcac aaatactctc gataagttgg   3000
ggttaaactg gagatggaac aatgtcgata tctcgacgca tgcgacgtcg ggcccaattc   3060
gccctatagt gagtcgtatt acaattcact ggccgtcgtt ttacaacgtc gtgactggga   3120
aaaccctggc gttacccaac ttaatcgcct tgcagcacat ccccctttcg ccagctggcg   3180
taatagcgaa gaggcccgca ccgatcgccc ttcccaacag ttgcgcagcc tgaatggcga   3240
atggacgcgc cctgtagcgg cgcattaagc gcggcgggtg tggtggttac gcgcagcgtg   3300
accgctacac ttgccagcgc cctagcgccc gctcctttcg ctttcttccc ttcctttctc   3360
gccacgttcg ccggctttcc ccgtcaagct ctaaatcggg ggctcccttt agggttccga   3420
tttagtgctt tacggcacct cgaccccaaa aaacttgatt agggtgatgg ttcacgtagt   3480
gggccatcgc cctgatagac ggttttcgc cctttgacgt tggagtccac gttctttaat   3540
agtggactct tgttccaaac tggaacaaca ctcaaccta tctcggtcta ttcttttgat   3600
ttataaggga ttttgccgat ttcggcctat tggttaaaaa atgagctgat ttaacaaaaa   3660
tttaacgcga attttaacaa aatattaacg cttacaattt cctgatgcgg tattttctcc   3720
ttacgcatct gtgcggtatt tcacaccgca tcaggtggca cttttcgggg aaatgtgcgc   3780 ggaacccta tttgtttatt tttctaaata cattcaaata tgtatccgct catgagacaa   3840
taaccctgat aaatgcttca ataatattga aaaaggaaga gtatgagtat tcaacatttc   3900
cgtgtcgccc ttattccctt ttttgcggca ttttgccttc ctgtttttgc tcacccagaa   3960
acgctggtga aagtaaaaga tgctgaagat cagttgggtg cacgagtggg ttacatcgaa   4020
ctggatctca acagcggtaa gatccttgag agttttcgcc ccgaagaacg ttttccaatg   4080
atgagcactt ttaaagttct gctatgtggc gcggtattat cccgtattga cgccgggcaa   4140
gagcaactcg gtcgccgcat acactattct cagaatgact tggttgagta ctcaccagtc   4200
acagaaaagc atcttacgga tggcatgaca gtaagagaat tatgcagtgc tgccataacc   4260
atgagtgata acactgcggc caacttactt ctgacaacga tcgaggacc gaaggagcta   4320 accgcttttt tgcacaacat gggggatcat gtaactcgcc ttgatcgttg ggaaccggag   4380
ctgaatgaag ccataccaaa cgacgagcgt gacaccacga tgcctgtagc aatggcaaca   4440
acgttgcgca aactattaac tggcgaacta cttactctag cttcccggca acaattaata   4500
gactggatgg aggcggataa agttgcagga ccacttctgc gctcggccct tccggctggc   4560
tggtttattg ctgataaatc tggagccggt gagcgtgggt ctcgcggtat cattgcagca   4620
ctggggccag atggtaagcc ctcccgtatc gtagttatct acacgacggg gagtcaggca   4680
```

```
actatggatg aacgaaatag acagatcgct gagataggtg cctcactgat taagcattgg   4740
taactgtcag accaagttta ctcatatata ctttagattg atttaaaact tcatttttaa   4800
tttaaaagga tctaggtgaa gatcctttt gataatctca tgaccaaaat cccttaacgt   4860
gagttttcgt tccactgagc gtcagacccc gtagaaaaga tcaaaggatc ttcttgagat   4920
ccttttttc tgcgcgtaat ctgctgcttg caaacaaaaa aaccaccgct accagcggtg   4980
gtttgtttgc cggatcaaga gctaccaact cttttccga aggtaactgg cttcagcaga   5040
gcgcagatac caaatactgt tcttctagtg tagccgtagt taggccacca cttcaagaac   5100
tctgtagcac cgcctacata cctcgctctg ctaatcctgt taccagtggc tgctgccagt   5160
ggcgataagt cgtgtcttac cgggttggac tcaagacgat agttaccgga taaggcgcag   5220
cggtcgggct gaacggggg ttcgtgcaca cagcccagct tggagcgaac gacctacacc   5280
gaactgagat acctacagcg tgagctatga gaaagcgcca cgcttcccga agggagaaag   5340
gcggacaggt atccggtaag cggcagggtc ggaacaggag agcgcacgag ggagcttcca   5400
gggggaaacg cctggtatct ttatagtcct gtcgggtttc gccacctctg acttgagcgt   5460
cgatttttgt gatgctcgtc agggggggcgg agcctatgga aaacgccag caacgcggcc   5520
tttttacggt tcctggcctt ttgctggcct tttgctcaca tgttctttcc tgcgttatcc   5580
cctgattctg tggataaccg tattaccgcc tttgagtgag ctgataccgc tcgccgcagc   5640
cgaacgaccg agcgcagcga gtcagtgagc gaggaagcgg aagagcgccc aatacgcaaa   5700
ccgcctctcc ccgcgcgttg gccgattcat taatgcagct ggcgcgccac caatcacaat   5760
tctgaaaagc acatcttgat ctcctcattg cggggagtcc aacggtggtc ttattcccc   5820
gaatttcccg ctcaatctcg ttccagaccg accgggacac agtgcttaac gccgttccga   5880
aactctaccg cagatatgct ccaacggact gggctgcata gatgtgatcc tcggcttgga   5940
gaaatggata aaagccggcc aaaaaaaag cggaaaaaag cggaaaaaaa gagaaaaaaa   6000
atcgcaaaat ttgaaaaata gggggaaaag acgcaaaaac gcaaggaggg gggagtatat   6060
gacactgata agcaagctca caacggttcc tcttatttt ttcctcatct tctgcctagg   6120
ttcccaaaat cccagatgct tctctccagt gccaaaagta agtaccccac aggtttttcgg   6180
ccgaaaattc cacgtgcagc aacgtcgtgt ggggtgttaa aatgtgggg ggggaacca   6240
ggacaagagg ctcttgtggg agccgaatga gagcacaaag cgggcgggtg tgataagggc   6300
atttttgccc attttccctt ctcctgtctc tccgacggtg atggcgttgt gcgtcctcta   6360
ttttctttta tttctttttg tttatttct ctgactaccg atttggtttg atttcctcaa   6420
ccccacacaa ataagctcgg gccgaggaat atatatatac acggacacag tcgccctgtg   6480
gacaacacgt cactacctct acgatacaca ccgtacgata gttagtagac aacaatcgat   6540
agttggagca agggagaaat gtagagtgtg aaagactcac tatggtccgg gcttatctcg   6600
accaatagcc aaagtctgga gtttctgaga gaaaaaggca agatacgtat gtaacaaagc   6660
gacgcatggt acaataatac cggaggcatg tatcatagag agttagtggt tcgatgatgg   6720
cactggtgcc tggtatgact ttatacggct gactacatat ttgtcctcag acatacaatt   6780
acagtcaagc acttacccctt ggacatctgt aggtaccccc cggccaagac gatctcagcg   6840
tgtcgtatgt cggattggcg tagctccctc gctcgtcaat tggctcccat ctactttctt   6900
ctgcttggct acacccagca tgtctgctat ggctcgtttt cgtgccttat ctatcctccc   6960
agtattacca actctaaatg acatgatgtg attgggtcta cactttcata tcagagataa   7020
```

```
ggagtagcac agttgcataa aaagcccaac tctaatcagc ttcttccttt cttgtaatta    7080
gtacaaaggt gattagcgaa atctggaagc ttagttggcc ctaaaaaaat caaaaaaagc    7140
aaaaaacgaa aaacgaaaaa ccacagtttt gagaacaggg aggtaacgaa ggatcgtata    7200
tatatatata tatatatata cccacggatc ccgagaccgg cctttgattc ttccctacaa    7260
ccaaccattc tcaccaccct aattcacaac catggccttt ccctgggcag ataagtgggc    7320
agccgatgcg tctgcatcta cagggctgcc tccggacctc ctcaagattg cattcactct    7380
ggtcatgtct tatccgctga gttctctcat gaaacggctg ccagatgacg ccaaaaacct    7440
caagatcatc tatatcatct ccgtgtccat cttctacatg gtgggtgtct tctccctcta    7500
tggcggagct gccactctgc tcttctcctc aatgggtacc ttcttcatca cccaatggaa    7560
gagcccttac atgccctggg tcaattttgg ttttgtcatg acccatctct tcgtcaatca    7620
cctgcgttcg cagttttttcc ccgaaacata cgaccccaat gtcattgaca tcaccggagc    7680
acagatggtt ctgtgtatga agctatcgtc ttttggatgg aacgtctacg atggatggca    7740
gattgagaag ggtgagcagc tcagcgagtt ccagactaaa agggctgttc tcaagcaccc    7800
cagtcttatg gacttcctag cttttgtgtt ctacttccct tccattctga caggtccttc    7860
ttacgactat atggagttcc ataactggct cgatctcagc ctgttcaagg agctggagaa    7920
agataaggac cccaagcgag ctgctcgacg aaagcgacac aagatccccc gatctggaat    7980
cgctgcttcc aagaaactcg ccgctggtat cttctggatc gttctgtgga cccaggtgga    8040
ctctcgaatc tccaccgcct acgcttactc agacgcattc accaaggagc acaacatctt    8100
tggacgaatt gtgtacctct acatgctcgg tttcatgtac cgactcaagt actacggagc    8160
ctggtccatt tccgagggag cctgcatctt gtctggcctc ggattccatg cgtggaccc    8220 caaaactggc aagtacaagt gggaccgtgt ccagaacgtg gacccgtggg gattcgaaac    8280
tggtcaaaac acaaaggctc tgctggaggc ctggaaccag aacactaaca agtggctacg    8340
aaactatgtg tacctccgag tggtgcccaa aggccaaaag cctggattcc gagccactat    8400
cttcacattt gtggttttccg ccttctggca tggaactcga cctggctact atctcacctt    8460
tgtgaccgct gccatgtacc agtctgttgg taagttcttc cgacgatacc tgcgaccctt    8520
cttcatggag tctgatggaa agactgccgg tccctataag atctactacg acattgtgtg    8580
ttggatcgtt gtccaaaccg catttggata cgctacccag tcctttatga ttctagactt    8640
ctggctgtcg ctcaagtgtt ggaagaactc ctggttcctg taccacattg ctctgggcgc    8700
catctttgca atttctagcc cctacaaggc atgggcgatt cccaagatca agaaaaagca    8760
ggctggagcc gtcactgaca agaaggacgc caaggaggag gtgaagaagg acaccatcaa    8820
gaccaagtaa gcggccgcat gagaagataa atatataaat acattgagat attaaatgcg    8880
ctagattaga gagcctcata ctgctcggag agaagccaag acgagtactc aaaggggatt    8940
acaccatcca tatccacaga cacaagctgg ggaaaggttc tatatacact ttccggaata    9000
ccgtagtttc cgatgttatc aatgggggca gccaggattt caggcacttc ggtgtctcgg    9060
ggtgaaatgg cgttcttggc ctccatcaag tcgtaccatg tcttcatttg cctgtcaaag    9120
taaaacagaa gcagatgaag aatgaacttg aagtgaagga atttaaatgt aacgaaactg    9180
aaatttgacc agatattgtg tccgcggtgg agctccagct tttgttccct ttagtgaggg    9240
ttaatttcga gcttggcgta atcatggtca tagctgtttc ctgtgtgaaa ttgttatccg    9300
ctcacaagct tccacacaac                                                9320
```

<210> SEQ ID NO 84
<211> LENGTH: 8726
<212> TYPE: DNA
<213> ORGANISM: Artificial Sequence
<220> FEATURE:
<223> OTHER INFORMATION: Plasmid pY208

<400> SEQUENCE: 84

| | | | | | |
|---|---|---|---|---|---|
| gtacgataac | ttcgtatagc | atacattata | cgaagttatc | gcgtcgacga gtatctgtct | 60 |
| gactcgtcat | tgccgccttt | ggagtacgac | tccaactatg | agtgtgcttg gatcactttg | 120 |
| acgatacatt | cttcgttgga | ggctgtgggt | ctgacagctg | cgttttcggc gcggttggcc | 180 |
| gacaacaata | tcagctgcaa | cgtcattgct | ggctttcatc | atgatcacat ttttgtcggc | 240 |
| aaaggcgacg | cccagagagc | cattgacgtt | ctttctaatt | tggaccgata gccgtatagt | 300 |
| ccagtctatc | tataagttca | actaactcgt | aactattacc | ataacatata cttcactgcc | 360 |
| ccagataagg | ttccgataaa | aagttctgca | gactaaattt | atttcagtct cctcttcacc | 420 |
| accaaaatgc | cctcctacga | agctcgagct | aacgtccaca | agtccgcctt tgccgctcga | 480 |
| gtgctcaagc | tcgtggcagc | caagaaaacc | aacctgtgtg | cttctctgga tgttaccacc | 540 |
| accaaggagc | tcattgagct | tgccgataag | gtcggacctt | atgtgtgcat gatcaaaacc | 600 |
| catatcgaca | tcattgacga | cttcacctac | gccggcactg | tgctcccct caaggaactt | 660 |
| gctcttaagc | acggtttctt | cctgttcgag | gacagaaagt | tcgcagatat tggcaacact | 720 |
| gtcaagcacc | agtaccggtg | tcaccgaatc | gccgagtggt | ccgatatcac caacgcccac | 780 |
| ggtgtacccg | gaaccggaat | cattgctggc | ctgcgagctg | gtgccgagga aactgtctct | 840 |
| gaacagaaga | aggaggacgt | ctctgactac | gagaactccc | agtacaagga gttcctagtc | 900 |
| ccctctccca | acgagaagct | ggccagaggt | ctgctcatgc | tggccgagct gtcttgcaag | 960 |
| ggctctctgg | ccactggcga | gtactccaag | cagaccattg | agcttgcccg atccgacccc | 1020 |
| gagtttgtgg | ttggcttcat | tgcccagaac | cgacctaagg | gcgactctga ggactggctt | 1080 |
| attctgaccc | ccggggtggg | tcttgacgac | aagggagacg | ctctcggaca gcagtaccga | 1140 |
| actgttgagg | atgtcatgtc | taccggaacg | gatatcataa | ttgtcggccg aggtctgtac | 1200 |
| ggccagaacc | gagatcctat | tgaggaggcc | aagcgatacc | agaaggctgg ctgggaggct | 1260 |
| taccagaaga | ttaactgtta | gaggttagac | tatggatatg | taatttaact gtgtatatag | 1320 |
| agagcgtgca | agtatggagc | gcttgttcag | cttgtatgat | ggtcagacga cctgtctgat | 1380 |
| cgagtatgta | tgatactgca | caacctgtgt | atccgcatga | tctgtccaat ggggcatgtt | 1440 |
| gttgtgtttc | tcgatacgga | gatgctgggt | acagtgctaa | tacgttgaac tacttatact | 1500 |
| tatatgaggc | tcgaagaaag | ctgacttgtg | tatgacttat | tctcaactac atccccagtc | 1560 |
| acaataccac | cactgcacta | ccactacacc | aaaaccatga | tcaaaccacc catggacttc | 1620 |
| ctggaggcag | aagaacttgt | tatggaaaag | ctcaagagag | agatcataac ttcgtatagc | 1680 |
| atacattata | cgaagttatc | ctgcaggtaa | aggaattcag | gagagaccgg ttggcggcg | 1740 |
| tatttgtgtc | ccaaaaaaca | gccccaattg | ccccaattga | ccccaaattg acccagtagc | 1800 |
| gggcccaacc | ccggcgagag | ccccccttcac | cccacatatc | aaacctcccc cggttcccac | 1860 |
| acttgccgtt | aagggcgtag | ggtactgcag | tctggaatct | acgcttgttc agactttgta | 1920 |
| ctagtttctt | tgtctggcca | tccgggtaac | ccatgccgga | cgcaaaatag actactgaaa | 1980 |
| atttttttgc | tttgtggttg | ggactttagc | caagggtata | aaagaccacc gtccccgaat | 2040 |
| taccttttcct | cttcttttct | ctctctcctt | gtcaactcac | acccgaaatc gttaagcatt | 2100 |

```
tccttctgag tataagaatc attcaccatg gacttcctgg aggcagaaga acttgttatg    2160
gaaaagctca agagagagaa gccaagatac tatcaagaca tgtgtcgcaa cttaattaag    2220
atgacgacat ttgcgagctg gacgaggaat agatggagcg tgtgttctga gtcgatgttt    2280
tctatggagt tgtgagtgtt agtagacatg atgggtttat atatgatgaa tgaatagatg    2340
tgattttgat ttgcacgatg gaattgagaa ctttgtaaac gtacatggga atgtatgaat    2400
gtggggttt tgtgactgga taactgacgg tcagtgacg ccgttgttca aatatccaag      2460
agatgcgaga aactttgggt caagtgaaca tgtcctctct gttcaagtaa accatcaact    2520
atgggtagta tatttagtaa ggacaagagt tgagattctt tggagtccta gaaacgtatt    2580
ttcgcgttcc aagatcaaat tagtagagta atacgggcac gggaatccat tcatagtctc    2640
aattttccca taggtgtgct acaaggtgtt gagatgtggt acagtaccac catgattcga    2700
ggtaaagagc ccagaagtca ttgatgaggt caagaaatac acagatctac agctcaatac    2760
aatgaatatc ttcttttcata ttcttcaggt gacaccaagg gtgtctattt tccccagaaa    2820
tgcgtgaaaa ggcgcgtgtg tagcgtggag tatgggttcg gttggcgtat ccttcatata    2880
tcgacgaaat agtagggcaa gagatgacaa aaagtatcta tatgtagaca gcgtagaata    2940
tggatttgat tggtataaat tcatttattg cgtgtctcac aaatactctc gataagttgg    3000
ggttaaactg gagatggaac aatgtcgata tctcgacgca tgcgacgtcg ggcccaattc    3060
gccctatagt gagtcgtatt acaattcact ggccgtcgtt ttacaacgtc gtgactggga    3120
aaaccctggc gttacccaac ttaatcgcct tgcagcacat ccccctttcg ccagctggcg    3180
taatagcgaa gaggcccgca ccgatcgccc ttcccaacag ttgcgcagcc tgaatggcga    3240
atggacgcgc cctgtagcgg cgcattaagc gcggcgggtg tggtggttac gcgcagcgtg    3300
accgctacac ttgccagcgc cctagcgccc gctcctttcg ctttcttccc ttcctttctc    3360
gccacgttcg ccggctttcc ccgtcaagct ctaaatcggg ggctcccttt agggttccga    3420
tttagtgctt tacggcacct cgaccccaaa aaacttgatt agggtgatgg ttcacgtagt    3480
gggccatcgc cctgatagac ggttttcgc cctttgacgt tggagtccac gttctttaat     3540
agtggactct tgttccaaac tggaacaaca ctcaaccta tctcggtcta ttcttttgat     3600
ttataaggga ttttgccgat ttcggcctat tggttaaaaa atgagctgat ttaacaaaaa    3660
tttaacgcga attttaacaa atattaacg cttacaattt cctgatgcgg tattttctcc     3720
ttacgcatct gtgcggtatt tcacaccgca tcaggtggca cttttcgggg aaatgtgcgc    3780
ggaacccta tttgtttatt tttctaaata cattcaaata tgtatccgct catgagacaa     3840
taaccctgat aaatgcttca ataatattga aaaggaaga gtatgagtat tcaacatttc    3900
cgtgtcgccc ttattccctt ttttgcggca ttttgccttc ctgttttgc tcacccagaa     3960
acgctggtga agtaaaaga tgctgaagat cagttgggtg cacgagtggg ttacatcgaa    4020
ctggatctca acagcggtaa gatccttgag agttttcgcc ccgaagaacg ttttccaatg    4080
atgagcactt ttaaagttct gctatgtggc gcggtattat cccgtattga cgccgggcaa    4140
gagcaactcg gtcgccgcat acactattct cagaatgact tggttgagta ctcaccagtc    4200
acagaaaagc atcttacgga tggcatgaca gtaagagaat tatgcagtgc tgccataacc    4260
atgagtgata acactgcggc caacttactt ctgacaacga tcggaggacc gaaggagcta    4320
accgcttttt tgcacaacat gggggatcat gtaactcgcc ttgatcgttg ggaaccggag    4380
ctgaatgaag ccataccaaa cgacgagcgt gacaccacga tgcctgtagc aatggcaaca    4440
acgttgcgca aactattaac tggcgaacta cttactctag cttcccggca acaattaata    4500
```

```
gactggatgg aggcggataa agttgcagga ccacttctgc gctcggccct tccggctggc    4560
tggtttattg ctgataaatc tggagccggt gagcgtgggt ctcgcggtat cattgcagca    4620
ctggggccag atggtaagcc ctcccgtatc gtagttatct acacgacggg gagtcaggca    4680
actatggatg aacgaaatag acagatcgct gagataggtg cctcactgat taagcattgg    4740
taactgtcag accaagttta ctcatatata ctttagattg atttaaaact tcattttttaa    4800 tttaaaagga tctaggtgaa gatccttttt gataatctca tgaccaaaat cccttaacgt    4860
gagttttcgt tccactgagc gtcagacccc gtagaaaaga tcaaaggatc ttcttgagat    4920 ccttttttc tgcgcgtaat ctgctgcttg caaacaaaaa aaccaccgct accagcggtg    4980
gtttgtttgc cggatcaaga gctaccaact cttttccga aggtaactgg cttcagcaga    5040
gcgcagatac caaatactgt tcttctagtg tagccgtagt taggccacca cttcaagaac    5100
tctgtagcac cgcctacata cctcgctctg ctaatcctgt taccagtggc tgctgccagt    5160
ggcgataagt cgtgtcttac cgggttggac tcaagacgat agttaccgga taaggcgcag    5220
cggtcgggct gaacggggggg ttcgtgcaca cagcccagct tggagcgaac gacctacacc    5280
gaactgagat acctacagcg tgagctatga gaaagcgcca cgcttcccga agggagaaag    5340
gcggacaggt atccggtaag cggcagggtc ggaacaggag agcgcacgag ggagcttcca    5400
gggggaaacg cctggtatct ttatagtcct gtcgggtttc gccacctctg acttgagcgt    5460
cgatttttgt gatgctcgtc aggggggcgg agcctatgga aaaacgccag caacgcggcc    5520
tttttacggt tcctggcctt ttgctggcct tttgctcaca tgttctttcc tgcgttatcc    5580
cctgattctg tggataaccg tattaccgcc tttgagtgag ctgataccgc tcgccgcagc    5640
cgaacgaccg agcgcagcga gtcagtgagc gaggaagcgg aagagcgccc aatacgcaaa    5700
ccgcctctcc ccgcgcgttg gccgattcat taatgcagct ggcgcgccac caatcacaat    5760
tctgaaaagc acatcttgat ctcctcattg cggggagtcc aacggtggtc ttattcccc    5820 gaatttcccg ctcaatctcg ttccagaccg acccggacac agtgcttaac gccgttccga    5880
aactctaccg cagatatgct ccaacggact gggctgcata gatgtgatcc tcggcttgga    5940
gaaatggata aaagccggcc aaaaaaaaag cggaaaaaag cggaaaaaaa gagaaaaaaa    6000
atcgcaaaat ttgaaaaata gggggaaaag acgcaaaaac gcaaggaggg gggagtatat    6060
gacactgata agcaagctca caacggttcc tcttattttt ttcctcatct tctgcctagg    6120
ttcccaaaat cccagatgct tctctccagt gccaaaagta agtacccac aggttttcgg    6180 ccgaaaattc cacgtgcagc aacgtcgtgt ggggtgttaa aatgtggggg ggggaacca    6240 ggacaagagg ctcttgtggg agccgaatga gagcacaaag cgggcgggtg tgataagggc    6300 attttttgccc attttccctt ctcctgtctc tccgacggtg atggcgttgt gcgtcctcta    6360 tttctttttta tttctttttg ttttatttct ctgactaccg atttggtttg atttcctcaa    6420
ccccacacaa ataagctcgg gccgaggaat atatatatac acgacacag tcgccctgtg    6480 gacaacacgt cactacctct acgatacaca ccgtacgata gttagtagac aacaatcgat    6540
agttggagca agggagaaat gtagagtgtg aaagactcac tatggtccgg gcttatctcg    6600
accaatagcc aaagtctgga gtttctgaga gaaaaaggca agatacgtat gtaacaaagc    6660
gacgcatggt acaataatac cggaggcatg tatcatagag agttagtggt tcgatgatgg    6720
cactggtgcc tggtatgact ttatacggct gactacatat ttgtcctcag acatacaatt    6780
acagtcaagc acttacccctt ggacatctgt aggtacccc cggccaagac gatctcagcg    6840
```

```
tgtcgtatgt cggattggcg tagctccctc gctcgtcaat tggctcccat ctactttctt   6900
ctgcttggct acaccagca tgtctgctat ggctcgtttt cgtgccttat ctatcctccc    6960
agtattacca actctaaatg acatgatgtg attgggtcta cactttcata tcagagataa   7020
ggagtagcac agttgcataa aaagcccaac tctaatcagc ttcttccttt cttgtaatta   7080
gtacaaaggt gattagcgaa atctggaagc ttagttggcc ctaaaaaaat caaaaaaagc   7140
aaaaaacgaa aaacgaaaaa ccacagtttt gagaacaggg aggtaacgaa ggatcgtata   7200
tatatatata tatatatata cccacggatc ccgagaccgg cctttgattc ttccctacaa   7260
ccaaccattc tcaccaccct aattcacaac catgtctatt ggttcgtcca accccgtgct   7320
cttggctgcg attcccttcg tctacctgtt tgtcctccca cgagtcctgg ctttcctgcc   7380
tcagaaggct cagttcctgg ccaaatgtat tgtggtcctg attgccacgc ttatcatgtc   7440
cgttgcaggc tgcttcatct cgatcgtgtg cgctcttctg acaagagat acgtcatcaa    7500 ttacgttgtg tcgcgattgt tctccttcct tgccgctcga ccgtgtggtg tgacctataa   7560
gattgttggt gaggaacacc tcgataagta ccctgctatc gtggtctgta accatcaatc   7620
ctctatggat atgatggttt tgggacgagt ttttccaaag cactgcgttg tcatggcgaa   7680
gaaggaactc ctgtactttc ccttttttggg aatgtttatg aaactgagca acgctatctt  7740
catcgaccgg aagaaccaca agaaagccat cgagtctacc acccaagccg tggcggacat   7800
gaagaagcac aactctggaa tctggatttt cccagagggc acccggtcta actggacaa    7860 ggcagacctg ctgcccttca agaaaggtgc ctttcatctt gcaattcagg cccagctccc   7920
tattctcccc attatctcgc agggctattc ccatatctac gactcttcga gcggtactt    7980 ccccggtgga gagctcgaga tcagagtcct ggagcccatt cctacaactg gcctcactac   8040
tgatgatgtg aacgacctga tggacaagac acgaaacctt atgctcaagc acttgaagga   8100
gatggattcc cagtattcgt cgagcactgc tgaaaatgga tccacgcaca tcgacgccga   8160
tattgccaag tctacagcca ccagcattgg caacactgac gacgcaatta caaaacgtcg   8220
tacccctaag gaataagcgg ccgcatgaga agataaatat ataaatacat tgagatatta   8280
aatgcgctag attagagagc ctcatactgc tcggagagaa gccaagacga gtactcaaag   8340
gggattacac catccatatc cacagacaca agctggggaa aggttctata tacactttcc   8400
ggaataccgt agtttccgat gttatcaatg ggggcagcca ggatttcagg cacttcggtg   8460
tctcggggtg aaatggcgtt cttggcctcc atcaagtcgt accatgtctt catttgcctg   8520
tcaaagtaaa acagaagcag atgaagaatg aacttgaagt gaaggaattt aaatgtaacg   8580
aaactgaaat ttgaccagat attgtgtccg cggtggagct ccagcttttg ttcccttag    8640 tgagggttaa tttcgagctt ggcgtaatca tggtcatagc tgtttcctgt gtgaaattgt   8700
tatccgctca caagcttcca cacaac                                       8726
```

<210> SEQ ID NO 85
<211> LENGTH: 31
<212> TYPE: DNA
<213> ORGANISM: Artificial Sequence
<220> FEATURE:
<223> OTHER INFORMATION: Primer 856

<400> SEQUENCE: 85
tcacaacaca tgtccgttgc atccaagctc g                                   31

<210> SEQ ID NO 86
<211> LENGTH: 28

```
<212> TYPE: DNA
<213> ORGANISM: Artificial Sequence
<220> FEATURE:
<223> OTHER INFORMATION: Primer 857

<400> SEQUENCE: 86
tttagcggcc gcctactgag tcttctgg                                          28

<210> SEQ ID NO 87
<211> LENGTH: 8630
<212> TYPE: DNA
<213> ORGANISM: Artificial Sequence
<220> FEATURE:
<223> OTHER INFORMATION: Plasmid pY207

<400> SEQUENCE: 87
gtacgataac ttcgtatagc atacattata cgaagttatc gcgtcgacga gtatctgtct     60
gactcgtcat tgccgccttt ggagtacgac tccaactatg agtgtgcttg atcactttg    120
acgatacatt cttcgttgga ggctgtgggt ctgacagctg cgttttcggc gcggttggcc    180
gacaacaata tcagctgcaa cgtcattgct ggctttcatc atgatcacat ttttgtcggc    240
aaaggcgacg cccagagagc cattgacgtt ctttctaatt tggaccgata gccgtatagt    300
ccagtctatc tataagttca actaactcgt aactattacc ataacatata cttcactgcc    360
ccagataagg ttccgataaa aagttctgca gactaaattt atttcagtct cctcttcacc    420
accaaaatgc cctcctacga agctcgagct aacgtccaca gtccgccttt gccgctcga    480
gtgctcaagc tcgtggcagc caagaaaacc aacctgtgtg cttctctgga tgttaccacc    540
accaaggagc tcattgagct tgccgataag gtcggacctt atgtgtgcat gatcaaaacc    600
catatcgaca tcattgacga cttcacctac gccggcactg tgctccccct caaggaactt    660
gctcttaagc acggtttctt cctgttcgag acagaaagt tcgcagatat tggcaacact    720
gtcaagcacc agtaccggtg tcaccgaatc gccgagtggt ccgatatcac caacgcccac    780
ggtgtacccg gaaccggaat cattgctggc ctgcgagctg gtgccgagga aactgtctct    840
gaacagaaga aggaggacgt ctctgactac gagaactccc agtacaagga gttcctagtc    900
ccctctccca acgagaagct ggccagaggt ctgctcatgc tggccgagct gtcttgcaag    960
ggctctctgg ccactggcga gtactccaag cagaccattg agcttgcccg atccgacccc   1020
gagtttgtgg ttggcttcat tgcccagaac cgacctaagg gcgactctga ggactggctt   1080
attctgaccc ccggggtggg tcttgacgac aagggagacg ctctcggaca gcagtaccga   1140
actgttgagg atgtcatgtc taccggaacg gatatcataa ttgtcggccg aggtctgtac   1200
ggccagaacc gagatcctat tgaggaggcc aagcgatacc agaaggctgg ctgggaggct   1260
taccagaaga ttaactgtta gaggttagac tatggatatg taatttaact gtgtatatag   1320
agagcgtgca agtatggagc gcttgttcag cttgtatgat ggtcagacga cctgtctgat   1380
cgagtatgta tgatactgca caacctgtgt atccgcatga tctgtccaat ggggcatgtt   1440
gttgtgtttc tcgatacgga gatgctgggt acagtgctaa tacgttgaac tacttatact   1500
tatatgaggc tcgaagaaag ctgacttgtg tatgacttat tctcaactac atccccagtc   1560
acaataccac cactgcacta ccactacacc aaaaccatga tcaaaccacc catgggcttc   1620
ctggaggcag aagaacttgt tatggaaaag ctcaagagag agatcataac ttcgtatagc   1680
atacattata cgaagttatc ctgcaggtaa aggaattcag gagagaccgg gttggcggcg   1740
tatttgtgtc ccaaaaaaca gccccaattg ccccaattga ccccaaattg acccagtagc   1800
```

```
gggcccaacc ccggcgagag ccccctteac cccacatatc aaacctcccc cggttcccac    1860
acttgccgtt aagggcgtag ggtactgcag tctggaatct acgcttgttc agactttgta    1920
ctagtttctt tgtctggcca tccgggtaac ccatgccgga cgcaaaatag actactgaaa    1980
attttttgc tttgtggttg ggactttagc caagggtata aaagaccacc gtccccgaat     2040
tacctttcct cttcttttct ctctctcctt gtcaactcac acccgaaatc gttaagcatt    2100
tccttctgag tataagaatc attcaccatg gacttcctgg aggcagaaga acttgttatg    2160
gaaaagctca agagagagaa gccaagatac tatcaagaca tgtgtcgcaa cttaattaag    2220
atgacgacat tgcgagctg gacgaggaat agatggagcg tgtgttctga gtcgatgttt     2280
tctatggagt tgtgagtgtt agtagacatg atgggtttat atatgatgaa tgaatagatg    2340
tgattttgat ttgcacgatg gaattgagaa cttttgtaaac gtacatggga atgtatgaat   2400
gtggggttt tgtgactgga taactgacgg tcagtggacg ccgttgttca aatatccaag     2460
agatgcgaga actttgggt caagtgaaca tgtcctctct gttcaagtaa accatcaact     2520
atgggtagta tatttagtaa ggacaagagt tgagattctt tggagtccta gaaacgtatt    2580
ttcgcgttcc aagatcaaat tagtagagta atacgggcac gggaatccat tcatagtctc    2640
aattttccca taggtgtgct acaaggtgtt gagatgtggt acagtaccac catgattcga    2700
ggtaaagagc ccagaagtca ttgatgaggt caagaaatac acagatctac agctcaatac    2760
aatgaatatc ttctttcata ttcttcaggt gacaccaagg gtgtctattt tccccagaaa    2820
tgcgtgaaaa ggcgcgtgtg tagcgtggag tatgggttcg gttggcgtat ccttcatata    2880
tcgacgaaat agtagggcaa gagatgacaa aaagtatcta tatgtagaca gcgtagaata    2940
tggatttgat tggtataaat tcatttattg cgtgtctcac aaatactctc gataagttgg    3000
ggttaaactg gagatggaac aatgtcgata tctcgacgca tgcgacgtcg ggcccaattc    3060
gccctatagt gagtcgtatt acaattcact ggccgtcgtt ttacaacgtc gtgactggga   3120
aaacctggc gttacccaac ttaatcgcct tgcagcacat ccccctttcg ccagctggcg    3180
taatagcgaa gaggcccgca ccgatcgccc ttcccaacag ttgcgcagcc tgaatggcga    3240
atggacgcgc cctgtagcgg cgcattaagc gcggcgggtg tggtggttac gcgcagcgtg    3300
accgctacac ttgccagcgc cctagcgccc gctcctttcg ctttcttccc ttcctttctc    3360
gccacgttcg ccggctttcc ccgtcaagct ctaaatcggg ggctcccttt agggttccga    3420
tttagtgctt tacggcacct cgaccccaaa aaacttgatt agggtgatgg ttcacgtagt    3480
gggccatcgc cctgatagac ggttttttcgc cctttgacgt tggagtccac gttctttaat   3540
agtggactct tgttccaaac tggaacaaca ctcaacccta tctcggtcta ttctttgat    3600
ttataaggga ttttgccgat ttcggcctat tggttaaaaa atgagctgat ttaacaaaaa    3660
tttaacgcga attttaacaa atattaacg cttacaattt cctgatgcgg tattttctcc     3720
ttacgcatct gtgcggtatt tcacaccgca tcaggtggca cttttcgggg aaatgtgcgc    3780
ggaacccta tttgtttatt tttctaaata cattcaaata tgtatccgct catgagacaa     3840
taaccctgat aaatgcttca ataatattga aaaggaaga gtatgagtat tcaacatttc    3900
cgtgtcgccc ttattccctt ttttgcggca ttttgcttc ctgttttgc tcacccagaa      3960
acgctggtga agtaaaaga tgctgaagat cagttgggtg cacgagtggg ttacatcgaa     4020
ctggatctca acagcggtaa gatccttgag agttttcgcc ccgaagaacg ttttccaatg    4080
atgagcactt ttaaagttct gctatgtggc gcggtattat cccgtattga cgccgggcaa    4140
gagcaactcg gtcgccgcat acactattct cagaatgact tggttgagta ctcaccagtc    4200
```

```
acagaaaagc atcttacgga tggcatgaca gtaagagaat tatgcagtgc tgccataacc   4260
atgagtgata acactgcggc caacttactt ctgacaacga tcggaggacc gaaggagcta   4320
accgcttttt tgcacaacat gggggatcat gtaactcgcc ttgatcgttg ggaaccggag   4380
ctgaatgaag ccataccaaa cgacgagcgt gacaccacga tgcctgtagc aatggcaaca   4440
acgttgcgca aactattaac tggcgaacta cttactctag cttcccggca caattaata   4500 gactggatgg aggcggataa agttgcagga ccacttctgc gctcggccct tccggctggc   4560
tggtttattg ctgataaatc tggagccggt gagcgtgggt ctcgcggtat cattgcagca   4620
ctggggccag atggtaagcc ctcccgtatc gtagttatct acacgacggg gagtcaggca   4680
actatggatg aacgaaatag acagatcgct gagataggtg cctcactgat taagcattgg   4740
taactgtcag accaagttta ctcatatata ctttagattg atttaaaact tcattttaa   4800 tttaaaagga tctaggtgaa gatcctttt gataatctca tgaccaaaat cccttaacgt   4860
gagttttcgt tccactgagc gtcagacccc gtagaaaaga tcaaaggatc ttcttgagat   4920
cctttttttc tgcgcgtaat ctgctgcttg caaacaaaaa aaccaccgct accagcggtg   4980
gtttgtttgc cggatcaaga gctaccaact cttttttccga aggtaactgg cttcagcaga   5040
gcgcagatac caaatactgt tcttctagtg tagccgtagt taggccacca cttcaagaac   5100
tctgtagcac cgcctacata cctcgctctg ctaatcctgt taccagtggc tgctgccagt   5160
ggcgataagt cgtgtcttac cgggttggac tcaagacgat agttaccgga taaggcgcag   5220
cggtcgggct gaacgggggg ttcgtgcaca gcccagct tggagcgaac gacctacacc   5280
gaactgagat acctacagcg tgagctatga gaaagcgcca cgcttcccga agggagaaag   5340
gcggacaggt atccggtaag cggcagggtc ggaacaggag agcgcacgag ggagcttcca   5400
gggggaaacg cctggtatct ttatagtcct gtcgggtttc gccacctctg acttgagcgt   5460
cgatttttgt gatgctcgtc aggggggcgg agcctatgga aaaacgccag caacgcggcc   5520 ttttttacggt tcctggcctt ttgctggcct tttgctcaca tgttctttcc tgcgttatcc   5580
cctgattctg tggataaccg tattaccgcc tttgagtgag ctgataccgc tcgccgcagc   5640
cgaacgaccg agcgcagcga gtcagtgagc gaggaagcgg aagagcgccc aatacgcaaa   5700
ccgcctctcc ccgcgcgttg gccgattcat taatgcagct ggcgcgccac caatcacaat   5760
tctgaaaagc acatcttgat ctcctcattg cggggagtcc aacggtggtc ttattccccc   5820
gaatttcccg ctcaatctcg ttccagaccg acccggacac agtgcttaac gccgttccga   5880
aactctaccg cagatatgct ccaacggact gggctgcata gatgtgatcc tcggcttgga   5940
gaaatggata aaagccggcc aaaaaaaaag cggaaaaaag cggaaaaaaa gagaaaaaaa   6000
atcgcaaaat ttgaaaaata ggggaaaag acgcaaaaac gcaaggaggg gggagtatat   6060
gacactgata agcaagctca caacggttcc tcttattttt ttcctcatct tctgcctagg   6120
ttcccaaaat cccagatgct tctctccagt gccaaaagta agtacccac aggttttcgg   6180 ccgaaaattc cacgtgcagc aacgtcgtgt ggggtgttaa aatgtgggg ggggaacca   6240 ggacaagagg ctcttgtggg agccgaatga gagcacaaag cggcgggtg tgataagggc   6300 attttttgccc attttccctt ctcctgtctc tccgacggtg atggcgttgt gcgtcctcta   6360
tttcttttta tttcttttg ttttatttct ctgactaccg atttggtttg atttcctcaa   6420
ccccacacaa ataagctcgg gccgaggaat atatatatac acggacacag tcgccctgtg   6480
gacaacacgt cactacctct acgatacaca ccgtacgata gttagtagac aacaatcgat   6540
```

```
agttggagca agggagaaat gtagagtgtg aaagactcac tatggtccgg gcttatctcg    6600
accaatagcc aaagtctgga gtttctgaga gaaaaaggca agatacgtat gtaacaaagc    6660
gacgcatggt acaataatac cggaggcatg tatcatagag agttagtggt tcgatgatgg    6720
cactggtgcc tggtatgact ttatacggct gactacatat ttgtcctcag acatacaatt    6780
acagtcaagc acttacccct tggacatctgt aggtacccc cggccaagac gatctcagcg    6840
tgtcgtatgt cggattggcg tagctccctc gctcgtcaat ggctcccat ctactttctt    6900
ctgcttggct acacccagca tgtctgctat ggctcgtttt cgtgccttat ctatcctccc    6960
agtattacca actctaaatg acatgatgtg attgggtcta cactttcata tcagagataa    7020
ggagtagcac agttgcataa aaagcccaac tctaatcagc ttcttccttt cttgtaatta    7080
gtacaaaggt gattagcgaa atctggaagc ttagttggcc ctaaaaaaat caaaaaaagc    7140
aaaaaacgaa aaacgaaaaa ccacagtttt gagaacaggg aggtaacgaa ggatcgtata    7200
tatatatata tatatatata cccacggatc ccgagaccgg cctttgattc ttccctacaa    7260
ccaaccattc tcaccaccct aattcacaac catgtccgtt gcatccaagc tcgtcttcta    7320
cgtccgcgcc gccatcgccg tggtcatctt tgccgcctgt gccacctacg gcgtgctggc    7380
gtccaccatt ctcaccgcca tcggcaagca gggcctggcc caatgaccg ttgccagagc    7440
cttctactac tcggtgcgca tcttcctggg tatcagcatc aagctgcgta gccggcaggt    7500
gaccggaacc gccggtctgg atgcctccaa gatccaggtc gccaacacca ccaagcccat    7560
tgacgacatc accaaacacc tgccccgacc atgcattctg atttccaacc accagaacga    7620
aatggacatt ctggtgctcg gtcgcatctt cccccagtac tgctccgtca ccgccaaaaa    7680
ggccctcaag tggtaccctc tgctgggcca gttcatggcg ctgtccggca ccatcttcct    7740
ggaccgaaag gaccgaacca agtccgtgca gaccctcggc ggcgccgtca agaccatcca    7800
gagcggcaac ggaggcaagg gccagagcgt cttcatgttc cccgagggaa cccgatccta    7860
ctccaaggac gtcggcatca tgcccttcaa gaagggctgt ttccacctgg cggtccagtc    7920
gggcgctccc attgtccccg tggtggtcca gaacacctcc cgaatgtttt ctttcggccg    7980
aggcaagctg gacgccggag agatccttgt cgacgtcctg agccccattg agaccaaggg    8040
tctggacgcc agcaacgtcg acgctctcat ggccaccact tataaggcca tgtgcgagac    8100
tgccgaccag attggctacg ctggccagaa gactcagtag gcggccgcat gagaagataa    8160
atatataaat acattgagat attaaatgcg ctagattaga gagcctcata ctgctcggag    8220
agaagccaag acgagtactc aaaggggatt acaccatcca tatccacaga cacaagctgg    8280
ggaaaggttc tatatacact ttccggaata ccgtagtttc cgatgttatc aatgggggca    8340
gccaggattt caggcacttc ggtgtctcgg ggtgaaatgg cgttcttggc ctccatcaag    8400
tcgtaccatg tcttcatttg cctgtcaaag taaaacagaa gcagatgaag aatgaacttg    8460
aagtgaagga atttaaatgt aacgaaactg aaatttgacc agatattgtg tccgcggtgg    8520
agctccagct tttgttccct ttagtgaggg ttaatttcga gcttggcgta atcatggtca    8580
tagctgtttc ctgtgtgaaa ttgttatccg ctcacaagct tccacacaac                8630
```

<210> SEQ ID NO 88
<211> LENGTH: 8630
<212> TYPE: DNA
<213> ORGANISM: Artificial Sequence
<220> FEATURE:
<223> OTHER INFORMATION: Plasmid pY175

<400> SEQUENCE: 88

-continued

```
gtacgataac ttcgtatagc atacattata cgaagttatc gcgtcgacga gtatctgtct    60
gactcgtcat tgccgccttt ggagtacgac tccaactatg agtgtgcttg gatcactttg   120
acgatacatt cttcgttgga ggctgtgggt ctgacagctg cgttttcggc gcggttggcc   180
gacaacaata tcagctgcaa cgtcattgct ggctttcatc atgatcacat ttttgtcggc   240
aaaggcgacg cccagagagc cattgacgtt ctttctaatt tggaccgata gccgtatagt   300
ccagtctatc tataagttca actaactcgt aactattacc ataacatata cttcactgcc   360
ccagataagg ttccgataaa aagttctgca gactaaattt atttcagtct cctcttcacc   420
accaaaatgc cctcctacga agctcgagct aacgtccaca agtccgcctt tgccgctcga   480
gtgctcaagc tcgtggcagc caagaaaacc aacctgtgtg cttctctgga tgttaccacc   540
accaaggagc tcattgagct tgccgataag gtcggacctt atgtgtgcat gatcaaaacc   600
catatcgaca tcattgacga cttcacctac gccggcactg tgctccccct caaggaactt   660
gctcttaagc acggtttctt cctgttcgag gacagaaagt tcgcagatat tggcaacact   720
gtcaagcacc agtaccggtg tcaccgaatc gccgagtggt ccgatatcac caacgcccac   780
ggtgtacccg gaaccggaat cattgctggc ctgcgagctg gtgccgagga aactgtctct   840
gaacagaaga aggaggacgt ctctgactac gagaactccc agtacaagga gttcctagtc   900
ccctctccca acgagaagct ggccagaggt ctgctcatgc tggccgagct gtcttgcaag   960
ggctctctgg ccactggcga gtactccaag cagaccattg agcttgcccg atccgacccc  1020
gagtttgtgg ttggcttcat tgcccagaac cgacctaagg gcgactctga ggactggctt  1080
attctgaccc ccggggtggg tcttgacgac aagggagacg ctctcggaca gcagtaccga  1140
actgttgagg atgtcatgtc taccggaacg gatatcataa ttgtcggccg aggtctgtac  1200
ggccagaacc gagatcctat tgaggaggcc aagcgatacc agaaggctgg ctgggaggct  1260
taccagaaga ttaactgtta gaggttagac tatggatatg taatttaact gtgtatatag  1320
agagcgtgca agtatggagc gcttgttcag cttgtatgat ggtcagacga cctgtctgat  1380
cgagtatgta tgatactgca caacctgtgt atccgcatga tctgtccaat ggggcatgtt  1440
gttgtgtttc tcgatacgga gatgctgggt acagtgctaa tacgttgaac tacttatact  1500
tatatgaggc tcgaagaaag ctgacttgtg tatgacttat tctcaactac atccccagtc  1560
acaataccac cactgcacta ccactacacc aaaaccatga tcaaaccacc catggacttc  1620
ctggaggcag aagaacttgt tatggaaaag ctcaagagag agatcataac ttcgtatagc  1680
atacattata cgaagttatc ctgcaggtaa aggaattcag gagagaccgg gttggcggcg  1740
tatttgtgtc ccaaaaaaca gccccaattg ccccaattga ccccaaattg acccagtagc  1800
gggcccaacc ccgcgagag ccccttcac cccacatatc aaacctcccc cggttcccac  1860
acttgccgtt aagggcgtag ggtactgcag tctggaatct acgcttgttc agactttgta  1920
ctagtttctt tgtctggcca tccgggtaac ccatgccgga cgcaaaatag actactgaaa  1980
attttttgc tttgtggttg ggactttagc caagggtata aaagaccacc gtccccgaat  2040
tacctttcct cttctttctct ctctctcctt gtcaactcac acccgaaatc gttaagcatt  2100
tccttctgag tataagaatc attccaccatg gacttcctgg aggcagaaga acttgttatg  2160
gaaaagctca agagagagaa gccaagatac tatcaagaca tgtgtcgcaa cttaattaag  2220
atgacgacat ttgcgagctg gacgaggaat agatggagcg tgttctga gtcgatgttt  2280
tctatggagt tgtgagtgtt agtagacatg atgggtttat atatgatgaa tgaatagatg  2340
```

```
tgattttgat ttgcacgatg gaattgagaa ctttgtaaac gtacatggga atgtatgaat   2400
gtggggttt tgtgactgga taactgacgg tcagtggacg ccgttgttca aatatccaag    2460
agatgcgaga aactttgggt caagtgaaca tgtcctctct gttcaagtaa accatcaact   2520
atgggtagta tatttagtaa ggacaagagt tgagattctt tggagtccta gaaacgtatt   2580
ttcgcgttcc aagatcaaat tagtagagta atacgggcac gggaatccat tcatagtctc   2640
aattttccca taggtgtgct acaaggtgtt gagatgtggt acagtaccac catgattcga   2700
ggtaaagagc ccagaagtca ttgatgaggt caagaaatac acagatctac agctcaatac   2760
aatgaatatc ttcttcata ttcttcaggt gacaccaagg gtgtctattt tccccagaaa    2820
tgcgtgaaaa ggcgcgtgtg tagcgtggag tatgggttcg gttggcgtat ccttcatata   2880
tcgacgaaat agtagggcaa gagatgacaa aaagtatcta tatgtagaca gcgtagaata   2940
tggatttgat tggtataaat tcatttattg cgtgtctcac aaatactctc gataagttgg   3000
ggttaaactg gagatggaac aatgtcgata tctcgacgca tgcgacgtcg ggcccaattc   3060
gccctatagt gagtcgtatt acaattcact ggccgtcgtt ttacaacgtc gtgactggga   3120
aaaccctggc gttacccaac ttaatcgcct tgcagcacat ccccctttcg ccagctggcg   3180
taatagcgaa gaggcccgca ccgatcgccc ttcccaacag ttgcgcagcc tgaatggcga   3240
atggacgcgc cctgtagcgg cgcattaagc gcggcgggtg tggtggttac gcgcagcgtg   3300
accgctacac ttgccagcgc cctagcgccc gctccttttcg ctttcttccc ttcctttctc   3360
gccacgttcg ccggctttcc ccgtcaagct ctaaatcggg ggctcccttt agggttccga   3420
tttagtgctt tacggcacct cgaccccaaa aaacttgatt agggtgatgg ttcacgtagt   3480
gggccatcgc cctgatagac ggttttcgc cctttgacgt tggagtccac gttctttaat    3540
agtggactct tgttccaaac tggaacaaca ctcaaccta tctcggtcta ttcttttgat    3600
ttataaggga ttttgccgat tcggcctat tggttaaaaa atgagctgat ttaacaaaaa    3660
tttaacgcga attttaacaa atattaacg cttacaattt cctgatgcgg tattttctcc    3720
ttacgcatct gtgcggtatt tcacaccgca tcaggtggca cttttcgggg aaatgtgcgc   3780
ggaaccccta tttgttattt ttctaaata cattcaaata tgtatccgct catgagacaa    3840
taaccctgat aaatgcttca ataatattga aaaggaaga gtatgagtat tcaacatttc   3900
cgtgtcgccc ttattccctt ttttgcggca ttttgccttc ctgttttgc tcacccagaa    3960
acgctggtga agtaaaaga tgctgaagat cagttgggtg cacgagtggg ttacatcgaa   4020
ctggatctca acagcggtaa gatccttgag agttttcgcc ccgaagaacg ttttccaatg   4080
atgagcactt ttaaagttct gctatgtggc gcggtattat cccgtattga cgccgggcaa   4140
gagcaactcg gtcgccgcat acactattct cagaatgact tggttgagta ctcaccagtc   4200
acagaaaagc atcttacgga tggcatgaca gtaagagaat tatgcagtgc tgccataacc   4260
atgagtgata acactgcggc caacttactt ctgacaacga tcggaggacc gaaggagcta   4320
accgcttttt tgcacaacat ggggatcat gtaactcgcc ttgatcgttg ggaaccggag   4380
ctgaatgaag ccataccaaa cgacgagcgt gacaccacga tgcctgtagc aatggcaaca   4440
acgttgcgca aactattaac tggcgaacta cttactctag cttcccggca acaattaata   4500
gactggatgg aggcggataa agttgcagga ccacttctgc gctcggccct tccggctggc   4560
tggtttattg ctgataaatc tggagccggt gagcgtgggt ctcgcggtat cattgcagca   4620
ctggggccag atggtaagcc ctcccgtatc gtagttatct acacgacggg gagtcaggca   4680
actatggatg aacgaaatag acagatcgct gagataggtg cctcactgat taagcattgg   4740
```

```
taactgtcag accaagttta ctcatatata ctttagattg atttaaaact tcatttttaa    4800
tttaaaagga tctaggtgaa gatccttttt gataatctca tgaccaaaat cccttaacgt    4860
gagttttcgt tccactgagc gtcagacccc gtagaaaaga tcaaaggatc ttcttgagat    4920
ccttttttc tgcgcgtaat ctgctgcttg caaacaaaaa aaccaccgct accagcggtg    4980
gtttgtttgc cggatcaaga gctaccaact cttttccga aggtaactgg cttcagcaga    5040
gcgcagatac caaatactgt tcttctagtg tagccgtagt taggccacca cttcaagaac    5100
tctgtagcac cgcctacata cctcgctctg ctaatcctgt taccagtggc tgctgccagt    5160
ggcgataagt cgtgtcttac cgggttggac tcaagacgat agttaccgga taaggcgcag    5220
cggtcgggct gaacggggggg ttcgtgcaca cagcccagct tggagcgaac gacctacacc    5280
gaactgagat acctacagcg tgagctatga gaaagcgcca cgcttcccga agggagaaag    5340
gcggacaggt atccggtaag cggcagggtc ggaacaggag agcgcacgag ggagcttcca    5400
gggggaaacg cctggtatct ttatagtcct gtcgggtttc gccacctctg acttgagcgt    5460
cgattttgt gatgctcgtc aggggggcgg agcctatgga aaaacgccag caacgcggcc    5520
ttttacggt tcctggcctt ttgctggcct tttgctcaca tgttctttcc tgcgttatcc    5580
cctgattctg tggataaccg tattaccgcc tttgagtgag ctgataccgc tcgccgcagc    5640
cgaacgaccg agcgcagcga gtcagtgagc gaggaagcgg aagagcgccc aatacgcaaa    5700
ccgcctctcc ccgcgcgttg gccgattcat taatgcagct ggcgcgccac caatcacaat    5760
tctgaaaagc acatcttgat ctcctcattg cggggagtcc aacggtggtc ttattccccc    5820
gaatttcccg ctcaatctcg ttccagaccg acccggacac agtgcttaac gccgttccga    5880
aactctaccg cagatatgct ccaacggact gggctgcata gatgtgatcc tcggcttgga    5940
gaaatggata aaagccggcc aaaaaaaaag cggaaaaaag cggaaaaaaa gagaaaaaaa    6000
atcgcaaaat ttgaaaaata gggggaaaag acgcaaaaac gcaaggaggg gggagtatat    6060
gacactgata agcaagctca caacggttcc tcttattttt ttcctcatct tctgcctagg    6120
ttcccaaaat cccagatgct tctctccagt gccaaaagta agtacccac aggttttcgg    6180
ccgaaaattc cacgtgcagc aacgtcgtgt ggggtgttaa aatgtggggg ggggaacca    6240
ggacaagagg ctcttgtggg agccgaatga gagcacaaag cgggcgggtg tgataagggc    6300
attttttgccc attttcccctt ctcctgtctc tccgacggtg atggcgttgt gcgtcctcta    6360
tttcttttta tttcttttg ttttatttct ctgactaccg atttggtttg atttcctcaa    6420
ccccacacaa ataagctcgg gccgaggaat atatatatac acggacacag tcgccctgtg    6480
gacaacacgt cactacctct acgatacaca ccgtacgata gttagtagac aacaatcgat    6540
agttggagca agggagaaat gtagagtgtg aaagactcac tatggtccgg gcttatctcg    6600
accaatagcc aaagtctgga gtttctgaga gaaaaggca agatacgtat gtaacaaagc    6660
gacgcatggt acaataatac cggaggcatg tatcatagag agttagtggt tcgatgatgg    6720
cactggtgcc tggtatgact ttatacggct gactacatat ttgtcctcag acatacaatt    6780
acagtcaagc acttacccct tggacatctgt aggtacccc cggccaagac gatctcagcg    6840
tgtcgtatgt cggattggcg tagctccctc gctcgtcaat ggctcccat ctactttctt    6900
ctgcttggct acacccagca tgtctgctat ggctcgtttt cgtgccttat ctatcctccc    6960
agtattacca actctaaatg acatgatgtg attgggtcta cactttcata tcagagataa    7020
ggagtagcac agttgcataa aaagcccaac tctaatcagc ttcttccttt cttgtaatta    7080
```

-continued

```
gtacaaaggt gattagcgaa atctggaagc ttagttggcc ctaaaaaaat caaaaaaagc   7140
aaaaaacgaa aaacgaaaaa ccacagtttt gagaacaggg aggtaacgaa ggatcgtata   7200
tatatatata tatatatata cccacggatc ccgagaccgg cctttgattc ttccctacaa   7260
ccaaccattc tcaccaccct aattcacaac catgggagaac ttctggtcca tcgtcgtgtt   7320
ctttctgctc tccattctgt tcatcctcta caacatttcg acagtctgcc actactacat   7380
gcgaatctcc ttctactact ttaccatcct gcttcacggc atggaggtgt gcgttaccat   7440
gattccctct tggctcaacg gcaagggtgc cgactacgtg tttcactcgt tcttctactg   7500
gtgcaagtgg actggagtcc acaccactgt gtatggctac gagaagaccc aggtcgaagg   7560
tcctgccgtg gtcatctgca accatcagtc ctcgctcgac attctgtcta tggcttccat   7620
ctggcccaag aactgtgttg tcatgatgaa gcggattctt gcctacgttc ccttcttcaa   7680
cctgggagcc tacttttcca acaccatctt catcgaccga tacaaccgag agcgagctat   7740
ggcttctgtc gactactgtg cctccgagat gaagaaccga aacctgaagc tctgggtgtt   7800
tcccgaaggc actcggaatc gagagggtgg attcattccc ttcaagaaag gtgccttcaa   7860
catcgctgtt cgagcccaga ttcccatcat tcctgtcgtg ttctctgact atcgagactt   7920
ctactccaag cctggccgat acttcaagaa cgatggagag tcgtgatcc gagtcctgga   7980 tgccattccc accaagggtc tgaccctcga tgacgtctct gagctttcgg acatgtgtcg   8040
agacgtcatg ctggctgcct acaaggaagt taccctcgag gctcagcaac gaaacgccac   8100
tcgaagagga gagaccaagg acggcaagaa atccgagtaa gcggccgcat gagaagataa   8160
atatataaat acattgagat attaaatgcg ctagattaga gagcctcata ctgctcggag   8220
agaagccaag acgagtactc aaagggggat acaccatcca tatccacaga cacaagctgg   8280
ggaaaggttc tatatacact ttccggaata ccgtagtttc cgatgttatc aatgggggca   8340
gccaggattt caggcacttc ggtgtctcgg ggtgaaatgg cgttcttggc ctccatcaag   8400
tcgtaccatg tcttcatttg cctgtcaaag taaaacagaa gcagatgaag aatgaacttg   8460
aagtgaagga atttaaatgt aacgaaactg aaatttgacc agatattgtg tccgcggtgg   8520
agctccagct tttgttccct ttagtgaggg ttaatttcga gcttggcgta atcatggtca   8580
tagctgtttc ctgtgtgaaa ttgttatccg ctcacaagct tccacacaac                8630
```

<210> SEQ ID NO 89
<211> LENGTH: 8237
<212> TYPE: DNA
<213> ORGANISM: Artificial Sequence
<220> FEATURE:
<223> OTHER INFORMATION: Plasmid pY153

<400> SEQUENCE: 89

```
cgataccatg gtcgggcaat gagaacggca gcaactgcaa tcacagcgac atatatccaa     60
ctgttcatgt ttggttttcg gatagtcaca caccttaatt ttgatgcacg ctttatggag   120
tctctctctc ttttctctc tctcttgtcg tcgctctttc ttgttttttca accacccact   180 tgattcctgc aaacaaacta cccacactaa tttttttcg ctgcataccc tcaaatgagc   240
ctaattggcg tgtgtctccg cacaaaaaca caccatgcac ggctgggctt gttgggaaac   300
tttgtcaggg gggtccaggg ggccattggc agacttggcc acgtgtgctc atctcggctt   360
cgtcgttatt acgtgtctgt gtaatcaaag tcgggcgttt tttgcgccat gtgtccgcat   420
gaaattggcc cctcttgaag tcccttgtgc acctacacgt gccgaaatga aggttggagt   480
cagcggggtc atgccgtggt attatgctgt ggcatgtggc attaagctgt ggcatcaagc   540
```

| | |
|---|---|
| cgtggaatca agccgtggtt cacgcccttg attgcgcagg cacatggcgc cattcttgcc | 600 |
| tctgctgtaa gcccggcttt gtgtgattca gagacgctgc taccgcacaa ctgcccatac | 660 |
| tccttctcct actgtataca tccacccctc atgctgataa cattatcatc tcatctcaac | 720 |
| tcaacatttc caccaacttg ggatcaaaaa cacgttctaa tactgtacac tgtctacgat | 780 |
| ataattaccg tacagtgtgg ttataatgaa catctattag agagaattgt tgttgctcg | 840 |
| tatcagtcat tgggaagcgg gataccatgt cattttcacc tatatcaacc atgaaactac | 900 |
| agtatgtaca gtagaagtat atactgtact gttttgtaac tatatgtaca gtagaagtat | 960 |
| atactatact gttattaact atacttgtga ctagtgttcc aaactacaag tatatactgt | 1020 |
| acttgtacac gactatccga ccagtatcca gtatacaata accaactact ctacgtacgt | 1080 |
| actaaactaa acaaatagat caatgctcaa tgtcgagctc cagcttttgt tccctttagt | 1140 |
| gagggttaat ttcgagcttg gcgtaatcat ggtcatagct gtttcctgtg tgaaattgtt | 1200 |
| atccgctcac aattccacac aacatacgag ccggaagcat aaagtgtaaa gcctggggtg | 1260 |
| cctaatgagt gagctaactc acattaattg cgttgcgctc actgcccgct ttccagtcgg | 1320 |
| gaaacctgtc gtgccagctg cattaatgaa tcggccaacg cgcggggaga ggcggtttgc | 1380 |
| gtattgggcg ctcttccgct tcctcgctca ctgactcgct gcgctcggtc gttcggctgc | 1440 |
| ggcgagcggt atcagctcac tcaaaggcgg taatacggtt atccacagaa tcaggggata | 1500 |
| acgcaggaaa gaacatgtga gcaaaaggcc agcaaaaggc caggaaccgt aaaaaggccg | 1560 |
| cgttgctggc gtttttccat aggctccgcc cccctgacga gcatcacaaa aatcgacgct | 1620 |
| caagtcagag gtggcgaaac ccgacaggac tataaagata ccaggcgttt ccccctggaa | 1680 |
| gctccctcgt gcgctctcct gttccgaccc tgccgcttac cggatacctg tccgcctttc | 1740 |
| tcccttcggg aagcgtggcg ctttctcata gctcacgctg taggtatctc agttcggtgt | 1800 |
| aggtcgttcg ctccaagctg ggctgtgtgc acgaaccccc cgttcagccc gaccgctgcg | 1860 |
| ccttatccgg taactatcgt cttgagtcca acccggtaag acacgactta tcgccactgg | 1920 |
| cagcagccac tggtaacagg attagcagag cgaggtatgt aggcggtgct acagagttct | 1980 |
| tgaagtggtg gcctaactac ggctacacta aaggacagt atttggtatc tgcgctctgc | 2040 |
| tgaagccagt taccttcgga aaagagttg gtagctcttg atccggcaaa caaaccaccg | 2100 |
| ctggtagcgg tggtttttt gtttgcaagc agcagattac gcgcagaaaa aaaggatctc | 2160 |
| aagaagatcc tttgatcttt tctacggggt ctgacgctca gtggaacgaa aactcacgtt | 2220 |
| aagggatttt ggtcatgaga ttatcaaaaa ggatcttcac ctagatcctt ttaaattaaa | 2280 |
| aatgaagttt taaatcaatc taaagtatat atgagtaaac ttggtctgac agttaccaat | 2340 |
| gcttaatcag tgaggcacct atctcagcga tctgtctatt tcgttcatcc atagttgcct | 2400 |
| gactccccgt cgtgtagata actacgatac gggagggctt accatctggc cccagtgctg | 2460 |
| caatgatacc gcgagaccca cgctcaccgg ctccagattt atcagcaata aaccagccag | 2520 |
| ccggaagggc cgagcgcaga agtggtcctg caactttatc cgcctccatc cagtctatta | 2580 |
| attgttgccg ggaagctaga gtaagtagtt cgccagttaa tagtttgcgc aacgttgttg | 2640 |
| ccattgctac aggcatcgtg gtgtcacgct cgtcgtttgg tatggcttca ttcagctccg | 2700 |
| gttcccaacg atcaaggcga gttacatgat cccccatgtt gtgcaaaaaa gcggttagct | 2760 |
| ccttcggtcc tccgatcgtt gtcagaagta agttggccgc agtgttatca ctcatggtta | 2820 |
| tggcagcact gcataattct cttactgtca tgccatccgt aagatgcttt tctgtgactg | 2880 |

```
gtgagtactc aaccaagtca ttctgagaat agtgtatgcg gcgaccgagt tgctcttgcc    2940
cggcgtcaat acgggataat accgcgccac atagcagaac tttaaaagtg ctcatcattg    3000
gaaaacgttc ttcggggcga aaactctcaa ggatcttacc gctgttgaga tccagttcga    3060
tgtaacccac tcgtgcaccc aactgatctt cagcatcttt tactttcacc agcgtttctg    3120
ggtgagcaaa aacaggaagg caaaatgccg caaaaaggg aataagggcg acacggaaat    3180
gttgaatact catactcttc ctttttcaat attattgaag catttatcag gttattgtc    3240 tcatgagcgg atacatattt gaatgtattt agaaaaataa acaaataggg gttccgcgca    3300
catttccccg aaaagtgcca cctgacgcgc cctgtagcgg cgcattaagc gcggcgggtg    3360
tggtggttac gcgcagcgtg accgctacac ttgccagcgc cctagcgccc gctcctttcg    3420
ctttcttccc ttcctttctc gccacgttcg ccggctttcc ccgtcaagct ctaaatcggg    3480
ggctcccttt agggttccga tttagtgctt tacggcacct cgaccccaaa aaacttgatt    3540
agggtgatgg ttcacgtagt gggccatcgc cctgatagac ggtttttcgc cctttgacgt    3600
tggagtccac gttctttaat agtggactct tgttccaaac tggaacaaca ctcaaccta    3660 tctcggtcta ttcttttgat ttataaggga ttttgccgat ttcggcctat tggttaaaaa    3720
atgagctgat ttaacaaaaa tttaacgcga attttaacaa atattaacg cttacaattt    3780 ccattcgcca ttcaggctgc gcaactgttg gaagggcga tcggtgcggg cctcttcgct    3840
attacgccag ctggcgaaag ggggatgtgc tgcaaggcga ttaagttggg taacgccagg    3900
gttttcccag tcacgacgtt gtaaaacgac ggccagtgaa ttgtaatacg actcactata    3960
gggcgaattg ggtaccgggc cccccctcga gtctagagca gggtgttgga ggggatggag    4020
aggttgagta aagcggaagt tgcggttgc tggtcgcgtt ttaatcttct tttgtaattt    4080
aatctcggta tgccgacgtg tttcggcgag ttaattttag ctgtcaaaaa aatggatcac    4140
caggatagac aaagaagaga gtgggacaag gatctttcca gccgctaata tcggccagtt    4200
taagagcaat tcacggtccc tggagtccat ataacaacgc caatctcgca cttgtctgct    4260
ccctcgtcac ccgtccaact gtccaatcca atctatgcct ctcatgatca tcttcacact    4320
acagtagagt aggtaaaggt agacttatgg gctcctcgaa taattggact ctgtctaaac    4380
cttgtgaagt tacctcggtc ggtagagttc ggctggaagg ccatgattac taacaacatc    4440
gtacagagag aaatcaagat gagtaataca atctcgatga gtaatacaat ctcgatgagt    4500
aatacaatct cgatgagtaa gactaggtgg tgtcacgact tttagaggaa tgagcagctt    4560
tcagggttat tatagagaca cgtccgcgga cgaagtagct ggtacatcga gcataagcat    4620
ggtacaagta ggagtagact aaaaaccaac agtttgaata gtccatgaca gtacgggcgg    4680
gtacgactga tctaagagaa ctggggtata cacgatatag cacagtacag agaaagtggg    4740
ctcgttttgc gttggtaatc gaggtagatt tcgttgctat attaatccat tcacccatag    4800
ctccacagcc aatggttcgc cgtgggtgtc gatctgaaaa atgtttcata ttacctatct    4860
ctctcctaaa gtagctacaa gcacttcttg tgctgcagtc tgcggccgct tactcggatt    4920
tcttgccgtc cttggtctct cctcttcgag tggcgtttcg ttgctgagcc tcgagggtaa    4980
cttccttgta ggcagccagc atgacgtctc gacacatgtc cgaaagctca gagcgtcat    5040 cgagggtcag acccttggtg ggaatggcat ccaggactcg gatcacgacc tctccatcgt    5100
tcttgaagta tcggccaggc ttggagtaga agtctcgata gtcagagaac acgacaggaa    5160
tgatgggaat ctgggctcga acagcgatgt tgaaggcacc tttcttgaag ggaatgaatc    5220
caccctctcg attccgagtg ccttcgggaa acacccagag cttcaggttt cggttcttca    5280
```

```
tctcggaggc acagtagtcg acagaagcca tagctcgctc tcggttgtat cggtcgatga    5340
agatggtgtt ggaaaagtag gctcccaggt tgaagaaggg aacgtaggca agaatccgct    5400
tcatcatgac aacacagttc ttgggccaga tggaagccat agacagaatg tcgagcgagg    5460
actgatggtt gcagatgacc acggcaggac cttcgacctg ggtcttctcg tagccataca    5520
cagtggtgtg gactccagtc cacttgcacc agtagaagaa cgagtgaaac acgtagtcgg    5580 caccctttgcc gttgagccaa gagggaatca tggtaacgca cacctccatg ccgtgaagca    5640
ggatggtaaa gtagtagaag gagattcgca tgtagtagtg gcagactgtc gaaatgttgt    5700
agaggatgaa cagaatggag agcagaaaga acacgacgat ggaccagaag ttctccatgg    5760
taccagagct gggttagttt gtgtagagag tgtgtgttgc tagcgacttt cggattgtgt    5820
cattacacaa aacgcgtcgt ctcgacactg atcttgtcgt ggatactcac ggctcggaat    5880
tctgtgatgt gtagtttaga tttcgaatct gtggggaaag aaaggaaaaa agagactggc    5940
aaccgattgg gagagccact gtttatatat accctagaca agccccccgc ttgtaagatg    6000
ttggtcaatg taaaccagta ttaaggttgg caagtgcagg agaagcaagg tgtgggtatc    6060
gagcaatgga aatgtgcgga aggcaaaaaa atgaggccac ggcctattgt cggggctata    6120 tccaggggc gattgaagta cactaacatg acatgtgtcc acagaccctc aatctggcct    6180
gatgagccaa atccatacgc gctttcgcag ctctaaaggc tataacaagt cacaccaccc    6240
tgctcgacct cagcgccctc acttttgtt aagacaaact gtacacgctg ttccagcgtt    6300
ttctgcctgc acctggtggg acatttggtg caacctaaag tgctcggaac ctctgtggtg    6360
tccagatcag cgcagcagtt ccgaggtagt tttgaggccc ttagatgatg caatggtgtc    6420
agtcgctgga tcacgagtct taatggcagt attcgttctt atttgtgcca ttgagccccg    6480
ttatcctcgt atcttctacc ccccatccca tccctttgtt ggtgcaaccc tacccattta    6540
ttgttgggtg cagcccaacc gacgtggaga gcttggcttg gccatataaa aaggcccccc    6600
cctagtggca atggcagaaa gtcagctgtg agttgttgaa tttgtcatct aggcggcctg    6660
gccgtcttct ccggggcaat ttaaatgttc ctctatagta gatctgcgta cactgtttaa    6720
acgtcgacga gtatctgtct gactcgtcat tgccgccttt ggagtacgac tccaactatg    6780
agtgtgcttg gatcactttg acgatacatt cttcgttgga ggctgtgggt ctgacagctg    6840
cgttttcggc gcggttggcc gacaacaata tcagctgcaa cgtcattgct ggctttcatc    6900
atgatcacat ttttgtcggc aaaggcgacg cccagagagc cattgacgtt ctttctaatt    6960
tggaccgata gccgtatagt ccagtctatc tataagttca actaactcgt aactattacc    7020
ataacatata cttcactgcc ccagataagg ttccgataaa agttctgca gactaaattt    7080 atttcagtct cctcttcacc accaaaatgc cctcctacga agctcgagct aacgtccaca    7140
agtccgcctt tgccgctcga gtgctcaagc tcgtggcagc caagaaaacc aacctgtgtg    7200
cttctctgga tgttaccacc accaaggagc tcattgagct tgccgataag gtcggacctt    7260
atgtgtgcat gatcaaaacc catatcgaca tcattgacga cttcacctac gccggcactg    7320 tgctcccccct caaggaactt gctcttaagc acggtttctt cctgttcgag gacagaaagt    7380
tcgcagatat tggcaacact gtcaagcacc agtaccggtg tcaccgaatc gccgagtggt    7440
ccgatatcac caacgcccac ggtgtacccg gaaccggaat cattgctggc ctgcgagctg    7500
gtgccgagga aactgtctct gaacagaaga aggaggacgt ctctgactac gagaactccc    7560
agtacaagga gttcctagtc ccctctccca acgagaagct ggccagaggt ctgctcatgc    7620
```

```
tggccgagct gtcttgcaag ggctctctgg ccactggcga gtactccaag cagaccattg    7680
agcttgcccg atccgacccc gagtttgtgg ttggcttcat tgcccagaac cgacctaagg    7740
gcgactctga ggactggctt attctgaccc ccggggtggg tcttgacgac aagggagacg    7800
ctctcggaca gcagtaccga actgttgagg atgtcatgtc taccggaacg gatatcataa    7860
ttgtcggccg aggtctgtac ggccagaacc gagatcctat tgaggaggcc aagcgatacc    7920
agaaggctgg ctgggaggct taccagaaga ttaactgtta gaggttagac tatggatatg    7980
taatttaact gtgtatatag agagcgtgca agtatggagc gcttgttcag cttgtatgat    8040
ggtcagacga cctgtctgat cgagtatgta tgatactgca caacctgtgt atccgcatga    8100
tctgtccaat ggggcatgtt gttgtgtttc tcgatacgga gatgctgggt acagtgctaa    8160
tacgttgaac tacttatact tatatgaggc tcgaagaaag ctgacttgtg tatgacttaa    8220
ttaattactg tcgaaat                                                   8237
```

<210> SEQ ID NO 90
<211> LENGTH: 1350
<212> TYPE: DNA
<213> ORGANISM: Euglena gracilis
<220> FEATURE:
<221> NAME/KEY: CDS
<222> LOCATION: (1)..(1350)
<223> OTHER INFORMATION: mutant delta-5 desaturase

<400> SEQUENCE: 90

```
atg gct ctc agt ctt acc aca gaa cag ctg tta gaa cgc cct gat ttg      48
Met Ala Leu Ser Leu Thr Thr Glu Gln Leu Leu Glu Arg Pro Asp Leu
1               5                   10                  15 gtt gcg att gat ggc atc ctc tac gac ctt gaa ggg ctt gcc aaa gtt      96
Val Ala Ile Asp Gly Ile Leu Tyr Asp Leu Glu Gly Leu Ala Lys Val
            20                  25                  30 cat cca gga tcc gat ttg att ctc gct tct ggt gcc tct gat gcc tcc     144
His Pro Gly Ser Asp Leu Ile Leu Ala Ser Gly Ala Ser Asp Ala Ser
        35                  40                  45 cct ctc ttt tat tca atg cat cca tac gtc aaa ccg gag aac tcc aaa     192
Pro Leu Phe Tyr Ser Met His Pro Tyr Val Lys Pro Glu Asn Ser Lys
    50                  55                  60 ttg ctt caa cag ttc gtc cga ggg aag cat gac cgc acc tcg aag gac     240
Leu Leu Gln Gln Phe Val Arg Gly Lys His Asp Arg Thr Ser Lys Asp
65                  70                  75                  80 att gtc tac acg tat gat tct ccc ttc gca caa gac gtt aag cgg aca     288
Ile Val Tyr Thr Tyr Asp Ser Pro Phe Ala Gln Asp Val Lys Arg Thr
                85                  90                  95 atg cgc gag gtg atg aaa ggg agg aac tgg tac gca acc cct ggc ttc     336
Met Arg Glu Val Met Lys Gly Arg Asn Trp Tyr Ala Thr Pro Gly Phe
            100                 105                 110 tgg ctg cgc acc gtt ggg atc atc gcc gtg acg gcc ttt tgc gag tgg     384
Trp Leu Arg Thr Val Gly Ile Ile Ala Val Thr Ala Phe Cys Glu Trp
        115                 120                 125 cac tgg gct acc acg ggg atg gtg ctg tgg ggc ctg ttg act gga ttc     432
His Trp Ala Thr Thr Gly Met Val Leu Trp Gly Leu Leu Thr Gly Phe
    130                 135                 140 atg cac atg cag atc ggc tta tcc atc cag cat gat gcg tcc cac ggg     480
Met His Met Gln Ile Gly Leu Ser Ile Gln His Asp Ala Ser His Gly
145                 150                 155                 160 gcc atc agc aag aag cct tgg gtc aac gcc ctc ttc gcc tac ggc att     528
Ala Ile Ser Lys Lys Pro Trp Val Asn Ala Leu Phe Ala Tyr Gly Ile
                165                 170                 175 gac gtc atc gga tcg tcc cgg tgg att tgg ctg cag tcg cac atc atg     576
Asp Val Ile Gly Ser Ser Arg Trp Ile Trp Leu Gln Ser His Ile Met
```

```
                Asp Val Ile Gly Ser Ser Arg Trp Ile Trp Leu Gln Ser His Ile Met
                            180                 185                 190 cgg cac cac acc tac acc aac cag cac ggc ctc gac ctg gat gcg gag        624
Arg His His Thr Tyr Thr Asn Gln His Gly Leu Asp Leu Asp Ala Glu
                195                 200                 205 tcg gca gag ccg ttc ctg gtg ttc cac aac tac ccc gcc gca aac acc        672
Ser Ala Glu Pro Phe Leu Val Phe His Asn Tyr Pro Ala Ala Asn Thr
210                 215                 220 gcc cga aag tgg ttc cac cgc ttc cag gct tgg tac atg tac ctt gtg        720
Ala Arg Lys Trp Phe His Arg Phe Gln Ala Trp Tyr Met Tyr Leu Val
225                 230                 235                 240 ctg ggg gca tac ggg gta tcg ctg gtg tac aac ccg ctc tac att ttc        768
Leu Gly Ala Tyr Gly Val Ser Leu Val Tyr Asn Pro Leu Tyr Ile Phe
                245                 250                 255 cgg atg cag cac aat gac acc atc cca gag tct gtc acg gcc atg cgg        816
Arg Met Gln His Asn Asp Thr Ile Pro Glu Ser Val Thr Ala Met Arg
                260                 265                 270 gaa aat ggc ttt ctg cgg cgc tac cgc aca ctt gca ttc gtg atg cga        864
Glu Asn Gly Phe Leu Arg Arg Tyr Arg Thr Leu Ala Phe Val Met Arg
                275                 280                 285 gct ttc ttc atc ttc cgg acc gca ttc ttg ccc tgg tac ctc act ggg        912
Ala Phe Phe Ile Phe Arg Thr Ala Phe Leu Pro Trp Tyr Leu Thr Gly
290                 295                 300 acc tca ttg ctg atc acc att cct ctg gtg ccc acc gca act ggt gcc        960
Thr Ser Leu Leu Ile Thr Ile Pro Leu Val Pro Thr Ala Thr Gly Ala
305                 310                 315                 320 ttc ttg acg ttc ttc ttc att ttg tcc cac aat ttt gat ggc tcc gaa       1008
Phe Leu Thr Phe Phe Phe Ile Leu Ser His Asn Phe Asp Gly Ser Glu
                325                 330                 335 cgg atc ccc gac aag aac tgc aag gtt aag cga tct gag aag gac gtt       1056
Arg Ile Pro Asp Lys Asn Cys Lys Val Lys Arg Ser Glu Lys Asp Val
                340                 345                 350 gag gct gac caa att gac tgg tat cgg gcg cag gtg gag acg tcc tcc       1104
Glu Ala Asp Gln Ile Asp Trp Tyr Arg Ala Gln Val Glu Thr Ser Ser
                355                 360                 365 aca tac ggt ggc ccc atc gcc atg ttc ttc act ggc ggt ctc aat ttc       1152
Thr Tyr Gly Gly Pro Ile Ala Met Phe Phe Thr Gly Gly Leu Asn Phe
370                 375                 380 cag atc gag cac cac ctc ttt ccc cgg atg tcg tct tgg cac tac ccc       1200
Gln Ile Glu His His Leu Phe Pro Arg Met Ser Ser Trp His Tyr Pro
385                 390                 395                 400 ttc gtc cag cag gcg gtc cgg gag tgt tgc gaa cga cat gga gtg cga       1248
Phe Val Gln Gln Ala Val Arg Glu Cys Cys Glu Arg His Gly Val Arg
                405                 410                 415 tat gtt ttc tac cct acc atc gtc ggc aac atc atc tcc acc ctg aag       1296
Tyr Val Phe Tyr Pro Thr Ile Val Gly Asn Ile Ile Ser Thr Leu Lys
                420                 425                 430 tac atg cat aag gtg ggt gtc gtc cac tgc gtg aag gac gca cag gat       1344
Tyr Met His Lys Val Gly Val Val His Cys Val Lys Asp Ala Gln Asp
                435                 440                 445 tcc taa                                                               1350
Ser

<210> SEQ ID NO 91
<211> LENGTH: 449
<212> TYPE: PRT
<213> ORGANISM: Euglena gracilis

<400> SEQUENCE: 91

Met Ala Leu Ser Leu Thr Thr Glu Gln Leu Leu Glu Arg Pro Asp Leu
```

-continued

```
1               5                   10                  15
Val Ala Ile Asp Gly Ile Leu Tyr Asp Leu Glu Gly Leu Ala Lys Val
            20                  25                  30
His Pro Gly Ser Asp Leu Ile Leu Ala Ser Gly Ala Ser Asp Ala Ser
            35                  40                  45
Pro Leu Phe Tyr Ser Met His Pro Tyr Val Lys Pro Glu Asn Ser Lys
            50                  55                  60
Leu Leu Gln Gln Phe Val Arg Gly Lys His Asp Arg Thr Ser Lys Asp
65                  70                  75                  80
Ile Val Tyr Thr Tyr Asp Ser Pro Phe Ala Gln Asp Val Lys Arg Thr
                85                  90                  95
Met Arg Glu Val Met Lys Gly Arg Asn Trp Tyr Ala Thr Pro Gly Phe
                100                 105                 110
Trp Leu Arg Thr Val Gly Ile Ile Ala Val Thr Ala Phe Cys Glu Trp
                115                 120                 125
His Trp Ala Thr Thr Gly Met Val Leu Trp Gly Leu Thr Gly Phe
                130                 135                 140
Met His Met Gln Ile Gly Leu Ser Ile Gln His Asp Ala Ser His Gly
145                 150                 155                 160
Ala Ile Ser Lys Lys Pro Trp Val Asn Ala Leu Phe Ala Tyr Gly Ile
                165                 170                 175
Asp Val Ile Gly Ser Ser Arg Trp Ile Trp Leu Gln Ser His Ile Met
                180                 185                 190
Arg His His Thr Tyr Thr Asn Gln His Gly Leu Asp Leu Asp Ala Glu
                195                 200                 205
Ser Ala Glu Pro Phe Leu Val Phe His Asn Tyr Pro Ala Ala Asn Thr
210                 215                 220
Ala Arg Lys Trp Phe His Arg Phe Gln Ala Trp Tyr Met Tyr Leu Val
225                 230                 235                 240
Leu Gly Ala Tyr Gly Val Ser Leu Val Tyr Asn Pro Leu Tyr Ile Phe
                245                 250                 255
Arg Met Gln His Asn Asp Thr Ile Pro Glu Ser Val Thr Ala Met Arg
                260                 265                 270
Glu Asn Gly Phe Leu Arg Arg Tyr Arg Thr Leu Ala Phe Val Met Arg
                275                 280                 285
Ala Phe Phe Ile Phe Arg Thr Ala Phe Leu Pro Trp Tyr Leu Thr Gly
                290                 295                 300
Thr Ser Leu Leu Ile Thr Ile Pro Leu Val Pro Thr Ala Thr Gly Ala
305                 310                 315                 320
Phe Leu Thr Phe Phe Ile Leu Ser His Asn Phe Asp Gly Ser Glu
                325                 330                 335
Arg Ile Pro Asp Lys Asn Cys Lys Val Lys Arg Ser Glu Lys Asp Val
                340                 345                 350
Glu Ala Asp Gln Ile Asp Trp Tyr Arg Ala Gln Val Glu Thr Ser Ser
                355                 360                 365
Thr Tyr Gly Gly Pro Ile Ala Met Phe Phe Thr Gly Gly Leu Asn Phe
                370                 375                 380
Gln Ile Glu His His Leu Phe Pro Arg Met Ser Ser Trp His Tyr Pro
385                 390                 395                 400
Phe Val Gln Gln Ala Val Arg Glu Cys Cys Glu Arg His Gly Val Arg
                405                 410                 415
Tyr Val Phe Tyr Pro Thr Ile Val Gly Asn Ile Ile Ser Thr Leu Lys
                420                 425                 430
```

```
Tyr Met His Lys Val Gly Val His Cys Val Lys Asp Ala Gln Asp
        435                 440                 445
Ser

<210> SEQ ID NO 92
<211> LENGTH: 1254
<212> TYPE: DNA
<213> ORGANISM: Mortierella alpina
<220> FEATURE:
<221> NAME/KEY: CDS
<222> LOCATION: (1)..(1254)
<223> OTHER INFORMATION: GenBank Accession No. CQ891250
<300> PUBLICATION INFORMATION:
<302> TITLE: Novel plant acyltransferases specific for long-chained,
      multiply unsaturated fatty acids
<310> PATENT DOCUMENT NUMBER: WO 2004/087902
<311> PATENT FILING DATE: 2004-03-26
<312> PUBLICATION DATE: 2004-10-14
<313> RELEVANT RESIDUES IN SEQ ID NO: (1)..(1254)

<400> SEQUENCE: 92 atg gat gaa tcc acc acg acc acc acg cac cac tca gag acc agc agc        48
Met Asp Glu Ser Thr Thr Thr Thr Thr His His Ser Glu Thr Ser Ser
1               5                   10                  15 aag acg tcc tcg cac ccc cgc cgg ctc ggt ccc gag atg aac cct atc        96
Lys Thr Ser Ser His Pro Arg Arg Leu Gly Pro Glu Met Asn Pro Ile
            20                  25                  30 tac aag ggt ctg cga gcc att gtc tgg gcc ttt tac ttc aac ctg gga       144
Tyr Lys Gly Leu Arg Ala Ile Val Trp Ala Phe Tyr Phe Asn Leu Gly
        35                  40                  45 gcg tcg ctt ata tcg atc acg cag gtg ctg tcg ctg cct ctg gcg ttg       192
Ala Ser Leu Ile Ser Ile Thr Gln Val Leu Ser Leu Pro Leu Ala Leu
    50                  55                  60 att gct cca ggg gtc tac cag tgg cac atc agc aaa aca cag ggt cac       240
Ile Ala Pro Gly Val Tyr Gln Trp His Ile Ser Lys Thr Gln Gly His
65                  70                  75                  80 ttt gga gct ttc ctg ctc cgg atg aac cag ctc ttt gcg ccg tca gat       288
Phe Gly Ala Phe Leu Leu Arg Met Asn Gln Leu Phe Ala Pro Ser Asp
                85                  90                  95 att gtc ttg aca ggg gac gag agt gtc agg gga atc gtc aag gtc tac       336
Ile Val Leu Thr Gly Asp Glu Ser Val Arg Gly Ile Val Lys Val Tyr
            100                 105                 110 aaa gga cgg aac ctg aag gag gcc ggt gag cca ggc agc ggt cag gga       384
Lys Gly Arg Asn Leu Lys Glu Ala Gly Glu Pro Gly Ser Gly Gln Gly
        115                 120                 125 gag gac att ctt ctg gat atg ccc gag agg atg gtt ttc att gcg aac       432
Glu Asp Ile Leu Leu Asp Met Pro Glu Arg Met Val Phe Ile Ala Asn
    130                 135                 140 cac cag atc tac tct gac tgg atg tac ctc tgg tgc ttc tcc tat ttt       480
His Gln Ile Tyr Ser Asp Trp Met Tyr Leu Trp Cys Phe Ser Tyr Phe
145                 150                 155                 160 gca gag agg cac agg gca ctg aag att att ctt cgg ggc gac ctg acc       528
Ala Glu Arg His Arg Ala Leu Lys Ile Ile Leu Arg Gly Asp Leu Thr
                165                 170                 175 tgg atc cct gtc ttt ggc tgg ggt atg cgg ttc ttt gac ttt atc ttt       576
Trp Ile Pro Val Phe Gly Trp Gly Met Arg Phe Phe Asp Phe Ile Phe
            180                 185                 190 ttg aaa cgt aat gac tgg gca cac gat cgc gtg gcc att gag gaa aac       624
Leu Lys Arg Asn Asp Trp Ala His Asp Arg Val Ala Ile Glu Glu Asn
        195                 200                 205 ttg gga cgt gtc aag gaa aag gat ccc ctc tgg ctc gtg gtc ttc ccc       672
Leu Gly Arg Val Lys Glu Lys Asp Pro Leu Trp Leu Val Val Phe Pro
```

```
gag gga aca gtc gtc tcc aag gaa acg cgt ctc cga tcc gtt gcc ttt      720
Glu Gly Thr Val Val Ser Lys Glu Thr Arg Leu Arg Ser Val Ala Phe
225                 230                 235                 240 tca aag aag gct agt ctg tcg gat cac cgc cat gtg ctg ctt cca agg      768
Ser Lys Lys Ala Ser Leu Ser Asp His Arg His Val Leu Leu Pro Arg
                245                 250                 255 acc agc ggt ctg ttt gtg tgc atc aac aag ttg cgt gga tct gtc gac      816
Thr Ser Gly Leu Phe Val Cys Ile Asn Lys Leu Arg Gly Ser Val Asp
            260                 265                 270 tac ttg tac gat gca acc gtt ggc tac tcg aat gtc gag tat ggc gag      864
Tyr Leu Tyr Asp Ala Thr Val Gly Tyr Ser Asn Val Glu Tyr Gly Glu
        275                 280                 285 att ccg cag gag ctt tac ccg tta cca gga ctg tat atc aac aaa gca      912
Ile Pro Gln Glu Leu Tyr Pro Leu Pro Gly Leu Tyr Ile Asn Lys Ala
    290                 295                 300 cag ccc aag gag atc aac atg cac ctg cgt cga ttt gcg atc aag gat      960
Gln Pro Lys Glu Ile Asn Met His Leu Arg Arg Phe Ala Ile Lys Asp
305                 310                 315                 320 atc ccc acg tca gaa ccc gaa ttt gtg gaa tgg gtc cga gct cgg tgg     1008
Ile Pro Thr Ser Glu Pro Glu Phe Val Glu Trp Val Arg Ala Arg Trp
                325                 330                 335 gtg gag aag gat gag ttg atg gaa gag ttt tat acc aag ggc cga ttt     1056
Val Glu Lys Asp Glu Leu Met Glu Glu Phe Tyr Thr Lys Gly Arg Phe
            340                 345                 350 cca tca caa ctg acg gcc gcc gac att ggt gag aag gag gtc aag acg     1104
Pro Ser Gln Leu Thr Ala Ala Asp Ile Gly Glu Lys Glu Val Lys Thr
        355                 360                 365 gca gga ggt cca acg gag gga cag agt gtc agg atc ccg ctc aag gcg     1152
Ala Gly Gly Pro Thr Glu Gly Gln Ser Val Arg Ile Pro Leu Lys Ala
    370                 375                 380 cga ggc atg atg gac tac ctc atg ccc tcg gtc atg aat ctg atc gcc     1200
Arg Gly Met Met Asp Tyr Leu Met Pro Ser Val Met Asn Leu Ile Ala
385                 390                 395                 400 ctt cct gtg ctg gcg ttt gcg atg aga tat gca gtg cag caa gca tcg     1248
Leu Pro Val Leu Ala Phe Ala Met Arg Tyr Ala Val Gln Gln Ala Ser
                405                 410                 415 ggc tga                                                              1254
Gly

<210> SEQ ID NO 93
<211> LENGTH: 417
<212> TYPE: PRT
<213> ORGANISM: Mortierella alpina

<400> SEQUENCE: 93

Met Asp Glu Ser Thr Thr Thr Thr His His Ser Glu Thr Ser Ser
1               5                   10                  15

Lys Thr Ser Ser His Pro Arg Arg Leu Gly Pro Glu Met Asn Pro Ile
                20                  25                  30

Tyr Lys Gly Leu Arg Ala Ile Val Trp Ala Phe Tyr Phe Asn Leu Gly
            35                  40                  45

Ala Ser Leu Ile Ser Ile Thr Gln Val Leu Ser Leu Pro Leu Ala Leu
        50                  55                  60

Ile Ala Pro Gly Val Tyr Gln Trp His Ile Ser Lys Thr Gln Gly His
65                  70                  75                  80

Phe Gly Ala Phe Leu Leu Arg Met Asn Gln Leu Phe Ala Pro Ser Asp
                85                  90                  95
```

```
Ile Val Leu Thr Gly Asp Glu Ser Val Arg Gly Ile Val Lys Val Tyr
            100                 105                 110
Lys Gly Arg Asn Leu Lys Glu Ala Gly Glu Pro Gly Ser Gly Gln Gly
        115                 120                 125
Glu Asp Ile Leu Leu Asp Met Pro Glu Arg Met Val Phe Ile Ala Asn
    130                 135                 140
His Gln Ile Tyr Ser Asp Trp Met Tyr Leu Trp Cys Phe Ser Tyr Phe
145                 150                 155                 160
Ala Glu Arg His Arg Ala Leu Lys Ile Ile Leu Arg Gly Asp Leu Thr
                165                 170                 175
Trp Ile Pro Val Phe Gly Trp Gly Met Arg Phe Phe Asp Phe Ile Phe
            180                 185                 190
Leu Lys Arg Asn Asp Trp Ala His Asp Arg Arg Ala Ile Glu Glu Asn
        195                 200                 205
Leu Gly Arg Val Lys Glu Lys Asp Pro Leu Trp Leu Val Val Phe Pro
    210                 215                 220
Glu Gly Thr Val Val Ser Lys Glu Thr Arg Leu Arg Ser Val Ala Phe
225                 230                 235                 240
Ser Lys Lys Ala Ser Leu Ser Asp His Arg His Val Leu Leu Pro Arg
                245                 250                 255
Thr Ser Gly Leu Phe Val Cys Ile Asn Lys Leu Arg Gly Ser Val Asp
            260                 265                 270
Tyr Leu Tyr Asp Ala Thr Val Gly Tyr Ser Asn Val Glu Tyr Gly Glu
        275                 280                 285
Ile Pro Gln Glu Leu Tyr Pro Leu Pro Gly Leu Tyr Ile Asn Lys Ala
    290                 295                 300
Gln Pro Lys Glu Ile Asn Met His Leu Arg Arg Phe Ala Ile Lys Asp
305                 310                 315                 320
Ile Pro Thr Ser Glu Pro Glu Phe Val Glu Trp Val Arg Ala Arg Trp
                325                 330                 335
Val Glu Lys Asp Glu Leu Met Glu Glu Phe Tyr Thr Lys Gly Arg Phe
            340                 345                 350
Pro Ser Gln Leu Thr Ala Ala Asp Ile Gly Glu Lys Glu Val Lys Thr
        355                 360                 365
Ala Gly Gly Pro Thr Glu Gly Gln Ser Val Arg Ile Pro Leu Lys Ala
    370                 375                 380
Arg Gly Met Met Asp Tyr Leu Met Pro Ser Val Met Asn Leu Ile Ala
385                 390                 395                 400
Leu Pro Val Leu Ala Phe Ala Met Arg Tyr Ala Val Gln Gln Ala Ser
                405                 410                 415
Gly

<210> SEQ ID NO 94
<211> LENGTH: 1170
<212> TYPE: DNA
<213> ORGANISM: Mortierella alpina
<220> FEATURE:
<221> NAME/KEY: CDS
<222> LOCATION: (1)..(1170)
<223> OTHER INFORMATION: Gen Bank Accession No. CQ891252
<300> PUBLICATION INFORMATION:
<302> TITLE: Novel plant acyltransferases specific for long-chained,
      multiply unsaturated fatty acids
<310> PATENT DOCUMENT NUMBER: WO 2004/087902
<311> PATENT FILING DATE: 2004-03-26
<312> PUBLICATION DATE: 2004-10-14
<313> RELEVANT RESIDUES IN SEQ ID NO: (1)..(1170)
```

-continued

<400> SEQUENCE: 94

| | | | | | | | | | | | | | | | | |
|---|---|---|---|---|---|---|---|---|---|---|---|---|---|---|---|---|
| atg | aac | cct | atc | tac | aag | ggt | ctg | cga | gcc | att | gtc | tgg | gcc | ttt | tac | 48 |
| Met | Asn | Pro | Ile | Tyr | Lys | Gly | Leu | Arg | Ala | Ile | Val | Trp | Ala | Phe | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttc | aac | ctg | gga | gcg | tcg | ctt | ata | tcg | atc | acg | cag | gtg | ctg | tcg | ctg | 96 |
| Phe | Asn | Leu | Gly | Ala | Ser | Leu | Ile | Ser | Ile | Thr | Gln | Val | Leu | Ser | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| cct | ctg | gcg | ttg | att | gct | cca | ggg | gtc | tac | cag | tgg | cac | atc | agc | aaa | 144 |
| Pro | Leu | Ala | Leu | Ile | Ala | Pro | Gly | Val | Tyr | Gln | Trp | His | Ile | Ser | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| aca | cag | ggt | cac | ttt | gga | gct | ttc | ctg | ctc | cgg | atg | aac | cag | ctc | ttt | 192 |
| Thr | Gln | Gly | His | Phe | Gly | Ala | Phe | Leu | Leu | Arg | Met | Asn | Gln | Leu | Phe | |
| | 50 | | | | | 55 | | | | | 60 | | | | | |

| | | | | | | | | | | | | | | | | |
|---|---|---|---|---|---|---|---|---|---|---|---|---|---|---|---|---|
| gcg | ccg | tca | gat | att | gtc | ttg | aca | ggg | gac | gag | agt | gtc | agg | gga | atc | 240 |
| Ala | Pro | Ser | Asp | Ile | Val | Leu | Thr | Gly | Asp | Glu | Ser | Val | Arg | Gly | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtc | aag | gtc | tac | aaa | gga | cgg | aac | ctg | aag | gag | gcc | ggt | gag | cca | ggc | 288 |
| Val | Lys | Val | Tyr | Lys | Gly | Arg | Asn | Leu | Lys | Glu | Ala | Gly | Glu | Pro | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| agc | ggt | cag | gga | gag | gac | att | ctt | ctg | gat | atg | ccc | gag | agg | atg | gtt | 336 |
| Ser | Gly | Gln | Gly | Glu | Asp | Ile | Leu | Leu | Asp | Met | Pro | Glu | Arg | Met | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| ttc | att | gcg | aac | cac | cag | atc | tac | tct | gac | tgg | atg | tac | ctc | tgg | tgc | 384 |
| Phe | Ile | Ala | Asn | His | Gln | Ile | Tyr | Ser | Asp | Trp | Met | Tyr | Leu | Trp | Cys | |
| | | 115 | | | | | 120 | | | | | 125 | | | | |

| | | | | | | | | | | | | | | | | |
|---|---|---|---|---|---|---|---|---|---|---|---|---|---|---|---|---|
| ttc | tcc | tat | ttt | gca | gag | agg | cac | agg | gca | ctg | aag | att | att | ctt | cgg | 432 |
| Phe | Ser | Tyr | Phe | Ala | Glu | Arg | His | Arg | Ala | Leu | Lys | Ile | Ile | Leu | Arg | |
| | 130 | | | | | 135 | | | | | 140 | | | | | |

| | | | | | | | | | | | | | | | | |
|---|---|---|---|---|---|---|---|---|---|---|---|---|---|---|---|---|
| ggc | gac | ctg | acc | tgg | atc | cct | gtc | ttt | ggc | tgg | ggt | atg | cgg | ttc | ttt | 480 |
| Gly | Asp | Leu | Thr | Trp | Ile | Pro | Val | Phe | Gly | Trp | Gly | Met | Arg | Phe | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gac | ttt | atc | ttt | ttg | aaa | cgt | aat | gac | tgg | gca | cac | gat | cgc | cgt | gcc | 528 |
| Asp | Phe | Ile | Phe | Leu | Lys | Arg | Asn | Asp | Trp | Ala | His | Asp | Arg | Arg | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| att | gag | gaa | aac | ttg | gga | cgt | gtc | aag | gaa | aag | gat | ccc | ctc | tgg | ctc | 576 |
| Ile | Glu | Glu | Asn | Leu | Gly | Arg | Val | Lys | Glu | Lys | Asp | Pro | Leu | Trp | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| gtg | gtc | ttc | ccc | gag | gga | aca | gtc | gtc | tcc | aag | gaa | acg | cgt | ctc | cga | 624 |
| Val | Val | Phe | Pro | Glu | Gly | Thr | Val | Val | Ser | Lys | Glu | Thr | Arg | Leu | Arg | |
| | | 195 | | | | | 200 | | | | | 205 | | | | |

| | | | | | | | | | | | | | | | | |
|---|---|---|---|---|---|---|---|---|---|---|---|---|---|---|---|---|
| tcc | gtt | gcc | ttt | tca | aag | aag | gct | agt | ctg | tcg | gat | cac | cgc | cat | gtg | 672 |
| Ser | Val | Ala | Phe | Ser | Lys | Lys | Ala | Ser | Leu | Ser | Asp | His | Arg | His | Val | |
| | 210 | | | | | 215 | | | | | 220 | | | | | |

| | | | | | | | | | | | | | | | | |
|---|---|---|---|---|---|---|---|---|---|---|---|---|---|---|---|---|
| ctg | ctt | cca | agg | acc | agc | ggt | ctg | ttt | gtg | tgc | atc | aac | aag | ttg | cgt | 720 |
| Leu | Leu | Pro | Arg | Thr | Ser | Gly | Leu | Phe | Val | Cys | Ile | Asn | Lys | Leu | Arg | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gga | tct | gtc | gac | tac | ttg | tac | gat | gca | acc | gtt | ggc | tac | tcg | aat | gtc | 768 |
| Gly | Ser | Val | Asp | Tyr | Leu | Tyr | Asp | Ala | Thr | Val | Gly | Tyr | Ser | Asn | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| gag | tat | ggc | gag | att | ccg | cag | gag | ctt | tac | ccg | tta | cca | gga | ctg | tat | 816 |
| Glu | Tyr | Gly | Glu | Ile | Pro | Gln | Glu | Leu | Tyr | Pro | Leu | Pro | Gly | Leu | Tyr | |
| | | | 260 | | | | | 265 | | | | | 270 | | | |

| | | | | | | | | | | | | | | | | |
|---|---|---|---|---|---|---|---|---|---|---|---|---|---|---|---|---|
| atc | aac | aaa | gca | cag | ccc | aag | gag | atc | aac | atg | cac | ctg | cgt | cga | ttt | 864 |
| Ile | Asn | Lys | Ala | Gln | Pro | Lys | Glu | Ile | Asn | Met | His | Leu | Arg | Arg | Phe | |
| | | 275 | | | | | 280 | | | | | 285 | | | | |

| | | | | | | | | | | | | | | | | |
|---|---|---|---|---|---|---|---|---|---|---|---|---|---|---|---|---|
| gcg | atc | aag | gat | atc | ccc | acg | tca | gaa | ccc | gaa | ttt | gtg | gaa | tgg | gtc | 912 |
| Ala | Ile | Lys | Asp | Ile | Pro | Thr | Ser | Glu | Pro | Glu | Phe | Val | Glu | Trp | Val | |
| | 290 | | | | | 295 | | | | | 300 | | | | | |

| | | | | | | | | | | | | | | | | |
|---|---|---|---|---|---|---|---|---|---|---|---|---|---|---|---|---|
| cga | gct | cgg | tgg | gtg | gag | aag | gat | gag | ttg | atg | gaa | gag | ttt | tat | acc | 960 |

```
Arg Ala Arg Trp Val Glu Lys Asp Glu Leu Met Glu Glu Phe Tyr Thr
305                 310                 315                 320 aag ggc cga ttt cca tca caa ctg acg gcc gcc gac att ggt gag aag      1008
Lys Gly Arg Phe Pro Ser Gln Leu Thr Ala Ala Asp Ile Gly Glu Lys
                325                 330                 335 gag gtc aag acg gca gga ggt cca acg gag gga cag agt gtc agg atc      1056
Glu Val Lys Thr Ala Gly Gly Pro Thr Glu Gly Gln Ser Val Arg Ile
                340                 345                 350 ccg ctc aag gcg cga ggc atg atg gac tac ctc atg ccc tcg gtc atg      1104
Pro Leu Lys Ala Arg Gly Met Met Asp Tyr Leu Met Pro Ser Val Met
                355                 360                 365 aat ctg atc gcc ctt cct gtg ctg gcg ttt gcg atg aga tat gca gtg      1152
Asn Leu Ile Ala Leu Pro Val Leu Ala Phe Ala Met Arg Tyr Ala Val
        370                 375                 380 cag caa gca tcg ggc tga                                              1170
Gln Gln Ala Ser Gly
385

<210> SEQ ID NO 95
<211> LENGTH: 389
<212> TYPE: PRT
<213> ORGANISM: Mortierella alpina

<400> SEQUENCE: 95

Met Asn Pro Ile Tyr Lys Gly Leu Arg Ala Ile Val Trp Ala Phe Tyr
1               5                   10                  15

Phe Asn Leu Gly Ala Ser Leu Ile Ser Ile Thr Gln Val Leu Ser Leu
                20                  25                  30

Pro Leu Ala Leu Ile Ala Pro Gly Val Tyr Gln Trp His Ile Ser Lys
            35                  40                  45

Thr Gln Gly His Phe Gly Ala Phe Leu Leu Arg Met Asn Gln Leu Phe
        50                  55                  60

Ala Pro Ser Asp Ile Val Leu Thr Gly Asp Glu Ser Val Arg Gly Ile
65                  70                  75                  80

Val Lys Val Tyr Lys Gly Arg Asn Leu Lys Glu Ala Gly Glu Pro Gly
                85                  90                  95

Ser Gly Gln Gly Glu Asp Ile Leu Leu Asp Met Pro Glu Arg Met Val
            100                 105                 110

Phe Ile Ala Asn His Gln Ile Tyr Ser Asp Trp Met Tyr Leu Trp Cys
        115                 120                 125

Phe Ser Tyr Phe Ala Glu Arg His Arg Ala Leu Lys Ile Ile Leu Arg
    130                 135                 140

Gly Asp Leu Thr Trp Ile Pro Val Phe Gly Trp Gly Met Arg Phe Phe
145                 150                 155                 160

Asp Phe Ile Phe Leu Lys Arg Asn Asp Trp Ala His Asp Arg Arg Ala
                165                 170                 175

Ile Glu Glu Asn Leu Gly Arg Val Lys Glu Lys Asp Pro Leu Trp Leu
            180                 185                 190

Val Val Phe Pro Glu Gly Thr Val Val Ser Lys Glu Thr Arg Leu Arg
        195                 200                 205

Ser Val Ala Phe Ser Lys Lys Ala Ser Leu Ser Asp His Arg His Val
    210                 215                 220

Leu Leu Pro Arg Thr Ser Gly Leu Phe Val Cys Ile Asn Lys Leu Arg
225                 230                 235                 240

Gly Ser Val Asp Tyr Leu Tyr Asp Ala Thr Val Gly Tyr Ser Asn Val
                245                 250                 255
```

```
Glu Tyr Gly Glu Ile Pro Gln Glu Leu Tyr Pro Leu Pro Gly Leu Tyr
            260                 265                 270

Ile Asn Lys Ala Gln Pro Lys Glu Ile Asn Met His Leu Arg Arg Phe
        275                 280                 285

Ala Ile Lys Asp Ile Pro Thr Ser Glu Pro Glu Phe Val Glu Trp Val
290                 295                 300

Arg Ala Arg Trp Val Glu Lys Asp Glu Leu Met Glu Glu Phe Tyr Thr
305                 310                 315                 320

Lys Gly Arg Phe Pro Ser Gln Leu Thr Ala Ala Asp Ile Gly Glu Lys
                325                 330                 335

Glu Val Lys Thr Ala Gly Gly Pro Thr Glu Gly Gln Ser Val Arg Ile
            340                 345                 350

Pro Leu Lys Ala Arg Gly Met Met Asp Tyr Leu Met Pro Ser Val Met
        355                 360                 365

Asn Leu Ile Ala Leu Pro Val Leu Ala Phe Ala Met Arg Tyr Ala Val
370                 375                 380

Gln Gln Ala Ser Gly
385
```

<210> SEQ ID NO 96
<211> LENGTH: 926
<212> TYPE: DNA
<213> ORGANISM: Saccharomyces cerevisiae
<220> FEATURE:
<221> NAME/KEY: CDS
<222> LOCATION: (4)..(915)

<400> SEQUENCE: 96

```
aac atg tct gtt att gga cga ttt ctt tac tac ctg aga tcg gtg ctc      48
    Met Ser Val Ile Gly Arg Phe Leu Tyr Tyr Leu Arg Ser Val Leu
    1               5                   10                  15 gtc gtt ttg gcc ctc gct gga tgt ggc ttc tat ggc gtg att gcc tct      96
Val Val Leu Ala Leu Ala Gly Cys Gly Phe Tyr Gly Val Ile Ala Ser
                20                  25                  30 atc ctg tgt act ctc atc ggc aag cag cat ctc gcg caa tgg att acc     144
Ile Leu Cys Thr Leu Ile Gly Lys Gln His Leu Ala Gln Trp Ile Thr
            35                  40                  45 gcc cga tgc ttt tac cac gtg atg aaa ctg atg ctg gga ttg gac gtc     192
Ala Arg Cys Phe Tyr His Val Met Lys Leu Met Leu Gly Leu Asp Val
        50                  55                  60 aaa gtc gtg ggt gaa gag aac ctg gct aag aag ccc tat atc atg atc     240
Lys Val Val Gly Glu Glu Asn Leu Ala Lys Lys Pro Tyr Ile Met Ile
65                  70                  75 gct aac cac cag tcc acc ctc gat atc ttt atg ctc ggc aga atc ttc     288
Ala Asn His Gln Ser Thr Leu Asp Ile Phe Met Leu Gly Arg Ile Phe
80                  85                  90                  95 cct ccc gga tgc acc gtt acc gca aag aag agc ctt aag tac gtc ccc     336
Pro Pro Gly Cys Thr Val Thr Ala Lys Lys Ser Leu Lys Tyr Val Pro
                100                 105                 110 ttc ctg ggc tgg ttt atg gcg ctt tcc ggt aca tac ttc ctc gac cgt     384
Phe Leu Gly Trp Phe Met Ala Leu Ser Gly Thr Tyr Phe Leu Asp Arg
            115                 120                 125 tcc aag cgg caa gag gct att gat acc ctg aac aaa gga ctg gag aac     432
Ser Lys Arg Gln Glu Ala Ile Asp Thr Leu Asn Lys Gly Leu Glu Asn
        130                 135                 140 gtc aaa aag aat aag cga gcc ctc tgg gtt ttt ccc gaa ggt acc cgg     480
Val Lys Lys Asn Lys Arg Ala Leu Trp Val Phe Pro Glu Gly Thr Arg
145                 150                 155 tct tac acg tcg gag ctt acc atg ctg ccg ttc aag aag ggc gcc ttt     528
```

| | | |
|---|---|---|
| Ser Tyr Thr Ser Glu Leu Thr Met Leu Pro Phe Lys Lys Gly Ala Phe<br>160                            165                          170                          175 | |
| cat ttg gcc cag cag gga aag atc cct atc gtc cca gtg gtt gtg tct<br>His Leu Ala Gln Gln Gly Lys Ile Pro Ile Val Pro Val Val Val Ser<br>                            180                          185                          190 | 576 |
| aac act agc acg ctc gtc agc cct aag tac ggt gtg ttc aac cga ggc<br>Asn Thr Ser Thr Leu Val Ser Pro Lys Tyr Gly Val Phe Asn Arg Gly<br>            195                          200                          205 | 624 |
| tgt atg att gtc cga att ctg aag ccc atc tcg act gag aac ctg aca<br>Cys Met Ile Val Arg Ile Leu Lys Pro Ile Ser Thr Glu Asn Leu Thr<br>                  210                          215                          220 | 672 |
| aaa gat aag att ggc gag ttc gct gag aaa gtg cga gat cag atg gtt<br>Lys Asp Lys Ile Gly Glu Phe Ala Glu Lys Val Arg Asp Gln Met Val<br>225                          230                          235 | 720 |
| gac aca ctg aag gaa atc ggt tat tcc ccc gca atc aac gac acc acc<br>Asp Thr Leu Lys Glu Ile Gly Tyr Ser Pro Ala Ile Asn Asp Thr Thr<br>240                          245                          250                          255 | 768 |
| ctt cct ccg cag gca att gag tac gcc gca ttg cag cat gac aag aag<br>Leu Pro Pro Gln Ala Ile Glu Tyr Ala Ala Leu Gln His Asp Lys Lys<br>                  260                          265                          270 | 816 |
| gtg aac aaa aag att aag aac gaa cct gtt cca tcg gtg tcc att tct<br>Val Asn Lys Lys Ile Lys Asn Glu Pro Val Pro Ser Val Ser Ile Ser<br>275                          280                          285 | 864 |
| aat gat gtg aat act cac aac gaa gga tcg tct gtc aag aag atg cac<br>Asn Asp Val Asn Thr His Asn Glu Gly Ser Ser Val Lys Lys Met His<br>            290                          295                          300 | 912 |
| tag gcggccgcat g | 926 |

<210> SEQ ID NO 97
<211> LENGTH: 303
<212> TYPE: PRT
<213> ORGANISM: Saccharomyces cerevisiae

<400> SEQUENCE: 97

Met Ser Val Ile Gly Arg Phe Leu Tyr Tyr Leu Arg Ser Val Leu Val
1                        5                          10                          15

Val Leu Ala Leu Ala Gly Cys Gly Phe Tyr Gly Val Ile Ala Ser Ile
                  20                          25                          30

Leu Cys Thr Leu Ile Gly Lys Gln His Leu Ala Gln Trp Ile Thr Ala
            35                          40                          45

Arg Cys Phe Tyr His Val Met Lys Leu Met Leu Gly Leu Asp Val Lys
    50                          55                          60

Val Val Gly Glu Glu Asn Leu Ala Lys Lys Pro Tyr Ile Met Ile Ala
65                        70                          75                          80

Asn His Gln Ser Thr Leu Asp Ile Phe Met Leu Gly Arg Ile Phe Pro
                  85                          90                          95

Pro Gly Cys Thr Val Thr Ala Lys Lys Ser Leu Lys Tyr Val Pro Phe
                100                        105                        110

Leu Gly Trp Phe Met Ala Leu Ser Gly Thr Tyr Phe Leu Asp Arg Ser
          115                        120                        125

Lys Arg Gln Glu Ala Ile Asp Thr Leu Asn Lys Gly Leu Glu Asn Val
    130                        135                        140

Lys Lys Asn Lys Arg Ala Leu Trp Val Phe Pro Glu Gly Thr Arg Ser
145                        150                          155                        160

Tyr Thr Ser Glu Leu Thr Met Leu Pro Phe Lys Lys Gly Ala Phe His
                165                        170                        175

Leu Ala Gln Gln Gly Lys Ile Pro Ile Val Pro Val Val Val Ser Asn

```
                    180                 185                 190
Thr Ser Thr Leu Val Ser Pro Lys Tyr Gly Val Phe Asn Arg Gly Cys
                195                 200                 205

Met Ile Val Arg Ile Leu Lys Pro Ile Ser Thr Glu Asn Leu Thr Lys
            210                 215                 220

Asp Lys Ile Gly Glu Phe Ala Glu Lys Val Arg Asp Gln Met Val Asp
225                 230                 235                 240

Thr Leu Lys Glu Ile Gly Tyr Ser Pro Ala Ile Asn Asp Thr Thr Leu
                245                 250                 255

Pro Pro Gln Ala Ile Glu Tyr Ala Ala Leu Gln His Asp Lys Lys Val
            260                 265                 270

Asn Lys Lys Ile Lys Asn Glu Pro Val Pro Ser Val Ser Ile Ser Asn
        275                 280                 285

Asp Val Asn Thr His Asn Glu Gly Ser Ser Val Lys Lys Met His
    290                 295                 300

<210> SEQ ID NO 98
<211> LENGTH: 32
<212> TYPE: DNA
<213> ORGANISM: Artificial Sequence
<220> FEATURE:
<223> OTHER INFORMATION: Primer 869

<400> SEQUENCE: 98
acttggcgcg ccactgccga gatccagtct ac                                    32

<210> SEQ ID NO 99
<211> LENGTH: 28
<212> TYPE: DNA
<213> ORGANISM: Artificial Sequence
<220> FEATURE:
<223> OTHER INFORMATION: Primer 870

<400> SEQUENCE: 99
tcagcctagg agcatccgtt gatttccg                                          28

<210> SEQ ID NO 100
<211> LENGTH: 7891
<212> TYPE: DNA
<213> ORGANISM: Artificial Sequence
<220> FEATURE:
<223> OTHER INFORMATION: Plasmid pY222

<400> SEQUENCE: 100
tcgaccgtac gatagttagt agacaacaat cgatagttgg agcaagggag aaatgtagag      60
tgtgaaagac tcactatggt ccgggcttat ctcgaccaat agccaaagtc tggagtttct     120
gagagaaaaa ggcaagatac gtatgtaaca aagcgacgca tggtacaata ataccggagg     180
catgtatcat agagagttag tggttcgatg atggcactgg tgcctggtat gactttatac     240
ggctgactac atatttgtcc tcagacatac aattacagtc aagcacttac ccttggacat     300
ctgtaggtac cccccggcca agacgatctc agcgtgtcgt atgtcggatt ggcgtagctc     360
cctcgctcgt caattggctc ccatctactt tcttctgctt ggctacaccc agcatgtctg     420
ctatggctcg ttttcgtgcc ttatctatcc tcccagtatt accaactcta atgacatga     480 tgtgattggg tctacacttt catatcagag ataaggagta gcacagttgc ataaaaagcc     540
caactctaat cagcttcttc ctttcttgta attagtacaa aggtgattag cgaaatctgg     600
aagcttagtt ggccctaaaa aaatcaaaaa agcaaaaaa cgaaaaacga aaaccacag      660
```

```
ttttgagaac agggaggtaa cgaaggatcg tatatatata tatatatata tatacccacg    720
gatcccgaga ccggcctttg attcttccct acaaccaacc attctcacca ccctaattca    780
caaccatgtc tgttattgga cgatttcttt actacctgag atcggtgctc gtcgttttgg    840
ccctcgctgg atgtggcttc tatggcgtga ttgcctctat cctgtgtact ctcatcggca    900
agcagcatct cgcgcaatgg attaccgccc gatgctttta ccacgtgatg aaactgatgc    960
tgggattgga cgtcaaagtc gtgggtgaag agaacctggc taagaagccc tatatcatga   1020
tcgctaacca ccagtccacc ctcgatatct ttatgctcgg cagaatcttc cctcccggat   1080
gcaccgttac cgcaaagaag agccttaagt acgtcccctt cctgggctgg tttatggcgc   1140
tttccggtac atacttcctc gaccgttcca agcggcaaga ggctattgat accctgaaca   1200
aaggactgga gaacgtcaaa aagaataagc gagccctctg gttttttccc gaaggtaccc   1260
ggtcttacac gtcggagctt accatgctgc cgttcaagaa gggcgccttt catttggccc   1320
agcagggaaa gatccctatc gtcccagtgg ttgtgtctaa cactagcacg ctcgtcagcc   1380
ctaagtacgg tgtgttcaac cgaggctgta tgattgtccg aattctgaag cccatctcga   1440
ctgagaacct gacaaaagat aagattggcg agttcgctga gaaagtgcga gatcagatgg   1500
ttgacacact gaaggaaatc ggttattccc ccgcaatcaa cgacaccacc cttcctccgc   1560
aggcaattga gtacgccgca ttgcagcatg acaagaaggt gaacaaaaag attaagaacg   1620
aacctgttcc atcggtgtcc atttctaatg atgtgaatac tcacaacgaa ggatcgtctg   1680
tcaagaagat gcactaggcg gccgcatgag aagataaata tataaataca ttgagatatt   1740
aaatgcgcta gattagagag cctcatactg ctcggagaga agccaagacg agtactcaaa   1800
ggggattaca ccatccatat ccacagacac aagctgggga aaggttctat atacactttc   1860
cggaataccg tagtttccga tgttatcaat ggggcagcc aggatttcag gcacttcggt   1920
gtctcggggt gaaatggcgt tcttggcctc catcaagtcg taccatgtct tcatttgcct   1980
gtcaaagtaa aacagaagca gatgaagaat gaacttgaag tgaaggaatt taaatgtaac   2040
gaaactgaaa tttgaccaga tattgtgtcc gcggtggagc tccagctttt gttccctta   2100
gtgagggtta atttcgagct tggcgtaatc atggtcatag ctgtttcctg tgtgaaattg   2160
ttatccgctc acaagcttcc acacaacgta cgagccggaa gcataaagtg taaagcctgg   2220
ggtgcctaat gagtgagcta actcacatta ttgcgttgc gctcactgcc cgcttttccag   2280
tcgggaaacc tgtcgtgcca gctgcattaa tgaatcggcc aacgcgcggg gagaggcggt   2340
ttgcgtattg ggcgctcttc cgcttcctcg ctcactgact cgctgcgctc ggtcgttcgg   2400
ctgcggcgag cggtatcagc tcactcaaag gcggtaatac ggttatccac agaatcaggg   2460
gataacgcag gaaagaacat gtgagcaaaa ggccagcaaa aggccaggaa ccgtaaaaag   2520
gccgcgttgc tggcgttttt ccataggctc cgcccccctg acgagcatca caaaaatcga   2580
cgctcaagtc agaggtggcg aaacccgaca ggactataaa gataccaggc gtttccccct   2640
ggaagctccc tcgtgcgctc tcctgttccg accctgccgc ttaccggata cctgtccgcc   2700
tttctccctt cggaagcgt ggcgctttct catagctcac gctgtaggta tctcagttcg   2760
gtgtaggtcg ttcgctccaa gctgggctgt gtgcacgaac cccccgttca gcccgaccgc   2820
tgcgccttat ccggtaacta tcgtcttgag tccaacccgg taagacacga cttatcgcca   2880
ctggcagcag ccactggtaa caggattagc agagcgaggt atgtaggcgg tgctacagag   2940
ttcttgaagt ggtggcctaa ctacggctac actagaagga cagtatttgg tatctgcgct   3000
ctgctgaagc cagttacctt cggaaaaaga gttggtagct cttgatccgg caaacaaacc   3060
```

```
accgctggta gcggtggttt ttttgtttgc aagcagcaga ttacgcgcag aaaaaaagga    3120
tctcaagaag atcctttgat cttttctacg gggtctgacg ctcagtggaa cgaaaactca    3180
cgttaaggga ttttggtcat gagattatca aaaggatctt caacctagat cttttaaat    3240
taaaaatgaa gttttaaatc aatctaaagt atatatgagt aaacttggtc tgacagttac    3300
caatgcttaa tcagtgaggc acctatctca gcgatctgtc tatttcgttc atccatagtt    3360
gcctgactcc ccgtcgtgta gataactacg atacgggagg gcttaccatc tggccccagt    3420
gctgcaatga taccgcgaga cccacgctca ccggctccag atttatcagc aataaaccag    3480
ccagccggaa gggccgagcg cagaagtggt cctgcaactt tatccgcctc catccagtct    3540
attaattgtt gccgggaagc tagagtaagt agttcgccag ttaatagttt gcgcaacgtt    3600
gttgccattg ctacaggcat cgtggtgtca cgctcgtcgt ttggtatggc ttcattcagc    3660
tccggttccc aacgatcaag gcgagttaca tgatccccca tgttgtgcaa aaaagcggtt    3720
agctccttcg gtcctccgat cgttgtcaga agtaagttgg ccgcagtgtt atcactcatg    3780
gttatggcag cactgcataa ttctcttact gtcatgccat ccgtaagatg cttttctgtg    3840
actggtgagt actcaaccaa gtcattctga gaatagtgta tgcggcgacc gagttgctct    3900
tgcccggcgt caatacggga taataccgcg ccacatagca gaactttaaa agtgctcatc    3960
attggaaaac gttcttcggg gcgaaaactc tcaaggatct taccgctgtt gagatccagt    4020
tcgatgtaac ccactcgtgc acccaactga tcttcagcat cttttacttt caccagcgtt    4080
tctgggtgag caaaaacagg aaggcaaaat gccgcaaaaa agggaataag ggcgacacgg    4140
aaatgttgaa tactcatact cttccttttt caatattatt gaagcattta tcagggttat    4200
tgtctcatga gcggatacat atttgaatgt atttagaaaa ataaacaaat aggggttccg    4260
cgcacatttc cccgaaaagt gccacctgac gcgccctgta gcggcgcatt aagcgcggcg    4320
ggtgtggtgg ttacgcgcag cgtgaccgct acacttgcca gcgccctagc gcccgctcct    4380
ttcgctttct tcccttcctt tctcgccacg ttcgccggct ttccccgtca gctctaaat    4440
cgggggctcc ctttagggtt ccgatttagt gctttacggc acctcgaccc caaaaaactt    4500
gattagggtg atggttcacg tagtgggcca tcgccctgat agacggtttt tcgccctttg    4560
acgttggagt ccacgttctt taatagtgga ctcttgttcc aaactggaac aacactcaac    4620
cctatctcgg tctattcttt tgatttataa gggattttgc cgatttcggc ctattggtta    4680
aaaaatgagc tgatttaaca aaaatttaac gcgaattta caaaatatt aacgcttaca    4740
atttccattc gccattcagg ctgcgcaact gttgggaagg gcgatcggtg cgggcctctt    4800
cgctattacg ccagctggcg aaagggggat gtgctgcaag gcgattaagt tgggtaacgc    4860
cagggttttc ccagtcacga cgttgtaaaa cgacggccag tgaattgtaa tacgactcac    4920
tatagggcga attgggtacc gggccccccc tcgaggtcga tggtgtcgat aagcttgata    4980
tcgaattcat gtcacacaaa ccgatcttcg cctcaaggaa acctaattct acatccgaga    5040
gactgccgag atccagtcta cactgattaa ttttcgggcc aataatttaa aaaaatcgtg    5100
ttatataata ttatatgtat tatatatata catcatgatg atactgacag tcatgtccca    5160
ttgctaaata gacagactcc atctgccgcc tccaactgat gttctcaata tttaaggggt    5220
catctcgcat tgtttaataa taaacagact ccatctaccg cctccaaatg atgttctcaa    5280
aatatattgt atgaacttat ttttattact tagtattatt agacaactta cttgctttat    5340
gaaaaacact tcctatttag gaaacaattt ataatggcag ttcgttcatt taacaattta    5400
```

```
tgtagaataa atgttataaa tgcgtatggg aaatcttaaa tatggatagc ataaatgata    5460
tctgcattgc ctaattcgaa atcaacagca acgaaaaaaa tcccttgtac aacataaata    5520
gtcatcgaga aatatcaact atcaaagaac agctattcac acgttactat tgagattatt    5580
attggacgag aatcacacac tcaactgtct ttctctcttc tagaaataca ggtacaagta    5640
tgtactattc tcattgttca tacttctagt catttcatcc cacatattcc ttggatttct    5700
ctccaatgaa tgacattcta tcttgcaaat tcaacaatta taataagata taccaaagta    5760
gcggtatagt ggcaatcaaa aagcttctct ggtgtgcttc tcgtatttat ttttattcta    5820
atgatccatt aaaggtatat atttatttct tgttatataa tccttttgtt tattacatgg    5880
gctggataca taaaggtatt tgatttaat ttttttgctta aattcaatcc cccctcgttc    5940
agtgtcaact gtaatggtag gaaattacca tacttttgaa gaagcaaaaa aaatgaaaga    6000
aaaaaaaaat cgtatttcca ggttagacgt tccgcagaat ctagaatgcg gtatgcggta    6060
cattgttctt cgaacgtaaa agttgcgctc cctgagatat tgtacatttt tgcttttaca    6120
agtacaagta catcgtacaa ctatgtacta ctgttgatgc atccacaaca gtttgttttg    6180
tttttttttg ttttttttttt ttctaatgat tcattaccgc tatgtatacc tacttgtact    6240
tgtagtaagc cggttattg gcgttcaatt aatcatagac ttatgaatct gcacggtgtg    6300
cgctgcgagt tacttttagc ttatgcatgc tacttgggtg taatattggg atctgttcgg    6360
aaatcaacgg atgctcaatc gatttcgaca gtaattaatt aagtcataca caagtcagct    6420
ttcttcgagc ctcatataag tataagtagt tcaacgtatt agcactgtac ccagcatctc    6480
cgtatcgaga aacacaacaa catgcccccat tggacagatc atgcggatac acaggttgtg    6540
cagtatcata catactcgat cagacaggtc gtctgaccat catacaagct gaacaagcgc    6600
tccatacttg cacgctctct atatacacag ttaaattaca tatccatagt ctaacctcta    6660
acagttaatc ttctggtaag cctcccagcc agccttctgg tatcgcttgg cctcctcaat    6720
aggatctcgg ttctggccgt acagaccctcg gccgacaatt atgatatccg ttccggtaga    6780
catgacatcc tcaacagttc ggtactgctg tccgagagcg tctcccttgt cgtcaagacc    6840 cacccccgggg gtcagaataa gccagtcctc agagtcgccc ttaggtcggt tctgggcaat    6900
gaagccaacc acaaactcgg ggtcggatcg ggcaagctca atggtctgct tggagtactc    6960
gccagtggcc agagagccct tgcaagacag ctcggccagc atgagcagac ctctggccag    7020
cttctcgttg ggagagggga ctaggaactc cttgtactgg gagttctcgt agtcagagac    7080
gtcctccttc ttctgttcag agacagtttc ctcggcacca gctcgcaggc cagcaatgat    7140
tccggttccg ggtacaccgt gggcgttggt gatatcggac cactcggcga ttcggtgaca    7200
ccggtactgg tgcttgacag tgttgccaat atctgcgaac tttctgtcct cgaacaggaa    7260
gaaaccgtgc ttaagagcaa gttccttgag ggggagcaca gtgccggcgt aggtgaagtc    7320
gtcaatgatg tcgatatggg ttttgatcat gcacacataa ggtccgacct tatcggcaag    7380
ctcaatgagc tccttggtgg tggtaacatc cagagaagca cacaggttgg ttttcttggc    7440
tgccacgagc ttgagcactc gagcggcaaa ggcggacttg tggacgttag ctcgagcttc    7500
gtaggagggc attttggtgg tgaagaggag actgaaataa atttagtctg cagaactttt    7560
tatcggaacc ttatctgggg cagtgaagta tatgttatgg taatagttac gagttagttg    7620
aacttataga tagactggac tatacggcta tcggtccaaa ttagaaagaa cgtcaatggc    7680
tctctgggcg tcgcctttgc cgacaaaaat gtgatcatga tgaaagccag caatgacgtt    7740
gcagctgata ttgttgtcgg ccaaccgcgc cgaaaacgca gctgtcagac ccacagcctc    7800
```

| | |
|---|---|
| caacgaagaa tgtatcgtca aagtgatcca agcacactca tagttggagt cgtactccaa | 7860 |
| aggcggcaat gacgagtcag acagatactc g | 7891 |

<210> SEQ ID NO 101
<211> LENGTH: 9598
<212> TYPE: DNA
<213> ORGANISM: Artificial Sequence
<220> FEATURE:
<223> OTHER INFORMATION: Plasmid pY177

<400> SEQUENCE: 101

| | |
|---|---|
| gtacgataac ttcgtatagc atacattata cgaagttatc gcgtcgacga gtatctgtct | 60 |
| gactcgtcat tgccgccttt ggagtacgac tccaactatg agtgtgcttg atcactttg | 120 |
| acgatacatt cttcgttgga ggctgtgggt ctgacagctg cgttttcggc gcggttggcc | 180 |
| gacaacaata tcagctgcaa cgtcattgct ggctttcatc atgatcacat ttttgtcggc | 240 |
| aaaggcgacg cccagagagc cattgacgtt ctttctaatt tggaccgata gccgtatagt | 300 |
| ccagtctatc tataagttca actaactcgt aactattacc ataacatata cttcactgcc | 360 |
| ccagataagg ttccgataaa aagttctgca gactaaattt atttcagtct cctcttcacc | 420 |
| accaaaatgc cctcctacga agctcgagct aacgtccaca agtccgcctt tgccgctcga | 480 |
| gtgctcaagc tcgtggcagc caagaaaacc aacctgtgtg cttctctgga tgttaccacc | 540 |
| accaaggagc tcattgagct tgccgataag gtcggacctt atgtgtgcat gatcaaaacc | 600 |
| catatcgaca tcattgacga cttcacctac gccggcactg tgctcccct caaggaactt | 660 |
| gctcttaagc acggtttctt cctgttcgag gacagaaagt tcgcagatat tggcaacact | 720 |
| gtcaagcacc agtaccggtg tcaccgaatc gccgagtggt ccgatatcac caacgcccac | 780 |
| ggtgtacccg gaaccggaat cattgctggc ctgcgagctg gtgccgagga aactgtctct | 840 |
| gaacagaaga aggaggacgt ctctgactac gagaactccc agtacaagga gttcctagtc | 900 |
| ccctctccca acgagaagct ggccagaggt ctgctcatgc tggccgagct gtcttgcaag | 960 |
| ggctctctgg ccactggcga gtactccaag cagaccattg agcttgcccg atccgacccc | 1020 |
| gagtttgtgg ttggcttcat tgcccagaac cgacctaagg gcgactctga ggactggctt | 1080 |
| attctgaccc ccggggtggg tcttgacgac aagggagacg ctctcggaca gcagtaccga | 1140 |
| actgttgagg atgtcatgtc taccggaacg gatatcataa ttgtcggccg aggtctgtac | 1200 |
| ggccagaacc gagatcctat tgaggaggcc aagcgatacc agaaggctgg ctgggaggct | 1260 |
| taccagaaga ttaactgtta gaggttagac tatggatatg taatttaact gtgtatatag | 1320 |
| agagcgtgca agtatggagc gcttgttcag cttgtatgat ggtcagacga cctgtctgat | 1380 |
| cgagtatgta tgatactgca caacctgtgt atccgcatga tctgtccaat ggggcatgtt | 1440 |
| gttgtgtttc tcgatacgga gatgctgggt acagtgctaa tacgttgaac tacttatact | 1500 |
| tatatgaggc tcgaagaaag ctgacttgtg tatgacttat tctcaactac atccccagtc | 1560 |
| acaataccac cactgcacta ccactacacc aaaaccatga tcaaaccacc catggacttc | 1620 |
| ctggaggcag aagaacttgt tatggaaaag ctcaagagag agatcataac ttcgtatagc | 1680 |
| atacattata cgaagttatc ctgcaggtaa aggaattcag agagaccggg ttggcggcg | 1740 |
| tatttgtgtc ccaaaaaaca gccccaattg ccccaattga ccccaaattg acccagtagc | 1800 |
| gggcccaacc ccgcgagag ccccccttcac cccacatatc aaacctcccc cggttcccac | 1860 |
| acttgccgtt aagggcgtag ggtactgcag tctggaatct acgcttgttc agactttgta | 1920 |

```
ctagtttctt tgtctggcca tccgggtaac ccatgccgga cgcaaaatag actactgaaa    1980
atttttttgc tttgtggttg ggactttagc caagggtata aaagaccacc gtccccgaat    2040
tacctttcct cttcttttct ctctctcctt gtcaactcac acccgaaatc gttaagcatt    2100
tccttctgag tataagaatc attccacatg gacttcctgg aggcagaaga acttgttatg    2160
gaaaagctca agagagagaa gccaagatac tatcaagaca tgtgtcgcaa cttaattaag    2220
atgacgacat tgcgagctg acgaggaat agatggagcg tgtgttctga gtcgatgttt    2280
tctatggagt tgtgagtgtt agtagacatg atgggtttat atatgatgaa tgaatagatg    2340
tgattttgat ttgcacgatg gaattgagaa ctttgtaaac gtacatggga atgtatgaat    2400
gtggggtttt tgtgactgga taactgacgg tcagtggacg ccgttgttca aatatccaag    2460
agatgcgaga aactttgggt caagtgaaca tgtcctctct gttcaagtaa accatcaact    2520
atgggtagta tatttagtaa ggacaagagt tgagattctt tggagtccta gaaacgtatt    2580
ttcgcgttcc aagatcaaat tagtagagta atacgggcac gggaatccat tcatagtctc    2640
aattttccca taggtgtgct acaaggtgtt gagatgtggt acagtaccac catgattcga    2700
ggtaaagagc ccagaagtca ttgatgaggt caagaaatac acagatctac agctcaatac    2760
aatgaatatc ttctttcata ttcttcaggt gacaccaagg gtgtctattt tccccagaaa    2820
tgcgtgaaaa ggcgcgtgtg tagcgtggag tatgggttcg gttggcgtat ccttcatata    2880
tcgacgaaat agtagggcaa gagatgacaa aaagtatcta tatgtagaca gcgtagaata    2940
tggatttgat tggtataaat tcatttattg cgtgtctcac aaatactctc gataagttgg    3000
ggttaaactg gagatggaac aatgtcgata tctcgacgca tgcgacgtcg ggcccaattc    3060
gccctatagt gagtcgtatt acaattcact ggccgtcgtt ttacaacgtc gtgactggga    3120
aaaccctggc gttacccaac ttaatcgcct tgcagcacat ccccctttcg ccagctggcg    3180
taatagcgaa gaggcccgca ccgatcgccc ttcccaacag ttgcgcagcc tgaatggcga    3240
atggacgcgc cctgtagcgg cgcattaagc gcggcgggtg tggtggttac gcgcagcgtg    3300
accgctacac ttgccagcgc cctagcgccc gctccttttcg ctttcttccc ttcctttctc    3360
gccacgttcg ccggctttcc ccgtcaagct ctaaatcggg ggctcccttt agggttccga    3420
tttagtgctt tacggcacct cgaccccaaa aaacttgatt agggtgatgg ttcacgtagt    3480
gggccatcgc cctgatagac ggttttttcgc cctttgacgt tggagtccac gttctttaat    3540
agtggactct tgttccaaac tggaacaaca ctcaacccta tctcggtcta ttcttttgat    3600
ttataaggga ttttgccgat ttcggcctat tggttaaaaa atgagctgat ttaacaaaaa    3660
tttaacgcga atttaacaa aatattaacg cttacaattt cctgatgcgg tatttctcc    3720
ttacgcatct gtgcggtatt tcacaccgca tcaggtggca cttttcgggg aaatgtgcgc    3780
ggaacccta tttgtttatt tttctaaata cattcaaata tgtatccgct catgagacaa    3840
taaccctgat aaatgcttca ataatattga aaaggaaga gtatgagtat tcaacatttc    3900
cgtgtcgccc ttattccctt ttttgcggca ttttgccttc ctgtttttgc tcacccagaa    3960
acgctggtga agtaaaaga tgctgaagat cagttgggtg cacgagtggg ttacatcgaa    4020
ctggatctca acagcggtaa gatccttgag agttttcgcc ccgaagaacg ttttccaatg    4080
atgagcactt ttaaagttct gctatgtggc gcggtattat cccgtattga cgccgggcaa    4140
gagcaactcg gtcgccgcat acactattct cagaatgact tggttgagta ctcaccagtc    4200
acagaaaagc atcttacgga tggcatgaca gtaagagaat tatgcagtgc tgccataacc    4260
atgagtgata acactgcggc caacttactt ctgacaacga tcggaggacc gaaggagcta    4320
```

```
accgcttttt tgcacaacat gggggatcat gtaactcgcc ttgatcgttg ggaaccggag    4380
ctgaatgaag ccataccaaa cgacgagcgt gacaccacga tgcctgtagc aatggcaaca    4440
acgttgcgca aactattaac tggcgaacta cttactctag cttcccggca acaattaata    4500
gactggatgg aggcggataa agttgcagga ccacttctgc gctcggccct tccggctggc    4560
tggtttattg ctgataaatc tggagccggt gagcgtgggt ctcgcggtat cattgcagca    4620
ctggggccag atggtaagcc ctcccgtatc gtagttatct acacgacggg gagtcaggca    4680
actatggatg aacgaaatag acagatcgct gagataggtg cctcactgat taagcattgg    4740
taactgtcag accaagttta ctcatatata ctttagattg atttaaaact tcattttaa    4800 tttaaaagga tctaggtgaa gatcctttt gataatctca tgaccaaaat cccttaacgt    4860
gagttttcgt tccactgagc gtcagacccc gtagaaaaga tcaaaggatc ttcttgagat    4920
cctttttttc tgcgcgtaat ctgctgcttg caaacaaaaa aaccaccgct accagcggtg    4980
gtttgtttgc cggatcaaga gctaccaact cttttcccga aggtaactgg cttcagcaga    5040
gcgcagatac caaatactgt tcttctagtg tagccgtagt taggccacca cttcaagaac    5100
tctgtagcac cgcctacata cctcgctctg ctaatcctgt taccagtggc tgctgccagt    5160
ggcgataagt cgtgtcttac cgggttggac tcaagacgat agttaccgga taaggcgcag    5220
cggtcgggct gaacgggggg ttcgtgcaca cagcccagct tggagcgaac gacctacacc    5280
gaactgagat acctacagcg tgagctatga gaaagcgcca cgcttcccga agggagaaag    5340
gcggacaggt atccggtaag cggcagggtc ggaacaggag agcgcacgag ggagcttcca    5400
gggggaaacg cctggtatct ttatagtcct gtcgggtttc gccacctctg acttgagcgt    5460
cgatttttgt gatgctcgtc aggggggcgg agcctatgga aaaacgccag caacgcggcc    5520 ttttttacggt tcctggcctt tgctggcct tttgctcaca tgttctttcc tgcgttatcc    5580
cctgattctg tggataaccg tattaccgcc tttgagtgag ctgataccgc tcgccgcagc    5640
cgaacgaccg agcgcagcga gtcagtgagc gaggaagcgg aagagcgccc aatacgcaaa    5700
ccgcctctcc ccgcgcgttg gccgattcat taatgcagct ggcgcgccac tgccgagatc    5760
cagtctacac tgattaattt tcgggccaat aatttaaaaa aatcgtgtta tataatatta    5820
tatgtattat atatatacat catgatgata ctgacagtca tgtcccattg ctaaatagac    5880
agactccatc tgccgcctcc aactgatgtt ctcaatattt aaggggtcat ctcgcattgt    5940
ttaataataa acagactcca tctaccgcct ccaaatgatg ttctcaaaat atattgtatg    6000
aacttatttt tattacttag tattattaga caacttactt gctttatgaa aaacacttcc    6060
tatttaggaa acaatttata atggcagttc gttcatttaa caatttatgt agaataaatg    6120
ttataaatgc gtatgggaaa tcttaaatat ggatagcata aatgatatct gcattgccta    6180
attcgaaatc aacagcaacg aaaaaaatcc cttgtacaac ataaatagtc atcgagaaat    6240
atcaactatc aaagaacagc tattcacacg ttactattga gattattatt ggacgagaat    6300
cacacactca actgtctttc tctcttctag aaatacaggt acaagtatgt actattctca    6360
ttgttcatac ttctagtcat ttcatcccac atattccttg gatttctctc caatgaatga    6420
cattctatct tgcaaattca acaattataa taagatatac caaagtagcg gtatagtggc    6480
aatcaaaaag cttctctggt gtgcttctcg tatttatttt tattctaatg atccattaaa    6540
ggtatatatt tatttcttgt tatataatcc ttttgtttat tacatgggct ggatacataa    6600
aggtattttg atttaatttt ttgcttaaat tcaatcccc ctcgttcagt gtcaactgta    6660
```

```
atggtaggaa attaccatac ttttgaagaa gcaaaaaaaa tgaaagaaaa aaaaaatcgt    6720
atttccaggt tagacgttcc gcagaatcta gaatgcggta tgcggtacat tgttcttcga    6780
acgtaaaagt tgcgctccct gagatattgt acattttgc ttttacaagt acaagtacat    6840
cgtacaacta tgtactactg ttgatgcatc cacaacagtt tgttttgttt tttttttgttt   6900 ttttttttc taatgattca ttaccgctat gtatacctac ttgtacttgt agtaagccgg    6960
gttattggcg ttcaattaat catagactta tgaatctgca cggtgtgcgc tgcgagttac    7020
ttttagctta tgcatgctac ttgggtgtaa tattgggatc tgttcggaaa tcaacggatg    7080
ctcctaggtt cccaaaatcc cagatgcttc tctccagtgc caaaagtaag taccccacag    7140
gttttcggcc gaaaattcca cgtgcagcaa cgtcgtgtgg ggtgttaaaa tgtgggggg     7200 gggaaccagg acaagaggct cttgtgggag ccgaatgaga gcacaaagcg ggcgggtgtg   7260
ataagggcat ttttgcccat tttcccttct cctgtctctc cgacggtgat ggcgttgtgc    7320
gtcctctatt tcttttattt tcttttttgtt ttatttctct gactaccgat ttggtttgat   7380
ttcctcaacc ccacacaaat aagctcgggc cgaggaatat atatatacac ggacacagtc   7440
gccctgtgga caacacgtca ctacctctac gatacacacc gtacgatagt tagtagacaa    7500
caatcgatag ttggagcaag ggagaaatgt agagtgtgaa agactcacta tggtccgggc   7560
ttatctcgac caatagccaa agtctggagt ttctgagaga aaaaggcaag atacgtatgt    7620
aacaaagcga cgcatggtac aataataccg gaggcatgta tcatagagag ttagtggttc   7680
gatgatggca ctggtgcctg gtatgacttt atacggctga ctacatattt gtcctcagac    7740
atacaattac agtcaagcac ttacccttgg acatctgtag gtaccccccg gccaagacga    7800
tctcagcgtg tcgtatgtcg gattggcgta gctccctcgc tcgtcaattg gctcccatct    7860
actttcttct gcttggctac acccagcatg tctgctatgg ctcgttttcg tgccttatct    7920
atcctcccag tattaccaac tctaaatgac atgatgtgat tgggtctaca ctttcatatc    7980
agagataagg agtagcacag ttgcataaaa agcccaactc taatcagctt cttccttct    8040 tgtaattagt acaaaggtga ttagcgaaat ctggaagctt agttggccct aaaaaaatca    8100 aaaaagcaa aaaacgaaaa acgaaaaacc acagttttga gaacagggag gtaacgaagg    8160
atcgtatata tatatatata tatatatacc cacggatccc gagaccggcc tttgattctt    8220
ccctacaacc aaccattctc accaccctaa ttcacaacca tgtccgttgc atccaagctc    8280
gtcttctacg tccgcgccgc catcgccgtg gtcatctttg ccgcctgtgc cacctacggc    8340
gtgctggcgt ccaccattct caccgccatc ggcaagcagg gcctggccca atggaccgtt    8400
gccagagcct tctactactc ggtgcgcatc ttcctgggta tcagcatcaa gctgcgtagc    8460
cggcaggtga ccggaaccgc cggtctggat gcctccaaga tccaggtcgc caacaccacc    8520
aagcccattg acgacatcac caaacacctg cccgaccat gcattctgat ttccaaccac    8580
cagaacgaaa tggacattct ggtgctcggt cgcatcttcc cccagtactg ctccgtcacc    8640
gccaaaaagg ccctcaagtg gtaccctctg ctgggccagt tcatggcgct gtccggcacc    8700
atcttcctgg accgaaagga ccgaaccaag tccgtgcaga ccctcggcgg cgccgtcaag    8760
accatccaga gcggcaacgg aggcaagggc cagagcgtct tcatgttccc cgagggaacc    8820
cgatcctact ccaaggacgt cggcatcatg cccttcaaga agggctgttt ccacctggcg    8880
gtccagtcgg gcgctcccat tgtccccgtg gtggtccaga acacctcccg aatgttttct    8940
ttcggccgag gcaagctgga cgccggagag atccttgtcg acgtcctgag ccccattgag    9000
accaagggtc tggacgccag caacgtcgac gctctcatgg ccaccactta taaggccatg    9060
```

```
tgcgagactg ccgaccagat tggctacgct ggccagaaga ctcagtaggc ggccgcatga    9120
gaagataaat atataaatac attgagatat taaatgcgct agattagaga gcctcatact    9180
gctcggagag aagccaagac gagtactcaa aggggattac accatccata tccacagaca    9240
caagctgggg aaaggttcta tatacactttt ccggaatacc gtagtttccg atgttatcaa    9300
tgggggcagc caggatttca ggcacttcgg tgtctcgggg tgaaatggcg ttcttggcct    9360
ccatcaagtc gtaccatgtc ttcatttgcc tgtcaaagta aaacagaagc agatgaagaa    9420
tgaacttgaa gtgaaggaat ttaaatgtaa cgaaactgaa atttgaccag atattgtgtc    9480
cgcggtggag ctccagcttt tgttcccttt agtgagggtt aatttcgagc ttggcgtaat    9540
catggtcata gctgtttcct gtgtgaaatt gttatccgct cacaagcttc cacacaac     9598
```

LONG CHAIN OMEGA-3 AND OMEGA-6 POLYUNSATURATED FATTY ACID BIOSYNTHESIS BY EXPRESSION OF ACYL-COA LYSOPHOSPHOLIPID ACYLTRANSFERASES

This application is a divisional of application Ser. No. 12/814,764 (now U.S. Pat. No. 8,524,485), filed Jun. 14, 2010, which claims the benefit of U.S. Provisional Application Nos. 61/187,366, 61/187,368 and 61/187,359, each filed Jun. 16, 2009. The disclosures of all these prior applications are incorporated herein by reference in their entirety.

FIELD OF THE INVENTION

This invention is in the field of biotechnology. More specifically, this invention pertains to methods for increasing $C_{18}$ to $C_{20}$ elongation conversion efficiency and/or Δ4 desaturation conversion efficiency in long-chain polyunsaturated fatty acid ["LC-PUFA"]-producing recombinant oleaginous microbial host cells, based on over-expression of genes encoding acyl-CoA:lysophospholipid acyltransferases ["LPLATs"].

BACKGROUND OF THE INVENTION

Glycerophospholipids, the main component of biological membranes, contain a glycerol core with fatty acids attached as R groups at the sn-1 position and sn-2 position, and a polar head group joined at the sn-3 position via a phosphodiester bond. The specific polar head group (e.g., phosphatidic acid, chloline, ethanolamine, glycerol, inositol, serine, cardiolipin) determines the name given to a particular glycerophospholipid, thus resulting in phosphatidylcholines ["PC"], phosphatidylethanolamines ["PE"], phosphatidylglycerols ["PG"], phosphatidylinositols ["PI"], phosphatidylserines ["PS"] and cardiolipins ["CL"]. Glycerophospholipids possess tremendous diversity, not only resulting from variable phosphoryl head groups, but also as a result of differing chain lengths and degrees of saturation of their fatty acids. Generally, saturated and monounsaturated fatty acids are esterified at the sn-1 position, while polyunsaturated fatty acids are esterified at the sn-2 position.

Glycerophospholipid biosynthesis is complex. Table 1 below summarizes the steps in the de novo pathway, originally described by Kennedy and Weiss (*J. Biol. Chem.*, 222:193-214 (1956)):

Following their de novo synthesis, glycerophospholipids can undergo rapid turnover of the fatty acyl composition at the sn-2 position. This "remodeling", or "acyl editing", is important for membrane structure and function, biological response to stress conditions, and manipulation of fatty acid composition and quantity in biotechnological applications. Specifically, the remodeling has been attributed to deacylation of the glycerophospholipid and subsequent reacylation of the resulting lysophospholipid.

In the Lands' cycle (Lands, W. E., *J. Biol. Chem.*, 231:883-888 (1958)), remodeling occurs through the concerted action of: 1) a phospholipase, such as phospholipase $A_2$, that releases fatty acids from the sn-2 position of phosphatidylcholine; and, 2) acyl-CoA:lysophospholipid acyltransferases ["LPLATs"], such as lysophosphatidylcholine acyltransferase ["LPCAT"] that reacylates the lysophosphatidylcholine ["LPC"] at the sn-2 position. Other glycerophospholipids can also be involved in the remodeling with their respective lysophospholipid acyltransferase activity, including LPLAT enzymes having lysophosphatidylethanolamine acyltransferase ["LPEAT"] activity, lysophosphatidylserine acyltransferase ["LPLAT"] activity, lysophosphatidylglycerol acyltransferase ["LPGAT"] activity and lysophosphatidylinositol acyltransferase ["LPIAT"] activity. In all cases, LPLATs are responsible for removing acyl-CoA fatty acids from the cellular acyl-CoA pool and acylating various lysophospholipid substrates at the sn-2 position in the phospholipid pool. Finally, LPLATs also include LPAAT enzymes that are involved in the de novo biosynthesis of PA from LPA. LPCAT activity is associated with two structurally distinct protein families, wherein one belongs to the LPAAT family of proteins and the other belongs to the membrane bound O-acyltransferase ["MBOAT"] family of proteins.

In other cases, this sn-2 position remodeling has been attributed to the forward and reverse reactions of enzymes having LPCAT activity (Stymne S. and A. K. Stobart, *Biochem J.*, 223(2):305-314 (1984)).

Several recent reviews by Shindou et al. provide an overview of glycerophospholipid biosynthesis and the role of LPLATs (*J. Biol. Chem.*, 284(1):1-5 (2009); *J. Lipid Res.*, 50:S46-S51 (2009)). Numerous LPLATs have been reported in public and patent literature, based on a variety of conserved motifs.

The effect of LPLATs on polyunsaturated fatty acid ["PUFA"] production has also been contemplated, since fatty acid biosynthesis requires rapid exchange of acyl groups

TABLE 1

General Reactions Of de Novo Glycerophospholipid Biosynthesis

| | |
|---|---|
| sn-Glycerol-3-Phosphate → Lysophosphatidic Acid (1-acyl-sn-glycerol 3-phosphate or "LPA") | Glycerol-3-phosphate acyltransferase (GPAT) [E.C. 2.3.1.15] esterifies 1st acyl-CoA to sn-1 position of sn-glycerol 3-phosphate |
| LPA → Phosphatidic Acid (1,2-diacylglycerol phosphate or "PA") | Lysophosphatidic acid acyltransferase (LPAAT) [E.C. 2.3.1.51] esterifies 2nd acyl-CoA to sn-2 position of LPA |
| PA → 1,2-Diacylglycerol ("DAG") Or PA → Cytidine Diphosphate Diacylglycerol ("CDP-DG") | Phosphatidic acid phosphatase [E.C.3.1.3.4] removes a phosphate from PA; DAG can subsequently be converted to PC, PE or TAG (TAG synthesis requires either a diacylglycerol acyltransferase (DGAT) [E.C. 2.3.1.20] or a phospholipid: diacylglycerol acyltransferase (PDAT) [E.C.2.3.1.158]) CDP-diacylglycerol synthase [EC 2.7.7.41] causes condensation of PA and cytidine triphosphate, with elimination of pyrophosphate; CDP-DG can subsequently be converted to PI, PS, PG or CL | between the acyl-CoA pool and the phospholipid pool. Specifically, desaturations occur mainly at the sn-2 position of phospholipids, while elongation occurs in the acyl-CoA pool. For example, Intl. App. Pub. No. WO 2004/076617 describes the isolation of an LPCAT from *Caenorhabditis elegans* (clone T06E8.1) and reports increase in the efficiency of Δ6 desaturation and Δ6 elongation, as well as an increase in biosynthesis of the long-chain PUFAs eicosadienoic acid ["EDA"; 20:2] and eicosatetraenoic acid ["ETA"; 20:4], respectively, when the LPCAT was expressed in an engineered strain of *Saccharomyces cerevisiae* that was fed exogenous 18:2 or α-linolenic ["ALA"; 18:3] fatty acids, respectively.

Furthermore, Example 16 of Intl. App. Pub. No. WO 2004/087902 describes the isolation of *Mortierella alpina* LPAAT-like proteins (encoded by the proteins of SEQ ID NO:93 and SEQ ID NO:95, having 417 amino acids in length or 389 amino acids in length, respectively) that are identical except for an N-terminal extension of 28 amino acid residues in SEQ ID NO:93. Intl. App. Pub. No. WO 2004/087902 also reports expression of one of these proteins using similar methods to those of Intl. App. Pub. No. WO 2004/076617, which results in similar improvements in EDA and ETA biosynthesis.

Both Intl. App. Publications No. WO 2004/076617 and No. WO 2004/087902 teach that the improvements in EDA and ETA biosynthesis are due to reversible LPCAT activity in some LPAAT-like proteins, although not all LPAAT-like proteins have LPCAT activity. They do not teach that LPCAT expression would result in the improvements in strains that do not require exogenous feeding of fatty acid substrates or in microbial species other than *Saccharomyces cerevisiae*. They also do not teach that LPCAT expression in engineered microbes results in increased production of high LC-PUFAs other than EDA and ETA, such as ARA, EPA and DHA, or that LPCAT expression can result in improvement in alternate desaturation reactions, other than Δ6 desaturation. Neither reference teaches the effect of the LPCAT or LPAAT-like proteins on either Δ6 elongation without exogenous feeding of fatty acids or on Δ4 desaturation.

Numerous other references generally describe benefits of co-expressing LPLATs with PUFA biosynthetic genes, to increase the amount of a desired fatty acid in the oil of a transgenic organism, increase total oil content or selectively increase the content of desired fatty acids (e.g., Intl. App. Publications No. WO 2004/087902, No. WO 2006/069936, No. WO 2006/052870, No. WO 2009/001315, No. WO 2009/014140).

Despite the work describe above, to date no one has studied the effect of LPAATs and LPCATs in an oleaginous organism engineered for high-level production of LC-PUFAs other than EDA and ETA, such as eicosapentaenoic acid ["EPA"; cis-5,8,11,14,17-eicosapentaenoic acid] and/or docosahexaenoic acid ["DHA"; cis-4,7,10,13,16,19-docosahexaenoic acid] and for improved $C_{18}$ to $C_{20}$ elongation conversion efficiency, and/or improved Δ4 desaturation conversion efficiency without exogenously feeding fatty acids.

SUMMARY OF THE INVENTION

In one embodiment, the invention concerns a recombinant oleaginous microbial host cell for the improved production of at least one long-chain polyunsaturated fatty acid, said host cell comprising at least one isolated polynucleotide encoding a polypeptide having at least acyl-CoA:lysophospholipid acyltransferase activity wherein the polypeptide is selected from the group consisting of:

(i) a polypeptide having at least 45% amino acid identity, based on the Clustal W method of alignment, when compared to an amino acid sequence selected from the group consisting of SEQ ID NO:9 and SEQ ID NO:11;

(ii) a polypeptide having at least one membrane bound O-acyltransferase protein family motif selected from the group consisting of: SEQ ID NO:3, SEQ ID NO:4, SEQ ID NO:5 and SEQ ID NO:28;

(iii) a polypeptide having at least 90% amino acid identity, based on the Clustal W method of alignment, when compared to an amino acid sequence as set forth in SEQ ID NO:2;

(iv) a polypeptide having at least 43.9% amino acid identity, based on the Clustal W method of alignment, when compared to an amino acid sequence selected from the group consisting of SEQ ID NO:15, SEQ ID NO:17 and SEQ ID NO:18; and, (v) a polypeptide having at least one 1-acyl-sn-glycerol-3-phosphate acyltransferase family motif selected from the group consisting of: SEQ ID NO:19 and SEQ ID NO:20;

wherein the at least one isolated polynucleotide encoding a polypeptide having at least acyl-CoA:lysophospholipid acyltransferase activity is operably linked to at least one regulatory sequence, said regulatory sequence being the same or different, and further wherein the host cell has at least one improvement selected from the group consisting of:

a) an increase in $C_{18}$ to $C_{20}$ elongation conversion efficiency in at least one long-chain polyunsaturated fatty acid-producing oleaginous microbial host cell when compared to a control host cell;

b) an increase in Δ4 desaturation conversion efficiency in at least one long-chain polyunsaturated fatty acid-producing oleaginous microbial host cell when compared to a control host cell.

The recombinant oleaginous microbial host cell can be yeast, preferably, *Yarrowia lipolytica*.

In a second embodiment, the invention concerns a recombinant oleaginous microbial host cell for the improved production of at least one long-chain polyunsaturated fatty acid wherein the long-chain polyunsaturated fatty acid can be selected from the group consisting of: eicosadienoic acid, dihomo-γ-linolenic acid, arachidonic acid, eicosatrienoic acid, eicosatetraenoic acid, eicosapentaenoic acid, docosatetraenoic acid, ω-6 docosapentaenoic acid, ω-3 docosapentaenoic acid and docosahexaenoic acid.

In a third embodiment, the invention concerns a recombinant oleaginous microbial host cell for the improved production of at least one long-chain polyunsaturated fatty acid wherein the polynucleotide encoding a polypeptide having at least acyl-CoA:lysophospholipid acyltransferase activity is stably integrated; and, further wherein the host cell has at least one improvement selected from the group consisting of:

a) an increase in $C_{18}$ to $C_{20}$ elongation conversion efficiency of at least 4% in at least one long-chain polyunsaturated fatty acid-producing oleaginous microbial host cell when compared to a control host cell; and, b) an increase in Δ4 desaturation conversion efficiency of at least 5% in at least one long-chain polyunsaturated fatty acid-producing oleaginous microbial host cell when compared to a control host cell.

In a fourth embodiment, the improvement in production of at least one long-chain polyunsaturated fatty acid can be selected from the group consisting of:

a) an increase in $C_{18}$ to $C_{20}$ elongation conversion efficiency of at least 13% in an eicosapentaenoic acid-producing host cell when compared to a control host cell;

b) an increase in $C_{18}$ to $C_{20}$ elongation conversion efficiency of at least 4% in a docosahexaenoic acid-producing host cell when compared to a control host cell;

c) an increase in $\Delta 4$ desaturation conversion efficiency of at least 18% in a docosahexaenoic acid-producing host cell when compared to a control host cell;

d) an increase of at least 9 weight percent of eicosapentaenoic acid in an eicosapentaenoic acid-producing host cell measured as a weight percent of the total fatty acids when compared to a control host cell;

e) an increase of at least 2 weight percent of eicosapentaenoic acid in a docosahexaenoic acid-producing host cell measured as a weight percent of the total fatty acids when compared to a control host cell; and, f) an increase of at least 9 weight percent of docosahexaenoic acid in a docosahexaenoic acid-producing host cell measured as a weight percent of the total fatty acids when compared to a control host cell.

In a fifth embodiment, the invention concerns oil comprising eicosapentaenoic acid and/or docosahexaenoic acid obtained from the oleaginous microbial recombinant host cell of the invention.

In a sixth embodiment, the invention concerns a method for making an oil comprising eicosapentaenoic acid and/or docosahexaenoic acid comprising:

a) culturing the oleaginous microbial host cell of claim 3 wherein an oil comprising eicosapentaenoic acid and/or docosahexaenoic acid is produced; and, b) optionally recovering the microbial oil of step (a).

In a seventh embodiment, the invention concerns a method for increasing $C_{18}$ to $C_{20}$ elongation conversion efficiency in a long-chain polyunsaturated fatty acid-producing oleaginous microbial recombinant host cell, comprising:

a) introducing into said long-chain polyunsaturated fatty acid-producing recombinant host cell at least one isolated polynucleotide encoding a polypeptide having at least acyl-CoA:lysophospholipid acyltransferase activity wherein the polypeptide is selected from the group consisting of:
  (i) a polypeptide having at least 45% amino acid identity, based on the Clustal W method of alignment, when compared to an amino acid sequence selected from the group consisting of SEQ ID NO:9 and SEQ ID NO:11;
  (ii) a polypeptide having at least one membrane bound O-acyltransferase protein family motif selected from the group consisting of: SEQ ID NO:3, SEQ ID NO:4, SEQ ID NO:5 and SEQ ID NO:28;
  (iii) a polypeptide having at least 90% amino acid identity, based on the Clustal W method of alignment, when compared to an amino acid sequence as set forth in SEQ ID NO:2;
  (iv) a polypeptide having at least 43.9% amino acid identity, based on the Clustal W method of alignment, when compared to an amino acid sequence selected from the group consisting of SEQ ID NO:15, SEQ ID NO:17 and SEQ ID NO:18; and,
  (v) a polypeptide having at least one 1-acyl-sn-glycerol-3-phosphate acyltransferase protein family motif selected from the group consisting of: SEQ ID NO:19 and SEQ ID NO:20;
  wherein the at least one isolated polynucleotide encoding a polypeptide having at least acyl-CoA:lysophospholipid acyltransferase activity is operably linked to at least one regulatory sequence, said regulatory sequence being the same or different; and, b) growing the oleaginous microbial host cell;
wherein the $C_{18}$ to $C_{20}$ elongation conversion efficiency of the oleaginous microbial host cell is increased relative to the control host cell.

In a eighth embodiment, the invention concerns a method of the invention wherein:

a) the polynucleotide encoding a polypeptide having at least acyl-CoA:lysophospholipid acyltransferase activity is stably integrated; and, b) the increase in $C_{18}$ to $C_{20}$ elongation conversion efficiency is at least 13% in an eicosapentaenoic acid-producing host cell when compared to the control host cell and/or the increase in $C_{18}$ to $C_{20}$ elongation conversion efficiency is at least 4% in a docosahexaenoic acid-producing host cell when compared to the control host cell.

In an ninth embodiment, the invention concerns a method for increasing $\Delta 4$ desaturation conversion efficiency in a long-chain polyunsaturated fatty acid-producing oleaginous microbial recombinant host cell, comprising:

a) introducing into said long-chain polyunsaturated fatty acid-producing recombinant host cell at least one isolated polynucleotide encoding a polypeptide having at least acyl-CoA:lysophospholipid acyltransferase activity wherein the polypeptide is selected from the group consisting of:
  (i) a polypeptide having at least 45% amino acid identity, based on the Clustal W method of alignment, when compared to an amino acid sequence selected from the group consisting of SEQ ID NO:9 and SEQ ID NO:11;
  (ii) a polypeptide having at least one membrane bound O-acyltransferase protein family motif selected from the group consisting of: SEQ ID NO:3, SEQ ID NO:4, SEQ ID NO:5 and SEQ ID NO:28;
  (iii) a polypeptide having at least 90% amino acid identity, based on the Clustal W method of alignment, when compared to an amino acid sequence as set forth in SEQ ID NO:2;
  (iv) a polypeptide having at least 43.9% amino acid identity, based on the Clustal W method of alignment, when compared to an amino acid sequence selected from the group consisting of SEQ ID NO:15, SEQ ID NO:17 and SEQ ID NO:18; and,
  (v) a polypeptide having at least one 1-acyl-sn-glycerol-3-phosphate acyltransferase protein family motif selected from the group consisting of: SEQ ID NO:19 and SEQ ID NO:20;
  wherein the at least one isolated polynucleotide encoding a polypeptide having at least acyl-CoA:lysophospholipid acyltransferase activity is operably linked to at least one regulatory sequence, said regulatory sequence being the same or different, and, b) growing the oleaginous microbial host cell;
wherein the $\Delta 4$ desaturation conversion efficiency of the oleaginous microbial host cell is increased relative to the control host cell.

In a tenth embodiment, the invention concerns a method for increasing $\Delta 4$ desaturation conversion efficiency in a long-chain polyunsaturated fatty acid-producing oleaginous microbial recombinant host cell wherein:

a) the polynucleotide encoding a polypeptide having at least acyl-CoA:lysophospholipid acyltransferase activity is stably integrated; and, b) the increase in $\Delta 4$ desaturation conversion efficiency is at least 18% when compared to a control host cell.

BIOLOGICAL DEPOSITS

The following biological materials have been deposited with the American Type Culture Collection (ATCC), 10801

University Boulevard, Manassas, Va. 20110-2209, and bear the following designations, accession numbers and dates of deposit.

| Biological Material | Accession No. | Date of Deposit |
|---|---|---|
| *Yarrowia lipolytica* Y4128 | ATCC PTA-8614 | Aug. 23, 2007 |
| *Yarrowia lipolytica* Y8406 | ATCC PTA-10025 | May 14, 2009 |
| *Yarrowia lipolytica* Y8412 | ATCC PTA-10026 | May 14, 2009 |

The biological materials listed above were deposited under the terms of the Budapest Treaty on the International Recognition of the Deposit of Microorganisms for the Purposes of Patent Procedure. The listed deposit will be maintained in the indicated international depository for at least 30 years and will be made available to the public upon the grant of a patent disclosing it. The availability of a deposit does not constitute a license to practice the subject invention in derogation of patent rights granted by government action.

BRIEF DESCRIPTION OF THE DRAWINGS AND SEQUENCE DESCRIPTIONS

FIG. 1A and FIG. 1B illustrate the ω-3/ω-6 fatty acid biosynthetic pathway, and should be viewed together when considering the description of this pathway.

Figure 2:
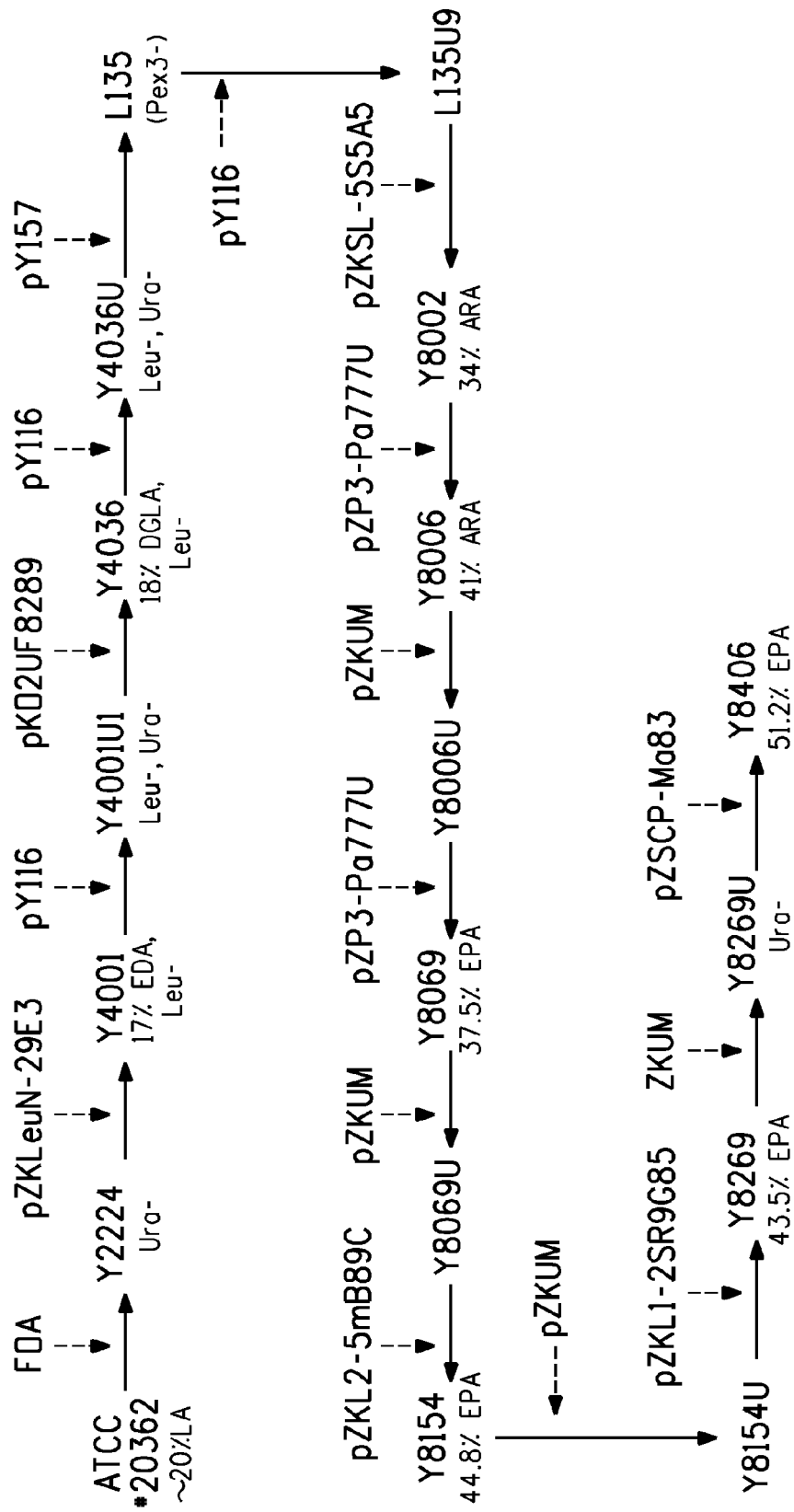

FIG. 2 diagrams the development of *Yarrowia lipolytica* strain Y8406, producing greater than 51.2 EPA % TFAs.

Figure 3:
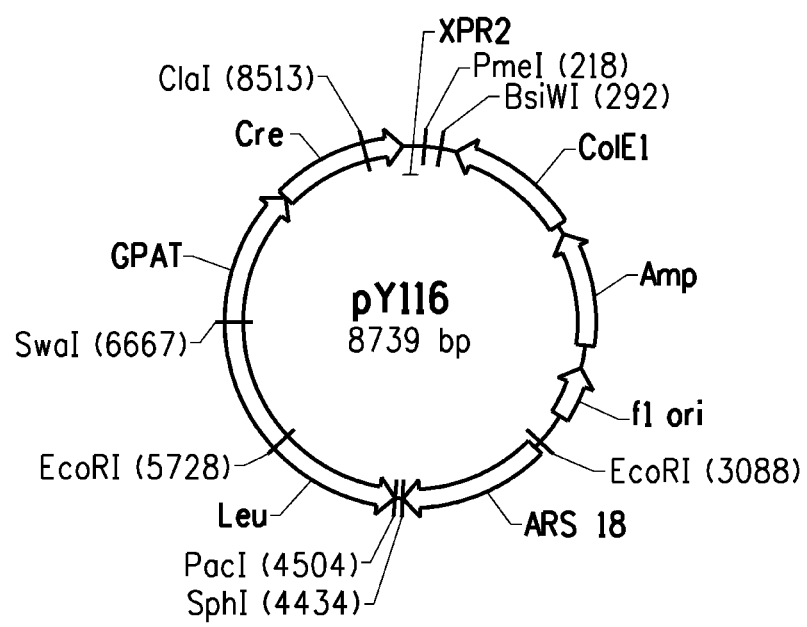

FIG. 3 provides a plasmid map for pY116.

Figure 4A:
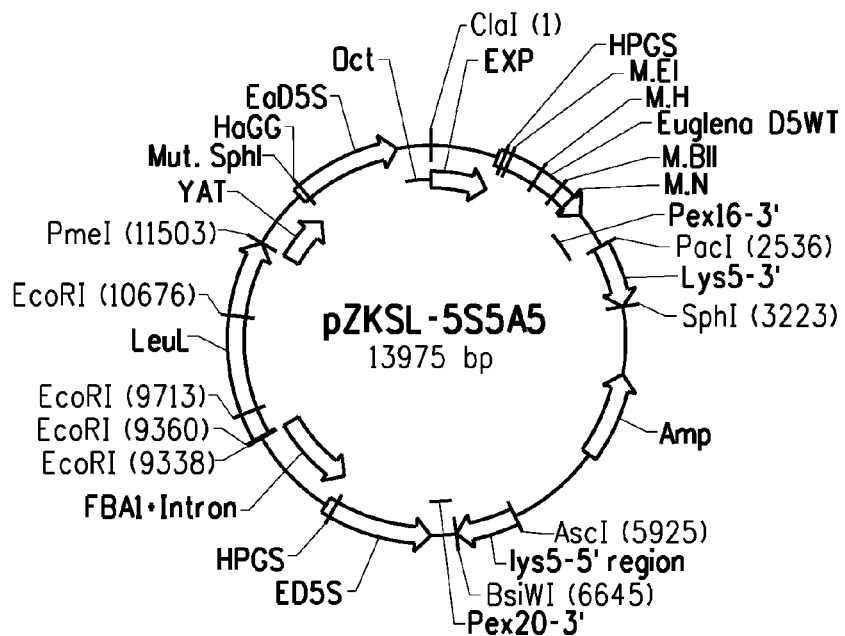
Figure 4B:
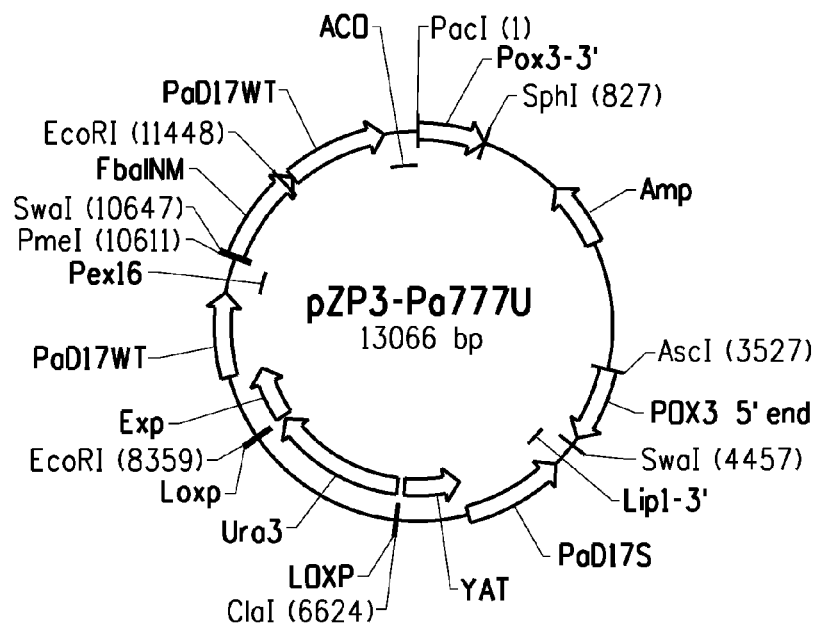

FIG. 4A provides a plasmid map for pZKSL-5S5A5; and FIG. 4B provides a plasmid map for pZP3-Pa777U.

Figure 5A:
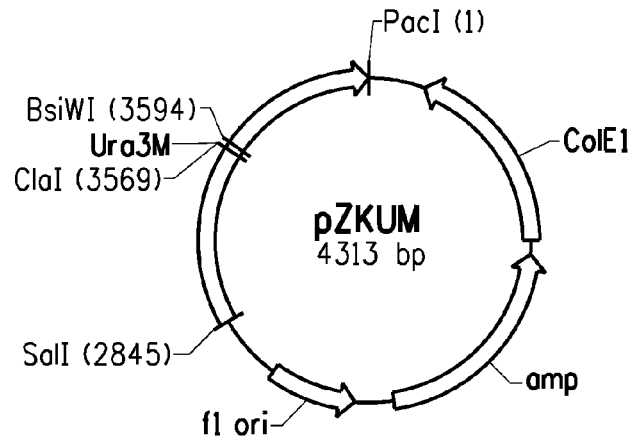
Figure 5B:
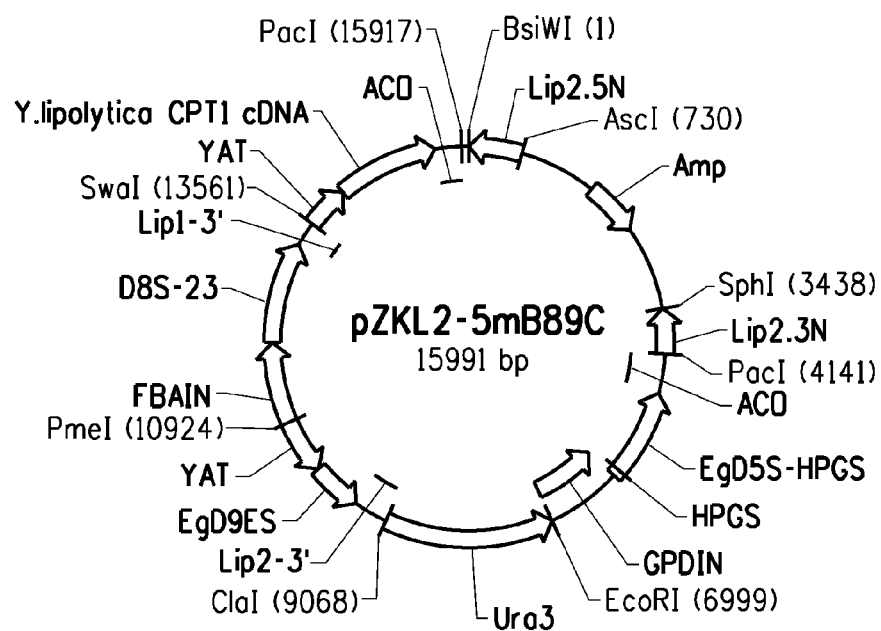

FIG. 5A provides a plasmid map for pZKUM; and FIG. 5B provides a plasmid map for pZKL2-5 mB89C.

Figure 6A:
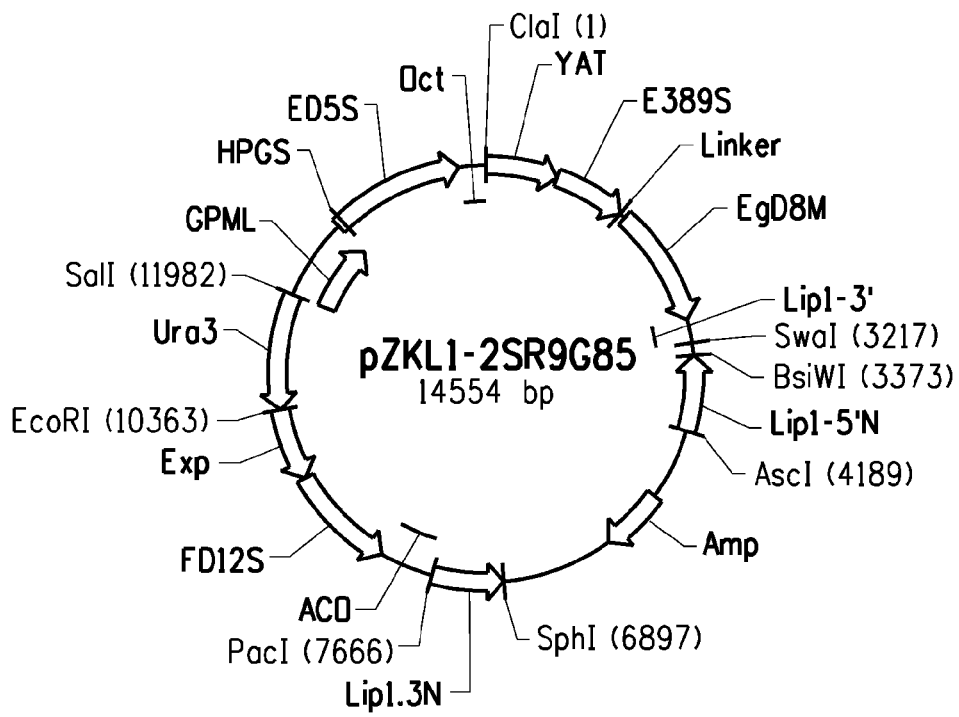
Figure 6B:
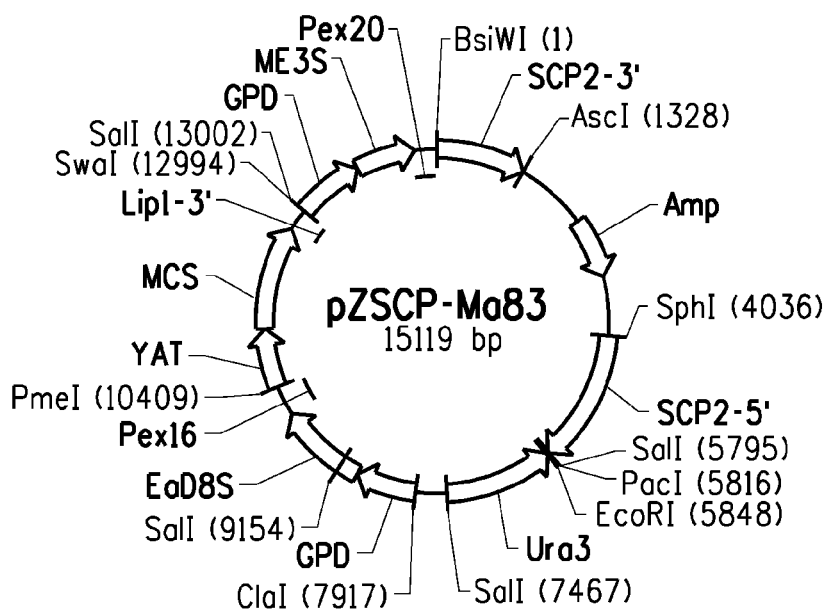

FIG. 6A provides a plasmid map for pZKL1-2SR9G85; and FIG. 6B provides a plasmid map for pZSCP-Ma83.

Figure 7:
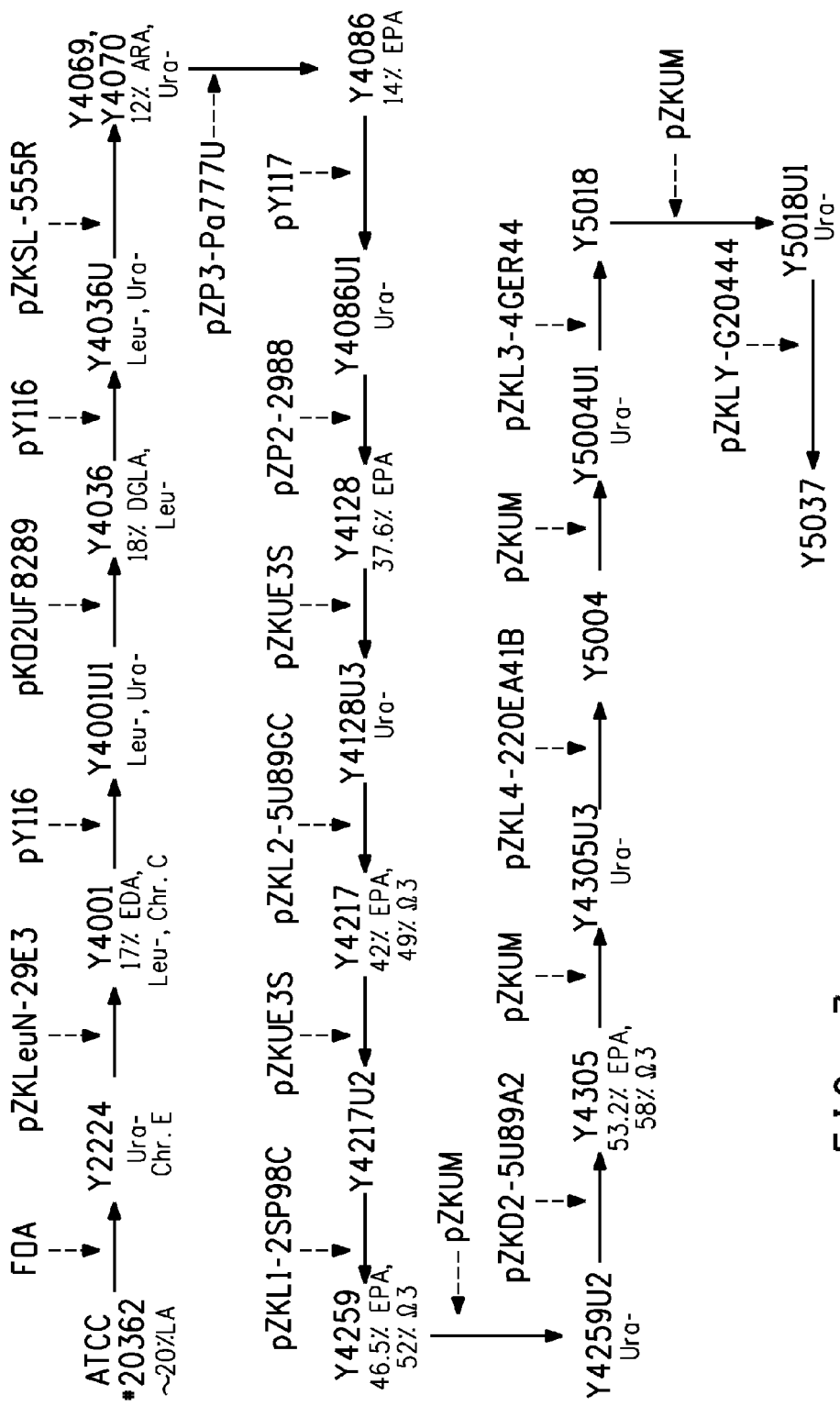

FIG. 7 diagrams the development of *Yarrowia lipolytica* strain Y5037, producing 18.6 EPA % TFAs, 22.8 DPA % TFAs and 9.7 DHA % TFAs.

Figure 8A:
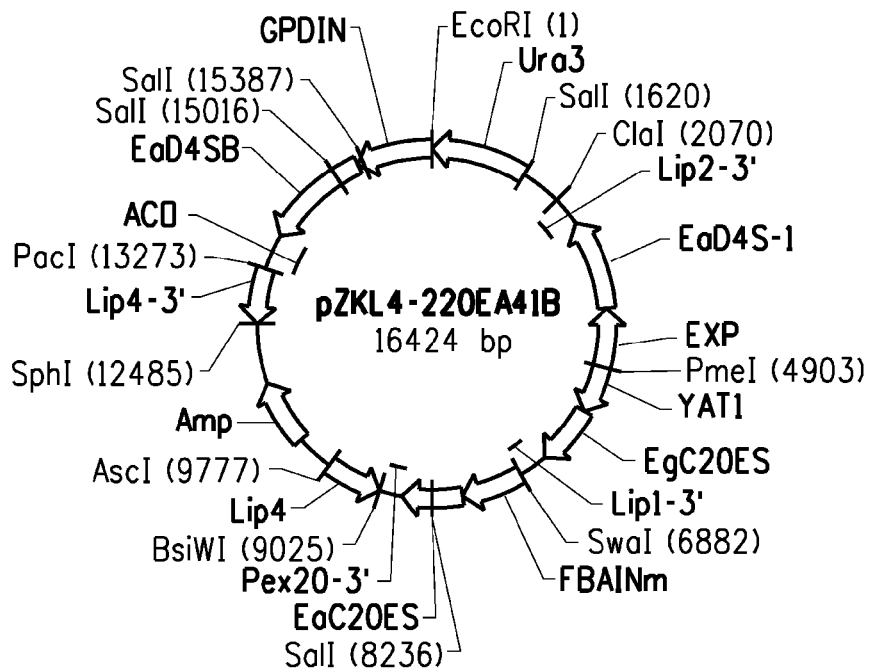
Figure 8B:
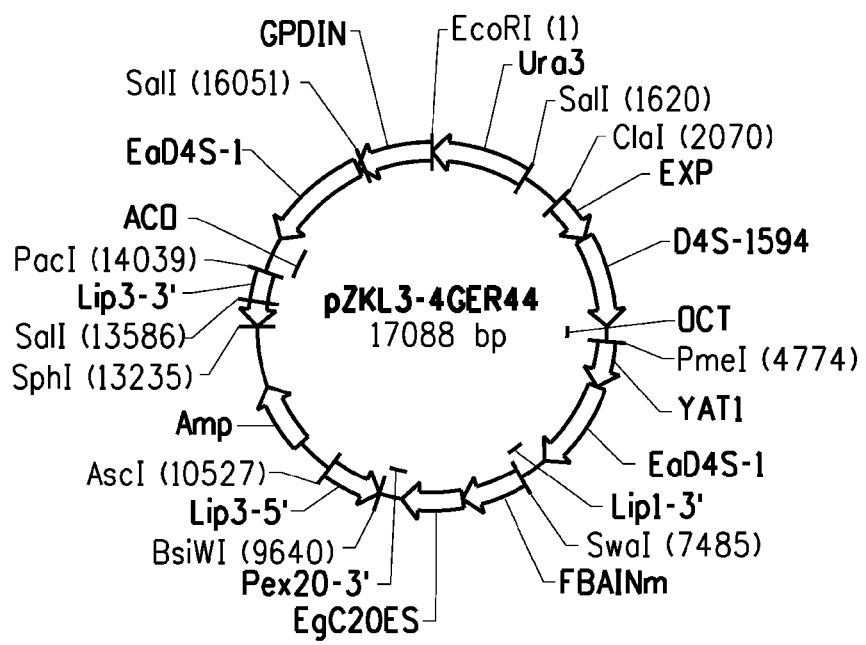

FIG. 8A provides a plasmid map for pZKL4-220EA41B; and FIG. 8B provides a plasmid map for pZKL3-4GER44.

Figure 9:
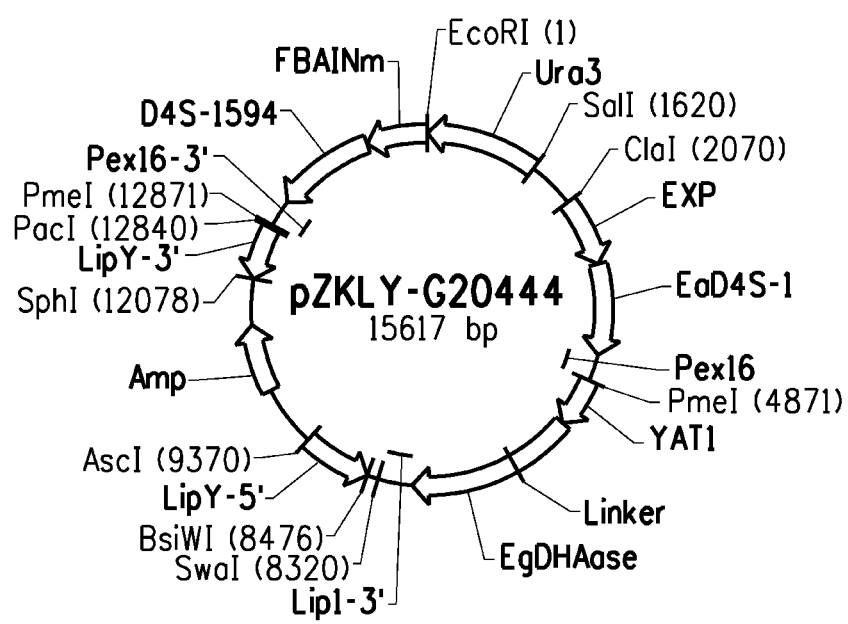

FIG. 9 provides a plasmid map for pZKLY-G20444.

Figure 10A:
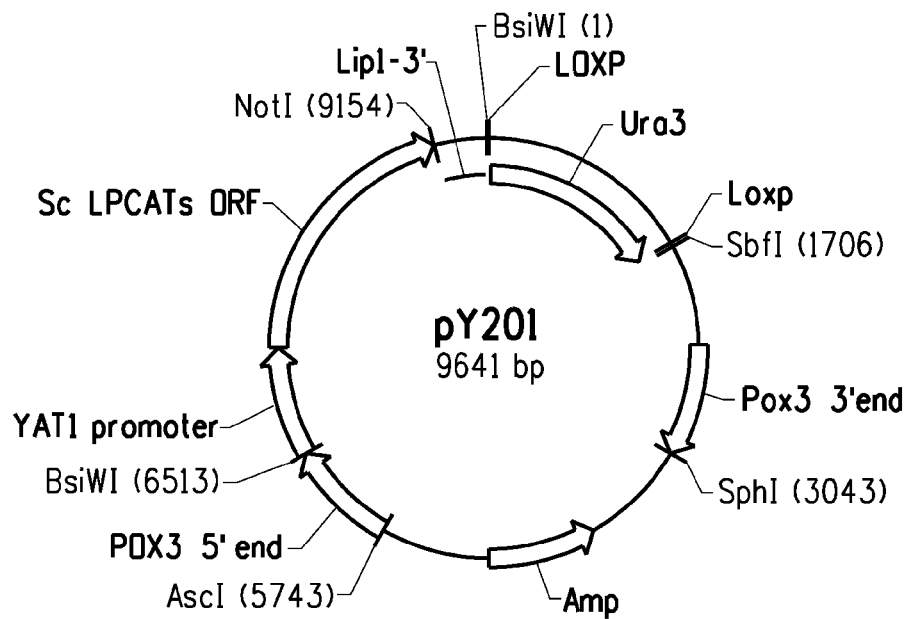
Figure 10B:
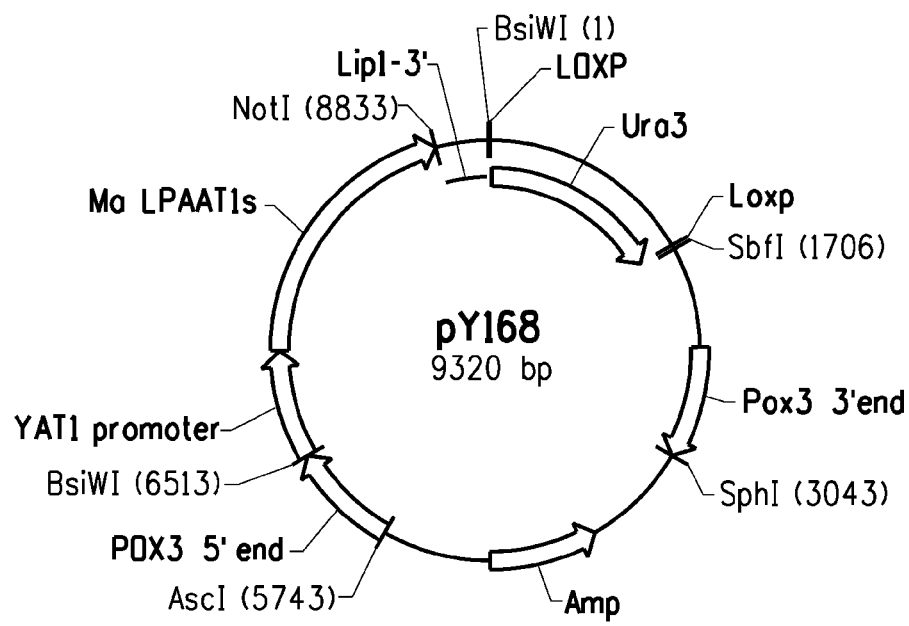

FIG. 10A provides a plasmid map for pY201, comprising a chimeric YAT1::ScAle1S::Lip1 gene; and FIG. 10B provides a plasmid map for pY168, comprising a chimeric YAT1::YlAle1::Lip1 gene.

Figure 11A:
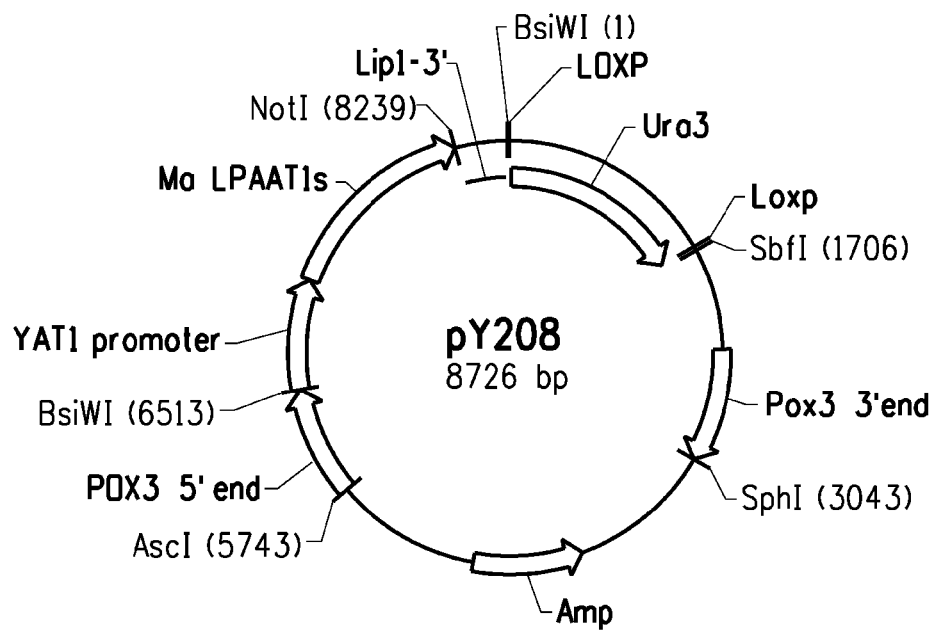
Figure 11B:
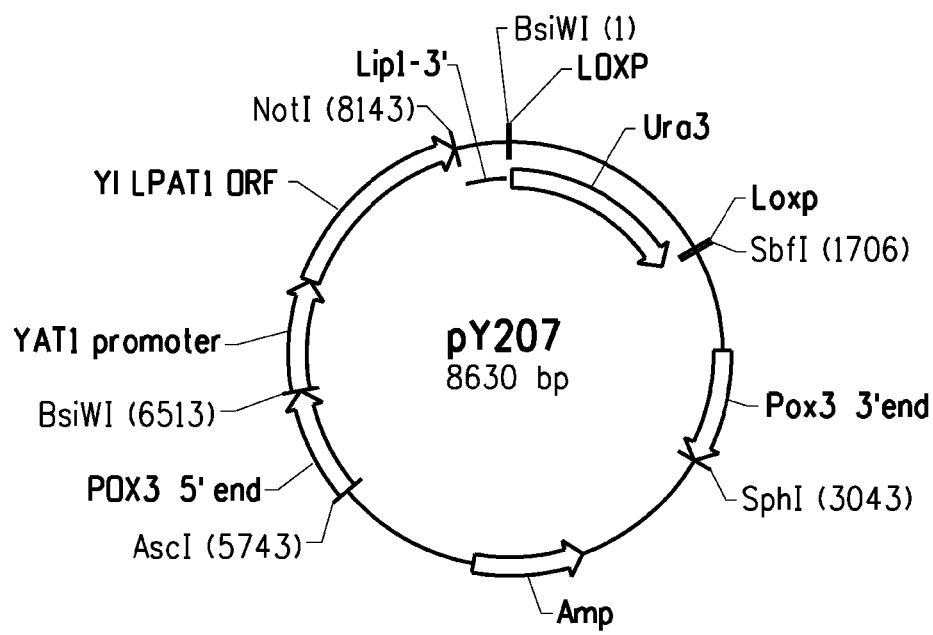

FIG. 11A provides a plasmid map for pY208, comprising a chimeric YAT1::MaLPAAT1S::Lip1 gene; and FIG. 11B provides a plasmid map for pY207, comprising a chimeric YAT1::YlLPAAT1::Lip1 gene.

Figure 12A:
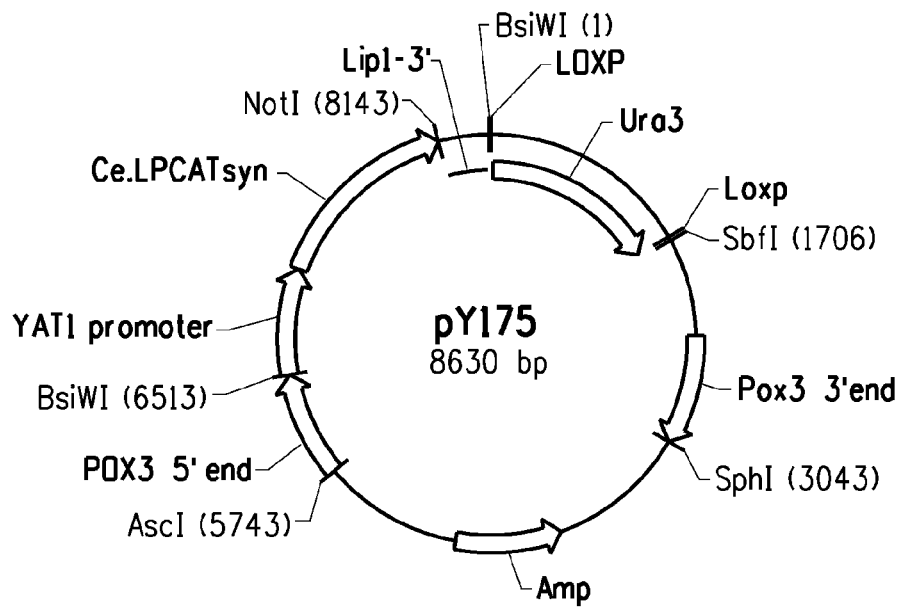
Figure 12B:
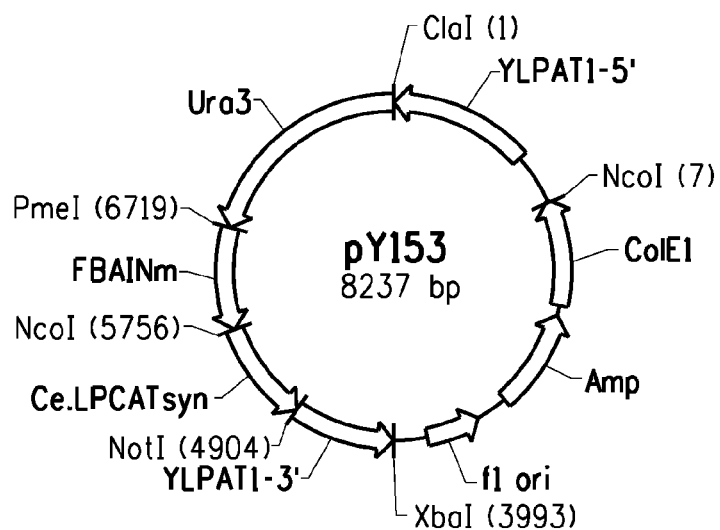

FIG. 12A provides a plasmid map for pY175, comprising a chimeric YAT1::CeLPCATS::Lip1 gene; and FIG. 12B provides a plasmid map for pY153, comprising a chimeric FBAIN::CeLPCATS::YlLPAAT1 gene.

Figure 13A:
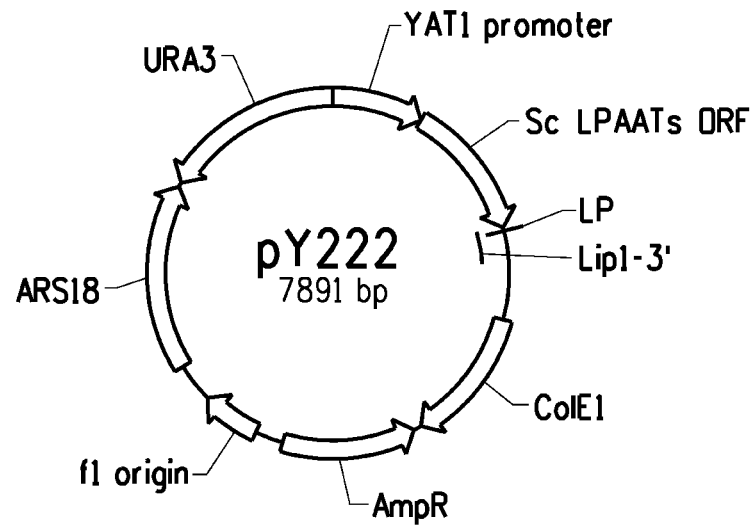
Figure 13B:
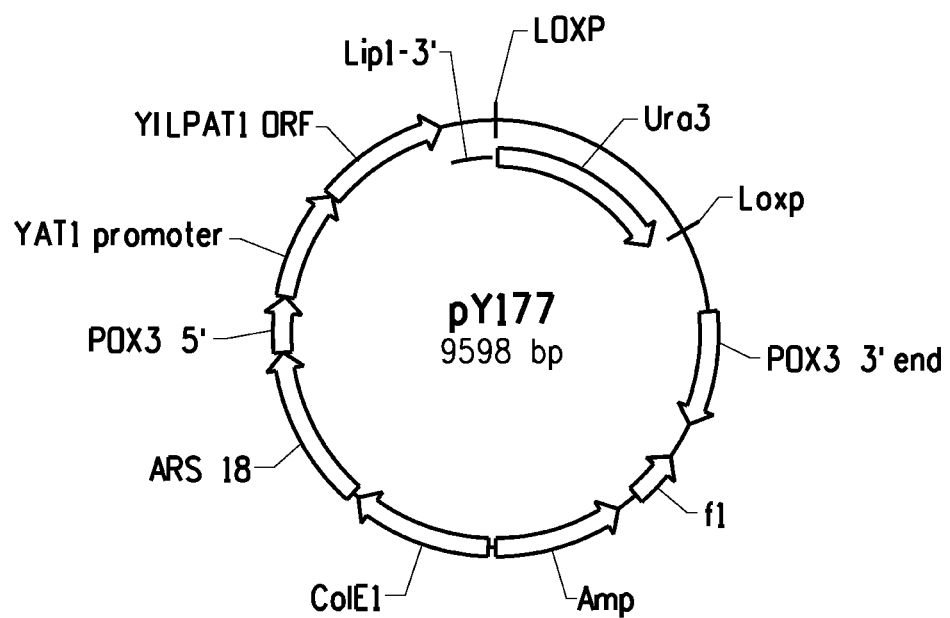

FIG. 13A provides a plasmid map for pY222, comprising a chimeric YAT1::ScLPAATS::Lip1 gene; and FIG. 13B provides a plasmid map for pY177, comprising a chimeric YAT1::YlLPAAT1::Lip1 gene.

The invention can be more fully understood from the following detailed description and the accompanying sequence descriptions, which form a part of this application.

The following sequences comply with 37 C.F.R. §1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-101 are ORFs encoding promoters, genes or proteins (or fragments thereof) or plasmids, as identified in Table 2.

TABLE 2

Summary of Gene and Protein SEQ ID Numbers

| Description | Nucleic acid SEQ ID NO. | Protein SEQ ID NO. |
|---|---|---|
| *Caenorhabditis elegans* LPCAT ("CeLPCAT") | 1 (849 bp) | 2 (282 AA) |
| membrane bound O-acyltransferase motif M(V/I)LxxKL | — | 3 |
| membrane bound O-acyltransferase motif RxKYYxxW | — | 4 |
| membrane bound O-acyltransferase motif SAxWHG | — | 5 |
| Synthetic LPCAT derived from *Caenorhabditis elegans*, codon-optimized for expression in *Yarrowia lipolytica* ("CeLPCATS") | 6 (859 bp) | 7 (282 AA) |
| *Saccharomyces cerevisiae* Ale1 ("ScAle1"; also ORF "YOR175C") | 8 (1860 bp) | 9 (619 AA) |
| *Yarrowia lipolytica* Ale1 ("YlAle1") | 10 (1539 bp) | 11 (512 AA) |
| Synthetic Ale1 derived from *Saccharomyces cerevisiae*, codon-optimized for expression in *Yarrowia lipolytica* ("ScAle1S") | 12 (1870 bp) | 13 (619 AA) |
| *Mortierella alpina* LPAAT1 ("MaLPAAT1") | 14 (945 bp) | 15 (314 AA) |
| *Yarrowia lipolytica* LPAAT1 ("YlLPAAT1") | 16 (1549 bp) | 17 (282 AA) |
| *Saccharomyces cerevisiae* LPAAT ("ScLPAAT"; also ORF "YDL052C") | — | 18 (303 AA) |
| 1-acyl-sn-glycerol-3-phosphate acyltransferase motif NHxxxxD | — | 19 |
| 1-acyl-sn-glycerol-3-phosphate acyltransferase motif EGTR | — | 20 |

TABLE 2-continued

Summary of Gene and Protein SEQ ID Numbers

| Description | Nucleic acid SEQ ID NO. | Protein SEQ ID NO. |
|---|---|---|
| Synthetic LPAAT1 derived from *Mortierella alpina*, codon-optimized for expression in *Yarrowia lipolytica* ("MaLPAAT1S") | 21 (955 bp) | 22 (314 AA) |
| Shindou et al. membrane bound O-acyltransferase motif WHGxxxGYxxxF | — | 23 |
| Shindou et al. membrane bound O-acyltransferase motif YxxxxF | — | 24 |
| Shindou et al. membrane bound O-acyltransferase motif YxxxYFxxH | — | 25 |
| U.S. patent Pub. No. 2008-0145867-A1 motif M-[V/I]-[L/I]-xxK-[L/V/I]-xxxxxxDG | — | 26 |
| U.S. patent Pub. No. 2008-0145867-A1 motif RxKYYxxWxxx-[E/D]-[A/G]xxxxGxG-[F/Y]-xG | — | 27 |
| U.S. patent Pub. No. 2008-0145867-A1 motif $EX_{11}WNX_2$-[T/V]-$X_2W$ | — | 28 |
| U.S. patent Pub. No. 2008-0145867-A1 motif SAxWHGxxPGYxx-[T/F]-F | — | 29 |
| Lewin, T. W. et al. & Yamashita et al. 1-acyl-sn-glycerol-3-phosphate acyltransferase motif GxxFI-[D/R]-R | — | 30 |
| Lewin, T. W. et al. 1-acyl-sn-glycerol-3-phosphate acyltransferase motif [V/I]-[P/X]-[I/V/L]-[I/V]-P-[V/I] | — | 31 |
| Yamashita et al. 1-acyl-sn-glycerol-3-phosphate acyltransferase motif IVPIVM | — | 32 |
| Plasmid pY116 | 33 (8739 bp) | — |
| Plasmid pZKSL-5S5A5 | 34 (13,975 bp) | — |
| Synthetic mutant Δ5 desaturase ("EgD5SM"), derived from *Euglena gracilis* ("EgD5S") (U.S. patent Pub. No. 2010-0075386-A1) | 35 (1350 bp) | 36 (449 AA) |
| Synthetic mutant Δ5 desaturase ("EaD5SM"), derived from *Euglena anabaena* ("EaD5S") (U.S. patent Pub. No. 2010-0075386-A1) | 37 (1365 bp) | 38 (454 AA) |
| Plasmid pZP3-Pa777U | 39 (13,066 bp) | — |
| Plasmjd pZKUM | 40 (4313 bp) | — |
| Plasmid pZKL2-5mB89C | 41 (15,991 bp) | — |
| *Yarrowia lipolytica* diacylglycerol cholinephosphotransferase gene ("YlCPT1") | 42 (1185 bp) | 43 (394 AA) |
| Synthetic mutant Δ8 desaturase ("EgD8M") (U.S. patent No. 7,709,239), derived from *Euglena gracilis* ("EgD8S") (U.S. Pat. No. 7,256,033) | 44 (1272 bp) | 45 (422 AA) |
| Synthetic Δ9 elongase derived from *Euglena gracilis*, codon-optimized for expression in *Yarrowia lipolytica* ("EgD9eS") | 46 (777 bp) | 47 (258 AA) |
| Plasmid pZKL1-2SR9G85 | 48 (14,554 bp) | — |
| DGLA synthase, comprising E389D9eS/EgD8M gene fusion | 49 (2127 bp) | 50 (708 AA) |
| Synthetic Δ12 desaturase derived from *Fusarium moniliforme*, codon-optimized for expression in *Yarrowia lipolytica* ("FmD12S") | 51 (1434 bp) | 52 (477 AA) |
| Plasmid pZSCP-Ma83 | 53 (15,119 bp) | — |
| Synthetic $C_{16/18}$ elongase derived from *Mortierella alpina* ELO3, codon-optimized for expression in *Yarrowia lipolytica* ("ME3S") | 54 (828 bp) | 55 (275 AA) |
| Synthetic malonyl-CoA synthetase derived from *Rhizobium leguminosarum* bv. *viciae* 3841 (GenBank Accession No. YP_766603), codon-optimized for expression in *Yarrowia lipolytica* ("MCS") | 56 (1518 bp) | 57 (505 AA) |
| Synthetic Δ8 desaturase derived from *Euglena anabaena* UTEX 373, codon-optimized for expression in *Yarrowia lipolytica* ("EaD8S") | 58 (1260 bp) | 59 (420 AA) |
| Plasmid pZKL4-220EA41B | 60 (16,424 bp) | — |
| Synthetic C20 elongase derived from *Euglena anabaena*, codon-optimized for expression in *Yarrowia lipolytica* ("EaC20ES") | 61 (900 bp) | 62 (299 AA) |
| Synthetic C20 elongase derived from *Euglena gracilis*, codon-optimized for expression in *Yarrowia lipolytica* ("EgC20ES") | 63 (912 bp) | 64 (303 AA) |

TABLE 2-continued

Summary of Gene and Protein SEQ ID Numbers

| Description | Nucleic acid SEQ ID NO. | Protein SEQ ID NO. |
|---|---|---|
| Truncated synthetic Δ4 desaturase derived from *Euglena anabaena*, codon-optimized for expression in *Yarrowia lipolytica* ("EaD4S-1") | 65 (1644 bp) | 66 (547 AA) |
| Truncated synthetic Δ4 desaturase version B derived from *Euglena anabaena*, codon-optimized for expression in *Yarrowia lipolytica* ("EaD4SB") | 67 (1644 bp) | 68 (547 AA) |
| Plasmid pZKL3-4GER44 | 69 (17,088 bp) | — |
| Synthetic Δ4 desaturase derived from *Eutreptiella cf_gymnastica* CCMP1594, codon-optimized for expression in *Yarrowia lipolytica* ("E1594D4S") | 70 (1548 bp) | 71 (515 AA) |
| Truncated synthetic Δ4 desaturase derived from *Euglena gracilis*, codon-optimized for expression in *Yarrowia lipolytica* ("EgD4S-1") | 72 (1542 bp) | 73 (513 AA) |
| Plasmid pZKLY-G20444 | 74 (15,617 bp) | — |
| Synthetic DHA synthase derived from *Euglena gracilis*, codon-optimized for expression in *Yarrowia lipolytica* ("EgDHAsyn1S") | 75 (2382 bp) | 76 (793 AA) |
| Plasmid pY201 | 77 (9641 bp) | — |
| *Escherichia coli* LoxP recombination site, recognized by a Cre recombinase enzyme | 78 (34 bp) | — |
| Primer 798 | 79 | — |
| Primer 799 | 80 | — |
| Primer 800 | 81 | — |
| Primer 801 | 82 | — |
| Plasmid pY168 | 83 (9320 bp) | — |
| Plasmid pY208 | 84 (8726 bp) | — |
| Primer 856 | 85 | — |
| Primer 857 | 86 | — |
| Plasmid pY207 | 87 (8630 bp) | — |
| Plasmid pY175 | 88 (8630 bp) | — |
| Plasmid pY153 | 89 (8237 bp) | — |
| Mutant Δ5 desaturase ("EgD5M"), derived from *Euglena gracilis* ("EgD5") (U.S. patent Pub. No. 2010-0075386-A1) | 90 (1350 bp) | 91 (449 AA) |
| *Mortierella alpina* LPAAT (corresponding to SEQ ID NOs: 16 and 17 within Intl. App. Pub. No. WO 2004/087902) | 92 (1254 bp) | 93 (417 AA) |
| *Mortierella alpina* LPAAT (corresponding to SEQ ID NOs: 18 and 19 within Intl. App. Pub. No. WO 2004/087902) | 94 (1170 bp) | 95 (389 AA) |
| Synthetic LPAAT derived from *Saccharomyces cerevisiae*, codon-optimized for expression in *Yarrowia lipolytica* ("ScLPAATS") | 96 (926 bp) | 97 (303 AA) |
| Primer 869 | 98 | — |
| Primer 870 | 99 | — |
| Plasmid pY222 | 100 (7891 bp) | — |
| Plasmid pY177 | 101 (9598 bp) | — |

DETAILED DESCRIPTION OF THE INVENTION

Described herein are methods for increasing $C_{18}$ to $C_{20}$ elongation conversion efficiency and/or Δ4 desaturation conversion efficiency in long-chain polyunsaturated fatty acid ["LC-PUFA"]-producing recombinant oleaginous microbial host cells, based on expression of polypeptides (e.g., Ale1, LPAAT, and LPCAT) having LPLAT activity. By increasing the conversion efficiency of $C_{18}$ to $C_{20}$ elongation and/or Δ4 desaturation, the concentration of the LC-PUFAs eicosapentaenoic acid ["EPA"; cis-5,8,11,14,17-eicosapentaenoic acid] and/or docosahexaenoic acid ["DHA"; cis-4,7,10,13, 16,19-docosahexaenoic acid] increased as a weight percent of the total fatty acids. Recombinant host cells are also claimed.

PUFAs, such as EPA and DHA (or derivatives thereof), are used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food and drink products and may find use as cardiovascular-protective, anti-depression, anti-inflammatory or cholesterol lowering agents. Optionally, the compositions may be used for pharmaceutical use, either human or veterinary.

All patents, patent applications, and publications cited herein are incorporated by reference in their entirety.

In this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

"Polyunsaturated fatty acid(s)" is abbreviated as "PUFA(s)".

"Diacylglycerol acyltransferase" is abbreviated as "DAG AT" or "DGAT".

"Triacylglycerols" are abbreviated as "TAGs".

"Co-enzyme A" is abbreviated as "CoA".

"Total fatty acids" are abbreviated as "TFAs".

"Fatty acid methyl esters" are abbreviated as "FAMEs".

"Dry cell weight" is abbreviated as "DCW".

"Long-chain polyunsaturated fatty acid(s)" is abbreviated as "LC-PUFA(s)".

"Acyl-CoA:lysophospholipid acyltransferase(s)" or "lysophospholipid acyltransferase(s)" is abbreviated as "LPLAT(s)".

The term "invention" or "present invention" as used herein is not meant to be limiting to any one specific embodiment of the invention but applies generally to any and all embodiments of the invention as described in the claims and specification.

The term "glycerophospholipids" refers to a broad class of molecules, having a glycerol core with fatty acids at the sn-1 position and sn-2 position, and a polar head group (e.g., phosphate, choline, ethanolamine, glycerol, inositol, serine, cardiolipin) joined at the sn-3 position via a phosphodiester bond. Glycerophospholipids thus include phosphatidylcholines ["PC"], phosphatidylethanolamines ["PE"], phosphatidylglycerols ["PG"], phosphatidylinositols ["PI"], phosphatidylserines ["PS"] and cardiolipins ["CL"].

"Lysophospholipids" are derived from glycerophospholipids, by deacylation of the sn-2 position fatty acid. Lysophospholipids include, e.g., lysophosphatidic acid ["LPA"], lysophosphatidylcholine ["LPC"], lysophosphatidyletanolamine ["LPE"], lysophosphatidylserine ["LPS"], lysophosphatidylglycerol ["LPG"] and lysophosphatidylinositol ["LPI"].

The term "acyltransferase" refers to an enzyme responsible for transferring an acyl group from a donor lipid to an acceptor lipid molecule.

The term "acyl-CoA:lysophospholipid acyltransferase" or "lysophospholipid acyltransferase" ["LPLAT"] refers to a broad class of acyltransferases, having the ability to acylate a variety of lysophospholipid substrates at the sn-2 position. More specifically, LPLATs include LPA acyltransferases ["LPAATs"] having the ability to catalyze conversion of LPA to PA, LPC acyltransferases ["LPCATs"] having the ability to catalyze conversion of LPC to PC, LPE acyltransferases ["LPEATs"] having the ability to catalyze conversion of LPE to PE, LPS acyltransferases ["LPLATs"] having the ability to catalyze conversion of LPS to PS, LPG acyltransferases ["LPGATs"] having the ability to catalyze conversion of LPG to PG, and LPI acyltransferases ["LPIATs"] having the ability to catalyze conversion of LPI to PI. Standardization of LPLAT nomenclature has not been formalized, so various other designations are used in the art (for example, LPAATs have also been referred to as acyl-CoA:1-acyl-sn-glycerol-3-phosphate 2-O-acyltransferases, 1-acyl-sn-glycerol-3-phosphate acyltransferases and/or 1-acylglycerolphosphate acyltransferases ["AGPATs"] and LPCATs are often referred to as acyl-CoA:1-acyl lysophosphatidyl-choline acyltransferases). Additionally, it is important to note that some LPLATs, such as the *Saccharomyces cerevisiae* Ale1 (ORF YOR175C; SEQ ID NO:9), have broad specificity and thus a single enzyme may be capable of catalyzing several LPLAT reactions, including LPAAT, LPCAT and LPEAT reactions (Tamaki, H. et al., *J. Biol. Chem.*, 282:34288-34298 (2007); Stahl, U. et al., *FEBS Letters*, 582:305-309 (2008); Chen, Q. et al., *FEBS Letters*, 581:5511-5516 (2007); Benghezal, M. et al., *J. Biol. Chem.*, 282:30845-30855 (2007); Riekhof, et al., *J. Biol. Chem.*, 282:28344-28352 (2007)).

More specifically, the term "polypeptide having at least lysophosphtidylcholine acyltransferase ["LPCAT"] activity" will refer to those enzymes capable of catalyzing the reaction: acyl-CoA+1-acyl-sn-glycero-3-phosphocholine=CoA+1,2-diacyl-sn-glycero-3-phosphocholine (EC 2.3.1.23). LPCAT activity has been described in two structurally distinct protein families, i.e., the LPAAT protein family (Hishikawa, et al., *Proc. Natl. Acad. Sci. U.S.A.*, 105:2830-2835 (2008); Intl. App. Pub. No. WO 2004/076617) and the ALE1 protein family (Tamaki, H. et al., supra; Stahl, U. et al., supra; Chen, Q. et al., supra; Benghezal, M. et al., supra; Riekhof, et al., supra).

The term "LPCAT" refers to a protein of the ALE1 protein family that: 1) has LPCAT activity (EC 2.3.1.23) and shares at least about 45% amino acid identity, based on the Clustal W method of alignment, when compared to an amino acid sequence selected from the group consisting of SEQ ID NO:9 (ScAle1) and SEQ ID NO:11 (YlAle1); and/or, 2) has LPCAT activity (EC 2.3.1.23) and has at least one membrane bound O-acyltransferase ["MBOAT"] protein family motif selected from the group consisting of: M(V/I)LxxKL (SEQ ID NO:3), RxKYYxxW (SEQ ID NO:4), SAxWHG (SEQ ID NO:5) and $EX_{11}WNX_2$— [T/V]-$X_2$W (SEQ ID NO:28). Examples of ALE1 polypeptides include ScAle1 and YlAle1.

The term "ScAle1" refers to a LPCAT (SEQ ID NO:9) isolated from *Saccharomyces cerevisiae* (ORF "YOR175C"), encoded by the nucleotide sequence set forth as SEQ ID NO:8. In contrast, the term "ScAle1S" refers to a synthetic LPCAT derived from *S. cerevisiae* that is codon-optimized for expression in *Yarrowia lipolytica* (i.e., SEQ ID NOs:12 and 13).

The term "YlAle1" refers to a LPCAT (SEQ ID NO:11) isolated from *Yarrowia lipolytica*, encoded by the nucleotide sequence set forth as SEQ ID NO:10.

The term "LPCAT" also refers to a protein that has LPCAT activity (EC 2.3.1.23) and shares at least about 90% amino acid identity, based on the Clustal W method of alignment, when compared to an amino acid sequence as set forth in SEQ ID NO:2 (CeLPCAT).

The term "CeLPCAT" refers to a LPCAT enzyme (SEQ ID NO:2) isolated from *Caenorhabditis elegans*, encoded by the nucleotide sequence set forth as SEQ ID NO:1. In contrast, the term "CeLPCATS" refers to a synthetic LPCAT derived from *C. elegans* that is codon-optimized for expression in *Yarrowia lipolytica* (i.e., SEQ ID NOs:6 and 7).

The term "polypeptide having at least lysophosphatidic acid acyltransferase ["LPAAT"] activity" will refer to those enzymes capable of catalyzing the reaction: acyl-CoA+1-acyl-sn-glycerol 3-phosphate=CoA+1,2-diacyl-sn-glycerol 3-phosphate (EC 2.3.1.51).

The term "LPAAT" refers to a protein that: 1) has LPAAT activity and shares at least about 43.9% amino acid identity, based on the Clustal W method of alignment, when compared to an amino acid sequence selected from the group consisting of SEQ ID NO:15 (MaLPAAT1), SEQ ID NO:17 (YILPAAT1) and SEQ ID NO:18 (ScLPAAT1); and/or, 2) has LPAAT activity and has at least one 1-acyl-sn-glycerol-3- phosphate acyltransferase family motif selected from the group consisting of: NHxxxxD (SEQ ID NO:19) and EGTR (SEQ ID NO:20). Examples of LPAAT polypeptides include ScLPAAT, MaLPAAT1 and YlLPAAT1.

The term "ScLPAAT" refers to a LPAAT (SEQ ID NO:18) isolated from *Saccharomyces cerevisiae* (ORF "YDL052C").

The term "MaLPAAT1" refers to a LPAAT (SEQ ID NO:15) isolated from *Mortierella alpina*, encoded by the nucleotide sequence set forth as SEQ ID NO:14. In contrast, the term "MaLPAAT1S" refers to a synthetic LPAAT derived from *M. alpina* that is codon-optimized for expression in *Yarrowia lipolytica* (i.e., SEQ ID NOs:21 and 22).

The term "YlLPAAT1" refers to a LPAAT (SEQ ID NO:17) isolated from *Yarrowia lipolytica*, encoded by the nucleotide sequence set forth as SEQ ID NO:16.

The term "ortholog" refers to a homologous protein from a different species that evolved from a common ancestor protein as evidenced by being in one clade of phylogenetic tree analysis and that catalyzes the same enzymatic reaction.

The term "conserved domain" or "motif" means a set of amino acids conserved at specific positions along an aligned sequence of evolutionarily related proteins. While amino acids at other positions can vary between homologous proteins, amino acids that are highly conserved at specific positions likely indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "oil" refers to a lipid substance that is liquid at 25° C. and usually polyunsaturated. In oleaginous organisms, oil constitutes a major part of the total lipid. "Oil" is composed primarily of triacylglycerols ["TAGs"] but may also contain other neutral lipids, phospholipids and free fatty acids. The fatty acid composition in the oil and the fatty acid composition of the total lipid are generally similar; thus, an increase or decrease in the concentration of PUFAs in the total lipid will correspond with an increase or decrease in the concentration of PUFAs in the oil, and vice versa.

"Neutral lipids" refer to those lipids commonly found in cells in lipid bodies as storage fats and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or triacylglycerol, respectively, or collectively, acylglycerols. A hydrolysis reaction must occur to release free fatty acids from acylglycerols.

The term "triacylglycerols" ["TAGs"] refers to neutral lipids composed of three fatty acyl residues esterified to a glycerol molecule. TAGs can contain LC-PUFAs and saturated fatty acids, as well as shorter chain saturated and unsaturated fatty acids.

The term "total fatty acids" ["TFAs"] herein refer to the sum of all cellular fatty acids that can be derivitized to fatty acid methyl esters ["FAMEs"] by the base transesterification method (as known in the art) in a given sample, which may be the biomass or oil, for example. Thus, total fatty acids include fatty acids from neutral lipid fractions (including diacylglycerols, monoacylglycerols and TAGs) and from polar lipid fractions (including the PC and the PE fractions), but not free fatty acids.

The term "total lipid content" of cells is a measure of TFAs as a percent of the dry cell weight ["DCW"], although total lipid content can be approximated as a measure of FAMEs as a percent of the DCW ["FAMEs DCW"]. Thus, total lipid content ["TFAs % DOW"] is equivalent to, e.g., milligrams of total fatty acids per 100 milligrams of DCW.

The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).

In some cases, it is useful to express the content of a given fatty acid(s) in a cell as its weight percent of the dry cell weight ["% DCW"]. Thus, for example, EPA % DCW would be determined according to the following formula: (EPA % TFAs)*(TFAs % DCW)]/100. The content of a given fatty acid(s) in a cell as its weight percent of the dry cell weight ["% DOW"] can be approximated, however, as: (EPA % TFAs)*(FAMEs % DCW)]/100.

The terms "lipid profile" and "lipid composition" are interchangeable and refer to the amount of individual fatty acids contained in a particular lipid fraction, such as in the total lipid or the oil, wherein the amount is expressed as a weight percent of TFAs. The sum of each individual fatty acid present in the mixture should be 100.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or "n-3"] are provided in U.S. Pat. No. 7,238,482, which is hereby incorporated herein by reference.

Nomenclature used to describe PUFAs herein is given in Table 3. In the column titled "Shorthand Notation", the omega-reference system is used to indicate the number of carbons, the number of double bonds and the position of the double bond closest to the omega carbon, counting from the omega carbon, which is numbered 1 for this purpose. The remainder of the Table summarizes the common names of ω-3 and ω-6 fatty acids and their precursors, the abbreviations that will be used throughout the specification and the chemical name of each compound.

TABLE 3

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-Linolenic | DGLA | cis-8,11,14-eicosatrienoic | 20:3 ω-6 |
| Arachidonic | ARA | cis-5,8,11,14-eicosatetraenoic | 20:4 ω-6 |

TABLE 3-continued

Nomenclature of Polyunsaturated Fatty Acids And Precursors

| Common Name | Abbreviation | Chemical Name | Shorthand Notation |
|---|---|---|---|
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Sciadonic | SCI | cis-5,11,14-eicosatrienoic | 20:3b ω-6 |
| Juniperonic | JUP | cis-5,11,14,17-eicosatetraenoic | 20:4b ω-3 |
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosa-tetraenoic | DTA | cis-7,10,13,16-docosatetraenoic | 22:4 ω-6 |
| Docosa-pentaenoic | DPAn-6 | cis-4,7,10,13,16-docosapentaenoic | 22:5 ω-6 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

The term "long-chain polyunsaturated fatty acid" ["LC-PUFA"] refers to those PUFAs that have chain lengths of $C_{20}$ or greater. Thus, the term LC-PUFA includes at least EDA, DGLA, ARA, ETrA, ETA, EPA, DTA, DPAn-6, DPA and DHA.

A metabolic pathway, or biosynthetic pathway, in a biochemical sense, can be regarded as a series of chemical reactions occurring in order within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to ω-6 fatty acids such as LA, EDA, GLA, DGLA, ARA, DRA, DTA and DPAn-6 and ω-3 fatty acids such as ALA, STA, ETrA, ETA, EPA, DPA and DHA. This process is well described in the literature (e.g., see Intl. App. Pub. No. WO 2006/052870). Briefly, this process involves elongation of the carbon chain through the addition of carbon atoms and desaturation of the molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode said enzymes) associated with the biosynthesis of a PUFA, including: Δ4 desaturase, Δ5 desaturase, Δ6 desaturase, Δ12 desaturase, Δ15 desaturase, Δ17 desaturase, Δ9 desaturase, Δ8 desaturase, Δ9 elongase, $C_{14/16}$ elongase, $C_{16/18}$ elongase, $C_{18/20}$ elongase and/or $C_{20/22}$ elongase.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are: Δ8 desaturases; Δ5 desaturases; Δ17 desaturases; Δ2 desaturases; Δ15 desaturases; Δ9 desaturases; Δ6 desaturases; and Δ4 desaturases. Δ17 desaturases, and also Δ5 desaturases, are also occasionally referred to as "omega-3 desaturases", "w-3 desaturases", and/or "ω-3 desaturases", based on their ability to convert ω-6 fatty acids into their ω-3 counterparts.

The term "elongase" refers to a polypeptide that can elongate a fatty acid carbon chain to produce an acid 2 carbons longer than the fatty acid substrate that the elongase acts upon. This process of elongation occurs in a multi-step mechanism in association with fatty acid synthase, as described in Intl. App. Pub. No. WO 2005/047480. Examples of reactions catalyzed by elongase systems are the conversion of GLA to DGLA, STA to ETA, ARA to DTA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., LA, ALA, GLA, STA) and a $C_{20/22}$ elongase (also known as a C20 elongase or Δ5 elongase as the terms can be used interchangeably) will utilize a $C_{20}$ substrate (e.g., ARA, EPA). For the purposes herein, two distinct types of $C_{18/20}$ elongases can be defined: a Δ6 elongase will catalyze conversion of GLA and STA to DGLA and ETA, respectively, while a Δ9 elongase is able to catalyze the conversion of LA and ALA to EDA and ETrA, respectively.

The terms "conversion efficiency" and "percent substrate conversion" refer to the efficiency by which a particular enzyme, such as a desaturase or elongase, can convert substrate to product. The conversion efficiency is measured according to the following formula: ([producty]/[substrate+product])*100, where 'product' includes the immediate product and all products in the pathway derived from it.

The term "$C_{18}$ to $C_{20}$ elongation conversion efficiency" refers to the efficiency by which $C_{18//20}$ elongases can convert $C_{18}$ substrates (i.e., LA, ALA, GLA, STA) to $C_{20}$ products (i.e., EDA, ETrA, DGLA, ETA). These $C_{18//20}$ elongases can be either Δ9 elongases or Δ6 elongases.

The terms "Δ9 elongation conversion efficiency" and "Δ9 elongase conversion efficiency" refer to the efficiency by which Δ9 elongase can convert $C_{18}$ substrates (i.e., LA, ALA) to $C_{20}$ products (i.e., EDA, ETrA).

The terms "Δ4 desaturation conversion efficiency" and "Δ4 desaturase conversion efficiency" refer to the efficiency by which Δ4 desaturase can convert substrates (i.e., DTA, DPAn-3) to products (i.e., DPAn-6, DHA).

The term "oleaginous" refers to those organisms that tend to store their energy source in the form of oil (Weete, In: Fungal Lipid Biochemistry, 2nd Ed., Plenum, 1980). Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. Oleaginous microorganisms include various bacteria, algae, euglenoids, moss, fungi (e.g., *Mortierella*), yeast and stramenopiles (e.g., *Schizochytrium*).

The term "oleaginous yeast" refers to those microorganisms classified as yeasts that can make oil. Examples of oleaginous yeast include, but are no means limited to, the following genera: *Yarrowia, Candida, Rhodotorula, Rhodosporidium, Cryptococcus, Trichosporon* and *Lipomyces*.

The term "fermentable carbon source" means a carbon source that a microorganism will metabolize to derive energy. Typical carbon sources include, but are not limited to:

monosaccharides, disaccharides, oligosaccharides, polysaccharides, alkanes, fatty acids, esters of fatty acids, glycerol, monoglycerides, diglycerides, triglycerides, carbon dioxide, methanol, formaldehyde, formate and carbon-containing amines.

As used herein the term "biomass" refers specifically to spent or used cellular material from the fermentation of a recombinant production host producing PUFAs in commercially significant amounts, wherein the preferred production host is a recombinant strain of an oleaginous yeast of the genus *Yarrowia*. The biomass may be in the form of whole cells, whole cell lysates, homogenized cells, partially hydrolyzed cellular material, and/or partially purified cellular material (e.g., microbially produced oil).

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, a nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* 2nd ed., Cold Spring Harbor Laboratory: Cold Spring Harbor, N.Y. (1989), which is hereby incorporated herein by reference, particularly Chapter 11 and Table 11.1.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.,* 215: 403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation, such as in situ hybridization of bacterial colonies or bacteriophage plaques. In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "complementary" is used to describe the relationship between nucleotide bases that are capable of hybridizing to one another. For example, with respect to DNA, adenosine is complementary to thymine and cytosine is complementary to guanine.

As used herein, the terms "homology" and "homologous" are used interchangeably. They refer to nucleic acid fragments wherein changes in one or more nucleotide bases do not affect the ability of the nucleic acid fragment to mediate gene expression or produce a certain phenotype. These terms also refer to modifications of the nucleic acid fragments such as deletion or insertion of one or more nucleotides that do not substantially alter the functional properties of the resulting nucleic acid fragment relative to the initial, unmodified fragment.

Moreover, the skilled artisan recognizes that homologous nucleic acid sequences are also defined by their ability to hybridize, under moderately stringent conditions, e.g., 0.5× SSC, 0.1% SDS, 60° C., with the sequences exemplified herein, or to any portion of the nucleotide sequences disclosed herein and which are functionally equivalent thereto. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995).

As used herein, the term "percent identity" refers to a relationship between two or more polypeptide sequences or two or more polynucleotide sequences, as determined by comparing the sequences. "Identity" also means the degree of sequence relatedness between polypeptide or polynucleotide sequences, as the case may be, as determined by the percentage of match between compared sequences. "Percent identity" and "percent similarity" can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: NY (1991).

Preferred methods to determine percent identity are designed to give the best match between the sequences tested. Methods to determine percent identity and percent similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, CABIOS, 5:151-153 (1989); Higgins, D. G. et al., *Comput. Appl. Biosci.,* 8:189-191 (1992)) and found in the MegAlign™ (version 8.0.2) program of the LASERGENE bioinformatics computing suite (DNASTAR Inc.). Default parameters for multiple protein alignment using the Clustal W method of alignment correspond to GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB with the 'slow-accurate' option. After alignment of the sequences using either Clustal program, it is possible to obtain a "percent identity" by viewing the "sequence distances" table in the program.

It is well understood by one skilled in the art that many levels of sequence identity are useful in identifying polypeptides, from other species, wherein such polypeptides have the same or similar function or activity. Useful examples of percent identities include any integer percentage from 34% to 100%, such as 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequence" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and which can be translated into protein by the cell. "cDNA" refers to a double-stranded DNA that is complementary to, and derived from, mRNA.

The term "operably linked" refers to the association of nucleic acid sequences on a single nucleic acid fragment so that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences in sense or antisense orientation.

The term "expression", as used herein, refers to the transcription and stable accumulation of sense (mRNA) or antisense RNA. Expression may also refer to translation of mRNA into a polypeptide.

"Transformation" refers to the transfer of a nucleic acid molecule into a host organism. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" or "transformant" organisms.

"Stable transformation" refers to the transfer of a nucleic acid fragment into the genome of a host organism, including both nuclear and organellar genomes, resulting in genetically stable inheritance (i.e., the nucleic acid fragment is "stably integrated"). In contrast, "transient transformation" refers to the transfer of a nucleic acid fragment into the nucleus, or DNA-containing organelle, of a host organism resulting in gene expression without integration or stable inheritance.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction that is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence ["ORF"]; and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

As previously described, genes encoding LPLATs are found in all eukaryotic cells, based on their intimate role in de novo synthesis and remodeling of glycerophospholipids, wherein LPLATs remove acyl-CoA fatty acids from the cellular acyl-CoA pool and acylate various lysophospholipid substrates at the sn-2 position in the phospholipid pool. Publicly available sequences encoding LPLATs include ScAle1 (SEQ ID NO:9), ScLPAAT (SEQ ID NO:18), MaLPAAT1 (SEQ ID NO:15) and CeLPCAT (SEQ ID NO:2). The ScAle1 (SEQ ID NO:9) and ScLPAAT (SEQ ID NO:18) protein sequences were used as a query to identify orthologs from the public *Y. lipolytica* protein database (the "Yeast project Genolevures" (Center for Bioinformatics, LaBR1, Talence Cedex, France) (see also Dujon, B. et al., *Nature*, 430(6995): 35-44 (2004)). Based on analysis of the best hits, the Ale1 and LPAAT orthologs from *Yarrowia lipolytica* are identified herein as YlAle1 (SEQ ID NO:11) and YlLPAAT1 (SEQ ID NO:17), respectively (see Example 5, infra).

When the sequence of a particular LPLAT gene or protein within a preferred host organism is not known, the LPLAT sequences set forth herein as SEQ ID NOs:2, 9, 11, 15, 17 and 18, or portions of them, may be used to search for LPLAT homologs in the same or other algal, fungal, oomycete, euglenoid, stramenopiles, yeast or plant species using sequence analysis software. In general, such computer software matches similar sequences by assigning degrees of homology to various substitutions, deletions, and other modifications. Use of software algorithms, such as the BLASTP method of alignment with a low complexity filter and the following parameters: Expect value=10, matrix=Blosum 62 (Altschul, et al., *Nucleic Acids Res.*, 25:3389-3402 (1997)), is well-known for comparing any LPLAT protein against a database of nucleic or protein sequences and thereby identifying similar known sequences within a preferred host organism.

Use of a software algorithm to comb through databases of known sequences is particularly suitable for the isolation of homologs having a relatively low percent identity to publicly available LPLAT sequences, such as those described in SEQ ID NOs:2, 9, 11, 15, 17 and 18. It is predictable that isolation would be relatively easier for LPLAT homologs of at least about 70%-85% identity to publicly available LPLAT sequences. Further, those sequences that are at least about 85%-90% identical would be particularly suitable for isolation and those sequences that are at least about 90%-95% identical would be the most facilely isolated.

LPLAT homologs can also be identified by the use of motifs unique to the LPLAT enzymes. These motifs likely represent regions of the LPLAT protein that are important to the structure, stability or activity of the protein and these motifs are useful as diagnostic tools for the rapid identification of novel LPLAT genes.

A variety of LPLAT motifs have been proposed, with slight variation based on the specific species that are included in analyzed alignments. For example, Shindou et al. (*Biochem. Biophys. Res. Comm.*, 383:320-325 (2009)) proposed the following membrane bound O-acyltransferase ["MBOAT"] family motifs to be important for LPLAT activity, based on alignment of sequences from *Homo sapiens, Gallus gallus, Danio rerio* and *Caenorhabditis elegans*: WD, WHGxxxGYxxxF (SEQ ID NO:23), YxxxxF (SEQ ID NO:24) and YxxxYFxxH (SEQ ID NO:25). Of these, the WD, WHGxxxGYxxxF and YxxxxF motifs are present in ScAle and YlAle1, but the YxxxYFxxH motif is not. Alternate non-plant motifs for Ale1 homologs are also described in U.S. Pat. Pub. No. 2008-0145867-A1; specifically, these include: M-[V/I]-[L/I]-xxK-[L/V/I]-xxxxxDG (SEQ ID NO:26), RxKYYxxWxxx-[E/D]-[A/G]xxxxGxG-[F/Y]-xG (SEQ ID NO:27), $EX_{11}WNX_2$-[T/V]-$X_2W$ (SEQ ID NO:28) and SAx-WHGxxPGYxx-[T/F]-F (SEQ ID NO:29).

Similarly, Lewin, T. W. et al. (*Biochemistry*, 38:5764-5771 (1999)) and Yamashita et al. (*Biochim, Biophys. Acta*, 1771: 1202-1215 (2007)) proposed the following 1-acyl-sn-glycerol-3-phosphate acyltransferase ["LPAAT"] family motifs to be important for LPLAT activity, based on alignment of sequences from bacteria, yeast, nematodes and mammals: NHxxxxD (SEQ ID NO:19), GxxFI-[D/R]-R (SEQ ID NO:30), EGTR (SEQ ID NO:20) and either [V/I]-[P/X]-[I/V/L]-[I/V]-P-[V/I] (SEQ ID NO:31) or IVPIVM (SEQ ID NO:32). The NHxxxxD and EGTR motifs are present in MaLPAAT1, YlLPAAT1 and CeLPCAT, but the other motifs are not.

Based on publicly available Ale1, LPCAT and LPAAT protein sequences, including those described herein, the instant invention concerns the following MBOAT family motifs: M(V/I)LxxKL (SEQ ID NO:3), RxKYYxxW (SEQ ID NO:4), SAxWHG (SEQ ID NO:5) and $EX_{11}WNX_2$-[T/V]-$X_2$W (SEQ ID NO:28). Similarly, 1-acyl-sn-glycerol-3-phosphate acyltransferase family motifs are those set forth as: NHxxxxD (SEQ ID NO:19) and EGTR (SEQ ID NO:20).

Alternatively, publicly available LPLAT sequences or their motifs may be hybridization reagents for the identification of homologs. Hybridization methods are well known to those of ordinary skill in the art as noted above.

Any of the LPLAT nucleic acid fragments or any identified homologs may be used to isolate genes encoding homologous proteins from the same or other algal, fungal, oomycete, euglenoid, stramenopiles, yeast or plant species. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies, such as polymerase chain reaction ["PCR"] (U.S. Pat. No. 4,683,202); ligase chain reaction ["LCR"](Tabor, S. et al., *Proc. Natl. Acad. Sci. U.S.A.*, 82:1074 (1985)); or strand displacement amplification ["SDA"] (Walker, et al., *Proc. Natl. Acad. Sci. U.S.A.*, 89:392 (1992)); and, 3) methods of library construction and screening by complementation.

For example, genes encoding proteins or polypeptides similar to publicly available LPLAT genes or their motifs could be isolated directly by using all or a portion of those publicly available nucleic acid fragments as DNA hybridization probes to screen libraries from any desired organism using well known methods. Specific oligonucleotide probes based upon the publicly available nucleic acid sequences can be designed and synthesized by methods known in the art (Maniatis, supra). Moreover, the entire sequences can be used directly to synthesize DNA probes by methods known to the skilled artisan, such as random primers DNA labeling, nick translation or end-labeling techniques, or RNA probes using available in vitro transcription systems. In addition, specific primers can be designed and used to amplify a part or the full length of the publicly available sequences or their motifs. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of available LPLAT sequences may be used in PCR protocols to amplify longer nucleic acid fragments encoding homologous genes from DNA or RNA. PCR may also be performed on a library of cloned nucleic acid fragments wherein the sequence of one primer is derived from the available nucleic acid fragments or their motifs. The sequence of the other primer takes advantage of the presence of the polyadenylic acid tracts to the 3' end of the mRNA precursor encoding genes.

Alternatively, the second primer sequence may be based upon sequences derived from the cloning vector. For example, the skilled artisan can follow the RACE protocol (Frohman et al., *Proc. Natl. Acad. Sci. U.S.A.*, 85:8998 (1988)) to generate cDNAs by using PCR to amplify copies of the region between a single point in the transcript and the 3' or 5' end. Primers oriented in the 3' and 5' directions can be designed from the available sequences. Using commercially available 3' RACE or 5' RACE systems (e.g., BRL, Gaithersburg, Md.), specific 3' or 5' cDNA fragments can be isolated (Ohara et al., *Proc. Natl. Acad. Sci. U.S.A.*, 86:5673 (1989); Loh et al., *Science*, 243:217 (1989)).

Based on any of these well-known methods just discussed, it would be possible to identify and/or isolate LPLAT gene homologs in any preferred eukaryotic organism of choice. The activity of any putative LPLAT gene can readily be confirmed by expression of the gene within a LC-PUFA-producing host organism, since the $C_{18}$ to $C_{20}$ elongation and/or Δ4 desaturation are increased relative to those within an organism lacking the LPLAT transgene (supra).

It has been previously hypothesized that LPCATs could be important in the accumulation of EPA in the TAG fraction of *Yarrowia lipolytica* (U.S. Pat. Pub. No. 2006-0115881-A1). As described therein, this hypothesis was based on the following studies: 1) Stymne S, and A. K. Stobart (*Biochem J.*, 223(2):305-314 (1984)), who hypothesized that the exchange between the acyl-CoA pool and PC pool may be attributed to the forward and backward reaction of LPCAT; 2) Domergue, F. et al. (*J. Bio. Chem.*, 278:35115 (2003)), who suggested that accumulation of GLA at the sn-2 position of PC and the inability to efficiently synthesize ARA in yeast was a result of the elongation step involved in PUFA biosynthesis occurring within the acyl-CoA pool, while Δ5 and Δ6 desaturation steps occurred predominantly at the sn-2 position of PC; 3) Abbadi, A. et al. (*The Plant Cell*, 16:2734-2748 (2004)), who suggested that LPCAT plays a criticial role in the successful reconstitution of a Δ6 desaturase/Δ6 elongase pathway, based on analysis on the constraints of PUFA accumulation in transgenic oilseed plants; and, 4) Intl. App. Pub. No. WO 2004/076617 A2 (Renz, A. et al.), who provided a gene encoding LPCAT from *Caenorhabditis elegans* (T06E8.1) ["CeLPCAT"] that substantially improved the efficiency of elongation in a genetically introduced Δ6 desaturase/Δ6 elongase pathway in *S. cerevisiae* fed with exogenous fatty acid substrates suitable for Δ6 elongation. Renz et al. concluded that LPCAT allowed efficient and continuous exchange of the newly synthesized fatty acids between phospholipids and the acyl-CoA pool, since desaturases catalyze the introduction of double bonds in PC-coupled fatty acids while elongases exclusively catalyze the elongation of CoA esterified fatty acids (acyl-CoAs). However, Intl. App. Pub. No. WO 2004/076617 did not teach the effect of CeLPCAT on Δ6 elongation conversion efficiency in host cells that were not exogenously fed fatty acids, Δ5 elongation conversion efficiency, or Δ4 desaturation conversion efficiency.

Herein, it is demonstrated that LPAAT and LPCAT are indeed important in the accumulation of EPA and DHA in the TAG fraction of *Yarrowia lipolytica*. However, unexpectedly, it was found that over-expression of LPLATs can result in an improvement in the Δ9 elongase conversion efficiency and/or Δ4 desaturase conversion efficiency. As previously defined, conversion efficiency is a term that refers to the efficiency by which a particular enzyme, such as a Δ4 desaturase or Δ9 elongase, can convert substrate to product. Thus, in a strain engineered to produce EPA, improvement in Δ9 elongase conversion efficiency was demonstrated to result in increased EPA % TFAs or EPA % DCW. Similarly, improvement in Δ9 elongase and/or Δ4 desaturase conversion efficiency in a strain engineered to produce DHA was demonstrated to result in increased DHA TFAs or DHA % DCW.

PUFA desaturations occur on phospholipids, while fatty acid elongations occur on acyl-CoAs. Based on previous studies, it was therefore expected that LPLAT over-expression would result in improved desaturations due to improved substrate availability in phospholipids, while expression of LPLATs was not expected to result in improved elongations that require improved substrate availability in the CoA pool.

Despite these assumptions, Example 5 demonstrates that LPLAT expression did not improve the conversion efficiency of all desaturations in strains of *Yarrowia* producing DHA, in a comparable manner. Specifically, the conversion efficiency of Δ4 desaturase was selectively improved, while similar improvements were not found in Δ2, Δ8, Δ5 or Δ17 desaturations. It is hypothesized that Δ4 desaturase was therefore limiting as a result of limited availability of the DPA substrate in phospholipids.

Additionally, Examples 4 and 5 demonstrate that LPLAT expression, based on at least one stably integrated polynucleotide encoding the LPLAT polypeptide, significantly improved the Δ9 elongase conversion efficiency in strains of *Yarrowia* producing EPA and DHA, respectively. Surprisingly, however, the LPLATs did not also result in a comparable improvement in the efficiency of the $C_{20/22}$ elongation of EPA to DPA in DHA strains. Generally, there was no significant change in the total lipid content in strains over-expressing LPLATs versus those that were not.

Clearly, broad generalizations are difficult concerning the effect of LPLAT over-expression in host cells producing PUFAs. Instead, the effect of LPLAT activity must be considered based on subsets of desaturases and elongases having specific activity (i.e., Δ2 desaturase, Δ8 desaturase, Δ5 desaturase, Δ17 desaturase, Δ4 desaturase, Δ9 elongase, $C_{14/16}$ elongase, $C_{16/18}$ elongase, $C_{18/20}$ elongase ["also Δ6 elongase"], $C_{20/22}$ elongase ["also Δ5 elongase"]).

On the basis of the above discussion, in one embodiment herein, methods for improving $C_{18}$ to $C_{20}$ elongation conversion efficiency in a LC-PUFA-producing recombinant oleaginous microbial host cell are provided, wherein said method comprises:
  a) introducing into said LC-PUFA-producing recombinant host cell at least one isolated polynucleotide encoding a polypeptide having at least acyl-CoA:lysophospholipid acyltransferase activity wherein the polypeptide is selected from the group consisting of:
    (i) a polypeptide having at least 45% amino acid identity, based on the Clustal W method of alignment, when compared to an amino acid sequence selected from the group consisting of SEQ ID NO:9 (ScAle1) and SEQ ID NO:11 (YlAle1);
    (ii) a polypeptide having at least one membrane bound O-acyltransferase protein family motif selected from the group consisting of: M(V/I)LxxKL (SEQ ID NO:3), RxKYYxxW (SEQ ID NO:4), SAxWHG (SEQ ID NO:5) and $EX_{11}WNX_2$-[T/V]-$X_2W$ (SEQ ID NO:28);
    (iii) a polypeptide having at least 90% amino acid identity, based on the Clustal W method of alignment, when compared to an amino acid sequence as set forth in SEQ ID NO:2 (CeLPCAT);
    (iv) a polypeptide having at least 43.9% amino acid identity, based on the Clustal W method of alignment, when compared to an amino acid sequence selected from the group consisting of SEQ ID NO:15 (MaLPAAT1), SEQ ID NO:17 (YlLPAAT1) and SEQ ID NO:18 (ScLPAAT1); and,
    (v) a polypeptide having at least one 1-acyl-sn-glycerol-3-phosphate acyltransferase protein family motif selected from the group consisting of: NHxxxxD (SEQ ID NO:19) and EGTR (SEQ ID NO:20);
  wherein the at least one isolated polynucleotide encoding a polypeptide having at least acyl-CoA:lysophospholipid acyltransferase activity is operably linked to at least one regulatory sequence, said regulatory sequence being the same or different; and,
  b) growing the oleaginous microbial host cell;
  wherein the $C_{18}$ to $C_{20}$ elongation conversion efficiency of the oleaginous microbial host cell is increased relative to the control host cell.

In preferred embodiments, the increase in $C_{18}$ to $C_{20}$ elongation conversion efficiency is at least 4% in at least one LC-PUFA-producing oleaginous microbial host cell, based on at least one stably integrated polynucleotide encoding the LPLAT polypeptide, when compared to the control host cell, although any increase in $C_{18}$ to $C_{20}$ elongation conversion efficiency greater than 4% is especially preferred, including increases of at least about 4-10%, more preferred at least about 10-20%, more preferred at least about 20-40%, and most preferred at least about 40-60% or greater.

For example, in one method demonstrated herein, the increase in $C_{18}$ to $C_{20}$ elongation conversion efficiency is at least 13% in an EPA-producing host cell when compared to the control host cell and the increase in $C_{18}$ to $C_{20}$ elongation conversion efficiency is at least 4% in a DHA-producing host cell when compared to the control host cell.

Similarly, methods are also described herein for increasing Δ4 desaturation conversion efficiency in a LC-PUFA-producing oleaginous microbial recombinant host cell, wherein said method comprises:
  a) introducing into said LC-PUFA-producing recombinant host cell at least one isolated polynucleotide encoding a polypeptide having at least acyl-CoA:lysophospholipid acyltransferase activity wherein the polypeptide is selected from the group consisting of:
    (i) a polypeptide having at least 45% amino acid identity, based on the Clustal W method of alignment, when compared to an amino acid sequence selected from the group consisting of SEQ ID NO:9 (ScAle1) and SEQ ID NO:11 (YlAle1);
    (ii) a polypeptide having at least one membrane bound O-acyltransferase protein family motif selected from the group consisting of: M(V/I)LxxKL (SEQ ID NO:3), RxKYYxxW (SEQ ID NO:4), SAxWHG (SEQ ID NO:5) and $EX_{11}WNX_2$-[T/V]-$X_2W$ (SEQ ID NO:28);
    (iii) a polypeptide having at least 90% amino acid identity, based on the Clustal W method of alignment, when compared to an amino acid sequence as set forth in SEQ ID NO:2 (CeLPCAT);

(iv) a polypeptide having at least 43.9% amino acid identity, based on the Clustal W method of alignment, when compared to an amino acid sequence selected from the group consisting of SEQ ID NO:15 (MaLPAAT1), SEQ ID NO:17 (YlLPAAT1) and SEQ ID NO:18 (ScLPAAT1); and, (v) a polypeptide having at least one 1-acyl-sn-glycerol-3-phosphate acyltransferase protein family motif selected from the group consisting of: NHxxxxD (SEQ ID NO:19) and EGTR (SEQ ID NO:20);

wherein the at least one isolated polynucleotide encoding a polypeptide having at least acyl-CoA:lysophospholipid acyltransferase activity is operably linked to at least one regulatory sequence, said regulatory sequence being the same or different; and, b) growing the oleaginous microbial host cell;

wherein the Δ4 desaturation conversion efficiency of the oleaginous microbial host cell is increased relative to the control host cell.

In preferred embodiments, the increase in Δ4 desaturation conversion efficiency is at least 5% in at least one LC-PUFA-producing oleaginous microbial host cell, based on at least one stably integrated polynucleotide encoding the LPLAT polypeptide, when compared to the control host cell, although any increase in Δ4 desaturation conversion efficiency greater than 5% is especially preferred, including increases of at least about 5-10%, more preferred at least about 10-20%, more preferred at least about 20-40%, and most preferred at least about 40-60% or greater.

For example, in one method demonstrated herein, the increase in Δ4 desaturation conversion efficiency in a DHA-producing host was at least 18% when compared to the control host cell.

Recombinant host cells are also described herein, in addition to the methods set forth above. Specifically, these recombinant host cells comprise at least one isolated polynucleotide encoding a polypeptide having at least acyl-CoA:lysophospholipid acyltransferase activity, wherein the polypeptide is selected from the group consisting of:

(a) a polypeptide having at least 45% amino acid identity, based on the Clustal W method of alignment, when compared to an amino acid sequence selected from the group consisting of SEQ ID NO:9 (ScAle1) and SEQ ID NO:11 (YlAle1);

(b) a polypeptide having at least one membrane bound O-acyltransferase protein family motif selected from the group consisting of: M(V/I)LxxKL (SEQ ID NO:3), RxKYYxxW (SEQ ID NO:4), SAxWHG (SEQ ID NO:5) and $EX_{11}WNX_2$-[T/V]-$X_2W$ (SEQ ID NO:28);

(c) a polypeptide having at least 90% amino acid identity, based on the Clustal W method of alignment, when compared to an amino acid sequence as set forth in SEQ ID NO:2 (CeLPCAT);

(d) a polypeptide having at least 43.9% amino acid identity, based on the Clustal W method of alignment, when compared to an amino acid sequence selected from the group consisting of SEQ ID NO:15 (MaLPAAT1), SEQ ID NO:17 (YlLPAAT1) and SEQ ID NO:18 (ScLPAAT1); and, (e) a polypeptide having at least one 1-acyl-sn-glycerol-3-phosphate acyltransferase family motif selected from the group consisting of: NHxxxxD (SEQ ID NO:19) and EGTR (SEQ ID NO:20);

wherein the at least one isolated polynucleotide encoding a polypeptide having at least acyl-CoA:lysophospholipid acyltransferase activity is operably linked to at least one regulatory sequence, said regulatory sequence being the same or different, and the recombinant host cells further have at least one improvement selected from the group consisting of:

a) an increase in $C_{18}$ to $C_{20}$ elongation conversion efficiency in at least one LC PUFA-producing oleaginous microbial host cell when compared to the control host cell;

b) an increase in Δ4 desaturation conversion efficiency in at least one LC PUFA-producing oleaginous microbial host cell when compared to the control host cell.

In preferred host cells, the polynucleotide encoding the polypeptide having at least acyl-CoA:lysophospholipid acyltransferase activity is stably integrated; and, further wherein the host cell has at least one improvement selected from the group consisting of:

a) an increase in $C_{18}$ to $C_{20}$ elongation conversion efficiency of at least 4% in at least one long-chain polyunsaturated fatty acid-producing oleaginous microbial host cell when compared to a control host cell; and, b) an increase in Δ4 desaturation conversion efficiency of at least 5% in at least one long-chain polyunsaturated fatty acid-producing oleaginous microbial host cell when compared to a control host cell.

In more preferred host cells, having at least one stably integrated polynucleotide encoding the LPLAT polypeptide, the at least one improvement is selected from the group consisting of:

a) an increase in $C_{18}$ to $C_{20}$ elongation conversion efficiency of at least 13% in an EPA-producing host cell when compared to the control host cell;

b) an increase of at least 9% EPA of TFAs in an EPA-producing host cell when compared to the control host cell;

c) an increase in $C_{18}$ to $C_{20}$ elongation conversion efficiency of at least of at least 4% in a DHA-producing host cell when compared to the control host cell;

d) an increase of at least 2% EPA of TFAs in a DHA-producing host cell when compared to the control host cell;

e) an increase in Δ4 desaturation conversion efficiency of at least 18% in a DHA-producing host cell when compared to the control host cell; and, f) an increase of at least 9% DHA of TFAs in a DHA-producing host cell when compared to the control host cell.

Of course, one of skill in the art should understand that the improvements described above should be considered as exemplary, but not limiting to the invention herein.

Based on the above improvements, one of skill in the art will appreciate the value of expressing a LPLAT in a recombinant host cell that is producing long-chain PUFAs, such EDA, DGLA, ARA, DTA, DPAn-6, ETrA, ETA, EPA, DPA and DHA, if it is desirable to optimize the production of these fatty acids.

Standard resource materials that are useful to make recombinant constructs describe, inter alia: 1) specific conditions and procedures for construction, manipulation and isolation of macromolecules, such as DNA molecules, plasmids, etc.; 2) generation of recombinant DNA fragments and recombinant expression constructs; and, 3) screening and isolation of clones. See, Sambrook, J., Fritsch, E. F. and Maniatis, T., Molecular Cloning: A Laboratory Manual, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

In general, the choice of sequences included in the construct depends on the desired expression products, the nature of the host cell and the proposed means of separating transformed cells versus non-transformed cells. The skilled artisan is aware of the genetic elements that must be present on the plasmid vector to successfully transform, select and propagate host cells containing the chimeric gene. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation, i.e., a promoter, the gene coding sequence, and a region 3' of the DNA fragment that controls transcriptional termination, i.e., a terminator. It is most preferred when both control regions are derived from genes from the transformed host cell, although they need not be derived from genes native to the production host.

Transcription initiation regions or promoters useful for driving expression of heterologous genes or portions of them in the desired host cell are numerous and well known. These control regions may comprise a promoter, enhancer, silencer, intron sequences, 3' UTR and/or 5' UTR regions, and protein and/or RNA stabilizing elements. Such elements may vary in their strength and specificity. Virtually any promoter, i.e., native, synthetic, or chimeric, capable of directing expression of these genes in the selected host cell is suitable, although transcriptional and translational regions from the host species are particularly useful. Expression in a host cell can occur in an induced or constitutive fashion. Induced expression occurs by inducing the activity of a regulatable promoter operably linked to the LPLAT gene of interest, while constitutive expression occurs by the use of a constituitive promoter.

3' non-coding sequences encoding transcription termination regions may be provided in a recombinant construct and may be from the 3' region of the gene from which the initiation region was obtained or from a different gene. A large number of termination regions are known and function satisfactorily in a variety of hosts when utilized in both the same and different genera and species from which they were derived. Termination regions may also be derived from various genes native to the preferred hosts. The termination region is usually selected more for convenience rather than for any particular property.

Particularly useful termination regions for use in yeast are derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. The 3'-region can also be synthetic, as one of skill in the art can utilize available information to design and synthesize a 3'-region sequence that functions as a transcription terminator. A termination region may be unnecessary, but is highly preferred.

The vector may also comprise a selectable and/or scorable marker, in addition to the regulatory elements described above. Preferably, the marker gene is an antibiotic resistance gene such that treating cells with the antibiotic results in growth inhibition, or death, of untransformed cells and uninhibited growth of transformed cells. For selection of yeast transformants, any marker that functions in yeast is useful with resistance to kanamycin, hygromycin and the amino glycoside G418 and the ability to grow on media lacking uracil, lysine, histine or leucine being particularly useful.

Merely inserting a gene (e.g., encoding a LPLAT) into a cloning vector does not ensure its expression at the desired rate, concentration, amount, etc. In response to the need for a high expression rate, many specialized expression vectors have been created by manipulating a number of different genetic elements that control transcription, RNA stability, translation, protein stability and location, oxygen limitation, and secretion from the host cell. Some of the manipulated features include: the nature of the relevant transcriptional promoter and terminator sequences, the number of copies of the cloned gene and whether the gene is plasmid-borne or integrated into the genome of the host cell, the final cellular location of the synthesized protein, the efficiency of translation and correct folding of the protein in the host organism, the intrinsic stability of the mRNA and protein of the cloned gene within the host cell and the codon usage within the cloned gene, such that its frequency approaches the frequency of preferred codon usage of the host cell. Each of these may be used in the methods and host cells described herein to further optimize expression of LPLAT genes.

For example, LPLAT expression can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Alternately, additional copies of the LPLAT genes may be introduced into the recombinant host cells to thereby increase EPA and/or DHA production and accumulation, either by cloning additional copies of genes within a single expression construct or by introducing additional copies into the host cell by increasing the plasmid copy number or by multiple integration of the cloned gene into the genome.

After a recombinant construct is created comprising at least one chimeric gene comprising a promoter, a LPLAT open reading frame ["ORF"] and a terminator, it is placed in a plasmid vector capable of autonomous replication in the host cell or is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When two or more genes are expressed from separate replicating vectors, each vector may have a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a host cell by any standard technique. These techniques include transformation, e.g., lithium acetate transformation (*Methods in Enzymology*, 194:186-187 (1991)), biolistic impact, electroporation, microinjection, vacuum filtration or any other method that introduces the gene of interest into the host cell.

For convenience, a host cell that has been manipulated by any method to take up a DNA sequence, for example, in an expression cassette, is referred to herein as "transformed" or "recombinant" or "transformant". The transformed host will have at least one copy of the expression construct and may have two or more, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be co-transformed with the desired construct, as many transformation techniques introduce many DNA molecules into host cells.

Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. Additional selection techniques are described in U.S. Pat. No. 7,238,482 and U.S. Pat. No. 7,259,255.

Regardless of the selected host or expression construct, multiple transformants must be screened to obtain a strain displaying the desired expression level and pattern. For example, Juretzek et al. (*Yeast*, 18:97-113 (2001)) note that the stability of an integrated DNA fragment in *Yarrowia lipolytica* is dependent on the individual transformants, the recipient strain and the targeting platform used. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western analysis of protein expression, phenotypic analysis or GC analysis of the PUFA products.

The metabolic process wherein oleic acid is converted to LC-PUFAs involves elongation of the carbon chain through the addition of carbon atoms and desaturation of the molecule through the addition of double bonds. This requires a series of special desaturation and elongation enzymes present in the endoplasmic reticulum membrane. However, as seen in FIGS. 1A and B and as described below, multiple alternate pathways exist for LC-PUFA production.

Specifically, FIGS. 1A and B depict the pathways described below. All pathways require the initial conversion of oleic acid to linoleic acid ["LA"], the first of the ω-6 fatty acids, by a Δ2 desaturase. Then, using the "Δ9 elongase/Δ8 desaturase pathway" and LA as substrate, long-chain ω-6 fatty acids are formed as follows: 1) LA is converted to eicosadienoic acid ["EDA"] by a Δ9 elongase; 2) EDA is converted to dihomo-γ-linolenic acid ["DGLA"] by a Δ8 desaturase; 3) DGLA is converted to arachidonic acid ["ARA"] by a Δ5 desaturase; 4) ARA is converted to docosatetraenoic acid ["DTA"] by a $C_{20/22}$ elongase; and, 5) DTA is converted to docosapentaenoic acid ["DPAn-6"] by a Δ4 desaturase.

The "Δ9 elongase/Δ8 desaturase pathway" can also use α-linolenic acid ["ALA"] as substrate to produce long-chain ω-3 fatty acids as follows: 1) LA is converted to ALA, the first of the ω-3 fatty acids, by a Δ15 desaturase; 2) ALA is converted to eicosatrienoic acid ["ETrA"] by a Δ9 elongase; 3) ETrA is converted to eicosatetraenoic acid ["ETA"] by a Δ8 desaturase; 4) ETA is converted to eicosapentaenoic acid ["EPA"] by a Δ5 desaturase; 5) EPA is converted to docosapentaenoic acid ["DPA"] by a $C_{20/22}$ elongase; and, 6) DPA is converted to docosahexaenoic acid ["DHA"] by a Δ4 desaturase. Optionally, ω-6 fatty acids may be converted to ω-3 fatty acids. For example, ETA and EPA are produced from DGLA and ARA, respectively, by Δ17 desaturase activity. Advantageously for the purposes herein, the Δ9 elongase/Δ8 desaturase pathway enables production of an EPA oil that lacks significant amounts of γ-linolenic acid ["GLA"].

Alternate pathways for the biosynthesis of ω-3/ω-6 fatty acids utilize a Δ6 desaturase and $C_{18/20}$ elongase, that is, the "Δ6 desaturase/Δ6 elongase pathway". More specifically, LA and ALA may be converted to to GLA and stearidonic acid ["STA"], respectively, by a Δ6 desaturase; then, a $C_{18/20}$ elongase converts GLA to DGLA and/or STA to ETA.

A LC-PUFA-producing recombinant host cell will possess at least one of the biosynthetic pathways described above, whether this pathway is native to the host cell or is genetically engineered. Preferably, the host cell will be capable of producing at least about 2-5% LC-PUFAs in the total lipids of the recombinant host cell, more preferably at least about 5-15% LC-PUFAs in the total lipids, more preferably at least about 15-35% LC-PUFAs in the total lipids, more preferably at least about 35-50% LC-PUFAs in the total lipids, more preferably at least about 50-65% LC-PUFAs in the total lipids and most preferably at least about 65-75% LC-PUFAs in the total lipids. The structural form of the LC-PUFAs is not limiting; thus, for example, the EPA or DHA may exist in the total lipids as free fatty acids or in esterified forms such as acylglycerols, phospholipids, sulfolipids or glycolipids.

A variety of eukaryotic microbial organisms, including bacteria, yeast, algae, stramenopile, oomycete, euglenoid and/or fungus, can produce (or can be engineered to produce) LC-PUFAs. These may include hosts that grow on a variety of feedstocks, including simple or complex carbohydrates, fatty acids, organic acids, oils, glycerols and alcohols, and/or hydrocarbons over a wide range of temperature and pH values.

Preferred microbial hosts are oleaginous organisms. These oleaginous organisms are naturally capable of oil synthesis and accumulation, wherein the total oil content can comprise greater than about 25% of the dry cell weight, more preferably greater than about 30% of the dry cell weight, and most preferably greater than about 40% of the dry cell weight. Various bacteria, algae, euglenoids, moss, fungi, yeast and stramenopiles are naturally classified as oleaginous. Within this broad group of hosts, of particular interest are those organisms that naturally produce ω-3/ω-6 fatty acids. For example, ARA, EPA and/or DHA is produced via *Cyclotella* sp., *Crypthecodinium* sp., *Mortierella* sp., *Nitzschia* sp., *Pythium*, *Thraustochytrium* sp. and *Schizochytrium* sp. Thus, for example, transformation of *Mortierella alpina*, which is commercially used for production of ARA, with any of the present LPLAT genes under the control of inducible or regulated promoters could yield a transformant organism capable of synthesizing increased quantities of ARA. The method of transformation of *M. alpina* is described by Mackenzie et al. (*Appl. Environ. Microbiol.*, 66:4655 (2000)). Similarly, methods for transformation of Thraustochytriales microorganisms (e.g., *Thraustochytrium*, *Schizochytrium*) are disclosed in U.S. Pat. No. 7,001,772. In alternate embodiments, a non-oleaginous organism can be genetically modified to become oleaginous, e.g., yeast such as *Saccharomyces cerevisiae* (U.S. Pat. Pub. No. 2007/0015237-A1).

In more preferred embodiments, the microbial host cells are oleaginous yeast. Genera typically identified as oleaginous yeast include, but are not limited to: *Yarrowia*, *Candida*, *Rhodotorula*, *Rhodosporidium*, *Cryptococcus*, *Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*). Most preferred is the oleaginous yeast *Yarrowia lipolytica*; and, in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., *Bioresour. Technol.*, 82(1):43-9 (2002)).

Specific teachings applicable for engineering ARA, EPA and DHA production in *Y. lipolytica* are provided in U.S. Pat. Pub. No. 2006-0094092-A1, U.S. Pat. Pub. No. 2006-0115881-A1, U.S. Pat. Pub. No. 2009-0093543-A1 and U.S. Pat. Pub. No. 2006-0110806-A1, respectively. These references also describe the preferred method of expressing genes in *Yarrowia lipolytica* by integration of a linear DNA fragment into the genome of the host, preferred promoters, termination regions, integration loci and disruptions, and preferred selection methods when using this particular host species.

One of skill in the art would be able to use the cited teachings in U.S. Pat. Pub. No. 2006-0094092-A1, U.S. Pat. Pub. No. 2006-0115881-A1, U.S. Pat. Pub. No. 2009-0093543-A1 and U.S. Pat. Pub. No. 2006-0110806-A1 to recombinantly engineer other host cells for PUFA production.

The transformed recombinant host cell is grown under conditions that optimize expression of chimeric genes (e.g., encoding desaturases, elongases, LPLATs, etc.) and produce the greatest and the most economical yield of LC-PUFA(s). In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest.

*Yarrowia lipolytica* are generally grown in a complex media such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source, such as are taught in U.S. Pat. No. 7,238,482 and U.S. patent application Ser. No. 12/641,929 (filed Dec. 19, 2009). Although it is contemplated that the source of carbon utilized may encompass a wide variety of carbon-containing sources, preferred carbon sources are sugars, glycerol and/or fatty acids. Most preferred is glucose, sucrose, invert sucrose, fructose and/or fatty acids containing between 10-22 carbons. For example, the fermentable carbon source can be selected from the group consisting of invert sucrose, glucose, fructose and combinations of these, provided that glucose is used in combination with invert sucrose and/or fructose.

The term "invert sucrose", also referred to herein as "invert sugar", refers to a mixture comprising equal parts of fructose and glucose resulting from the hydrolysis of sucrose. Invert sucrose may be a mixture comprising 25 to 50% glucose and 25 to 50% fructose. Invert sucrose may also comprise sucrose, the amount of which depends on the degree of hydrolysis.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the high EPA- and/or DHA-producing host cells and the promotion of the enzymatic pathways for EPA and/or DHA production. Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and host cells described herein are common commercially prepared media, such as Yeast Nitrogen Base (DIFCO Laboratories, Detroit, Mich.). Other defined or synthetic growth media may also be used and the appropriate medium for growth of *Yarrowia lipolytica* will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of EPA and/or DHA in *Yarrowia lipolytica*. This approach is described in U.S. Pat. No. 7,238,482, as are various suitable fermentation process designs (i.e., batch, fed-batch and continuous) and considerations during growth.

In some aspects, the primary product is oleaginous microbial biomass. As such, isolation and purification of the LC-PUFA-containing oils from the biomass may not be necessary (i.e., wherein the whole cell biomass is the product).

However, certain end uses and/or product forms may require partial and/or complete isolation/purification of the LC-PUFA-containing oil from the biomass, to result in partially purified biomass, purified oil, and/or purified LC-PUFAs. Fatty acids, including PUFAs, may be found in the host microorganisms as free fatty acids or in esterified forms such as acylglycerols, phospholipids, sulfolipids or glycolipids. These fatty acids may be extracted from the host cells through a variety of means well-known in the art. One review of extraction techniques, quality analysis and acceptability standards for yeast lipids is that of Z. Jacobs (*Critical Reviews in Biotechnology*, 12(5/6):463-491 (1992)). A brief review of downstream processing is also available by A. Singh and O. Ward (*Adv. Appl. Microbiol.*, 45:271-312 (1997)).

In general, means for the purification of fatty acids (including LC-PUFAs) may include extraction (e.g., U.S. Pat. No. 6,797,303 and U.S. Pat. No. 5,648,564) with organic solvents, sonication, supercritical fluid extraction (e.g., using carbon dioxide), saponification and physical means such as presses, or combinations thereof. See U.S. Pat. No. 7,238,482.

Many food and feed products incorporate ω-3 and/or ω-6 fatty acids, particularly ALA, GLA, ARA, EPA, DPA and DHA. It is contemplated that oleaginous yeast biomass comprising LC-PUFAs, partially purified biomass comprising LC-PUFAs, purified oil comprising LC-PUFAs, and/or purified LC-PUFAs made by the methods and host cells described herein impart the health benefits, upon ingestion of foods or feed improved by their addition. These oils can be added to food analogs, drinks, meat products, cereal products, baked foods, snack foods and dairy products, to name a few. See U.S. Pat. Appl. Pub. No. 2006-0094092.

These compositions may impart health benefits by being added to medical foods including medical nutritionals, dietary supplements, infant formula and pharmaceuticals. The skilled artisan will appreciate the amount of the oils to be added to food, feed, dietary supplements, nutriceuticals, pharmaceuticals, and other ingestible products as to impart health benefits. Health benefits from ingestion of these oils are described in the art, known to the skilled artisan and continuously investigated. Such an amount is referred to herein as an "effective" amount and depends on, among other things, the nature of the ingested products containing these oils and the physical conditions they are intended to address.

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and, 3) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2nd ed., Sinauer Associates Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), New England Biolabs, Inc. (Beverly, Mass.), GIBCO/BRL (Gaithersburg, Md.), or Sigma Chemical Company (St. Louis, Mo.), unless otherwise specified. *E. coli* strains were typically grown at 37° C. on Luria Bertani ["LB"] plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "pmole" mean micromole(s), "g" means gram(s), "μg" means microgram(s), "ng" means nanogram(s), "U" means unit(s), "bp" means base pair(s), "kB" means kilobase(s), "DCW" means dry cell weight, and "TFAs" means total fatty acids.

Nomenclature for Expression Cassettes

The structure of an expression cassette will be represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica*

*Yarrowia lipolytica* strain ATCC #20362 was purchased from the American Type Culture Collection (Rockville, Md.). *Yarrowia lipolytica* strains were routinely grown at 28-30° C. in several media (e.g., YPD agar medium, Basic Minimal Media ["MM"], Minimal Media+Uracil ["MMU"], Minimal Media+Leucine+Lysine ["MMLeuLys"], Minimal Media+5-Fluoroorotic Acid ["MM+5-FOA"], High Glucose Media ["HGM"] and Fermentation medium ["FM"]), as described in U.S. Pat. Appl. Pub. No. 2009-0093543-A1.

Transformation of *Y. lipolytica* was performed as described in U.S. Pat. Appl. Pub. No. 2009-0093543-A1.

Fatty Acid Analysis of *Yarrowia lipolytica*

For fatty acid ["FA"] analysis, cells were collected by centrifugation and lipids were extracted as described in Bligh, E. G. & Dyer, W. J. (*Can. J. Biochem. Physiol.*, 37:911-917 (1959)). Fatty acid methyl esters ["FAMEs"] were prepared by transesterification of the lipid extract with sodium methoxide (Roughan, G., and Nishida I., *Arch Biochem Biophys.*, 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* cells (0.5 mL culture) were harvested, washed once in distilled water, and dried under vacuum in a Speed-Vac for 5-10 min. Sodium methoxide (100 μl of 1%) and a known amount of C15:0 triacylglycerol (C15:0 TAG; Cat. No. T-145, Nu-Check Prep, Elysian, Minn.) was added to the sample, and then the sample was vortexed and rocked for 30 min at 50° C. After adding 3 drops of 1 M NaCl and 400 μl hexane, the sample was vortexed and spun. The upper layer was removed and analyzed by GC.

FAME peaks recorded via GC analysis were identified by their retention times, when compared to that of known fatty acids, and quantitated by comparing the FAME peak areas with that of the internal standard (C15:0 TAG) of known amount. Thus, the approximate amount (μg) of any fatty acid FAME ["μg FAME"] is calculated according to the formula: (area of the FAME peak for the specified fatty acid/area of the standard FAME peak)*(μg of the standard C15:0 TAG), while the amount (μg) of any fatty acid ["μg FA"] is calculated according to the formula: (area of the FAME peak for the specified fatty acid/area of the standard FAME peak)*(μg of the standard C15:0 TAG)*0.9503, since 1 μg of C15:0 TAG is equal to 0.9503 μg fatty acids. Note that the 0.9503 conversion factor is an approximation of the value determined for most fatty acids, which range between 0.95 and 0.96.

The lipid profile, summarizing the amount of each individual fatty acid as a weight percent of TFAs, was determined by dividing the individual FAME peak area by the sum of all FAME peak areas and multiplying by 100.

For quantitating the amount of an individual fatty acid or the total fatty acids as a weight percent of the dry cell weight ["% DCW"], cells from 10 mL of the culture were collected by centrifugation, washed once with 10 mL water and collected by centrifugation again. Cells were resuspended in 1-2 mL water, poured into a pre-weighed aluminium weighing pan, and rinsed with 1-2 mL water that was also added to the same weighing pan. The pan was placed under vacuum at 80° C. overnight. The pan was weighed and the DCW calculated by subtracting the weight of the empty pan. Determination of the fatty acid as a % DCW can then be calculated based on either μg FAME or μg FA as a fraction of the μg DCW (for example, FAME % DCW was calculated as μg FAME/μg DCW*100).

Example 1

Generation of *Yarrowia lipolytica* Strain Y8406 to Produce about 51% EPA of Total Fatty Acids The present Example describes the construction of strain Y8406, derived from *Yarrowia lipolytica* ATCC #20362, capable of producing about 51% EPA relative to the total lipids via expression of a Δ9 elongase/Δ8 desaturase pathway. This strain was used as the EPA-producing host cell in Example 4.

The development of strain Y8406 (FIG. 2) required the construction of strains Y2224, Y4001, Y4001U, Y4036, Y4036U, L135, L135U9, Y8002, Y8006U6, Y8069, Y8069U, Y8154, Y8154U, Y8269 and Y8269U.

Generation of Y4036U Strain

Briefly, strain Y8406 was derived from *Yarrowia lipolytica* ATCC #20362 via construction of strain Y2224 (a FOA resistant mutant from an autonomous mutation of the Ura3 gene of wildtype *Yarrowia* strain ATCC #20362), strain Y4001 (producing 17% EDA with a Leu– phenotype), strain Y4001U1 (Leu– and Ura–), strain Y4036 (producing 18% DGLA with a Leu– phenotype) and strain Y4036U (Leu– and Ura–). Further details regarding the construction of strains Y2224, Y4001, Y4001U, Y4036 and Y4036U are described in the General Methods of U.S. Pat. App. Pub. No. 2008-0254191, hereby incorporated herein by reference.

The final genotype of strain Y4036U with respect to wild type *Yarrowia lipolytica* ATCC #20362 was Ura3–, YAT1::ME3S::Pex16, EXP1::EgD9eS::Lip1, FBAINm::EgD9eS::Lip2, GPAT::EgD9e::Lip2, FBAINm::EgD8M::Pex20, EXP1::EgD8M::Pex16, GPD::FmD12::Pex20, YAT1::FmD12::OCT (wherein FmD12 is a *Fusarium moniliforme* Δ2 desaturase gene [U.S. Pat. No. 7,504,259]; ME3S is a codon-optimized C$_{16/18}$ elongase gene, derived from *Mortierella alpina* [U.S. Pat. No. 7,470,532]; EgD9e is a *Euglena gracilis* Δ9 elongase gene [U.S. Pat. No. 7,645,604]; EgD9eS is a codon-optimized Δ9 elongase gene, derived from *Euglena gracilis* [U.S. Pat. No. 7,645,604]; EgD8M is a synthetic mutant Δ8 desaturase [U.S. Pat. No. 7,709,239], derived from *Euglena gracilis* [U.S. Pat. No. 7,256,033]).

Generation of L135 Strain (Ura3+, Leu–, Δpex3) with Chromosomal Deletion Of Pex3

Construction of strain L135 is described in Example 12 of Intl. App. Pub. No. WO 2009/046248, hereby incorporated herein by reference. Briefly, construct pY157 was used to knock out the chromosomal gene encoding the peroxisome biogenesis factor 3 protein [peroxisomal assembly protein Peroxin 3 or "Pex3p"] in strain Y4036U, thereby producing strain L135 (also referred to as strain Y4036 (Δpex3)). Knockout of the chromosomal Pex3 gene in strain L135, as compared to in strain Y4036 (whose native Pex3p had not been knocked out) resulted in the following: higher lipid content (TFAs DCW) (ca. 6.0% versus 4.7%), higher DGLA % TFAs (46% versus 19%), higher DGLA % DCW (ca. 2.8% versus 0.9%) and reduced LA % TFAs (12% versus 30%). Additionally, the Δ9 elongase percent conversion efficiency was increased from ca. 48% in strain Y4036 to 83% in strain L135.

The final genotype of strain L135 with respect to wildtype *Yarrowia lipolytica* ATCC #20362 was Ura3+, Leu–, Pex3–, unknown1–, YAT1::ME3S::Pex16, EXP1::EgD9eS::Lip1, FBAINm::EgD9eS::Lip2, GPAT::EgD9e::Lip2, FBAINm::EgD8M::Pex20, EXP1::EgD8M::Pex16, GPD::FmD12::Pex20, YAT1::FmD12::OCT.

Generation of L135U9 (Leu–, Ura3–) Strain

Strain L135U was created via temporary expression of the Cre recombinase enzyme in plasmid pY116 (FIG. 3; SEQ ID NO:33; described in Example 7 of Intl. App. Pub. No. WO 2008/073367, hereby incorporated herein by reference) within strain L135 to produce a Leu– and Ura– phenotype. Plasmid pY116 was used for transformation of freshly grown L135 cells according to the General Methods. The transformant cells were plated onto MMLeuUra plates and maintained at 30° C. for 3 to 4 days. Three colonies were picked, inoculated into 3 mL liquid YPD media at 30° C. and shaken at 250 rpm/min for 1 day. The cultures were diluted to 1:50,000 with liquid MMLeuUra media, and 100 μL was plated onto new YPD plates and maintained at 30° C. for 2 days. Eight colonies were picked from each of three plates (24 colonies total) and streaked onto MMLeu and MMLeuUra selection plates. The colonies that could grow on MMLeuUra plates but not on MMLeu plates were selected and analyzed by GC to confirm the presence of C20:2 (EDA). One strain, having a Leu– and Ura– phenotype, was designated as L135U9.

Generation of Y8002 Strain to Produce about 32% ARA of TFAs

Construct pZKSL-5S5A5 (FIG. 4A; SEQ ID NO:34) was generated to integrate three Δ5 desaturase genes into the Lys loci of strain L135U9, to thereby enable production of ARA. The pZKSL-5S5A5 plasmid contained the following components:

TABLE 4

| Description of Plasmid pZKSL-5S5A5 (SEQ ID NO: 34) | |
|---|---|
| RE Sites And Nucleotides Within SEQ ID NO: 34 | Description Of Fragment And Chimeric Gene Components |
| AscI/BsiWI (5925-6645) | 720 bp 5' portion of *Yarrowia* Lys5 gene (GenBank Accession No. M34929; labeled as "lys5 5' region" in Figure) |
| PacI/SphI (2536-3225) | 689 bp 3' portion of *Yarrowia* Lys5 gene (GenBank Accession No. M34929; labeled as "Lys5-3'" in Figure) |
| EcoRI/BsiWI (9338-6645) | FBAIN::EgD5SM::Pex20, comprising: FBAIN: *Yarrowia lipolytica* FBAIN promoter (U.S. Pat. No. 7,202,356); EgD5SM: Synthetic mutant Δ5 desaturase (SEQ ID NO: 35; U.S. patent Pub. No. 2010-0075386-A1), derived from *Euglena gracilis* (U.S. patent No. 7,678,560) (labeled as "ED5S" in Figure); Pex20: Pex20 terminator sequence from *Yarrowia* Pex20 gene (GenBank Accession No. AF054613) |
| PmeI/ClaI (11503-1) | YAT1::EaD5SM::OCT, comprising: YAT1: *Yarrowia lipolytica* YAT1 promoter (labeled as "YAT" in Figure; U.S. patent application Pub. No. 2006-0094102-A1); EaD5SM: Synthetic, mutant Δ5 desaturase (SEQ ID NO: 37; U.S. patent Pub. No. 2010-0075386-A1), derived from *Euglena anabaena* (U.S. patent application Pub. No. 2008-0274521-A1) (labeled as "EaD5S" in Figure); |

TABLE 4-continued

Description of Plasmid pZKSL-5S5A5 (SEQ ID NO: 34)

| RE Sites And Nucleotides Within SEQ ID NO: 34 | Description Of Fragment And Chimeric Gene Components |
|---|---|
| | OCT: OCT terminator sequence of *Yarrowia* OCT gene (GenBank Accession No. X69988) |
| ClaI/PacI (1-2536) | EXP1::EgD5M::Pex16, comprising:<br>EXP1: *Yarrowia lipolytica* export protein (EXP1) promoter (labeled as "EXP" in Figure; Intl. App. Pub. No. WO 2006/052870);<br>EgD5M: Mutant Δ5 desaturase (SEQ ID NO: 90; U.S. patent Pub. No. 2010-0075386-A1) with elimination of internal EcoRI, BglII, HindIII and NcoI restriction enzyme sites, derived from *Euglena gracilis* (U.S. Pat. No. 7,678,560) (labeled as "*Euglena* D5WT" in Figure);<br>Pex16: Pex16 terminator sequence from *Yarrowia* Pex16 gene (GenBank Accession No. U75433) |
| EcoRI/PmeI (9360-11503) | *Yarrowia* Leu2 gene (GenBank Accession No. M37309) |

The pZKSL-5S5A5 plasmid was digested with AscI/SphI, and then used for transformation of strain L135U9 according to the General Methods. The transformant cells were plated onto MMUraLys plates and maintained at 30° C. for 2 to 3 days. Single colonies were then re-streaked onto MMUraLys plates, and then inoculated into liquid MMUraLys at 30° C. and shaken at 250 rpm/min for 2 days. The cells were subjected to fatty acid analysis, according to the General Methods.

GC analyses showed the presence of ARA in the transformants containing the 3 chimeric genes of pZKSL-5S5A5, but not in the parent L135U9 strain. Five strains (i.e., #28, #62, #73, #84 and #95) that produced about 32.2%, 32.9%, 34.4%, 32.1% and 38.6% ARA of TFAs were designated as strains Y8000, Y8001, Y8002, Y8003 and Y8004, respectively. Further analyses showed that the three chimeric genes of pZKSL-5S5A5 were not integrated into the Lys5 site in the Y8000, Y8001, Y8002, Y8003 and Y8004 strains. All strains possessed a Lys+ phenotype.

The final genotype of strains Y8000, Y8001, Y8002, Y8003 and Y8004 with respect to wildtype *Yarrowia lipolytica* ATCC #20362 was Ura−, Pex3− unknown 1−, unknown 2−, Leu+, Lys+, YAT1::ME3S::Pex16, GPD::FmD12::Pex20, YAT1::FmD12::Oct, GPAT::EgD9e::Lip2, FBAINm::EgD9eS::Lip2, EXP1::EgD9eS::Lip1, FBAINm::EgD8M::Pex20, EXP1::EgD8M::Pex16, FBAIN::EgD5SM::Pex20, EXP1::EgD5M::Pex16, YAT1::EaD5SM::Oct.

Generation of Y8006 Strains to Produce about 41% ARA of TFAs

Construct pZP3-Pa777U (FIG. 4B; SEQ ID NO:39; described in Table 9 of U.S. Pat. Appl. Pub. No. 2009-0093543-A1, hereby incorporated herein by reference) was generated to integrate three Δ17 desaturase genes into the Pox3 loci (GenBank Accession No. AJ001301) of strain Y8002.

The pZP3-Pa777U plasmid was digested with AscI/SphI, and then used for transformation of strain Y8002 according to the General Methods. The transformant cells were plated onto MM plates and maintained at 30° C. for 2 to 3 days. Single colonies were then re-streaked onto MM plates, and then inoculated into liquid MM at 30° C. and shaken at 250 rpm/min for 2 days. The cells were subjected to fatty acid analysis, according to the General Methods.

GC analyses showed the presence of 26% to 31% EPA of TFAs in most of the selected 96 transformants containing the 3 chimeric genes of pZP3-Pa777U, but not in the parent Y8002 strain. Strain #69 produced about 38% EPA of TFAs and was designated as Y8007. There was one strain (i.e., strain #9) that did not produce EPA, but produced about 41% ARA of TFAs. This strain was designated as Y8006. Based on the lack of EPA production in strain Y8006, its genotype with respect to wildtype *Yarrowia lipolytica* ATCC #20362 is assumed to be Pex3−, unknown 1−, unknown 2−, unknown 3−, Leu+, Lys+, Ura+, YAT1::ME3S::Pex16, GPD::FmD12::Pex20, YAT1::FmD12::Oct, GPAT::EgD9e::Lip2, FBAINm::EgD9eS::Lip2, EXP1::EgD9eS::Lip1, FBAINm::EgD8M::Pex20, EXP1::EgD8M::Pex16, FBAIN::EgD5SM::Pex20, EXP1::EgD5M::Pex16, YAT1::EaD5SM::Oct.

In contrast, the final genotype of strain Y8007 with respect to wildtype *Yarrowia lipolytica* ATCC #20362 was Pex3−, unknown 1−, unknown 2−, unknown 3−, Leu+, Lys+, Ura+, YAT1::ME3S::Pex16, GPD::FmD12::Pex20, YAT1::FmD12::Oct, GPAT::EgD9e::Lip2, FBAINm::EgD9eS::Lip2, EXP1::EgD9eS::Lip1, FBAINm::EgD8M::Pex20, EXP1::EgD8M::Pex16, FBAIN::EgD5SM::Pex20, EXP1::EgD5M::Pex16, YAT1::EaD5SM::Oct, YAT1::PaD17S::Lip1, EXP1::PaD17::Pex16, FBAINm::PaD17::Aco (wherein PaD17 is a *Pythium* aphanidermatum Δ17 desaturase [U.S. Pat. No. 7,556,949] and PaD17S is a codon-optimized Δ17 desaturase, derived from *Pythium aphanidermatum* [U.S. Pat. No. 7,556,949].

Integration of the 3 chimeric genes of pZP3-Pa777U into the Pox3 loci (GenBank Accession No. AJ001301) in strains Y8006 and Y8007 was not confirmed.

Generation of Strain Y8006U6 (Ura3−)

To disrupt the Ura3 gene, construct pZKUM (FIG. 5A; SEQ ID NO:40; described in Table 15 of U.S. Pat. Appl. Pub. No. 2009-0093543-A1, hereby incorporated herein by reference) was used to integrate a Ura3 mutant gene into the Ura3 gene of strain Y8006.

Plasmid pZKUM was digested with SalI/PacI, and then used to transform strain Y8006 according to the General Methods. Following transformation, cells were plated onto MM+5-FOA selection plates and maintained at 30° C. for 2 to 3 days.

A total of 8 transformants grown on MM+5-FOA plates were picked and re-streaked onto MM plates and MM+5-FOA plates, separately. All 8 strains had a Ura− phenotype (i.e., cells could grow on MM+5-FOA plates, but not on MM plates). The cells were scraped from the MM+5-FOA plates and subjected to fatty acid analysis, according to the General Methods.

GC analyses showed the presence of 22.9%, 25.5%, 23.6% 21.6%, 21.6% and 25% ARA of TFAs in the pZKUM-transformant strains #1, #2, #4, #5, #6 and #7, respectively, grown on MM+5-FOA plates. These six strains were designated as strains Y8006U1, Y8006U2, Y8006U3, Y8006U4, Y8006U5 and Y8006U6, respectively (collectively, Y8006U).

Generation of Y8069 Strain to Produce about 37.5% EPA of TFAs

Construct pZP3-Pa777U (FIG. 4B; SEQ ID NO:39; described in Table 9 of U.S. Pat. Appl. Pub. No. 2009-0093543-A1, hereby incorporated herein by reference) was used to integrate three Δ17 desaturase genes into the Pox3 loci (GenBank Accession No. AJ001301) of strain Y8006U6.

The pZP3-Pa777U plasmid was digested with AscI/SphI, and then used for transformation of strain Y8006U6 according to the General Methods. The transformant cells were plated onto MM plates and maintained at 30° C. for 2 to 3 days. Single colonies were then re-streaked onto MM plates, and then inoculated into liquid MM at 30° C. and shaken at 250 rpm/min for 2 days. The cells were subjected to fatty acid analysis, according to the General Methods.

GC analyses showed the presence of EPA in the transformants containing the 3 chimeric genes of pZP3-Pa777U, but not in the parent Y8006U6 strain. Most of the selected 24 strains produced 24-37% EPA of TFAs. Four strains (i.e., #1, #6, #11 and #14) that produced 37.5%, 43.7%, 37.9% and 37.5% EPA of TFAs were designated as Y8066, Y8067, Y8068 and Y8069, respectively. Integration of the 3 chimeric genes of pZP3-Pa777U into the Pox3 loci (GenBank Accession No. AJ001301) of strains Y8066, Y8067, Y8068 and Y8069 was not confirmed.

The final genotype of strains Y8066, Y8067, Y8068 and Y8069 with respect to wildtype *Yarrowia lipolytica* ATCC #20362 was Ura+, Pex3−, unknown 1−, unknown 2−, unknown 3−, unknown 4−, Leu+, Lys+, YAT1::ME3S:: Pex16, GPD::FmD12::Pex20, YAT1::FmD12::Oct, GPAT:: EgD9e::Lip2, FBAINm::EgD9eS::Lip2, EXP1::EgD9eS:: Lip1, FBAINm::EgD8M::Pex20, EXP1::EgD8M::Pex16, FBAIN::EgD5SM::Pex20, EXP1::EgD5M::Pex16, YAT1:: EaD5SM::Oct, YAT1::PaD17S::Lip1, EXP1::PaD17::Pex16, FBAINm::PaD17::Aco.

Generation of Strain Y8069U (Ura3−)

To disrupt the Ura3 gene, construct pZKUM (FIG. 5A; SEQ ID NO:40; described in Table 15 of U.S. Pat. Appl. Pub. No. 2009-0093543-A1) was used to integrate a Ura3 mutant gene into the Ura3 gene of strain Y8069, in a manner similar to that described for pZKUM transformation of strain Y8006 (supra). A total of 3 transformants were grown and identified to possess a Ura− phenotype.

GC analyses showed the presence of 22.4%, 21.9% and 21.5% EPA of TFAs in the pZKUM-transformant strains #1, #2 and #3, respectively, grown on MM+5-FOA plates. These three strains were designated as strains Y8069U1, Y8069U2, and Y8069U3, respectively (collectively, Y8069U).

Generation of Strain Y8154 to Produce about 44.8% EPA of TFAs

Construct pZKL2-5 mB89C (FIG. 5B; SEQ ID NO:41) was generated to integrate one Δ5 desaturase gene, one Δ9 elongase gene, one Δ8 desaturase gene, and one *Yarrowia lipolytica* diacylglycerol cholinephosphotransferase gene (CPT1) into the Lip2 loci (GenBank Accession No. AJ012632) of strain Y8069U3 to thereby enable higher level production of EPA. The pZKL2-5 mB89C plasmid contained the following components:

TABLE 5

Description of Plasmid pZKL2-5mB89C (SEQ ID NO: 41)

| RE Sites And Nucleotides Within SEQ ID NO: 41 | Description Of Fragment And Chimeric Gene Components |
|---|---|
| AscI/BsiWI (730-1) | 722 bp 5' portion of *Yarrowia* Lip2 gene (labeled as "Lip2.5N" in Figure; GenBank Accession No. AJ012632) |
| PacI/SphI (4141-3438) | 697 bp 3' portion of *Yarrowia* Lip2 gene (labeled as "Lip2.3N" in Figure; GenBank Accession No. AJ012632) |
| SwaI/BsiWI (13561-1) | YAT1::YlCPT1::Aco, comprising: YAT1: *Yarrowia lipolytica* YAT1 promoter (labeled as "YAT" in Figure; U.S. patent application Pub. No. 2006-0094102-A1); YlCPT1: *Yarrowia lipolytica* diacylglycerol cholinephosphotransferase gene (SEQ ID NO: 42) (labeled as "*Y. lipolytica* CPT1 cDNA" in Figure; Intl. App. Pub. No. WO 2006/052870); Aco: Aco terminator sequence from *Yarrowia* Aco gene (GenBank Accession No. AJ001300) |
| PmeI/SwaI (10924-13561) | FBAIN::EgD8M::Lip1 comprising: FBAIN: *Yarrowia lipolytica* FBAIN promoter (U.S. Pat. No. 7,202,356); EgD8M: Synthetic mutant Δ8 desaturase (SEQ ID NO: 44; U.S. Pat. No. 7,709,239), derived from *Euglena gracilis* ("EgD8S"; U.S. Pat. No. 7,256,033) (labeled as "D8S-23" in Figure); Lip1: Lip1 terminator sequence from *Yarrowia* Lip1 gene (GenBank Accession No. Z50020) |
| PmeI/ClaI (10924-9068) | YAT1::EgD9eS::Lip2, comprising: YAT1: *Yarrowia lipolytica* YAT1 promoter (labeled as "YAT" in Figure; U.S. patent application Pub. No. 2006-0094102-A1); EgD9eS: codon-optimized Δ9 elongase (SEQ ID NO: 46), derived from *Euglena gracilis* (U.S. Pat. No. 7,645,604); Lip2: Lip2 terminator sequence from *Yarrowia* Lip2 gene (GenBank Accession No. AJ012632) |

TABLE 5-continued

Description of Plasmid pZKL2-5mB89C (SEQ ID NO: 41)

| RE Sites And Nucleotides Within SEQ ID NO: 41 | Description Of Fragment And Chimeric Gene Components |
|---|---|
| ClaI/EcoRI (9068-6999) | *Yarrowia* Ura3 gene (GenBank Accession No. AJ306421) |
| EcoRI/PacI (6999-4141) | GPDIN::EgD5SM::ACO, comprising:<br>GPDIN: *Yarrowia lipolytica* GPDIN promoter (U.S. Pat. No. 7,459,546);<br>EgD5SM: Synthetic mutant Δ5 desaturase (SEQ ID NO: 35; U.S. patent Pub. No. 2010-0075386-A1), derived from *Euglena gracilis* (U.S. Pat. No. 7,678,560) (labeled as "EgD5S-HPGS" in Figure);<br>Aco: Aco terminator sequence from *Yarrowia* Aco gene (GenBank Accession No. AJ001300) |

The pZKL2-5 mB89C plasmid was digested with AscI/SphI, and then used for transformation of strain Y8069U3 according to the General Methods. The transformant cells were plated onto MM plates and maintained at 30° C. for 3 to 4 days. Single colonies were re-streaked onto MM plates, and then inoculated into liquid MM at 30° C. and shaken at 250 rpm/min for 2 days. The cells were collected by centrifugation, resuspended in HGM and then shaken at 250 rpm/min for 5 days. The cells were subjected to fatty acid analysis, according to the General Methods.

GC analyses showed that most of the selected 96 strains produced approximately 38-44% EPA of TFAs. Seven strains (i.e., #1, #39, #49, #62, #70, #85 and #92) that produced about 44.7%, 45.2%, 45.4%, 44.8%, 46.1%, 48.6% and 45.9% EPA of TFAs were designated as strains Y8151, Y8152, Y8153, Y8154, Y8155, Y8156 and Y8157, respectively. Knockout of the Lip2 gene was not confirmed in these EPA strains.

The final genotype of strains Y8151, Y8152, Y8153, Y8154, Y8155, Y8156 and Y8157 with respect to wildtype *Yarrowia lipolytica* ATCC #20362 was Ura+, Pex3−, unknown 1−, unknown 2−, unknown 3−, unknown 4−, unknown 5−, Leu+, Lys+, YAT1::ME3S::Pex16, FBAINm::EgD9eS::Lip2, EXP1::EgD9eS::Lip1, GPAT::EgD9e::Lip2, YAT1::EgD9eS::Lip2, FBAINm::EgD8M::Pex20, EXP1::EgD8M::Pex16, FBAIN::EgD8M::Lip1, GPD::FmD12::Pex20, YAT1::FmD12::Oct, EXP1::EgD5M::Pex16, YAT1::EaD5SM::Oct, FBAIN::EgD5SM::Pex20, GPDIN::EgD5SM::Aco, FBAINm::PaD17::Aco, EXP1::PaD17::Pex16, YAT1::PaD17S::Lip1, YAT1::YlCPT::Aco.

Generation of Strain Y8154U1 (Ura3−)

To disrupt the Ura3 gene, construct pZKUM (FIG. 5A; SEQ ID NO:40; described in Table 15 of U.S. Pat. Appl. Pub. No. 2009-0093543-A1) was used to integrate a Ura3 mutant gene into the Ura3 gene of strain Y8154, in a manner similar to that described for pZKUM transformation of strain Y8006 (supra). A total of 8 transformants were grown and identified to possess a Ura− phenotype.

GC analyses showed that there was 23.1% EPA of TFAs in the pZKUM-transformant strain #7. This strain was designated as strain Y8154U1.

Generation of Strain Y8269 to Produce about 45.3% EPA of TFAs

Construct pZKL1-2SR9G85 (FIG. 6A; SEQ ID NO:48) was generated to integrate one DGLA synthase, one Δ12 desaturase gene and one Δ5 desaturase gene into the Lip1 loci (GenBank Accession No. Z50020) of strain Y8154U1 to thereby enable higher level production of EPA. A DGLA synthase is a multizyme comprising a Δ9 elongase linked to a Δ8 desaturase (U.S. Pat. Appl. Pub. No. 2008-0254191-A1).

The pZKL1-2SR9G85 plasmid contained the following components:

TABLE 6

Description of Plasmid pZKL1-2SR9G85 (SEQ ID NO: 48)

| RE Sites And Nucleotides Within SEQ ID NO: 48 | Description Of Fragment And Chimeric Gene Components |
|---|---|
| AscI/BsiWI (4189-3373) | 809 by 5' portion of *Yarrowia* Lip1 gene (labeled as "Lip1-5'N" in Figure; GenBank Accession No. Z50020) |
| PacI/SphI (7666-6879) | 763 by 3' portion of *Yarrowia* Lip1 gene (labeled as "Lip1.3N" in Figure; GenBank Accession No. Z50020) |
| ClaI/SwaI (1-3217) | YAT1::E389D9eS/EgD8M::Lip1, comprising:<br>YAT1: *Yarrowia lipolytica* YAT1 promoter (labeled as "YAT" in Figure; U.S. patent application Pub. No. 2006-0094102-A1);<br>E389D9eS/EgD8M: gene fusion comprising a codon-optimized Δ9 elongase derived from *Eutreptiella* sp. CCMP389 ("E389D9eS"), a linker, and the synthetic mutant Δ8 desaturase derived from *Euglena gracilis* ("EgD8M") (SEQ ID NO: 49) (labeled individually as "E389S", "Linker" and "EgD8M" in Figure; U.S. patent application Pub. No. 2008-0254191-A1);<br>Lip1: Lip1 terminator sequence from *Yarrowia* Lip1 gene (GenBank Accession No. Z50020) |

TABLE 6-continued

Description of Plasmid pZKL1-2SR9G85 (SEQ ID NO: 48)

| RE Sites And Nucleotides Within SEQ ID NO: 48 | Description Of Fragment And Chimeric Gene Components |
|---|---|
| SalI/ClaI (11982-1) | GPM::EgD5SM::Oct comprising:<br>GPM: *Yarrowia lipolytica* GPM promoter (labeled as "GPML" in Figure; U.S. Pat. No. 7,202,356);<br>EgD5SM: Synthetic mutant Δ5 desaturase (SEQ ID NO: 35; U.S. patent Pub. No. 2010-0075386-A1), derived from *Euglena gracilis* (U.S. Pat. No. 7,678,560) (labeled as "ED5S" in Figure);<br>OCT: OCT terminator sequence of *Yarrowia* OCT gene (GenBank Accession No. X69988) |
| SalI/EcoRI (11982-10363) | *Yarrowia* Ura3 gene (GenBank Accession No. AJ306421) |
| EcoRI/PacI (10363-7666) | EXP1::FmD12S::ACO, comprising:<br>EXP1: *Yarrowia lipolytica* export protein (EXP1) promoter (labeled as "Exp" in Figure; Intl. App. Pub. No. WO 2006/052870);<br>FmD12S: codon-optimized Δ12 elongase (SEQ ID NO: 51), derived from *Fusarium moniliforme* (labeled as "FD12S" in Figure; U.S. Pat. No. 7,504,259);<br>Aco: Aco terminator sequence from *Yarrowia* Aco gene (GenBank Accession No. AJ001300) |

The pZKL1-2SR9G85 plasmid was digested with AscI/SphI, and then used for transformation of strain Y8154U1 according to the General Methods. The transformant cells were plated onto MM plates and maintained at 30° C. for 3 to 4 days. Single colonies were re-streaked onto MM plates, and then inoculated into liquid MM at 30° C. and shaken at 250 rpm/min for 2 days. The cells were collected by centrifugation, resuspended in HGM and then shaken at 250 rpm/min for 5 days. The cells were subjected to fatty acid analysis, according to the General Methods.

GC analyses showed that most of the selected 96 strains produced 40-44.5% EPA of total lipids. Five strains (i.e., #44, #46, #47, #66 and #87) that produced about 44.8%, 45.3%, 47%, 44.6% and 44.7% EPA of TFAs were designated as Y8268, Y8269, Y8270, Y8271 and Y8272, respectively. Knockout of the Lip1 loci (GenBank Accession No. Z50020) was not confirmed in these EPA strains.

The final genotype of strains Y8268, Y8269, Y8270, Y8271 and Y8272 with respect to wildtype *Yarrowia lipolytica* ATCC #20362 was Ura+, Pex3−, unknown 1−, unknown 2−, unknown 3−, unknown 4−, unknown 5−, unknown6−, YAT1::ME3S::Pex16, FBAINm::EgD9eS::Lip2, EXP1::EgD9eS::Lip1, GPAT::EgD9e::Lip2, YAT1::EgD9eS::Lip2, FBAINm::EgD8M::Pex20, EXP1::EgD8M::Pex16, FBAIN::EgD8M::Lip1, YAT1::E389D9eS/EgD8M::Lip1, GPD::FmD12::Pex20, YAT1::FmD12::Oct, EXP1::FmD12S::Aco, EXP1::EgD5M::Pex16, YAT1::EaD5SM::Oct, FBAIN::EgD5SM::Pex20, GPDIN::EgD5SM::Aco, GPM::EgD5SM::Oct, FBAINm::PaD17::Aco, EXP1::PaD17::Pex16, YAT1::PaD17S::Lip1, YAT1::YlCPT::Aco.

Generation of Strain Y8269U (Ura3−)

To disrupt the Ura3 gene, construct pZKUM (FIG. 5A; SEQ ID NO:40; described in Table 15 of U.S. Pat. Appl. Pub. No. 2009-0093543-A1) was used to integrate a Ura3 mutant gene into the Ura3 gene of strain Y8269, in a manner similar to that described for pZKUM transformation of strain Y8006 (supra). A total of 8 transformants were grown and identified to possess a Ura− phenotype.

GC analyses showed that there were 23.0%, 23.1% and 24.2% EPA of TFAs in pZKUM-transformant strains #2, #3 and #5, respectively. These strains were designated as strains Y8269U1, Y8269U2 and Y8269U3, respectively (collectively, Y8269U).

Generation of Strain Y8406 and Strain Y8412 to Produce about 51.2% EPA and 55.8% EPA of TFAs Construct pZSCP-Ma83 (FIG. 6B; SEQ ID NO:53) was generated to integrate one Δ8 desaturase gene, one $C_{16/18}$ elongase gene and one malonyl-CoA synthetase gene into the SCP2 loci (GenBank Accession No. XM_503410) of strain Y8269U1 to thereby enable higher level production of EPA. The pZSCP-Ma83 plasmid contained the following components:

TABLE 7

Description of Plasmid pZSCP-Ma83 (SEQ ID NO: 53)

| RE Sites And Nucleotides Within SEQ ID NO: 53 | Description Of Fragment And Chimeric Gene Components |
|---|---|
| BsiWI/AscI (1-1328) | 1327 bp 3' portion of *Yarrowia* SCP2 gene (labeled as "SCP2-3'" in Figure; GenBank Accession No. XM_503410) |
| SphI/PacI (4036-5816) | 1780 bp 5' portion of *Yarrowia* SCP2 gene (labeled as "SCP2-5'" in Figure; GenBank Accession No. XM_503410) |
| SwaI/BsiWI (12994-1) | GPD::ME3S::Pex20, comprising:<br>GPD: *Yarrowia lipolytica* GPD promoter (U.S. Pat. No. 7,259,255);<br>ME3S: codon-optimized $C_{16/18}$ elongase gene (SEQ ID |

TABLE 7-continued

Description of Plasmid pZSCP-Ma83 (SEQ ID NO: 53)

| RE Sites And Nucleotides Within SEQ ID NO: 53 | Description Of Fragment And Chimeric Gene Components |
|---|---|
| | NO: 54), derived from *M. alpina* (U.S. Pat. No. 7,470,532); Pex20: Pex20 terminator sequence from *Yarrowia* Pex20 gene (GenBank Accession No. AF054613) |
| PmeI/SwaI (10409-12994) | YAT1::MCS::Lip1 comprising: YAT1: *Yarrowia lipolytica* YAT1 promoter (labeled as "YAT" in Figure; U.S. patent application Pub. No. 2006/0094102-A1); MCS: codon-optimized malonyl-CoA synthetase gene (SEQ ID NO: 56), derived from *Rhizobium leguminosarum* bv. *viciae* 3841 (U.S. patent application No. 12/637877); Lip1: Lip1 terminator sequence from *Yarrowia* Lip1 gene (GenBank Accession No. Z50020) |
| ClaI/PmeI (7917-10409) | GPD::EaD8S::Pex16 comprising: GPD: *Yarrowia lipolytica* GPD promoter (U.S. Pat. No. 7,259,255); EaD8S: codon-optimized Δ8 desaturase gene (SEQ ID NO: 58), derived from *Euglena anabaena* (U.S. patent application Pub. No. 2008-0254521-A1); Pex16: Pex16 terminator sequence from *Yarrowia* Pex16 gene (GenBank Accession No. U75433) |
| SalI/EcoRI (7467-5848) | *Yarrowia* Ura3 gene (GenBank Accession No. AJ306421) |

The pZSCP-Ma83 plasmid was digested with AscI/SphI, and then used for transformation of strains Y8269U1, Y8269U2 and Y8269U3, separately, according to the General Methods. The transformant cells were plated onto MM plates and maintained at 30° C. for 3 to 4 days. Single colonies were re-streaked onto MM plates, and then inoculated into liquid MM at 30° C. and shaken at 250 rpm/min for 2 days. The cells were collected by centrifugation, resuspended in HGM and then shaken at 250 rpm/min for 5 days. The cells were subjected to fatty acid analysis, according to the General Methods.

A total of 96 strains resulting from each pZSCP-Ma83 transformation (i.e., into Y8269U1, Y8269U2 and Y8269U3) were analyzed by GC. Most of the selected 288 strains produced 43-47% EPA of TFAs. Seven strains of Y8269U1 transformed with pZSCP-Ma83 (i.e., #59, #61, #65, #67, #70, #81 and #94) that produced about 51.3%, 47.9%, 50.8%, 48%, 47.8%, 47.8% and 47.8% EPA of TFAs were designated as strains Y8404, Y8405, Y8406, Y8407, Y8408, Y8409 and Y8410, respectively. Three strains of Y8269U2 transformed with pZSCP-Ma83 (i.e., #4, #13 and #17) that produced about 48.8%, 50.8%, and 49.3% EPA of TFAs were designated as Y8411, Y8412 and Y8413, respectively. And, two strains of Y8269U3 transformed with pZSCP-Ma83 (i.e., #2, and #16) that produced about 49.3% and 53.5% EPA of TFAs were designated as Y8414 and Y8415, respectively.

Knockout of the SCP2 loci (GenBank Accession No. XM_503410) was not confirmed in any of these EPA strains, produced by transformation with pZSCP-Ma83.

The final genotype of strains Y8404, Y8405, Y8406, Y8407, Y8408, Y8409, Y8410, Y8411, Y8412, Y8413, Y8414 and Y8415 with respect to wildtype *Yarrowia lipolytica* ATCC #20362 was Ura+, Pex3−, unknown 1−, unknown 2−, unknown 3−, unknown 4−, unknown 5−, unknown6−, unknown 7−, YAT1::ME3S::Pex16, GPD::ME3S::Pex20, FBAINm::EgD9eS::Lip2, EXP1::EgD9eS::Lip1, GPAT:: EgD9e::Lip2, YAT1::EgD9eS::Lip2, FBAINm::EgD8M:: Pex20, EXP1::EgD8M::Pex16, FBAIN::EgD8M::Lip1, GPD::EaD8S::Pex16, YAT1::E389D9eS/EgD8M::Lip1, GPD::FmD12::Pex20, YAT1::FmD12::Oct, EXP1:: FmD12S::Aco, EXP1::EgD5M::Pex16, YAT1::EaD5SM:: Oct, FBAIN::EgD5SM::Pex20, GPDIN::EgD5SM::Aco, GPM::EgD5SM::Oct, FBAINm::PaD17::Aco, EXP1:: PaD17::Pex16, YAT1::PaD17S::Lip1, YAT1::YlCPT::Aco, YAT1::MCS::Lip1.

*Yarrowia lipolytica* strain Y8406 was deposited with the American Type Culture Collection on May 14, 2009 and bears the designation ATCC PTA-10025. *Yarrowia lipolytica* strain Y8412 was deposited with the American Type Culture Collection on May 14, 2009 and bears the designation ATCC PTA-10026.

Analysis of Total Lipid Content and Composition by Flask Assay

Cells from YPD plates of strains Y8404, Y8405, Y8406, Y8407, Y8408, Y8409, Y8410, Y8411, Y8412, Y8413, Y8414 and Y8415 were grown and analyzed for total lipid content and composition, as follows.

Specifically, one loop of freshly streaked cells was inoculated into 3 mL FM medium and grown overnight at 250 rpm and 30° C. The $OD_{600nm}$ was measured and an aliquot of the cells were added to a final $OD_{600nm}$ of 0.3 in 25 mL FM medium in a 125 mL flask. After 2 days in a shaker incubator at 250 rpm and at 30° C., 6 mL of the culture was harvested by centrifugation and resuspended in 25 mL HGM in a 125 mL flask. After 5 days in a shaker incubator at 250 rpm and at 30° C., a 1 mL aliquot was used for fatty acid analysis (supra) and 10 mL dried for dry cell weight ["DCW"] determination.

For DCW determination, 10 mL culture was harvested by centrifugation for 5 min at 4000 rpm in a Beckman GH-3.8 rotor in a Beckman GS-6R centrifuge. The pellet was resuspended in 25 mL of water and re-harvested as above. The washed pellet was re-suspended in 20 mL of water and transferred to a pre-weighed aluminum pan. The cell suspension was dried overnight in a vacuum oven at 80° C. The weight of the cells was determined.

Data from flask assays are presented as Table 8. The Table presents the total dry cell weight of the cells ["DCW'], the total lipid content of cells ["FAME % DCW"], the concentration of each fatty acid as a weight percent of TFAs ["% TFAs"] and the EPA content as a percent of the dry cell weight ["EPA FAME % DCW"]. More specifically, fatty acids will be identified as 16:0 (palmitate), 16:1 (palmitoleic acid), 18:0 (stearic acid), 18:1 (oleic acid), 18:2 (LA), ALA, EDA, DGLA, ARA, ETrA, ETA, EPA and other.

TABLE 8

Total Lipid Content And Composition In *Yarrowia* Strains Y8404, Y8405, Y8406, Y8407, Y8408, Y8409, Y8410, Y8411, Y8412, Y8413, Y8414 And Y8415 By Flask Assay

| Strain | DCW (g/L) | Total FAME % DCW | 16:0 | 16:1 | 18:0 | 18:1 | 18:2 | ALA | EDA | DGLA | ARA | EtrA | ETA | EPA | other | EPA FAME % DCW |
|---|---|---|---|---|---|---|---|---|---|---|---|---|---|---|---|---|
| Y8404 | 4.1 | 27.3 | 2.8 | 0.8 | 1.8 | 5.1 | 20.4 | 2.1 | 2.9 | 2.5 | 0.6 | 0.8 | 2.4 | 51.1 | 6.3 | 14.0 |
| Y8405 | 3.9 | 29.6 | 2.7 | 0.5 | 2.9 | 5.7 | 20.5 | 2.8 | 2.7 | 2.1 | 0.5 | 0.7 | 2.0 | 51.4 | 5.1 | 15.2 |
| Y8406 | 4.0 | 30.7 | 2.6 | 0.5 | 2.9 | 5.7 | 20.3 | 2.8 | 2.8 | 2.1 | 0.5 | 0.8 | 2.1 | 51.2 | 5.4 | 15.7 |
| Y8407 | 4.0 | 29.4 | 2.6 | 0.5 | 3.0 | 5.6 | 20.5 | 2.8 | 2.7 | 2.1 | 0.4 | 0.7 | 2.1 | 51.5 | 5.1 | 15.2 |
| Y8408 | 4.1 | 29.8 | 2.9 | 0.6 | 2.7 | 5.7 | 20.2 | 2.8 | 2.6 | 2.1 | 0.5 | 0.9 | 2.1 | 51.2 | 5.5 | 15.3 |
| Y8409 | 3.9 | 30.8 | 2.8 | 0.5 | 2.9 | 5.7 | 20.6 | 2.7 | 2.7 | 2.1 | 0.5 | 0.8 | 2.1 | 51.0 | 5.2 | 15.7 |
| Y8410 | 4.0 | 31.8 | 2.7 | 0.5 | 3.0 | 5.7 | 20.5 | 2.9 | 2.7 | 2.1 | 0.5 | 0.7 | 2.1 | 50.9 | 5.3 | 16.2 |
| Y8411 | 3.6 | 30.5 | 2.7 | 0.3 | 3.3 | 5.1 | 19.9 | 2.6 | 2.4 | 2.0 | 0.5 | 0.6 | 1.8 | 52.9 | 5.7 | 16.1 |
| Y8412 | 3.2 | 27.0 | 2.5 | 0.4 | 2.6 | 4.3 | 19.0 | 2.4 | 2.2 | 2.0 | 0.5 | 0.6 | 1.9 | 55.8 | 5.6 | 15.1 |
| Y8413 | 2.9 | 27.2 | 3.1 | 0.4 | 2.6 | 5.4 | 19.9 | 2.2 | 2.8 | 2.0 | 0.5 | 0.7 | 1.8 | 52.4 | 5.9 | 14.2 |
| Y8414 | 3.7 | 27.1 | 2.5 | 0.7 | 2.3 | 6.0 | 19.9 | 1.6 | 3.4 | 3.4 | 0.6 | 0.6 | 3.1 | 49.4 | 6.1 | 13.4 |
| Y8415 | 3.6 | 25.9 | 1.4 | 0.3 | 1.9 | 4.5 | 16.0 | 1.3 | 2.7 | 2.9 | 0.5 | 0.6 | 2.5 | 59.0 | 6.1 | 15.3 |

Generation of Strain Y8406U (Ura3−)

To disrupt the Ura3 gene, construct pZKUM (FIG. 5A; SEQ ID NO:40; described in Table 15 of U.S. Pat. Appl. Pub. No. 2009-0093543-A1) was used to integrate a Ura3 mutant gene into the Ura3 gene of strain Y8406 in a manner similar to that described for pZKUM transformation of strain Y8006 (supra). Several transformants were grown and identified to possess a Ura− phenotype.

GC analyses showed that there were 26.1% EPA of FAMEs in pZKUM-transformant strains #4 and #5. These two strains were designated as strains Y8406U1 and Y8406U2, respectively (collectively, Y8406U).

Example 2

Generation of *Yarrowia lipolytica* Strain Y5037 to Produce about 18.6% EPA, 22.8% DPA and 9.7% DHA of Total Fatty Acids The present Example describes the construction of strain Y5037, derived from *Yarrowia lipolytica* ATCC #20362, capable of producing about 18.6% EPA, 22.8% DPA and 9.7% DHA relative to the total lipids via expression of a Δ9 elongase/Δ8 desaturase pathway. This strain was used as the DHA-producing host cell in Example 5.

Briefly, as diagrammed in FIG. 7, strain Y5037 was derived from *Yarrowia lipolytica* ATCC #20362 via construction of strain Y2224 (a FOA resistant mutant from an autonomous mutation of the Ura3 gene of wildtype *Yarrowia* strain ATCC #20362), strain Y4001 (producing 17% EDA with a Leu− phenotype), strain Y4001U1 (Leu− and Ura−), strain Y4036 (producing 18% DGLA with a Leu− phenotype), strain Y4036U (Leu− and Ura−), strain Y4070 (producing 12% ARA with a Ura− phenotype), strain Y4086 (producing 14% EPA), strain Y4086U1 (Ura3−), strain Y4128 (producing 37% EPA; deposited with the American Type Culture Collection on Aug. 23, 2007, bearing the designation ATCC PTA-8614), strain Y4128U3 (Ura−), strain Y4217 (producing 42% EPA), strain Y4217U2 (Ura−), strain Y4259 (producing 46.5% EPA), strain Y4259U2 (Ura−), strain Y4305 (producing 53.2% EPA), strain Y4305U3 (Ura−), strain Y5004 (producing 17% EPA, 18.7% DPA and 6.4% DHA), strain Y5004U1 (Ura−), strain Y5018 (producing 25.4% EPA, 11.4% DPA and 9.4% DHA), strain Y5018U1 (Ura−) and strain Y5037 (producing 18.6% EPA, 22.8% DPA and 9.7% DHA relative to the total TFAs). Further details regarding the construction of strains Y2224, Y4001, Y4001U, Y4036, Y4036U, Y4070, Y4086, Y4086U1, Y4128, Y4128U3, Y4217, Y4217U2, Y4259, Y4259U2, Y4305 and Y4305U3 are described in the General Methods of U.S. Pat. App. Pub. No. 2008-0254191-A1 and in Examples 1-3 of U.S. Pat. App. Pub. No. 2009-0093543-A1, hereby incorporated herein by reference.

The complete lipid profile of strain Y4305 was as follows: 16:0 (2.8%), 16:1 (0.7%), 18:0 (1.3%), 18:1 (4.9%), 18:2 (17.6%), ALA (2.3%), EDA (3.4%), DGLA (2.0%), ARA (0.6%), ETA (1.7%), and EPA (53.2%). The total lipid content of cells ["TFAs % DCW"] was 27.5.

The final genotype of strain Y4305 with respect to wild type *Yarrowia lipolytica* ATCC #20362 was SCP2− (YALI0E01298g), YALI0C18711g−, Pex10−, YALI0F24167g−, unknown 1−, unknown 3−, unknown 8−, GPD::FmD12::Pex20, YAT1::FmD12::OCT, GPM/FBAIN:: FmD12S::OCT, EXP1::FmD12S::Aco, YAT1::FmD12S:: Lip2, YAT1::ME3S::Pex16, EXP1::ME3S::Pex20 (3 copies), GPAT::EgD9e::Lip2, EXP1::EgD9eS::Lip1, FBAINm:: EgD9eS::Lip2, FBA::EgD9eS::Pex20, GPD::EgD9eS::Lip2, YAT1::EgD9eS::Lip2, YAT1::E389D9eS::OCT, FBAINm:: EgD8M::Pex20, FBAIN::EgD8M::Lip1 (2 copies), EXP1:: EgD8M::Pex16, GPDIN::EgD8M::Lip1, YAT1::EgD8M:: Aco, FBAIN::EgD5::Aco, EXP1::EgD5S::Pex20, YAT1:: EgD5S::Aco, EXP1::EgD5S::ACO, YAT1::RD5S::OCT, YAT1::PaD17S::Lip1, EXP1::PaD17::Pex16, FBAINm:: PaD17::Aco, YAT1::YlCPT1::ACO, GPD::YlCPT1::ACO (wherein FmD12 is a *Fusarium moniliforme* Δ2 desaturase gene [U.S. Pat. No. 7,504,259]; FmD12S is a codon-optimized Δ2 desaturase gene, derived from *Fusarium moniliforme* [U.S. Pat. No. 7,504,259]; MESS is a codon-optimized $C_{16/18}$ elongase gene, derived from *Mortierella alpina* [U.S. Pat. No. 7,470,532]; EgD9e is a *Euglena gracilis* Δ9 elongase gene [U.S. Pat. No. 7,645,604]; EgD9eS is a codon-optimized Δ9 elongase gene, derived from *Euglena gracilis* [U.S. Pat. No. 7,645,604]; E389D9eS is a codon-optimized Δ9 elongase gene, derived from *Eutreptiella* sp. CCMP389 [U.S. Pat. No. 7,645,604]; EgD8M is a synthetic mutant Δ8 desaturase [U.S. Pat. No. 7,709,239], derived from *Euglena gracilis* [U.S. Pat. No. 7,256,033]; EgD5 is a *Euglena gracilis* Δ5 desaturase [U.S. Pat. No. 7,678,560]; EgD5S is a codon-optimized Δ5 desaturase gene, derived from *Euglena gracilis* [U.S. Pat. No. 7,678,560]; RD5S is a codon-optimized Δ5 desaturase, derived from *Peridinium* sp. CCMP626 [U.S. Pat. No. 7,695,950]; PaD17 is a *Pythium* aphanidermatum Δ17 desaturase [U.S. Pat. No. 7,556,949]; PaD17S is a codon-optimized Δ17 desaturase, derived from *Pythium* aphanidermatum [U.S. Pat. No. 7,556,949]; and, YlCPT1 is a *Yarrowia lipolytica* diacylglycerol cholinephosphotransferase gene [Intl. App. Pub. No. WO 2006/052870]).

Strain Y4305U (Ura3−) was generated via integrating a Ura3 mutant gene into the Ura3 gene of strain Y4305.

Generation of Y5004 Strain to Produce about 17.0% EPA, 18.7% DPA and 6.4% DHA of TFAs Construct pZKL4-220EA41B (FIG. 8A; SEQ ID NO:60) was constructed to integrate two $C_{20-22}$ elongase genes and two Δ4 desaturase genes into the lipase 4-like locus (GenBank Accession No. XM_503825) of strain Y4305U3. The pZKL4-220EA41B plasmid contained the following components:

GC analyses showed the presence of DHA in the transformants with pZKL4-220EA41B, but not in the parent Y4305U strain. Most of the selected 72 strains produced about 22% EPA, 18% DPA and 5% DHA of TFAs. Strain #2 produced 17% EPA, 18.7% DPA and 6.4% DHA, while strain #33 produced 21.5% EPA, 21% DPA and 5.5% DHA. These two strains were designated as Y5004 and Y5005, respectively.

Knockout of the lipase 4-like locus (GenBank Accession No. XM_503825) was not confirmed in either strain Y5004 or Y5005.

Generation of Strain Y5004U (Ura3−)

To disrupt the Ura3 gene, construct pZKUM (FIG. 5A; SEQ ID NO:40; described in Table 15 of U.S. Pat. App. Pub. No. 2009-0093543-A1) was used to integrate a Ura3 mutant

TABLE 9

Components Of Plasmid pZKL4-220EA41B (SEQ ID NO: 60)

| RE Sites And Nucleotides Within SEQ ID NO: 60 | Description Of Fragment And Chimeric Gene Components |
|---|---|
| AscI/BsiWI (9777-9025) | 745 bp 5' portion of the *Yarrowia* Lipase 4-like gene (GenBank Accession No. XM_503825; labeled as "Lip4" in Figure) |
| PacI/SphI (13273-12485) | 782 bp 3' portion of *Yarrowia* Lipase 4 like gene (GenBank Accession No. XM_503825; labeled as "Lip4-3'" in Figure) |
| SwaI/BsiWI (6882-9025) | FBAINm::EaC20ES::Pex20, comprising: FBAINm: *Yarrowia lipolytica* FBAINm promoter (U.S. Pat. No. 7,202,356) EaC20ES: codon-optimized C20 elongase gene (SEQ ID NO: 61), derived from *Euglena anabaena* (U.S. patent application Pub. No. 2008/0254191-A1); Pex20: Pex20 terminator sequence from *Yarrowia* Pex20 gene (GenBank Accession No. AF054613) |
| PmeI/SwaI (4903-6882) | YAT1::EgC20ES::Lip1, comprising: YAT1: *Yarrowia lipolytica* YAT1 promoter (U.S. patent application Pub. No. 2006/0094102-A1); EgC20ES: codon-optimized C20 elongase gene (SEQ ID NO: 63), derived from *Euglena gracilis* (U.S. patent application Pub. No. 2008/0254191-A1); Lip1: Lip1 terminator sequence from *Yarrowia* Lip1 gene (GenBank Accession No. Z50020) |
| PmeI/ClaI (4903-2070) | EXP1::EaD4S-1::Lip2, comprising: EXP1: *Yarrowia lipolytica* export protein (EXP1) promoter (Intl. App. Pub. No. WO 2006/052870); EaD4S-1: codon-optimized truncated Δ4 desaturase (SEQ ID NO: 65), derived from *Euglena anabaena* (U.S. patent application Pub. No. 2008/0254191-A1); Lip2: Lip2 terminator sequence from *Yarrowia* Lip2 gene (GenBank Accession No. AJ012632) |
| SalI/EcoRI (1620-1) | *Yarrowia* Ura3 gene (GenBank Accession No. AJ306421) |
| EcoRI/PacI (1-14039) | GPDIN::EaD4SB::Aco, comprising: GPDIN: *Yarrowia lipolytica* GPDIN promoter (U.S. Pat. No. 7,459,546); EaD4SB: codon-optimized truncated Δ4 desaturase version B (SEQ ID NO: 67), derived from *Euglena anabaena* (U.S. patent application Pub. No. 2008/0254191-A1); Aco: Aco terminator sequence from *Yarrowia* Aco gene (GenBank Accession No. AJ001300) |

The pZKL4-220EA41B plasmid was digested with AscI/SphI, and then used for transformation of strain Y4305U3 (supra), according to the General Methods. The transformants were selected on MM plates. After days growth at 30° C., 72 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, resuspended in HGM and then shaken at 250 rpm/min for 5 days. The cells were subjected to fatty acid analysis, according to the General Methods.

gene into the Ura3 gene of strain Y5004, in a manner similar to that described for pZKUM transformation of strain Y8006 (Example 1).

A total of 8 transformants grown on MM+5-FOA plates were picked and re-streaked onto MM plates and MM+5-FOA plates, separately. All 8 strains had a Ura− phenotype (i.e., cells could grow on MM+5-FOA plates, but not on MM plates). The cells were scraped from the MM+5-FOA plates and subjected to fatty acid analysis, according to the General Methods.

GC analyses showed the presence of 14.8% EPA, 17.4% DPA and 0.4% DHA of TFAs in transformant #5 and 15.3%

EPA, 17.2% DPA and 0.4% DHA of TFAs in transformant #8. These two strains were designated as strains Y5004U1 and Y5004U2, respectively (collectively, Y5004U).

Generation of Strain Y5018 to Produce about 25.4% EPA, 11.4% DPA and 9.4% DHA of TFAs Construct pZKL3-4GER44 (FIG. 8B; SEQ ID NO:69) was constructed to integrate one $C_{20/22}$ elongase gene and three Δ4 desaturase genes into the lipase 3-like locus (GenBank Accession No. XP_506121) of strain Y5004U1. The pZKL3-4GER44 plasmid contained the following components:

TABLE 10

Components Of Plasmid pZKL3-4GER44 (SEQ ID NO: 69)

| RE Sites And Nucleotides Within SEQ ID NO: 69 | Description Of Fragment And Chimeric Gene Components |
|---|---|
| AscI/BsiWI (10527-9640) | 887 bp 5' portion of the *Yarrowia* Lipase 3-like gene (GenBank Accession No. XP_506121) |
| PacI/SphI (14039-13235) | 804 bp 3' portion of *Yarrowia* Lipase 3-like gene (GenBank Accession No. XP_506121) |
| SwaI/BsiWI (7485-9640) | FBAINm::EgC20ES::Pex20, comprising: FBAINm: *Yarrowia lipolytica* FBAINm promoter (U.S. Pat. No. 7,202,356); EgC20ES: codon-optimized C20 elongase gene (SEQ ID NO: 63), derived from *Euglena gracilis* (U.S. patent application Pub. No. 2008/0254191-A1); Pex20: Pex20 terminator sequence from *Yarrowia* Pex20 gene (GenBank Accession No. AF054613) |
| PmeI/SwaI (4774-7485) | YAT1::EaD4S-1::Lip1, comprising: YAT1: *Yarrowia lipolytica* YAT1 promoter (U.S. patent application Pub. No. 2006/0094102-A1); EaD4S-1: codon-optimized truncated Δ4 desaturase (SEQ ID NO: 65), derived from *Euglena anabaena* (U.S. patent application Pub. No. 2008/0254191-A1); Lip1: Lip1 terminator sequence from *Yarrowia* Lip1 gene (GenBank Accession No. Z50020) |
| ClaI/PmeI (2070-4774) | EXP1::E1594D4S::Oct, comprising: EXP1: *Yarrowia lipolytica* export protein promoter (Intl. App. Pub. No. WO 2006/052870); E1594D4S: codon-optimized Δ4 desaturase (SEQ ID NO: 70), derived from *Eutreptiella cf_gymnastica* CCMP1594 (U.S. patent application Pub. No. 2009/0253188-A1) (labeled as "D4S-1594" in Figure); OCT: OCT terminator sequence of *Yarrowia* OCT gene (GenBank Accession No. X69988) |
| SalI/EcoRI (1620-1) | *Yarrowia* Ura3 gene (GenBank Accession No. AJ306421) |
| EcoRI/PacI (1-14039) | GPDIN::EgD4S-1::Aco, comprising: GPDIN: *Yarrowia lipolytica* GPDIN promoter (U.S. Pat. No. 7,459,546); EgD4S-1: codon-optimized truncated Δ4 desaturase (SEQ ID NO: 72), derived from *Euglena gracilis* (U.S. patent application Pub. No. 2008/0254191-A1); Aco: Aco terminator sequence from *Yarrowia* Aco gene (GenBank Accession No. AJ001300) |

The pZKL3-4GER44 plasmid was digested with AscI/SphI, and then used for transformation of strain Y5004U1, according to the General Methods. The transformants were selected on MM plates. After 5 days growth at 30° C., 96 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, resuspended in HGM and then shaken at 250 rpm/min for 5 days. The cells were subjected to fatty acid analysis, according to the General Methods.

GC analyses showed that most of the selected 96 strains produced about 19% EPA, 22% DPA and 7% DHA of TFAs. Strain #1 produced 23.3% EPA, 13.7% DPA and 8.9% DHA, while strain #49 produced 25.2% EPA, 11.4% DPA and 9.4% DHA. These two strains were designated as Y5011 and Y5018, respectively.

Knockout of the lipase 3-like locus (GenBank Accession No. XP_506121) was not confirmed in strains Y5011 and Y5018.

Generation of Strain Y5018U (Ura3−)

To disrupt the Ura3 gene, construct pZKUM (FIG. 5A; SEQ ID NO:40; described in Table 15 of U.S. Pat. App. Pub. No. 2009-0093543-A1) was used to integrate a Ura3 mutant gene into the Ura3 gene of strain Y5018, in a manner similar to that described for pZKUM transformation of strain Y8006 (Example 1). A total of 18 transformants were grown and identified to possess a Ura− phenotype.

GC analyses showed the presence of 16.6% EPA, 10.4% DPA and 0.0% DHA of FAMEs in pZKUM-transformant strain #2 and 17.0% EPA, 10.8% DPA and 0.0% DHA of FAMEs in pZKUM-transformant strain #4. These two strains were designated as strains Y5018U1 and Y5018U2, respectively (collectively, Y5018U).

Generation of Strain Y5037 to Produce about 18.6% EPA, 22.8% DPA and 9.7% DHA of TFAs Construct pZKLY-G20444 (FIG. 9; SEQ ID NO:74) was constructed to integrate one DHA synthase and two Δ4 desaturase genes into the lipase 7-like locus (GenBank Accession No. AJ549519) of strain Y5018U1. A DHA synthase is a multizyme comprising a C20 elongase linked to a Δ4 desaturase. The pZKLY-G20444 plasmid contained the following components:

TABLE 11

Components Of Plasmid pZKLY-G20444 (SEQ ID NO: 74)

| RE Sites And Nucleotides Within SEQ ID NO: 74 | Description Of Fragment And Chimeric Gene Components |
|---|---|
| AscI/BsiWI (9370-8476) | 887 bp 5' portion of the *Yarrowia* Lipase 7-like gene (labeled as "LipY-5'" in Figure; GenBank Accession No. AJ549519) |
| PacI/SphI (12840-12078) | 756 bp 3' portion of *Yarrowia* Lipase 7-like gene (labeled as "LipY-3'" in Figure; GenBank Accession No. AJ549519) |
| PmeI/SwaI (4871-8320) | YAT1::EgDHAsyn1S::Lip1, comprising: YAT1: *Yarrowia lipolytica* YAT1 promoter (U.S. patent application Pub. No. 2006/0094102-A1); EgDHAsyn1S: codon-optimized DHA synthase (SEQ ID NO: 75), derived from *Euglena gracilis* (labeled as "EgDHAase" in Figure; U.S. patent application Pub. No. 2008/0254191-A1); Lip1: Lip1 terminator sequence from *Yarrowia* Lip1 gene (GenBank Accession No. Z50020) |
| ClaI/PmeI (2070-4871) | EXP1::EaD4S-1::Pex16, comprising: EXP1: *Yarrowia lipolytica* export protein (EXP1) promoter (Intl. App. Pub. No. WO 2006/052870); EaD4S-1: codon-optimized truncated Δ4 desaturase (SEQ ID NO: 65), derived from *Euglena anabaena* (U.S. patent application Pub. No. 2008/0254191-A1); Pex16: Pex16 terminator sequence from *Yarrowia* Pex16 gene (GenBank Accession No. U75433) |
| SalI/EcoRI (1620-1) | *Yarrowia* Ura3 gene (GenBank Accession No. AJ306421) |
| EcoRI/PmeI (1-12871) | FBAINm::E1594D4S::Pex16, comprising: FBAINm: *Yarrowia lipolytica* FBAINm promoter (U.S. Pat. No. 7,202,356); E1594D4S: codon-optimized Δ4 desaturase (SEQ ID NO: 70), derived from *Eutreptiella cf_gymnastica* CCMP1594 (U.S. patent application Pub. No. 2009/0253188-A1) (labeled as "D4S-1594" in Figure); Pex16: Pex16 terminator sequence from *Yarrowia* Pex16 gene (GenBank Accession No. U75433) |

The pZKLY-G20444 plasmid was digested with AscI/SphI, and then used for transformation of strain Y5018U1, according to the General Methods. The transformants were selected on MM plates. After 5 days growth at 30° C., 96 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, resuspended in HGM and then shaken at 250 rpm/min for 5 days. The cells were subjected to fatty acid analysis, according to the General Methods.

GC analyses showed that most of the selected 96 strains produced about 19% EPA, 22% DPA and 9% DHA of TFAs. Strain #3 produced 18.6% EPA, 22.8% DPA and 9.7% DHA; strain #9 produced 18.4% EPA, 21% DPA and 9.6% DHA; strain #27 produced 17.8% EPA, 20.6% DPA and 10% DHA; and strain #40 produced 18.8% EPA, 21.2% DPA and 9.6% DHA. These four strains were designated as Y5037, Y5038, Y5039 and Y5040, respectively.

Knockout of the lipase 7-like locus (GenBank Accession No, AJ549519) was not confirmed in these knocked out strains.

The final genotype of strains Y5037, Y5038, Y5039 and Y5040 with respect to wild type *Yarrowia lipolytica* ATCC #20362 was SCP2-(YALI0E01298g), YALI0C18711g-, Pex10-, YALI0F24167g-, unknown 1-, unknown 3-, unknown 8-, unknown 9-, unknown10-, unknown 11-, GPD::FmD12::Pex20, YAT1::FmD12::OCT, GPM/FBAIN:: FmD12S::OCT, EXP1::FmD12S::Aco, YAT1::FmD12S:: Lip2, YAT1::ME3S::Pex16, EXP1::ME3S::Pex20 (3 copies), GPAT::EgD9e::Lip2, EXP1::EgD9eS::Lip1, FBAINm:: EgD9eS::Lip2, FBA::EgD9eS::Pex20, GPD::EgD9eS::Lip2, YAT1::EgD9eS::Lip2, YAT1::E389D9eS::OCT, FBAINm:: EgD8M::Pex20, FBAIN::EgD8M::Lip1 (2 copies), EXP1:: EgD8M::Pex16, GPDIN::EgD8M::Lip1, YAT1::EgD8M:: Aco, FBAIN::EgD5::Aco, EXP1::EgD5S::Pex20, YAT1:: EgD5S::Aco, EXP1::EgD5S::ACO, YAT1::RD5S::OCT, YAT1::PaD17S::Lip1, EXP1::PaD17::Pex16, FBAINm:: PaD17::Aco, YAT1::YlCPT1::ACO, GPD::YlCPT1::ACO, FBAINm::EaC20ES::Pex20, YAT1::EgC20ES::Lip1, FBAINm::EgC20ES::Pex20, EXP1::EaD4S-1::Lip2, EXP1::EaD4S-1::Pex16, YAT1::EaD4S-1::Lip1, GPDIN:: EaD4SB::Aco, EXP1::E1594D4S::Oct, FBAINm:: E1594D4S::Pex16, GPDIN::EgD4S-1::Aco, YAT1:: EgDHAsyn1S::Lip1.

Generation of Strain Y5037U (Ura3-)

To disrupt the Ura3 gene, construct pZKUM (FIG. 5A; SEQ ID NO:40; described in Table 15 of U.S. Pat. App. Pub. No. 2009-0093543-A1) was used to integrate a Ura3 mutant gene into the Ura3 gene of strain Y5037, in a manner similar to that described for pZKUM transformation of strain Y5004 (supra). A total of 12 transformants were grown and identified to possess a Ura- phenotype.

GC analyses showed the presence of 12.1% EPA, 10.2% DPA and 3.3% DHA in pZKUM-transformant strain #4 and 12.4% EPA, 10.3% DPA and 3.5% DHA in pZKUM-transformant strain #11. These two strains were designated as strains Y5037U1 and Y5037U2, respectively (collectively, Y5037U).

Example 3

Construction of Various Expression Vectors Comprising Different LPLAT ORFs

The present example describes the construction of a series of vectors, each comprising a LPLAT ORF, suitable for expression in *Yarrowia lipolytica*. LPLAT ORFs included the *Saccharomyces cerevisiae* Ale1, *Yarrowia lipolytica* Ale1, *Mortierella alpina* LPAAT1, *Yarrowia lipolytica* LPAAT1 and *Caenorhabditis elegans* LPCAT. Examples 4, 5 and 6 describe the results obtained following transformation of these vectors into *Yarrowia lipolytica*.

Origin of LPLATs

A variety of LPLATs have been identified in the patent and open literature, but the functionality of these genes has not been previously directly compared. Table 12 summarizes publicly available LPLATs (i.e., ScAle1, ScLPAAT, MaL-PAAT1 and CeLPCAT) and LPLAT orthologs identified herein (i.e., YlAle1 and YlLPAAT1) that are utilized in the Examples, following codon-optimization of heterologous genes for expression in *Yarrowia lipolytica* (infra).

TABLE 12

LPLATs Functionally Characterized

| LPLAT | Organism | ORF Designation | References | SEQ ID NO |
|---|---|---|---|---|
| Ale1 | *Saccharomyces cerevisiae** | ORF "YOR175C" or "ScAle1" | GenBank Accession No. NP_014818; U.S. patent application Pub. No. 20080145867 (and corresponding to Intl. App. Pub. No. WO 2008/076377); Intl. App. Pub. No. WO 2009/001315 | 8, 9 |
| | *Yarrowia lipolytica* | "YALI0F19514p" or "YlAle1" | GenBank Accession No. XP_505624; Intl. App. Pub. No. WO 2009/001315 | 10, 11 |
| LPAAT | *Saccharomyces cerevisiae* | ORF "YDL052C" or "ScLPAAT" | GenBank Accession No. NP_010231 | 18 |
| | *Mortierella alpina* | "MaLPAAT1" | U.S. patent application Pub. No. 2006-0115881-A1; U.S. patent application Pub. No. 2009-0325265-A1 | 14, 15 |
| | *Yarrowia lipolytica* | "YALI0E18964g" or "YlLPAAT1" | GenBank Accession No. XP_504127; U.S. Pat. No. 7,189,559 | 16, 17 |
| LPCAT | *Caenorhabditis elegans** | "clone T06E8.1" or "CeLPCAT" | GenBank Accession No. CAA98276; Intl. App. Pub. No. WO 2004/076617 (corresponding to U.S. patent application Pub. No. 2006-0168687-A1) | 1, 2 |

*The *Saccharomyces cerevisiae* Ale1 and *Caenorhabditis elegans* LPCAT were used as comparative Examples.

More specifically, the ScLPAAT (SEQ ID NO:18) and ScAle1 (SEQ ID NO:9) protein sequences were used as queries to identify orthologs from the public *Y. lipolytica* protein database of the "Yeast project *Genolevures*" (Center for Bioinformatics, LaBRI, Talence Cedex, France) (see also Dujon, B. et al., *Nature*, 430(6995):35-44 (2004)) using the Washington University in St. Louis School of Medicine BLAST 2.0 (WU-BLAST; http://blast.wustl.edu). Based on analysis of the best hits, the Ale1 and LPAAT orthologs from *Yarrowia lipolytica* are identified herein as YlAle1 (SEQ ID NO:11) and YlLPAAT (SEQ ID NO:17), respectively. The identity of YlAle1 and YlLPAAT1 as orthologs of ScAle1 and ScLPAAT, respectively, was further confirmed by doing a reciprocal BLAST, i.e., using SEQ ID NOs:11 and 17 as a query against the *Saccharomyces cerevisiae* public protein database to find ScAle1 and ScLPAAT, respectively, as the best hits.

The LPLAT proteins identified above as ScAle1 (SEQ ID NO:9), YlAle1 (SEQ ID NO:11), ScLPAAT (SEQ ID NO:18), MaLPAAT1 (SEQ ID NO:15), YlLPAAT1 (SEQ ID NO:17) and CeLPCAT (SEQ ID NO:2) were aligned using the method of Clustal W (slow, accurate, Gonnet option; Thompson et al., *Nucleic Acids Res.*, 22:4673-4680 (1994)) of the MegAlign™ program (version 8.0.2) of the LASER-GENE bioinformatics computing suite (DNASTAR, Inc., Madison, Wis.). This resulted in creation of Table 13, where percent similarity is shown in the upper triangle of the Table while percent divergence is shown in the lower triangle.

TABLE 13

Percent Identity And Divergence Among Various LPLATs

| YlLPAAT1 | CeLPCAT | MaLPAAT1 | ScAle1 | ScLPAAT | YlAle1 | |
|---|---|---|---|---|---|---|
| — | 26.6 | 34.0 | 9.6 | 43.9 | 11.7 | YlLPAAT1 |
| 184.3 | — | 36.4 | 11.3 | 32.4 | 14.5 | CeLPCAT |
| 137.5 | 126.4 | — | 11.1 | 34.6 | 15.0 | MaLPAAT1 |
| 545.0 | 442.0 | 456.0 | — | 13.5 | 45.0 | ScAle1 |
| 97.9 | 145.7 | 134.5 | 365.0 | — | 15.6 | ScLPAAT |
| 426.0 | 339.0 | 330.0 | 94.3 | 317.0 | — | YlAle1 |

The percent identities revealed by this method allowed determination of the minimum percent identity between each of the LPAAT polypeptides and the minimum percent identity between each of the Ale1 polypeptides. The range of identity between LPAAT polypeptides was 34.0% identity (MaLPAAT1 and YlLPAAT1) to 43.9% identity (ScLPAAT and YlLPAAT1), while identity between the ScAle1 and YlAle1 polypeptides was 45%.

Membrane Bound O-Acyltransferase ["MBOAT"] Family Motifs:

Orthologs of the ScAle1 protein sequence (SEQ ID NO:9) were identified by conducting a National Center for Biotechnology Information ["NCBI"] BLASTP 2.2.20 (protein-protein Basic Local Alignment Search Tool; Altschul et al., *Nucleic Acids Res.*, 25:3389-3402 (1997); and Altschul et al., *FEBS J.*, 272:5101-5109 (2005)) search using ScAle1 (SEQ ID NO:9) as the query sequence against fungal proteins in the "nr" protein database (comprising all non-redundant GenBank CDS translations, sequences derived from the 3-dimensional structure from Brookhaven Protein Data Bank ["PDB"], sequences included in the last major release of the SWISS-PROT protein sequence database, PIR and PRF excluding those environmental samples from WGS projects) using default parameters (expect threshold=10; word size=3; scoring parameters matrix=BLOSUM62; gap costs: existence=11, extension=1). The following hits were obtained:

TABLE 14

Fungal Orthologs Of ScAle1 (SEQ ID NO: 9) Based On BLAST Analysis

| Gen Bank Acession No. | Species |
|---|---|
| NP_014818.1 | *Saccharomyces cerevisiae* |
| XP_001643411.1 | *Vanderwaltozyma polyspora* DSM 70294 |
| XP_448977.1 | *Candida glabrata* |
| XP_455985.1 | *Kluyveromyces lactis* |
| NP_986937.1 | *Ashbya gossypii* ATCC 10895 |
| XP_001385654.2 | *Pichia stipitis* CBS 6054 |
| XP_001487052.1 | *Pichia guilliermondii* ATCC 6260 |
| EDK36331.2 | *Pichia guilliermondii* ATCC 6260 |
| XP_001525914.1 | *Lodderomyces elongisporus* NRRL YB-4239 |
| XP_461358.1 | *Debaryomyces hansenii* CBS767 |
| XP_713184.1 | *Candida albicans* SC5314 |
| XP_001645053.1 | *Vanderwaltozyma polyspora* DSM 70294 |
| XP_505624.1 | *Yarrowia lipolytica* |
| XP_001805526.1 | *Phaeosphaeria nodorum* SN15 |
| XP_001598340.1 | *Sclerotinia sclerotiorum* 1980 |
| XP_001907785.1 | *Podospora anserine* |
| XP_001931658.1 | *Pyrenophora tritici-repentis* Pt-1C-BFP |
| XP_001560657.1 | *Botryotinia fuckeliana* B05.10 |
| XP_963006.1 | *Neurospora crassa* OR74A |
| XP_364011.2 | *Magnaporthe grisea* 70-15 |
| XP_001209647.1 | *Aspergillus terreus* NIH2624 |
| XP_001822945.1 | *Aspergillus oryzae* RIB40 |
| XP_001257694.1 | *Neosartorya fischeri* NRRL 181 |
| XP_747591.2 | *Aspergillus fumigatus* Af293 |
| XP_001270060.1 | *Aspergillus clavatus* NRRL 1 |

TABLE 14-continued

Fungal Orthologs Of ScAle1 (SEQ ID NO: 9) Based On BLAST Analysis

| Gen Bank Acession No. | Species |
|---|---|
| NP_596779.1 | *Schizosaccharomyces pombe* |
| XP_001396584.1 | *Aspergillus niger* |
| XP_001229385.1 | *Chaetomium globosum* CBS 148.51 |
| XP_001248887.1 | *Coccidioides immitis* RS |
| XP_664134.1 | *Aspergillus nidulans* FGSC A4 |
| XP_566668.1 | *Cryptococcus neoformans* var. *neoformans* JEC21 |
| XP_001839338.1 | *Coprinopsis cinerea okayama* 7#130 |
| XP_757554.1 | *Ustilago maydis* 521 |

The yeast and fungal protein sequences of Table 14 were aligned using DNASTAR. Multiple sequence alignments and percent identity calculations were performed using the Clustal W method of alignment (supra).

More specifically, default parameters for multiple protein alignment using the Clustal W method of alignment correspond to: GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB with the 'slow-accurate' option. The resulting alignment was analyzed to determine the presence or absence of the non-plant motifs for Ale1 homologs, as identified in U.S. Pat. Pub. No. 2008-0145867-A1. Specifically, these include: M-[V/I]-[L/I]-xxK-[L/V/I]-xxxxxxDG (SEQ ID NO:26), RxKYYxxWxxx-[E/D]-[A/G]xxxxGxG-[F/Y]-xG (SEQ ID NO:27), $EX_{11}WNX_2$-[T/V]-$X_2$W (SEQ ID NO:28) and SAxWHGxxPGYxx-[T/F]-F (SEQ ID NO:29), wherein X encodes any amino acid residue. The H is residue in SEQ ID NO:29 has been reported to be a likely active site residue within the protein.

Only one motif, i.e., $EX_{11}WNX_2$-[T/V]-$X_2$W (SEQ ID NO:28), was completely conserved in all 33 of the organisms aligned. The remaining M-[V/I]-[L/I]-xxK-[L/V/I]-xxxxxxDG (SEQ ID NO:26), RxKYYxxWxxx-[E/D]-[A/G]xxxxGxG-[F/Y]-xG (SEQ ID NO:27) and SAxWHGxx-PGYxx-[T/F]-F (SEQ ID NO:29) motifs were only partially conserved. Thus, these motifs were appropriately truncated to fit with 0 mismatch (i.e., SAxWHG [SEQ ID NO:5]), 1 mismatch (i.e., RxKYYxxW [SEQ ID NO:4]), or 2 mismatches (i.e., M(V/I)(L/I)xxK(L/I) [SEQ ID NO:3]) for the purposes of the present methodologies.

1-Acyl-Sn-Glycerol-3-Phosphate Acyltransferase ["LPAAT"] Family Motifs:

Analysis of the protein alignment comprising ScLPAAT (SEQ ID NO:18), MaLPAAT1 (SEQ ID NO:15) and YlLPAAT1 (SEQ ID NO:17) revealed that the 1-acyl-sn-glycerol-3-phosphate acyltransferase family motif EGTR (SEQ ID NO:20) was present in each of the LPAAT orthologs. On this basis, MaLPAAT1 was identified as a likely LPAAT, that was clearly distinguishable from the Ma LPAAT-like proteins disclosed in Intl. App. Pub. No. WO 2004/087902 (i.e., SEQ ID NOs:93 and 95).

It is noteworthy that the EGTR (SEQ ID NO:20) motif, while lacking in the LPCAT sequences in Intl. App. Pub. No. WO 2004/087902, is present in CeLPCAT (SEQ ID NO:2). It appears that other residues distinguish LPAAT and LPCAT sequences in LPAAT-like proteins. One such residue could be the extension of the EGTR (SEQ ID NO:20) motif. Specifically, whereas the EGTR motif in ScLPAAT (SEQ ID NO:18), MaLPAAT1 (SEQ ID NO:15) and YlLPAAT1 (SEQ ID NO:17) is immediately followed by a serine residue, the EGTR motif in CeLPCAT is immediately followed by an asparagine residue. In contrast, the two LPCATs in Intl. App. Pub. No. WO 2004/087902 have a valine substituted for the arginine residue in the EGTR motif and the motif is immediately followed by a valine residue.

Construction of pY201, Comprising a Codon-Optimized *Saccharomyces cerevisiae* Ale1 Gene The *Saccharomyces cerevisiae* ORF designated as "ScAle1" (SEQ ID NO:8) was optimized for expression in *Yarrowia lipolytica*, by DNA 2.0 (Menlo Park, Calif.). In addition to codon optimization, 5' Pci1 and 3' Not1 cloning sites were introduced within the synthetic gene (i.e., ScAle1S; SEQ ID NO:12). None of the modifications in the ScAle1S gene changed the amino acid sequence of the encoded protein (i.e., the protein sequence encoded by the codon-optimized gene [i.e., SEQ ID NO:13] is identical to that of the wildtype protein sequence [i.e., SEQ ID NO:9]). ScAle1S was cloned into pJ201 (DNA 2.0) to result in pJ201: ScAle1S.

A 1863 bp Pci1/Not1 fragment comprising ScAle1S was excised from pJ201:ScAle1S and used to create pY201 (SEQ ID NO:77; Table 15; FIG. 10A). In addition to comprising a chimeric YAT1::ScAle1S::Lip1 gene, pY201 also contains a *Yarrowia lipolytica* URA3 selection marker flanked by LoxP sites for subsequent removal, if needed, by Cre recombinase-mediated recombination. Both the YAT1::ScAle1S::Lip1 chimeric gene and the URA3 gene were flanked by fragments having homology to 5' and 3' regions of the *Yarrowia lipolytica* Pox3 gene to facilitate integration by double homologous recombination, although integration into *Yarrowia lipolytica* is known to usually occur without homologous recombination. Thus, construct pY201 thereby contained the following components:

TABLE 15

Description of Plasmid pY201 (SEQ ID NO: 77)

| RE Sites And Nucleotides Within SEQ ID NO: 77 | Description Of Fragment And Chimeric Gene Components |
|---|---|
| BsiW1/Sbf1 (1-1706 bp) | LoxP::Ura3::LoxP, comprising: LoxP sequence (SEQ ID NO: 78) *Yarrowia lipolytica* Ura3 gene (GenBank Accession No. AJ306421); LoxP sequence (SEQ ID NO: 78) |
| Sbf1/Sph1 (1706-3043 bp) | 3' portion of *Yarrowia lipolytica* POX3 Acyl-CoA oxidase 3 (GenBank Accession No. YALI0D24750g) (i.e., bp 2215-3038 in pY201) |
| Sph1/AscI (3043-5743 bp) | ColE1 plasmid origin of replication; Ampicillin-resistance gene (Amp^R) for selection in *E. coli* (i.e., bp 3598-4758 [complementary] in pY201); *E. coli* f1 origin of replication |
| AscI/BsiWI (5743-6513 bp) | 5' portion of *Yarrowia lipolytica* POX3 Acyl-CoA oxidase 3 (GenBank Accession No. YALI0D24750g) (i.e., bp 5743-6512 in pY201) |

TABLE 15-continued

Description of Plasmid pY201 (SEQ ID NO: 77)

| RE Sites And Nucleotides Within SEQ ID NO: 77 | Description Of Fragment And Chimeric Gene Components |
|---|---|
| BsiWI/BsiWI (6514-1 bp) [a Not1 site, located between ScAle1S and Lip1 is present at bp 9154 bp] | YAT1::ScAle1S::Lip1, comprising: YAT1: *Yarrowia lipolytica* YAT1 promoter (U.S. patent application Pub. No. 2006/0094102-A1) (i.e., bp 6514-7291 in pY201) ScAle1S: codon-optimized Ale1 (SEQ ID NO: 12) derived from *Saccharomyces cerevisiae* YOR175C (i.e., bp 7292-9151 in pY201; labeled as "Sc LPCATs ORF" in Figure); Lip1: Lip1 terminator sequence from *Yarrowia* Lip1 gene (GenBank Accession No. Z50020) (i.e., bp 9160-9481 pY201; labeled as "Lip1-3'" in Figure) |

Construction of pY168, Comprising a *Yarrowia lipolytica* Ale1 Gene

The *Yarrowia lipolytica* ORF designated as "YlAle1" (GenBank Accession No. XP_505624; SEQ ID NO:10) was amplified by PCR from *Yarrowia lipolytica* ATCC #20362 cDNA library using PCR primers 798 and 799 (SEQ ID NOs:79 and 80, respectively). Additionally, the YAT promoter was amplified by PCR primers 800 and 801 (SEQ ID NOs:81 and 82, respectively) from pY201 (SEQ ID NO:77). Since the primer pairs were designed to create two PCR products having some overlap with one another, a YAT1::YlAle1 fusion fragment was then amplified by overlapping PCR using primers 798 and 801 (SEQ ID NOs:79 and 82, respectively) and the two PCR fragments as template. The PCR was carried out in a RoboCycler Gradient 40 PCR machine (Stratagene) using the manufacturer's recommendations and Pfu Ultra™ High-Fidelity DNA Polymerase (Stratagene, Cat. No. 600380). Amplification was carried out as follows: initial denaturation at 95° C. for 4 min, followed by 30 cycles of denaturation at 95° C. for 30 sec, annealing at 55° C. for 1 min, and elongation at 72° C. for 1 min. A final elongation cycle at 72° C. for 10 min was carried out, followed by reaction termination at 4° C.

The PCR product comprising the YAT1::Yl Ale1 fusion fragment was gel purified and digested with ClaI/NotI. This Cla1-Not1 fragment was ligated into pY201 that had been similarly digested (thereby removing the YAT1::ScAle1S fragment) to create pY168 (SEQ ID NO:83), comprising a chimeric YAT1::YlAle1::Lip1 gene. The DNA sequence of the *Yarrowia Ale1* ORF was confirmed by DNA sequencing. The components present in pY168 (FIG. 10B; SEQ ID NO:83) are identical to those present in pY201, with the exception of the YAT1::YlAle1::Lip1 gene in pY168, instead of the YAT1::ScAle1S::Lip1 gene in pY201 (FIG. 10A). Note that YlAle1 is labeled as "Yl LPCAT" in FIG. 10B.

Construction of pY208, Comprising a *Mortierella alpina* LPAAT1 Gene

The *Mortierella alpina* ORF designated as "MaLPAAT1" (SEQ ID NO:14) was optimized for expression in *Yarrowia lipolytica*, by DNA 2.0 (Menlo Park, Calif.). In addition to codon optimization, 5' Pci1 and 3' Not1 cloning sites were introduced within the synthetic gene (i.e., MaLPAAT1S; SEQ ID NO:21). None of the modifications in the MaLPAAT1S gene changed the amino acid sequence of the encoded protein (i.e., the protein sequence encoded by the codon-optimized gene [i.e., SEQ ID NO:22] is identical to that of the wildtype protein sequence [i.e., SEQ ID NO:15]). MaLPAAT1S was cloned into pJ201 (DNA 2.0) to result in pJ201:MaLPAAT1S.

A 945 bp PciI/NotI fragment comprising MaLPAAT1S was excised from pJ201:MaLPAAT1S and used to create pY208 (SEQ ID NO:84), in a 3-way ligation with two fragments of pY201 (SEQ ID NO:77). Specifically, the MaLPAAT1 fragment was ligated with a 3530 bp Sph-NotI pY201 fragment and a 4248 bp NcoI-SphI pY201 fragment to result in pY208. The components present in pY208 (FIG. 11A; SEQ ID NO:84) are identical to those present in pY201, with the exception of the YAT1::MaLPAAT1S::Lip1 gene in pY208, instead of the YAT1::Sc Ale1S::Lip1 gene in pY201 (FIG. 10A).

Construction of pY207, Comprising a *Yarrowia lipolytica* LPAAT1 Gene

A putative LPAAT1 from *Yarrowia lipolytica* (designated herein as "YlLPAAT1"; SEQ ID NO:17) was described in U.S. Pat. No. 7,189,559 and GenBank Accession No. XP_504127. The protein is annotated as "similar to uniprot|P33333 *Saccharomyces cerevisiae* YDL052c SLC1 fatty acyltransferase".

The YlLPAAT1 ORF (SEQ ID NO:16) was amplified by PCR using *Yarrowia lipolytica* ATCC #20362 cDNA library as a template and PCR primers 856 and 857 (SEQ ID NOs:85 and 86, respectively). The PCR was conducted using the same components and conditions as described above for amplification of the YAT1::Yl Ale1 fusion fragment, prior to synthesis of pY168.

The PCR product comprising YlLPAAT1 ORF was digested with PciI and NotI and then utilized in a 3-way ligation with two fragments from pY168. Specifically, the YlLPAAT1 fragment was ligated with a 3530 bp Sph-NotI pY168 fragment and a 4248 bp NcoI-SphI pY168 fragment, to produce pY207, comprising a chimeric YAT1::YlLPAAT1::Lip1 gene. The *Y. lipolytica* LPAAT1 ORF was confirmed by DNA sequencing. The components present in pY207 (FIG. 11B; SEQ ID NO:87) are identical to those present in pY201, with the exception of the chimeric YAT1::Yl LPAAT1::Lip1 gene in pY207, instead of the YAT1::ScAle1S::Lip1 gene in pY201 (FIG. 10A). Note that YlLPAAT1 is labeled as "Yl LPAT1 ORF" in FIG. 11B.

Construction of pY175, Comprising a *Caenorhabditis elegans* LPCAT Gene

The *Caenorhabditis elegans* ORF designated as "CeLPCAT" (SEQ ID NO:1) was optimized for expression in *Yarrowia lipolytica*, by GenScript Corporation (Piscataway, N.J.). In addition to codon optimization, 5' Nco1 and 3' Not1 cloning sites were introduced within the synthetic gene (i.e., CeLPCATS; SEQ ID NO:6). None of the modifications in the CeLPCATS gene changed the amino acid sequence of the encoded protein (i.e., the protein sequence encoded by the codon-optimized gene [i.e., SEQ ID NO:7] is identical to that of the wildtype protein sequence [i.e., SEQ ID NO:2]).

A Nco1-Not1 fragment comprising CeLPCATS was used to create pY175 (SEQ ID NO:88), in a 3-way ligation with two fragments from pY168 (SEQ ID NO:83). Specifically, the Nco1-Not1 fragment comprising CeLPCATS was ligated with a 3530 bp Sph-NotI pY168 fragment and a 4248 bp NcoI-SphI pY168 fragment to result in pY175. The components present in pY175 (FIG. 12A; SEQ ID NO:88) are identical to those present in pY201, with the exception of the YAT1::CeLPCATS::Lip1 gene in pY175, instead of the YAT1::ScAle1S::Lip1 gene in pY201 (FIG. 10A). Note that CeLPCATS is labeled as "Ce.LPCATsyn" in FIG. 12A.

Construction of pY153, Comprising a *Caenorhabditis elegans* LPCAT Gene

The NcoI-NotI fragment comprising CeLPCATS, supra, was used to create pY153 (SEQ ID NO:89; FIG. 12B). In addition to comprising a chimeric FBAIN::CeLPCATS::3' Yl LPAAT1 gene, pY153 also contains a *Yarrowia lipolytica* URA3 selection marker. Both the chimeric FBAIN::CeLPCATS::3' Yl LPAAT1 gene and the URA3 gene were flanked by fragments having homology to 5' and 3' regions of the *Yarrowia lipolytica* LPAAT1 gene to facilitate integration by double homologous recombination, although integration into *Yarrowia lipolytica* is known to usually occur without homologous recombination. Thus, construct pY153 thereby contained the following components:

TABLE 16

Description of Plasmid pY153 (SEQ ID NO: 89)

| RE Sites And Nucleotides Within SEQ ID NO: 89 | Description Of Fragment And Chimeric Gene Components |
|---|---|
| Cla1/Sap1 (1-1398 bp) | 5' portion of *Yarrowia lipolytica* gene encoding LPAAT1 (GenBank Accession No. XP_504127) (i.e., bp 1-1112 [complementary] in pY153); |
| Sap1/Xba1 (1398-3993 bp) | Vector backbone including:<br>ColE1 plasmid origin of replication (i.e., bp 1380-2260 in pY153);<br>Ampicillin-resistance gene (Amp$^R$) for selection in *E. coli* (i.e., bp 2330-3190 [complementary] in pY153);<br>*E. coli* f1 origin of replication (i.e., bp 3370-3770 in pY153) |
| Xba1/Pme1 (3993-6719 bp) [a Nco1 site, located between CeLPCATS and FBAIN is present at bp 5756; a Not1 site, located between CeLPCATS and YlLPAAT1 is present at bp 4904] | FBAIN::CeLPCATS::3' Yl LPAAT1, comprising:<br>FBAINm: *Yarrowia lipolytica* FBAIN promoter (U.S. Pat. No. 7,202,356) (i.e., bp 5756-6719 [complementary] in pY153);<br>CeLPCATS: codon-optimized LPCAT (SEQ ID NO: 6) derived from *Caenorhabditis elegans* T06E8.1 (GenBank Accession No. CAA98276) (i.e., bp 4910-5758 [complementary] in pY153; labeled as "Ce.LPCATsyn" in Figure);<br>3' Yl LPAAT1: 3' untranslated portion of *Yarrowia lipolytica* gene encoding LPAAT1 (GenBank Accession No. XP_504127) (i.e., bp 3987-4905 [complementary] in pY153) |
| Pme1-Cla1 (6719-1 bp) | *Yarrowia lipolytica* URA3 gene (GenBank Accession No. AJ306421) (i.e., bp 6729-1 [complementary] in pY153) |

Example 4

Functional Characterization of Different LPLATs in EPA-Producing *Yarrowia lipolytica* Strain Y8406

*Yarrowia lipolytica* strain Y8406U, producing EPA, was used to functionally characterize the effects of overexpression of the *Saccharomyces cerevisiae* Ale1, *Yarrowia lipolytica* Ale1, *Mortierella* alpina LPAAT1, *Yarrowia lipolytica* LPAAT1 and *Caenorhabditis elegans* LPCAT, following their stable integration into the *Yarrowia* host chromosome. This was in spite of the host containing its native LPLATs, i.e., Ale1 and LPAAT1.

Transformation and Growth

*Yarrowia lipolytica* strain Y8406U (Example 1) was individually transformed with linear SphI-AscI fragments of the integrating vectors described in Example 3, wherein each LPLAT was under the control of the *Yarrowia* YAT promoter. Specifically, vectors pY201 (YAT1::ScAle1S::Lip1), pY168 (YAT1::YlAle1::Lip1), pY208 (YAT1::MaLPAAT1S::Lip1), pY207 (YAT1::YlLPAAT1::Lip1) and pY175 (YAT1::CeLPCATS::Lip1) were transformed according to the General Methods.

Each transformation mix was plated on MM agar plates. Several resultant URA+ transformants were picked and inoculated into 3 mL FM medium (Biomyx Cat. No. CM-6681, Biomyx Technology, San Diego, Calif.) containing per L: 6.7 g Difco Yeast Nitrogen Base without amino acids, 5 g Yeast Extract, 6 g $KH_2PO_4$, 2 g $K_2HPO_4$, 1.5 g $MgSO_4.7H_2O$, 1.5 mg thiamine.HCl, and 20 g glucose. After 2 days growth on a shaker at 200 rpm and 30° C., the cultures were harvested by centrifugation and resuspended in 3 mL HGM medium (Cat. No. 2G2080, Teknova Inc., Hollister, Calif.) containing 0.63% monopotassium phosphate, 2.7% dipotassium phosphate, 8.0% glucose, adjusted to pH 7.5. After 5 days growth on a shaker at 200 rpm and at 30° C., 1 mL aliquots of the cultures were harvested by centrifugation and analyzed by GC. Specifically, the cultured cells were collected by centrifugation for 1 min at 13,000 rpm, total lipids were extracted, and fatty acid methyl esters ["FAMEs"] were prepared by trans-esterification, and subsequently analyzed with a Hewlett-Packard 6890 GC (General Methods).

Based on the fatty acid composition of the 3 mL cultures, selected transformants were further characterized by flask assay. Specifically, clones #5 and #11 of strain Y8406U transformed with expression vector pY201 (comprising ScAle1S) were selected and designated as "Y8406U::ScAle1S-5" and "Y8406U::ScAle1S-11", respectively; clone #16 of strain Y8406U transformed with expression vector pY168 (comprising YlAle1) was selected and designated as "Y8406U::YlAle1"; clone #8 of strain Y8406U transformed with expression vector pY208 (comprising MaLPAAT1S) was selected and designated as "Y8406U::MaLPAAT1S"; clone #21 of strain Y8406U transformed with expression vector pY207 (comprising YlLPAAT1) was selected and designated as "Y8406U::YlLPAAT1"; and clone #23 of strain Y8406U transformed with expression vector pY175 (comprising CeLPCATS) was selected and designated as "Y8406U::CeLPCATS". Additionally, strain Y8406 (a Ura+ strain that was parent to strain Y8406U (Ura−)) was used as a control.

Each selected transformant and the control was streaked onto MM agar plates. Then, one loop of freshly streaked cells was inoculated into 3 mL FM medium and grown overnight at 250 rpm and 30° C. The $OD_{600nm}$ was measured and an aliquot of the cells were added to a final $OD_{600nm}$ of 0.3 in 25 mL FM medium in a 125 mL flask. After 2 days in a shaker incubator at 250 rpm and at 30° C., 6 mL of the culture was harvested by centrifugation and resuspended in 25 mL HGM in a 125 mL flask. After 5 days in a shaker incubator at 250 rpm and at 30° C., a 1 mL aliquot was used for GC analysis (supra) and 10 mL dried for dry cell weight ["DCW"] determination.

For DCW determination, 10 mL culture was harvested by centrifugation for 5 min at 4000 rpm in a Beckman GH-3.8 rotor in a Beckman GS-6R centrifuge. The pellet was resuspended in 25 mL of water and re-harvested as above. The washed pellet was re-suspended in 20 mL of water and transferred to a pre-weighed aluminum pan. The cell suspension was dried overnight in a vacuum oven at 80° C. The weight of the cells was determined.

Lipid Content, Fatty Acid Composition and Conversion Efficiencies

A total of four separate experiments were conducted under identical conditions. Experiment 1 compared control strain Y8406 versus strain Y8406U::ScAle1S-5. Experiment 2 compared control strain Y8406 versus strain Y8406U::YlAle1. Experiment 3 compared control strain Y8406 versus strain Y8406U::YlAle1, strain Y8406U::ScAle1S-11, and strain Y8406U::MaLPAAT1S. Experiment 4 compared control strain Y8406 versus strain Y8406U::MaLPAAT1S, strain Y8406U::YlLPAAT1 and strain Y8406U::CeLPCATS.

In each experiment, the lipid content, fatty acid composition and EPA as a percent of the DCW are quantified for 1, 2 or 3 replicate cultures ["Replicates"] of the control Y8406 strain and the transformant Y8406U strain(s). Additionally, data for each Y8406U transformant is presented as a % of the Y8406 control. Table 17 below summarizes the total lipid content of cells ["TFAs % DCW"], the concentration of each fatty acid as a weight percent of TFAs ["% TFAs"] and the EPA content as a percent of the dry cell weight ["EPA % DCW"]. More specifically, fatty acids are identified as 16:0 (palmitate), 16:1 (palmitoleic acid), 18:0 (stearic acid), 18:1 (oleic acid), 18:2 (LA), ALA, EDA, DGLA, ARA, ETrA, ETA and EPA.

Table 18 summarizes the conversion efficiency of each desaturase and the Δ9 elongase functioning in the PUFA biosynthetic pathway and which are required for EPA production. Specifically, the Δ2 desaturase conversion efficiency ["Δ12 CE"], Δ8 desaturase conversion efficiency ["Δ8 CE"], Δ5 desaturase conversion efficiency ["Δ5 CE"], Δ17 desaturase conversion efficiency ["Δ17 CE"] and Δ9 elongation conversion efficiency ["Δ9e CE"] are provided for each control Y8406 strain and the transformant Y8406U strain(s); data for each Y8406U transformant is presented as a % of the Y8406 control. Conversion efficiency was calculated according to the formula: product(s)/(product(s)+substrate)*100, where product includes both product and product derivatives.

TABLE 17

Lipid Content And Composition In LPCAT Transformant Strains Of *Yarrowia lipolytica* Y8406

| Expt. | Strain | Replicates | TFA % DCW | % TFAs 16:0 | 16:1 | 18:0 | 18:1 | 18:2 | ALA | EDA | DGLA | ARA | ERA | ETA | EPA | EPA % DCW |
|---|---|---|---|---|---|---|---|---|---|---|---|---|---|---|---|---|
| 1 | Y8406 | AVG.3 | 17.6 | 3.8 | 0.7 | 3.3 | 6.4 | 22.6 | 2.5 | 2.8 | 2.2 | 0.5 | 1.9 | 2.0 | 48.9 | 8.6 |
|  | Y8406U:: | AVG.3 | 18.3 | 4.2 | 0.7 | 3.5 | 5.7 | 15.1 | 0.6 | 3.3 | 3.7 | 0.8 | 1.8 | 2.3 | 56.9 | 10.4 |
|  | ScAle1S-5 | % Ctrl | 104 | 111 | 100 | 106 | 89 | 67 | 24 | 118 | 168 | 160 | 95 | 115 | 116 | 121 |

TABLE 17-continued

Lipid Content And Composition In LPCAT Transformant Strains Of *Yarrowia lipolytica* Y8406

| Expt. | Strain | Replicates | TFA % DCW | 16:0 | 16:1 | 18:0 | 18:1 | 18:2 | ALA | EDA | DGLA | ARA | ERA | ETA | EPA | EPA % DCW |
|---|---|---|---|---|---|---|---|---|---|---|---|---|---|---|---|---|
| 2 | Y8406 | AVG.3 | 23.2 | 3.5 | 0.6 | 3.3 | 6.4 | 22.3 | 2.7 | 2.6 | 2.1 | 0.5 | 1.6 | 2.0 | 49.9 | 11.6 |
|   | Y8406U:: | AVG.3 | 22.3 | 3.8 | 0.7 | 2.9 | 3.9 | 12.7 | 0.4 | 3.0 | 3.8 | 0.8 | 1.6 | 2.4 | 60.9 | 13.6 |
|   | YlAle1 | % Ctrl | 96 | 109 | 117 | 88 | 61 | 57 | 15 | 115 | 181 | 160 | 100 | 120 | 122 | 117 |
| 3 | Y8406 | 1 | 26.1 | 2.7 | 0.7 | 2.8 | 6.5 | 20.5 | 2.5 | 3.2 | 2.3 | 0.7 | 0.8 | 0.0 | 50.8 | 13.3 |
|   | Y8406U:: | AVG.2 | 23.3 | 3.3 | 0.7 | 2.4 | 3.6 | 12.1 | 0.5 | 3.2 | 3.5 | 0.9 | 0.0 | 2.3 | 62.2 | 14.5 |
|   | YlAle1 | % Ctrl | 89 | 122 | 100 | 86 | 55 | 59 | 20 | 100 | 152 | 129 | 0 | na | 122 | 109 |
|   | Y8406U:: | AVG.2 | 28.0 | 3.0 | 0.7 | 3.0 | 5.5 | 13.1 | 0.6 | 3.5 | 3.8 | 0.9 | 0.0 | 2.4 | 58.5 | 16.4 |
|   | ScAle1S-11 | % Ctrl | 107 | 111 | 100 | 107 | 85 | 64 | 24 | 109 | 165 | 129 | 0 | na | 115 | 123 |
|   | Y8406U:: | AVG.2 | 23.7 | 4.4 | 0.8 | 4.2 | 6.6 | 11.2 | 0.7 | 2.7 | 3.7 | 0.9 | 0.0 | 2.5 | 57.0 | 13.5 |
|   | MaLPAAT1S | % Ctrl | 91 | 163 | 114 | 150 | 102 | 55 | 28 | 84 | 161 | 129 | 0 | na | 112 | 102 |
| 4 | Y8406 | AVG.2 | 27.9 | 2.8 | 0.6 | 3.1 | 6.2 | 20.6 | 2.9 | 2.9 | 2.0 | 0.6 | 0.7 | 2.0 | 49.4 | 13.8 |
|   | Y8406U:: | AVG.2 | 25.2 | 4.8 | 0.8 | 4.8 | 6.9 | 11.6 | 0.8 | 2.5 | 3.0 | 0.7 | 0.0 | 2.3 | 55.3 | 14.0 |
|   | MaLPAAT1S | % Ctrl | 90 | 171 | 133 | 155 | 111 | 56 | 28 | 86 | 150 | 117 | 0 | 115 | 112 | 101 |
|   | Y8406U:: | AVG.2 | 25.2 | 3.7 | 0.7 | 4.2 | 6.2 | 13.0 | 1.2 | 2.3 | 2.6 | 0.6 | 0.0 | 2.2 | 56.7 | 14.3 |
|   | YlLPAAT1 | % Ctrl | 90 | 132 | 117 | 135 | 100 | 63 | 41 | 79 | 130 | 100 | 0 | 110 | 115 | 104 |
|   | Y8406U:: | AVG.2 | 24.7 | 3.8 | 0.6 | 4.6 | 7.1 | 13.9 | 1.6 | 2.3 | 2.6 | 0.6 | 0.4 | 2.2 | 53.6 | 13.2 |
|   | CeLPCATS | % Ctrl | 89 | 136 | 100 | 148 | 115 | 67 | 55 | 79 | 130 | 100 | 0 | 57 | 110 | 109 | 96 |

TABLE 18

Desaturase And Elongase Conversion Efficiency In LPCAT Transformant Strains Of *Yarrowia lipolytica* Y8406

| Expt. | Strain | Replicates | Δ12 CE | Δ9e CE | Δ8 CE | Δ5 CE | Δ17 CE |
|---|---|---|---|---|---|---|---|
| 1 | Y8406 | AVG.3 | 93 | 70 | 92 | 92 | 90 |
|   | Y8406U::ScAle1S-5 | AVG.3 | 94 | 81 | 93 | 91 | 89 |
|   |  | % Ctrl | 101 | 116 | 101 | 98 | 98 |
| 2 | Y8406 | AVG.3 | 93 | 70 | 93 | 93 | 91 |
|   | Y8406U::YlAle1 | AVG.3 | 96 | 85 | 94 | 91 | 90 |
|   |  | % Ctrl | 103 | 121 | 101 | 98 | 98 |
| 3 | Y8406 | 1 | 93 | 72 | 93 | 96 | 89 |
|   | Y8406U::YlAle1 | AVG.2 | 96 | 85 | 96 | 92 | 89 |
|   |  | % Ctrl | 104 | 119 | 103 | 96 | 100 |
|   | Y8406U::ScAle1S-11 | AVG.2 | 94 | 83 | 95 | 91 | 88 |
|   |  | % Ctrl | 101 | 117 | 102 | 95 | 99 |
|   | Y8406U::MaLPAAT1S | AVG.2 | 92 | 85 | 96 | 90 | 89 |
|   |  | % Ctrl | 100 | 119 | 103 | 94 | 100 |
| 4 | Y8406 | AVG.2 | 93 | 71 | 94 | 93 | 91 |
|   | Y8406U::MaLPAAT1S | AVG.2 | 92 | 84 | 96 | 91 | 90 |
|   |  | % Ctrl | 99 | 118 | 102 | 99 | 100 |
|   | Y8406U::YlLPAAT1 | AVG.2 | 93 | 82 | 96 | 92 | 92 |
|   |  | % Ctrl | 100 | 115 | 103 | 100 | 101 |
|   | Y8406U::CeLPCATS | AVG.2 | 92 | 80 | 96 | 92 | 91 |
|   |  | % Ctrl | 99 | 113 | 102 | 99 | 100 |

Based on the data concerning Experiments 1, 2 and 3 in Table 17 and Table 18, overexpression of LPLAT in EPA strains Y8406U::ScAle1S-5, Y8406U::ScAle1S-11, Y8406U::YlAle1 and Y8406U::MaLPAAT1S results in significant reduction (to 67% or below of the control) of the concentration of LA (18:2) as a weight % of TFAs ["LA % TFAs"], an increase (to at least 12% of the control) in the concentration of EPA as a weight % of TFAs ["EPA % TFAs"], and an increase (to at least 16% of the control) in the conversion efficiency of the Δ9 elongase. Compared to Y8406U::ScAle1S-5 and Y8406U::ScAle1S-11, Y8406U::YlAle1 has lower LA % TFAs, higher EPA % TFAs, better Δ9 elongation conversion efficiency, and slightly lower TFAs % DCW and EPA % DCW. Y8406U::Yl Ale1 and Y8406U::MaLPAAT1S are similar except overexpression of MaLPAAT1S resulted in lower LA % TFAs, EPA % TFAs, and EPA % DCW.

Experiment 4 shows that overexpression of LPLAT in EPA strains Y8406U::YlLPAAT1, Y8406U::MaLPAAT1S and Y8406U::CeLPCATS results in significant reduction (to 67% or below of the control) of LA % TFAs, an increase (to at least 9% of the control) in EPA % TFAs, and an increase (to at least 13% of the control) in the conversion efficiency of the Δ9 elongase. Compared to Y8406U::CeLPCATS, Y8406U::YlLPAAT1 and Y8406U::MaLPAAT1S both have lower LA % TFAs, higher EPA % TFAs, higher EPA % DCW, and slightly better TFAs % DCW. Y8406U::YlLPAAT1 and Y8406U::MaLPAAT1S are similar except overexpression of MaLPAAT1S results in lower LA % TFAs, slightly lower EPA % TFAs and EPA % DCW, and slightly better Δ9 elongase conversion efficiency.

It is well known in the art that most desaturations occur at the sn-2 position of phospholipids, while fatty acid elongations occur on acyl-CoAs. Furthermore, ScAle1S, YlAle1, MaLPAAT1S and YlLPAAT1 were expected to only incorporate acyl groups from the acyl-CoA pool into the sn-2 position of lysophospholipids, such as lysophosphatidic acid ["LPA"]

and lysophosphatidylcholine ["LPC"]. Thus, it was expected that expression of ScAle1S, YlAle1, MaLPAAT1S, and YlLPAAT1 would result in improved desaturations due to improved substrate availability in phospholipids, and not result in improved elongations that require improved substrate availability in the CoA pool. Our data (supra) shows that unexpectedly, expression of ScAle1S, YlAle1, MaLPAAT1S, and YlLPAAT1 significantly improved the Δ9 elongase conversion efficiency in strains of *Yarrowia* producing EPA but did not improve the desaturations (measured as Δ2 desaturase conversion efficiency, Δ8 desaturase conversion efficiency, Δ5 desaturase conversion efficiency or Δ17 desaturase conversion efficiency).

CeLPCAT was previously shown to improve Δ6 elongation conversion efficiency in *Saccharomyces cerevisiae* fed LA or GLA (Intl. App. Pub. No. WO 2004/076617). This was attributed to its reversible LPCAT activity that released fatty acids from phospholipids into the CoA pool. An improvement in Δ9 elongation conversion efficiency in an oleaginous microbe, such as *Yarrowia lipolytica*, engineered for high level LC-PUFA production in the absence of feeding fatty acids was not contemplated in Intl. App. Pub. No. WO 2004/076617.

Furthermore, expression of ScAle1S, YlAle1, MaLPAAT1S, YlLPAAT1 and CeLPCATS did not significantly alter either the level of PUFAs accumulated or the total lipid content in strains of *Yarrowia* producing EPA.

Previous studies have shown that both Δ6 elongation and Δ9 elongation are bottlenecks in long chain PUFA biosynthesis due to poor transfer of acyl groups between phospholipid and acyl-CoA pools. Based on the improved Δ9 elongase conversion efficiency resulting from over-expression of LPLATs, demonstrated above, it is anticipated that the LPLATs described herein and their orthologs, such as Sc LPAAT, will also improve Δ6 elongation conversion efficiency.

Example 5

Functional Characterization of Different LPLATs in DHA-Producing *Y. lipolytica* Strain Y5037

*Yarrowia lipolytica* strain Y5037U, producing DHA, was used to functionally characterize the effects of overexpression of the *Saccharomyces cerevisiae* Ale1, *Mortierella alpina* LPAAT1 and *Caenorhabditis elegans* LPCAT, following their stable integration into the *Yarrowia* host chromosome. This was in spite of the host containing its native LPLATs, i.e., Ale1 and LPAAT1.

Transformation and Growth

*Yarrowia lipolytica* strain Y5037U (Example 2) was individually transformed with linear SphI-AscI fragments of the integrating vectors described in Example 3, wherein ScAle1S and MaLPAAT1S were under the control of the *Yarrowia* YAT promoter, while CeLPCATS was under the control of the *Yarrowia* FBAIN promoter. Specifically, vectors pY201 (YAT1::ScAle1S::Lip1), pY208 (YAT1::MaLPAAT1S::Lip1) and pY153 (FBAIN::CeLPCATS::YlLPAAT1) were transformed according to the General Methods.

Each transformation mix was plated on MM agar plates. Selected transformants were further characterized, as detailed below. More specifically, clone #7 of strain Y5037U, transformed with expression vector pY153 (comprising CeLPCATS) was selected and designated as "Y5037U::FBAIN-CeLPCATS"; clone #18 of strain Y5037U, transformed with expression vector pY201 (comprising ScAle1S) was selected and designated as "Y5037U::ScAle1S"; and clone #6 of strain Y5037U, transformed with expression vector pY208 (comprising MaLPAAT1S) was selected and designated as "Y5037U::MaLPAAT1S". Additionally, strain Y5037 (a Ura+ strain that was parent to strain Y5037 (Ura−)) was used as a control.

A total of four separate experiments were conducted in 3 mL culture based on variable culturing conditions and strains, to examine the effect of LPLAT overexpression on lipid content, fatty acid composition and conversion efficiencies. Experiment 1 compared control strain Y5037 versus strains Y5037U::FBAIN-CeLPCATS and Y5037U::ScAle1S after 2 days of growth in MM medium on a shaker at 200 rpm and 30° C., followed by 3 days of incubation in 3 mL HGM medium. MM medium (Cat. No. CML-MM, Biomyx Technology), pH 6.1, contains per L: 1.7 g yeast nitrogen base ["YNB"] without amino acids and $NH_4SO_4$, 1 g proline, 0.1 g adenine, 0.1 g lysine, and 20 g glucose.

Experiment 2 compared control strain Y5037 versus strain Y5037U::ScAle1S after 2 days of growth in CSM-U medium on a shaker at 200 rpm and 30° C., followed by 3 days of incubation in 3 mL HGM medium. CSM-U medium (Cat. No C8140, Teknova Inc, Hollister, Calif.) contains: 0.13% amino acid dropout powder minus uracil, 0.17% yeast nitrogen base, 0.5% $(NH_4)_2SO_4$, and 2.0% glucose.

Experiment 3 compared control strain Y5037 versus strains Y5037U::FBAIN-CeLPCATS and Y5037U::ScAle1S after 2 days of growth in MM medium on a shaker at 200 rpm and 30° C., followed by 5 days of incubation in 3 mL HGM medium.

Experiment 5 compared control strain Y5037 versus strain Y5037U::MaLPAAT1S after 2 days of growth in FM medium on a shaker at 200 rpm and 30° C., followed by 3 days of incubation in 3 mL HGM medium. The composition of FM medium is described in Example 4.

Following growth for 3 days (Experiments 1, 2, and 5) or 5 days (Experiment 3) in HGM, 1 mL aliquots of the cultures were harvested by centrifugation and analyzed by GC, as described in Example 4.

Experiment 4 compared control strain Y5037 versus strains Y5037U::FBAIN-CeLPCATS and Y5037U::ScAle1S after 2 days of growth in 25 mL FM medium followed by 5 days of incubation in HGM medium as described above. Specifically, one loop of freshly streaked cells from MM agar plates was inoculated into 3 mL FM medium and grown overnight at 250 rpm and 30° C. The $OD_{600nm}$ was measured and an aliquot of the cells were added to a final $OD_{600nm}$ of 0.3 in 25 mL FM medium in a 125 mL flask. After 2 days in a shaker incubator at 250 rpm and at 30° C., 6 mL of the culture was harvested by centrifugation and resuspended in 25 mL HGM in a 125 mL flask. After 5 days in a shaker incubator at 250 rpm and at 30° C., a 1 mL aliquot was used for GC analysis and 10 mL dried for dry cell weight ["DCW"] determination (supra, Example 4).

Lipid Content, Fatty Acid Composition and Conversion Efficiencies

In each experiment, the lipid content and fatty acid composition are quantified for 1, 2, 3 or 4 replicate cultures ["Replicates"] of the control Y5037 strain and the transformant Y5037U strain(s). Additionally, data for each Y5037U transformant is presented as a % of the Y5037 control. Table 19 below summarizes the concentration of each fatty acid as a weight percent of TFAs ["% TFAs"]. More specifically, fatty acids are identified as 16:0 (palmitate), 16:1 (palmitoleic acid), 18:0 (stearic acid), 18:1 (oleic acid), 18:2 (LA), ALA, EDA, DGLA, ARA, ETrA, ETA, EPA, DPA, DHA and EDD (corresponding to the sum of EPA plus DPA plus DHA). Additionally, the ratio of DHA % TFAs/DPA % TFAs is provided.

Table 20 summarizes the total DCW (mg/mL), the total lipid content of cells ["TFAs % DCW"], and the conversion efficiency of each desaturase and elongase functioning in the PUFA biosynthetic pathway and which are required for DHA production. Specifically, the Δ2 desaturase conversion efficiency ["Δ2 CE"], Δ8 desaturase conversion efficiency ["Δ8 CE"], Δ5 desaturase conversion efficiency ["Δ5 CE"], Δ17 desaturase conversion efficiency ["Δ17 CE"], Δ4 desaturase conversion efficiency ["Δ4 CE"], Δ9 elongation conversion efficiency ["Δ9e CE"] and Δ5 elongation conversion efficiency ["Δ5e CE"] are provided for each control Y5037 strain and the transformant Y5037U strain(s); data for each Y5037U transformant is presented as a % of the Y5037 control. Conversion efficiency was calculated according to the formula: product(s)/(product(s)+substrate)*100, where product includes both product and product derivatives.

TABLE 19

Lipid Content and Composition In LPCAT Transformant Strains Of *Yarrowia lipolytica* Y5037

| | | | | | | | | | | | % TFAs | | | | | | | | |
|---|---|---|---|---|---|---|---|---|---|---|---|---|---|---|---|---|---|---|---|
| Expt. | Strain | Replicates | 16:0 | 16:1 | 18:0 | 18:1 | 18:2 | ALA | EDA | DGLA | ARA | ETrA | ETA | EPA | DPA | DHA | EDD | DHA/DPA |
| 1 | Y5037 | AVG.4 | 4.1 | 1.1 | 3.2 | 5.4 | 21.8 | 0.5 | 2.9 | 1.7 | 0.7 | 1.3 | 1.8 | 18.1 | 20.6 | 6.5 | 45.2 | 0.3 |
| | Y5037U:: | 1 | 5.2 | 1.2 | 2.7 | 8.5 | 11.1 | 0.3 | 2.5 | 3.6 | 1.1 | 1.4 | 2.7 | 31.7 | 9.6 | 11.0 | 52.4 | 1.1 |
| | FBAIN-CeLPCATS | % Ctrl | 127 | 109 | 84 | 157 | 51 | 60 | 86 | 212 | 157 | 108 | 150 | 175 | 47 | 169 | 116 | 367 |
| | Y5037U:: | 1 | 4.4 | 1.4 | 2.0 | 4.4 | 15.7 | 0.5 | 3.5 | 2.7 | 1.0 | 1.2 | 2.2 | 22.0 | 16.8 | 14.4 | 53.3 | 0.9 |
| | ScAleIS | % Ctrl | 107 | 127 | 63 | 81 | 72 | 100 | 121 | 159 | 143 | 92 | 122 | 122 | 82 | 222 | 118 | 300 |
| 2 | Y5037 | AVG.2 | 4.4 | 1.1 | 3.9 | 5.4 | 21.8 | 0.5 | 3.4 | 1.6 | 0.8 | 1.1 | 1.7 | 17.0 | 21.0 | 6.7 | 44.7 | 0.3 |
| | Y5037U:: | 1 | 4.5 | 1.5 | 2.5 | 4.7 | 16.6 | 0.4 | 4.1 | 2.6 | 1.1 | 1.1 | 2.1 | 21.2 | 17.1 | 13.2 | 51.5 | 0.8 |
| | ScAleIS | % Ctrl | 102 | 136 | 64 | 87 | 76 | 80 | 121 | 163 | 138 | 100 | 124 | 125 | 81 | 197 | 115 | 267 |
| 3 | Y5037 | AVG.3 | 3.9 | 1.1 | 1.6 | 4.7 | 20.7 | 0.5 | 3.3 | 1.8 | 1.3 | 1.5 | 3.9 | 19.3 | 20.8 | 7.9 | 47.9 | 0.4 |
| | Y5037U:: | 1 | 5.8 | 1.1 | 2.6 | 8.0 | 10.0 | 0.3 | 3.0 | 3.6 | 1.9 | 2.2 | 2.7 | 31.0 | 9.9 | 11.8 | 52.7 | 1.2 |
| | FBAIN-CeLPCATS | % Ctrl | 149 | 100 | 163 | 170 | 48 | 60 | 91 | 200 | 146 | 147 | 69 | 161 | 48 | 149 | 110 | 300 |
| | Y5037U:: | 1 | 4.6 | 1.3 | 1.8 | 5.9 | 18.1 | 0.3 | 4.4 | 2.4 | 1.3 | 1.8 | 4.0 | 22.1 | 15.1 | 11.7 | 48.9 | 0.8 |
| | ScAleIS | % Ctrl | 118 | 118 | 113 | 126 | 87 | 60 | 133 | 133 | 100 | 120 | 103 | 115 | 73 | 148 | 102 | 200 |
| 5 | Y5037 | 1 | 5.1 | 1.3 | 1.6 | 4.7 | 22.5 | 2.7 | 3.9 | 1.9 | 1.4 | 1.3 | 1.7 | 20.4 | 20.7 | 8.9 | 50.1 | 0.4 |
| | Y5037U:: | 1 | 6.1 | 1.5 | 1.8 | 4.5 | 21.1 | 2.2 | 4.0 | 2.1 | 1.5 | 1.2 | 1.7 | 23.4 | 19.5 | 10.7 | 53.7 | 0.6 |
| | MaLPAT1 | % Ctrl | 120 | 115 | 113 | 96 | 94 | 81 | 103 | 111 | 107 | 92 | 100 | 115 | 94 | 120 | 107 | 150 |
| 4 | Y5037 | AVG.3 | 3.9 | 1.2 | 1.3 | 5.9 | 22.4 | 3.9 | 1.7 | 1.8 | 0.8 | 1.0 | 1.6 | 20.0 | 26.2 | 6.7 | 52.9 | 0.3 |
| | Y5037U:: | AVG.3 | 6.1 | 1.3 | 3.4 | 8.8 | 10.1 | 0.7 | 1.6 | 3.5 | 0.7 | 1.3 | 2.3 | 33.9 | 12.5 | 10.6 | 57.0 | 0.9 |
| | FBAIN-CeLPCATS | % Ctrl | 156 | 108 | 262 | 149 | 45 | 18 | 94 | 194 | 88 | 130 | 144 | 170 | 48 | 158 | 108 | 300 |
| | Y5037U:: | AVG.3 | 5.4 | 1.4 | 2.7 | 8.7 | 21.1 | 1.7 | 5.4 | 2.5 | 0.6 | 1.2 | 1.4 | 20.4 | 19.6 | 7.3 | 47.3 | 0.4 |
| | ScAleIS | % Ctrl | 138 | 117 | 208 | 147 | 94 | 44 | 318 | 139 | 75 | 120 | 88 | 102 | 75 | 109 | 89 | 133 |

TABLE 20

Desaturase And Elongase Conversion Efficiency In LPCAT Transformant Strains Of *Yarrowia lipolytica* Y5037

| Expt. | Strain | Replicates | DCW mg/mL | TFA % DCW | Δ12 CE | Δ9e CE | Δ8 CE | Δ5 CE | Δ17 CE | Δ5e CE | Δ4 CE |
|---|---|---|---|---|---|---|---|---|---|---|---|
| 1 | Y5037 | AVG.4 | nd | nd | 93 | 71 | 92 | 93 | 90 | 60 | 24 |
| | Y5037U:: | 1 | nd | nd | 90 | 85 | 94 | 89 | 89 | 39 | 53 |
| | FBAIN-CeLPCATS | % Ctrl | nd | nd | 96 | 120 | 102 | 96 | 98 | 66 | 221 |
| | Y5037U:: | 1 | nd | nd | 95 | 80 | 93 | 92 | 89 | 59 | 46 |
| | ScAleIS | % Ctrl | nd | nd | 102 | 113 | 101 | 99 | 98 | 98 | 191 |
| 2 | Y5037 | AVG.2 | nd | nd | 93 | 71 | 91 | 93 | 89 | 62 | 24 |
| | Y5037U:: | 1 | nd | nd | 94 | 79 | 92 | 92 | 88 | 59 | 44 |
| | ScAleIS | % Ctrl | nd | nd | 101 | 111 | 100 | 99 | 98 | 95 | 180 |
| 3 | Y5037 | AVG.3 | nd | nd | 94 | 74 | 92 | 90 | 89 | 60 | 27 |
| | Y5037U:: | 1 | nd | nd | 91 | 86 | 92 | 90 | 87 | 41 | 54 |
| | FBAIN-CeLPCATS | % Ctrl | nd | nd | 96 | 117 | 100 | 100 | 97 | 69 | 198 |
| | Y5037U:: | 1 | nd | nd | 93 | 77 | 90 | 89 | 87 | 55 | 44 |
| | ScAleIS | % Ctrl | nd | nd | 99 | 105 | 98 | 99 | 97 | 92 | 160 |
| 5 | Y5037 | 1 | nd | nd | 95 | 70 | 91 | 93 | 88 | 59 | 30 |
| | Y5037U:: | 1 | nd | nd | 95 | 73 | 92 | 93 | 88 | 56 | 36 |
| | MaLPAT1 | % Ctrl | nd | nd | 100 | 104 | 101 | 100 | 100 | 95 | 118 |
| 4 | Y5037 | AVG.3 | 3.7 | 19.7 | nd | 69 | 95 | 94 | 93 | 62 | 20 |
| | Y5037U:: | AVG.3 | 3.0 | 14.0 | nd | 86 | 96 | 91 | 91 | 40 | 46 |
| | FBAIN-CeLPCATS | % Ctrl | 82 | 71 | nd | 124 | 100 | 97 | 98 | 65 | 226 |
| | Y5037U:: | AVG.3 | 3.7 | 31.6 | nd | 72 | 89 | 92 | 85 | 57 | 27 |
| | ScAleIS | % Ctrl | 101 | 157 | nd | 104 | 93 | 98 | 92 | 92 | 133 |

Based on the data in Table 19 and Table 20, overexpression of LPLAT in DHA strains Y5037U::CeLPCATS, Y5037U::ScAle1S and Y5037U::MaLPAAT1S results in reduction of the concentration of LA as a weight % of TFAs ["LA % TFAs"], an increase in the concentration of EPA as a weight % of TFAs ["EPA % TFAs"], an increase in the concentration of DHA as a weight % of TFAs ["DHA % TFAs"], an increase in the concentration of EPA+DPA+DHA as a weight % of TFAs ["EDD % TFAs"] (with the exception of strain Y5037U::ScAle1S in Experiment 4), an increase in the ratio of DHA % TFAs to DPA % TFAs ["DHA/DPA"], an increase in the conversion efficiency of the Δ9 elongase and an increase in the conversion efficiency of the Δ4 desaturase.

More specifically, depending on the culture conditions, CeLPCATS overexpression in Y5037U::CeLPCATS can reduce LA % TFAs to 45%, increase EPA % TFAs to 175%, increase DHA % TFAs to 169%, increase Δ9 elongation CE to 124%, and increase Δ4 desaturation CE to 226%, as compared to the control. Similarly, depending on the culture conditions, ScAle1S overexpression in Y5037U::ScAle1S can reduce LA % TFAs to 72%, increase EPA % TFAs to 125%, increase DHA % TFAs to 222%, increase Δ9 elongation CE to 113%, and increase Δ4 desaturation CE to 191%, as compared to the control. Finally, overexpression of MaLPAAT1 in Y5037U::MaLPAAT1S can reduce LA % TFAs to 94%, increase EPA % TFAs to 115%, increase DHA % TFAs to 120%, increase Δ9 elongation CE to 104%, and increase Δ4 desaturation CE to 118%, as compared to the control.

Although Y5037U::CeLPCATS possessed a significantly lower total lipid content ["TFAs % DCW"] in Experiment 4, the total lipid content was significantly improved in strain Y5037U::ScAle1S. This increase in lipid content is a likely explanation for the lower EDD % TFAs in strain Y5037U::ScAle1S.

DHA biosynthesis via EPA involves two steps: elongation of EPA to DPA by $C_{20/22}$ elongase (also known as either a "C20" elongase or a Δ5 elongase) and desaturation of DPA to DHA by Δ4 desaturase. An important bottleneck in the production of DHA from EPA has been the Δ4 desaturation step, evident by the build up of DPA, although the mechanistic details for this limitation were unknown. The results above show that expression of ScAle1S, YlAle1, YlLPAAT1, MaLPAAT1S, and CeLPCATS proteins significantly improved Δ4 desaturation. Thus, Δ4 desaturation was not limiting because of Δ4 desaturase activity per se. Instead, Δ4 desaturation was limiting because of limited availability of the DPA substrate at the sn-2 position of phospholipids. The results showed unexpectedly that (unlike other desaturation substrates), limited DPA incorporation into phospholipid can be overcome by overexpression of Ale1, LPAAT and LPCAT proteins.

Previously, Intl. App. Pub. No. WO 2004/076617 showed that expression of CeLPCAT (SEQ ID NO:2) in *Saccharomyces cerevisiae* improved Δ6 elongation of exogenously provided GLA to DGLA. It hypothesized that CeLPCAT removed an acyl chain from the sn-2 position of phospholipids, thereby making the removed acyl group available for elongation in the CoA pool. It was shown in the present studies that the expression of the codon-optimized CeLPCATS, under control of the YAT1 promoter, in strains of *Yarrowia lipolytica* engineered to produce high levels of EPA (Example 4) and DHA (Example 5), respectively, improves Δ9 elongation of endogenously produced LA to EDA. However, expression of CeLPCATS in DHA-producing strain Y5037U::CeLPCATS unexpectedly did not result in improved Δ5 elongation of EPA to DPA. In contrast, expression of CeLPCATS in DHA-producing strain Y5037U::CeLPCATS very significantly improved Δ4 desaturation of DPA to DHA (supra). This is especially unexpected since desaturations occur mainly at the sn-2 position of phospholipids and elongation occurs in the CoA pool.

Based on the improved Δ4 desaturation conversion efficiency resulting from over-expression of LPLATs, demonstrated above, it is anticipated that the LPLATs described herein and their orthologs, such as ScLPAAT, will also improve Δ4 desaturation conversion efficiency.

Example 6

Functional Characterization of Different LPLATs in ARA-Producing *Y. lipolytica* Strain Y8006U

*Yarrowia lipolytica* strain Y8006U, producing ARA, is used to functionally characterize the effects of overexpression of the *Saccharomyces cerevisiae* Ale1, *Mortierella alpina* LPAAT1 and *Caenorhabditis elegans* LPCAT, following their integration into the *Yarrowia* host chromosome. This was in spite of the host containing its native LPLATs, i.e., Ale1 and LPAAT1.

Transformation and Growth

*Yarrowia lipolytica* strain Y8006U (Example 1) will be individually transformed with linear SphI-AscI fragments of the integrating vectors described in Example 3, in a manner comparable to that utilized in Example 4. URA+ transformants will be selected, grown for 2 days in FM medium and 5 days in HGM medium and then 1 mL aliquots of the cultures will be harvested by centrifugation and analyzed by GC (Example 4). Based on the fatty acid composition of the 3 mL cultures, selected transformants will be further characterized using strain Y8006 (a Ura+ strain that was parent to strain Y8006U (Ura−)) as a control.

Each selected transformant and the control will be re-grown in FM and HGM medium, as described in Example 4, and then subjected to GC analysis and DCW determination.

The lipid content, fatty acid composition and ARA as a percent of the DCW will be quantified for the control Y8006 strain and the transformant Y8006U strain(s). Additionally, data for each Y8006U transformant will be determined as a % of the Y8006 control. The conversion efficiency of each desaturase and the Δ9 elongase functioning in the PUFA biosynthetic pathway and which is required for ARA production will also be determined and compared to the control, in a manner similar to that in Examples 4 and 5.

It is hypothesized that overexpression of the ScAle1S, YlAle1, MaLPAAT1S, YlLPAAT1 and CeLPCATS LPLATs in the ARA strains will result in a reduction of the concentration of LA (18:2) as a weight % of TFAs ["LA % TFAs"], an increase in the concentration of ARA as a weight % of TFAs ["ARA % TFAs"], and an increase in the conversion efficiency of the Δ9 elongase.

Example 7

Construction of Expression Vectors Comprising LPAAT ORFs and an Autonomously Replicating Sequence The present example describes the construction of vectors comprising autonomously replicating sequences ["ARS"] and LPAAT ORFs suitable for LPAAT gene expression without integration in *Yarrowia lipolytica*. ORFs included the *Saccharomyces cerevisiae* LPAAT encoding SEQ ID NO:18 and the *Yarrowia lipolytica* LPAAT1 encoding SEQ ID NO:17. Example 8 describes the results obtained following transformation of these vectors into *Y. lipolytica*.

Construction of pY222, Comprising a Codon-Optimized *Saccharomyces cerevisiae* LPAAT Gene The *Saccharomyces cerevisiae* ORF designated as "ScLPAAT" (SEQ ID NO:18) was optimized for expression in *Yarrowia lipolytica*, by DNA 2.0 (Menlo Park, Calif.). In addition to codon optimization, 5' Pci1 and 3' Not1 cloning sites were introduced within the synthetic gene (i.e., ScLPAATS; SEQ ID NO:96). None of the modifications in the ScLPAATS gene changed the amino acid sequence of the encoded protein (i.e., the protein sequence encoded by the codon-optimized gene [i.e., SEQ ID NO:97] is identical to that of the wildtype protein sequence [i.e., SEQ ID NO:18]). ScLPAATS was cloned into pJ201 (DNA 2.0) to result in pJ201:ScLPAATS.

A 926 bp Pci1/Not1 fragment comprising ScLPAATS was excised from pJ201:ScLPAATS and cloned into NcoI-Not1 cut pYAT-DG2-1 to create pY222 (SEQ ID NO:100; Table 21; FIG. 13A). Thus, pY222 contained the following components:

TABLE 21

| Description of Plasmid pY222 (SEQ ID NO: 100) | |
|---|---|
| RE Sites And Nucleotides Within SEQ ID NO: 100 | Description Of Fragment And Chimeric Gene Components |
| SalI/SwaI (1-2032) | YAT1::ScLPAATS::Lip1, comprising: YAT1: *Yarrowia lipolytica* YAT1 promoter (U.S. patent application Pub. No. 2006/0094102-A1); ScLPAATS: codon-optimized ScLPAATS (SEQ ID NO: 96) (labeled as "Sc LPAATs ORF" in Figure); Lip1: Lip1 terminator sequence from *Yarrowia* Lip1 gene (GenBank Accession No. Z50020) (labeled as "Lip1-3'" in Figure) |
| SwaI/AvaI (2032-4946) | ColE1 plasmid origin of replication; Ampicillin-resistance gene ($Amp^R$) for selection in *E. coli*; *E. coli* f1 origin of replication |
| AvaI-SphI (4946-6330) | *Yarrowia lipolytica* centromere and autonomously replicating sequence ["ARS"] 18 locus |
| SphI-SalI (6330-1) | *Yarrowia lipolytica* URA3 gene (GenBank Accession No. AJ306421) |

Construction of pY177, Comprising a *Yarrowia lipolytica* LPAAT1 Gene

The *Yarrowia lipolytica* centromere and autonomously replicating sequence ["ARS"] was amplified by standard PCR using primer 869 (SEQ ID NO:98) and primer 870 (SEQ ID NO:99), with plasmid pYAT-DG2-1 as template. The PCR product was digested with AscI/AvrII and cloned into AscI-AvrII digested pY207 (SEQ ID NO:87; Example 3) to create pY177 (SEQ ID NO:101; Table 22; FIG. 13B). Thus, the components present in pY177 are identical to those in pY207 (FIG. 11B), except for the replacement of the 373 bp pY207 sequence between AscI and AvrII with the 1341 bp sequence containing ARS. More specifically, pY177 contained the following components:

TABLE 22

| Description of Plasmid pY177 (SEQ ID NO: 101) | |
|---|---|
| RE Sites And Nucleotides Within SEQ ID NO: 101 | Description Of Fragment And Chimeric Gene Components |
| BsiW1/Sbf1 (1-1706 bp) | LoxP::Ura3::LoxP, comprising: LoxP sequence (SEQ ID NO: 78) *Yarrowia lipolytica* Ura3 gene (GenBank Accession No. AJ306421); LoxP sequence (SEQ ID NO: 78) |
| Sbf1/Sph1 (1706-3043 bp) | 3' portion of *Yarrowia lipolytica* POX3 Acyl-CoA oxidase 3 (GenBank Accession No. YALI0D24750g) |
| SphI/AscI (3043-5743 bp) | ColE1 plasmid origin of replication; Ampicillin-resistance gene ($Amp^R$) for selection in *E. coli*; *E. coli* f1 origin of replication |
| AscI/BsiWI (5743-6513 bp) | 5' portion of *Yarrowia lipolytica* POX3 Acyl-CoA oxidase 3 (GenBank Accession No. YALI0D24750g) |
| AscI/AvrII (5743-7084 bp) | *Yarrowia lipolytica* centromere and autonomously replicating sequence ["ARS"] 18 locus |
| AvrII/BsiWI | 5' portion of *Yarrowia lipolytica* POX3 Acyl-CoA oxidase 3 |

TABLE 22-continued

Description of Plasmid pY177 (SEQ ID NO: 101)

| RE Sites And Nucleotides Within SEQ ID NO: 101 | Description Of Fragment And Chimeric Gene Components |
|---|---|
| (7084-7481 bp) BsiWI/BsiWI (7481-1 bp) | (GenBank Accession No. YALI0D24750g) YAT1::YlLPAAT1::Lip1, comprising: YAT1: *Yarrowia lipolytica* YAT1 promoter (U.S. patent application Pub. No. 2006/0094102-A1); YlLPAAT1: *Yarrowia lipolytica* LPAAT1 ("YALI0E18964g"; GenBank Accession No. XP_504127) (SEQ ID NO: 16) (labeled as "Yl LPAT1 ORF" in Figure); Lip1: Lip1 terminator sequence from *Yarrowia* Lip1 gene (GenBank Accession No. Z50020) (labeled as "Lip1-3'" in Figure) |

Example 8

Functional Characterization of Different LPAATs in EPA-Producing *Yarrowia lipolytica* Strain Y8406

*Yarrowia lipolytica* strain Y8406U, producing EPA, was used to functionally characterize the effects of expression of the *Saccharomyces cerevisiae* LPAATS (SEQ ID NO:96) and *Yarrowia lipolytica* LPAAT1 (SEQ ID NO:16) without integration on self-replicating plasmids. This was in spite of the host containing its native LPAATs.

Transformation and Growth

*Yarrowia lipolytica* strain Y8406U (Example 1) was individually transformed with uncut plasmids from Example 7. Specifically, vectors pY177 (YAT1::YlLPAAT1::Lip1) [SEQ ID NO:101] and pY222 (YAT1::ScLPAATS::Lip1) [SEQ ID NO:100] were transformed according to the General Methods.

Each transformation mix was plated on MM agar plates. Several resultant URA+ transformants were picked and inoculated into 3 mL CSM-U medium (Teknova Cat. No. C8140, Teknova Inc., Hollister, Calif.), wherein CSM-U medium refers to CM Broth with glucose minus uracil containing 0.13% amino acid dropout powder minus uracil, 0.17% yeast nitrogen base, 0.5% $(NH_4)_2SO_4$, and 2.0% glucose. After 2 days growth on a shaker at 200 rpm and 30° C., the cultures were harvested by centrifugation and resuspended in 3 mL HGM medium (Cat. No. 2G2080, Teknova Inc.). After 5 days growth on a shaker, 1 mL aliquots of the cultures were harvested and analyzed by GC, as described in Example 4.

Based on the fatty acid composition of the 3 mL cultures, selected transformants were further characterized by flask assay. Specifically, clones #5 and #6 of strain Y8406U transformed with expression vector pY222 (comprising ScLPAATS) were selected and designated as "Y8406U:: ScLPAATS-5" and "Y8406U::ScLPAATS-6", respectively; clone #1 of strain Y8406U transformed with expression vector pY177 (comprising YlLPAAT1) was selected and designated as "Y8406U::YlLPAAT1". Additionally, strain Y8406 (a Ura+ strain that was parent to strain Y8406U (Ura-)) was used as a control.

Each selected transformant and the control was streaked onto MM agar plates. Then, one loop of freshly streaked cells was inoculated into 3 mL CSM-U medium and grown overnight at 250 rpm and 30° C. The $OD_{600nm}$ was measured and an aliquot of the cells were added to a final $OD_{600nm}$ of 0.3 in 25 mL CSM-U medium in a 125 mL flask. After 2 days in a shaker incubator at 250 rpm and at 30° C., 6 mL of the culture was harvested by centrifugation and resuspended in 25 mL HGM in a 125 mL flask. After 5 days in a shaker incubator at 250 rpm and at 30° C., a 1 mL aliquot was used for GC analysis and 10 mL dried for dry cell weight ["DCW"] determination, as described in Example 4.

Lipid Content, Fatty Acid Composition and Conversion Efficiencies

The lipid content, fatty acid composition and EPA as a percent of the DCW are quantified for 2 replicate cultures ["Replicates"] of the control Y8406 strain and the transformant Y8406U strain(s). Additionally, data for each Y8406U transformant is presented as a % of the Y8406 control. Table 23 below summarizes the total lipid content of cells ["TFAs % DCW"], the concentration of each fatty acid as a weight percent of TFAs ["% TFAs"] and the EPA content as a percent of the dry cell weight ["EPA % DCW"]. More specifically, fatty acids are identified as 16:0 (palmitate), 16:1 (palmitoleic acid), 18:0 (stearic acid), 18:1 (oleic acid), 18:2 (LA), ALA, EDA, DGLA, ARA, ETrA, ETA and EPA.

Table 24 summarizes the conversion efficiency of each desaturase and the Δ9 elongase functioning in the PUFA biosynthetic pathway and which are required for EPA production, in a manner identical to that described in Example 4.

TABLE 23

Lipid Content And Composition In ScLPAATS and YlLPAAT1 Transformant Strains Of *Yarrowia lipolytica* Y8406

| Strain | Replicates | TFA % DCW | 16:0 | 16:1 | 18:0 | 18:1 | 18:2 | ALA | EDA | DGLA | ARA | ERA | ETA | EPA | EPA % DCW |
|---|---|---|---|---|---|---|---|---|---|---|---|---|---|---|---|
| Y8406 | AVG.2 | 22.0 | 2 | 0 | 2 | 4 | 19 | 2 | 3 | 4 | 1 | 2 | 3 | 55 | 12 |
| Y8406U:: YlLPAAT1 | AVG.2 | 24.6 | 2 | 1 | 2 | 6 | 14 | 1 | 3 | 5 | 1 | 2 | 3 | 55 | 14 |
| | % Ctrl | 112 | 98 | 153 | 102 | 148 | 76 | 50 | 120 | 144 | 101 | 109 | 123 | 101 | 113 |
| Y8406U:: ScLPAATS-5 | AVG.2 | 21.6 | 3 | 1 | 3 | 6 | 14 | 1 | 3 | 4 | 1 | 2 | 3 | 57 | 12 |
| | % Ctrl | 98 | 131 | 137 | 125 | 131 | 74 | 56 | 100 | 117 | 86 | 101 | 108 | 104 | 102 |

TABLE 23-continued

Lipid Content And Composition In ScLPAATS and YlLPAAT1 Transformant Strains Of *Yarrowia lipolytica* Y8406

| Strain | Replicates | TFA % DCW | 16:0 | 16:1 | 18:0 | 18:1 | 18:2 | ALA | EDA | DGLA | ARA | ERA | ETA | EPA | EPA % DCW |
|---|---|---|---|---|---|---|---|---|---|---|---|---|---|---|---|
| Y8406U:: ScLPAATS-6 | AVG.2 | 21.4 | 3 | 1 | 3 | 5 | 14 | 1 | 3 | 4 | 1 | 2 | 3 | 58 | 12 |
|  | % Ctrl | 97 | 125 | 133 | 121 | 124 | 72 | 52 | 97 | 119 | 88 | 102 | 111 | 106 | 103 |

TABLE 24

Desaturase And Elongase Conversion Efficiency In ScLPAATS and YlLPAAT1 Transformant Strains Of *Yarrowia lipolytica* Y8406

| Strain | Replicates | $\Delta12$ CE | $\Delta9e$ CE | $\Delta8$ CE | $\Delta5$ CE | $\Delta17$ CE |
|---|---|---|---|---|---|---|
| Y8406 | AVG.2 | 95 | 77 | 92 | 90 | 92 |
| Y8406U::YlLPAAT1 | AVG.2 | 93 | 82 | 92 | 87 | 90 |
|  | % Ctrl | 98 | 107 | 99 | 97 | 98 |
| Y8406U::ScLPAATS-5 | AVG.2 | 94 | 83 | 93 | 89 | 92 |
|  | % Ctrl | 98 | 108 | 100 | 99 | 100 |
| Y8406U::ScLPAATS-6 | AVG.2 | 94 | 83 | 93 | 89 | 92 |
|  | % Ctrl | 99 | 109 | 101 | 99 | 100 |

Based on the data in Table 23 and Table 24 above, overexpression of both ScLPAATS and YlLPAAT1 in EPA strains Y8406U::YlLPAAT1, Y8406U::ScLPAATS-5 and Y8406U::ScLPAATS-6 resulted in reduction (to 76% or below of the control) of the concentration of LA (18:2) as a weight % of TFAs ["LA % TFAs"], and an increase (to at least 7% of the control) in the conversion efficiency of the Δ9 elongase. ScLPAATS and YlLPAAT1 have a similar effect on lipid profile.

The results obtained above were then compared to those obtained in Example 4, although different means were utilized to characterize the LPLATs. Specifically, in Example 4, linearized DNA carrying the LPLATs were transformed by chromosomal integration, since the vectors lacked ARS sequences. This resulted in stable integrations and the strains were grown in the relatively rich, non-selective FM growth medium during both preculture and 2 days growth prior to being transferred to HGM.

In Example 8, the functional characterization of YlL-PAAT1 and ScLPAATS was done on a replicating plasmid. Thus, *Yarrowia lipolytica* strain Y8406 was transformed with circular DNA carrying each LPAAT and ARS sequence. To maintain these plasmids and assay gene expression without integration, it was necessary to grow the transformants on selective medium (i.e., CSM-U medium) during both preculture and 2 days growth prior to being transferred to HGM.

These differences described above can contribute to differences in lipid profile and content, as illustrated by the expression of YlLPAAT1 in Examples 4 and 8. The change over control in LA % TFAs, EPA % TFAs, and Δ9 elongase conversion efficiency were 63%, 115%, and 115%, respectively, upon expression of YlLPAAT in Example 4, whereas the change over control in LA % TFAs, EPA % TFAs, and Δ9 elongase conversion efficiency were were 76%, 101%, and 107%, respectively, upon expression of YlLPAAT in Example 8. Thus, the improvements in Δ9 elongation and LC-PUFA biosynthesis in Example 8 are minimized when compared to those observed in Example 4. These differences can be attributed to the "position effects" of chromosomal integration and/or different growth conditions.

Since the improvements in LC-PUFA biosynthesis (measured as reduction in LA % TFAs, increase in EPA % TFAs and increase in Δ9 elongase conversion efficiency) are similar for both ScLPAATS and YlLPAAT when transformed in *Yarrowia lipolytica* strain Y8406 on a replicating plasmid, it is anticipated that both LPLAATs will also function similarly when stably integrated into the host chromosome. Thus, ScLPAATS will likely improve the lipid profile in a manner similar to that observed in Examples 4 and 5, when YlL-PAAT1 was stably integrated into the host chromosome.

What is claimed is:

1. A recombinant oleaginous microbial host cell for improved production of at least one long-chain polyunsaturated fatty acid, said host cell comprising at least one isolated polynucleotide encoding a polypeptide having at least acyl-CoA:lysophospholipid acyltransferase activity, wherein the polypeptide comprises (i) at least 90% amino acid identity, based on the Clustal W method of alignment, compared to the amino acid sequence of SEQ ID NO:11, and (ii) at least one membrane bound O-acyltransferase protein family motif selected from the group consisting of: SEQ ID NO:3, SEQ ID NO:4, SEQ ID NO:5 and SEQ ID NO:28;
  wherein the isolated polynucleotide is operably linked to at least one regulatory sequence, and further wherein the host cell has at least one improvement selected from the group consisting of:
  (i) an increase in $C_{18}$ to $C_{20}$ elongation conversion efficiency compared to a control host cell, and
  (ii) an increase in delta-4 desaturation conversion efficiency compared to a control host cell.

2. The recombinant host cell of claim 1, wherein the at least one long-chain polyunsaturated fatty acid is selected from the group consisting of: eicosadienoic acid, dihomo-gamma-linolenic acid, arachidonic acid, eicosatrienoic acid, eicosatetraenoic acid, eicosapentaenoic acid, docosatetraenoic acid, omega-6 docosapentaenoic acid, omega-3 docosapentaenoic acid and docosahexaenoic acid.

3. The recombinant host cell of claim 1, wherein the isolated polynucleotide is stably integrated in the host cell; and further wherein the improvement is selected from the group consisting of:
  a) an increase in $C_{18}$ to $C_{20}$ elongation conversion efficiency of at least 4% compared to a control host cell; and
  b) an increase in delta-4 desaturation conversion efficiency of at least 5% compared to a control host cell.

4. The recombinant host cell of claim 3, wherein the improvement is selected from the group consisting of:
  a) an increase in $C_{18}$ to $C_{20}$ elongation conversion efficiency of at least 13% compared to a control host cell, wherein the recombinant host cell produces eicosapentaenoic acid;
  b) an increase in $C_{18}$ to $C_{20}$ elongation conversion efficiency of at least 4% compared to a control host cell, wherein the recombinant host cell produces docosahexaenoic acid;
  c) an increase in delta-4 desaturation conversion efficiency of at least 18% compared to a control host cell, wherein the recombinant host cell produces docosahexaenoic acid;
  d) an increase of at least 9% of eicosapentaenoic acid measured as a weight percent of the total fatty acids compared to a control host cell;
  e) an increase of at least 2% of eicosapentaenoic acid measured as a weight percent of the total fatty acids compared to a control host cell, wherein the recombinant host cell produces docosahexaenoic acid; and
  f) an increase of at least 9% of docosahexaenoic acid measured as a weight percent of the total fatty acids compared to a control host cell.

5. The recombinant host cell of claim 1, wherein the host cell is a yeast.

6. The recombinant host cell of claim 5, wherein the yeast is *Yarrowia lipolytica*.

7. The recombinant host cell of claim 1, wherein the polypeptide comprises at least 95% amino acid identity compared to the amino acid sequence of SEQ ID NO:11.

8. The recombinant host cell of claim 1, wherein the regulatory sequence comprises a heterologous promoter.

9. A method for making an oil comprising eicosapentaenoic acid and/or docosahexaenoic acid comprising:
  a) culturing the recombinant host cell of claim 1, wherein an oil comprising eicosapentaenoic acid and/or docosahexaenoic acid is produced; and
  b) optionally recovering the oil of step (a).

10. The method of claim 9, wherein the recovered oil of step (b) is further processed.

11. The method of claim 9, wherein the host cell is an oleaginous yeast.

12. The method of claim 11, wherein the oleaginous yeast is *Yarrowia lipolytica*.

* * * * *